US009169250B2

(12) United States Patent
Zhang et al.

(10) Patent No.: US 9,169,250 B2
(45) Date of Patent: Oct. 27, 2015

(54) COMPOUNDS MODULATING C-FMS AND/OR C-KIT ACTIVITY AND USES THEREFOR

(71) Applicant: Plexxikon Inc., Berkeley, CA (US)

(72) Inventors: Jiazhong Zhang, Burlingame, CA (US); Prabha N. Ibrahim, Mountain View, CA (US); Ryan Bremer, Emeryville, CA (US)

(73) Assignee: Plexxikon Inc., Berkeley, CA (US)

( * ) Notice: Subject to any disclaimer, the term of this patent is extended or adjusted under 35 U.S.C. 154(b) by 0 days.

(21) Appl. No.: 14/250,331

(22) Filed: Apr. 10, 2014

(65) Prior Publication Data

US 2014/0243365 A1    Aug. 28, 2014

Related U.S. Application Data

(60) Continuation of application No. 13/776,547, filed on Feb. 25, 2013, now Pat. No. 8,722,702, which is a continuation of application No. 13/546,923, filed on Jul. 11, 2012, now Pat. No. 8,404,700, which is a continuation of application No. 12/958,379, filed on Dec. 1, 2010, now Pat. No. 8,461,169, which is a division of application No. 11/986,667, filed on Nov. 21, 2007, now Pat. No. 7,893,075.

(60) Provisional application No. 60/860,749, filed on Nov. 22, 2006.

(51) Int. Cl.
*A61K 31/497* (2006.01)
*A61K 31/506* (2006.01)
*C07D 471/04* (2006.01)
*A61K 31/444* (2006.01)
*A61K 31/5377* (2006.01)

(52) U.S. Cl.
CPC ............ *C07D 471/04* (2013.01); *A61K 31/444* (2013.01); *A61K 31/497* (2013.01); *A61K 31/506* (2013.01); *A61K 31/5377* (2013.01)

(58) Field of Classification Search
CPC .......................... A61K 31/497; A61K 31/506
See application file for complete search history.

(56) References Cited

U.S. PATENT DOCUMENTS

| | | | |
|---|---|---|---|
| 2,234,705 | A | 3/1941 | Normington et al. |
| 2,413,258 | A | 12/1946 | Soday et al. |
| 4,150,949 | A | 4/1979 | Smith |
| 4,301,159 | A | 11/1981 | Ogata et al. |
| 4,439,444 | A | 3/1984 | Nisato et al. |
| 4,568,649 | A | 2/1986 | Bertoglio-Matte |
| 4,595,780 | A | 6/1986 | Ogata et al. |
| 4,626,513 | A | 12/1986 | Burton et al. |
| 4,634,701 | A | 1/1987 | de Vincentiis |
| 4,714,693 | A | 12/1987 | Targos |
| 4,727,395 | A | 2/1988 | Oda et al. |
| 4,863,945 | A | 9/1989 | Friebe et al. |
| 5,120,782 | A | 6/1992 | Hubsch et al. |
| 5,143,854 | A | 9/1992 | Pirrung et al. |
| 5,338,849 | A | 8/1994 | Festal et al. |
| 5,360,882 | A | 11/1994 | Dougherty et al. |
| 5,426,039 | A | 6/1995 | Wallace et al. |
| 5,432,177 | A | 7/1995 | Baker et al. |
| 5,434,049 | A | 7/1995 | Okano et al. |
| 5,449,614 | A | 9/1995 | Danos et al. |
| 5,474,935 | A | 12/1995 | Chatterjee et al. |
| 5,486,525 | A | 1/1996 | Summers et al. |
| 5,556,752 | A | 9/1996 | Lockhart et al. |
| 5,576,319 | A | 11/1996 | Baker et al. |
| 5,580,859 | A | 12/1996 | Felgner et al. |
| 5,631,236 | A | 5/1997 | Woo et al. |
| 5,632,957 | A | 5/1997 | Heller et al. |
| 5,658,775 | A | 8/1997 | Gilboa |
| 5,681,959 | A | 10/1997 | Bishop et al. |
| 5,700,637 | A | 12/1997 | Southern |
| 5,700,809 | A | 12/1997 | Leeson et al. |
| 5,712,285 | A | 1/1998 | Curtis et al. |
| 5,721,118 | A | 2/1998 | Scheffler |
| 5,744,305 | A | 4/1998 | Fodor et al. |
| 5,747,276 | A | 5/1998 | Hoch et al. |
| 5,763,198 | A | 6/1998 | Hirth et al. |
| 5,770,456 | A | 6/1998 | Holmes |
| 5,800,992 | A | 9/1998 | Fodor et al. |
| 5,807,522 | A | 9/1998 | Brown et al. |
| 5,830,645 | A | 11/1998 | Pinkel et al. |
| 5,840,485 | A | 11/1998 | Lebl et al. |
| 5,856,174 | A | 1/1999 | Lipshutz et al. |

(Continued)

FOREIGN PATENT DOCUMENTS

| | | |
|---|---|---|
| CA | 2 550 361 | 7/2005 |
| DE | 24 13 258 A1 | 10/1975 |

(Continued)

OTHER PUBLICATIONS

Abou-Khalil, et al., "Delayed bone regeneration is linked to chronic inflammation in murine muscular dystrophy," *J. Bone Miner. Res.*, DOI 10.1002/jbmr.2038 (2013).
Ahmad, K., "BRAF mutation common to 70% of thyroid carcinomas," The Lancet, Oncology, (2003), 4:330.
Alfthan, K., "Surface Plasmon Resonance Biosensors as a Tool in Antibody Engineering," Biosensors & Bioelectronics, (1998), 13:653-663.
Allegretti, et al., "Palladium-Catalysed Functionalisation at 4- and 6-Position of the 7-Azaindole System," Synlett, (2001), 5:609-612.
Al-Obeidi, et al., Peptide and Peptidomimetic Libraries, Mol Biotechnol., (1998), 9:205-223.
Alvarez, et al., "Synthesis of 3-Aryl- and 3-Heteroaryl-7-Azaindoles," Synthesis, (1999), 4:615-620.
Amersdorfer, et al., "Phage Libraries for Generation of Anti-Botulinum scFv Antibodies," Methods in Molecular Biology, (2000), 145:219-240.

(Continued)

*Primary Examiner* — Paul Zarek
(74) *Attorney, Agent, or Firm* — Sheppard Mullin Richter & Hampton LLP

(57) ABSTRACT

Compounds active on the receptor protein tyrosine kinases c-kit and/or c-fms are provided herewith. Also provided herewith are compositions useful for treatment of c-kit mediated diseases or conditions and/or c-fms-mediated diseases or conditions, and methods for the use thereof.

17 Claims, No Drawings

(56) References Cited

U.S. PATENT DOCUMENTS

| | | |
|---|---|---|
| 5,877,007 A | 3/1999 | Housey |
| 5,908,401 A | 6/1999 | Henley |
| 5,952,362 A | 9/1999 | Cournoyer et al. |
| 5,958,930 A | 9/1999 | Gangjee |
| 5,959,098 A | 9/1999 | Goldberg et al. |
| 5,965,452 A | 10/1999 | Kovacs |
| 6,013,440 A | 1/2000 | Lipshutz et al. |
| 6,022,963 A | 2/2000 | McGall et al. |
| 6,025,155 A | 2/2000 | Hadlaczky et al. |
| 6,045,996 A | 4/2000 | Cronin et al. |
| 6,048,695 A | 4/2000 | Bradley et al. |
| 6,054,270 A | 4/2000 | Southern |
| 6,090,912 A | 7/2000 | Lebl et al. |
| 6,096,718 A | 8/2000 | Weitzman et al. |
| 6,107,478 A | 8/2000 | Pedersen et al. |
| 6,110,456 A | 8/2000 | During |
| 6,110,458 A | 8/2000 | Freeman et al. |
| 6,113,913 A | 9/2000 | Brough et al. |
| 6,117,681 A | 9/2000 | Salmons et al. |
| 6,161,776 A | 12/2000 | Byles |
| 6,178,384 B1 | 1/2001 | Kolossvary |
| 6,235,769 B1 | 5/2001 | Clary |
| 6,243,980 B1 | 6/2001 | Bronstein et al. |
| 6,258,606 B1 | 7/2001 | Kovacs |
| 6,261,776 B1 | 7/2001 | Pirrung et al. |
| 6,277,489 B1 | 8/2001 | Abbott et al. |
| 6,277,628 B1 | 8/2001 | Johann et al. |
| 6,288,234 B1 | 9/2001 | Griffin |
| 6,294,330 B1 | 9/2001 | Michnick et al. |
| 6,310,074 B1 | 10/2001 | Depreux et al. |
| 6,350,786 B1 | 2/2002 | Albano et al. |
| 6,545,014 B2 | 4/2003 | Verner |
| 6,653,309 B1 | 11/2003 | Saunders et al. |
| 6,858,860 B2 | 2/2005 | Hosono et al. |
| 6,897,207 B2 | 5/2005 | Cox et al. |
| 7,259,165 B2 | 8/2007 | Bernotas et al. |
| 7,271,262 B2 | 9/2007 | La Greca et al. |
| 7,361,763 B2 | 4/2008 | Arnold et al. |
| 7,361,764 B2 | 4/2008 | Arnold et al. |
| 7,452,993 B2 | 11/2008 | Arnold et al. |
| 7,498,342 B2 | 3/2009 | Ibrahim et al. |
| 7,504,509 B2 | 3/2009 | Ibrahim et al. |
| 7,582,637 B2 | 9/2009 | Arnold et al. |
| 7,601,839 B2 | 10/2009 | Arnold et al. |
| 7,626,021 B2 | 12/2009 | Arnold et al. |
| 7,846,941 B2 | 12/2010 | Zhang et al. |
| 7,863,288 B2 | 1/2011 | Ibrahim et al. |
| 7,863,289 B2 | 1/2011 | Spevak et al. |
| 7,893,075 B2 | 2/2011 | Zhang et al. |
| 7,994,185 B2 | 8/2011 | Rheault |
| 8,067,638 B2 | 11/2011 | Kai et al. |
| 8,129,404 B2 | 3/2012 | Ibrahim et al. |
| 8,143,271 B2 | 3/2012 | Ibrahim et al. |
| 8,404,700 B2 | 3/2012 | Ibrahim et al. |
| 8,415,345 B2 | 4/2013 | Adabeng et al. |
| 8,415,469 B2 | 4/2013 | Ibrahim et al. |
| 8,461,169 B2 | 6/2013 | Zhang et al. |
| 8,507,484 B2 | 8/2013 | Lida et al. |
| 8,722,702 B2 | 5/2014 | Zhang et al. |
| 2001/0001449 A1 | 5/2001 | Kiliany et al. |
| 2001/0008765 A1 | 7/2001 | Shinoki et al. |
| 2001/0012537 A1 | 8/2001 | Anderson et al. |
| 2001/0014448 A1 | 8/2001 | Chappa et al. |
| 2001/0016322 A1 | 8/2001 | Caren et al. |
| 2001/0018642 A1 | 8/2001 | Balaban et al. |
| 2001/0019827 A1 | 9/2001 | Dawson et al. |
| 2003/0003004 A1 | 1/2003 | Stones et al. |
| 2003/0219489 A1 | 11/2003 | Curatolo et al. |
| 2004/0002534 A1 | 1/2004 | Lipson et al. |
| 2004/0022534 A1 | 2/2004 | Amano et al. |
| 2004/0073274 A1 | 4/2004 | Cook et al. |
| 2004/0077595 A1 | 4/2004 | Cheng et al. |
| 2004/0142864 A1 | 7/2004 | Bremer et al. |
| 2004/0167030 A1 | 8/2004 | Bernotas et al. |
| 2005/0026792 A1 | 2/2005 | Cartwright |
| 2005/0031692 A1 | 2/2005 | Beyerinck et al. |
| 2005/0085463 A1 | 4/2005 | Weiner et al. |
| 2005/0154014 A1 | 7/2005 | Bloxham et al. |
| 2005/0164300 A1 | 7/2005 | Artis et al. |
| 2005/0170431 A1 | 8/2005 | Ibrahim et al. |
| 2005/0256151 A1 | 11/2005 | Salom et al. |
| 2006/0018726 A1 | 1/2006 | Hall |
| 2006/0024361 A1 | 2/2006 | Odidi et al. |
| 2006/0035898 A1 | 2/2006 | Arnold et al. |
| 2006/0058324 A1 | 3/2006 | Capraro et al. |
| 2006/0058339 A1 | 3/2006 | Ibrahim et al. |
| 2006/0058340 A1 | 3/2006 | Ibrahim et al. |
| 2006/0167403 A1 | 7/2006 | Henley et al. |
| 2007/0032519 A1 | 2/2007 | Zhang et al. |
| 2007/0049615 A1 | 3/2007 | Ibrahim et al. |
| 2007/0054963 A1 | 3/2007 | Lifshitz-Liron et al. |
| 2007/0072862 A1 | 3/2007 | Dimauro et al. |
| 2007/0161666 A1 | 7/2007 | Blumenkopf et al. |
| 2007/0218138 A1 | 9/2007 | Bittorf et al. |
| 2007/0225306 A1 | 9/2007 | Choi et al. |
| 2007/0287711 A1 | 12/2007 | Arnold et al. |
| 2008/0004661 A1 | 1/2008 | Silverstone |
| 2008/0079906 A1 | 4/2008 | Finn |
| 2008/0167338 A1 | 7/2008 | Spevak et al. |
| 2008/0188514 A1 | 8/2008 | Wu et al. |
| 2009/0005356 A1 | 1/2009 | Blaney et al. |
| 2009/0076046 A1 | 3/2009 | Zhang et al. |
| 2009/0143352 A1 | 6/2009 | Arnold et al. |
| 2009/0286783 A1 | 11/2009 | Ibrahim et al. |
| 2009/0306056 A1 | 12/2009 | Arnold et al. |
| 2009/0306086 A1 | 12/2009 | Ibrahim et al. |
| 2009/0306087 A1 | 12/2009 | Ibrahim et al. |
| 2010/0286142 A1 | 11/2010 | Ibrahim et al. |
| 2010/0286178 A1 | 11/2010 | Ibrahim et al. |
| 2010/0310659 A1 | 12/2010 | Desai et al. |
| 2011/0028511 A1 | 2/2011 | Hildbrand et al. |
| 2011/0092538 A1 | 4/2011 | Speval et al. |
| 2011/0152258 A1 | 6/2011 | Ibrahim et al. |
| 2011/0183988 A1 | 7/2011 | Ibrahim et al. |
| 2012/0053177 A1 | 3/2012 | Ibrahim et al. |
| 2012/0165366 A1 | 6/2012 | Ibrahim et al. |
| 2012/0245174 A1 | 9/2012 | Ibrahim et al. |
| 2013/0172375 A1 | 7/2013 | Albano et al. |
| 2013/0261117 A1 | 10/2013 | Ibrahim et al. |
| 2013/0274259 A1 | 10/2013 | Zhang et al. |
| 2013/0303534 A1 | 11/2013 | Ibrahim et al. |
| 2014/0028373 A1 | 1/2014 | Voelker et al. |
| 2014/0037617 A1 | 2/2014 | Bollag et al. |
| 2014/0094611 A1 | 4/2014 | Ibrahim et al. |
| 2014/0128373 A1 | 5/2014 | Ibrahim et al. |
| 2014/0288070 A1 | 9/2014 | Ibrahim et al. |

FOREIGN PATENT DOCUMENTS

| | | |
|---|---|---|
| EP | 0 344 603 B1 | 5/1989 |
| EP | 0 154 734 | 8/1990 |
| EP | 0 465 970 | 1/1992 |
| EP | 0 580 860 B1 | 4/1992 |
| EP | 0 901 786 B1 | 7/1998 |
| EP | 1 057 826 | 12/2000 |
| EP | 1 368 001 B1 | 2/2002 |
| EP | 0 870 768 | 5/2002 |
| EP | 1 267 111 A1 | 12/2002 |
| EP | 1 388 541 | 2/2004 |
| EP | 1 749 829 | 2/2007 |
| EP | 2 036 990 | 4/2014 |
| FR | 2264804 A1 | 10/1975 |
| GB | 1 198 301 A | 5/1973 |
| GB | 2 292 143 | 2/1996 |
| GB | 2 292 145 | 2/1996 |
| GB | 2 298 198 | 8/1996 |
| GB | 2 299 581 | 10/1996 |
| JP | 06-135946 | 5/1994 |
| JP | 10-087629 | 4/1998 |
| JP | 10-130269 | 5/1998 |
| JP | 2000-95708 | 4/2000 |
| JP | 2001-278886 | 10/2001 |
| JP | 15-073357 | 3/2003 |
| WO | WO-93/13099 | 7/1993 |

(56) References Cited

FOREIGN PATENT DOCUMENTS

| | | |
|---|---|---|
| WO | WO-94/14808 | 7/1994 |
| WO | WO-94/20459 | 9/1994 |
| WO | WO-94/20497 | 9/1994 |
| WO | WO-95/04742 | 2/1995 |
| WO | WO-95/07910 | 3/1995 |
| WO | WO-95/28387 | 10/1995 |
| WO | WO-96/00226 | 1/1996 |
| WO | WO-96/11929 | 2/1996 |
| WO | WO-96/05200 | 4/1996 |
| WO | WO-96/17958 | 6/1996 |
| WO | WO-96/18738 | 6/1996 |
| WO | WO-96/38131 | 12/1996 |
| WO | WO-97/03967 | 2/1997 |
| WO | WO-97/46313 | 12/1997 |
| WO | WO-97/46558 | 12/1997 |
| WO | WO-97/49703 | 12/1997 |
| WO | WO-98/06433 | 2/1998 |
| WO | WO-98/22457 | 5/1998 |
| WO | WO-98/47899 | 10/1998 |
| WO | WO-99/00386 | 1/1999 |
| WO | WO-99/09217 | 2/1999 |
| WO | WO-99/32106 | 7/1999 |
| WO | WO-99/32433 | 7/1999 |
| WO | WO-99/51231 | 10/1999 |
| WO | WO-99/51232 | 10/1999 |
| WO | WO-99/51233 | 10/1999 |
| WO | WO-99/51234 | 10/1999 |
| WO | WO-99/51595 | 10/1999 |
| WO | WO-99/51596 | 10/1999 |
| WO | WO-99/51773 | 10/1999 |
| WO | WO-00/09162 | 2/2000 |
| WO | WO-00/12074 | 3/2000 |
| WO | WO-00/12514 | 3/2000 |
| WO | WO-00/17202 | 3/2000 |
| WO | WO-00/29411 | 5/2000 |
| WO | WO-00/53582 | 9/2000 |
| WO | WO-00/55153 | 9/2000 |
| WO | WO-00/64898 | 11/2000 |
| WO | WO-00/71506 A2 | 11/2000 |
| WO | WO-00/71537 | 11/2000 |
| WO | WO-00/75139 | 12/2000 |
| WO | WO-01/09121 | 2/2001 |
| WO | WO-01/24236 | 4/2001 |
| WO | WO-01/29036 | 4/2001 |
| WO | WO-01/46196 | 6/2001 |
| WO | WO-01/60822 | 8/2001 |
| WO | WO-01/62255 | 8/2001 |
| WO | WO-01/32174 | 10/2001 |
| WO | WO-01/74786 | 11/2001 |
| WO | WO-01/98299 | 12/2001 |
| WO | WO-02/00657 | 1/2002 |
| WO | WO-02/18346 | 3/2002 |
| WO | WO-02/076447 | 10/2002 |
| WO | WO-02/078780 | 10/2002 |
| WO | WO-02/083175 | 10/2002 |
| WO | WO-02/085896 | 10/2002 |
| WO | WO-02/092087 | 11/2002 |
| WO | WO-02/102783 | 12/2002 |
| WO | WO-03/000258 | 1/2003 |
| WO | WO-03/000267 | 1/2003 |
| WO | WO-03/003004 A2 | 1/2003 |
| WO | WO-03/004472 | 1/2003 |
| WO | WO-03/006459 | 1/2003 |
| WO | WO-03/008422 | 1/2003 |
| WO | WO-03/011868 | 2/2003 |
| WO | WO-03/020698 | 3/2003 |
| WO | WO-03/028724 | 4/2003 |
| WO | WO-03/037862 | 5/2003 |
| WO | WO-03/051838 | 6/2003 |
| WO | WO-03/064413 | 8/2003 |
| WO | WO-03/068221 | 8/2003 |
| WO | WO-03/082289 | 10/2003 |
| WO | WO-03/082868 | 10/2003 |
| WO | WO-03/082869 | 10/2003 |
| WO | WO-03/087087 | 10/2003 |
| WO | WO-03/062236 | 12/2003 |
| WO | WO-03/101990 | 12/2003 |
| WO | WO-2004/005283 | 1/2004 |
| WO | WO-2004/009600 | 1/2004 |
| WO | WO-2004/009601 | 1/2004 |
| WO | WO-2004/014369 | 2/2004 |
| WO | WO-2004/016609 | 2/2004 |
| WO | WO-2004/016610 | 2/2004 |
| WO | WO-2004/024895 | 3/2004 |
| WO | WO-2004/052880 | 6/2004 |
| WO | WO-2004/054581 | 7/2004 |
| WO | WO-2004/056830 A | 7/2004 |
| WO | WO-2004/065393 | 8/2004 |
| WO | WO-2004/065394 | 8/2004 |
| WO | WO-2004/069138 | 8/2004 |
| WO | WO-2004/054974 | 9/2004 |
| WO | WO-2004/074278 | 9/2004 |
| WO | WO-2004/074286 | 9/2004 |
| WO | WO-2004/078756 | 9/2004 |
| WO | WO-2004/078923 | 9/2004 |
| WO | WO-2004/101565 | 11/2004 |
| WO | WO-2005/005426 | 1/2005 |
| WO | WO-2005/028475 | 3/2005 |
| WO | WO-2005/028624 | 3/2005 |
| WO | WO-2005/030128 | 4/2005 |
| WO | WO-2005/030709 | 4/2005 |
| WO | WO-2005/034869 | 4/2005 |
| WO | WO-2005/044181 | 5/2005 |
| WO | WO-2005/058891 | 6/2005 |
| WO | WO-2005/062795 | 7/2005 |
| WO | WO-2005/063746 | 7/2005 |
| WO | WO-2005/063747 | 7/2005 |
| WO | WO-2005/066347 | 7/2005 |
| WO | WO-2005/082367 | 9/2005 |
| WO | WO-2005/085244 | 9/2005 |
| WO | WO-2005/086904 | 9/2005 |
| WO | WO-2005/092896 | 10/2005 |
| WO | WO-2005/095400 | 10/2005 |
| WO | WO-2005/103050 | 11/2005 |
| WO | WO-2005/115363 | 12/2005 |
| WO | WO-2005/115374 | 12/2005 |
| WO | WO-2005/116035 | 12/2005 |
| WO | WO-2006/004984 | 1/2006 |
| WO | WO-2006/009755 | 1/2006 |
| WO | WO-2006/009797 | 1/2006 |
| WO | WO-2006/010637 | 2/2006 |
| WO | WO-2006/015123 | 2/2006 |
| WO | WO-2006/015124 | 2/2006 |
| WO | WO-2006/063167 | 6/2006 |
| WO | WO-2006/114180 | 11/2006 |
| WO | WO-2006/114520 | 11/2006 |
| WO | WO-2006/127587 | 11/2006 |
| WO | WO-2006/137376 | 12/2006 |
| WO | WO-2007/002325 | 1/2007 |
| WO | WO-2007/002433 | 1/2007 |
| WO | WO-2007/009799 | 1/2007 |
| WO | WO-2007/013896 | 2/2007 |
| WO | WO-2007/022380 | 2/2007 |
| WO | WO-2007/106236 | 9/2007 |
| WO | WO-2008/058341 | 5/2008 |
| WO | WO-2008/065417 | 6/2008 |
| WO | WO-2008/063888 | 7/2008 |
| WO | WO-2008/079906 | 7/2008 |
| WO | WO-2008/076779 | 8/2008 |
| WO | WO-2008/064265 | 11/2008 |
| WO | WO-2008/138755 | 11/2008 |
| WO | WO 2008/138755 | 11/2008 |
| WO | WO-2009/012283 | 1/2009 |
| WO | WO-2009/012791 | 1/2009 |
| WO | WO-2009/111277 | 9/2009 |
| WO | WO-2009/111279 | 9/2009 |
| WO | WO-2009/111280 | 9/2009 |
| WO | WO-2009/115084 | 9/2009 |
| WO | WO-2009/143024 | 11/2009 |
| WO | WO-2010/020905 | 2/2010 |
| WO | WO 2010/104945 | 9/2010 |
| WO | WO-2010/104973 | 9/2010 |
| WO | WO 2010/114928 | 10/2010 |
| WO | WO-2010/129567 | 11/2010 |

(56) References Cited

FOREIGN PATENT DOCUMENTS

| WO | WO-2010/129570 | 11/2010 |
|---|---|---|
| WO | WO-2011/015522 | 2/2011 |
| WO | WO 2011/060216 | 5/2011 |
| WO | WO-2011/063159 | 5/2011 |
| WO | WO-2011/079133 | 6/2011 |
| WO | WO-2011/133637 A2 | 10/2011 |
| WO | WO-2012/032236 | 3/2012 |
| WO | WO-2012/037060 | 5/2012 |
| WO | WO-2012/138809 | 10/2012 |
| WO | WO-2012/158957 | 11/2012 |
| WO | WO-2012/161776 | 11/2012 |

OTHER PUBLICATIONS

Amiel, et al., "Hirschsprung disease, associated syndromes and genetics: a review," J Med Genet., (2008), 45:1-14.
Anderson, et al., "Cooperative Catalyst Effects in Palladium-Mediated Cyanation Reactions of Aryl Halides and Triflates," J. Org. Chem., (1998), 63:8224-8228.
Antonini, et al., "Synthesis of 4-Amino-1-β-D-Ribofuranosyl-1H-pyrrolo[2,3-b]pyridine (1-Deazatubercidin) as a Potential Antitumor Agent," J. Med. Chem., (1982), 25:1258-1261.
Ashman, et al., "The biology of stem cell factor and its receptor C-kit," The International Journal of Biochemistry & Cell Biology, (1999), 31:1037-1051.
Baghestanian, et al., "A Case of Malignant Mastocytosis with Circulating Mast Cell Precursors: Biologic and Phenotypic Characterization of the Malignant Clone," Leuk., (1996), 10:159-166.
Bagshaw, et al., "Measurement of Ligand Binding to Proteins," Spectrophotometry and Spectrofluorometry: A Practical Approach, (1987), 4:91-114.
Bagshawe, K., "Antibody-Directed Enzyme Prodrug Therapy: A Review," Drug Dev. Res., (1995), 34:220-230.
Balak, et. al., "Novel D761Y and Common Secondary T790M Mutations in Epidermal Growth Factor Receptor 13 Mutant Lung Adenocarcinomas with Acquired Resistance to Kinase Inhibitors," Clin Cancer Res., (2006), 12:6494-501.
Bancalari, et al., "Blood Markers of Early and Late Airway Responses to Allergen in Asthmatic Subjects. Relationship with Functional Findings," Allergy, (1997), 52:32-40.
Bartlett, et al., "CAVEAT: A Program to Facilitate the Structure-Derived Design of Biologically Active Molecules," Royal Society of Chemistry, (1989), 78:I80-I96.
Barton, et al., "The chemistry of pentavalent organobismuth reagants. Part X. Studies on the phenylation and oxidation of phenols," Tetrahedron, (1987), 43(2):323-332.
Bashford, et al., "Measurement of Ligand Binding to Proteins," Spectrophotometry and Spectrofluorimetry: A Practical Approach, (1987), 4:91-113.
Basta, et al., "High-dose Intravenous Immunoglobulin Exerts Its Beneficial Effect in Patients with Dermatomyositis by Blocking Endomysial Deposition of Activated Complement Fragments," J Clin Invest., (1994), 94:1729-1735.
Basto, et al., "Mutation analysis of B-RAF gene in human gliomas," Acta Neuropathol., (2005), 109:207-210.
Baston et al., The Chemistry of pentavalent organobismuth reagents-past-X . . . .
Bedi, et al., "BCR-ABL-Mediated Inhibition of Apoptosis With Delay of G2/M Transition After DNA Damage: A Mechanism of Resistance to Multiple Anticancer Agents," Blood, (1995), 86:1148-1158.
Bell, J.E., "Fluorescence: Solution Studies" Spectroscopy in Biochemistry I, (1981),(4):155-194.
Bellone, et al., "Growth Stimulation of Colorectal Carcinoma Cells Via the c-Kit Receptor is Inhibited by TGF-β1," J. Cell Physiol., (1997), 172:1-11.
Berdel, et al., "Recombinant Human Stem Cell Factor Stimulates Growth of a Human Glioblastoma Cell Line Expressing c-kit Protooncogene," Canc. Res., (1992), 52:3498-3502.
Bertolini, et al., "A new Rational Hypothesis for the Pharmacophore of the Active Metabolite of Leflunomide, a Potent Immunosuppressive Drug," J. Med. Chem., (1997), 40:2011-2016.
Bjorntrop, "Neuroendocrine Pertuirbations as a Cause of Insulin Resistance," Diabetes Metab Res. Rev., (1999), 15:427-441.
Bloom, et al., "The Preparation of 2-Alkylaminobenzimidazoles," J. Org. Chem., (1939), 14-19.
Blundell, et al., "Knowledge-Based Protein Modelling and Design," Eur. J. Biochem., (1988), 172:513-520.
Bode, et al., "Mutations in the tyrosine kinase domain of the EGFR gene are rare in synovial sarcoma," Modern Pathology, (2006), 19:541-547.
Bohm, H-J., "On the Use of LUDI to Search the Fine Chemicals Directory for Ligands of Proteins of Known Three-Dimensional Structure," J. Comp. Aided Molec. Design, (1994), 8:623-632.
Bokenmeyer, et al., "Expression of Stem-Cell Factor and Its Receptor c-kit Protein in Normal Testicular Tissue and Malignant Germ-Cell Tumours," J. Cancer Res. Clin. Oncol., (1996), 122:301-306.
Bolger, et al., "Computer Modeling of Combining Site Structure of Anti-Hapten Monoclonal Antibodies," Methods Enz., (1991), 203:21-45.
Bongarzone, et al., "High Frequency of Activation of Tyrosine Kinase Oncogenes in Human Papillary Thyroid Carcinoma," Oncogene, (1989), 4(12):1457-1462.
Bothwell, M., "Keeping Track of Neurotrophin Receptors," Cell, (1991), 65:915-918.
Bouzakri, et al., "MAP4K4 Gene silencing in Human Skeletal Muscle Prevents Tumor Necrosis Factor-a-induced Insulin Resistance," J. Biol. Chem., (2007), 282:7783-7789.
Bowtell, D., "Options Available From Start to Finish for Obtaining Expression Data by Microarray," Nature Genetics Supp., (1999), 21:25-32.
Breindl, "No Melanocyte is an Island: In Melanoma, Interfeon, Roles Need Rethinking," *BioWorld Today*, (2011), 22(17): 1; 5.
Brenner, et al., "Encoded Combinatorial Chemistry," Proc. Natl. Acad. Sci. USA, (1992), 89:5381-5383.
Broudy, V., "Stem Cell Factor and Hematopoiesis," Blood, (1997), 90:1345-1364.
Brunger, A. T., "Free R Value: a Novel Statistical Quantity for Assessing the Accuracy of Crystal Structures," Nature, (1992), 355:472-475.
Buchschacher, et al., "Human Immunodeficiency Virus Vectors for Inducible Expression of Foreign Genes," J. Virol., (1992), 66:2731-2739.
Calabresi, et al., "Section IX: Chemotherapy of neoplastic diseases," Goodman & Gilman's The Pharmacological Basis of Therapeutics, Tenth Edition, McGraw-Hill Medical Publishing Division (2001), pp. 1381, 1383-1385 and 1388.
Capon, et al., "Designing CD4 Immunoadhesins for AIDS Therapy," Nature, (1989), 337:525-531.
Carell, et al., "New Promise in Combinatorial Chemistry: Synthesis, Characterization, and Screening of Small-Molecule Libraries in Solution," Chem. Biol., (1995), 2:171-183.
Carpino, et al., "p62dok: A Constitutively Tyrosine-Phosphorylated, GAP-Associated Protein in Chronic Myelogenous Leukemia Progenitor Cells," Cell, (1997), 88:197-204.
Castelle, et al., "The Presence of Membrane-Bound Stem Cell Factor on Highly Immature Nonmetachromatic Mast Cells in the Peripheral Blood of a Patient with Aggressive Systemic Mastocytosis," J. Aller. Clin. Immunol., (1996), 98:831-840.
Castellone, et al., "A novel de novo germ-line V292M mutation in the extracellular region of RET in a patient with phaeochromocytoma and medullary thyroid carcinoma: functional characterization," Clinical Endocrinology, (2010), 73:529-534.
Castro, et al. "Utilizacion de dispersiones solidas como estrategia para aumentar la velocidad de disolucion de farmacos", Nuestra Farmcia, (2008), 25:24-29 (No English Translation Available).
Chabala, J., "Solid-Phase Combinatorial Chemistry and Novel Tagging Methods for Identifying Leads," Curr Opin Biotechnol., (1995), 6:632-639.
Chayer, et al., "Synthesis of Carboranylpyrroles," Tetrahedron Lett., (2001), 42(44):7759-7761.

(56) References Cited

OTHER PUBLICATIONS

Checovich, et al., "Fluorescence Polarization—a New Tool for Cell and Molecular Biology," Nature, (1995), 375:254-256.
Chou, et al., "Chemotherapeutic Synergism, Potentiation and Antagonism," Encyclopedia of Human Biology, Academic Press, (1991), 2:371-379.
Chou, et al., "Computerized Quantitation of Synergism and Antagonism of Taxol, Topotecan, and Cisplatin Against Human Teratocarcinoma Cell Growth: a Rational Approach to Clinical Protocol Design," J. Natl. Cancer Inst., (1994), 86:1517-1524.
Chou, et al., "Quantitative analysis of Dose-Effect Relationships: The Combined Effects of Multiple Drugs or Enzyme Inhibitors," Adv. Enzyme Regul., (1984), 22:27-55.
Chou, et al., "Synergism and Antagonism in Chemotherapy," Academic Press, (1991), Chapter 2, 61-102.
Clark, et al., "PRO_LIGAND: An Approach to De Novo Molecular Design. 1. Application to the Design of Organic Molecules," J. Comp. Aided Molec. Design, (1995), 9:13-32.
Clohisy, et al., "Review of Cellular Mechanisms of Tumor Osteolysis," Clin. Orthop., (2000), 373:104-114.
Coe, et al., "Solution-Phase Combinatorial Chemistry," Mol Divers., (1999), 4:31-38.
Coelho, et al., "Studies of RET gene expression and acetylcholinesterase activity in a series of sporadic Hirschsprung's disease," Pediatr Surg Int, (2008), 24:1017-1021.
Cohen, et al., "Expression of Stem Cell Factor and C-Kit in Human Neuroblastoma," Blood, (1994), 84:3465-3472.
Collins, et al., "A small interfereing RNA screen for modulators of tumor cell motility identifies MAP4K4 as a prommigratory kinase," Proc. Natl. Acad. Sci. USA, (2006), 103:3775-3780.
Collioud, et al., "Oriented and Covalent Immobilization of Target Molecules to Solid Supports: Synthesis and Application of a Light-Activatable and Thiol-Reactive Cross-Linking Reagent," Bioconjugate Chem., (1993), 4:528-536.
Colman, P.M., "Structure-Based Drug Design," Current Opinion in Struc. Biol., (1994), 4:868-874.
Columbo, et al., "The Human Recombinant c-kit Receptor Ligand, rhSCF, Induces Mediator Release From Human Cutaneous Mast Cells and Enhances IgE-Dependent Mediator Release From Both Skin Mast Cells and Peripheral Blood Basophils," J. Immunol., (1992), 149:599-608.
Communication Pursuant to Article 94(3) EPC for European Appln. No. 04814626.0 dated Jun. 6, 2011.
Communication Pursuant to Article 94(3) EPC for European Appln. No. 04814626.0 dated Dec. 15, 2009.
Communication Pursuant to Article 94(3) EPC for European Appln. No. 05789913.0 dated Feb. 15, 2010.
Communication Pursuant to Article 94(3) EPC for European Appln. No. 06773861.7 dated Jul. 9, 2009.
Communication Pursuant to Article 94(3) EPC for European Appln. No. 06773861.7 dated Dec. 21, 2009.
Communication Pursuant to Article 94(3) EPC for European Appln. No. 06773861.7 dated Apr. 22, 2010.
Communication Pursuant to Article 94(3) EPC for European Appln. No. 06813186.1 dated Apr. 17, 2009.
Communication Pursuant to Article 94(3) EPC for European Appln. No. 06813186.1 dated Sep. 15, 2009.
Communication Pursuant to Article 94(3) EPC for European Appln. No. 07864681.7 dated Oct. 8, 2012.
Communication Pursuant to Article 94(3) EPC for European Appln. No. 07864681.7 dated Dec. 2, 2009.
Communication Pursuant to Article 94(3) EPC for European Appln. No. 10722860.3 dated Mar. 27, 2013.
Communication Pursuant to Article 94(3) EPC for European Appln. No. 11173701.1 dated Jan. 4, 2013.
Coniglio, et al., "Microglial stimulation of glioblastoma invasion involves epidermal growth factor receptor (EGFR) and colony stimulating factor 1 receptor (CSF-1R) signaling," Mol. Med., (2012), 18:519-527.
Costa, et al., "The Cells of the Allergic Response," JAMA, (1997), 278:1815-1822.
Coste, et al., "Coupling N-Methylated Amino Acids Using PyBroP1 and PyCloP Halogenophosphonium Salts: Mechanism and Fields of Application," Journal of Organic Chemistry, (1994), 59:2437-2446.
Coulie, et al., "Recombinant Human Neurotropic Factors Accelerate Colonic Transit and Relieve Constipation in Humans," Gastroenterology, (2000), 119:41-50.
Creighton, T., "An Empirical Approach to Protein Conformation Stability and Flexibility," Biopolymers, (1983), 22(1):49-58.
Crouch, et al., "The use of ATP bioluminescence as a measure of cell proliferation and cytotoxicity," Journal of Immunological Methods, (1993), 160:81-88.
Crump, M., "Inhibition of Raf Kinase in the Treatment of Acute Myeloid Leukemia," Curr. Pharm. Design, (2002), 8(25):2243-2248.
Curtin, et al., "Discovery and Evaluation of a Series of 3-Acylindole Imidazopyridine Platelet-Activating Factor Antagonists," J. Med. Chem., (1998), 41:74-95.
Curtin, et al., "Somatic activation of KIT in distinct subtypes of melanoma," J. of Clinical Oncology, (2006), 24(26): 4340-4345.
Cwirla, et al., "Peptides on Phage: A Vast Library of Peptides for Identifying Ligands," Biochemistry, (1990), 87:6378-6382.
Dai, et al., "Targeted disruption of the mouse colony-stimulating factor 1 receptor gene results in osteopetrosis, mononuclear phagocyte deficiency, increased primitive progenitor cell frequencies, and reproductive defects," Blood, (2002), 99: 111-120.
Dandliker, et al., "Equilibrium and Kinetic Inhibition Assays Based Upon Fluorescence Polarization," Methods in Enzymology, (1981), 74:3-28.
Das-Gupta et al., "Acridine Derivatives, Part VI," J. Indian Chem. Society, (1941), 18:25-28.
Dastych, et al., "Stem Cell Factor Induces Mast Cell Adhesion to Fibronectin," J. Immunol., (1994), 152:213-219.
Davies, et al., "Mutations of the BRAF gene in human cancer," Nature, (2002), 417:949-954.
Demetri, et al., "Differential properties of current tyrosine kinase inhibitors in gastrointestinal stromal tumors," Seminars in Oncology, 38:(2), (2011), Suppl 1: S10-S19.
Demetri, G.D., "Targeting c-kit mutations in solid tumors: Scientific rationale and novel therapeutic options," Seminars in Oncology, (2001), 28(5), Supp. 17, 19-26.
Denardo, et al., "Leukocyte complexity predicts breast cancer survival and functionally regulates response to chemotherapy," Cancer Discovery, (2011), 54-67.
Dewar, et al., "Inhibition of c-fms by Imatinib Expanding the Spectrum of Treatment," Cell Cycle, (2005), 4(7):851-853.
Dobeli, et al., "Recombinant Fusion Proteins for the Industrial Production of Disulfide Bridge containing Peptides: Purification, Oxidation without Cancatamer Formation, and Selective Cleavage," Protein Expr. Purif., (1998), 12:404-414.
Dolle, et al., "Comprehensive Survey of Combinatorial Library Synthesis: 1998," J Comb Chem., (1999), 1:235-282.
Dong, et al., "BRAF Oncogenic Mutations Correlate with Progression rather than Initiation of Human Melanoma," Cancer Research, (2003), 63:3883-3885.
Donis-Keller, et al., "Mutations in the RET Proto-Oncogene are Associated with MEN 2A and FMTC," Hum Mol Genet., (1993), 2(7):851-856.
Douma, et al., "Suppression of anoikis and induction of metastasis by the neurotropic receptor TrkB," Nature, (2004), 430:1034-1039.
Doyle, eta al., "Alkyl Nitrite-metal halide Deamination Reactions. 6. Direct Synthesis of Arenediazonium Tetrafluoroborate Salts from Aromatic Amines, tert-Butyl Nitrite, and Boron Trifluoride Etherate in Anhydrous Media," J. Org. Chem., (1979), 44:1572.
Dube, et al., "Reductive N-Alkylation of Amides, Carbamates and Ureas," Tetrahedron Lett., (1999), 40:2295-2298.
Durbec, et al., "GDNF Signalling Through the Ret Receptor Tyrosine Kinase," Nature, (1996), 381:789-793.
Dutcher et al., "Studies of the C11H8N2OS Degradation Product of Gliotoxin," J. Am. Chem. Soc., (1951), 73:4139-4141.
Dyson, et al., "The Human Papilloma Virus 13 16 E7 Oncoprotein is Able to Bind to the Retinoblastoma Gene Product," Science, (1989), 243:934-937.

(56) References Cited

OTHER PUBLICATIONS

Eklund, et al., "Treatment of rheumatoid arthritis with imatinib mesylate: clinical improvements in three refractory cases," Annals of Medicine, (2003), 35:362-367.
Eliseev, et al., "Dynamic Combinatorial Chemistry: Evolutionary Formation and Screening of Molecular Libraries," Current Topics in Microbiology & Immunology, (1999), 243:159-172.
Enjalbal, et al., "Mass Spectrometry in Combinatorial Chemistry," Mass Spectrometry Reviews, (2000), 19:139-161.
Escribano, et al., "Expression of the c-kit (CD117) Molecule in Normal and Malignant Hematopoiesis," Leuk. Lymph., (1998), 30:459-466.
Examination Report dated Mar. 13, 2012 in related Australian Patent Application Serial No. 2007323644 (039363-4138).
Examination Report dated Mar. 14, 2012 in related New Zealand Patent Application Serial No. 577011 (039363-4127).
Examination Report for GCC Patent Application No. GCC/P/2005/4795.
Felder, E.R., "The Challenge of Preparing and Testing Combinatorial Compound Libraries in the Fast Lane, at the Front End of Drug Development," Chimia., (1994), 48:531-541.
Feng, et al., "Stable in Vivo Gene Transduction Via a Novel Adenoviral/Retroviral Chimeric Vector," Nature Biotechnology, (1997), 15:866-870.
Feng, et al., "Tyrosines 559 and 807 in the Cytoplasmic Tail of the Macrophage colony-Stimulating Factor Receptor Play Distinct Roles in Osteoclast Differentiation and Function," Endocrinology, (2002), 143: 4868-4874.
Finotto, et al., "Glucocorticoids Disease Tissue Mast Cell Number by Reducing the Production of the c-kit Ligand, Stem Cell Factor, by Resident Cells," J. Clin. Invest., (1997), 99:1721-1728.
Fivash, et al., "BIAcore for macromolecular interaction," Current Opinion in Biotechnology, (1998), 9:97-101.
Flanagan, et al., "Update on the biologic effects of macrophage colony-stimulating factor," Curr Opin Hematol., (1998), 5:181-185.
Franz, et al., "Sulfuranes. X. A Reagent for the Facile Cleavage of Secondary Amides," JACS, (1973), 95(6):2017-2019.
Friesen et al., "Hydroxypropyl Methylcellulose Acetate Succinate-Based Spray-Dried Dispersions: An Overview," Molecular Pharmaceutics, 5(6):1003-1019 (2008).
Furitsu, et al., "Identification of Mutations in the Coding Sequence of the Proto-oncogene c-kit in a Human Mast Cell Leukemia Cell Line Causing Ligand-independent Activation of the c-kit Product," J. Clin. Invest., (1993), 92:1736-1744.
Furuta, et al., "Stem Cell Factor Influences Mast Cell Mediator Release in Response to Eosinophil-Derived Granule Major Basic Protein," Blood, (1998), 92:1055-1061.
Gallop, et al., "Applications of Combinatorial Technologies to Drug Discovery. 1. Background and Peptide Combinatorial Libraries," J. Med. Chem. (1994), 37:1233-1251.
Gassman, et al., "Specific Ortho Substitution of Aromatic Heterocyclic Amines," J Am Chem Society, (1973), 95(13):4453-4455.
Ghebre-Sellassie, Isaac; Martin, Charles., Pharmaceuticast Extrusion Technology. Mercer Dekker, Inc., New York. Basel. CRC Press, 2003 p. 238.
Gimbel, et al., "Braf mutations are associated with increased mortality in colorectal cancer," Journal of the American College of Surgeons, (2004), 199:S91-S92.
Girgis, et.al., "The Synthesis of 5-Azaindoles by Substitution-Rearrangement of 7-Azaindoles upon Treatment with Certain Primary Amines," J. Heterocyclic. Chem., (1989), 26:317-325.
Golkar, et al., "Mastocytosis," Lancet, (1997), 349:1379-1385.
Golub, et al., "Molecular Classifcation of Cancer: Class Discovery and Class Prediction by Gene Expression Monitoring," Science, (1999), 286:531-537.
Goodford, P.J., "A Computational Procedure for Determining Energetically Favorable Binding Sites on Biologically Important Macromolecules," J. Med. Chem., (1985), 28:849-857.
Goodsell, et al., "Automated Docking of Substrates to Proteins by Simulated Annealing," Proteins: Structure, Function, and Genetics, (1990), 8:195-202.
Gordon et al., "Detection of Peroxides and Their Removal," The Chemist's Companion: A Handbook of Practical Data, Techniques, and References, (1972), p. 437.
Gordon, et al., "Applications of Combinatorial Technologies to Drug Discovery. 2. Combinatorial Organic Synthesis, Library Screening Strategies, and Future Directions," J. Med. Chem., (1994), 37:1385-1401.
Gram, H., "Phage Display in Proteolysis and Signal Transduction," Combinatorial Chemistry & High Throughput Screening, (1999), 2:19-28.
Gravert, et al., "Synthesis on Soluble Polymers: New Reactions and the Construction of Small Molecules," Curr Opin Chem Biol., (1997), 1:107-113.
Greer, J., "Model Structure for the Inflammatory Protein C5a," Science, (1985), 228:1055-1060.
Grieco, et al., "PTC is a Novel Rearranged Form of the ret Proto-Oncogene and is Frequently Detected in Vivo in Human Thyroid Papillary Carcinomas," Cell, (1990), 60(4):557-563.
Guida, W., "Software for Structure-Based Drug Design," Current Opinion in Struc. Biol., (1994), 4:777-781.
Hafner, et al., "Isothermal Amplification and Multimerization of DNA by Bst DNA Polymerase," Biotechniques, (2001), 30(4):852-867.
Hallek, et al., "Interaction of the Receptor Tyrosine Kinase p145c-kit with the p210bcr/abl Kinase in Myeloid Cells," Brit. J Haem., (1996), 94:5-16.
Halvorson, et al., "A Blocking Antibody to Nerve Growth Factor Attenuates Skeletal Pain Induced by Prostate Tumor Cells Growing in Bone," Cancer Res., (2005), 65:9426-9435.
Hamel, et al., "The Road Less Traveled: c-kit and Stem Cell Factor," J. Neuro-Onc., (1997), 35:327-333.
Hancock et al., "Characteristics and Significance of the Amorphous State in Pharmaceutical Systems," Journal of Pharmaceutical Sciences 86(1):1-12 (1997).
Hands, et al., "A convenient Method for the Preparation of 5-, 6- and 7-Azaindoles and Their Derivatives," Synthesis, (1996), 877-882.
Hanselman, et al., "A cDNA-Dependant Scintillation Proximity Assay for Quantifying Apolipoprotein A1," J. Lipid Res., (1997), 38:2365-2373.
Hassan, et al., "Expression of Protooncogene c-kit and Its Ligand Stem Cell Factor (SCF) in Gastric Carcinoma Cell Lines," Digest. Dis. Science, (1998), 43:8-14.
Hassan, et al., "Stem Cell Factor as a Survival and Growth Factor in Human Normal and Malignant Hematopoiesis," Acta. Hem., (1996), 95:257-262.
Hayashi, et al., "Dichloro[1,1 19-bis(diphenylophosphino)ferrocene]pallladium-(II), An Effective Catalyst for Cross-Coupling of Secondary and Primary Alkyl Grignard and Alkylzinc Reagents with Organic Halides," J. Am. Chem. Soc., (1984), 106:158-163.
Haydock et al., "Analogues of clofibrate and clobuzarit containing fluorine in the side chains," Eur. J. Med. Chem., (1984), 19(3):205-214.
Haydock, et al., "Analogues of clofibrate and clobuzarit containing fluorine in the side chains," European Journal of Medicinal Chemistry, (1984), 19:205-214.
He et al. "c-Fms Signaling Mediates Neurofibromatosis Type-1 Osteoclast Gain-In-Functions," PLoS ONE, (2012), 7(11): 1-9.
He, et al., "Gamma-secretase activating protein, a therapeutic target for Alzheimer's disease," Nature (2010) 467(7311):95-98.
Heacock et al., "Orientation and Relative Reaction Rate Factors in Aromatic Substitution by the Benzenesulfonimido Radical," J. of the Am. Chem. Society, (1960), 82:3460-3463.
Heim, et al., "Engineering Green Fluorescent Protein for Improved Brightness, Longer Wavelengths and Fluorescence Resonance Energy Transfer," Curr. Biol., (1996), 6:178-182.
Heinrich, et al., "PDGFRA Activating Mutations in Gastrointestinal Stromal Tumors," Science, (2003), 299:708-710.

(56) References Cited

OTHER PUBLICATIONS

Heinrich, M. C. et al., "Inhibition of KIT Tyrosine Kinase Activity: A Novel Molecular Approach to the Treatment of KIT-Positive Malignancies," J. Clin. Oncol., vol. 20, No. 6, pp. 1692-1703, Mar. 15, 2002.
Herbst, et al., "Differential Effects of W Mutations on p145c-kit Tyrosine Kinase Activity and Substrate Interaction," J. Biol. Chem., (1992), 267:13210-13216.
Hibi, et al., "Coexpression of the stem cell factor and the c-kit genes in small-cell lung cancer," Oncogene, (1991), 6:2291-2296.
Hirota, et al., "Gain-of-function Mutations of c-kit in Human Gastrointestinal Stromal Tumors," Science, (1998), 279:577-580.
Hoffmann, "m-Trifluoromethylbenzenesulfonyl Chloride," Organic Syntheses, (1981), 60:121-126.
Hogaboam, et al., "Novel Role of Transmembrane SCF for Mast Cell Activation and Eotaxin Production in Mast Cell-Fibroblast Interactions," J. Immunol., (1998), 160:6166-6171.
Holmes, et al., "Long-term effects of Aβ42 immunisation in Alzheimer's disease: follow-up of a randomised, placebo-controlled phase I trail," Lancet (2008) 372:216-233.
Hood, et al., "Tumor Regression by Targeted Gene Delivery to the Neovasculature," Science, (2002), 296: 2404-2407.
Houghten, et al., "Generation and Use of Synthetic Peptide Combinatorial Libraries for Basic Research and Drug Discovery," Nature, (1991), 354:84-86.
Houghten, R., "Parallel Array and Mixture-Based Synthetic Combinatorial Chemistry: Tools for the Next Millennium," Annu Rev Pharmacol Toxicol., (2000), 40:273-282.
Houghten, R., "Peptide Libraries: Criteria and Trends," Trends Genet., (1993), 9:235-239.
Hudson, et al., "A Simple Method for the Determination of Serum Acid Phosphatase," J. Urology, (1947), 58:89-92.
Hughes-Jones, et al., "Synthesis of Rh Fv Phage-Antibodies Using VH and VL Germline Genes," British Journal of Haematology, (1999), 105:811-816.
Iemura, et al., "The c-kit Ligand, Stem Cell Factor, Promotes Mast Cell Survival by Suppressing Apoptosis," Amer. J. Pathol., (1994), 144:321-328.
Inoue, et al., "Coexpression of the c-kit Receptor and the Stem Cell Factor in Gynecological Tumors," Cancer Res., (1994), 54:3049-3053.
International Search Report and Written Opinion of International Application No. PCT/US2004/042470 dated Nov. 25, 2005 (039363-1904).
International Search Report and Written Opinion of International Application No. PCT/US2005/021231 dated Apr. 20, 2006 (039363-2122).
International Search Report and Written Opinion of International Application No. PCT/US2006/018726 dated Apr. 4, 2007 (039363-2193).
International Search Report and Written Opinion of International Application No. PCT/US2006/024361 dated Oct. 24, 2006 (039363-2850).
International Search Report and Written Opinion of International Application No. PCT/US2006/024524 dated Oct. 24, 2006 (039363-2804).
International Search Report and Written Opinion of International Application No. PCT/US2007/083910 dated Jun. 5, 2008 (039363-4101).
International Search Report and Written Opinion of International Application No. PCT/US2007/085289 dated Jun. 5, 2008 (039363-4101A).
International Search Report and Written Opinion of International Application No. PCT/US2007/085299 dated Jul. 28, 2008 (036393-4150).
International Search Report and Written Opinion of International Application No. PCT/US2007/088231 dated Jun. 4, 2008 (039363-3503).
International Search Report and Written Opinion of International Application No. PCT/US2007/088237 dated Jun. 4, 2008 (039363-3550).
International Search Report and Written Opinion of International Application No. PCT/US2007/088243 dated Jun. 5, 2008 (039363-3403).
International Search Report and Written Opinion of International Application No. PCT/US2007/088412 dated Nov. 17, 2008 (039363-3350).
International Search Report and Written Opinion of International Application No. PCT/US2007/088443 dated Jul. 25, 2008 (039363-3303).
International Search Report and Written Opinion of International Application No. PCT/US2010/029489 dated Oct. 5, 2010 (039363-6904).
International Search Report and Written Opinion of International Application No. PCT/US2012/025965 dated May 31, 2012 (039363-7506).
Isbel, et al., "Local macrophage proliferation correlates with increased renal M-CSF expression in human glomerulonephritis," Nephrol Dial Transplant, (2001), 16:1638-1647.
Ishizaka, et al., "Human ret Proto-Oncogene Mapped to Chromsome 10q11.2," Oncogene, (1989), 4(12):1519-1521.
Isozaki, et al., "Deficiency of c-kit cells in patients with a myopathic form of chronic idiopathic intestinal pseudo-obstruction," Amer. J. of Gast., (1997), 9:332-334.
Ivanisevic et al., "Uses of X-Ray Powder Diffraction in the Pharmaceutical Industry," Pharm Sci Encyc:DDDM, (2010), 1-42.
Iwane, et al., "Myosin Subfragment-1 is Fully Equipped with Factors Essential for Motor Function," Biochem. and Biophys. Res. Comm., (1997), 230:76-80.
Izquierdo, et al., "Differential Expression of the c-kit Proto-Oncogene in Germ Cel Tumours," J. Pathol., (1995), 177:253-258.
Jarugula, et al., "Nonlinear Pharmacokinetics of 5-Fluorouracil in Rats," J Pharm Sci., (1997), 86(6):756-757.
Jensen, et al., "Pharmacological targeting of the KIT growth factor receptor: a therapeutic consideration for mast cell disorders," Brit J Pharmacology, (2008), 154:1572-1582.
Jing, et al., "GDNF-Induced Activation of the Ret Protein Tyrosine Kinase is Mediated by GDNFR-a, a Novel Receptor for GDNF," Cell, (1996), 85:1113-1124.
Johann, et al., "GLVR1, a Receptor for gibbon Ape Leukemia Virus, Is Homologous to a Phosphate Permease of *Neurospora crassa* and is Expressed at High Levels in the Brain and Thymus," J. Virol., (1992), 66:1635-1640.
Johnston, M., "Gene Chips: Array of hope for understanding gene regulation," Curr. Biol., (1998), 8:R171-R174.
Jones et al., "Antiestrogens. 2. Structure-Activity Studies in a Series of 3-Aroyl-2-arylbenzo[b]thiophene Derivatives Leading to [6-Hydroxy-2-(4-hydroxyphenyl)benzo[b]thien-3-yl][4-[2-(1-piperidinyl)ethoxy]-phenyl]methanone Hydrochloride (LY156758), a Remarkably Effective Estrogen Antagonist with Only Minimal Intrinsic Estrogenicity," J. Med. Chem., (1984), 27(8):1057-1066.
Jones, R., "Biology and Treatment of Chronic Myeloid Leukemia," Curr. Opin. Onc., (1997), 9:3-7.
Jones, T., "Interactive Computer Graphics: FRODO," Methods in Enzymology, (1985), 115:157-171.
Jose, et al., "Blockade or Macrophage colony-Stimulating Factor Reduces Macrophage Proliferation and Accumulation in Renal Allograft Rejection," Am J Transplant, (2003), 3(3):294-300.
Joseph-McCarthy, D., "Computational Approaches to Structure-Based Ligand Design," Pharmacology & Therapeutics, (1999), 84:179-191.
Kahl, et al., "A Multiple-Approach Scintillation Proximity Assay to Measure the Association Between Ras and Raf," Anal. Biochem., (1996), 243:282-283.
Kassel, et al., "Local increase in the Number of mast cells and expression of nerve growth factor in the bronchus of asthmatic patients after repeated inhalation of allergen at low-dose," Clin. Exp. Allergy, (2001), 31:1432-1440.
Katritzky, et al., "Regiospecific C-Acylation of Pyrroles and Indoles Using N-Acylbenzotriazoles," J. Org. Chem., (2003), 68:5720-5723.

(56) References Cited

OTHER PUBLICATIONS

Kay, et al., "Eosinophils and Eosinophil-Associated Cytokines in Allergic Inflammation," Int. Arch. Aller. Immunol., (1997), 113:196-199.

Kern, et al., "Direct Hybridization of Large-Insert Genomic Clones on High-Density Gridded cDNA Filter Arrays," Biotechniques, (1997), 23:120-124.

Kim, et al., "A Merger of Rational Drug Design and Combinatorial Chemistry: Development and Application of Peptide Secondary Structure Mimetics," Combinatorial Chemistry & High Throughput Screening, (2000), 3:167-183.

Kim, et al., Database CAS on STN (Columbus, OH, USA) No. 138:55974, Preparation of 2-anilino-4-indolyl pyrimidines as tyrosine kinase inhibitors, abstract, 2002) see whole article.

Kinashi, et al., "Steel Factor and c-kit Cell-Matrix Adhesion," Blood, (1994), 83:1033-1038.

Kirkpatrick, et al., "Structure-Based Drug Design: Combinatorial Chemistry and Molecular Modeling," Combinatorial Chemistry & High Throughput Screening, (1999), 2:211-221.

Kitamura, et al., "Synthesis of Quinolines and 2H-Dihydropyrroles by Nucleophilic Substitution at the Nitrogen Atom of Oxime Derivatives," Synthesis, (2003), 15:2415-2426.

Kline, et al., "Studies by 1H Nuclear Magnetic Resonance and Distance Geometry of the Solution Conformation of the x-Amylase Inhibitor Tendamistat," J. Mol. Biol., (1986), 189:377-382.

Knighton, et al., "Structural Basis of the Intrasteric Regulation of Myosin Light Chain Kinases," Science, (1992), 258:130-I35.

Kodama, et al., "Congenital Osteoclast Deficiency in Osteopetrotic (op/op) Mice Is Cured by Injections of Macrophage colony-stimulating Factor," J. Exp,. Med.,(1991), 173:269-272.

Kolaskar, et al., "A Semi-Empirical Method for Prediction of Antigenic Determinants on Protein Antigens," FEBS Lett., (1990), 276:172-174.

Komoyira, et al., "Design, synthesis and biological activity of amidinobicyclic compounds (derivatives of DX-9065a) as a factor Xa inhibitors: SAR study of S1 and aryl binding sites," Bioorg. Med. Chem., (2004), 12: 2099-2114.

Kondoh, et al., "An in vivo model for receptor tyrosine kinase autocrine/paracrine activation: auto-stimulated Kit receptor acts as a tumor promoting factor in papillomavirus-induced tumorigenesis," Oncogene, (1995), 10:341-347.

Kondoh, et al., "Establishment and Further Characterization of a Line of Transgenic Mice Showing Testicular Tumorigenesis at 100% Incidence," J. Urol., (1994), 152:2151-2154.

Kondoh, et al., "Very High Incidence of Germ Cell tumorigenesis (Seminomagenesis) in Human Papillomavirus Type 16 Transgenic Mice," J. Virol., (1991), 65:3335-3339.

Konishi, et al., "Overexpression of leucocyte common antigen (LAR) P-subunit in thyroid carcinomas," Brit J Cancer, (2003), 88:1223-1228.

Konno et al., "Influence of Different Polymers on the Crystallization Tendency of Molecularly Dispersed Amorphous Felodipine," Journal of Pharmaceutical Sciences 95(12):2692-2705 (2006).

Kroll, et al., "A Malfunctional Prokaryotic Protein Expression System: Overproduction, Affinity Purification, and Selective Detection," DNA Cell. Biol., (1993), 12:441-453.

Kundu, et al., "Combinatorial Chemistry: Polymer Supported Synthesis of Peptide and Non-Peptide Libraries," Progress in Drug Research, (1999), 53:89-156.

Kunisada, et al., "Murine Cutaneous Mastocytosis and Epidermal Melanocytosis Induced by Keratinocyte Expression of Transgenic Stem Cell Factor," J. Exp. Med., (1998), 187:1565-1573.

Kunkel, T., "Rapid and Efficient Site-Specific Mutagenesis Without Phenotypic Selection," Methods in Enzymology, (1987), 154:367-382.

Kunkel, T., "Rapid and Efficient Site-Specific Mutagenesis Without Phenotypic Selection" *Proc. Natl. Acad. Sci. USA*, (1985), 82: 488-492.

Kunnimalaiyaan, et al., "The Raf-1 pathway: a molecular target for treatment of select neuroendocrine tumors?" Anticancer Drugs, (2006), 17(2):139-42.

Kuntz, et al., "A Geometric Approach to Macromolecule-Ligand Interactions," J. Mol. Biol., (1982), 161:269-288.

Kuntz, et al., "Structure-Based Molecular Design," Acc. Chem. Res., (1994), 27:117-123.

Lahm, et al., "Interleukin 4 Down-Regulates Expression of c-kit and Autocrine Stem Cell Factor in Human Colorectal Carcinoma Cells," Cell Growth & Differ., (1995), 6:1111-1118.

Lala, et al., "Role of nitric oxide in tumor progression: Lessons from experimental tumors," Cancer and Metastasis Reviews, (1998), 17:91-106.

Lam, et al., "A new type of synthetic peptide library for identifying ligand-binding activity," Nature, (1991), 354: 82-84.

Langham et al., "Metalation and Halogen-Metal Interconversion Reactions of Some Halogenated Phenyl Ethers," J. of the Am. Chem. Society, (1941), 63:545-549.

Lawicki, et al., "The pretreratment plasma level and disgnostic utility of M-CSF in benign breast tumor and breast cancer patients," Clinica Chimica Acta., (2006), 371:112-116.

Le Meur, et al., "Macrophage accumulation at a site of renal inflammation is dependent on the M-CSF/c-fms pathway," J Leukocyte Biology, (2002), 72:530-537.

Lebl, et al., "One-Bead-One-Structure Combinatorial Libraries," Biopolymers, (1995), 37:177-198.

Lee, et al., "HLA-DR-Triggered Inhibition of Hemopoiesis Involves Fas/Fas Ligand Interactions and is Prevented by c-kit Ligand," J. Immunol., (1997), 159:3211-3219.

Lee, et al., "Mast Cells: A Cellular Link Between Autoantibodies and Inflammatory Arthritis," Science, (2002), 297:1689-1692.

Leuner, et al., "Improving drug solubility for oral delivery using solid dispersions", European J. of Pharm. Biopharm., (2000), 50:47-60.

Leuner, et al., "Improving drug solubility for oral delivery using solid dispersions," European Journal of Pharma. and Biopharma., (2000), 50(1):47-60.

Levin, et al., "Neoplasms of the Central Nervous System," Cancer Principles & Practice of Oncology, (1997), 2:2022-2082.

Li, et al., "Abrogation of c-kit/Steel Factor-Dependent Tumorigenesis by Kinase Defective Mutants of the c-kit Receptor: c-kit Kinase Defective Mutants as Candidate Tools for Cancer Gene Therapy," Canc. Res., (1996), 56:4343-4346.

Libby, P., "Inflammation in atherosclerosis," Nature, (2002), 420:868-874.

Liparoto, et al., "Biosensor Analysis of the Interleukin-2 Receptor Complex," Journal of Molecular Recognition, (1999), 12:316-321.

Lipinski, et al., "Experimental and Computational Approaches to Estimate Solubility and Permeability in Drug Discovery and Development Settings," Advanced Drug Delivery Reviews, (1997), 23:3-25.

Lipschultz, et al., "Experimental design for analysis of complex kinetics using surface plasmon resonance," Methods, (2000), 20(3):310-318.

Liu, et al., "Sorafenib Blocks the RAF/MEK/ERK Pathway, Inhibits Tumor Angiogenesis, and Induces Tumor Cell Apoptosis in Hepatocellular Carcinoma Model PLC/PRF/5," Cancer Res., (2006), 66:11852-11858.

Liu, et al., "CD68 Expression is Markedly Different in Crohn's Disease and the Colitis Associated with Chronic Granulomatous Disease," *Inflamm. Bowel Dis*., (2009), 15(8): 1213-1217.

London, et al., "Expression of Stem Cell Factor Receptor (c-kit) by the Malignant Mast Cells from Spontaneous Canine Mast Cell Tumors," J. Compar. Pathol., (1996), 115:399-414.

Longley, et al., "Altered Metabolism of Mast-cell Growth Factor (c-kit Ligand) in Cutaneous Mastocytosis," New Engl. J. Med., (1993), 328:1302-1307.

Longley, et al., "Chymase Cleavage of Stem Cell Factor Yields a Bioactive Soluble Product," Proc. Natl. Acad. Sci., (1997), 94:9017-9021.

Longley, et al., "Somatic c-KIT Activating Mutation in Urticaria Pigmentosa and Aggressive Mastocytosis: Establishment of Clonality in a Human Mast Cell Neoplasm," Nat. Gen., (1996), 12:312-314.

(56) References Cited

OTHER PUBLICATIONS

Louvet et al., "Tyrosine kinase inhibitors reverse type 1 diabetes in nonobese diabetic mice," Proc. Nat. Acad. Sci., (2008), 105(48): 18895-18900.
Loveland, et al., "Stem Cell Factor and c-kit in the Mammalian Testis: Lessons Originating from Mother Nature 19s Gene Knockouts," J. Endocrinol., (1997), 153:337-344.
Lu, et al., "Oriented Immobilization of Fab 19 Fragments on Silica Surfaces," Anal. Chem., (1995), 67:83-87.
Lukacs, et al., "Stem Cell Factor (c-kit Ligand) Influences Eosinophil Recruitment and Histamine Levels in Allergic Airway Inflammation," J. Immunol., (1996), 156:3945-3951.
Luo, et al., "Close Linkage with the RET Proto-Oncogene and Boundaries of Deletion Mutations in Autosomal Dominant Hirschsprung Disease," Hum Mol Genet., (1993), 2(11):1803-1808.
Lyman, et al., "c-kit Ligand and Flt3 Ligand: Stem/Progenitor Cell Factors With Overlapping Yet Distinct Activities," Blood, (1998), 91:1101-1134.
Ma, et al., "Indolinone Derivatives Inhibit Constitutively Activated KIT Mutants and Kill Neoplastic Mast Cells," J Invest Dermatol., (2000), 114:392-394.
Ma, et al., "The c-KIT Mutation Causing Human Mastocytosis is Resistant to ST1571 and Other KIT Kinase Inhibitors; Kinases with Enzymatic Site Mutations Show Different Inhibitor Sensitivity Profiles Than Wild-type Kinases and Those With Regulatory-Type Mutations," Blood, (2002), 99:1741-1744.
Machens, et al., "Modification of multiple endocrine neoplasia 2A phenotype by cell membrane proximity of RET mutations in exon 10," Endocrine-Related Cancer, (2009), 16:171-177.
Machida, et al., "Mitogen-activated Protein Kinase Kinase Kinase Kinase 4 as a Putative Effector of Rap2 to Activate the c-Jun N-terminal Kinase," J. Biol. Chem., (2004), 279:15711-15714.
Mack, et al., "Functional identification of kinases essential for T-cell activation through a genetic suppression screen," Immunol. Lett., (2005), 96:129-145.
Madden, et al., "Synthetic Combinatorial Libraries: Views on Techniques and Their Application," Perspectives in Drug Discovery and Design, (1994), 2:269-285.
Malaysian Examination Report dated Aug. 15, 2012 in related Malaysian Application Serial No. PI20092547 (039363-3576).
Malaysian Substantive Examination Report dated Aug. 15, 2012 in related Malaysian Application Serial No. PI20092040 (039363-4125).
Malmborg, et al., "BIAcore as a Tool in Antibody Engineering," Journal of Immunological Methods, (1995), 183:7-13.
Malmqvist, et al., "Biomolecular Interaction Analysis: Affinity Biosensor Technologies for Functional Analysis of Proteins," Current Opinion in Chemical Biology, (1997), 1:378-383.
Malmqvist, M., "BIACORE: An Affinity Biosensor System for Characterization of Biomolecular Interactions," Biochemical Society Transactions, (1999), 27:335-340.
Markiewicz, et al., "Synthetic Oligonucleotide Combinatorial Libraries and Their Applications," II Farmaco, (2000), 55:174-177.
Marshall, et al., "Blockade of colony stimulating Factor-1 (CSF-1) Leads to inhibition of DSS-induced colitis," Inflamm. Bowel Dis., (2007), 13(2): 219-224.
Martin, Y., "Computer-Assisted Rational Drug Design," Methods Enz., (1991), 203:587-613.
Matayoshi, et al., "Actions of brain-derived neurotrophic factor on spinal nociceptive transmission during inflammation in the rat," J Physiol., (2005), 569:685-95.
Matsumoto, et al., "Physical properties of solid molecular dispersions of indomethacin with poly(vinylpyrrolindone) and poly(vinylpyrrolidone-co-vinyl-acetate) in relation to indomethacin crystallization," Pharmaceutical Research, (1999), 16(11):1722-1728.
Mazeas, et. al., "Synthesis of new melatoninergic ligands including azaindole moiety," Heterocycles, (1999), 50:1065-1080.
McCall, et al., "Characterization of Anti-Mouse FcγRII Single-Chain Fv Fragments Derived from Human Phage Display Libraries," Immunotechnology, (1998), 4:71-87.
McPherson, A., "Current Approaches to Macromolecule Crystallization," Eur. J. Biochem., (1990), 189:1-23.
Mekori, et al., "The Role of c-Kit and Its Ligand, Stem Cell Factor, in Mast Cell Apoptosis," Int. Arch. Allergy Immunol., (1995), 107:136-138.
Mekori, et al., "Transforming Growth Factor-β Prevents Stem Cell Factor-Mediated Rescue of Mast Cells from Apoptosis After IL-3 Deprivation," J. Immunol., (1994), 153:2194-2203.
Meltzer, E. O., "The pharmacological basis for the treatment of perennial allergic rhinitis and non-allergic rhinitis with topical corticosteroids," Aller., (1997), 52:33-40.
Meng, et al., "Automated Docking with Grid-Based Energy Evaluation," J. Compt. Chem., (1992), 13:505-524.
Menke et al., "Sunlight triggers cutaneous lupus through a CSF-1-dependent mechanism in MRL-$Fas^{lpr}$ mice," Journal of Immunology, (2008), 181: 7367-7379.
Merour, et al., "Synthesis and Reactivity of 7-Azaindoles (1H-Pyrrolo[2,3-b]pyridine)," Curr. Org. Chem., (2001), 5:471-506.
Merritt, A., "Solution Phase Combinatorial Chemistry," Comb Chem High Throughput Screen, (1998), 1:57-72.
Metcalf, D., "Lineage Commitment in the Progeny of Murine Hematopoietic Preprogenitor Cells: Influence of Thrombopoietin and Interleukin 5," Proc. Natl. Acad. Sci., (1998), 95:6408-6412.
Metcalfe, D. "Classification and Diagnosis of Mastocytosis: Current Status," J. Invest. Derm., (1991), 93:2S-4S.
Metcalfe, et al., "Mast Cells," Physiol. Rev., (1997), 77:1033-1079.
Meula Pomeda, et al., "Efecto De Codisolventes Y Dispersiones Solida De Polivinilpirrolidona K-30 En La Solubilidad Tel Tiabendazol," Departamento de Farmacia y Tecnologia Farmaceutica. Facultad de Farmacia. Universidad de Alcala, pp. 85-87 (2002) (No English Translation Available).
Miller et al., "FLOG: A System to Select Quasi-Flexible Ligands Complementary to a Receptor of Known Three-Dimensional Structure," J. Comp. Aided Molec. Design, (1994), 8:153-174.
Minakata, et al., "Functionalization of 1H-Pyrrolo[2,3-b]pyridine," Bulletin of the Chemical Society of Japan, (1992), 65(11):2992-2997.
Minakata, et al., "Regioselective Funtionalization of 1H-Pyrrolo[2,3-b]pyridine Via its N-Oxide," Synthesis, (1992), 661-663.
Miranker, at al., "Functionality Maps of Binding Sites: A Multiple Copy Simultaneous Search Method," Proteins: Structure, Function, and Genetics, (1991), 11:29-34.
Mitra, et al., "Fluorescence Resonance Energy Transfer Between Blue-Emitting and Red-Shifted Excitation Derivatives of the Green Fluorescent Protein," Gene, (1996), 173:13-17.
Miyaura, et al., "Palladium-Catalyzed Cross-Coupling Reactions of Organoboron Compounds," Chem. Rev., (1995), 95:2457-2483.
Mokhtari, et al., "Potential utility of small tyrosine kinase inhibitors in the treatment of diabetes," Clinical Science, (2010), 118(4):241-247.
Mol, et al., "Structural Basis for the Autoinhibition and STI-571 Inhibition of c-Kit Tyrosine Kinase," J. Biol. Chem., (2004), 279:31655-31663.
Mol, et al., "Structure of a c-Kit Product Complex Reveals the Basis for Kinase Transactivation," J. Biol. Chem., (2003), 278:31461-31464.
Morgan, et al., "Isolation and Characterization of a Cloned Growth Factor Dependent Macrophage Cell Line, BAC1.2F5," J. of Cell. Physiology, (1987), 130:420-427.
Motoyoshi, K., "Biological activities and clinical application of M-CSF," Int J Hematol. (1998), 67:109-122.
Murphy, et al., "Expression of macrophage colony-stimulating factor receptor is increased in the $A\beta BPP^{V717F}$ transgenic mouse model of Alzheimer's disease," Am. J. of Pathology, (2000), 157:(3) 895-904.
Murty, et al., "A Genetic Perspective of Male Germ Cell Tumors," Sem. Oncol., (1998), 25:133-144.
Naclerio, et al., "Rhinitis and Inhalant Allergens," JAMA, (1997), 278:1842-1848.

(56) References Cited

OTHER PUBLICATIONS

Nagafuji, et al., "A General Synthesis of Pyrroles and Fused Pyrrole Systems from Ketones and Amino Acids," J. Org. Chem., (1996), 61:4999-5003.

Nagata, et al., "Elevated Expression of the Proto-Oncogene c-kit in Patients with Mastocytosis," Leukemia, (1998), 12:175-181.

Nahm et al., "N-Methoxy-N-Methylamides as Effective Acylating Agents," Tetrahedron Lett., (1981), 22(39):3815-3818.

Nakagawara, et al., "Expression and Function of TRK-B an BDNF in Human Neuroblastomas," Mol. Cell Biol., (1994), 14:759-767.

Nakai et al., "New Potent Antagonists of Leukotrienes C4 and D4. 01. Synthesis and Structure-Activity Relationships," J. Med. Chem., (1988), 31:(1):84-91.

Nassentein, et al., "The Neurotrophins Nerve Growth Factor, Brain-derived Neurotrophic Factor, Neurotrophin-3, and Neurotrophin-4 Are Survival and Activation Factors for Eosinophils in Patients with Allergic Bronchial Asthma," J. Exp. Med., (2003), 198:455-467.

Natali, et al., "Breast cancer is associated with loss of the c-kit oncogene product," Int. J. Cancer (1992) 52:713-717.

Navaza, J., "AMoRe: an Automated Package for Molecular Replacement," Acta Cryst., (1994), A50:157-163.

Neidle, et al., "Molecular Modeling to Study DNA Intercalation by Anti-Tumor Drugs," Methods Enz., (1991), 203:433-458.

Ng, et al., "Engineering Protein-Lipid Interactions: Targeting of Histidine-Tagged Proteins to Metal-Chelating Lipid Monolayers," Langmuir, (1995), 11:4048-4055.

Nicholls, et al., "Protein Folding and Association: Insights From the Interfacial and Thermodynamic Properties of Hydrocarbons," Proteins, (1991), 11:281-296.

Nichols, et al., "Development of a Scintillation Proximity Assay for Peroxisome Proliferator-Activated Receptor y Ligand Binding Domain," Anal. Biochem., (1998), 257:112-119.

Niihori, et al., "Germline KRAS and BRAF mutations in cardio-facio-cutaneous syndrome," Nature Genet., (2006), 38(3):294-296.

Notice of Allowance for U.S. Appl. No. 12/082,665 dated Jul. 26, 2011 (039363-1917).

Ochs, et al., "A phase I/II trial of recombinant methionyl human brain derived neurotrophic factor administered by intrathecal infusion to patients with amyotrophic lateral sclerosis," Amyotroph Lateral Scler Other Motor Neuron Disord., (2000), 1:201-206.

Odegaard et al. "Macrophage-specific PPARγ controls alternative activation and improves insulin resistance," Nature, (2007), 447: 1116-1121.

Office Action in Australian Application No. 2006261993 dated Aug. 15, 2011 (039363-2862).

Office Action in Australian Application No. 2006272951 dated Mar. 8, 2011 (039363-4001).

Office Action in Canadian Application No. 2,738,573 dated Jan. 10, 2012 (039363-6914).

Office Action in Chilean Application No. 3326-2007 dated Sep. 28, 2011 (039363-4103).

Office Action in Chinese Application No. 200680030326 dated Mar. 30, 2010 (039363-2864).

Office Action in Chinese Application No. 200780050245.3 dated Jul. 20, 2011(039363-4117).

Office Action in Colombian Application No. 08-005.567 dated Sep. 9, 2011 (039363-2865).

Office Action in Dominican Republic Application No. P2011-0291 dated Apr. 23, 2012 (039363-6922) (English Translation).

Office Action in Ecuador Application No. 2009117475/04 dated Jul. 26, 2011 (039363-4131).

Office Action in Egyptian Application PCT 1439/2007 dated Mar. 30, 2011 (039363-2868).

Office Action in European Application No. 04751431.0 dated Dec. 14, 2009.

Office Action in Israeli Application No. 188248 dated Mar. 7, 2011 (039363-2871).

Office Action in Israeli Application No. 198624 dated Apr. 18, 2012 (039363-4124) (English Translation).

Office Action in Israeli Application No. 199194 dated Apr. 23, 2012 (with English Translation) (0393633574).

Office Action in Japanese Application No. 2006-545481 dated Oct. 27, 2011(039363-1908).

Office Action in Japanese Application No. 2008-518402 dated Nov. 29, 2011 (039363-2873) (English Translation).

Office Action in Japanese Application No. 2009-538496 dated Jan. 29, 2013 (039363-4140).

Office Action in Japanese Application No. 2009-538496 dated Aug. 20, 2013 (039363-4140).

Office Action in Mexican Application No. MX/a/2009/005428 dated May 16, 2012 (039363-4126).

Office Action in Mexican Application No. MX/a/2009/006162 dated Sep. 8, 2011 (039363-3577).

Office Action in New Zealand Application No. 577612 dated Mar. 21, 2012(039363-3579).

Office Action in New Zealand Application No. 594398 dated Aug. 16, 2012 (039363-6938).

Office Action in Norwegian Application No. 20076659 dated Aug. 15, 2012 (039363-2878) (With English Translation).

Office Action in Panama Application No. 1796-2007 dated Sep. 15, 2011(039363-3556).

Office Action in Panama Application No. 88694 dated Mar. 15, 2011 (039363-6909).

Office Action in Peruvian Application No. 1602-2007 dated Sep. 2, 2011 (039363-4110).

Office Action in Philippine Application No. 12009501009 dated Jul. 27, 2012 (039363-4130).

Office Action in Philippine Application No. 12009501009 dated Nov. 24, 2011 (039363-4130).

Office Action in Philippine Application No. 1-2009-501241 dated Jul. 27, 2012 (039363-3582).

Office Action in Russian Application No. 2008100933/04(001022) dated Apr. 14, 2010 (039363-2881).

Office Action in Russian Application No. 2009122436 (039363-3583) dated Dec. 2, 2011 (OA with English Translation).

Office Action in Taiwan Application No. 095122373 dated Dec. 9, 2011 (039363-2858) (English Translation).

Office Action in Taiwan Application No. 099110011 dated Jun. 26, 2012 (039363-6911)(With English Translation).

Ohno, et al. "A c-fms tyrosine kinase inhibitor, KI202227, suppresses osteoclast differentiation and osteolytic bone destruction in a bone metastasis model," Mol. Cancer Ther., (2006), 5(11):2634-2643. 2634-43, 5, 2006.

Ohno, et al., "The orally-active and selective c_FMS tyrosine kinase inhibitor Ki20227 inhibits disease progression in a collagen-induced arthritis mouse model," Eur. J Immunol., (2008), 38: 1-9.

Okada, et al., "Gene Therapy Against an Experimental Glioma Using Adeno-Associated Virus Vectors," Gene Ther., (1996), 3:957-964.

Okayama, et al., "Activation of Eosinophils with Cytokines Produced by Lung Mast Cells," Int. Arch. Aller. Immunol., (1997), 114(suppl. 1):75-77.

Okayama, et al., "Human Lung Mast Cells are Enriched in the Capacity to Produce Granulocyte-Macrophage Colony-Stimulating Factor in Response to IgE-Dependent Stimulation," Eur. J. Immunol., (1998), 28:708-715.

Olah, et al., "Synthetic Methods and Reactions: Part 209. Improved Preparation of Aldehydes and Ketones from N,N-Dimethylamides and Grignard Reagents," Synthesis, (1984), 228-230.

O'Shannessy, D., "Determination of Kinetic Rate and Equilibrium Binding Constants for Macromolecular Interactions: a Critique of the Surface Plasmon Resonance Literature," Current Opinions in Biotechnology, (1994), 5:65-71.

O'Shannessy, et al., "Interpretation of Deviations From Pseudo-First-Order Kinetic Behavior in the Characterization of Ligand Binding by Biosensor Technology," Analytical Biochemistry, (1996), 236:275-283.

Ottoni, et al., "Efficient and Simple Methods for the Introduction of the Sulfonyl, Acyl and Alkyl Protecting Groups on the Nitrogen of Indole and its Derivatives," Tetrahedron, (1998), 54:13915-13928.

Otwinowski, Z., "Maximum Likelihood Refinement of Heavy Atom Parameters," Dept. of Molecular Biophysics and Biochemistry, (1991), 80-86.

(56) References Cited

OTHER PUBLICATIONS

Owicki, et al., Application of Fluorescence Polarization Assays in High-Throughput Screening, Genetic Engineering News, (1997), 17:27.
Parker, et al., "Development of High Throughput Screening Assays Using Fluorescence Polarization: Nuclear Receptor-Ligand-Binding and Kinase/Phosphatase Assays," J Biomol Screen, (2000), 5:77-88.
Patani et al, "Bioisosterism: a rational approach in drug design," Chem Rev, (1996), 96:3147-3176.
Perrin, D., "Nucleic Acids for Recognition and Catalysis: Landmarks, Limitations, and Looking to the Future," Combinatorial Chemistry & High Throughput Screening, (2000), 3:243-269.
Petty, et al., "The effect of systemically administered recombinant human nerve growth factor in healthy human subjects," Ann Neurol., (1994), 36:244-246.
Pflugrath, et al., "Crystal Structure Determination, Refinement and the Molecular Model of the x-Amylase Inhibitor Hoe-467A," J. Mol. Biol., (1986), 189:383-386.
Pierce et al., "Local Anesthetics. I. beta-Monoalkylaminoethyl Esters of Alkoxybenzoic Acids," J. of Am. Chem. Society, (1942), 64:1691-1694.
Pignon, J.M., "C-kit mutations and mast cell disorders a model of activating mutations of growth factor receptors," Hermatol Cell Ther., (1997), 39:114-116.
Plunkett, et al., "A Silicon-Based Linker for Traceless Solid-Phase Synthesis," J. Org. Chem., (1995), 60:6006-6007.
Poul, et al., "Selection of Tumor-Specific Internalizing Human Antibodies from Phage Libraries," J. Mol. Biol., (2000), 301:1149-1161.
Prada et al., "Neurofibroma-associated Macrophages Play Roles in Tumor Growth and Response to Pharmacological Inhibition," Acta Neuropathol, (2013), 125: 159-168.
Price, et al., "Summary report on the ISOBM TD-4 Workshop: analysis of 56 monoclonal antibodies against the MUC1 mucin," Tumour Biology, (1998), 19:1-20.
Qiao, et. al., "Role of Macrophage Colony-Stimulating Factor in Atherosclerosis," Am. J. Path., (1997), 150:1687-1699.
Rajavashisth, et. al., "Heterozygous Osteopetrotic (op) Mutation Reduces Atherosclerosis in LDL Receptor-deficient Mice," J. Clin. Invest., (1998), 101:2702-2710.
Rajpert-De Meyts, et al., "Expression of the c-kit Protein Product in Carcinoma-in-situ and Invasive Testicular Germ Cell Tumours," Int. J. Androl., (1994), 17:85-92.
Rapp, et al., "Raf kinases in lung tumor development," Advan. Enzyme Regul. (2003) 43:183-195.
Ricotti, et al., "c-kit Is Expressed in Soft Tissue Sarcoma of Neuroectodermic Origin and Its Ligand Prevents Apoptosis of Neoplastic Cells," Blood, (1998), 91:2397-2405.
Ridge, et al., "FMS mutations in myelodysplastic, leukemic, and normal subjects," Proc. Nat. Acad. Sci., (1990), 87:1377-1380.
Ritz, et al., "Elevated blood levels of inflammatory monocytes (CD14$^+$CD16$^+$) in patients with complex regional pain syndrome," Clin. Exper. Immunology, (2011), 1-10.
Roberts et al., "Targeting the Raf-MEK-ERK mitogen-activated protein kinase cascade for the treatment of cancer," Oncogene (2007) 26:3291-3310.
Roberts, et al., "Generation of an antibody with enhanced affinity and specificity for its antigen by protein engineering," Nature, (1987), 328:731-734.
Robinson, et al., "Stimulation of Bone Marrow Colony Growth In Vitro by Human Urine," Blood, (1969), 33:396-399.
Robison, et al., "7-Azaindole. I. Synthesis and Conversion to 7-Azatryptophan and Other Derivatives," J. Am. Chem. Soc., (1955), 77:457-460.
Rodan, et al., "Therapeutic Approaches to Bone Diseases," Science, (2000), 289:1508-1514.
Rodriguez-Viciana, et al., "Germline Mutations in Genes Within the MAPK Pathway Cause Cardio-facio-cutaneous Syndrome," Science, (2006), 311:1287-1290.
Rosenfeld, M.A., "Human artificial chromosomes get real," Nat. Genet., (1997), 15:333-335.
Ryan, et al., "Role for the Stem Cell Factor/KIT Complex in Schwann Cell Neoplasia and Mast Cell Proliferation Associated with Neurofibromatosis," J. Neuro. Res. (1994), 37:415-432.
Saify, et al., "Database CAS on STN (Columbus, OH, USA) No. 124:170379, Synthesis of some 2-azaindole derivatives: their cyctotoxicity and antibacterial activity," abstract, (1996), See RN 271-63-6.
Saify, et al., "Synthesis of some 7-azaindole derivatives: Their cytotoxicity and antibacterial activity," Pakistan Journal of Scientific and Industrial Research, (1994), 37(10):439-441.
Saiki, R.K., "Amplification of Genomic DNA," PCR Protocols, A Guide to Methods and Applications, (1990), 13-20.
Sambrook, et al., "Introduction of Recombinant Vectors into Mammalian Cells," Molecular Cloning: A Laboratory Manual, (1989), 2:16.30-16.37.
Sandlow, et al., "Expression of c-KIT and its Ligand, Stem Cell Factor, in Normal and Subfertile Human Testicular Tissue," J. Androl., (1996), 17:403-408.
Santoro, et al., "The ret Proto-Oncogene is Consistently Expressed in Human Pheochromocytomas and Thyroid Medullary Carcinomas," Oncogene, (1990), 5(10):1595-1598.
Sathornsumetee, et al., "AAL881, a Novel Small Molecule Inhibitor of RAF and Vascular Endothelial Growth Factor Receptor Activities, Blocks the Growth of Malignant Glioma," Cancer Res., (2006), 66:8722-8730.
Sawada, et al., "4-(Benzoylindolizinyl)butyric acids; Novel nonsteroidal inhibitors of steroid 5;1-reductase. III," Chemical and Pharmaceutical Bulletin, (2001), 49(7):799-813.
Sawada, et al., "Role of Cytokines in Leukemic type Growth of Myelodysplastic CD34+ Cells," Blood, (1996), 88:319-327.
Sawai, et al., "Aberrant growth of granulocyte-macrophage progenitors in juvenile chronic myelogenous leukemia in serum-free culture," Exp. Hem., (1996), 2:116-122.
Scheffner, et al., "The E6 Oncoprotein Encoded by Human Papillomavirus Types 16 and 18 Promotes the Degredation of p53," Cell, (1990), 63:1129-1136.
Schiemann, et al., "p-Fluorobenzoic Acid," Org. Syn. Coll., (1943), 2:299-301.
Schneider, et al., "Functional Purification of a Bacterial ATP-Binding Cassette Transporter Protein (MalK) from the Cytoplasmic Fraction of an Overproducing Strain," Protein Expr. Purif., (1995), 6:10-14.
Schneller, et. al., "Synthesis of 4-Amino-1 H-pyrrolo[2,3-b]pyridine {1,7-Dideazaadenine) and 1H-Pyrrolo[2,3-b]pyridine-4-ol (1,7-Dideazahypoxanthine)," J. Org. Chem., (1980), 45:4045-4048.
Schuhmann, et al., "Immobilization of Enzymes on Langmuir-Blodgett Films via a Membrane-Bound Receptor. Possible Applications for Amperometric Biosensors," Adv. Mater., (1991), 3:388-391.
Schummer, et al., "Inexpensive Handheld Device for the Construction of High-Density Nucleic Acid Arrays," Biotechniques, (1997), 23:1087-1092.
Schweizer, et al., "Combinatorial Synthesis of Carbohydrates," Curr Opin Chem Biol, (1999), 3(3):291-298.
Sclabas, et al., "Overexpression of Tropomysin-Related Kinase B in Metastatic Human Pancreatic Cancer Cells," Clin. Cancer. Res., (2005), 11:440-449.
Search Report for European Application No. 04814626.0 dated Aug. 4, 2009.
Search Report for European Application No. 11173701.1 dated Mar. 6, 2012.
Search Report for European Application No. 11173701.1 dated Oct. 26, 2011.
Search Report for Taiwan Patent Application No. 094120055 dated Aug. 25, 2011 (039363-2153).
Secor, et al., "Mast cells are essential for early onset and severe disease in a murine model of multiple sclerosis," J. Exp. Med., (2000), 5:813-821.
Selvin, P., "Fluorescence Resonance Energy Transfer," Meth. Enzymol., (1995), 246:300-345.
Shan, et al., "Prodrug strategies based on intramolecular cyclization reactions," Journal of Pharmaceutical Sciences, (1997), 86(7):765-767.

(56) References Cited

OTHER PUBLICATIONS

Sheets, et al., "Efficient Construction of a Large Nonimmune Phage Antibody Library: The Production of High-Affinity Human Single-Chain Antibodies to Protein Antigens," Proc Natl Acad Sci USA., (1998), 95:6157-6162.
Shibata, et al., "Alveolar macrophage deficiency in osteopetrotic mice deficient in macrophage colony-stimulating factor is spontaneously corrected with age and associated with matrix metalloproteinase expression and emphysema," Blood, (2001), 98:2845-2852.
Siegel, et al., "Mass Spectral Analysis of a Protein Complex Using Single-Chain Antibodies Selected on a Peptide Target: Applications to Functional Genomics," Journal of Molecular Biology, (2000), 302:285-293.
Sigal, et al., "A Self-Assembled Monolayer for the Binding and Study of histidine-Tagged Proteins by Surface Plasmon Resonance," Anal. Chem., (1996), 68:490-497.
Smaley, et al., "c-KIT signaling as the driving oncogenic event in sub-groups of melanomas," Histol Histopathol, (2009), 24:643-650.
Smith, et al., "The Role of kinase inhibitors in the treatment of patients with acute myeloid leukemia," (2013), *Am Soc Clin Oncol Educ Book*, (2013), 313-318.
Solinas-Toldo, et al., "Matrix-Based Comparative Genomic Hybridization Biochips to Screen for Genomic Imbalances," Genes, Chromosomes & Cancer, (1997), 20:399-407.
Song, et al., "Isomerism of Bis(7-azaindolyl)methane," Organic Letters (2002), 4(23):4049-4052, Table of content p. 1-16 and Supporting information p. 1-15.
Sperling, et al., "Expression of the Stem Cell Factor Receptor C-Kit (CD117) in Acute Leukemias," Haemat., (1997), 82:617-621.
Stanulla, et al., "Coexpression of Stem Cell Factor and Its Receptor c-Kit in Human Malignant Glioma Cell Lines," Act Neuropath., (1995), 89:158-165.
Steinman, L., "Multiple sclerosis: A coordinated immunological attack against myelin in the central nervous system," Cell, (1996), 85:299-302.
Strohmeyer, et al., "Expression of the C-kit Proto-Oncogene and its Ligand Stem Cell Factor (SCF) in Normal and Malignant Human Testicular Tissue," J. Urol., (2005), 153:511-515.
Strohmeyer, et al., "Expression of the hst-1 and c-kit Protooncogenes in Human Testicular Germ Cell Tumors," Canc. Res., (1991), 51:1811-1816.
Su, et al., "Synthesis of bromo-substituted Idoxyl Esters for Cytochemical Demonstration of Enzyme Activity," J. Am. Chem. Soc., (1960), 82:1187-1189.
Sun, C., "Recent Advances in Liquid-Phase Combinatorial Chemistry," Comb. Chem. & High Throughput Screening, (1999), 2:299-318.
Sun, et al., "Design, Synthesis, and Evaluations of Substituted 3-[(3- or 4-Carboxyethylpyrrol-2-yl) Methylidenyl]indolin-2-Ones as Inhibitors of VEGF, PGF, and PDGF Receptor Tyrosine Kinases," J. Med. Chem., (1999), 42:5120-5130.
Tada, et al., "Analysis of Cytokine Receptor Messenger RNA Expression in Human Glioblastoma Cells and Normal Astrocytes by Reverse-Transcription Polymerase Chain Reaction," J. Neuro., (1994), 80:1063-1073.
Takahashi, et al., "Activation of a Novel Human Transforming Gene, ret, by DNA Rearrangement," Cell, (1985), 42(2):581-588.
Takahashi, et al., "Cloning and Expression of the ret Proto-Oncogene Encoding a Tyrosine Kinase with Two Potential Transmembrane Domains," Oncogene, (1988), 3(5):571-578.
Takahashi, et al., "ret Transforming Gene Encodes a Fusion Protein Homologous to Tyrosine Kinases," Mol Cell Biol., (1987), 7:1378-1385.
Tang, et al., "An RNA interference-based screen identifies MAP4K4/NIK as a negative regulator of PPARy, adipogenesis, and insulin-responsive hexose transport," Proc. Natl. Acad. Sci., (2006), 103:2087-2092.
Tanno et al., "Evaluation of Hypromellose Acetate Succinate (HPMCAS) as a Carrier in Solid Dispersions," Drug Development and Industrial Pharmacy 30(1):9-17 (2004).
Taylor, et al., "The Rapid Generation of Oligonucleotide-directed Mutations at High Frequency Using Phosphorothloate-Modified DNA," Nucl. Acids Res., (1985), 13:8764-8785.
Teitelbaum, S.L., "Bone Resorption by Osteoclasts," Science, (2000), 289:1504-1508.
Thibault, et. al., "Concise and Efficient Synthesis of 4-fluoro-1H-pyrrolo[2,3-b] pyridine," Org. Lett., (2003), 5:5023-5025.
Thomas, et al., "The Eosinophil and its Role in Asthma," Gen. Pharmac., (1996), 27:593-597.
Thomas, et. al., "Light-Emitting Carbazole Derivatives: Potential Electroluminescent Materials," J. Am. Chem. Soc., (2001), 123:9404-9411.
Toste, et al., "A Versatile Procedure for the Preparation of Aryl Thiocyanates Using N-Thiocyanatosuccinimide (NTS)," Synth. Comm., (1995), 25(8):1277-1286.
Toy et al., "Enhanced ovarian cancer tumorigenesis and metastasis by the macrophage colony-stimulating factor," *Neoplasia*, (2009), 11:(2) 136-144.
Toyota, et al., "Expression of c-kit and kit Ligand in Human Colon Carcinoma Cells," Turn Biol., (1993), 14:295-302.
Trupp, et al., "Functional Receptor for GDNF Encoded by the c-ret Proto-Oncogene," Nature., (1996), 381:785-789.
Tsuda, et al., "Microglia and Intractable Chronic Pain," (2012), *GLIA*, 1-7.
Tsujimura, et al., "Ligand-Independent Activation of c-kit Receptor Tyrosine Kinase in a Murine Mastocytoma Cell Line P-815 Generated by a Point Mutation," Blood, (1994), 9:2619-2626.
Tsujimura, et al., "Substitution of an Aspartic Acid Results in Constitutive Activation of c-kit Receptor Tyrosine Kinase in a Rat Tumor Mast Cell Line RBL-2H3," Int. Arch. Aller. Immunol., (1995), 106:377-385.
Tsujimura, T., "Role of c-kit Receptor Tyrosine Kinase in the Development, Survival and Neoplastic Transformation of Mast Cells," Pathol Int., (1996), 46:933-938.
Turner, et al., "Nonhematopoeietic Tumor Cell Lines Express Stem Cell Factor and Display c-kit Receptors," Blood, (1992), 80:374-381.
Udenfriend, et al., "Scintillation Proximity Assay: A Sensitive and Continuous Isotopic Method for Monitoring Ligand/Receptor and Antigen/Antibody Interactions," Anal. Biochem, (1987), 161:494-500.
Uemura et al., "The Selective M-CSF Receptor Tyrosine Kinase Inhibitor Ki20227 Suppresses Experimental Autoimmune Encephalomyelitis," *J. Neuroimmunology*, (2008), 195: 73-80.
Uritskaya, et al., STN Accession No. 1974-27133; Document No. 08:27133; Abstract of Khimiya Geterotsiklicheskikh Soedinenii (1973), 10:1370-1373.
US Notice of Allowance of U.S. Appl. No. 11/016,350 dated Dec. 26, 2007 (039363-1903).
US Notice of Allowance of U.S. Appl. No. 11/154,988 dated Jun. 6, 2008 (039363-2121).
US Notice of Allowance of U.S. Appl. No. 11/154,988 dated Jul. 23, 2008 (039363-2121).
US Notice of Allowance of U.S. Appl. No. 11/154,988 dated Sep. 8, 2008 (039363-2121).
US Notice of Allowance of U.S. Appl. No. 11/435,381 dated May 27, 2010 (039363-2192).
US Notice of Allowance of U.S. Appl. No. 11/473,347 dated Jun. 18, 2010 (039363-2803).
US Notice of Allowance of U.S. Appl. No. 11/473,347 dated Sep. 8, 2010 (039363-2803).
US Notice of Allowance of U.S. Appl. No. 11/960,590 dated Aug. 11, 2010 (039363-3502).
US Notice of Allowance of U.S. Appl. No. 11/961,901 dated May 17, 2012 (039363-3402).
US Notice of Allowance of U.S. Appl. No. 11/962,044 dated Aug. 13, 2010 (039363-3302).
US Notice of Allowance of U.S. Appl. No. 11/986,667 dated Aug. 6, 2010 (039363-4152).
US Notice of Allowance of U.S. Appl. No. 12/244,730 dated Jan. 6, 2011 (039363-2128).

(56) References Cited

OTHER PUBLICATIONS

US Notice of Allowance of U.S. Appl. No. 12/616,079 dated Oct. 25, 2012 (039363-2805).
US Notice of Allowance of U.S. Appl. No. 13/216,200 dated Dec. 8, 2011 (039363-2807).
US Notice of Allowance of U.S. Appl. No. 13/546,923 dated Nov. 19, 2012 (039363-4155).
US Office Action in U.S. Appl. No. 11/016,350 dated Jun. 6, 2007 (039363-1903).
US Office Action in U.S. Appl. No. 11/016,350 dated Aug. 2, 2007 (039363-1903).
US Office Action in U.S. Appl. No. 11/016,350 dated Oct. 26, 2007 (039363-1903).
US Office Action in U.S. Appl. No. 11/154,988 dated Jan. 4, 2008 (039363-2121).
US Office Action in U.S. Appl. No. 11/154,988 dated Oct. 19, 2007 (039363-2121).
US Office Action in U.S. Appl. No. 11/435,381 dated Feb. 19, 2010 (039363-2192).
US Office Action in U.S. Appl. No. 11/435,381 dated Mar. 4, 2009 (039363-2192).
US Office Action in U.S. Appl. No. 11/435,381 dated Jun. 1, 2009 (039363-2192).
US Office Action in U.S. Appl. No. 11/473,347 dated Dec. 18, 2009 (039363-2803).
US Office Action in U.S. Appl. No. 11/487,134 dated May 15, 2008 (039363-1915).
US Office Action in U.S. Appl. No. 11/487,134 dated Aug. 22, 2007 (039363-1915).
US Office Action in U.S. Appl. No. 11/961,901 dated Jan. 23, 2012 (039363-3402).
US Office Action in U.S. Appl. No. 11/961,901 dated Aug. 4, 2011 (039363-3402).
US Office Action in U.S. Appl. No. 11/962,044 dated Feb. 17, 2010 (039363-3302).
US Office Action in U.S. Appl. No. 11/962,044 dated Sep. 23, 2009 (039363-3302).
US Office Action in U.S. Appl. No. 11/986,667 dated Feb. 26, 2010 (039363-4152).
US Office Action in U.S. Appl. No. 11/986,667 dated Sep. 22, 2009 (039363-4152).
US Office Action in U.S. Appl. No. 12/082,665 dated Nov. 8, 2010 (039363-1917).
US Office Action in U.S. Appl. No. 12/244,730 dated Jul. 22, 2010 (039363-2128).
US Office Action in U.S. Appl. No. 12/616,079 dated Feb. 9, 2012 (039363-2805).
US Office Action in U.S. Appl. No. 12/616,079 dated Jun. 29, 2012 (039363-2805).
US Office Action in U.S. Appl. No. 12/752,035 dated Oct. 3, 2012 (039363-6903).
US Office Action in U.S. Appl. No. 12/906,980 dated Feb. 29, 2012 (039363-2806).
US Office Action in U.S. Appl. No. 12/906,980 dated Oct. 17, 2012 (039363-2806).
US Office Action in U.S. Appl. No. 12/958,376 dated Apr. 18, 2012 (039363-2196).
US Office Action in U.S. Appl. No. 12/958,379 dated Jul. 17, 2012 (039363-4153).
US Office Action in U.S. Appl. No. 12/958,379 dated Nov. 14, 2012 (039363-4153).
US Office Action in U.S. Appl. No. 12/981,427 dated Mar. 5, 2013 (039363-3504).
US Office Action in U.S. Appl. No. 13/546,923 dated Sep. 18, 2012 (039363-4155).
Vachon, et al., "The influence of microencapsulation using Eudragit RS100 on the hydrolysis kinetics of acetylsalicylic acid," J. Microencapsulation, (1997), 14(3):281-301.
Valent, P., "Biology, Classification and Treatment of Human Mastocytosis," Wein/Klin Wochenschr., (1996), 108:385-397.
Van Heyningen, V., "One Gene—Four Syndromes," Nature, (1994), 367:319-320.
Van Regenmortel, M.H.V., "Use of biosensors to characterize recombinant proteins," Developments in Biological Standardization, (1994), 83:143-151.
Vandelli, et al., "Analysis of release data in the evaluation of the physical state of progesterone in matrix systems," J. Microencapsulation, (1993), 10(1):55-65.
Vely, et al., "BIAcore Analysis to Test Phosphopeptide-SH2 Domain Interactions," Methods in Molecular Biology, (2000), 121:313-321.
Verfaillie, C.M., "Chronic myelogenous leukemia: too much or too little growth, or both?" Leukemia, (1998), 12:136-138.
Viskochil, D., "It Takes Two to Tango: Mast Cell and Schwann Cell Interactions in Neurofibromas," J Clin Invest., (2003), 112:1791-1793.
Vliagoftis, et al., "The protooncogene c-kit and c-kit ligand in human disease," Journ. Clin. Immunol, (1997), 100:435-440.
Waldo et al., "Heterogeneity of human macrophages in culture and in atherosclerotic plaques," *Am. J. of Pathology*, 172(4): 1112-1126 (2008).
Weber, P., "Physical Principles of Protein Crystallization," Adv. Protein Chem., (1991), 41:1-36.
Wells, et al., "Targeting the RET Pathway in Thyroid Cancer," Clin Cancer Res., (2009), 15(23):7119-7123.
Wendt, et al., "Identification of novel binding interactions in the development of potent, selective 2-naphthamidine inhibitors of urokinase, synthesis, structural analysis, and SAR of y-Phenyl amide 6-substitution," J. Med. Chem., (2004), 47(2):303-324.
Wentworth et al., "Pro-Inflammatory $CD11C^+CD206^+$Adipose Tissue Macrophages Are Associated With Insulin Resistance in Human Obesity," *Diabetes*, (2010), 59:1648-1656.
Werness, et al., "Association of Human Papillomavirus Types 16 and 18 E6 Proteins with p53," Science, (1990), 248:76-79.
Wessjohann, L., "Synthesis of Natural-Product-Based Compound Libraries," Curr Opin Chem Biol., (2000), 4:303-309.
Wharam, et al., "Specific Detection of DNA and RNA Targets Using a Novel Isothermal Nucleic Acid Amplification Assay Based on the Formation of a Three-Way Junction Structure," Nucleic Acids Res., (2001), 29:1-8.
Wild, et al., "Antibodies to Nerve Growth Factor Reverse Established Tactile Allodynia in Rodent Models of Neuropathic Pain without Tolerance," J. Pharmacol. Exp. Ther., (2007), 322:282-287.
Williams, et al., "Dissection of the Extracellular Human Interferon y Receptor a-Chain into two Immunoglobulin-like domains. Production in an *Escherichia coli* Thioredoxin Gene Fusion Expression system and Recognition by Neutralizing Antibodies," Biochemistry, (1995), 34:1787-1797.
Woon, et al., "Construction and Characterization of a 10-Fold Genome Equivalent Rat P1-Derived Artificial Chromosome Library," Genomics, (1998), 50:306-316.
Wright, et al., "The STE20 Kinase KGK Is Broadly Expressed in Human tumor Cells and Can Modulate Cellular Transformation, Invasion, and Adhesion," Mol. Cell. Biol., (2003), 23:2068-2082.
Wuthrich, K., "Chapter 10: Three-Dimensional Protein Structures by NMR," NMR of Proteins and Nucleic Acids, (1986), 10:176-199.
Wyckoff, et al., "Direct visualization of macrophage-assisted tumor cell intravasation in mammary tumors," Cancer Research, (2007), 67(6):2649-2656.
Xing, et al., "BRAF Mutation Predicts a Poorer Clinical Prognosis for Papillary Thyroid Cancer," J. Clin. Endocrinol. Metab., (2005), 90(12):6373-6379.
Xing, M., "BRAF mutation in thyroid cancer," Endocrine-Related Cancer, (2005), 12:245-262.
Xu et al., "CSF1R signaling blockade stanches tumor-infiltrating myeloid cells and improves the efficacy of radiotherapy in prostate cancer," *Cancer Res.*, (2013), 73(9): 2782-94.
Xu, et al., "Modulation of Endothelial Cell function by Normal Polyspecific Human Intraveneous immunoglobulins," Am. J. Path., (1998), 153:1257-1266.
Yakhontov, et al., "Derivatives of 7-azaindole. XV. Electrophilic substitution of 4-methyl-7-azaindole and its derivatives," Zhurnal Obshchei Khimii, (1965), 1(11):2032-2040 (English abstract only).

(56) References Cited

OTHER PUBLICATIONS

Yamaguchi, et al., "Calcium Restriction Allows cAMP Activation of the B-Raf/ERK Pathway, Switching Cells to a cAMP-dependent Growth-stimulated Phenotype*," The Journal of Biological Chemistry, (2004), 279:40419-40430.
Yamaguchi, et al., "Cyclic AMP activates B-Raf and ERK in cyst epithelial cells from autosomal-dominant polycystic kidneys," Kidney International, (2003), 63:1983-1994.
Yang, et al., "Identification of Brain-Derived Neurotrophic Factor as a Novel Functional Protein in Hepatocellular Carcinoma," Cancer Res., (2005), 65:219-225.
Yang, et al., "Neurofibromin-Deficient Schwann Cells Secrete a Potent Migratory Stimulus for NF1+/– Mast Cells," J Clin Invest., (2003), 112:1851-1861.
Yang, et al., "Nf1-Dependent tumors require a microenvironment containing Nf1+/_-and c-kit-Dependent bone marrow," Cell, (2008), 135:437-448.
Yang, et al., "Synthesis of some 5-substituted indoles," Heterocycles, (1992), 34:1169-1175.
Yao, et al., "A Novel Human STE20-related Protein Kinase, HGK, That Specifically Activates the c-Jun N-terminal Kinase Signaling Pathway," J. Biol. Chem., (1999), 274:2118-2125.
Yee, et al., "Role of kit-Ligand in Proliferation and Suppression of Apoptosis in Mast Cells: Basis for Radiosensitivity of White Spotting and Steel Mutant Mice," J. Exp. Med., (1994), 179:1777-1787.
Yeung, et al., "Friedel-Crafts acylation of indoles in acidic imidazolium chloroaluminate ionic liquid at room temperature," Tetrahedron Letters, (2002), 43(33), 5793-5795.
Yuan, et al., Human Peripheral Blood Eosinophils Express a Functional c-kit Receptor for Stem Cell Factor that Stimulates Very Late Antigen 4 (VLA-4)-Mediated Cell Adhesion to Fibronectin and Vascular Cell Adhesion Molecule 1 (VCAM-1), J. Exp. Med., (1997), 186:313-323.
Zaidi et al., "Interferon-γ links ultraviolet radiation to melanomagenesis in mice." Nature, (2011), 469: 548-553.
Zanon, et. al., "Copper-Catalyzed Domino Halide Exchange-Cyanation of Aryl Bromides," J. Am. Chem. Soc., (2003), 125:2890-2891.
Zhang, et al., "An effective procedure for the acylation of azaindoles at C-3," Journal of Organic Chemistry, (2002), 67(17):6226-6227.
Zhang, et al., "Design and pharmacology of a highly specific dual FMS and KIT kinase inhibitor," Proc. Natl. Acad. Sci., (2013), 110:(14) 5689-5694.
U.S. Appl. No. 61/054,445, filed May 19, 2008, Ibrahim et al.
U.S. Appl. No. 61/060,418, filed Jun. 10, 2008, Ibrahim et al.
Arbiser, "Why targeted therapy hasn't worked in advanced cancer," The Journal of Clinical Investigation, (2007), 117(10):2762-2765.
Arthan et al., "Leukemia inhibitory factor can mediate Ras/Raf/MEK/ERK-induced growth inhibitory signaling in medullary thyroid cancer cells," Cancer Letters (2010), 297:31-41.
Banker, G.S. et al, "Modern Pharmaceutics, 3ed.", Marcel Dekker, New York, (1996), p. 596.
Bayindir et al., "Cellular mesoblastic nephroma (infantile renal fibrosarcoma): institutional review of clinical, diagnostic imaging, and pathologic features of a distinctive neoplasm of infancy," Pediatr. Radiol., (2009), 39(10):1066-74.
Beaucage et al., "Advances in Synthesis of Oligonucleotides by the Phosphoramidite Approach," Tetrahedron, (1992), 48:2223-2311.
Bouzas-Rodriguez et al., Neurotrophin-3 production promotes human neuroblastoma cell survival by inhibiting TrkC-induced apoptosis, J. Clin. Invest., 120(3):850-8 (2010).
Bundgaard, "Design of produdrugs: Bioreversible derivatives for various functional groups and chemical entitites," Design of Produgs,(1985), p. 1.
Burns et al., "c-FMS Inhibitars: A Patent Review," Expert Opinion Ther. Patents, (2011), 21(2):147-165.
Chappell et al., "Ras/Raf/MEK/ERK and PI3K/PTEN/Akt/mTOR Inhibitors: Rationale and Importance to Inhibiting These Pathways in Human Health," Oncotarget, (2011), 2(3):135-164.
Damasio, "Alzheimer's Disease and Related Dementias," Cecil Textbook of Medicine, 20th Edition, (1996), 2:1992-1996.

Dorwald, "Side Reactions in Organic Synthesis: A Guide to Successful Synthesis Design," Wiley-VCH, (2005), Preface p. IX.
Dumas, "Protein kinase inhibitors: emerging pharmacophores 1997-2000," Exp. Opin. Ther. Patents, (2001), 11 (3):405-429.
Engelman et al., "Effective use of PI3K and MEK inhibitors to treat mutant Kras G12D and PIK3CA H1047R murine lung cancers," Nature Medicine, (2008), 14(12):1351-1356.
Ertl et al., "Fast calculation of molecular polar surface area as a sum of fragment-based contributions i I and its application to the prediction of drug transport properties," J Med Chem, (2000), 43:3714-3717.
Fischer et al., "Targeting receptor tyrosine kinase signalling in small cell lung cancer (SCLC): What have we learned so far?," Cancer Treatment Reviews, (2007), 33:391-406.
Gallego et al., "Increased opioid dependence in a mouse model of panic disorder," Front Behav. Neurosci., (2010), 3:60.
Gallop, et al., "Applications of Combinatorial Technologies to Drug Discovery. 1. Background and Peptide Combinatorial Libraries," J. Med. Chem., (1994), 37:1233-1251.
Galofre, et al., "Evaluation and Treatment of Thyroid Nodules: A Clinical Guide," Mt Sinai J Med., (2008), 75:299-311.
Garzya et al., "Indium(III)-catalysed aryl sulfonylation reactions," Tetrahedron Letters, (2004), 45:1499-1501.
Gura, "Systems for identifying New Drugs Are Often Faulty, Cancer Models," Science, (1997), 278(5340):1041-1042.
Hasegawa et al., "Visualizing Mechanosensory Endings of TrkC-Expressing Neurons in HS3ST-2-hPLAP Mice," J Comp. Neurol., (2008), 511(4):543-556.
Hentschel et al., "BCR-ABL-and Ras-independent activiation of Raf as a novel mechanism of Imatinib resistance in CML," (2012), http://www.ncbi.nlm.nih.gov/pubmed/2163917.
Ibrahim et al., "Pyrrolo[2,3-b]pyridine derivatives as protein kinase inhibitors and their preparation, pharmaceutical compositions and use in the treatment of diseases," Caplus, (2007) 11300.
Jaiswal et al., Combined Targeting of BRAF and CRAF or BRAF and PI3K Effector Pathways is Requred for Efficacy in NRAS Mutant Tumors, PLoS One, (2009), 4(5):e5717.
Johnson et al., Relationships between drug activity in NCI preclinical in vitro and in vivo models and early clinical trials, British Journal of Cancer, (2001), 64(10):1424-1431.
Jongh et al. "The Role of Interleukin-6 in Nociception and Pain," Anesth Analg, (2003), (96):1096-103.
Joule et al., "Indole and its Derivatives," Science of Synthesis, (2001), 10:618-652.
Khazak et al., "Selective Raf Inhibition in Cancer Therapy," (2012), http://www.ncbu.nlm.nih.gov/pms/articles/PMC2720036.
Kubo et al., "Resequencing Analysis of the Human Tyrosine Kinase Gene Family in Pancreatic Cancer," Pancreas, (2009), 38(7):e200-e206.
Kubo et al., "Resequencing and copy number analysis of the human tyrosine kinase gene family in poorly differentiated gastric cancer," Carcinogenesis, (2009), 30(11 ):1857-1864.
Lambros et al., "Genomic profile of a secretory breast cancer with an ETV6-NTRK3 duplication," J. Clin. Pathol., (2009), 62(7):604-12.
Layzer, "Degenerative Diseases of the Nervous System," Cecil Textbook of Medicine, 20th Edition, (1996), 2:2050-2057.
Lee et al., "FMS-like tyrosine kinase 3 inhibitors: a patent review," Expert Opinion Ther. Patents, (2011), 21(4):483-503.
Levis et al., "A FLT3 tyrosine kinase inhibitor is selectively cytotoxic to acute myeloid leukemia blasts harboring FL T3 internal tandem duplication mutations," Blood, (2001), 98:885-887.
Madhusdan et al., "Tyrosine kinase inhibitors in cancer therapy," Clinical Biochemistry, (2004), 37:618-635.
Marchetti et al., "Frequent Mutations in the Neurotrophic Tyrosine Receptor Kinase Gene Family in Large Cell Neuroendocrine Carcinoma of the Lung," Hum. Mutat., (2008), 29(5):609-16.
McDermott et al., "Identification of genotype-correlated sensitivity to selective kinase inhibitors by using high throughput tumor cell line profiling," PNAS,(2007), 104(50):19936-19941.
Mettey et al., "Aloisines, a New family of CDK.GSK-3 Inhibitors. SAR Study, Crystal Structure in Complex with CDK2, Enzyme Selectivity, and Cellular Effects," J. Med. Chem., (2003), 46:222-236.

(56) References Cited

OTHER PUBLICATIONS

Panitumumab, (2011),"In Combination with Cisplatin/Gemacitabine", http://clinicaltrials.gov/ct2/show/NCT0132054.

Pearce et al., "Failure modes in anticancer drug discovery and development," *Cancer Drug Design and Discovery Edited by Stephen Neidle*, (2008), Chapter 18: 424-435.

Pratilas et al., "Marker gene showing changes in levels of expression in response to antineoplastic drug therapy and their use of chemotherapy", *Hcalplus*, (2008) 670875.

Prien, "Target-family-oriented focused libraries for kinases—Conceptual design aspects and commercial availability," *ChemBioChem*, (2005), 6:500-505.

Remington: *The Science and Practice of Pharmacy, vol. II*, (1995), pp. 1454-1460.

Rosnet et al., "Isolation and Chromosomal Localization of a Novel FMS-like Tyrosine Kinase Gene," *Genomics*, (1991), 9: 380-385.

Sclabas et al., "Overexpression of Tropomysin-Related Kinase Bin Metastatic Human Pancreatic Cancer Cells," *Clin. Cancer. Res*,(2005), VII: 440-449. Duplicate.

Serajuddin, A. T. M., "Solid Dispersion of Poorly Water-Soluble Drugs: Early Promises, Subsequent Problems, and Recent Breakthroughs," *J. Pharm. Sci.*, (1999), 8(10), 1058-1066.

Shah et al., "Development of Novel Microprecipitated Bulk Power(MBP) Technology for Manufacturing Stable Amorphous Formulations of Poorly Soluble Drugs", *International Journal of Pharmaceutics*, (2012), 438:53-60.

Shah et al., "Improved Human Bioavailability of Vemurafenib, A Practically Insoluble Drug, Using an Amorphous Polymer-Stabilized Solid Dispersion Prepared by a Solvent-Controlled Coprecipitation Process," *Journal of Pharmceutical Sciences*, (2012), pp. 1-15.

Silverman, Prodrugs and Drug Delivery Systems, *The Organic Chemistry of Drug Design and Drug Action, Academic Press, Inc.* (1992), pp. 352-399.

Simone, "Oncology: Introduction," *Cecil Textbook of Medicine, 20th Edition*, (1996), 1:1004-1010.

Small et al., "STK-I, the human homolog ofFlk-2/Flt-3, is selectively expressed in CD34+ human bone marrow cells and is involved in the proliferation of early progenitor/stem cells," *Proc. Nat. Acad. Sci.*, (1994), 91:459-463.

Soreafenib, (2012), http://www.cancer.gov/cancertopics/druginfo/sorafenibtosylate.

Specchia et al., "Constitutive expression ofiL-Iβ, M-CSF and c-fms during the myeloid blastic phase of chronic myelogenous leukaemia," *Br J Haematol.*, (1992), 80(3):310-316.

Wakefield, Basil "Fluorinated Pharmaceuticals" Innovations in Pharmaceutical Technology, (2003), 74:76-78. Online "http://web.archive/org/web/20030905122408/http://www.iptonline.com/articles/public/IPTFOUR74NP.pdf." (accessed via Wayback machine Nov. 20, 2009 showing web availability as of Sep. 2003).

Willmore-Payne, C., et al. "Human malignant melanoma. detection of BRAF- and c-kit-activating mutations by high-resolution amplicon melting analysis," *Humon Pathology*, (2005), 36:486-493.

Wolff, Manfred E. "Burger's Medicinal Chemistry, 5ed, Part 1", John Wiley & Sons, (1995), pp. 975-977.

Yoshida et al., "Studies on anti-helicobacter pylori agents, Part 1: Benzyloxyisoquinoline derivatives," *Bioorganic & Medicinal Chemistry, Elsevier Science Ltd*,(1999), 7(11):2647-2666.

Office Action in U.S. Appl. No. 11/016,350 dated Aug. 2, 2007 (039363-1903).

Supplementary Search Report for European Application No. 04814626.0 dated Aug. 4, 2009 (039363-1907).

Notice of Allowance for U.S. Appl. No. 12/244,730 dated Jul. 27, 2010 (039363-2128).

Examination Report dated Jun. 27, 2008 for GCC Patent Application No. GCC/P/2005/4795 (039363-2144).

Examination Report for Guatemala Patent Application No. PI-2005-00164 dated Jul. 2, 2008 (039363-2145).

Notice of Allowance for U.S. Appl. No. 11/435,381 dated Jul. 27, 2010 (039363-2192).

Office Action in U.S. Appl. No. 13/243,748 dated Jun. 27, 2013 (039363-2808).

Office Action in U.S. Appl. No. 13/786,219 dated Jul. 21, 2014 (039363-2809).

Office Action in U.S. Appl. No. 13/786,219 dated Nov. 8, 2013 (039363-2809).

Office Action in U.S. Appl. No. 13/866,469 dated Oct. 31, 2013 (039363-2810).

Office Action in Taiwan Application No. 102123382 dated Nov. 16, 2013 (039363-2847).

Novelty Search Report dated Sep. 24, 2009 for Gulf Cooperation Council Application No. GCC/P/2006/6469 (039363-2853).

Examination Report for Pakistan Patent Application No. 0679/2006 (039363-2854).

Office Action for Ukraine Application No. A200800780 dated Jul. 12, 2010 (039363-2883).

Office Action for European Application No. 11173701.1 dated Jan. 13, 2014 (039363-2894).

Office Action in Malaysian Applictaion No. PI2011004969 dated Apr. 30, 2014 (039363-2898).

Notification Prior to Examination for Israeli Application No. 199194 dated May 4, 2010 (039363-3574).

Office Action in Korean Application No. 10-2009-7012836 dated May 29, 2014 (039363-4134).

Office Action in Canadian Application No. 2670362 dated Dec. 5, 2013 (039363-4139).

Office Action in Canadian Application No. 2670362 dated Jul. 14, 2014 (039363-4139).

Office Action in U.S. Appl. No. 12/467,194 dated Feb. 3, 2011 (039363-4302).

Notice of Allowance for U.S. Appl. No. 12/467,194 dated Dec. 5, 2011 (039363-4302).

Office Action in U.S. Appl. No. 12/467,194 dated Jun. 24, 2011 (039363-4302).

International Search Report and Written Opinion dated Feb. 18, 2010 for PCT Patent Application No. PCT/US2009/044151 (039363-4308).

International Search Report and Written Opinion dated Sep. 22, 2009 for PCT Patent Application No. PCT/US2009/046598 (039363-4612).

Notice of Allowance for U.S. Appl. No. 12/773,798 dated Feb. 9, 2012 (039363-4902).

Office Action in U.S. Appl. No. 12/733,798 dated Jan. 20, 2011 (039363-4902).

Office Action in U.S. Appl. No. 12/773,798 dated Jul. 25, 2011 (039363-4902).

International Search Report dated Sep. 13, 2010 in PCT Application No. PCT/US2010/033571 (039363-4903).

International Preliminary Report on Patentability dated Nov. 9, 2011 in PCT Aapplication No. PCT/US2010/033576 (039363-4950).

International Search Report and Written Opinion dated Jun. 30, 2010 for PCT Application No. PCT/US2010/033576 (039363-4950).

International Search Report and Written Opinion dated Sep. 23, 2011 for PCT Patent Application No. PCT/US2010/061601 (039363-5204).

Extended European Search Report for EP Application 100840075.5 dated May 13, 2013.(039363-5217).

Office Action in Japanese Application No. 2012-546158 dated Dec. 2, 2014 (039363-5219).

International Search Report and Written Opinion dated Jan. 14, 2011 for PCT Patent Application No. PCT/US2010/055519 (039363-5303).

Office Action in Chinese Application No. 201080060838.X dated Oct. 29, 2014 (039363-5317).

Office Action in Israeli Application No. 219418 dated Oct. 6, 2014 (039363-5327).

Office Action and Search Report for Taiwanese Application No. 100113512 dated Dec. 15, 2014 (039363-5404).

International Search Report dated Dec. 19, 2011 in PCT Application No. PCT/US2011/033192 (039363-5406).

Supplementary European Search Report for EP Application No. 11772612, dated Oct. 21, 2013 (039363-5421).

(56) References Cited

OTHER PUBLICATIONS

International Search Report and Written Opinion dated Jan. 25, 2011 for PCT Patent Application No. PCT/US2010/057293 (039363-5504).
Extended European Search Report for EP Application 10832209.0 dated Apr. 17, 2013 (039363-5511).
Office Action in Russian Application No. 2012125070 dated Dec. 5, 2014 (039363-5524).
International Search Report and Written Opinion dated Jun. 11, 2010 for PCT Patent Application No. PCT/US2010/026816 (039363-6002).
Office Action in U.S. Appl. No. 12/721,500 dated May 13, 2011 (039363-6701).
Notice of Allowance for U.S. Appl. No. 12/721,500 dated Nov. 2, 2011 (039363-6701).
International Search Report and Written Opinion dated Jun. 11, 2010 for PCT Patent Application No. US2010/026856 (039363-6702).
Office Action in U.S. Appl. No. 12/752,035 dated Jun. 18, 2013 (039363-6903).
Examiners Report in Australian Application No. 2010232670 dated Jun. 6, 2014 (039363-6916).
Office Action in Chinese Application No. 201080012888.0 dated Mar. 10, 2014 (039363-6918).
Office Action in Chinese Application No. 20108001288.0 dated Oct. 21, 2014 (039363-6918).
Office Action in Eurasion Application No. 20119098 dated Jun. 16, 2014 (039363-6925).
Office Action in Eurasian Application No. 201190098 dated Apr. 13, 2014 (039363-6925).
Office Action in Indonesian Application No. W-00 2011-02778 dated Nov. 7, 2014 (039363-6930).
Office Action in Israeli Application No. 214328 dated Jul. 31, 2013 (039363-6931).
Office Action in Japense Patent Application No. 2012-503676 dated May 21, 2013 (039363-6932).
Office Action in Mexican Application No. MX/a/2011/008303 dated Sep. 11, 2014 (039363-6934).
Office Action in Peru Applicantion No. 1471-2011 dated Mar. 23, 2014 (039363-6939).
Office Action in Ukraine Application No. A 2011 09548 dated Jun. 4, 2014 (039363-6945).
Office Action in European Application 10722860.3 dated Aug. 21, 2014 (039363-6947).
International Search Report and Written Opinion dated May 31, 2012 for PCT Patent Application No. PCT/US2012/023543 (039363-7211).
Office Action in Australian Application No. 2012214762 dated Mar. 23, 2014 (039363-7213).
Office Action for Chinese Application No. 2012800170177 dated Jul. 8, 2014 (039363-7217).
Search Report for European Application No. 12745360.3 dated Jul. 23, 2014 (039363-7223).
Office Action in Japanese Application No. 2013-552610 dated Nov. 4, 2014 (039363-7227).
Examination Report in New Zealand Application No. 613786 dated May 5, 2014 (039363-7231).
Office Action for Thai Application No. 1301004352 dated Sep. 29, 2014 (039363-7235).
International Search Report for PCT/US2012/038417 dated Aug. 10, 2012 (039363-7303).
Office Action in New Zealand Application No. 617526 dated Aug. 14, 2014 (039363-7303NZ).
Exam Report in Australian Application No. 2012200933 dated Jul. 3, 2013 (039363-7801).
Office Action in U.S. Appl. No. 12/669,450 dated Dec. 27, 2012 (039363-7851).
International Search Report and Written Opinion dated May 7, 2013 for PCT Patent Application No. PCT/US2013/032835 (039363-7910).
International Preliminary Report on Patentability dated Sep. 23, 2014 for PCT Application No. PCT/US2013/032835 (039363-7910).
Office Action in U.S. Appl. No. 13/793,917 dated Jul. 21, 2014 (039363-8002).
International Search Report and Written Opinion dated Jul. 22, 2013 for PCT Patent Application No. PCT/US2013/043400 (039363-8010).
Fan et al., "Ester Prodrugs of Ampicillin Tailored for Intracellular Accumulation," Bioorganic & Medicinal Chem. Letters, (1997), 7(24):3107-3112.
Office Action in Chinese Application No. 201310470059.2 dated Nov. 4, 2014.
Office Action in Colombian Application No. 09-052-610 dated Dec. 23, 2013.
Office Action in Indian Application No. 1879/KOLNP/2009 dated Jun. 24, 2014.
Report of Reconsideration in Japanese Application No. 2009-538496 dated Feb. 10, 2014.
Office Action in Japanese Application No. 2013-262181 dated Jan. 6, 2015.
Sikora, et al., "Cancer Drug Development in the Post-Genomic Age," *Current Science,* (2001), 81(5):549-554.
Technical Report for El Salvador Application No. 2007002813 dated Jan. 27, 2015.
Zips, et al., "New Anticancer Agents In Vitro and In Vivo Evaluation," In Vivo, (2005), 19:1-8.

COMPOUNDS MODULATING C-FMS AND/OR C-KIT ACTIVITY AND USES THEREFOR

RELATED PATENT APPLICATIONS

This application is a continuation of U.S. application Ser. No. 13/776,547, filed Feb. 25, 2013, which is a continuation of U.S. patent application Ser. No. 13/546,923, filed Jul. 11, 2012, now U.S. Pat. No. 8,404,700, which is a continuation of U.S. patent application Ser. No. 12/958,379, filed Dec. 1, 2010, now U.S. Pat. No. 8,461,169, which is a divisional application of U.S. patent application Ser. No. 11/986,667, filed Nov. 21, 2007, now U.S. Pat. No. 7,893,075, issued Feb. 22, 2011, which claims priority to U.S. Provisional App. No. 60/860,749, filed Nov. 22, 2006, and is related to U.S. patent application Ser. No. 11/435,381, filed May 16, 2006, now U.S. Pat. No. 7,846,941, which claims the benefit of U.S. Provisional App. No. 60/682,063, filed May 17, 2005, U.S. Provisional App. No. 60/682,051, filed May 17, 2005, U.S. Provisional App. No. 60/682,042, filed May 17, 2005, U.S. Provisional App. No. 60/692,750, filed Jun. 22, 2005, and U.S. Provisional App. No. 60/692,960, filed Jun. 22, 2005, all of which are incorporated herein by reference in their entireties and for all purposes.

FIELD OF THE INVENTION

This invention relates to ligands for c-fms and c-kit, and to methods for use thereof. The information provided is intended solely to assist the understanding of the reader. None of the information provided nor references cited is admitted to be prior art to the present invention. Each of the references cited is incorporated herein in its entirety and for any purpose.

BACKGROUND OF THE INVENTION

C-fms and c-kit are both type III transmembrane receptor protein tyrosine kinases (RPTKs) that regulate key signal transduction cascades that control cellular growth and proliferation. Both receptors have similar structural features comprising five extracellular immunoglobulin (IG) domains, a single transmembrane domain, and a split cytoplasmic kinase domain separated by a kinase insert segment.

c-Fms

C-fms is a member of the family of genes originally isolated from the Susan McDonough strain of feline sarcoma viruses. The cellular proto-oncogene FMS (c-fms, cellular feline McDonough sarcoma) codes for the receptor for the macrophage colony-stimulating factor (M-CSF). C-fms is crucial for the growth and differentiation of the monocyte-macrophage lineage, and upon binding of M-CSF to the extracellular domain of c-fms, the receptor dimerizes and trans-autophosphorylates cytoplasmic tyrosine residues.

M-CSF, first described by Robinson and co-workers (Blood. 1969, 33:396-9), is a cytokine that controls the production, differentiation, and function of macrophages. M-CSF stimulates differentiation of progenitor cells to mature monocytes, and prolongs the survival of monocytes. Furthermore, M-CSF enhances cytotoxicity, superoxide production, phagocytosis, chemotaxis, and secondary cytokine production of additional factors in monocytes and macrophages. Examples of such additional factors include granulocyte colony stimulating factor (G-CSF), interleukin-6 (IL-6), and interleukin-8 (IL-8). M-CSF stimulates hematopoiesis, promotes differentiation and proliferation of osteoclast progenitor cells, and has profound effects on lipid metabolism. Furthermore, M-CSF is important in pregnancy. Physiologically, large amounts of M-CSF are produced in the placenta, and M-CSF is believed to play an essential role in trophoblast differentiation (Motoyoshi, Int J Hematol. 1998, 67:109-22). The elevated serum levels of M-CSF in early pregnancy may participate in the immunologic mechanisms responsible for the maintenance of the pregnancy (Flanagan & Lader, Curr Opin Hematol. 1998, 5:181-5).

Related to c-fms and c-kit are two platelet-derived growth factor receptors, alpha (i.e., pdgfra) and beta (pdgfrb) (PDGF). The gene coding for pdgfra is located on chromosome 4q11-q12 in the same region of chromosome 4 as the oncogene coding for c-kit. The genes coding for pdgfra and c-fms appear to have evolved from a common ancestral gene by gene duplication, inasmuch as these two genes are tandemly linked on chromosome 5. They are oriented head-to-tail with the 5-prime exon of the c-fms gene located only 500 bp from the last 3-prime exon of the gene coding for pdgfra. Most gastrointestinal stromal tumors (GIST) have activating mutations in c-kit, and most patients with GISTs respond well to Gleevec, which inhibits c-kit. Heinrich et al. (Science 2003, 299:708-10) have shown that approximately 35% of GISTs lacking c-kit mutations have intragenic activation mutations in the gene encoding pdgfra, and that tumors expressing c-kit or pdgfra are indistinguishable with respect to activation of downstream signaling intermediates and cytogenetic changes associated with tumor progression. Thus, c-kit and pdgfra mutations appear to be alternative and mutually exclusive oncogenic mechanisms in GISTs.

Similarly, the observation that production of M-CSF, the major macrophage growth factor, is increased in tissues during inflammation points out a role for c-fms in diseases, such as for example inflammatory diseases. More particularly, because elevated levels of M-CSF are found in the disease state, modulation of the activity of c-fms can ameliorate disease associated with increased levels of M-CSF.

c-Kit

The Stem Cell Factor (SCF) receptor c-kit plays an important role in the development of melanocytes and mast, germ and hematopoietic cells. Stem Cell Factor (SCF) is a protein encoded by the S1 locus, and has also been called "kit ligand" (KL) and mast cell growth factor (MGF), based on the biological properties used to identify it (reviewed in Tsujimura, Pathol Int 1996, 46:933-938; Loveland, et al., J. Endocrinol 1997, 153:337-344; Vliagoftis, et al., Clin Immunol 1997, 100:435-440; Broudy, Blood 1997, 90:1345-1364; Pignon, Hermatol Cell Ther 1997, 39:114-116; and Lyman, et al., Blood 1998, 91:1101-1134.). Herein the abbreviation SCF refers to the physiological ligand for c-kit.

SCF is synthesized as a transmembrane protein with a molecular weight of 220 or 248 Dalton, depending on alternative splicing of the mRNA to encode exon 6. The larger protein can be proteolytically cleaved to form a soluble, glycosylated protein which noncovalently dimerizes. Both the soluble and membrane-bound forms of SCF can bind to and activate c-kit. For example, in the skin, SCF is predominantly expressed by fibroblasts, keratinocytes, and endothelial cells, which modulate the activity of melanocytes and mast cells expressing c-kit. In bone, marrow stromal cells express SCF and regulate hematopoiesis of c-kit expressing stem cells. In the gastrointestinal tract, intestinal epithelial cells express SCF and affect the interstitial cells of Cajal and intraepithelial lymphocytes. In the testis, sertoli cells and granulosa cells express SCF which regulates spermatogenesis by interaction with c-kit on germ cells.

SUMMARY OF THE INVENTION

The present invention relates to compounds active on c-fms, c-kit, or both c-fms and c-kit. In accordance with one aspect of the present invention, it has been discovered that in the treatment of diseases amenable to treatment by an effective amount of a modulator of either c-fms alone or c-kit alone, the efficacy of treatment can be enhanced if said compounds are dual inhibitors of both c-fms and c-kit. In another aspect of the present invention, compounds active on c-fms, c-kit, or both c-fms and c-kit are also active on one or more of TrkA, TrkB and HGK. In particular, the invention provides compounds of Formula I, and all sub-generic formulae thereof, as well as methods of using such compounds as described below. Thus, the invention provides methods of using compounds that can be used therapeutically and/or prophylactically involving modulation of c-fms, c-kit, or both c-fms and c-kit, or involving one or more of TrkA, TrkB and HGK in addition to c-fms, c-kit, or both c-fms and c-kit.

The compounds of Formula I have the following structure:

Formula I all salts, prodrugs, tautomers, and isomers thereof,
wherein:
  $X_1$ is N or $CR^2$, $X_2$ is N or $CR^6$, $Y_1$ is N or $CR^4$, and $Y_2$ is N or $CR^5$, provided, however, that not more than one of $X_2$, $Y_1$ and $Y_2$ is N;
  $L^1$ is selected from the group consisting of optionally substituted lower alkylene, —S–, —O—, —C(O)—, —C(S)—, —S(O)—, —S(O)$_2$—, and —NR$^7$—;
  $L^2$ is selected from the group consisting of a bond, optionally substituted lower alkylene, -(alk)$_a$-S-(alk)$_b$-, -(alk)$_a$-O-(alk)$_b$-, -(alk)$_a$-OC(O)-(alk)$_b$-, -(alk)$_a$-C(O)O-(alk)$_b$-, -(alk)$_a$-OC(S)-(alk)$_b$-, -(alk)$_a$-C(S)O-(alk)$_b$-, -(alk)$_a$-C(O)-(alk)$_b$-, -(alk)$_a$-C(S)-(alk)$_b$-, -(alk)$_a$-C(O)NR$^9$—(alk)$_b$-, -(alk)$_a$-OC(O)NR$^9$-(alk)$_b$-, -(alk)$_a$-OC(S)NR$^9$—(alk)$_b$-, -(alk)$_a$-C(S)NR$^9$-(alk)$_b$-, -(alk)$_a$-S(O)-(alk)$_b$-, -(alk)$_a$-S(O)$_2$-(alk)$_b$-, -(alk)$_a$-S(O)NR$^9$—(alk)$_b$-, -(alk)$_a$-NR$^9$—(alk)$_b$-, -(alk)$_a$-NR$^9$C(O)-(alk)$_b$-, -(alk)$_a$-NR$^9$C(S)-(alk)$_b$-, -(alk)$_a$-NR$^9$C(O)NR$^9$—(alk)$_b$-, -(alk)$_a$-NR$^9$C(S)NR$^9$—(alk)$_b$-, -(alk)$_a$-NR$^9$C(O)O-(alk)$_b$-, -(alk)$_a$-NR$^9$C(S)O-(alk)$_b$-, -(alk)$_a$-NR$^9$S(O)$_2$-(alk)$_b$-, and -(alk)$_a$-NR$^9$S(O)$_2$NR$^9$—(alk)$_b$-, wherein alk is optionally substituted $C_{1-3}$ alkylene and a and b are independently 0 or 1;
  $R^1$ is selected from the group consisting of optionally substituted lower alkyl, optionally substituted cycloalkyl, optionally substituted heterocycloalkyl, optionally substituted aryl, and optionally substituted heteroaryl;
  $R^2$, $R^4$, $R^5$ and $R^6$ are independently selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —NR$^{10}$R$^{11}$, —NHR$^3$, —OR$^3$, —SR$^3$, —C(O)R$^3$, —C(S)R$^3$, —S(O)R$^3$, —S(O)$_2$R$^3$, —C(O)OR$^3$, —C(S)OR$^3$, —C(O)NHR$^3$, —C(O)NR$^3$R$^3$, —C(S)NHR$^3$, —C(S)NR$^3$R$^3$, —S(O)$_2$NHR$^3$, —S(O)$_2$NR$^3$R$^3$, —NHC(O)R$^3$, —NR$^3$C(O)R$^3$, —NHC(S)R$^3$, —NR$^3$C(S)R$^3$, —NHS(O)$_2$R$^3$, —NR$^3$S(O)$_2$R$^3$, —NHC(O)OR$^3$, —NR$^3$C(O)OR$^3$, —NR$^3$C(O)OR$^3$, —NHC(S)OR$^3$, —NR$^3$C(S)OH, —NR$^3$C(S)OR$^3$, —NHC(O)NHR$^3$, —NHC(O)NR$^3$R$^3$, —NR$^3$C(O)NH$_2$, —NR$^3$C(O)NHR$^3$, —NR$^3$C(O)NR$^3$R$^3$, —NHC(S)NHR$^3$, —NHC(S)NR$^3$R$^3$, —NR$^3$C(S)NH$_2$, —NR$^3$C(S)NHR$^3$, —NR$^3$C(S)NR$^3$R$^3$, —NHS(O)$_2$NHR$^3$, —NHS(O)$_2$NR$^3$R$^3$, —NR$^3$S(O)$_2$NH$_2$, —NR$^3$S(O)$_2$NHR$^3$, and —NR$^3$S(O)$_2$NR$^3$R$^3$;

Ar$_1$ is a 5 or 6 membered optionally substituted heteroarylene having the structure

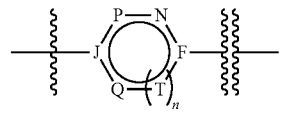

wherein

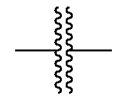

indicates the point of attachment of $L^1$ and

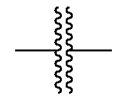

indicates the point of attachment of $L^2$, and wherein the indicated N is either =N— or —N=;
  n is 0 or 1;
  F and J are both C or one of F and J is C and the other of F and J is N;
  P and Q are independently selected from CR, N, NR, O or S;
  T is selected from CR or N;
    wherein
      when n is 1, F and J are C, and P, T and Q are CR, or any one of P, T and Q is N and the other two of P, T and Q are CR,
      when n is 0 and F and J are both C, then one of P and Q are CR, N or NR and the other of P and Q is C, N, NR, O or S, provided both P and Q are not CR,
      when n is 0, one of F and J is N and the other of F and J is C, then one of P and Q is N and the other of P and Q is CR or both P and Q are CR, and
      R is hydrogen or an optional substituent as defined herein for optionally substituted heteroarylene that provides a stable compound;
  $R^3$ at each occurrence is independently selected from the group consisting of optionally substituted lower alkyl, optionally substituted lower alkenyl, provided, however, that no alkene carbon thereof is bound to any —C(O)—, —C(S)—, —S(O)—, —S(O)$_2$—, —O—, —S—, or —N— of any of —OR$^3$, —SR$^3$, —C(O)R$^3$, —C(S)R$^3$, —S(O)R$^3$, —S(O)$_2$R$^3$, —C(O)OR$^3$, —C(S)OR$^3$, —C(O)NHR$^3$, —C(O)NR$^3$R$^3$, —C(S)NHR$^3$, —C(S)NR$^3$R$^3$, —S(O)$_2$NHR$^3$, —S(O)$_2$NR$^3$R$^3$, —NHR$^3$, —NHC(O)R$^3$, —NR$^3$C(O)R$^3$, —NHC(S)R$^3$, —NR$^3$C (S)R³, —NHS(O)₂R³, —NR³S(O)₂R³, —NHC(O)
OR³, —NR³C(O)OH, —NR³C(O)OR³, —NHC(S)
OR³, NR³C(S)OH, —NR³C(S)OR³, —NHC(O)NHR³,
—NHC(O)NR³R³, —NR³C(O)NH₂, —NR³C(O)
NHR³, —NR³C(O)NR³R³, —NHC(S)NHR³, —NHC
(S)NR³R³, —NR³C(S)NH₂, —NR³C(S)NHR³,
—NR³C(S)NR³R³, —NHS(O)₂NHR³,
—NHS(O)₂NR³R³, —NR³S(O)₂NH₂,
—NR³S(O)₂NHR³, or —NR³S(O)₂NR³R³, optionally
substituted lower alkynyl, provided, however, that no
alkyne carbon thereof is bound to any —C(O)—,
—C(S)—, —S(O)—, —S(O)₂—, —O—, —S—, or
—N— of any of —OR³, —SR³, —C(O)R³, —C(S)R³,
—S(O)R³, —S(O)₂R³, —C(O)OR³, —C(S)OR³,
—C(O)NHR³, —C(O)NR³R³, —C(S)NHR³, —C(S)
NR³R³, —S(O)₂NHR³, —S(O)₂NR³R³, —NHR³,
—NHC(O)R³, —NR³C(O)R³, —NHC(S)R³, —NR³C
(S)R³, —NHS(O)₂R³, —NR³S(O)₂R³, —NHC(O)
OR³, —NR³C(O)OH, —NR³C(O)OR³, —NHC(S)
OR³, —NR³C(S)OH, —NR³C(S)OR³, —NHC(O)
NHR³, —NHC(O)NR³R³, —NR³C(O)NH₂, —NR³C
(O)NHR³, —NR³C(O)NR³R³, —NHC(S)NHR³,
—NHC(S)NR³R³, —NR³C(S)NH₂, —NR³C(S)NHR³,
—NR³C(S)NR³R³, —NHS(O)₂NHR³,
—NHS(O)₂NR³R³, —NR³S(O)₂NH₂,
—NR³S(O)₂NHR³, or —NR³S(O)₂NR³R³, optionally
substituted cycloalkyl, optionally substituted heterocycloalkyl, optionally substituted aryl, and optionally substituted heteroaryl;

R⁷ is selected from the group consisting of hydrogen, optionally substituted lower alkyl, optionally substituted cycloalkyl, optionally substituted heterocycloalkyl, optionally substituted aryl, optionally substituted heteroaryl, —C(O)R⁸, and —S(O)₂R⁸;

R⁸ is selected from the group consisting of optionally substituted lower alkyl, optionally substituted cycloalkyl, optionally substituted heterocycloalkyl, optionally substituted aryl and optionally substituted heteroaryl;

R⁹ at each occurrence is independently selected from the group consisting of hydrogen, lower alkyl, and lower alkyl substituted with one or more substituents selected from the group consisting of fluoro, —OH, —NH₂, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and —NR¹²R¹³, provided, however, that when R⁹ is substituted lower alkyl, any substitution on the alkyl carbon bound to the —N— of —NR⁹— is fluoro;

R¹⁰ and R¹¹ at each occurrence are independently selected from the group consisting of optionally substituted lower alkyl, optionally substituted lower alkenyl, provided, however, that no alkene carbon thereof is bound to the nitrogen of NR¹⁰R¹¹, optionally substituted lower alkynyl, provided, however, that no alkyne carbon thereof is bound to the nitrogen of —NR¹⁰R¹¹, optionally substituted cycloalkyl, optionally substituted heterocycloalkyl, optionally substituted aryl, and optionally substituted heteroaryl; or R¹⁰ and R¹¹ together with the nitrogen to which they are attached form a monocyclic 5-7 membered optionally substituted heterocycloalkyl or a monocyclic 5 or 7 membered optionally substituted nitrogen containing heteroaryl; and R¹² and R¹³ combine with the nitrogen to which they are attached to form a 5-7 membered heterocycloalkyl or 5-7 membered heterocycloalkyl substituted with one or more substituents selected from the group consisting of fluoro, —OH, —NH₂, lower alkyl, fluoro substituted lower alkyl, lower alkoxy, fluoro substituted lower alkoxy, lower alkylthio, and fluoro substituted lower alkylthio;

provided, however that when compounds have the structure

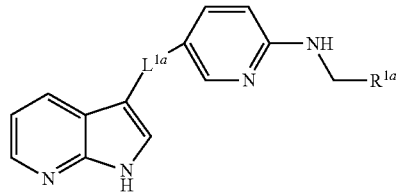

and L¹ᵃ is —CH₂—, —CH(OH)—, or —C(O)—, then R¹ᵃ is not phenyl, 4-trifluoromethyl-phenyl, 4-methoxy-phenyl, 4-chloro-phenyl, 4-fluoro-phenyl, 4-methyl-phenyl, 3-fluoro-phenyl or thiophen-2-yl, and compounds do not have the structure

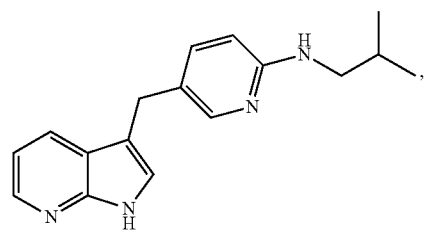

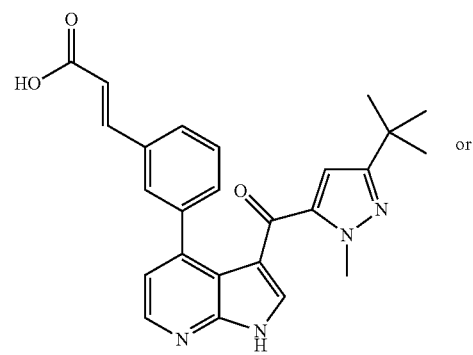

or

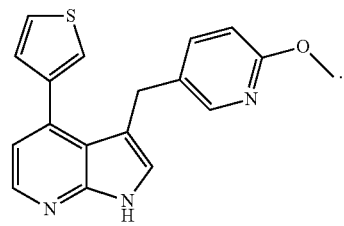

In reference to Formula I, the core structure shown above with X₁, X₂, Y₁ and Y₂ as CH and with L¹-Ar₁-L²-R¹ replaced with H is referred to as the "azaindole core." For that azaindole core, reference to ring atoms or ring positions is as shown in the following structure:

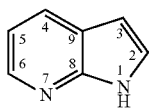

In one embodiment of compounds of Formula I, compounds have a structure selected from the following:

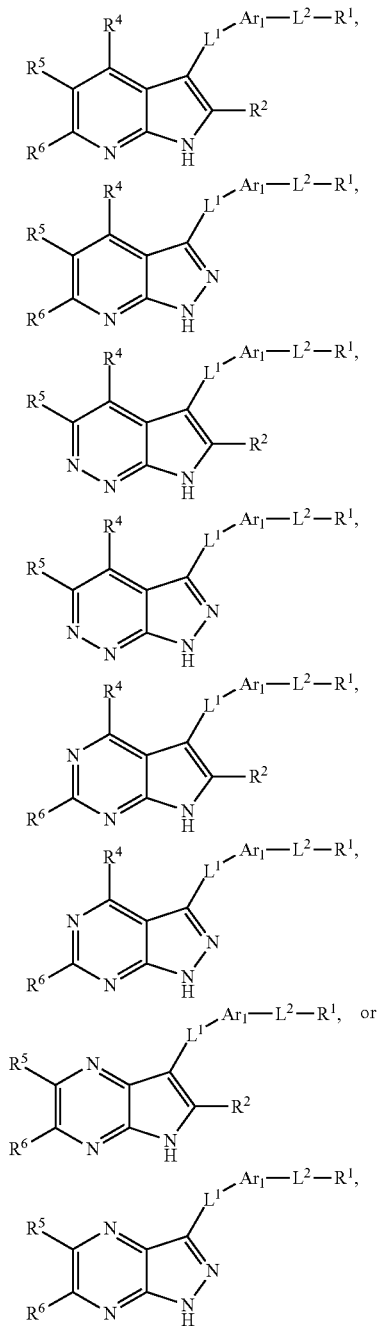

wherein $L^1$, $Ar_1$, $L^2$, $R^1$, $R^2$, $R^4$, $R^5$ and $R^6$ are as defined for Formula I.

In one embodiment of compounds of Formula I, $X_1$ and $X_2$ are N or CH. In another embodiment, $X_1$, $X_2$ and $Y_1$ are N or CH, where in a further embodiment, $Y_2$ is $CR^5$ and $R^5$ is other than hydrogen. In another embodiment, $X_1$, $X_2$ and $Y_2$ are N or CH, where in a further embodiment $Y_1$ is $CR^4$ and $R^4$ is other than hydrogen. In another embodiment, $X_1$, $X_2$ and $Y_1$ are CH, where in a further embodiment, $Y_2$ is $CR^5$ and $R^5$ is other than hydrogen. In another embodiment, $X_1$, $X_2$ and $Y_2$ are CH, where in a further embodiment $Y_1$ is $CR^4$ and $R^4$ is other than hydrogen.

In one embodiment of compounds of Formula I, wherein $X_1$, $X_2$, $Y_1$ and $Y_2$ are independently $CR^2$, $CR^6$, $CR^4$ and $CR^5$ respectively, one of $R^4$ or $R^5$ is other than hydrogen, preferably where $R^2$ and $R^6$ are hydrogen. In one embodiment, wherein $X_1$, $X_2$, $Y_1$ and $Y_2$ are independently $CR^2$, $CR^6$, $CR^4$ and $CR^5$ respectively, $R^2$, $R^5$ and $R^6$ are hydrogen and $R^4$ is other than hydrogen. In one embodiment, wherein $X_1$, $X_2$, $Y_1$ and $Y_2$ are independently $CR^2$, $CR^6$, $CR^4$ and $CR^5$ respectively, $R^2$, $R^4$ and $R^6$ are hydrogen and $R^5$ is other than hydrogen.

In one embodiment of compounds of Formula I, $X_1$ and $X_2$ are N or CH, preferably wherein both $X_1$ and $X_2$ are CH.

In one embodiment of compounds of Formula I, $L^1$ is selected from the group consisting of S, O, lower alkylene, —C(O)—, —C(S)—, —S(O)—, —S(O)$_2$—, and —NR$^7$—, wherein lower alkylene is optionally substituted with fluoro, and wherein when $L^2$ is optionally substituted lower alkylene or comprises optionally substituted $C_{1-3}$ alkylene, the alkylene is optionally substituted with fluoro or lower alkyl. In one embodiment, $L^1$ is selected from the group consisting of S, O, —CH$_2$—, —CF$_2$—, —C(O)—, —C(S)—, —S(O)—, —S(O)$_2$—, and —NH—.

In one embodiment of compounds of Formula I, $L^2$ is selected from the group consisting of a bond, optionally substituted lower alkylene, —O-(alk)$_b$-, —OC(O)-(alk)$_b$-, —C(O)O-(alk)$_b$-, —OC(S)-(alk)$_b$-, —C(S)O-(alk)$_b$-, —C(O)-(alk)$_b$-, —C(S)-(alk)$_b$-, —C(O)NR$^9$—(alk)$_b$-, —OC(O)NR$^9$—(alk)$_b$-, —OC(S)NR$^9$—(alk)$_b$-, —C(S)NR$^9$—(alk)$_b$-, —S(O)-(alk)$_b$-, —S(O)$_2$-(alk)$_b$-, S(O)$_2$NR$^9$—(alk)$_b$-, —NR$^9$—(alk)$_b$-, —NR$^9$C(O)-(alk)$_b$-, —NR$^9$C(O)O-(alk)$_b$-, —NR$^9$C(S)-(alk)$_b$-, —NR$^9$C(S)O-(alk)$_b$-, —NR$^9$C(O)NR$^9$—(alk)$_b$-, —NR$^9$C(S)NR$^9$—(alk)$_b$-, —NR$^9$S(O)$_2$-(alk)$_b$-, and —NR$^9$S(O)$_2$NR$^9$—(alk)$_b$-.

Further to any of the above embodiments of Formula I, when $L^1$ is substituted lower alkylene or when $L^2$ is substituted lower alkylene or comprises substituted $C_{1-3}$ alkylene, the alkylene is substituted with one or more, preferably 1, 2, or 3 substituents selected from the group consisting of fluoro, —OH, —NH$_2$, lower alkoxy, lower alkylthio, mono-alkylamino, di-alkylamino, and —NR$^{12}$R$^{13}$, wherein the alkyl chain(s) of lower alkoxy, lower alkylthio, mono-alkylamino or di-alkylamino are optionally substituted with one or more, preferably 1, 2, or 3 substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, or cycloalkylamino.

In one embodiment of the compounds of Formula I, the variables P, J, Q, T, F, and n are selected to provide structures of $Ar_1$ selected from the group consisting of

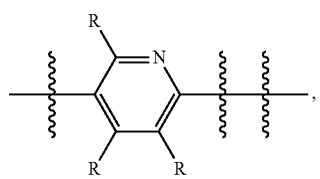

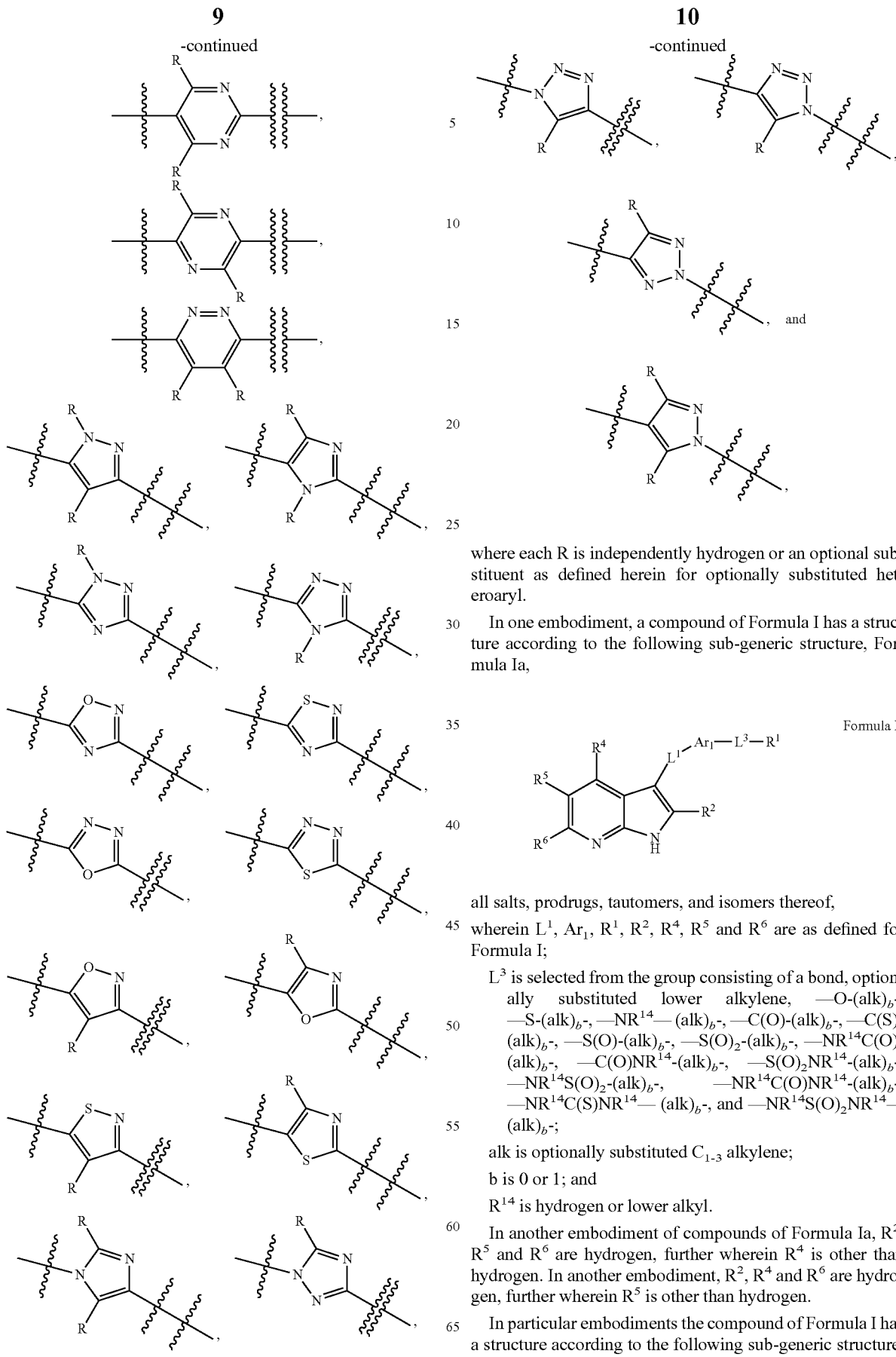

where each R is independently hydrogen or an optional substituent as defined herein for optionally substituted heteroaryl.

In one embodiment, a compound of Formula I has a structure according to the following sub-generic structure, Formula Ia, all salts, prodrugs, tautomers, and isomers thereof, wherein $L^1$, $Ar_1$, $R^1$, $R^2$, $R^4$, $R^5$ and $R^6$ are as defined for Formula I;

$L^3$ is selected from the group consisting of a bond, optionally substituted lower alkylene, —O-(alk)$_b$-, —S-(alk)$_b$-, —NR$^{14}$—(alk)$_b$-, —C(O)-(alk)$_b$-, —C(S)-(alk)$_b$-, —S(O)-(alk)$_b$-, —S(O)$_2$-(alk)$_b$-, —NR$^{14}$C(O)-(alk)$_b$-, —C(O)NR$^{14}$-(alk)$_b$-, —S(O)$_2$NR$^{14}$-(alk)$_b$-, —NR$^{14}$S(O)$_2$-(alk)$_b$-, —NR$^{14}$C(O)NR$^{14}$-(alk)$_b$-, —NR$^{14}$C(S)NR$^{14}$—(alk)$_b$-, and —NR$^{14}$S(O)$_2$NR$^{14}$—(alk)$_b$-;

alk is optionally substituted $C_{1-3}$ alkylene;

b is 0 or 1; and $R^{14}$ is hydrogen or lower alkyl.

In another embodiment of compounds of Formula Ia, $R^2$, $R^5$ and $R^6$ are hydrogen, further wherein $R^4$ is other than hydrogen. In another embodiment, $R^2$, $R^4$ and $R^6$ are hydrogen, further wherein $R^5$ is other than hydrogen.

In particular embodiments the compound of Formula I has a structure according to the following sub-generic structure, Formula Ib,

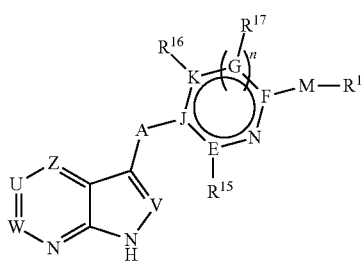

Formula Ib all salts, prodrugs, tautomers, and isomers thereof,
wherein:
V and W are independently selected from the group consisting of N and CH;
U and Z are independently selected from the group consisting of N and $CR^{18}$, provided, however, that not more than one of W, U and Z is N;
A is selected from the group consisting of $-CR^{19}R^{20}-$, $-C(O)-$, $-C(S)-$, $-S-$, $-S(O)-$, $-S(O)_2-$, $-NR^{21}-$, and $-O-$;
n is 0 or 1;
F and J are both C or one of F and J is C and the other of F and J is N;
E and K are selected from C, N, O or S;
G is selected from C or N;
    wherein
        when n is 1, F and J are C, and E, G and K are C, or any one of E, G and K is N and the other two of E, G and K are C, provided that when E, G or K is N, $R^{15}$, $R^{17}$ and $R^{16}$, respectively, are absent,
        when n is 0 and F and J are both C, then one of E and K is C or N and the other of E and K is C, N, O or S, provided both E and K are not C, and provided that when both E and K are N, one of $R^{15}$ and $R^{16}$ is absent, and provided that when one of E and K are N and the other is O or S, $R^{15}$ and $R^{16}$ are absent,
        when n is 0, one of F and J is N and the other of F and J is C, then one of E and K is N and the other of E and K is C, or both E and K are C, provided that when E is N, $R^{15}$ is absent and when K is N, $R^{16}$ is absent;
$R^1$ is selected from the group consisting of optionally substituted lower alkyl, optionally substituted cycloalkyl, optionally substituted heterocycloalkyl, optionally substituted aryl and optionally substituted heteroaryl;
$R^{15}$ is selected from the group consisting of hydrogen, optionally substituted lower alkyl, $-OR^{22}$, $-SR^{22}$ and halogen when E is C, is absent when E is O or S or when n=1 and E is N, and is absent or selected from the group consisting of hydrogen and optionally substituted lower alkyl when n=0 and E is N;
$R^{16}$ is selected from the group consisting of hydrogen, optionally substituted lower alkyl, $-OR^{22}$, $-SR^{22}$ and halogen when K is C, is absent when K is O or S or when n=1 and K is N, and is absent or selected from the group consisting of hydrogen and optionally substituted lower alkyl when n=0 and K is N;
$R^{17}$ is selected from the group consisting of hydrogen, optionally substituted lower alkyl, $-OR^{22}$, $-SR^{22}$ and halogen when G is C, or is absent when G is N;
$R^{18}$ is selected from the group consisting of hydrogen, halogen, optionally substituted lower alkyl, optionally substituted aryl, optionally substituted heteroaryl, $-OH$, $-NH_2$, $-NO_2$, $-CN$, $-NHC(O)NH_2$, $-NHC$(S)$NH_2$, $-NHS(O)_2NH_2$, $-NR^{24}R^{25}$, $-NHR^{23}$, $-OR^{23}$, $-SR^{23}$, $-NHC(O)R^{23}$, $-NR^{23}C(O)R^{23}$, $-NHC(S)R^{23}$, $-NR^{23}C(S)R^{23}$, $-NHS(O)_2R^{23}$, $-NR^{23}S(O)_2R^{23}$, $-NHC(O)NHR^{23}$, $-NR^{23}C(O)NH_2$, $-NR^{23}C(O)NHR^{23}$, $-NHC(O)NR^{23}R^{23}$, $-NR^{23}C(O)NR^{23}R^{23}$, $-NHC(S)NHR^{23}$, $-NR^{23}C(S)NH_2$, $-NR^{23}C(S)NHR^{23}$, $-NHC(S)NR^{23}R^{23}$, $-NR^{23}C(S)NR^{23}R^{23}$, $-NHS(O)_2NHR^{23}$, $-NR^{23}S(O)_2NH_2$, $-NR^{23}S(O)_2NHR^{23}$, $-NHS(O)_2NR^{23}R^{23}$, and $-NR^{23}S(O)_2NR^{23}R^{23}$;
M is selected from the group consisting of a bond, $-(CR^{19}R^{20})_u-$, $-(CR^{19}R^{20})_t-C(O)-(CR^{19}R^{20})_s-$, $-(CR^{19}R^{20})_t-C(S)-(CR^{19}R^{20})_s-$, $-(CR^{19}R^{20})_t-C(O)O-(CR^{19}R^{20})_s-$, $-(CR^{19}R^{20})_t-C(S)O-(CR^{19}R^{20})_s-$, $-(CR^{19}R^{20})_t-C(O)NR^{26}-(CR^{19}R^{20})_s-$, $-(CR^{19}R^{20})_t-C(S)NR^{26}-(CR^{19}R^{20})_s-$, $-(CR^{19}R^{20})_t-S(O)-(CR^{19}R^{20})_s-$, $-(CR^{19}R^{20})_t-S(O)_2-(CR^{19}R^{20})_s-$, $-(CR^{19}R^{20})_t-S(O)_2NR^{26}-(CR^{19}R^{20})_s-$, $-(CR^{19}R^{20})_t-O-(CR^{19}R^{20})_s-$, $-(CR^{19}R^{20})_t-OC(O)-(CR^{19}R^{20})_s-$, $-(CR^{19}R^{20})_t-OC(S)-(CR^{19}R^{20})_s-$, $-(CR^{19}R^{20})_t-OC(O)NR^{26}-(CR^{19}R^{20})_s-$, $-(CR^{19}R^{20})_t-OC(S)NR^{26}-(CR^{19}R^{20})_s-$, $-(CR^{19}R^{20})_t-S-(CR^{19}R^{20})_s-$, $-(CR^{19}R^{20})_t-NR^{26}-(CR^{19}R^{20})_s-$, $-(CR^{19}R^{20})_t-NR^{26}C(O)-(CR^{19}R^{20})_s-$, $-(CR^{19}R^{20})_t-NR^{26}C(S)-(CR^{19}R^{20})_s-$, $-(CR^{19}R^{20})_t-NR^{26}C(O)O-(CR^{19}R^{20})_s-$, $-(CR^{19}R^{20})_t-NR^{26}C(S)O-(CR^{19}R^{20})_s-$, $-(CR^{19}R^{20})_t-NR^{26}C(O)NR^{26}-(CR^{19}R^{20})_s-$, $-(CR^{19}R^{20})_t-NR^{26}C(S)NR^{26}-(CR^{19}R^{20})_s-$, $-(CR^{19}R^{20})_t-NR^{26}S(O)_2-(CR^{19}R^{20})_s-$, and $-(CR^{19}R^{20})_t-NR^{26}S(O)_2NR^{26}-(CR^{19}R^{20})_s-$;
wherein $R^{19}$ and $R^{20}$ at each occurrence are independently selected from the group consisting of hydrogen, fluoro, $-OH$, $-NH_2$, lower alkyl, lower alkoxy, lower alkylthio, mono-alkylamino, di-alkylamino, and $-NR^{27}R^{28}$, wherein the alkyl chain(s) of lower alkyl, lower alkoxy, lower alkylthio, mono-alkylamino, or di-alkylamino are optionally substituted with one or more substituents selected from the group consisting of fluoro, $-OH$, $-NH_2$, lower alkoxy, fluoro substituted lower alkoxy, lower alkylthio, fluoro substituted lower alkylthio, mono-alkylamino, di-alkylamino, and cycloalkylamino; or
any two of $R^{19}$ and $R^{20}$ on the same or different carbons combine to form a 3-7 membered monocyclic cycloalkyl or 5-7 membered monocyclic heterocycloalkyl and any others of $R^{19}$ and $R^{20}$ are independently selected from the group consisting of hydrogen, fluoro, $-OH$, $-NH_2$, lower alkyl, lower alkoxy, lower alklylthio, mono-alkylamino, di-alkylamino, and $-NR^{27}R^{28}$, wherein the alkyl chain(s) of lower alkyl, lower alkoxy, lower alkylthio, mono-alkylamino, or di-alkylamino are optionally substituted with one or more substituents selected from the group consisting of fluoro, $-OH$, $-NH_2$, lower alkoxy, fluoro substituted lower alkoxy, lower alkylthio, fluoro substituted lower alkylthio, mono-alkylamino, di-alkylamino, and cycloalkylamino, and wherein the monocyclic cycloalkyl or monocyclic heterocycloalkyl are optionally substituted with one or more substituents selected from the group consisting of halogen, $-OH$, $-NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;
$R^{21}$ and $R^{22}$ at each occurrence are independently hydrogen or optionally substituted lower alkyl;

R²³ at each occurrence is independently selected from the group consisting of optionally substituted lower alkyl, optionally substituted lower alkenyl, provided, however, that no alkene carbon thereof is bound to any —C(O)—, —C(S)—, —S(O)₂—, —O—, —S—, or —N— of any of —NHR²³, —OR²³, —SR²³, —NHC(O)R²³, —NR²³C(O)R²³, —NHC(S)R²³, —NR²³C(S)R²³, —NHS(O)₂R²³, —NR²³S(O)₂R²³, —NHC(O)NHR²³, —NR²³C(O)NH₂, —NR²³C(O)NHR²³, —NHC(O)NR²³R²³, —NR²³C(O)NR²³R²³, —NHC(S)NHR²³, —NR²³C(S)NH₂, —NR²³C(S)NHR²³, —NHC(S)NR²³R²³, —NR²³C(S)NR²³R²³, —NHS(O)₂NHR²³, —NR²³S(O)₂NH₂, —NR²³S(O)₂NHR²³, —NHS(O)₂NR²³R²³, or —NR²³S(O)₂NR²³R²³, optionally substituted lower alkynyl, provided, however, that no alkyne carbon thereof is bound to any —C(O)—, —C(S)—, —S(O)—, —S(O)₂—, —O—, —S—, or —N— of any of —NHR²³, —OR²³, —SR²³, —NHC(O)R²³, —NR²³C(O)R²³, —NHC(S)R²³, —NR²³C(S)R²³, —NHS(O)₂R²³, —NR²³S(O)₂R²³, —NHC(O)NHR²³, —NR²³C(O)NH₂, —NR²³C(O)NHR²³, —NHC(O)NR²³R²³, —NR²³C(O)NR²³R²³, —NHC(S)NHR²³, —NR²³C(S)NH₂, —NR²³C(S)NHR²³, —NHC(S)NR²³R²³, —NR²³C(S)NR²³R²³, —NHS(O)₂NHR²³, —NR²³S(O)₂NH₂, —NR²³S(O)₂NHR²³, —NHS(O)₂NR²³R²³, or —NR²³S(O)₂NR²³R²³, optionally substituted cycloalkyl, optionally substituted heterocycloalkyl, optionally substituted aryl, and optionally substituted heteroaryl;

R²⁴ and R²⁵ at each occurrence are independently selected from the group consisting of optionally substituted lower alkyl, optionally substituted lower alkenyl, provided, however, that no alkene carbon thereof is bound to the nitrogen of —NR²⁴R²⁵, optionally substituted lower alkynyl, provided, however, that no alkyne carbon thereof is bound to the nitrogen of —NR²⁴R²⁵, optionally substituted cycloalkyl, optionally substituted heterocycloalkyl, optionally substituted aryl, and optionally substituted heteroaryl; or R²⁴ and R²⁵ together with the nitrogen to which they are attached form a monocyclic 5-7 membered optionally substituted heterocycloalkyl or a monocyclic 5 or 7 membered optionally substituted nitrogen containing heteroaryl;

R²⁶ at each occurrence is independently selected from the group consisting of hydrogen, lower alkyl, and lower alkyl substituted with one or more substituents selected from the group consisting of fluoro, —OH, —NH₂, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and NR²⁷R²⁸, provided, however, that when R²⁶ is substituted lower alkyl, any substitution on the lower alkyl carbon bound to the —N— of —NR²⁶— is fluoro;

R²⁷ and R²⁸ combine with the nitrogen to which they are attached to form a 5-7 membered heterocycloalkyl or 5-7 membered heterocycloalkyl substituted with one or more substituents selected from the group consisting of fluoro, —OH, —NH₂, lower alkyl, fluoro substituted lower alkyl, lower alkoxy, fluoro substituted lower alkoxy, lower alkylthio, and fluoro substituted lower alkylthio;

u is 1-6;
t is 0-3; and
s is 0-3;

provided that when V, W, U and Z are CH, n=1, E, F, G, J, and K are C, R¹⁵, R¹⁶ and R¹⁷ are H, A is —CH₂—, —CH(OH)—, or —C(O)—, and M is —NHCH₂—, then R¹ is not phenyl, 4-trifluoromethyl-phenyl, 4-methoxy-phenyl, 4-chloro-phenyl, 4-fluoro-phenyl, 4-methyl-phenyl, 3-fluoro-phenyl or thiophen-2-yl, when V, W, U and Z are CH, n=1, E, F, G, J, and K are C, R¹⁵, R¹⁶ and R¹⁷ are H, and A is —CH₂—, then M-R¹ is not —NHCH₂CH(CH₃)₂, when V, W, and U are CH, n=1, E, F, G, J, and K are C, R¹⁵, R¹⁶ and R¹⁷ are H, A is —CH₂—, M-R¹ is —OCH₃, and Z is CR¹⁸, then R¹⁸ is not thiophen-3-yl, and when V, W, and U are CH, n=0, F, J, and K are C, E is N, R¹⁵ is CH₃, R¹⁶ is H, A is —C(O)—, M-R¹ is CH(CH₃)₃, and Z is CR¹⁸, then R¹⁸ is not 3-((E)-2-carboxy-vinyl)phenyl.

In one embodiment of the compounds of Formula Ib, E, J, K, G, F, n, R¹⁵, R¹⁶ and R¹⁷ are selected to provide structures selected from the group consisting of

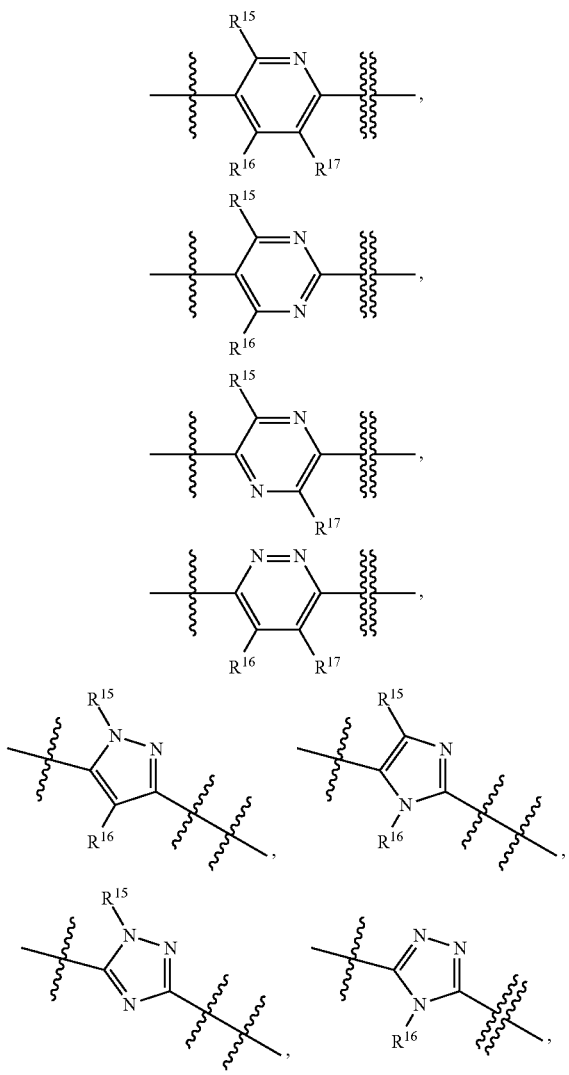

-continued

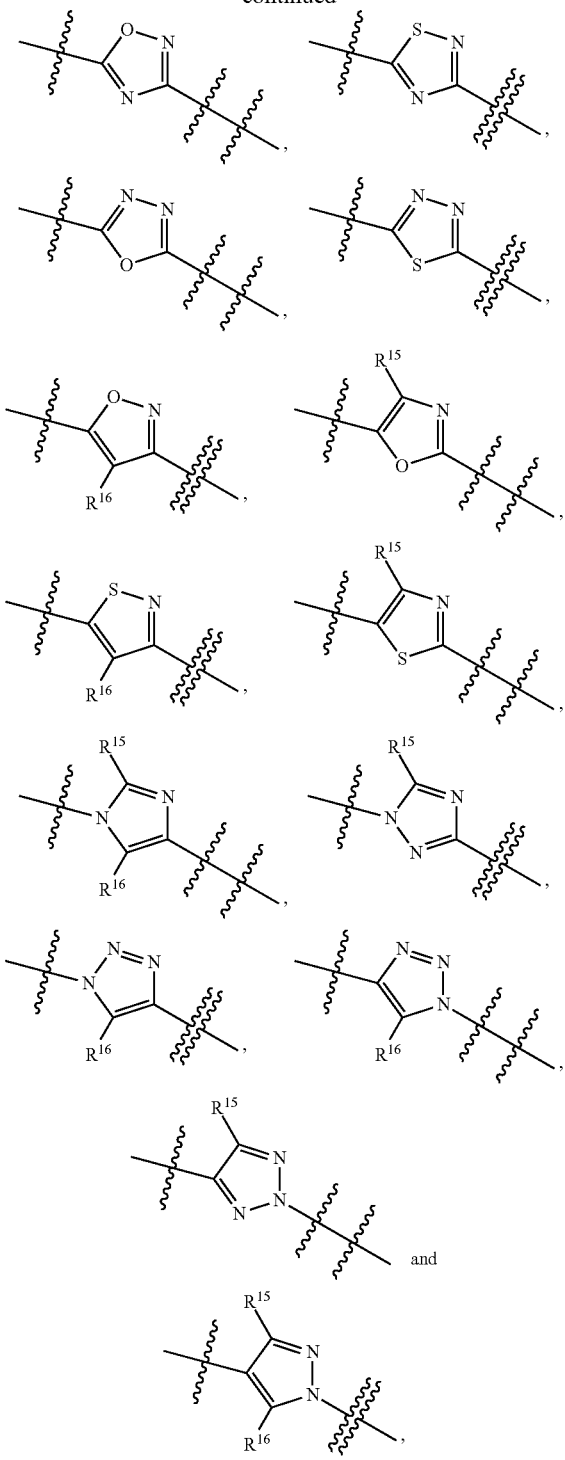

wherein $R^{15}$, $R^{16}$ and $R^{17}$ are as defined for compounds of Formula Ib and wherein

indicates the point of attachment of A and indicates the point of attachment of M.

In one embodiment of compounds of Formula Ib, M is selected from the group consisting of —O—$(CR^{19}R^{20})_s$—, —S—$(CR^{19}R^{20})_s$—, —OC(O)—$(CR^{19}R^{20})_s$—, —OC(S)—$(CR^{19}R^{20})_s$—, —OC(O)$NR^{26}$—$(CR^{19}R^{20})_s$—, —OC(S)$NR^{26}$—$(CR^{19}R^{20})_s$—, —C(O)$NR^{26}$—$(CR^{19}R^{20})_s$—, —C(S)$NR^{26}$—$(CR^{19}R^{20})_s$—, —S(O)$_2NR^{26}$—$(CR^{19}R^{20})_s$—, —$NR^{26}$—$(CR^{19}R^{20})_s$—, —$NR^{26}$C(O)—$(CR^{19}R^{20})_s$—, —$NR^{26}$C(S)—$(CR^{19}R^{20})_s$—, —$NR^{26}$C(O)O—$(CR^{19}R^{20})_s$—, —$NR^{26}$C(S)O—$(CR^{19}R^{20})_s$—, —$NR^{26}$C(O)$NR^{26}$—$(CR^{19}R^{20})_s$—, —$NR^{26}$C(S)$NR^{26}$—$(CR^{19}R^{20})_s$—, —$NR^{26}$S(O)$_2$—$(CR^{19}R^{20})_s$—, and —$NR^{26}$S(O)$_2NR^{26}$—$(CR^{19}R^{20})_s$—.

In one embodiment of compounds of Formula Ib, $R^{26}$ at each occurrence is independently selected from the group consisting of hydrogen, lower alkyl, and lower alkyl substituted with 1, 2, or 3 substituents selected from the group consisting of fluoro, —OH, —$NH_2$, alkoxy, lower alkylthio, mono-alkylamino, di-alkylamino and cycloalkylamino, provided that any substitution on the carbon that is bound to the nitrogen of —$NR^{26}$ is fluoro.

In one embodiment of compounds of Formula Ib, $R^1$ is selected from the group consisting of optionally substituted aryl and optionally substituted heteroaryl.

In one embodiment of the compounds of Formula Ib, Z is N or CH, n is 1, E-$R^{15}$ is N or CH, K—$R^{16}$ is N or CH, and G-$R^{17}$ is N or CH, provided no more than one of E-$R^{15}$, K—$R^{16}$ and G-$R^{17}$ is N. In one embodiment, Z is N or CH, n is 1, and E-$R^{15}$, K—$R^{16}$ and G-$R^{17}$ are CH.

In one embodiment of the compounds of Formula Ib, V, W and Z are CH, U is $CR^{18}$, n is 1, E-$R^{15}$ is N or CH, K—$R^{16}$ is N or CH, and G-$R^{17}$ is N or CH, provided no more than one of E-$R^{15}$, K—$R^{16}$ and G-$R^{17}$ is N. In another embodiment, V, W and Z are CH, U is $CR^{18}$, n is 1, and E-$R^{15}$, K—$R^{16}$ and G-$R^{17}$ are CH.

In one embodiment of the compounds of Formula Ib, Z is N or CH, n is 1, E-$R^{15}$, K—$R^{16}$ and G-$R^{17}$ are CH, A is —$CH_2$—, M is —$NHCH_2$—, further wherein $R^1$ is optionally substituted phenyl. In another embodiment, V, Z, U and W are CH, n is 1, E-$R^{15}$ is N or CH, K—$R^{16}$ is N or CH, and G-$R^{17}$ is N or CH, provided no more than one of E-$R^{15}$, K—$R^{16}$ and G-$R^{17}$ is N.

In one embodiment of the compounds of Formula Ib, Z is N or CH, n is 1, E-$R^{15}$ is N or CH, K—$R^{16}$ is N or CH, and G-$R^{17}$ is N or CH, provided no more than one of E-$R^{15}$, K—$R^{16}$ and G-$R^{17}$ is N, and $R^1$ is phenyl optionally substituted with one or more substituents selected from the group consisting of halogen, —OH, —$NH_2$, —$NO_2$, —CN, optionally substituted lower alkyl and —$OR^{29}$, where $R^{29}$ is selected from the group consisting of optionally substituted lower alkyl, optionally substituted cycloalkyl, optionally substituted heterocycloalkyl, optionally substituted aryl and optionally substituted heteroaryl.

In one embodiment of the compounds of Formula Ib, V, Z, U and W are CH, n is 1, E-$R^{15}$, K—$R^{16}$ and G-$R^{17}$ are CH, A is —$CH_2$—, M is —$NHCH_2$, and $R^1$ is optionally substituted phenyl, further wherein $R^1$ is phenyl optionally substituted with one or more substituents selected from the group consisting of halogen, —OH, —$NH_2$, —$NO_2$, —CN, optionally substituted lower alkyl and —$OR^{29}$, where $R^{29}$ is selected from the group consisting of optionally substituted lower alkyl, optionally substituted cycloalkyl, optionally substituted heterocycloalkyl, optionally substituted aryl and optionally substituted heteroaryl.

In one embodiment of the compounds of Formula Ib, V, W and Z are CH, U is $CR^{18}$, n is 1, E-$R^{15}$, K—$R^{16}$ and G-$R^{17}$ are CH, A is —$CH_2$—, M is —$NHCH_2$, and $R^1$ is optionally substituted phenyl, further wherein $R^1$ is phenyl optionally substituted with one or more substituents selected from the group consisting of halogen, —OH, —$NH_2$, —$NO_2$, —CN, optionally substituted lower alkyl and —$OR^{29}$, where $R^{29}$ is selected from the group consisting of optionally substituted lower alkyl, optionally substituted cycloalkyl, optionally substituted heterocycloalkyl, optionally substituted aryl and optionally substituted heteroaryl.

In one embodiment of the compounds of Formula Ib, when n is 1, and E, K and G are C, at least one of $R^{15}$, $R^{16}$ and $R^{17}$ is other than hydrogen. In another embodiment, n is 1, one of E, K, and G are N and the other two of E, K, and G are C and at least one of $R^{15}$, $R^{16}$ and $R^{17}$ is other than hydrogen. In another embodiment, n is 1, E, K and G are C, and at least one of $R^{15}$, $R^{16}$ and $R^{17}$ is other than hydrogen.

In one embodiment of the compounds of Formula Ib, n is 1, V and W are CH, U and Z are independently $CR^{18}$, one of E, K, and G are N and the other two of E, K, and G are C and at least one of $R^{15}$, $R^{16}$ and $R^{17}$ is other than hydrogen. In another embodiment, n is 1, V and W are CH, U and Z are independently $CR^{18}$, E, K and G are C, and at least one of $R^{15}$, $R^{16}$ and $R^{17}$ is other than hydrogen.

In one embodiment of the compounds of Formula Ib, n is 1, one of E, K, and G are N and the other two of E, K, and G are C, at least one of $R^{15}$, $R^{16}$ and $R^{17}$ is other than hydrogen, A is —$CH_2$—, M is —$NHCH_2$—, further wherein $R^1$ is optionally substituted phenyl. In another embodiment, n is 1, E, K, and G are C, at least one of $R^{15}$, $R^{16}$ and $R^{17}$ is other than hydrogen, A is —$CH_2$—, M is —$NHCH_2$—, further wherein $R^1$ is optionally substituted phenyl.

In one embodiment of the compounds of Formula Ib, n is 1, V, Z, U and W are CH, one of E, K, and G are N and the other two of E, K, and G are C and at least one of $R^{15}$, $R^{16}$ and $R^{17}$ is other than hydrogen. In another embodiment, V, Z, U and W are CH, E, K and G are C, and at least one of $R^{15}$, $R^{16}$ and $R^{17}$ is other than hydrogen.

In one embodiment of the compounds of Formula Ib, Z is $CR^{18}$, wherein $R^{18}$ is other than hydrogen, n is 1, E-$R^{15}$ is N or CH, K—$R^{16}$ is N or CH and G-$R^{17}$ is N or CH. In another embodiment, Z is $CR^{18}$, wherein $R^{18}$ is other than hydrogen, n is 1, and E-$R^{15}$, K—$R^{16}$ and G-$R^{17}$ are CH. In another embodiment, Z is $CR^{18}$, wherein $R^{18}$ is other than hydrogen, U is $CR^{18}$, V and W are CH, n is 1, and E-$R^{15}$, K—$R^{16}$ and G-$R^{17}$ are CH, further wherein U is CH.

In one embodiment of the compounds of Formula Ib, Z is $CR^{18}$, wherein $R^{18}$ is other than hydrogen, n is 1, E-$R^{15}$, K—$R^{16}$ and G-$R^{17}$ are CH, A is —$CH_2$—, M is —$NHCH_2$—, further wherein $R^1$ is optionally substituted phenyl. In a further embodiment, Z is $CR^{18}$, wherein $R^{18}$ is other than hydrogen, U is $CR^{18}$, V and W are CH, n is 1, E-$R^{15}$, K—$R^{16}$ and G-$R^{17}$ are CH, A is —$CH_2$—, M is —$NHCH_2$—, further wherein $R^1$ is optionally substituted phenyl. In a further embodiment, Z is $CR^{18}$, wherein $R^{18}$ is other than hydrogen, V, U and W are CH, n is 1, E-$R^{15}$, K—$R^{16}$ and G-$R^{17}$ are CH, A is —$CH_2$—, M is —$NHCH_2$—, further wherein $R^1$ is optionally substituted phenyl.

In one embodiment of the compounds of Formula Ib, U is $CR^{18}$, wherein $R^{18}$ is other than hydrogen, n is 1, E-$R^{15}$ is N or CH, K—$R^{16}$ is N or CH and G-$R^{17}$ is N or CH. In another embodiment, U is $CR^{18}$, wherein $R^{18}$ is other than hydrogen, n is 1, and E-$R^{15}$, K—$R^{16}$ and G-$R^{17}$ are CH. In another embodiment, U is $CR^{18}$, wherein $R^{18}$ is other than hydrogen, Z is $CR^{18}$, V and W are CH, n is 1, and E-$R^{15}$, K—$R^{16}$ and G-$R^{17}$ are CH, further wherein Z is CH.

In one embodiment of the compounds of Formula Ib, U is $CR^{18}$, wherein $R^{18}$ is other than hydrogen, n is 1, E-$R^{15}$, K—$R^{16}$ and G-$R^{17}$ are CH, A is —$CH_2$—, M is —$NHCH_2$—, further wherein $R^1$ is optionally substituted phenyl. In a further embodiment, U is $CR^{18}$, wherein $R^{18}$ is other than hydrogen, Z is $CR^{18}$, V and W are CH, n is 1, E-$R^{15}$, K—$R^{16}$ and G-$R^{17}$ are CH, A is —$CH_2$—, M is —$NHCH_2$—, further wherein $R^1$ is optionally substituted phenyl. In a further embodiment, U is $CR^{18}$, wherein $R^{18}$ is other than hydrogen, V, Z and W are CH, n is 1, E-$R^{15}$, K—$R^{16}$ and G-$R^{17}$ are CH, A is —$CH_2$—, M is —$NHCH_2$—, further wherein $R^1$ is optionally substituted phenyl.

In one embodiment of the compounds of Formula Ib, further to any of the above embodiments, $R^{15}$, $R^{16}$ and $R^{17}$ are independently selected from the group consisting of halogen, —OH, lower alkyl, fluoro substituted lower alkyl, lower alkoxy, and fluoro substituted lower alkoxy. Further to any of these embodiments $R^1$ is phenyl optionally substituted with one or more substituents selected from the group consisting of halogen, —OH, —$NH_2$, —$NO_2$, —CN, optionally substituted lower alkyl and —$OR^{29}$, where $R^{29}$ is selected from the group consisting of optionally substituted lower alkyl, optionally substituted cycloalkyl, optionally substituted heterocycloalkyl, optionally substituted aryl and optionally substituted heteroaryl.

In one embodiment of the compounds of Formula Ib, further to any of the above embodiments, $R^{18}$ is selected from the group consisting of halogen, —OH, optionally substituted lower alkyl and —$OR^{29}$, where $R^{29}$ is selected from the group consisting of optionally substituted lower alkyl, optionally substituted cycloalkyl, optionally substituted heterocycloalkyl, optionally substituted aryl and optionally substituted heteroaryl. Further to any of these embodiments, $R^1$ is phenyl optionally substituted with one or more substituents selected from the group consisting of halogen, —OH, —$NH_2$, —$NO_2$, —CN, optionally substituted lower alkyl and —$OR^{29}$, where $R^{29}$ is selected from the group consisting of optionally substituted lower alkyl, optionally substituted cycloalkyl, optionally substituted heterocycloalkyl, optionally substituted aryl and optionally substituted heteroaryl.

In another embodiment of compounds of Formula Ib, M is a bond and $R^1$ is other than thiophenyl.

In another embodiment of the compounds of Formula Ib, Z is N or $CR^{18}$ wherein $R^{18}$ is not hydrogen. Further to this embodiment, as allowed in the description of Formula Ib, E is $NR^{15}$ or $CR^{15}$, K is $NR^{16}$ or $CR^{16}$ and G is $CR^{17}$, or combinations thereof, wherein at least one of $R^{15}$, $R^{16}$ and $R^{17}$ is not hydrogen.

In one embodiment, a compound of Formula I has a structure according to the following sub-generic structure, Formula Ig,

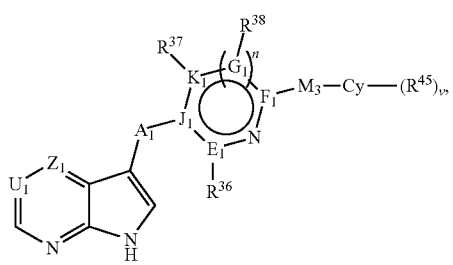

Formula Ig all salts, prodrugs, tautomers, and isomers thereof, wherein:

$Z_1$ is selected from the group consisting of N and $CR^{34}$;

$U_1$ is selected from the group consisting of N and $CR^{35}$;

$A_1$ is selected from the group consisting of —$CH_2$— and —C(O)—;

$M_3$ is selected from the group consisting of a bond, —$NR^{39}$—, —S—, —O—, —$NR^{39}CH_2$—, —$NR^{39}CH(R^{40})$—, —$SCH_2$—, —$OCH_2$—, —$C(O)NR^{39}$—, —$S(O)_2NR^{39}$—, —$CH_2NR^{39}$—, —$CH(R^{40})NR^{39}$—, —$NR^{39}C(O)$—, and —$NR^{39}S(O)_2$—;

n is 0 or 1;

v is 0, 1, 2 or 3;

$F_1$ and $J_1$ are both C or one of $F_1$ and $J_1$ is C and the other of $F_1$ and $J_1$ is N;

$E_1$ and $K_1$ are independently selected from C, N, O or S;

$G_1$ is selected from C or N;

wherein when n is 1, $F_1$ and $J_1$ are C, and $E_1$, $G_1$ and $K_1$ are C, or any one of $E_1$, $G_1$ and $K_1$ is N and the other two of $E_1$, $G_1$ and $K_1$ are C, provided that when $E_1$, $G_1$ or $K_1$ is N, $R^{36}$, $R^{37}$ and $R^{38}$, respectively, are absent;

when n is 0 and $F_1$ and $J_1$ are both C, then one of $E_1$ and $K_1$ is C or N and the other of $E_1$ and $K_1$ is C, N, O or S, provided both $E_1$ and $K_1$ are not C, and provided that when both $E_1$ and $K_1$ are N, one of $R^{36}$ and $R^{37}$ is absent, and provided that when one of $E_1$ and $K_1$ are N and the other is O or S, $R^{36}$ and $R^{37}$ are absent;

when n is 0, one of $F_1$ and $J_1$ is N and the other of $F_1$ and $J_1$ is C, then one of $E_1$ and $K_1$ is N and the other of $E_1$ and $K_1$ is C, or both $E_1$ and $K_1$ are C, provided that when $E_1$ is N, $R^{36}$ is absent and when $K_1$ is N, $R^{37}$ is absent;

Cy is selected from the group consisting of cycloalkyl, heterocycloalkyl, aryl and heteroaryl;

$R^{34}$ and $R^{35}$ are independently selected from the group consisting of hydrogen, —$OR^{41}$, —$SR^{41}$, —$NHR^{41}$, —$NR^{41}R^{41}$, —$NR^{39}C(O)R^{41}$, —$NR^{39}S(O)_2R^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{34}$ or $R^{35}$, or as substituents of lower alkyl are optionally substituted with one or more substituents selected from the group consisting of —OH, —$NH_2$, —CN, —$NO_2$, —$S(O)_2NH_2$, —$C(O)NH_2$, —$OR^{42}$, —$SR^{42}$, —$NHR^{42}$, —$NR^{42}R^{42}$, —$NR^{39}C(O)R^{42}$, —$NR^{39}S(O)_2R^{42}$, —$S(O)_2R^{42}$, halogen, lower alkyl, fluoro substituted lower alkyl, and cycloalkylamino;

$R^{45}$ at each occurrence is independently selected from the group consisting of —$OR^{41}$, —$SR^{41}$, —$NHR^{41}$, —$NR^{41}R^{41}$, —$NR^{39}C(O)R^{41}$, —$NR^{39}S(O)_2R^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{45}$, or as substituents of lower alkyl are optionally substituted with one or more substituents selected from the group consisting of —OH, —$NH_2$, —CN, —$NO_2$, —$S(O)_2NH_2$, —$C(O)NH_2$, —$OR^{42}$, —$SR^{42}$, —$NHR^{42}$, —$NR^{42}R^{42}$, —$NR^{39}C(O)R^{42}$, —$NR^{39}S(O)_2R^{42}$, —$S(O)_2R^{42}$, halogen, lower alkyl, fluoro substituted lower alkyl, and cycloalkylamino;

$R^{36}$ is selected from the group consisting of hydrogen, halogen, lower alkyl, fluoro substituted lower alkyl, lower alkoxy, and fluoro substituted lower alkoxy when $E_1$ is C, is absent when $E_1$ is O or S or when n=1 and $E_1$ is N, and is absent or selected from the group consisting of hydrogen, lower alkyl, and fluoro substituted lower alkyl when n=0 and $E_1$ is N;

$R^{37}$ is selected from the group consisting of hydrogen, halogen, lower alkyl, fluoro substituted lower alkyl, lower alkoxy, and fluoro substituted lower alkoxy when $K_1$ is C, is absent when $K_1$ is O or S or when n=1 and $K_1$ is N, and is absent or selected from the group consisting of hydrogen, lower alkyl, and fluoro substituted lower alkyl when n=0 and $K_1$ is N;

$R^{38}$ is selected from the group consisting of hydrogen, halogen, lower alkyl, fluoro substituted lower alkyl, lower alkoxy, and fluoro substituted lower alkoxy when $G_1$ is C, or is absent when $G_1$ is N;

$R^{39}$ at each occurrence is independently hydrogen or lower alkyl;

$R^{40}$ is lower alkyl or fluoro substituted lower alkyl;

$R^{41}$ is selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{41}$ or as substituents of lower alkyl are optionally substituted with one or more substituents selected from the group consisting of —OH, —$NH_2$, —CN, —$NO_2$, —$S(O)_2NH_2$, —$C(O)NH_2$, —$OR^{42}$, —$SR^{42}$, —$NHR^{42}$, —$NR^{42}R^{42}$, —$NR^{39}C(O)R^{42}$, —$NR^{39}S(O)_2R^{42}$, —$S(O)_2R^{42}$, halogen, lower alkyl, fluoro substituted lower alkyl, and cycloalkylamino; and $R^{42}$ at each occurrence is independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, and heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy.

In one embodiment of compounds of Formula Ig, n is 1, $G_1$ and $K_1$ are C, and E is N or C, preferably wherein E is C.

In one embodiment of compounds of Formula Ig, $M_3$ is selected from the group consisting of —$NR^{39}$—, —O—, —$NR^{39}CH_2$—, —$NR^{39}CH(R^{40})$—, —$SCH_2$—, —$OCH_2$—, —$CH_2NR^{39}$—, —$NR^{39}C(O)$—, and —$NR^{39}S(O)_2$—, preferably wherein $M_3$ is —$NR^{39}CH_2$—, —$NR^{39}CH(R^{40})$—, —$SCH_2$—, —$OCH_2$—, or —$CH_2NR^{39}$—.

In one embodiment of compounds of Formula Ig, n is 1, $G_1$ and $K_1$ are C, and E is N or C, preferably wherein E is C, and $M_3$ is selected from the group consisting of —$NR^{39}$—, —O—, $NR^{39}CH_2$—, —$NR^{39}CH(R^{40})$—, —$SCH_2$—, —$OCH_2$—, —$CH_2NR^{39}$—, —$NR^{39}C(O)$—, and —$NR^{39}S(O)_2$—, preferably wherein $M_3$ is —$NR^{39}CH_2$—, —$NR^{39}CH(R^{40})$—, —$SCH_2$—, —$OCH_2$—, or —$CH_2NR^{39}$—.

In one embodiment of compounds of Formula Ig, each $R^{45}$ is selected from the group consisting of —OH, —$NH_2$, —CN, —$NO_2$, halogen, lower alkyl, fluoro substituted lower alkyl, lower alkoxy, fluoro substituted lower alkoxy, lower thioalkyl, fluoro substituted lower thioalkyl, mono-alkylamino, di-alkylamino and cycloalkylamino, preferably wherein v is 0, 1, or 2, also 0 or 1.

In one embodiment of compounds of Formula Ig, n is 1, $G_1$ and $K_1$ are C, and E is N or C, preferably wherein E is C, $M_3$ is selected from the group consisting of —$NR^{39}$—, —O—, —$NR^{39}CH_2$—, —$NR^{39}CH(R^{40})$—, —$SCH_2$—, —$OCH_2$—, —$CH_2NR^{39}$—, —$NR^{39}C(O)$—, and —$NR^{39}S(O)_2$—, preferably wherein $M_3$ is —$NR^{39}CH_2$—, —$NR^{39}CH(R^{40})$—, —$SCH_2$—, —$OCH_2$—, or —$CH_2NR^{39}$—, and each $R^{45}$ is selected from the group consisting of —OH, —$NH_2$, —CN, —$NO_2$, halogen, lower alkyl, fluoro substituted lower alkyl, lower alkoxy, fluoro substituted lower alkoxy, lower thioalkyl, fluoro substituted lower thioalkyl, mono-alkylamino, di-alkylamino and cycloalkylamino, preferably wherein v is 0, 1, or 2, also 0 or 1.

In one embodiment of compounds of Formula Ig, $Z_1$ is $CR^{34}$, $U_1$ is $CR^{35}$, and $R^{34}$ and $R^{35}$ are both hydrogen. In one embodiment, $Z_1$ is $CR^{34}$, $U_1$ is $CR^{35}$, and $R^{34}$ and $R^{35}$ are independently selected from the group consisting of hydrogen, —$OR^{41}$, halogen, lower alkyl, cycloalkyl, heterocycloalkyl, aryl and heteroaryl, wherein cycloalkyl, heterocycloalkyl, aryl and heteroaryl are optionally substituted with one or more substituents selected from the group consisting of —OH, —$NH_2$, —CN, —$NO_2$, —$S(O)_2NH_2$, —$C(O)NH_2$, —$OR^{42}$, —$SR^{42}$, —$NHR^{42}$, —$NR^{42}R^{42}$, —$NR^{39}C(O)R^{42}$, —$NR^{39}S(O)_2R^{42}$, —$S(O)_2R^{42}$, halogen, lower alkyl, fluoro substituted lower alkyl, and cycloalkylamino, and wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino. In a further embodiment, one of $R^{34}$ and $R^{35}$ is hydrogen, and the other of $R^{34}$ and $R^{35}$ is selected from the group consisting of hydrogen, halogen, lower alkyl, lower alkoxy, aryl and heteroaryl, wherein aryl and heteroaryl are optionally substituted with one or more substituents selected from the group consisting of —OH, —$NH_2$, —CN, —$NO_2$, —$S(O)_2NH_2$, —$C(O)NH_2$, —$OR^{42}$, —$SR^{42}$, —$NHR^{42}$, —$NR^{42}R^{42}$, —$NR^{39}C(O)R^{42}$, —$NR^{39}S(O)_2R^{42}$, —$S(O)_2R^{42}$, halogen, lower alkyl, fluoro substituted lower alkyl, and cycloalkylamino, and wherein lower alkyl and lower alkoxy are optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, further wherein the other of $R^{34}$ and $R^{35}$ is selected from the group consisting of halogen, lower alkyl, and lower alkoxy, wherein lower alkyl and lower alkoxy are optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino.

In one embodiment of compounds of Formula Ig, each $R^{45}$ is independently selected from the group consisting of —OH, —$NH_2$, —CN, —$NO_2$, halogen, lower alkyl, fluoro substituted lower alkyl, lower alkoxy, fluoro substituted lower alkoxy, lower thioalkyl, fluoro substituted lower thioalkyl, mono-alkylamino, di-alkylamino and cycloalkylamino, preferably wherein v is 0, 1, or 2, also 0 or 1, $Z_1$ is $CR^{34}$, $U_1$ is $CR^{35}$, and $R^{34}$ and $R^{35}$ are independently selected from the group consisting of hydrogen, —$OR^{41}$, halogen, lower alkyl, cycloalkyl, heterocycloalkyl, aryl and heteroaryl, wherein cycloalkyl, heterocycloalkyl, aryl and heteroaryl are optionally substituted with one or more substituents selected from the group consisting of —OH, —$NH_2$, —CN, —$NO_2$, —$S(O)_2NH_2$, —$C(O)NH_2$, —$OR^{42}$, —$SR^{42}$, —$NHR^{42}$, —$NR^{42}R^{42}$, —$NR^{39}C(O)R^{42}$, —$NR^{39}S(O)_2R^{42}$, —$S(O)_2R^{42}$, halogen, lower alkyl, fluoro substituted lower alkyl, and cycloalkylamino, and wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino. In a further embodiment, both of $R^{34}$ and $R^{35}$ are hydrogen.

In one embodiment of compounds of Formula Ig, each $R^{45}$ is selected from the group consisting of —OH, —$NH_2$, —CN, —$NO_2$, halogen, lower alkyl, fluoro substituted lower alkyl, lower alkoxy, fluoro substituted lower alkoxy, lower thioalkyl, fluoro substituted lower thioalkyl, mono-alkylamino, di-alkylamino and cycloalkylamino, preferably wherein v is 0, 1, or 2, also 0 or 1, $Z_1$ is $CR^{34}$, $U_1$ is $CR^{35}$, one of $R^{34}$ and $R^{35}$ is hydrogen, and the other of $R^{34}$ and $R^{35}$ is selected from the group consisting of hydrogen, halogen, lower alkyl, lower alkoxy, aryl and heteroaryl, wherein aryl and heteroaryl are optionally substituted with one or more substituents selected from the group consisting of —OH, —$NH_2$, —CN, —$NO_2$, —$S(O)_2NH_2$, —$C(O)NH_2$, —$OR^{42}$, —$SR^{42}$, —$NHR^{42}$, —$NR^{42}R^{42}$, —$NR^{39}C(O)R^{42}$, —$NR^{39}S(O)_2R^{42}$, —$S(O)_2R^{42}$, halogen, lower alkyl, fluoro substituted lower alkyl, and cycloalkylamino, and wherein lower alkyl and lower alkoxy are optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, further wherein the other of $R^{34}$ and $R^{35}$ is selected from the group consisting of halogen, lower alkyl, and lower alkoxy, wherein lower alkyl and lower alkoxy are optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino.

In one embodiment of compounds of Formula Ig, n is 1, $G_1$ and $K_1$ are C, and E is N or C, preferably wherein E is C, $M_3$ is selected from the group consisting of —$NR^{39}$—, —O—, —$NR^{39}CH_2$—, —$NR^{39}CH(R^{40})$—, —$SCH_2$—, —$OCH_2$—, —$CH_2NR^{39}$—, —$NR^{39}C(O)$—, and —$NR^{39}S(O)_2$—, preferably wherein $M_3$ is —$NR^{39}CH_2$—, —$NR^{39}CH(R^{40})$—, —$SCH_2$—, —$OCH_2$—, or —$CH_2NR^{39}$—, each $R^{45}$ is selected from the group consisting of —OH, —$NH_2$, —CN, —$NO_2$, halogen, lower alkyl, fluoro substituted lower alkyl, lower alkoxy, fluoro substituted lower alkoxy, lower thioalkyl, fluoro substituted lower thioalkyl, mono-alkylamino, di-alkylamino and cycloalkylamino, preferably wherein v is 0, 1, or 2, also 0 or 1, $Z_1$ is $CR^{34}$, $U_1$ is $CR^{35}$, and $R^{34}$ and $R^{35}$ are both hydrogen.

In one embodiment of compounds of Formula Ig, n is 1, $G_1$ and $K_1$ are C, and E is N or C, preferably wherein E is C, $M_3$ is selected from the group consisting of —$NR^{39}$—, —O—, —$NR^{39}CH_2$—, —$NR^{39}CH(R^{40})$—, —$SCH_2$—, —$OCH_2$—, —$CH_2NR^{39}$—, —$NR^{39}C(O)$—, and —$NR^{39}S(O)_2$—, preferably wherein $M_3$ is —$NR^{39}CH_2$—, —$NR^{39}CH(R^{40})$—, —$SCH_2$—, —$OCH_2$—, or —$CH_2NR^{39}$—, each $R^{45}$ is selected from the group consisting of —OH, —$NH_2$, —CN, —$NO_2$, halogen, lower alkyl, fluoro substituted lower alkyl, lower alkoxy, fluoro substituted lower alkoxy, lower thioalkyl, fluoro substituted lower thioalkyl, mono-alkylamino, di-alkylamino and cycloalkylamino, preferably wherein v is 0, 1, or 2, also 0 or 1, $Z_1$ is $CR^{34}$ and $U_1$ is $CR^{35}$, and $R^{34}$ and $R^{35}$ are independently selected from the group consisting of hydrogen, —$OR^{41}$, halogen, lower alkyl, cycloalkyl, heterocycloalkyl, aryl and heteroaryl, wherein cycloalkyl, heterocycloalkyl, aryl and heteroaryl are optionally substituted with one or more substituents selected from the group consisting of —OH, —$NH_2$, —CN, —$NO_2$, —$S(O)_2NH_2$, —$C(O)NH_2$, —$OR^{42}$, —$SR^{42}$, —$NHR^{42}$, —$NR^{42}R^{42}$, —$NR^{39}C(O)R^{42}$, —$NR^{39}S(O)_2R^{42}$, —$S(O)_2R^{42}$, halogen, lower alkyl, fluoro substituted lower alkyl, and cycloalkylamino, and wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino. In a further embodiment, one of $R^{34}$ and $R^{35}$ is hydrogen, and the other of $R^{34}$ and $R^{35}$ is selected from the group consisting of halogen, lower alkyl, lower alkoxy, aryl and heteroaryl, wherein aryl and heteroaryl are optionally substituted with one or more substituents selected from the group consisting of —OH, —$NH_2$, —CN, —$NO_2$, —$S(O)_2NH_2$, —$C(O)NH_2$, —$OR^{42}$, —$SR^{42}$, —$NHR^{42}$, —$NR^{42}R^{42}$, —$NR^{39}C(O)R^{42}$, —$NR^{39}S(O)_2R^{42}$, —$S(O)_2R^{42}$, halogen, lower alkyl, fluoro substituted lower alkyl, and cycloalkylamino, and wherein lower alkyl and lower alkoxy are optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, further wherein the other of $R^{34}$ and $R^{35}$ is selected from the group consisting of halogen, lower alkyl, and lower alkoxy, wherein lower alkyl and lower alkoxy are optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, further wherein $R^{34}$ is hydrogen.

In one embodiment, a compound of Formula I has a structure according to the following sub-generic structure, Formula II,

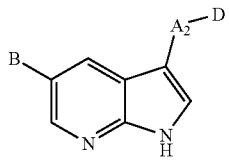

Formula II all salts, prodrugs, tautomers, and isomers thereof, wherein:

D has a structure selected from the group consisting of

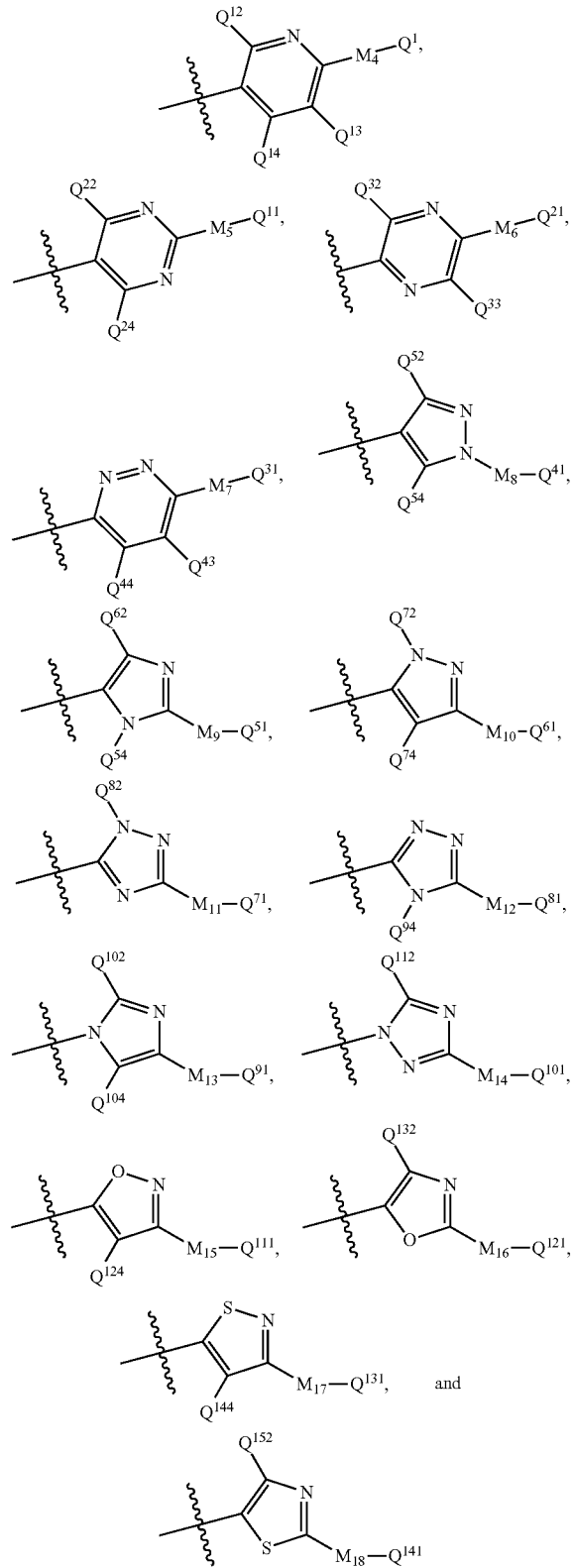

in which

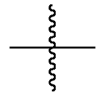

indicates the attachment point of D to $A_2$ of Formula II;

$A_2$ is selected from the group consisting of —$CR^{19}R^{20}$—, —C(O)—, —C(S)—, —S—, —S(O)—, —$S(O)_2$—, —$NR^{21}$—, and —O—, provided, however, that when $A_2$ is $NR^{21}$, N is not bound to a nitrogen of D;

B is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —$NH_2$, —$NO_2$, —CN, —$NHC(O)NH_2$, —$NHC(S)NH_2$, —$NHS(O)_2NH_2$, —$C(O)NH_2$, —$C(S)NH_2$, —$S(O)_2NH_2$, —$NR^{24}R^{25}$, —$NHR^{23}$, —$OR^{23}$, —$SR^{23}$, —$C(O)R^{23}$, —$C(S)R^{23}$, —$S(O)R^{23}$, —$S(O)_2R^{23}$, —$C(O)NHR^{23}$, —$C(O)NR^{23}R^{23}$, —$C(S)NHR^{23}$, —$C(S)NR^{23}R^{23}$, —$S(O)_2NHR^{23}$, —$S(O)_2NR^{23}R^{23}$, —$NHC(O)R^{23}$, —$NR^{23}C(O)R^{23}$, —$NHC(S)R^{23}$, —$NR^{23}C(S)R^{23}$, —$NHS(O)_2R^{23}$, —$NR^{23}S(O)_2R^{23}$, —$NHC(O)NHR^{23}$, —$NR^{23}C(O)NH_2$, —$NR^{23}C(O)NHR^{23}$, —$NHC(O)NR^{23}R^{23}$, —$NR^{23}C(O)NR^{23}R^{23}$, —$NHC(S)NHR^{23}$, —$NR^{23}C(S)NH_2$, —$NR^{23}C(S)NHR^{23}$, —$NHC(S)NR^{23}R^{23}$, —$NR^{23}C(S)NR^{23}R^{23}$, —$NHS(O)_2NHR^{23}$, —$NR^{23}S(O)_2NH_2$, —$NR^{23}S(O)_2NHR^{23}$, —$NHS(O)_2NR^{23}R^{23}$, and —$NR^{23}S(O)_2NR^{23}R^{23}$;

$M_4$ is —$NR^{39}CH_2$—, —$NR^{39}CH(R^{40})$—, —$NR^{39}CH_2CH_2$—, or —$NR^{39}C(O)$—;

$M_5, M_6, M_7, M_9, M_{10}, M_{11}, M_{12}, M_{13}, M_{14}, M_{15}, M_{16}, M_{17}$ and $M_{18}$ are selected from the group consisting of a bond, —$(CR^{19}R^{20})_u$—, —$(CR^{19}R^{20})_t$—C(O)—$(CR^{19}R^{20})_s$—, —$(CR^{19}R^{20})_t$—C(S)—$(CR^{19}R^{20})_s$—, —$(CR^{19}R^{20})_t$—C(O)O—$(CR^{19}R^{20})_s$—, —$(CR^{19}R^{20})_t$—C(S)O—$(CR^{19}R^{20})_s$—, —$(CR^{19}R^{20})_t$—C(O)$NR^{26}$—$(CR^{19}R^{20})_s$—, —$(CR^{19}R^{20})_t$—C(S)$NR^{26}$—$(CR^{19}R^{20})_s$—, —$(CR^{19}R^{20})_t$—S(O)—$(CR^{19}R^{20})_s$—, —$(CR^{19}R^{20})_t$—$S(O)_2$—$(CR^{19}R^{20})_s$—, —$(CR^{19}R^{20})_t$—$S(O)_2NR^{26}$—$(CR^{19}R^{20})_s$—, —$(CR^{19}R^{20})_t$—O—$(CR^{19}R^{20})_s$—, —$(CR^{19}R^{20})_t$—OC(O)—$(CR^{19}R^{20})_s$—, —$(CR^{19}R^{20})_t$—OC(S)—$(CR^{19}R^{20})_s$—, —$(CR^{19}R^{20})_t$—OC(O)$NR^{26}$—$(CR^{19}R^{20})_s$—, —$(CR^{19}R^{20})_t$—OC(S)$NR^{26}$—$(CR^{19}R^{20})_s$—, —$(CR^{19}R^{20})_t$—S—$(CR^{19}R^{20})_s$—, —$(CR^{19}R^{20})_t$—$NR^{26}$—$(CR^{19}R^{20})_s$—, —$(CR^{19}R^{20})_t$—$NR^{26}C(O)$—$(CR^{19}R^{20})_s$—, —$(CR^{19}R^{20})_t$—$NR^{26}C(S)$—$(CR^{19}R^{20})_s$—, —$(CR^{19}R^{20})_t$—$NR^{26}C(O)O$—$(CR^{19}R^{20})_s$—, —$(CR^{19}R^{20})_t$—$NR^{26}C(S)O$—$(CR^{19}R^{20})_s$—, —$(CR^{19}R^{20})_t$—$NR^{26}C(O)NR^{26}$—$(CR^{19}R^{20})_s$—, —$(CR^{19}R^{20})_t$—$NR^{26}C(S)NR^{26}$—$(CR^{19}R^{20})_s$—, —$(CR^{19}R^{20})_t$—$NR^{26}S(O)_2$—$(CR^{19}R^{20})_s$—, and —$(CR^{19}R^{20})_t$—$NR^{26}S(O)_2NR^{26}$—$(CR^{19}R^{20})_s$—;

$M_8$ is selected from the group consisting of a bond, —$(CR^{19}R^{20})_u$—, —$(CR^{19}R^{20})_t$—C(O)—$(CR^{19}R^{20})_s$—, —$(CR^{19}R^{20})_t$—C(S)—$(CR^{19}R^{20})_s$—, —$(CR^{19}R^{20})_t$—C(O)O—$(CR)^{19}R^{20})_s$—, —$(CR^{19}R^{20})_t$—C(S)O—$(CR^{19}R^{20})_s$—, —$(CR^{19}R^{20})_t$—C(O)$NR^{26}$—$(CR^{19}R^{20})_s$—, —$(CR^{19}R^{20})_t$—C(S)$NR^{26}$—$(CR^{19}R^{20})_s$—, —$(CR^{19}R^{20})_t$—S(O)—$(CR^{19}R^{20})_s$—, —$(CR^{19}R^{20})_t$—$S(O)_2$—$(CR^{19}R^{20})_s$—, —$(CR^{19}R^{20})_t$—$S(O)_2NR^{26}$—$(CR^{19}R^{20})_s$—, —$(CR^{19}R^{20})_t$—O—$(CR^{19}R^{20})_s$—, —$(CR^{19}R^{20})_w$—OC(O)—$(CR^{19}R^{20})_s$—, —$(CR^{19}R^{20})_w$—OC(S)—$(CR^{19}R^{20})_s$—, —$(CR^{19}R^{20})_w$—OC(O)$NR^{26}$—$(CR^{19}R^{20})_s$—, —$(CR^{19}R^{20})_w$—OC(S)$NR^{26}$—$(CR^{19}R^{20})_s$—, —$(CR^{19}R^{20})_w$—S—$(CR^{19}R^{20})_s$—, —$(CR^{19}R^{20})_w$—$NR^{26}$—$(CR^{19}R^{20})_s$—, —$(CR^{19}R^{20})_w$—$NR^{26}C(O)$—$(CR^{19}R^{20})_s$—, —$(CR^{19}R^{20})_w$—$NR^{26}C(S)$—$(CR^{19}R^{20})_s$—, —$(CR^{19}R^{20})_w$—$NR^{26}C(O)O$—$(CR^{19}R^{20})_s$—, —$(CR^{19}R^{20})_w$—$NR^{26}C(S)O$—$(CR^{19}R^{20})_s$—, —$(CR^{19}R^{20})_w$—$NR^{26}C(O)NR^{26}$—$(CR^{19}R^{20})_s$—, —$(CR^{19}R^{20})_w$—$NR^{26}C(S)NR^{26}$—$(CR^{19}R^{20})_s$—, —$(CR^{19}R^{20})_w$—$NR^{26}S(O)_2$—$(CR^{19}R^{20})_s$—, and —$(CR^{19}R^{20})_w$—$NR^{26}S(O)_2NR^{26}$—$(CR^{19}R^{20})_s$—;

$Q^1$ is aryl or heteroaryl, wherein aryl or heteroaryl are optionally substituted with one or more substituents selected from the group consisting of halogen, lower alkyl, fluoro substituted lower alkyl, —$NHS(O)_2R^{43}$, —$NHC(O)R^{43}$, —$NHR^{43}$, —$NR^{43}R^{43}$, —$OR^{43}$, $SR^{43}$, $S(O)R^{43}$, and —$S(O)_2R^{43}$;

$Q^{11}, Q^{21}, Q^{31}, Q^{41}, Q^{51}, Q^{61}, Q^{71}, Q^{81}, Q^{91}, Q^{101}, Q^{111}, Q^{121}, Q^{131}$, and $Q^{141}$ are selected from the group consisting of optionally substituted lower alkyl, optionally substituted cycloalkyl, optionally substituted heterocycloalkyl, optionally substituted aryl and optionally substituted heteroaryl;

$Q^{12}$ is fluoro, chloro or —$CF_3$;

$Q^{13}$ and $Q^{14}$ are independently hydrogen, fluoro, chloro, lower alkyl, or fluoro substituted lower alkyl;

$Q^{22}, Q^{24}, Q^{32}, Q^{33}, Q^{43}, Q^{44}, Q^{52}, Q^{54}, Q^{102}$ and $Q^{104}$ are independently selected from the group consisting of hydrogen, halogen, lower alkyl, fluoro substituted lower alkyl, —$NR^{44}R^{44}$, —$OR^{44}$, and —$SR^{44}$, provided, however, that at least one of $Q^{22}$ and $Q^{24}$, at least one of $Q^{32}$ and $Q^{33}$, at least one of $Q^{43}$ and $Q^{44}$, at least one of $Q^{52}$ and $Q^{54}$, and at least one of $Q^{102}$ and $Q^{104}$ is hydrogen, fluoro, chloro, lower alkyl or fluoro substituted lower alkyl;

$Q^{62}, Q^{74}, Q^{112}, Q^{124}, Q^{132}, Q^{144}$, and $Q^{152}$ are hydrogen, fluoro, chloro, lower alkyl, fluoro substituted lower alkyl, —$NR^{44}R^{44}$, —$OR^{44}$, or —$SR^{44}$;

$Q^{64}, Q^{72}, Q^{82}$, and $Q^{94}$ are hydrogen, lower alkyl or fluoro substituted lower alkyl;

$R^{43}$ at each occurrence is independently optionally substituted lower alkyl, optionally substituted cycloalkyl, optionally substituted heterocycloalkyl, optionally substituted aryl or optionally substituted heteroaryl;

$R^{39}$ and $R^{40}$ are as defined for Formula Ig;

each $R^{44}$ is independently hydrogen, lower alkyl or fluoro substituted lower alkyl;

w is 1, 2, or 3; and $R^{19}, R^{20}, R^{21}, R^{23}, R^{24}, R^{25}, R^{26}$, s, t and u are as defined for Formula Ib;

provided, however, that the compound is not

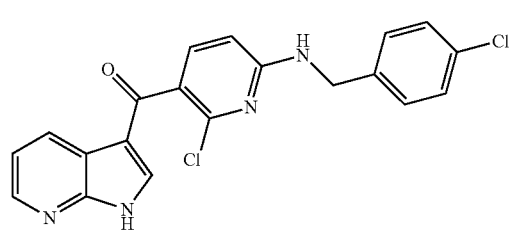

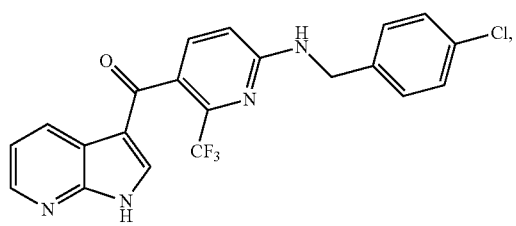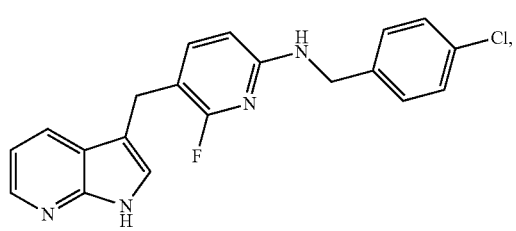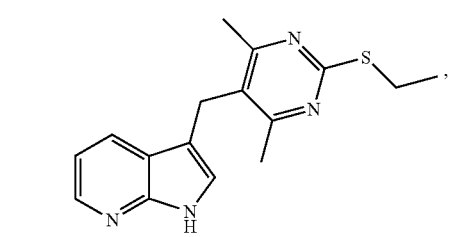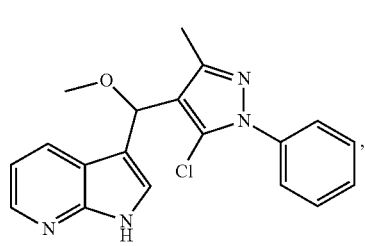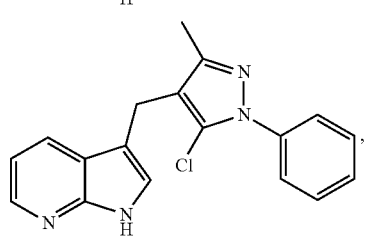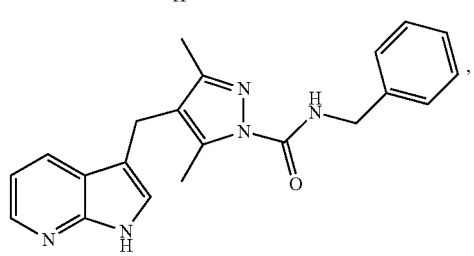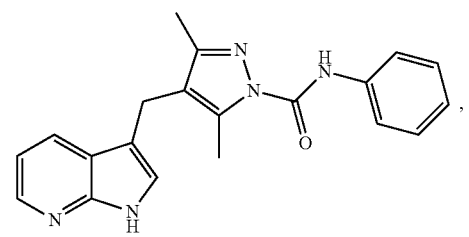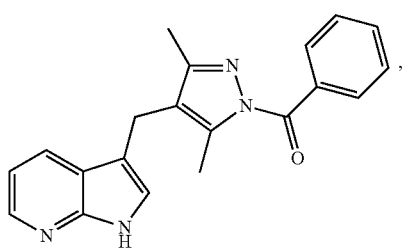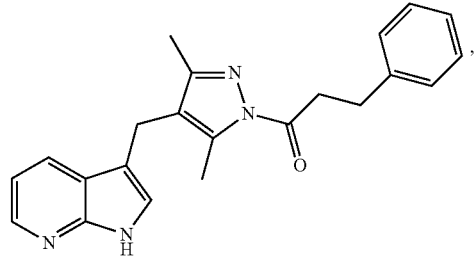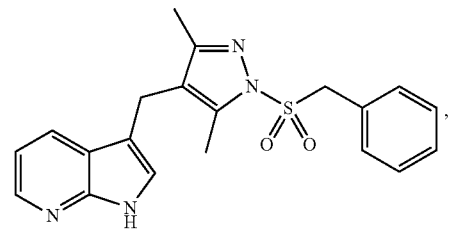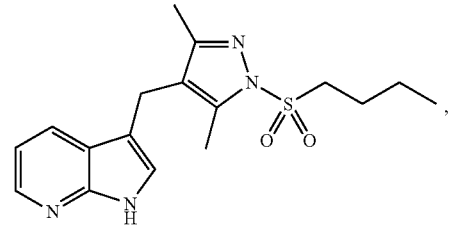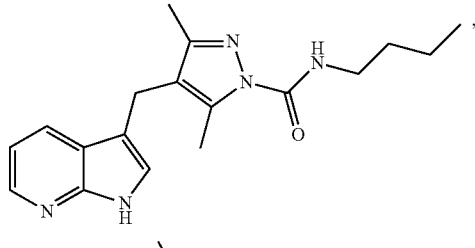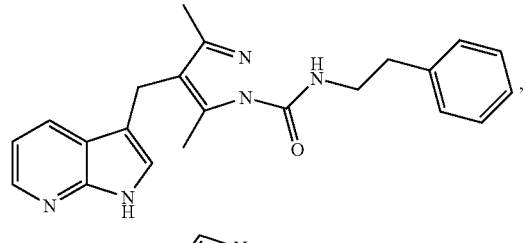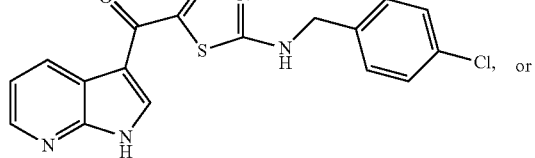

-continued

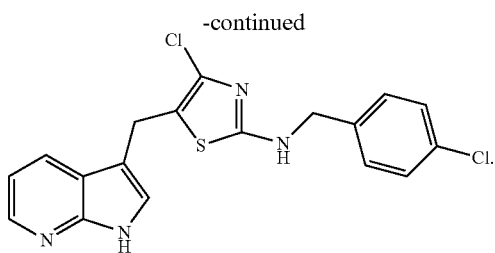

In one embodiment of compounds of Formula II,
D has a structure selected from the group consisting of

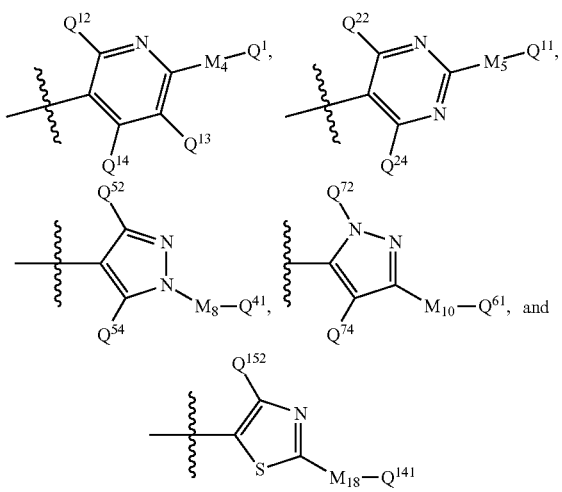

in which

indicates the attachment point of D to $A_2$ of Formula II;
$A_2$ is selected from the group consisting of —$CR^{19}R^{20}$—, —C(O)—, —C(S)—, —S—, —S(O)—, —S(O)$_2$—, —$NR^{21}$—, and —O—, provided, however, that when $A_2$ is $NR^{21}$, N is not bound to a nitrogen of D, preferably $A_2$ is —CH$_2$— or —C(O)—;
B is selected from the group consisting of hydrogen, —CN, —OR$^{41}$, —SR$^{41}$, —NHR$^{41}$, —NR$^{41}$R$^{41}$, —NR$^{39}$C(O)R$^{41}$, NR$^{39}$S(O)$_2$R$^{41}$, —C(O)NR$^{39}$R$^{41}$, —C(O)R$^{41}$, —S(O)$_2$NR$^{39}$R$^{41}$, —S(O)$_2$R$^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as B, or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$^2$R$^{42}$, —S(O)$_2$R$^{42}$, halogen, lower alkyl, fluoro substituted lower alkyl, and cycloalkylamino;

$M_4$ is —NR$^{39}$CH$_2$—, —NR$^{39}$CH(R$^{40}$)—, —NR$^{39}$CH$_2$CH$_2$—, or —NR$^{39}$C(O)—, preferably —NHCH$_2$— or —NHC(O)—;
$M_5$, $M_{10}$, and $M_{18}$ are selected from the group consisting of a bond, —(CR$^{19}$R$^{20}$)$_u$—, —(CR$^{19}$R$^{20}$)$_t$—C(O)—(CR$^{19}$R$^{20}$)$_s$—, —(CR$^{19}$R$^{20}$)$_t$—C(S)—(CR$^{19}$R$^{20}$)$_s$—, —(CR$^{19}$R$^{20}$)$_t$—C(O)O—(CR$^{19}$R$^{20}$)$_s$—, —(CR$^{19}$R$^{20}$)$_t$—C(S)O—(CR$^{19}$R$^{20}$)$_s$—, —(CR$^{19}$R$^{20}$)$_t$—C(O)NR$^{26}$—(CR$^{19}$R$^{20}$)$_s$—, —(CR$^{19}$R$^{20}$)$_t$—C(S)NR$^{26}$—(CR$^{19}$R$^{20}$)$_s$—, —(CR$^{19}$R$^{20}$)$_t$—S(O)—(CR$^{19}$R$^{20}$)$_s$—, —(CR$^{19}$R$^{20}$)$_t$—S(O)$_2$—(CR$^{19}$R$^{20}$)$_s$—, —(CR$^{19}$R$^{20}$)$_t$—S(O)$_2$NR$^{26}$—(CR$^{19}$R$^{20}$)$_s$—, —(CR$^{19}$R$^{20}$)$_t$—O—(CR$^{19}$R$^{20}$)$_s$—, —(CR$^{19}$R$^{20}$)$_t$—OC(O)—(CR$^{19}$R$^{20}$)$_s$—, —(CR$^{19}$R$^{20}$)$_t$—OC(S)—(CR$^{19}$R$^{20}$)$_s$—, —(CR$^{19}$R$^{20}$)$_t$—OC(O)NR$^{26}$—(CR$^{19}$R$^{20}$)$_s$—, —(CR$^{19}$R$^{20}$)$_t$—OC(S)NR$^{26}$—(CR$^{19}$R$^{20}$)$_s$—, —(CR$^{19}$R$^{20}$)$_t$—S—(CR$^{19}$R$^{20}$)$_s$—, —(CR$^{19}$R$^{20}$)$_t$—NR$^{26}$—(CR$^{19}$R$^{20}$)$_s$—, —(CR$^{19}$R$^{20}$)$_t$—NR$^{26}$C(O)—(CR$^{19}$R$^{20}$)$_s$—, —(CR$^{19}$R$^{20}$)$_t$—NR$^{26}$C(S)—(CR$^{19}$R$^{20}$)$_s$—, —(CR$^{19}$R$^{20}$)$_t$—NR$^{26}$C(O)O—(CR$^{19}$R$^{20}$)$_s$—, —(CR$^{19}$R$^{20}$)$_t$—NR$^{26}$C(S)O—(CR$^{19}$R$^{20}$)$_s$—, —(CR$^{19}$R$^{20}$)$_t$—NR$^{26}$C(O)NR$^{26}$—(CR$^{19}$R$^{20}$)$_s$—, —(CR$^{19}$R$^{20}$)$_t$—NR$^{26}$C(S)NR$^{26}$—(CR$^{19}$R$^{20}$)$_s$—, —(CR$^{19}$R$^{20}$)$_t$—NR$^{26}$S(O)$_2$—(CR$^{19}$R$^{20}$)$_s$—, and —(CR$^{19}$R$^{20}$)$_t$—NR$^{26}$S(O)$_2$NR$^{26}$—(CR$^{19}$R$^{20}$)$_s$—, preferably a bond, —NR$^{39}$—, —S—, —O—, —NR$^{39}$CH$_2$—, —NR$^{39}$CH$_2$CH$_2$—, —NR$^{39}$CH(R$^{40}$)—, —SCH$_2$—, —OCH$_2$—, —C(O)NR$^{39}$—, —S(O)$_2$NR$^{39}$—, —CH$_2$NR$^{39}$—, —CH(R$^{40}$)NR$^{39}$—, —NR$^{39}$C(O)—, or —NR$^{39}$S(O)$_2$—, more preferably —NR$^{39}$CH$_2$—, —NR$^{39}$CH(R$^{40}$)— or —NR$^{39}$C(O)—, more preferably —NHCH$_2$—, —NHCH(CH$_3$)— or —NHC(O)—;
$M_8$ is selected from the group consisting of a bond, —(CR$^{19}$R$^{20}$)$_u$—, —(CR$^{19}$R$^{20}$)$_t$—C(O)—(CR$^{19}$R$^{20}$)$_s$—, —(CR$^{19}$R$^{20}$)$_t$—C(S)—(CR$^{19}$R$^{20}$)$_s$—, —(CR$^{19}$R$^{20}$)$_t$—C(O)O—(CR$^{19}$R$^{20}$)$_s$—, —(CR$^{19}$R$^{20}$)$_t$—C(S)O—(CR$^{19}$R$^{20}$)$_s$—, —(CR$^{19}$R$^{20}$)$_t$—C(O)NR$^{26}$—(CR$^{19}$R$^{20}$)$_s$—, —(CR$^{19}$R$^{20}$)$_t$—C(S)NR$^{26}$—(CR$^{19}$R$^{20}$)$_s$—, —(CR$^{19}$R$^{20}$)$_t$—S(O)—(CR$^{19}$R$^{20}$)$_s$—, —(CR$^{19}$R$^{20}$)$_t$—S(O)$_2$—(CR$^{19}$R$^{20}$)$_s$—, —(CR$^{19}$R$^{20}$)$_t$—S(O)$_2$NR$^{26}$—(CR$^{19}$R$^{20}$)$_s$—, —(CR$^{19}$R$^{20}$)$_w$—O—(CR$^{19}$R$^{20}$)$_s$—, —(CR$^{19}$R$^{20}$)$_w$—OC(O)—(CR$^{19}$R$^{20}$)$_s$—, —(CR$^{19}$R$^{20}$)$_w$—OC(S)—(CR$^{19}$R$^{20}$)$_s$—, —(CR$^{19}$R$^{20}$)$_w$—OC(O)NR$^{26}$—(CR$^{19}$R$^{20}$)$_s$—, —(CR$^{19}$R$^{20}$)$_w$—OC(S)NR$^{26}$—(CR$^{19}$R$^{20}$)$_s$—, —(CR$^{19}$R$^{20}$)$_w$—S—(CR$^{19}$R$^{20}$)$_s$—, —(CR$^{19}$R$^{20}$)$_w$—NR$^{26}$—(CR$^{19}$R$^{20}$)$_s$—, —(CR$^{19}$R$^{20}$)$_w$—NR$^{26}$C(O)—(CR$^{19}$R$^{20}$)$_s$—, —(CR$^{19}$R$^{20}$)$_w$—NR$^{26}$C(S)—(CR$^{19}$R$^{20}$)$_s$—, —(CR$^{19}$R$^{20}$)$_w$—NR$^{26}$C(O)O—(CR$^{19}$R$^{20}$)$_s$—, —(CR$^{19}$R$^{20}$)$_w$—NR$^{26}$C(S)O—(CR$^{19}$R$^{20}$)$_s$—, —(CR$^{19}$R$^{20}$)$_w$—NR$^{26}$C(O)NR$^{26}$—(CR$^{19}$R$^{20}$)$_s$—, —(CR$^{19}$R$^{20}$)$_w$—NR$^{26}$C(S)NR$^{26}$—(CR$^{19}$R$^{20}$)$_s$—, —(CR$^{19}$R$^{20}$)$_w$—NR$^{26}$S(O)$_2$—(CR$^{19}$R$^{20}$)$_s$—, and —(CR$^{19}$R$^{20}$)$_w$—NR$^{26}$S(O)$_2$NR$^{26}$—(CR$^{19}$R$^{20}$)$_s$—, preferably a bond, —CH$_2$—, —CH$_2$C(O)—, —S(O)$_2$—, —S(O)$_2$CH$_2$—, —S(O)$_2$CH(CH$_3$)—, —S(O)$_2$CH$_2$CH$_2$—, —S(O)$_2$NR$^{39}$—, —S(O)$_2$NR$^{39}$CH$_2$—, —S(O)$_2$NR$^{39}$CH(CH$_3$)—, —S(O)$_2$NR$^{39}$CH$_2$CH$_2$—, —C(O)—, —C(O)CH$_2$—, —C(O)CH(CH$_3$)—, —C(O)CH$_2$CH$_2$—, —C(O)NR$^{39}$—, —C(O)NR$^{39}$CH$_2$—, —C(O)NR$^{39}$CH(CH$_3$)—, and —C(O)NR$^{39}$CH$_2$CH$_2$—, more preferably —C(O)NR$^{39}$CH$_2$—, —C(O)NR$^{39}$CH(R$^{40}$)— or —C(O)NR$^{39}$CH$_2$CH$_2$—, more preferably —C(O)NHCH$_2$—, —C(O)NHCH(CH$_3$)— or —C(O)NHCH$_2$CH$_2$—;

$Q^1$, $Q^{11}$, $Q^{41}$, $Q^{61}$, and $Q^{141}$ are aryl or heteroaryl, wherein aryl or heteroaryl are optionally substituted with one or more substituents selected from the group consisting of, —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as a substituent of $Q^1$, $Q^{11}$, $Q^{41}$, $Q^{61}$, or $Q^{141}$, or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino, preferably $Q^1$, $Q^{11}$, $Q^{41}$, $Q^{61}$, and $Q^{141}$ are aryl or heteroaryl, wherein aryl or heteroaryl are optionally substituted with one or more halogen, lower alkyl, fluoro substituted lower alkyl, —NHS(O)$_2$R$^{41}$, —NHC(O)R$^{41}$, —NHR$^{41}$, —NR$^{41}$R$^{41}$, —OR$^{41}$ or —S(O)$_2$R$^{41}$;

$Q^{12}$ is fluoro, chloro or —CF$_3$;

$Q^{13}$ and $Q^{14}$ are independently hydrogen, fluoro, chloro, lower alkyl, or fluoro substituted lower alkyl;

$Q^{22}$, $Q^{24}$, $Q^{52}$ and $Q^{54}$ are independently selected from the group consisting of hydrogen, halogen, lower alkyl, fluoro substituted lower alkyl, —NR$^{44}$R$^{44}$, —OR$^{44}$, and —SR$^{44}$, provided, however, that at least one of $Q^{22}$ and $Q^{24}$ and at least one of $Q^{52}$ and $Q^{54}$ is hydrogen, fluoro, chloro, lower alkyl or fluoro substituted lower alkyl;

$Q^{74}$ and $Q^{152}$ are hydrogen, fluoro, chloro, lower alkyl, fluoro substituted lower alkyl, —NR$^{44}$R$^{44}$, —OR$^{44}$, or SR$^{44}$;

$Q^{72}$ is hydrogen, lower alkyl or fluoro substituted lower alkyl;

R$^{39}$, R$^{40}$ and R$^{41}$ are as defined for Formula Ig;

each R$^{44}$ is independently hydrogen, lower alkyl or fluoro substituted lower alkyl; and R$^{19}$, R$^{20}$, R$^{21}$, R$^{26}$, s, t and u are as defined for Formula Ib.

In one embodiment, a compound of Formula II has a structure according to the following sub-generic structure, Formula IIa, Formula IIa

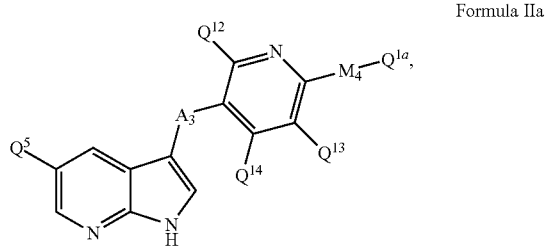

all salts, prodrugs, tautomers, and isomers thereof, wherein:

A$_3$ is —CH$_2$— or —C(O)—;

$Q^{1a}$ is aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, and —OR$^{41}$;

$Q^5$ is hydrogen, —OR$^{43}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{43}$, —NR$^{43}$R$^{43}$, —OR$^{43}$ and —S(O)$_2$R$^{43}$; and M$_4$, $Q^{12}$, $Q^{13}$, $Q^{14}$, R$^{41}$, and R$^{43}$ are as defined for Formula II;

provided, however, that the compound is not

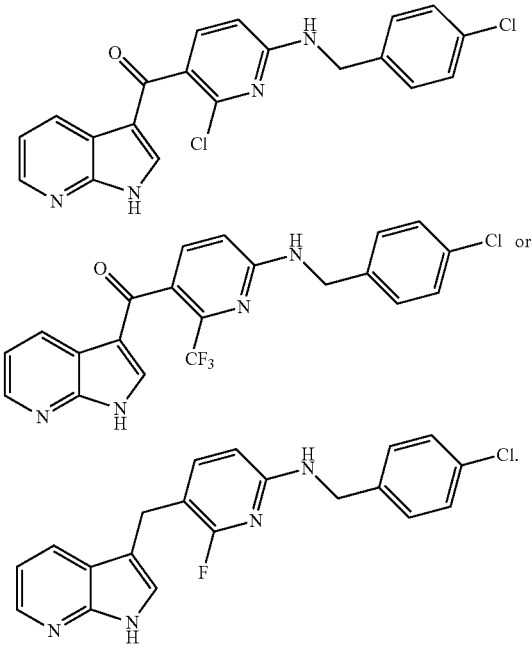

In one embodiment of compounds of Formula IIa, A$_3$ is —CH$_2$— and M$_4$ is —NHCH$_2$—. In one embodiment A$_3$ is —C(O)— and M$_4$ is —NHCH$_2$—. In one embodiment A$_3$ is —C(O)— and M$_4$ is —NHC(O)—. In one embodiment A$_3$ is —CH$_2$— and M$_4$ is —NHC(O)—.

In one embodiment of compounds of Formula IIa, A$_3$ is —CH$_2$—, M$_4$ is —NHCH$_2$—, $Q^5$ is —OR$^{43}$, —CN, C$_{1-3}$ alkyl, fluoro substituted C$_{1-3}$ alkyl, fluoro, chloro, aryl or heteroaryl, wherein aryl or heteroaryl are optionally substituted with one or more substituents selected from the group consisting of halogen, lower alkyl, fluoro substituted lower alkyl, —NHR$^{43}$, —NR$^{43}$R$^{43}$, —OR$^{43}$ and —S(O)$_2$R$^{43}$, and $Q^{13}$ and $Q^{14}$ are hydrogen.

In one embodiment of compounds of Formula IIa, A$_3$ is —C(O)—, M$_4$ is —NHCH$_2$—, $Q^5$ is —OR$^{43}$, —CN, C$_{1-3}$ alkyl, fluoro substituted C$_{1-3}$ alkyl, fluoro, chloro, aryl or heteroaryl, wherein aryl or heteroaryl are optionally substituted with one or more substituents selected from the group consisting of halogen, lower alkyl, fluoro substituted lower alkyl, —NHR$^{43}$, —NR$^{43}$R$^{43}$, —OR$^{43}$ and —S(O)$_2$R$^{43}$, and $Q^{13}$ and $Q^{14}$ are hydrogen.

In one embodiment of compounds of Formula IIa, A$_3$ is —C(O)—, M$_4$ is —NHC(O)—, $Q^5$ is —OR$^{43}$, —CN, C$_{1-3}$ alkyl, fluoro substituted C$_{1-3}$ alkyl, fluoro, chloro, aryl or heteroaryl, wherein aryl or heteroaryl are optionally substituted with one or more substituents selected from the group consisting of halogen, lower alkyl, fluoro substituted lower alkyl, —NHR$^{43}$, —NR$^{43}$R$^{43}$, —OR$^{43}$ and —S(O)$_2$R$^{43}$, and Q$^{13}$ and Q$^{14}$ are hydrogen.

In one embodiment of compounds of Formula IIa, A$_3$ is —CH$_2$—, M$_4$ is —NHC(O)—, Q$^5$ is —OR$^{43}$, —CN, C$_{1-3}$ alkyl, fluoro substituted C$_{1-3}$ alkyl, fluoro, chloro, aryl or heteroaryl, wherein aryl or heteroaryl are optionally substituted with one or more substituents selected from the group consisting of halogen, lower alkyl, fluoro substituted lower alkyl, —NHR$^{43}$, —NR$^{43}$R$^{43}$, —OR$^{43}$ and —S(O)$_2$R$^{43}$, and Q$^{13}$ and Q$^{14}$ are hydrogen.

In one embodiment of compounds of Formula IIa, A$_3$ is —CH$_2$— or —C(O)—; Q$^{1a}$ is aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, and —OR$^{41}$; Q$^5$ is hydrogen, —CN, —OR$^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, and —OR$^{41}$; M$_4$ is —NR$^{39}$CH$_2$—, —NR$^{39}$CH(R$^{40}$)—, —NR$^{39}$CH$_2$CH$_2$—, or —NR$^{39}$C(O)—; Q$^{12}$ is fluoro, chloro or —CF$_3$; and Q$^{13}$ and Q$^{14}$ are independently hydrogen, fluoro, chloro, lower alkyl, or fluoro substituted lower alkyl, wherein R$^{41}$ is as defined for Formula II.

In one embodiment, further to any of the embodiments of Formula IIa above, R$^{43}$ is R$^{41}$ as defined for Formula Ig. In one embodiment, further to any of the embodiments of Formula IIa above, R$^{43}$ is R$^{42}$ as defined for Formula Ig.

In one embodiment, further to any of the embodiments of Formula IIa above, Q$^{1a}$ is phenyl or pyridinyl, wherein phenyl or pyridinyl are substituted with 1 or 2 substituents selected from the group consisting of fluoro, chloro, methyl, methoxy, trifluoromethyl, difluoromethoxy and trifluoromethoxy; A$_3$ is —CH$_2$—; M$_4$ is —NHCH$_2$—; and Q$^5$ is —CN, fluoro, chloro, methyl, trifluoromethyl, methoxy, difluoromethoxy, trifluoromethoxy, aryl or heteroaryl, wherein aryl or heteroaryl are optionally substituted with one or more halogen, lower alkyl, fluoro substituted lower alkyl, lower alkoxy, or fluoro substituted lower alkoxy. In one embodiment, further to any of the embodiments of Formula IIa above, Q$^{1a}$ is phenyl mono substituted with chloro, preferably at the 4-position; A$_3$ is —CH$_2$—; M$_4$ is —NHCH$_2$—; and Q$^5$ is —CN, fluoro, chloro, methyl, trifluoromethyl, methoxy, difluoromethoxy, trifluoromethoxy, aryl or heteroaryl, wherein aryl or heteroaryl are optionally substituted with one or more halogen, lower alkyl, fluoro substituted lower alkyl, lower alkoxy, or fluoro substituted lower alkoxy. In one embodiment, further to any of the embodiments of Formula IIa, Q$^{1a}$ is pyridin-3-yl monosubstituted with methyl, methoxy, trifluoromethyl, difluoromethoxy or trifluoromethoxy, preferably at the 6-position; A$_3$ is —CH$_2$—; M$_4$ is —NHCH$_2$—; Q$^5$ is —CN, fluoro, chloro, methyl, trifluoromethyl, methoxy, difluoromethoxy, trifluoromethoxy, aryl or heteroaryl, wherein aryl or heteroaryl are optionally substituted with one or more halogen, lower alkyl, fluoro substituted lower alkyl, lower alkoxy, or fluoro substituted lower alkoxy.

In one embodiment of compounds of Formula IIa, A$_3$ is —CH$_2$—; M$_4$ is —NHCH$_2$—; Q$^{1a}$ is phenyl or pyridinyl, wherein phenyl or pyridinyl are substituted with 1 or 2 substituents selected from the group consisting of fluoro, chloro, methyl, methoxy, trifluoromethyl, difluoromethoxy and trifluoromethoxy; Q$^5$ is hydrogen, fluoro, chloro, methyl, methoxy, trifluoromethyl, trifluoromethoxy, —CN, or 1-methyl-1H-pyrazole-4-yl; Q$^{12}$ is fluoro or chloro; and Q$^{13}$ and Q$^{14}$ are hydrogen. In one embodiment, A$_3$ is —CH$_2$—; M$_4$ is —NHCH$_2$—; Q$^{1a}$ is phenyl mono substituted with chloro, preferably at the 4-position, Q$^5$ is hydrogen, chloro, methyl, methoxy, or CN; Q$^{12}$ is fluoro or chloro; and Q$^{13}$ and Q$^{14}$ are hydrogen. In one embodiment, A$_3$ is —C$_2$—; M$_4$ is —NHCH$_2$—; Q$^{1a}$ is pyridin-3-yl monosubstituted with methyl, methoxy, trifluoromethyl, difluoromethoxy or trifluoromethoxy, preferably at the 6-position; Q$^5$ is hydrogen, chloro, methyl, methoxy, —CN, or 1-methyl-1H-pyrazole-4-yl; Q$^{12}$ is fluoro or chloro; and Q$^{13}$ and Q$^{14}$ are hydrogen.

In one embodiment of compounds of Formula IIa, the compound is selected from the group consisting of:

(4-Chloro-benzyl)-[5-(5-chloro-1H-pyrrolo[2,3-b]pyridin-3-ylmethyl)-6-fluoro-pyridin-2-yl]-amine (P-0132), (4-Chloro-benzyl)-[6-chloro-5-(1-pyrrolo[2,3-b]pyridin-3-ylmethyl)-pyridin-2-yl]-amine (P-0161),

[6-Chloro-5-(1H-pyrrolo[2,3-b]pyridin-3-ylmethyl)-pyridin-2-yl]-(6-trifluoromethyl-pyridin-3-ylmethyl)-amine (P-0174),

[6-Chloro-5-(5-chloro-1H-pyrrolo[2,3-b]pyridin-3-ylmethyl)-pyridin-2-yl]-(6-trifluoromethyl-pyridin-3-ylmethyl)-amine (P-0176), {6-Chloro-5-[5-(1-methyl-1H-pyrazol-4-yl)-1H-pyrrolo[2,3-b]pyridin-3-ylmethyl]-pyridin-2-yl}-(6-trifluoromethyl-pyridin-3-ylmethyl)-amine (P-0179),

[5-(5-Chloro-1H-pyrrolo[2,3-b]pyridin-3-ylmethyl)-6-fluoro-pyridin-2-yl]-(6-trifluoromethyl-pyridin-3-ylmethyl)-amine (P-0186),

[6-Fluoro-5-(5-methoxy-1H-pyrrolo[2,3-b]pyridin-3-ylmethyl)-pyridin-2-yl]-(6-trifluoromethyl-pyridin-3-ylmethyl)-amine (P-0187),

[6-Fluoro-5-(1H-pyrrolo[2,3-b]pyridin-3-ylmethyl)-pyridin-2-yl]-(6-trifluoromethyl-pyridin-3-ylmethyl)-amine (P-0188), 3-{2-Chloro-6-[(6-trifluoromethyl-pyridin-3-ylmethyl)-amino]-pyridin-3-ylmethyl}-1H-pyrrolo[2,3-b]pyridine-5-carbonitrile (P-0232),

[6-Chloro-5-(5-methyl-1H-pyrrolo[2,3-b]pyridin-3-ylmethyl)-pyridin-2-yl]-(6-trifluoromethyl-pyridin-3-ylmethyl)-amine (P-0233),

[6-Chloro-5-(5-methyl-1H-pyrrolo[2,3-b]pyridin-3-ylmethyl)-pyridin-2-yl]-(6-trifluoromethyl-pyridin-3-ylmethyl)-amine (P-0234),

[6-Fluoro-5-(1H-pyrrolo[2,3-b]pyridin-3-ylmethyl)-pyridin-2-yl]-(6-methoxy-pyridin-3-ylmethyl)-amine (P-0378),

[5-(5-Chloro-1H-pyrrolo[2,3-b]pyridin-3-ylmethyl)-6-fluoro-pyridin-2-yl]-(6-methoxy-pyridin-3-ylmethyl)-amine (P-0379), (5-Fluoro-pyridin-3-ylmethyl)-[6-fluoro-5-(1H-pyrrolo[2,3-b]pyridin-3-ylmethyl)-pyridin-2-yl]-amine (P-0414), 3-{2-Fluoro-6-[(5-fluoro-pyridin-3-ylmethyl)-amino]-pyridin-3-ylmethyl}-1H-pyrrolo[2,3-b]pyridine-5-carbonitrile (P-0415), 3-[6-(4-Chloro-benzylamino)-2-fluoro-pyridin-3-ylmethyl]-1H-pyrrolo[2,3-b]pyridine-5-carbonitrile (P-0432), and all salts, prodrugs, tautomers, and isomers thereof.

In one embodiment, a compound of Formula II has a structure according to the following sub-generic structure, Formula IIb, Formula IIb

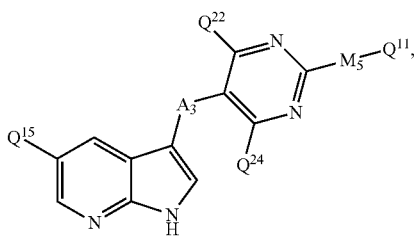

all salts, prodrugs, tautomers, and isomers thereof,
wherein:
$A_2$ is selected from the group consisting of —$CR^{19}R^{20}$—, —C(O)—, —C(S)—, —S—, —S(O)—, —$S(O)_2$—, —$NR^{21}$—, and —O—;
$Q^{15}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —$NH_2$, —$NO_2$, —CN, —NHC(O)$NH_2$, —NHC(S)$NH_2$, —NHS(O)$_2NH_2$, —C(O)$NH_2$, —C(S)$NH_2$, —S(O)$_2NH_2$, —$NR^{24}R^{25}$, —$NHR^{23}$, —$OR^{23}$, —$SR^{23}$, —C(O)$R^{23}$, —C(S)$R^{23}$, —S(O)$R^{23}$, —S(O)$_2R^{23}$, —C(O)$NHR^{23}$, —C(O)$NR^{23}R^{23}$, —C(S)$NHR^{23}$, —C(S)$NR^{23}R^{23}$, —S(O)$NHR^{23}$, —S(O)$_2NHR^{23}$, —NHC(O)$R^{23}$, —$NR^{23}$C(O)$R^{23}$, —NHC(S)$R^{23}$, —$NR^{23}$C(S)$R^{23}$, —NHS(O)$_2R^{23}$, —$NR^{23}$S(O)$_2R^{23}$, —NHC(O)$NHR^{23}$, —$NR^{23}$C(O)$NH_2$, —$NR^{23}$C(O)$NHR^{23}$, —NHC(O)$NR^{23}R^{23}$, —$NR^{23}$C(O)$NR^{23}R^{23}$, —NHC(S)$NHR^{23}$, —$NR^{23}$C(S)$NH_2$, —$NR^{23}$C(S)$NHR^{23}$, —NHC(S)$NR^{23}R^{23}$, —$NR^{23}$C(S)$NR^{23}R^{23}$, —NHS(O)$_2NHR^{23}$, —$NR^{23}$S(O)$_2NH_2$, —$NR^{23}$S(O)$_2NHR^{23}$, —NHS(O)$_2NR^{23}R^{23}$, and —$NR^{23}$S(O)$_2NR^{23}R^{23}$; $M_5$, $Q^{11}$, $Q^{22}$ and $Q^{24}$ are as defined for Formula II; and $R^{19}$, $R^{20}$, $R^{21}$, $R^{23}$, $R^{24}$, and $R^{25}$ are as defined for Formula Ib;
provided, however, that the compound is not

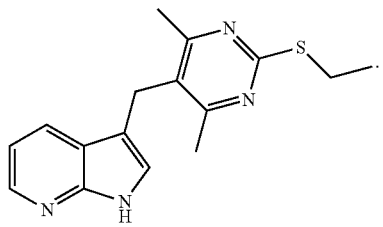 [SMILES: CCSc1nc(C)c(Cc2c[nH]c3ncccc23)c(C)n1]

In one embodiment of compounds of Formula IIb, $M_5$ is —$(CR^{19}R^{20})_t$—$NR^{26}$—$(CR^{19}R^{20})_s$— or —$(CR^{19}R^{20})_t$—$NR^{26}$C(O)—$(CR^{19}R^{20})_s$—, preferably —$NR^{26}$—$(CR^{19}R^{20})_s$— or —$NR^{26}$C(O)—$(CR^{19}R^{20})_s$—, more preferably —$NR^{39}CH_2$—, —$NR^{39}$CH($R^{40}$)— or —$NR^{39}$C(O)—, wherein $R^{39}$ is hydrogen or lower alkyl and $R^{40}$ is lower alkyl or fluoro substituted lower alkyl. In one embodiment, $A_2$ is —$CR^{19}R^{20}$— or —C(O)—, preferably —$CH_2$— or —C(O)—. In one embodiment, $Q^{11}$ is cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —S(O)$_2R^{23}$ and $Q^{15}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —S(O)$_2R^{23}$. Further to any of the above embodiments, $Q^{22}$ and $Q^{24}$ are independently hydrogen, fluoro, chloro, or —$CF_3$, preferably $Q^{22}$ and $Q^{24}$ are hydrogen.

In one embodiment of compounds of Formula IIb, $M_5$ is —$(CR^{19}R^{20})_t$—$NR^{26}$—$(CR^{19}R^{20})_s$— or —$(CR^{19}R^{20})_t$—$NR^{26}$C(O)—$(CR^{19}R^{20})_s$—, preferably —$NR^{26}$—$(CR^{19}R^{20})_s$— or —$NR^{26}$C(O)—$(CR^{19}R^{20})_s$—, more preferably —$NR^{39}CH_2$—, —$NR^{39}$CH($R^{40}$)— or —$NR^{39}$C(O)—, and $A_2$ is —$CR^{19}R^{20}$— or —C(O)—, preferably —$CH_2$— or —C(O)—. In one embodiment, $M_5$ is —$(CR^{19}R^{20})_t$—$NR^{26}$—$(CR^{19}R^{20})_s$— or —$(CR^{19}R^{20})_t$—$NR^{26}$C(O)—$(CR^{19}R^{20})_s$—, preferably —$NR^{26}$—$(CR^{19}R^{20})_s$— or —$NR^{26}$C(O)—$(CR^{19}R^{20})_s$—, more preferably —$NR^{39}CH_2$—, —$NR^{39}$CH($R^{40}$)— or —$NR^{39}$C(O)—; $A_2$ is —$CR^{19}R^{20}$— or —C(O)—, preferably —$CH_2$— or —C(O)—; $Q^{11}$ is cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —S(O)$_2R^{23}$; $Q^{15}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —S(O)$_2R^{23}$. In one embodiment, $M_5$ is —$(CR^{19}R^{20})_t$—$NR^{26}$—$(CR^{19}R^{20})_s$— or —$(CR^{19}R^{20})_t$—$NR^{26}$C(O)—$(CR^{19}R^{20})_s$—, preferably)-$NR^{26}$—$(CR^{19}R^{20})_s$— or —$NR^{26}$C(O)—$(CR^{19}R^{20})_s$—, more preferably —$NR^{39}CH_2$—, —$NR^{39}$CH($R^{40}$)— or —$NR^{39}$C(O)—; $A_2$ is —$CR^{19}R^{20}$— or —C(O)—, preferably —$CH_2$— or —C(O)—; $Q^{11}$ is cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —S(O)$_2R^{23}$; $Q^{15}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —S(O)$_2R^{23}$; and $Q^{22}$ and $Q^{24}$ are independently hydrogen, fluoro, chloro, or —$CF_3$, preferably $Q^{22}$ and $Q^{24}$ are hydrogen.

In one embodiment of compounds of Formula IIb, $M_5$ is —$NR^{39}CH_2$—, —$NR^{39}$CH($R^{40}$)—, —$NR^{39}CH_2CH_2$—, or —$NR^{39}$C(O)—; $A_2$ is —$CH_2$— or —C(O)—, preferably —$CH_2$—; $Q^{11}$ is cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{41}$, —$NR^{41}R^{41}$, —$OR^{41}$ and —S(O)$_2R^{41}$; $Q^{15}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_1$R$^{41}$; Q$^{22}$ and Q$^{24}$ are independently hydrogen, fluoro, chloro, lower alkyl, or fluoro substituted lower alkyl, preferably hydrogen, fluoro, chloro, or —CF$_3$, more preferably both Q$^{22}$ and Q$^{24}$ are hydrogen, wherein R$^{41}$ is as defined for Formula Ig.

In one embodiment of compounds of Formula IIb, A$_2$ is —CH$_2$— or —C(O)—, preferably —CH$_2$—; Q$^{11}$ is cycloalkyl, heterocycloalkyl, aryl or heteroaryl, wherein cycloalkyl, heterocycloalkyl, aryl or heteroaryl are optionally substituted with one or more substituents selected from the group consisting of —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of Q$^{11}$, or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino; Q$^{15}$ is hydrogen, —CN, —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, and —OR$^{41}$; M$_5$ is a bond, —NR$^{39}$—, —S—, —O—, —NR$^{39}$CH$_2$—, —NR$^{39}$CH$_2$CH$_2$—, —NR$^{39}$CH(R$^{40}$)—, —SCH$_2$—, —OCH$_2$—, —C(O)NR$^{39}$—, —S(O)$_2$NR$^{39}$—, —CH$_2$NR$^{39}$—, —CH(R$^{40}$)NR$^{39}$—, —NR$^{39}$C(O)—, or —NR$^{39}$S(O)$_2$—; and Q$^{22}$, and Q$^{24}$ are independently hydrogen, halogen, lower alkyl, fluoro substituted lower alkyl, —NR$^{44}$R$^{44}$, —OR$^{44}$, or —SR$^{44}$, provided, however, that at least one of Q$^{22}$ and Q$^{24}$ is hydrogen, fluoro, chloro, lower alkyl or fluoro substituted lower alkyl, wherein R$^{39}$, R$^{40}$, R$^{41}$, and R$^{42}$ are as defined for Formula Ig, and R$^{44}$ is as defined for Formula II.

In one embodiment of compounds of Formula IIb, A$_2$ is —CH$_2$—; Q$^{11}$ is aryl or heteroaryl, wherein aryl or heteroaryl are optionally substituted with one or more substituents selected from the group consisting of fluoro, chloro, lower alkyl, fluoro substituted lower alkyl, lower alkoxy, fluoro substituted lower alkoxy, di-alkylamino, and heterocycloalkyl; Q$^{15}$ is hydrogen, —CN, fluoro, chloro, lower alkyl, fluoro substituted lower alkyl, lower alkoxy, or fluoro substituted lower alkoxy; M$_5$ is —NR$^{39}$CH$_2$—, —NR$^{39}$CH$_2$CH$_2$—, or —NR$^{39}$CH(R$^{40}$)—; and Q$^{22}$ and Q$^{24}$ are independently hydrogen, halogen, lower alkyl, fluoro substituted lower alkyl, lower alkoxy, or fluoro substituted lower alkoxy, provided, however, that at least one of Q$^{22}$ and Q$^{24}$ is hydrogen, fluoro, chloro, lower alkyl or fluoro substituted lower alkyl.

In one embodiment, further to any of the embodiments of Formula IIb above, each occurrence of R$^{41}$ is R$^{42}$ as defined for Formula Ig.

In one embodiment of compounds of Formula IIb, M$_5$ is —NHCH$_2$CH$_2$—, —NHCH$_2$—, —N(CH$_3$)CH$_2$—, or —NHCH(CH$_3$)—, preferably —NHCH$_2$—; A$_2$ is —CH$_2$—; Q$^{11}$ is cycloalkyl, heterocycloalkyl, phenyl or heteroaryl, wherein phenyl or heteroaryl are optionally substituted with 1 or 2 substituents selected from the group consisting of halogen, lower alkyl, fluoro substituted lower alkyl, lower alkoxy, fluoro substituted lower alkoxy, di-alkylamino, and heterocycloalkyl; Q$^{15}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, lower alkoxy, and fluoro substituted lower alkoxy; and Q$^{22}$ and Q$^{24}$ are independently hydrogen, fluoro, chloro, lower alkyl, or fluoro substituted lower alkyl, preferably hydrogen, fluoro, chloro, or —CF$_3$, more preferably both Q$^{22}$ and Q$^{24}$ are hydrogen.

In one embodiment of compounds of Formula IIb, M$_5$ is —NHCH$_2$—; A$_2$ is —CH$_2$—; Q$^{11}$ is phenyl substituted with 1 or 2 substituents selected from the group consisting of fluoro, chloro, methyl, fluoro substituted methyl, methoxy, and fluoro substituted methoxy; Q$^{15}$ is hydrogen, —CN, fluoro, chloro, lower alkyl, fluoro substituted lower alkyl, lower alkoxy, fluoro substituted lower alkoxy, preferably hydrogen or chloro; and Q$^{22}$ and Q$^{24}$ are hydrogen.

In one embodiment of compounds of Formula IIb, the compound is selected from the group consisting of:
(4-Chloro-benzyl)-[5-(5-chloro-1H-pyrrolo[2,3-b]pyridin-3-ylmethyl)-pyrimidin-2-yl]-amine (P-0260),
[5-(5-Chloro-1H-pyrrolo[2,3-b]pyridin-3-ylmethyl)-pyrimidin-2-yl]-(2,6-difluoro-benzyl)-amine (P-0261),
[5-(5-Chloro-1H-pyrrolo[2,3-b]pyridin-3-ylmethyl)-pyrimidin-2-yl]-(2-trifluoromethyl-benzyl)-amine (P-0262),
(2-Chloro-benzyl)-[5-(5-chloro-1H-pyrrolo[2,3-b]pyridin-3-ylmethyl)-pyrimidin-2-yl]-amine (P-0263),
[5-(5-Chloro-1H-pyrrolo[2,3-b]pyridin-3-ylmethyl)-pyrimidin-2-yl]-(2-fluoro-benzyl)-amine (P-0264),
[5-(5-Chloro-1H-pyrrolo[2,3-b]pyridin-3-ylmethyl)-pyrimidin-2-yl]-(2,4-difluoro-benzyl)-amine (P-0265),
[5-(5-Chloro-1H-pyrrolo[2,3-b]pyridin-3-ylmethyl)-pyrimidin-2-yl]-(4-trifluoromethyl-benzyl)-amine (P-0266),
[5-(5-Chloro-1H-pyrrolo[2,3-b]pyridin-3-ylmethyl)-pyrimidin-2-yl]-(2,5-difluoro-benzyl)-amine (P-0267),
[5-(5-Chloro-1H-pyrrolo[2,3-b]pyridin-3-ylmethyl)-pyrimidin-2-yl]-(3-trifluoromethyl-benzyl)-amine (P-0268),
[5-(5-Chloro-1H-pyrrolo[2,3-b]pyridin-3-ylmethyl)-pyrimidin-2-yl]-(2-fluoro-5-trifluoromethyl-benzyl)-amine (P-0289),
(2-Fluoro-5-trifluoromethyl-benzyl)-[5-(1H-pyrrolo[2,3-b]pyridin-3-ylmethyl)-pyrimidin-2-yl]-amine (P-0291),
(2,5-Difluoro-benzyl)-[5-(1H-pyrrolo[2,3-b]pyridin-3-ylmethyl)-pyrimidin-2-yl]-amine (P-0292),
(2-Chloro-5-trifluoromethyl-benzyl)-[5-(1H-pyrrolo[2,3-b]pyridin-3-ylmethyl)-pyrimidin-2-yl]-amine (P-0293),
(3-Fluoro-5-trifluoromethyl-benzyl)-[5-(1H-pyrrolo[2,3-b]pyridin-3-ylmethyl)-pyrimidin-2-yl]-amine (P-0294),
(3,5-Difluoro-benzyl)-[5-(1H-pyrrolo[2,3-b]pyridin-3-ylmethyl)-pyrimidin-2-yl]-amine (P-0295),
(2-Fluoro-benzyl)-[5-(1H-pyrrolo[2,3-b]pyridin-3-ylmethyl)-pyrimidin-2-yl]-amine (P-0300),
(2-Chloro-benzyl)-[5-(1H-pyrrolo[2,3-b]pyridin-3-ylmethyl)-pyrimidin-2-yl]-amine (P-0301),
[5-(1H-Pyrrolo[2,3-b]pyridin-3-ylmethyl)-pyrimidin-2-yl]-(2-trifluoromethyl-benzyl)-amine (P-0302),
[5-(1H-Pyrrolo[2,3-b]pyridin-3-ylmethyl)-pyrimidin-2-yl]-(2-trifluoromethoxy-benzyl)-amine (P-0303),
(5-Chloro-2-fluoro-benzyl)-[5-(1H-pyrrolo[2,3-b]pyridin-3-ylmethyl)-pyrimidin-2-yl]-amine (P-0304),
(2,4-Dichloro-benzyl)-[5-(1H-pyrrolo[2,3-b]pyridin-3-ylmethyl)-pyrimidin-2-yl]-amine (P-0305), (2,4-Difluoro-benzyl)-[5-(1H-pyrrolo[2,3-b]pyridin-3-ylmethyl)-pyrimidin-2-yl]-amine (P-0306),
(4-Chloro-benzyl)-[5-(1H-pyrrolo[2,3-b]pyridin-3-ylmethyl)-pyrimidin-2-yl]-amine (P-0307),
[5-(1H-Pyrrolo[2,3-b]pyridin-3-ylmethyl)-pyrimidin-2-yl]-(4-trifluoromethyl-benzyl)-amine (P-0308),
(2-Fluoro-3-trifluoromethyl-benzyl)-[5-(1H-pyrrolo[2,3-b]pyridin-3-ylmethyl)-pyrimidin-2-yl]-amine (P-0309),
(2,5-Dichloro-benzyl)-[5-(1H-pyrrolo[2,3-b]pyridin-3-ylmethyl)-pyrimidin-2-yl]-amine (P-0310),
(3-Chloro-2-fluoro-benzyl)-[5-(1H-pyrrolo[2,3-b]pyridin-3-ylmethyl)-pyrimidin-2-yl]-amine (P-0311),
(2-Difluoromethoxy-benzyl)-[5-(1H-pyrrolo[2,3-b]pyridin-3-ylmethyl)-pyrimidin-2-yl]-amine (P-0312),
(2,3-Dichloro-benzyl)-[5-(1H-pyrrolo[2,3-b]pyridin-3-ylmethyl)-pyrimidin-2-yl]-amine (P-0313),
(4-Chloro-2-fluoro-benzyl)-[5-(1H-pyrrolo[2,3-b]pyridin-3-ylmethyl)-pyrimidin-2-yl]-amine (P-0314),
(5-Fluoro-2-trifluoromethyl-benzyl)-[5-(1H-pyrrolo[2,3-b]pyridin-3-ylmethyl)-pyrimidin-2-yl]-amine (P-0315),
(2-Chloro-4-fluoro-benzyl)-[5-(1H-pyrrolo[2,3-b]pyridin-3-ylmethyl)-pyrimidin-2-yl]-amine (P-0316),
(5-Chloro-2-methyl-benzyl)-[5-(1H-pyrrolo[2,3-b]pyridin-3-ylmethyl)-pyrimidin-2-yl]-amine (P-0317),
(5-Fluoro-2-methyl-benzyl)-[5-(1H-pyrrolo[2,3-b]pyridin-3-ylmethyl)-pyrimidin-2-yl]-amine (P-0318),
(2-Fluoro-4-trifluoromethyl-benzyl)-[5-(1H-pyrrolo[2,3-b]pyridin-3-ylmethyl)-pyrimidin-2-yl]-amine (P-0319),
(4-Fluoro-2-trifluoromethyl-benzyl)-[5-(1H-pyrrolo[2,3-b]pyridin-3-ylmethyl)-pyrimidin-2-yl]-amine (P-0320),
[5-(5-Chloro-1H-pyrrolo[2,3-b]pyridin-3-ylmethyl)-pyrimidin-2-yl]-(2-difluoromethoxy-benzyl)-amine (P-0390),
[5-(5-Chloro-1H-pyrrolo[2,3-b]pyridin-3-ylmethyl)-pyrimidin-2-yl]-(5-fluoro-2-trifluoromethyl-benzyl)-amine (P-0391),
(3-Chloro-2-fluoro-benzyl)-[5-(5-chloro-1H-pyrrolo[2,3-b]pyridin-3-ylmethyl)-pyrimidin-2-yl]-amine (P-0392),
[5-(5-Chloro-1H-pyrrolo[2,3-b]pyridin-3-ylmethyl)-pyrimidin-2-yl]-(2-fluoro-3-trifluoromethyl-benzyl)-amine (P-0393),
[5-(5-Chloro-1H-pyrrolo[2,3-b]pyridin-3-ylmethyl)-pyrimidin-2-yl]-(2-fluoro-4-trifluoromethyl-benzyl)-amine (P-0394),
[5-(5-Chloro-1H-pyrrolo[2,3-b]pyridin-3-ylmethyl)-pyrimidin-2-yl]-(2,3-difluoro-benzyl)-amine (P-0395),
(2-Chloro-4-fluoro-benzyl)-[5-(5-chloro-1H-pyrrolo[2,3-b]pyridin-3-ylmethyl)-pyrimidin-2-yl]-amine (P-0396),
[5-(5-Chloro-1H-pyrrolo[2,3-b]pyridin-3-ylmethyl)-pyrimidin-2-yl]-(2-trifluoromethoxy-benzyl)-amine (P-0402),
(2-Chloro-5-fluoro-benzyl)-[5-(1H-pyrrolo[2,3-b]pyridin-3-ylmethyl)-pyrimidin-2-yl]-amine (P-0407),
(2-Chloro-5-fluoro-benzyl)-[5-(5-chloro-1H-pyrrolo[2,3-b]pyridin-3-ylmethyl)-pyrimidin-2-yl]-amine (P-0408),
[5-(5-Chloro-1H-pyrrolo[2,3-b]pyridin-3-ylmethyl)-pyrimidin-2-yl]-pyridin-4-ylmethyl-amine (P-0416),
[5-(5-Chloro-1H-pyrrolo[2,3-b]pyridin-3-ylmethyl)-pyrimidin-2-yl]-(2-pyrrolidin-1-yl-ethyl)-amine (P-0417),
Benzyl-[5-(5-chloro-1H-pyrrolo[2,3-b]pyridin-3-ylmethyl)-pyrimidin-2-yl]-amine (P-0418),
Benzyl-[5-(5-chloro-1H-pyrrolo[2,3-b]pyridin-3-ylmethyl)-pyrimidin-2-yl]-methyl-amine (P-0419),
[5-(5-Chloro-1H-pyrrolo[2,3-b]pyridin-3-ylmethyl)-pyrimidin-2-yl]-(4-trifluoromethoxy-benzyl)-amine (P-0420),
(3-Chloro-benzyl)-[5-(5-chloro-1H-pyrrolo[2,3-b]pyridin-3-ylmethyl)-pyrimidin-2-yl]-amine (P-0421),
[5-(5-Chloro-1H-pyrrolo[2,3-b]pyridin-3-ylmethyl)-pyrimidin-2-yl]-pyridin-3-ylmethyl-amine (P-0422),
[5-(5-Chloro-1H-pyrrolo[2,3-b]pyridin-3-ylmethyl)-pyrimidin-2-yl]-(4-fluoro-benzyl)-amine (P-0423),
(3-Chloro-benzyl)-[5-(5-chloro-1H-pyrrolo[2,3-b]pyridin-3-ylmethyl)-pyrimidin-2-yl]-methyl-amine (P-0424),
[5-(5-Chloro-1H-pyrrolo[2,3-b]pyridin-3-ylmethyl)-pyrimidin-2-yl]-(3,5-difluoro-benzyl)-amine (P-0425),
[5-(5-Chloro-1H-pyrrolo[2,3-b]pyridin-3-ylmethyl)-pyrimidin-2-yl]-[1-(2-fluoro-phenyl)-ethyl]-amine (P-0426),
[1-(4-Chloro-phenyl)-ethyl]-[5-(5-chloro-1H-pyrrolo[2,3-b]pyridin-3-ylmethyl)-pyrimidin-2-yl]-amine (P-0427),
[5-(5-Chloro-1H-pyrrolo[2,3-b]pyridin-3-ylmethyl)-pyrimidin-2-yl]-[(S)-1-(4-fluoro-phenyl)-ethyl]-amine (P-0428),
[5-(5-Chloro-1H-pyrrolo[2,3-b]pyridin-3-ylmethyl)-pyrimidin-2-yl]-(6-trifluoromethyl-pyridin-3-ylmethyl)-amine (P-0429),
(2-Chloro-benzyl)-[5-(5-chloro-1H-pyrrolo[2,3-b]pyridin-3-ylmethyl)-pyrimidin-2-yl]-methyl-amine (P-0430),
[5-(5-Chloro-1H-pyrrolo[2,3-b]pyridin-3-ylmethyl)-pyrimidin-2-yl]-(2-methyl-benzyl)-amine (P-0431),
[5-(5-Chloro-1H-pyrrolo[2,3-b]pyridin-3-ylmethyl)-pyrimidin-2-yl]-(2-methoxy-benzyl)-amine (P-0433),
[5-(5-Chloro-1H-pyrrolo[2,3-b]pyridin-3-ylmethyl)-pyrimidin-2-yl]-(2-morpholin-4-yl-ethyl)-amine (P-0434),
[5-(5-Chloro-1H-pyrrolo[2,3-b]pyridin-3-ylmethyl)-pyrimidin-2-yl]-cyclohexylmethyl-amine (P-0435),
[5-(5-Chloro-1H-pyrrolo[2,3-b]pyridin-3-ylmethyl)-pyrimidin-2-yl]-pyridin-2-ylmethyl-amine (P-0436),
[2-(4-Chloro-phenyl)-ethyl]-[5-(5-chloro-1H-pyrrolo[2,3-b]pyridin-3-ylmethyl)-pyrimidin-2-yl]-amine (P-0437),
[5-(5-Chloro-1H-pyrrolo[2,3-b]pyridin-3-ylmethyl)-pyrimidin-2-yl]-(4-difluoromethoxy-benzyl)-amine (P-0438),
[5-(5-Chloro-1H-pyrrolo[2,3-b]pyridin-3-ylmethyl)-pyrimidin-2-yl]-(4-methoxy-benzyl)-amine (P-0439),
[5-(5-Chloro-1H-pyrrolo[2,3-b]pyridin-3-ylmethyl)-pyrimidin-2-yl]-(4-methyl-benzyl)-amine (P-0440),
[5-(5-Chloro-1H-pyrrolo[2,3-b]pyridin-3-ylmethyl)-pyrimidin-2-yl]-(2-methoxy-ethyl)-amine (P-0441),
[5-(5-Chloro-1H-pyrrolo[2,3-b]pyridin-3-ylmethyl)-pyrimidin-2-yl]-(3-fluoro-benzyl)-amine (P-0442),
(3-Chloro-4-fluoro-benzyl)-[5-(5-chloro-1H-pyrrolo[2,3-b]pyridin-3-ylmethyl)-pyrimidin-2-yl]-amine (P-0443),
[5-(5-Chloro-1H-pyrrolo[2,3-b]pyridin-3-ylmethyl)-pyrimidin-2-yl]-(2-ethoxy-benzyl)-amine (P-0444),
[5-(5-Chloro-1H-pyrrolo[2,3-b]pyridin-3-ylmethyl)-pyrimidin-2-yl]-(4-morpholin-4-yl-benzyl)-amine (P-0445),
[5-(5-Chloro-1H-pyrrolo[2,3-b]pyridin-3-ylmethyl)-pyrimidin-2-yl]-(3-difluoromethoxy-benzyl)-amine (P-0446),
(4-Chloro-3-fluoro-benzyl)-[5-(5-chloro-1H-pyrrolo[2,3-b]pyridin-3-ylmethyl)-pyrimidin-2-yl]-amine (P-0447),
[5-(5-Chloro-1H-pyrrolo[2,3-b]pyridin-3-ylmethyl)-pyrimidin-2-yl]-[1-(3-fluoro-phenyl)-ethyl]-amine (P-0448),
[5-(5-Chloro-1H-pyrrolo[2,3-b]pyridin-3-ylmethyl)-pyrimidin-2-yl]-(2-dimethylamino-benzyl)-amine (P-0449), and
all salts, prodrugs, tautomers, and isomers thereof.

In one embodiment, a compound of Formula II has a structure according to the following sub-generic structure, Formula IIc,

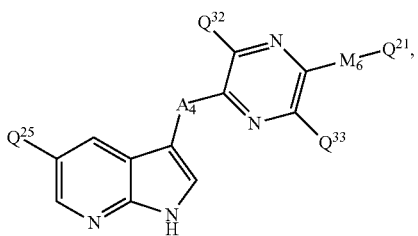

Formula IIc all salts, prodrugs, tautomers, and isomers thereof,
wherein:
- $A_4$ is selected from the group consisting of —$CR^{19}R^{20}$—, —C(O)—, —C(S)—, —S—, —S(O)—, —S(O)$_2$—, —$NR^{21}$—, and —O—;
- $Q^{25}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —$NH_2$, —$NO_2$, —CN, —NHC(O)$NH_2$, —NHC(S)$NH_2$, —NHS(O)$_2NH_2$, —C(O)$NH_2$, —C(S)$NH_2$, —S(O)$_2NH_2$, —$NR^{24}R^{25}$, —$NHR^{23}$, —$OR^{23}$, —$SR^{23}$, —C(O)$R^{23}$, —C(S)$R^{23}$, —S(O)$R^{23}$, —S(O)$_2R^{23}$, —C(O)$NHR^{23}$, —C(O)$NR^{23}R^{23}$, —C(S)$NHR^{23}$, —C(S)$NR^{23}R^{23}$, —S(O)$NHR^{23}$, —S(O)$_2NR^{23}R^{23}$, —NHC(O)$R^{23}$, —$NR^{23}$C(O)$R^{23}$, —NHC(S)$R^{23}$, —$NR^{23}$C(S)$R^{23}$, —NHS(O)$_2R^{23}$, —$NR^{23}$S(O)$_2R^{23}$, —NHC(O)$NHR^{23}$, —$NR^{23}$C(O)$NH_2$, —$NR^{23}$C(O)$NHR^{23}$, —NHC(O)$NR^{23}R^{23}$, —$NR^{23}$C(O)$NR^{23}R^{23}$, —NHC(S)$NHR^{23}$, —$NR^{23}$C(S)$NH_2$, —$NR^{23}$C(S)$NHR^{23}$, —NHC(S)$NR^{23}R^{23}$, —$NR^{23}$C(S)$NR^{23}R^{23}$, —NHS(O)$_2NHR^{23}$, —$NR^{23}$S(O)$_2NH_2$, —$NR^{23}$S(O)$_2NHR^{23}$, —NHS(O)$_2NR^{23}R^{23}$, and —$NR^{23}$S(O)$_2NR^{23}R^{23}$;
- $M_6$, $Q^{21}$, $Q^{32}$ and $Q^{33}$ are as defined for Formula II; and
- $R^{19}$, $R^{20}$, $R^{21}$, $R^{23}$, $R^{24}$, and $R^{25}$ are as defined for Formula Ib.

In one embodiment of compounds of Formula IIc, $M_6$ is —$(CR^{19}R^{20})_t$—$NR^{26}$—$(CR^{19}R^{20})_s$— or —$(CR^{19}R^{20})_t$—$NR^{26}$C(O)—$(CR^{19}R^{20})_s$—, preferably —$NR^{26}$—$(CR^{19}R^{20})_s$— or —$NR^{26}$C(O)—$(CR^{19}R^{20})_s$—, more preferably —$NR^{39}CH_2$—, —$NR^{39}CH(R^{40})$— or —$NR^{39}$C(O)—, wherein $R^{39}$ is hydrogen or lower alkyl and $R^{40}$ is lower alkyl or fluoro substituted lower alkyl. In one embodiment, $A_4$ is —$CR^{19}R^{20}$— or —C(O)—, preferably —$CH_2$— or —C(O)—. In one embodiment, $Q^{21}$ is aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —S(O)$_2R^{23}$ and $Q^{25}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —S(O)$_2R^{23}$. Further to any of the above embodiments, $Q^{32}$ and $Q^{33}$ are independently hydrogen, fluoro, chloro, or —$CF_3$.

In one embodiment of compounds of Formula IIc, $M_6$ is —$(CR^{19}R^{20})_t$—$NR^{26}$—$(CR^{19}R^{20})_s$— or —$(CR^{19}R^{20})_t$—$NR^{26}$C(O)—$(CR^{19}R^{20})_s$—, preferably —$NR^{26}$—$(CR^{19}R^{20})_s$— or —$NR^{26}$C(O)—$(CR^{19}R^{20})_s$—, more preferably —$NR^{39}CH_2$—, —$NR^{39}CH(R^{40})$— or —$NR^{39}$C(O)—, and $A_4$ is —$CR^{19}R^{20}$— or —C(O)—, preferably —$CH_2$— or —C(O)—. In one embodiment, $M_5$ is —$(CR^{19}R^{20})_t$—$NR^{26}$—$(CR^{19}R^{20})_s$— or —$(CR^{19}R^{20})_t$—$NR^{26}$C(O)—$(CR^{19}R^{20})_s$—, preferably —$NR^{26}$—$(CR^{19}R^{20})_s$— or —$NR^{26}$C(O)—$(CR^{19}R^{20})_s$—, more preferably —$NR^{39}CH_2$—, —$NR^{39}CH(R^{40})$— or —$NR^{39}$C(O)—; $A_4$ is —$CR^{19}R^{20}$— or —C(O)—, preferably —$CH_2$— or —C(O)—; $Q^{21}$ is aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —S(O)$_2R^{23}$; and $Q^{25}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —S(O)$_2R^{23}$; and $Q^{32}$ and $Q^{33}$ are independently hydrogen, fluoro, chloro, or —$CF_3$.

In one embodiment of compounds of Formula IIc, $M_6$ is —$NR^{39}CH_2$—, —$NR^{39}CH(R^{40})$— or —$NR^{39}$C(O)—, preferably —$NHCH_2$—; $A_4$ is —$CH_2$— or —C(O)—, preferably —$CH_2$—; $Q^{21}$ is aryl or heteroaryl, wherein aryl or heteroaryl are optionally substituted with one or more substituents selected from the group consisting of halogen, lower alkyl, fluoro substituted lower alkyl, —$NHR^{41}$, —$NR^{41}R^{41}$, —$OR^{41}$ and —S(O)$_2R^{41}$; $Q^{25}$ is hydrogen, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{41}$, —$NR^{41}R^{41}$, —$OR^{41}$ and —S(O)$_2R^{41}$; $Q^{32}$ and $Q^{33}$ are independently hydrogen, fluoro, chloro, lower alkyl, or fluoro substituted lower alkyl, preferably $Q^{32}$ and $Q^{33}$ are independently hydrogen fluoro, chloro, or —$CF_3$, wherein $R^{41}$ is as defined for Formula Ig.

In one embodiment of compounds of Formula IIc, $A_4$ is —$CH_2$— or —C(O)—, preferably —$CH_2$—; $Q^{21}$ is aryl or heteroaryl, wherein aryl or heteroaryl are optionally substituted with one or more substituents selected from the group consisting of —$OR^{41}$, —$SR^{41}$, —S(O)$R^{41}$, —S(O)$_2R^{41}$, —$NHR^{41}$, —$NR^{41}R^{41}$, —$NR^{39}$C(O)$R^{41}$, —$NR^{39}$S(O)$_2R^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of $Q^{21}$, or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino; $Q^{25}$ is hydrogen, —CN, —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, and —OR$^{41}$; $M_6$ is a bond, —NR$^{39}$—, —S—, —O—, —NR$^{39}$CH$_2$—, —NR$^{39}$CH$_2$CH$_2$—, —NR$^{39}$CH(R$^{40}$)—, —SCH$_2$—, —OCH$_2$—, —C(O)NR$^{39}$—, —S(O)$_2$NR$^{39}$—, —CH$_2$NR$^{39}$—, —CH(R$^{40}$)NR$^{39}$—, —NR$^{39}$C(O)—, or —NR$^{39}$S(O)$_2$—; and $Q^{32}$ and $Q^{33}$ are independently hydrogen, halogen, lower alkyl, fluoro substituted lower alkyl, —NR$^{44}$R$^{44}$, —OR$^{44}$, or —SR$^{44}$, provided, however, that at least one of $Q^{32}$ and $Q^{33}$ is hydrogen, fluoro, chloro, lower alkyl or fluoro substituted lower alkyl, wherein R$^{39}$, R$^{40}$, R$^{41}$, R$^{42}$ and R$^{44}$ are as defined for Formula II.

In one embodiment of compounds of Formula IIc, $A_4$ is —CH$_2$—; $Q^{21}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; $Q^{25}$ is hydrogen, —CN, fluoro, chloro, lower alkyl, fluoro substituted lower alkyl, lower alkoxy, or fluoro substituted lower alkoxy; $M_6$ is —NR$^{39}$CH$_2$—, —NR$^{39}$CH$_2$CH$_2$—, or —NR$^{39}$CH(R$^{40}$)—; and $Q^{32}$ and $Q^{33}$ are independently hydrogen, halogen, lower alkyl, fluoro substituted lower alkyl, lower alkoxy, or fluoro substituted lower alkoxy, provided, however, that at least one of $Q^{32}$ and $Q^{33}$ is hydrogen, fluoro, chloro, lower alkyl or fluoro substituted lower alkyl.

In one embodiment, further to any of the embodiments of Formula IIc above, each occurrence of R$^{41}$ is R$^{42}$ as defined for Formula Ig.

In one embodiment, a compound of Formula II has a structure according to the following sub-generic structure, Formula IId,

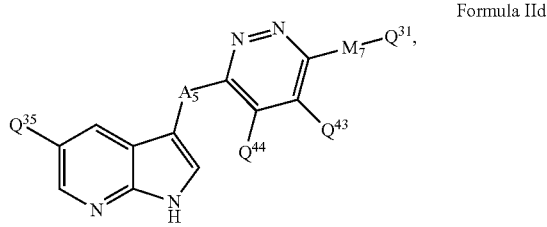

Formula IId all salts, prodrugs, tautomers, and isomers thereof,
wherein:
  $A_5$ is selected from the group consisting of —CR$^{19}$R$^{20}$—, —C(O)—, —C(S)—, —S—, —S(O)—, —S(O)$_2$—, —NR$^{21}$—, and —O—;
  $Q^{35}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —NH$_2$, —NO$_2$, —CN, —NHC(O)NH$_2$, —NHC(S)NH$_2$, —NHS(O)$_2$NH$_2$, —C(O)NH$_2$, —C(S)NH$_2$, —S(O)$_2$NH$_2$, —NR$^{24}$R$^{25}$, —NHR$^{23}$, —OR$^{23}$, —SR$^{23}$, —C(O)R$^{23}$, —C(S)R$^{23}$, —S(O)R$^{23}$, —S(O)$_2$R$^{23}$, —C(O)NHR$^{23}$, —C(O)NR$^{23}$R$^{23}$, —C(S)NHR$^{23}$, —C(S)NR$^{23}$R$^{23}$, —S(O)$_2$NHR$^{23}$, —S(O)$_2$NR$^{23}$R$^{23}$, —NHC(O)R$^{23}$, —NR$^{23}$C(O)R$^{23}$, —NHC(S)R$^{23}$, —NR$^{23}$C(S)R$^{23}$, —NHS(O)$_2$R$^{23}$, —NR$^{23}$S(O)$_2$R$^{23}$, —NHC(O)NHR$^{23}$, —NR$^{23}$C(O)NH$_2$, —NR$^{23}$C(O)NHR$^{23}$, —NHC(O)NR$^{23}$R$^{23}$, —NR$^{23}$C(O)NR$^{23}$R$^{23}$, —NHC(S)NHR$^{23}$, —NR$^{23}$C(S)NH$_2$, —NR$^{23}$C(S)NHR$^{23}$, —NHC(S)NR$^{23}$R$^{23}$, —NR$^{23}$C(S)NR$^{23}$R$^{23}$, —NHS(O)$_2$NHR$^{23}$, —NR$^{23}$S(O)$_2$NH$_2$, —NR$^{23}$S(O)$_2$NHR$^{23}$, —NHS(O)$_2$NR$^{23}$R$^{23}$, and —NR$^{23}$S(O)$_2$NR$^{23}$R$^{23}$;
  $M_7$, $Q^{31}$, $Q^{43}$ and $Q^{44}$ are as defined for Formula II; and R$^{19}$, R$^{20}$, R$^{21}$, R$^{23}$, R$^{24}$, and R$^{25}$ are as defined for Formula Ib.

In one embodiment of compounds of Formula IId, $M_7$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CH$_2$—, —NR$^{39}$CH(R$^{40}$)— or —NR$^{39}$C(O)—, wherein R$^{39}$ is hydrogen or lower alkyl and R$^{40}$ is lower alkyl or fluoro substituted lower alkyl. In one embodiment, $A_5$ is —CR$^{19}$R$^{20}$— or —C(O)—, preferably —CH$_2$— or —C(O)—. In one embodiment, $Q^{31}$ is aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$ and $Q^{35}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$. Further to any of the above embodiments, $Q^{43}$ and $Q^{44}$ are independently hydrogen, fluoro, chloro, or —CF$_3$.

In one embodiment of compounds of Formula IId, $M_7$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CH$_2$—, —NR$^{39}$CH(R$^{40}$)— or —NR$^{39}$C(O)—, and $A_5$ is —CR$^{19}$R$^{20}$— or —C(O)—, preferably —CH$_2$— or —C(O)—. In one embodiment, $M_7$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CH$_2$—, —NR$^{39}$CH(R$^{40}$)— or —NR$^{39}$C(O)—; $A_5$ is —CR$^{19}$R$^{20}$— or —C(O)—, preferably —CH$_2$— or —C(O)—; $Q^{31}$ is aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and $Q^{35}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$. In one embodiment, $M_7$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CH$_2$—, —NR$^{39}$CH(R$^{40}$)— or —NR$^{39}$C(O)—; $A_5$ is —CR$^{19}$R$^{20}$— or —C(O)—, preferably —CH$_2$— or —C(O)—; Q$^{31}$ is aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; Q$^{35}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and Q$^{43}$ and Q$^{44}$ are independently hydrogen, fluoro, chloro, or —CF$_3$.

In one embodiment of compounds of Formula IId, M$_7$ is —NR$^{39}$CH$_2$—, —NR$^{39}$CH(R$^{40}$)— or —NR$^{39}$C(O)—, preferably —NHCH$_2$—; A$_5$ is —CH$_2$— or —C(O)—, preferably —CH$_2$—; Q$^{31}$ is aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; Q$^{35}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; Q$^{43}$ and Q$^{44}$ are independently hydrogen, fluoro, chloro, lower alkyl, or fluoro substituted lower alkyl, preferably Q$^{43}$ and Q$^{44}$ are independently hydrogen, fluoro, chloro, or —CF$_3$, wherein R$^{41}$ is as defined for Formula Ig.

In one embodiment of compounds of Formula IId, A$_5$ is —CH$_2$— or —C(O)—, preferably —CH$_2$—; Q$^{31}$ is aryl or heteroaryl, wherein aryl or heteroaryl are optionally substituted with one or more substituents selected from the group consisting of —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of Q$^{31}$, or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino; Q$^{35}$ is hydrogen, —CN, —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, and —OR$^{41}$; M$_7$ is a bond, —NR$^{39}$—, —S—, —O—, —NR$^{39}$CH$_2$—, —NR$^{39}$CH$_2$CH$_2$—, —NR$^{39}$CH(R$^{40}$)—, —SCH$_2$—, —OCH$_2$—, —C(O)NR$^{39}$—, —S(O)$_2$NR$^{39}$—, —CH$_2$NR$^{39}$—, —CH(R$^{40}$)NR$^{39}$—, —NR$^{39}$C(O)—, or —NR$^{39}$S(O)$_2$—; and Q$^{43}$ and Q$^{44}$ are independently hydrogen, halogen, lower alkyl, fluoro substituted lower alkyl, —NR$^{44}$R$^{44}$, —OR$^{44}$, or —SR$^{44}$, provided, however, that at least one of Q$^{43}$ and Q$^{44}$ is hydrogen, fluoro, chloro, lower alkyl or fluoro substituted lower alkyl, wherein R$^{39}$, R$^{40}$, R$^{41}$, R$^{42}$ and R$^{44}$ are as defined for Formula II.

In one embodiment of compounds of Formula IId, A$_5$ is —CH$_2$—; Q$^{31}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; Q$^{35}$ is hydrogen, —CN, fluoro, chloro, lower alkyl, fluoro substituted lower alkyl, lower alkoxy, or fluoro substituted lower alkoxy; M$_7$ is —NR$^{39}$CH$_2$—, —NR$^{39}$CH$_2$CH$_2$—, or —NR$^{39}$CH(R$^{40}$)—; and Q$^{43}$ and Q$^{44}$ are independently hydrogen, halogen, lower alkyl, fluoro substituted lower alkyl, lower alkoxy, or fluoro substituted lower alkoxy, provided, however, that at least one of Q$^{43}$ and Q$^{44}$ is hydrogen, fluoro, chloro, lower alkyl or fluoro substituted lower alkyl.

In one embodiment, further to any of the embodiments of Formula IId above, each occurrence of R$^{41}$ is R$^{42}$ as defined for Formula Ig.

In one embodiment, a compound of Formula II has a structure according to the following sub-generic structure, Formula IIe,

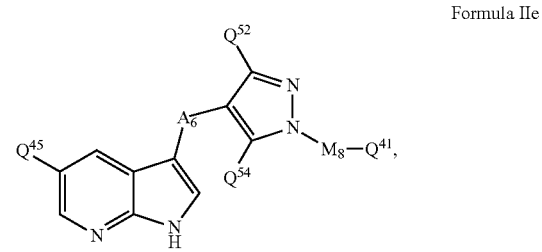

Formula IIe all salts, prodrugs, tautomers, and isomers thereof,
wherein:

A$_6$ is selected from the group consisting of —CR$^{19}$R$^{20}$—, —C(O)—, —C(S)—, —S—, —S(O)—, —S(O)$_2$—, —NR$^{21}$—, and —O—;

Q$^{45}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —NH$_2$, —NO$_2$, —CN, —NHC(O)NH$_2$, —NHC(S)NH$_2$, —NHS(O)$_2$NH$_2$, —C(O)NH$_2$, —C(S)NH$_2$, —S(O)$_2$NH$_2$, —NR$^{24}$R$^{25}$, —NHR$^{23}$, —OR$^{23}$, —SR$^{23}$, —C(O)R$^{23}$, —C(S)R$^{23}$, —S(O)R$^{23}$, —S(O)$_2$R$^{23}$, —C(O)NHR$^{23}$, —C(O)NR$^{23}$R$^{23}$, —C(S)NHR$^{23}$, —C(S)NR$^{23}$R$^{23}$, —S(O)$_2$NHR$^{23}$, —S(O)$_2$NR$^{23}$R$^{23}$, —NHC(O)R$^{23}$, —NR$^{23}$C(O)R$^{23}$, —NHC(S)R$^{23}$, —NR$^{23}$C(S)R$^{23}$, —NHS(O)$_2$R$^{23}$, —NR$^{23}$S(O)$_2$R$^{23}$, —NHC(O)NHR$^{23}$, —NR$^{23}$C(O)NH$_2$, —NR$^{23}$C(O)NHR$^{23}$, —NHC(O)NR$^{23}$R$^{23}$, —NR$^{23}$C(O)NR$^{23}$R$^{23}$, —NHC(S)NHR$^{23}$, —NR$^{23}$C(S)NH$_2$, —NR$^{23}$C(S)NHR$^{23}$, —NHC(S)NR$^{23}$R$^{23}$, —NR$^{23}$C(S)NR$^{23}$R$^{23}$, —NHS(O)$_2$NHR$^{23}$, —NR$^{23}$S(O)$_2$NH$_2$, —NR$^{23}$S(O)$_2$NHR$^{23}$, —NHS(O)$_2$NR$^{23}$R$^{23}$, and —NR$^{23}$S(O)$_2$NR$^{23}$R$^{23}$;

M$_8$, Q$^{41}$, Q$^{52}$ and Q$^{54}$ are as defined in Formula II; and $R^{19}$, $R^{20}$, $R^{21}$, $R^{23}$, $R^{24}$, and $R^{25}$ are as defined for Formula Ib;

provided, however, that the compound is not

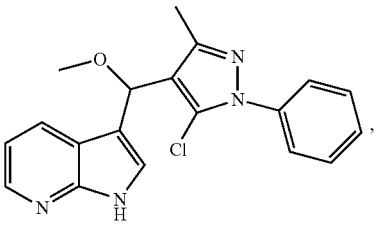,

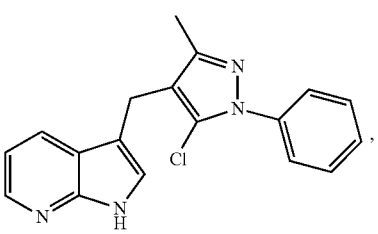,

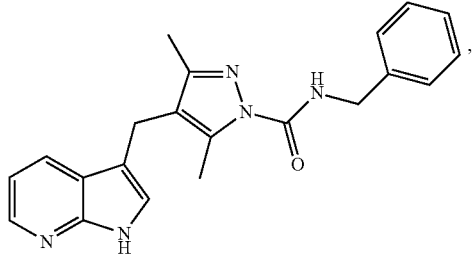,

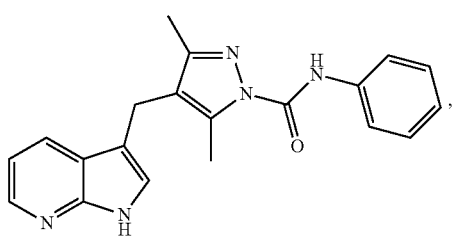,

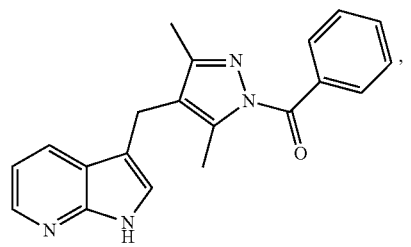,

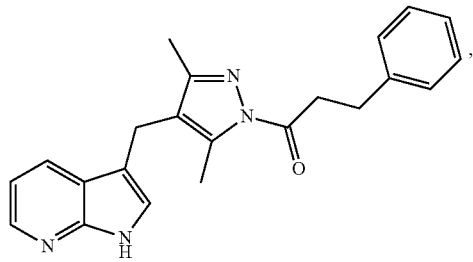,

-continued

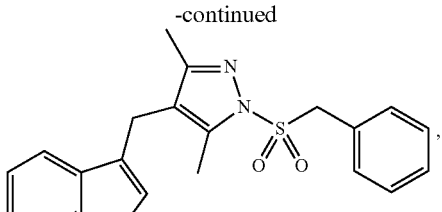,

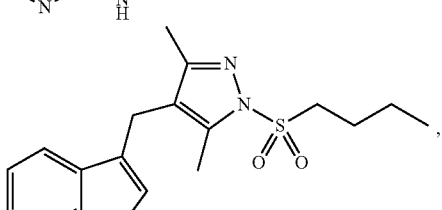,

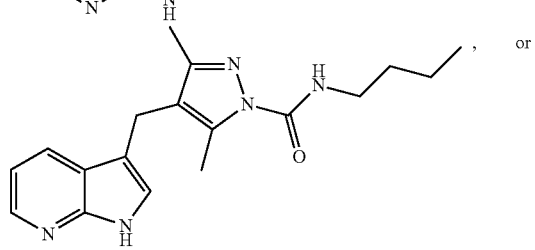, or

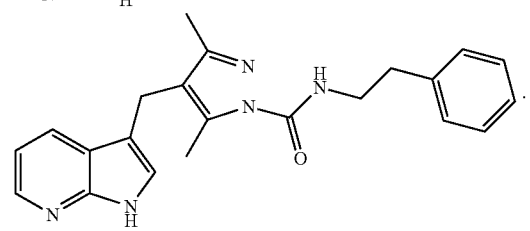.

In one embodiment of compounds of Formula IIe, $M_8$ is $-(CR^{19}R^{20})_t-C(O)NR^{26}-(CR^{19}R^{20})_s-$, preferably $-C(O)NR^{26}-(CR^{19}R^{20})_s-$, more preferably $-C(O)NR^{39}-CR^{80}R^{80}-$ or $-C(O)NR^{39}-(CR^{80}R^{80})_2-$, wherein $R^{39}$ is hydrogen or lower alkyl and $R^{80}$ is hydrogen, lower alkyl or fluoro substituted lower alkyl, preferably hydrogen. In one embodiment, $A_6$ is $-CR^{19}R^{20}-$ or $-C(O)-$, preferably $-CH_2-$ or $-C(O)-$. In one embodiment, $Q^{41}$ is aryl or heteroaryl, wherein aryl or heteroaryl are optionally substituted with one or more substituents selected from the group consisting of halogen, lower alkyl, fluoro substituted lower alkyl, $-NHR^{23}$, $-NR^{23}R^{23}$, $-OR^{23}$ and $-S(O)_2R^{23}$ and $Q^{45}$ is hydrogen, $-OR^{23}$, $-CN$, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, $-NHR^{23}$, $-NR^{23}R^{23}$, $-OR^{23}$ and $-S(O)_2R^{23}$. Further to any of the above embodiments, $Q^{52}$ and $Q^{54}$ are independently hydrogen, fluoro, chloro, methyl, or $-CF_3$.

In one embodiment of compounds of Formula IIe, Mg is $-(CR^{19}R^{20})_t-C(O)NR^{26}-(CR^{19}R^{20})_s-$, preferably $-C(O)NR^{26}-(CR^{19}R^{20})_s-$, more preferably $-C(O)NR^{39}-CR^{80}R^{80}-$ or $-C(O)NR^{39}-(CR^{80}R^{80})_2-$, and $A_6$ is $-CR^{19}R^{20}-$ or $-C(O)-$, preferably $-CH_2-$ or $-C(O)-$. In one embodiment, $M_8$ is $-(CR^{19}R^{20})_t-C(O)NR^{26}-(CR^{19}R^{20})_s-$, preferably $-C(O)NR^{26}-(CR^{19}R^{20})_s-$, more preferably $-C(O)NR^{39}-CR^{80}R^{80}-$ or $-C(O)NR^{39}-(CR^{80}R^{80})_2-$; $A_6$ is $-CR^{19}R^{20}-$ or —C(O)—, preferably —CH$_2$— or —C(O)—; Q$^{41}$ is aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and Q$^{45}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$. In one embodiment, M$_8$ is —(CR$^{19}$R$^{20}$)$_t$—C(O)NR$^{26}$—(CR$^{19}$R$^{20}$)$_s$—, preferably —C(O)NR$^{26}$—(CR$^{19}$R$^{20}$)$_s$—, more preferably —C(O)NR$^{39}$—CR$^{80}$R$^{80}$— or —C(O)NR$^{39}$—(CR$^{80}$R$^{80}$)$_2$—; A$_6$ is —CR$^{19}$R$^{20}$— or —C(O)—, preferably —CH$_2$— or —C(O)—; Q$^{41}$ is aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; Q$^{45}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and Q$^{52}$ and Q$^{54}$ are independently hydrogen, fluoro, chloro, methyl, or —CF$_3$.

In one embodiment of compounds of Formula IIe, M$_8$ is —C(O)NR$^{39}$—CH$_2$—, —C(O)NR$^{39}$CH(CH$_3$)—, or —C(O)NR$^{39}$—(CH$_2$)$_2$—; A$_6$ is —CH$_2$— or —C(O)—, preferably —CH$_2$—; Q$^{41}$ is aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; Q$^{45}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; and Q$^{52}$ and Q$^{54}$ are independently hydrogen, fluoro, chloro, lower alkyl, or fluoro substituted lower alkyl, preferably Q$^{52}$ and Q$^{54}$ are independently fluoro, chloro, methyl, or —CF$_3$, wherein R$^{41}$ is as defined in Formula Ig.

In one embodiment of compounds of Formula IIe, A$_6$ is —CH$_2$— or —C(O)—, preferably —CH$_2$—; Q$^{41}$ is aryl or heteroaryl, wherein aryl or heteroaryl are optionally substituted with one or more substituents selected from the group consisting of —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of Q$^{41}$, or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino; Q$^{45}$ is hydrogen, —CN, —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, and —OR$^{41}$; M$_8$ is —C(O)NR$^{39}$CH$_2$—, —C(O)NR$^{39}$CH(R$^{40}$)—, or —C(O)NR$^{39}$CH$_2$CH$_2$—; and Q$^{52}$ and Q$^{54}$ are independently hydrogen, halogen, lower alkyl, fluoro substituted lower alkyl, —NR$^{44}$R$^{44}$, —OR$^{44}$, or —SR$^{44}$, provided, however, that at least one of Q$^{52}$ and Q$^{54}$ is hydrogen, fluoro, chloro, lower alkyl or fluoro substituted lower alkyl, wherein R$^{39}$, R$^{40}$, R$^{41}$, R$^{42}$ and R$^{44}$ are as defined for Formula II.

In one embodiment of compounds of Formula IIe, A$_6$ is —CH$_2$—; Q$^{41}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; Q$^{45}$ is hydrogen, —CN, fluoro, chloro, lower alkyl, fluoro substituted lower alkyl, lower alkoxy, or fluoro substituted lower alkoxy; M$_8$ is —C(O)NR$^{39}$CH$_2$—, —C(O)NR$^{39}$CH(R$^{40}$)—, or —C(O)NR$^{39}$CH$_2$CH$_2$—; and Q$^{52}$ and Q$^{54}$ are independently hydrogen, halogen, lower alkyl, fluoro substituted lower alkyl, lower alkoxy, or fluoro substituted lower alkoxy, provided, however, that at least one of Q$^{52}$ and Q$^{54}$ is hydrogen, fluoro, chloro, lower alkyl or fluoro substituted lower alkyl.

In one embodiment, further to any of the embodiments of Formula IIe above, each occurrence of R$^{41}$ is R$^{42}$ as defined for Formula Ig.

In one embodiment of compounds of Formula IIe, M$_8$ is —C(O)NHCH$_2$—, —C(O)NH—CH(CH$_3$)— or —C(O)NH—(CH$_2$)$_2$—; A$_6$ is —CH$_2$— or —C(O)—, preferably —CH$_2$—; Q$^{41}$ is aryl or heteroaryl, wherein aryl or heteroaryl are optionally substituted with 1 or 2 substituents selected from the group consisting of fluoro, chloro, methyl, fluoro substituted methyl, methoxy, and fluoro substituted methoxy; Q$^{45}$ is hydrogen, —CN, fluoro, chloro, lower alkyl, fluoro substituted lower alkyl, lower alkoxy, or fluoro substituted lower alkoxy, preferably hydrogen or chloro; and Q$^{52}$ and Q$^{54}$ are independently hydrogen, fluoro, chloro, lower alkyl, or fluoro substituted lower alkyl, preferably Q$^{52}$ and Q$^{54}$ are methyl.

In one embodiment of compounds of Formula IIe, the compound is selected from the group consisting of:

3-(1-Benzyl-3,5-dimethyl-1H-pyrazol-4-ylmethyl)-1H-pyrrolo[2,3-b]pyridine (P-0133), 2-[3,5-Dimethyl-4-(1H-pyrrolo[2,3-b]pyridin-3-ylmethyl)-pyrazol-1-yl]-1-phenyl-ethanone (P-0134), 3,5-Dimethyl-4-(1H-pyrrolo[2,3-b]pyridin-3-ylmethyl)-pyrazole-1-carboxylic acid 4-methoxy-benzylamide (P-0135), 3,5-Dimethyl-4-(1H-pyrrolo[2,3-b]pyridin-3-ylmethyl)-pyrazole-1-carboxylic acid 2-chloro-benzylamide (P-0136), 3,5-Dimethyl-4-(1H-pyrrolo[2,3-b]pyridin-3-ylmethyl)-pyrazole-1-carboxylic acid 2-fluoro-benzylamide (P-0137), 3-[3,5-Dimethyl-1-(5-trifluoromethyl-furan-2-ylmethyl)-1H-pyrazol-4-ylmethyl]-1H-pyrrolo[2,3-b]pyridine (P-0138), 3-[3,5-Dimethyl-1-(5-methyl-isoxazol-3-ylmethyl)-1H-pyrazol-4-ylmethyl]-1H-pyrrolo[2,3-b]pyridine (P-0139), 3,5-Dimethyl-4-(1H-pyrrolo[2,3-b]pyridin-3-ylmethyl)-pyrazole-1-carboxylic acid 4-chloro-benzylamide (P-0140), 3,5-Dimethyl-4-(1H-pyrrolo[2,3-b]pyridin-3-ylmethyl)-pyrazole-1-carboxylic acid [2-(4-methoxy-phenyl)-ethyl]-amide (P-0141), 3,5-Dimethyl-4-(1H-pyrrolo[2,3-b]pyridin-3-ylmethyl)-pyrazole-1-carboxylic acid 3-methoxy-benzylamide (P-0142), 3-{3,5-Dimethyl-1-[4-methyl-2-(4-trifluoromethyl-phenyl)-thiazol-5-ylmethyl]-1H-pyrazol-4-ylmethyl}-1H-pyrrolo[2,3-b]pyridine (P-0143), 3-[3,5-Dimethyl-1-(4-methyl-2-phenyl-thiazol-5-ylmethyl)-1H-pyrazol-4-ylmethyl]-1H-pyrrolo[2,3-b]pyridine (P-0144), 3,5-Dimethyl-4-(1H-pyrrolo[2,3-b]pyridin-3-ylmethyl)-pyrazole-1-carboxylic acid 2-methoxy-benzylamide (P-0145), 3,5-Dimethyl-4-(1H-pyrrolo[2,3-b]pyridin-3-ylmethyl)-pyrazole-1-carboxylic acid [2-(2,4-dichloro-phenyl)-ethyl]-amide (P-0146), 3,5-Dimethyl-4-(1H-pyrrolo[2,3-b]pyridin-3-ylmethyl)-pyrazole-1-carboxylic acid [2-(4-fluoro-phenyl)-ethyl]-amide (P-0147), 3,5-Dimethyl-4-(1H-pyrrolo[2,3-b]pyridin-3-ylmethyl)-pyrazole-1-carboxylic acid [2-(2-fluoro-phenyl)-ethyl]-amide (P-0148), 3,5-Dimethyl-4-(1H-pyrrolo[2,3-b]pyridin-3-ylmethyl)-pyrazole-1-carboxylic acid ((S)-1-phenyl-ethyl)-amide (P-0149), 3,5-Dimethyl-4-(1H-pyrrolo[2,3-b]pyridin-3-ylmethyl)-pyrazole-1-carboxylic acid 3-fluoro-benzylamide (P-0150), 3,5-Dimethyl-4-(1H-pyrrolo[2,3-b]pyridin-3-ylmethyl)-pyrazole-1-carboxylic acid 4-fluoro-benzylamide (P-0151), 3,5-Dimethyl-4-(1H-pyrrolo[2,3-b]pyridin-3-ylmethyl)-pyrazole-1-carboxylic acid 4-methyl-benzylamide (P-0152), 3,5-Dimethyl-4-(1H-pyrrolo[2,3-b]pyridin-3-ylmethyl)-pyrazole-1-carboxylic acid 2-methyl-benzylamide (P-0153), 4-(5-Chloro-1H-pyrrolo[2,3-b]pyridin-3-ylmethyl)-3,5-dimethyl-pyrazole-1-carboxylic acid [2-(4-fluoro-phenyl)-ethyl]-amide (P-0157), 4-(5-Chloro-1H-pyrrolo[2,3-b]pyridin-3-ylmethyl)-3,5-dimethyl-pyrazole-1-carboxylic acid 4-fluoro-benzylamide (P-0158), 4-(5-Chloro-1H-pyrrolo[2,3-b]pyridin-3-ylmethyl)-3,5-dimethyl-pyrazole-1-carboxylic acid 4-chloro-benzylamide (P-0159), 4-(5-Chloro-1H-pyrrolo[2,3-b]pyridin-3-ylmethyl)-3,5-dimethyl-pyrazole-1-carboxylic acid [(S)-1-(4-fluoro-phenyl)-ethyl]-amide (P-0160), and all salts, prodrugs, tautomers, and isomers thereof.

In one embodiment, a compound of Formula II has a structure according to the following sub-generic structure, Formula IIf,

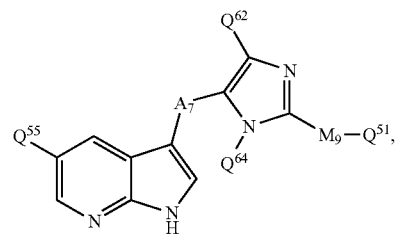

Formula IIf all salts, prodrugs, tautomers, and isomers thereof,
wherein:

$A_7$ is selected from the group consisting of —$CR^{19}R^{20}$—, —C(O)—, —C(S)—, —S—, —S(O)—, —$S(O)_2$—, —$NR^{21}$—, and —O—;

$Q^{55}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —$NH_2$, —$NO_2$, —CN, —NHC(O)$NH_2$, —NHC(S)$NH_2$, —NHS(O)$_2NH_2$, —C(O)$NH_2$, —C(S)$NH_2$, —S(O)$_2NH_2$, —$NR^{24}R^{25}$, —$NHR^{23}$, —$OR^{23}$, —$SR^{23}$, —$C(O)R^{23}$, —$C(S)R^{23}$, —$S(O)R^{23}$, —$S(O)_2R^{23}$, —$C(O)NHR^{23}$, —$C(O)NR^{23}R^{23}$, —$C(S)NHR^{23}$, —$C(S)NR^{23}R^{23}$, —$S(O)_2NHR^{23}$, —$S(O)_2NR^{23}R^{23}$, —$NHC(O)R^{23}$, —$NR^{23}C(O)R^{23}$, —$NHC(S)R^{23}$, —$NR^{23}C(S)R^{23}$, —$NHS(O)_2R^{23}$, —$NR^{23}S(O)_2R^{23}$, —$NHC(O)NHR^{23}$, —$NR^{23}C(O)NH_2$, —$NR^{23}C(O)NHR^{23}$, —NHC(O)$NR^{23}R^{23}$, —$NR^{23}C(O)NR^{23}R^{23}$, —$NHC(S)NHR^{23}$, —$NR^{23}C(S)NH_2$, —$NR^{23}C(S)NHR^{23}$, —NHC(S)$NR^{23}R^{23}$, —$NR^{23}C(S)NR^{23}R^{23}$, —$NHS(O)_2NHR^{23}$, —$NR^{23}S(O)_2NH_2$, —$NR^{23}S(O)_2NHR^{23}$, —$NHS(O)_2NR^{23}R^{23}$, and —$NR^{23}S(O)_2NR^{23}R^{23}$;

$M_9$, $Q^{51}$, $Q^{62}$, and $Q^{64}$ are as defined for Formula II; and $R^{19}$, $R^{20}$, $R^{21}$, $R^{23}$, $R^{24}$, and $R^{25}$ are as defined for Formula Ib.

In one embodiment of compounds of Formula IIf, $M_9$ is —$(CR^{19}R^{20})_t$—$NR^{26}$—$(CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$— or —$NR^{39}(CR^{80}R^{80})_2$—, wherein $R^{39}$ is hydrogen or lower alkyl and $R^{80}$ is hydrogen, lower alkyl or fluoro substituted lower alkyl, preferably hydrogen. In one embodiment, $A_7$ is —$CR^{19}R^{20}$— or —C(O)—, preferably —$CH_2$— or —C(O)—. In one embodiment, $Q^{51}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$ and $Q^{55}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$. Further to any of the above embodiments, $Q^{62}$ is hydrogen, fluoro, chloro, lower alkyl or fluoro substituted lower alkyl.

In one embodiment of compounds of Formula IIf, $M_9$ is —$(CR^{19}R^{20})_t$—$NR^{26}$—$(CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$— or —$NR^{39}(CR^{80}R^{80})_2$—, and $A_7$ is —CR$^{19}$R$^{20}$— or —C(O)—, preferably —CH$_2$— or —C(O)—. In one embodiment, M$_9$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CR$^{80}$R$^{80}$—, or —NR$^{39}$(CR$^{80}$R$^{80}$)$_2$—; A$_7$ is —CR$^{19}$R$^{20}$— or —C(O)—, preferably —CH$_2$— or —C(O)—; Q$^{51}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and Q$^{55}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$. In one embodiment, M$_9$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CR$^{80}$R$^{80}$—, —NR$^{39}$(CR$^{80}$R$^{80}$)$_2$—; A$_7$ is —CR$^{19}$R$^{20}$— or —C(O)—, preferably —CH$_2$— or —C(O)—; Q$^{51}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; Q$^{55}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and Q$^{62}$ is hydrogen, fluoro, chloro, lower alkyl or fluoro substituted lower alkyl.

In one embodiment of compounds of Formula IIf, M$_9$ is —NR$^{39}$CH$_2$— or —NR$^{39}$—(CH$_2$)$_2$—; A$_7$ is —CH$_2$— or —C(O)—, preferably —CH$_2$—; Q$^{51}$ is aryl or heteroaryl, wherein aryl or heteroaryl are optionally substituted with one or more substituents selected from the group consisting of halogen, lower alkyl, fluoro substituted lower alkyl, —NHR$^{41}$; —NR$^{41}$R$^{41}$, —OR$^{41}$ and —S(O)$_2$R$^{41}$; Q$^{55}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; and Q$^{62}$ is hydrogen, fluoro, chloro, lower alkyl or fluoro substituted lower alkyl, wherein R$^{41}$ is as defined in Formula Ig.

In one embodiment of compounds of Formula IIf, A$_7$ is —CH$_2$— or —C(O)—, preferably —CH$_2$—; Q$^{51}$ is aryl or heteroaryl, wherein aryl or heteroaryl are optionally substituted with one or more substituents selected from the group consisting of —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of Q$^{51}$, or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino; Q$^{55}$ is hydrogen, —CN, —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$ fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, and —OR$^{41}$; M$_9$ is a bond, —NR$^{39}$—, —S—, —O—, —NR$^{39}$CH$_2$—, —NR$^{39}$CH$_2$CH$_2$—, —NR$^{39}$CH(R$^{40}$)—, —SCH$_2$—, —OCH$_2$—, —C(O)NR$^{39}$—, —S(O)$_2$NR$^{39}$—, —CH$_2$NR$^{39}$—, —CH(R$^{40}$)NR$^{39}$—, —NR$^{39}$C(O)—, or —NR$^{39}$S(O)$_2$—; Q$^{62}$ is hydrogen, fluoro, chloro, lower alkyl, fluoro substituted lower alkyl, —NR$^{44}$R$^{44}$, —OR$^{44}$, or —SR$^{44}$; and Q$^{64}$ is hydrogen, lower alkyl, or fluoro substituted lower alkyl, wherein R$^{39}$, R$^{40}$, R$^{41}$, R$^{42}$ and R$^{44}$ are as defined for Formula II.

In one embodiment of compounds of Formula IIf, A$_7$ is —CH$_2$—; Q$^{51}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; Q$^{55}$ is hydrogen, —CN, fluoro, chloro, lower alkyl, fluoro substituted lower alkyl, lower alkoxy, or fluoro substituted lower alkoxy; M$_9$ is —NR$^{39}$CH$_2$—, —NR$^{39}$CH$_2$CH$_2$—, or —NR$^{39}$CH(R$^{40}$)—; Q$^{62}$ is hydrogen, fluoro, chloro, lower alkyl, fluoro substituted lower alkyl, lower alkoxy, or fluoro substituted lower alkoxy; and Q$^{64}$ is hydrogen, lower alkyl, or fluoro substituted lower alkyl.

In one embodiment, further to any of the embodiments of Formula IIf above, each occurrence of R$^{41}$ is R$^{42}$ as defined for Formula Ig.

In one embodiment, a compound of Formula II has a structure according to the following sub-generic structure, Formula IIg,

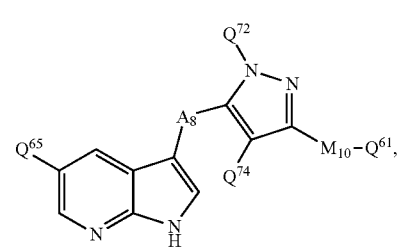

Formula IIg all salts, prodrugs, tautomers, and isomers thereof, wherein:

A$_8$ is selected from the group consisting of —CR$^{19}$R$^{20}$—, —C(O)—, —C(S)—, —S—, —S(O)—, —S(O)$_2$—, —NR$^{21}$—, and —O—;

Q$^{65}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —NH$_2$, —NO$_2$, —CN, —NHC(O)NH$_2$, —NHC(S)NH$_2$, —NHS(O)$_2$NH$_2$, —C(O)NH$_2$, —C(S)NH$_2$, —S(O)$_2$NH$_2$, —NR$^{24}$R$^{25}$, —NHR$^{23}$, —OR$^{23}$, —SR$^{23}$, —C(O)R$^{23}$, —C(S)R$^{23}$, —S(O)R$^{23}$, —S(O)$_2$R$^{23}$, —C(O)NHR$^{23}$, —C(O)NR$^{23}$R$^{23}$, —C(S)NHR$^{23}$, —C(S)NR$^{23}$R$^{23}$, —S(O)$_2$NHR$^{23}$, —S(O)$_2$NR$^{23}$R$^{23}$, —NHC(O)R$^{23}$, —NR$^{23}$C(O)R$^{23}$, —NHC(S)R$^{23}$, —NR$^{23}$C(S)R$^{23}$, —NHS(O)$_2$R$^{23}$, —NR$^{23}$S(O)$_2$R$^{23}$, —NHC(O)NHR$^{23}$, —NR$^{23}$C(O)NH$_2$, —NR$^{23}$C(O)NHR$^{23}$, —NHC(O)NR$^{23}$R$^{23}$, —NR$^{23}$C(O)NR$^{23}$R$^{23}$, —NHC(S)NHR$^{23}$, —NR$^{23}$C(S)NH$_2$, —NR$^{23}$C(S)NHR$^{23}$, —NHC(S)NR$^{23}$R$^{23}$, —NR$^{23}$C(S)NR$^{23}$R$^{23}$, —NHS(O)$_2$NHR$^{23}$, —NR$^{23}$S(O)$_2$NH$_2$, —NR$^{23}$S(O)$_2$NHR$^{23}$, —NHS(O)$_2$NR$^{23}$R$^{23}$, and —NR$^{23}$S(O)$_2$NR$^{23}$R$^{23}$;

$M_{10}$, $Q^{61}$, $Q^{72}$, $Q^{74}$ are as defined for Formula II; and $R^{19}$, $R^{20}$, $R^{21}$, $R^{23}$, $R^{24}$, and $R^{25}$, $R^{26}$ are as defined for Formula Ib.

In one embodiment of compounds of Formula IIg, $M_{10}$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CR$^{80}$R$^{80}$— or —NR$^{39}$(CR$^{80}$R$^{80}$)$_2$—, wherein R$^{39}$ is hydrogen or lower alkyl and R$^{80}$ is hydrogen, lower alkyl or fluoro substituted lower alkyl, preferably hydrogen. In one embodiment, $A_8$ is —CR$^{19}$R$^{20}$— or —C(O)—, preferably —CH$_2$— or —C(O)—. In one embodiment, $Q^{61}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$ and $Q^{65}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$. Further to any of the above embodiments, $Q^{74}$ is hydrogen, fluoro, chloro, lower alkyl or fluoro substituted lower alkyl.

In one embodiment of compounds of Formula IIg, $M_{10}$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CR$^{80}$R$^{80}$— or —NR$^{39}$(CR$^{80}$R$^{80}$)$_2$—, and $A_8$ is —CR$^{19}$R$^{20}$— or —C(O)—, preferably —CH$_2$— or —C(O)—. In one embodiment, $M_{10}$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CR$^{80}$R$^{80}$— or —NR$^{39}$(CR$^{80}$R$^{80}$)$_2$—; $A_8$ is —CR$^{19}$R$^{20}$— or —C(O)—, preferably —CH$_2$— or —C(O)—; $Q^{61}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and $Q^{65}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and $Q^{74}$ is hydrogen, fluoro, chloro, lower alkyl or fluoro substituted lower alkyl.

In one embodiment of compounds of Formula IIg, $M_{10}$ is —NR$^{39}$CH$_2$— or —NR$^{39}$—(CH$_2$)$_2$—; $A_8$ is —CH$_2$— or —C(O)—, preferably —CH$_2$—; $Q^{61}$ is aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; $Q^{65}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; and $Q^{74}$ is hydrogen, fluoro, chloro, lower alkyl or fluoro substituted lower alkyl, wherein R$^{41}$ is as defined for Formula Ig.

In one embodiment of compounds of Formula IIg, $A_8$ is —CH$_2$— or —C(O)—, preferably —CH$_2$—; $Q^{61}$ is aryl or heteroaryl, wherein aryl or heteroaryl are optionally substituted with one or more substituents selected from the group consisting of —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of $Q^{61}$, or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino; $Q^{65}$ is hydrogen, —CN, —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, and —OR$^{41}$; $M_{10}$ is a bond, —NR$^{39}$—, —S—, —O—, —NR$^{39}$CH$_2$—, —NR$^{39}$CH$_2$CH$_2$—, —NR$^{39}$CH(R$^{40}$)—, —SCH$_2$—, —OCH$_2$—, —C(O)NR$^{39}$—, —S(O)$_2$NR$^{39}$—, —CH$_2$NR$^{39}$—, —CH(R$^{40}$)NR$^{39}$—, —NR$^{39}$C(O)—, or —NR$^{39}$S(O)$_2$—; $Q^{74}$ is hydrogen, fluoro, chloro, lower alkyl, fluoro substituted lower alkyl, —NR$^{44}$R$^{44}$, —OR$^{44}$, or —SR$^{44}$; and $Q^{72}$ is hydrogen, lower alkyl, or fluoro substituted lower alkyl, wherein R$^{39}$, R$^{40}$, R$^{41}$, R$^{42}$ and R$^{44}$ are as defined for Formula II.

In one embodiment of compounds of Formula IIg, $A_8$ is —$CH_2$—; $Q^{61}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; $Q^{65}$ is hydrogen, —CN, fluoro, chloro, lower alkyl, fluoro substituted lower alkyl, lower alkoxy, or fluoro substituted lower alkoxy; $M_{10}$ is —$NR^{39}CH_2$—, —$NR^{39}CH_2CH_2$—, or —$NR^{39}CH(R^{40})$—; $Q^{74}$ is hydrogen, fluoro, chloro, lower alkyl, fluoro substituted lower alkyl, lower alkoxy, or fluoro substituted lower alkoxy; and $Q^{72}$ is hydrogen, lower alkyl, or fluoro substituted lower alkyl.

In one embodiment, further to any of the embodiments of Formula IIg above, each occurrence of $R^{41}$ is $R^{42}$ as defined for Formula Ig.

In one embodiment of compounds of Formula IIg, $M_{10}$ is —$NHCH_2$—, $A_8$ is —$CH_2$—, $Q^{61}$ is phenyl optionally substituted with 1 or 2 substituents selected from the group consisting of fluoro, chloro, methyl, trifluoromethyl, methoxy, difluoromethoxy, or trifluoromethoxy, $Q^{65}$ is hydrogen, fluoro, —CN, or 1-methyl-pyrazol-4-yl, $Q^{72}$ is lower alkyl or fluoro substituted lower alkyl, and $Q^{74}$ is hydrogen, fluoro, chloro, lower alkyl, or fluoro substituted lower alkyl. In one embodiment, $M_{10}$ is —$NHCH_2$—, $A_8$ is —$CH_2$—, $Q^{61}$ is 4-fluoro-phenyl, $Q^{65}$ is hydrogen, chloro, —CN, or 1-methyl-pyrazol-4-yl, $Q^{72}$ is methyl or ethyl and $Q^{74}$ is hydrogen or chloro.

In one embodiment, the compound of Formula IIg is selected from the group consisting of:

[1-Ethyl-5-(1H-pyrrolo[2,3-b]pyridin-3-ylmethyl)-1H-pyrazol-3-yl]-(4-fluoro-benzyl)-amine (P-0165), (4-Fluoro-benzyl)-[1-methyl-5-(1H-pyrrolo[2,3-b]pyridin-3-ylmethyl)-1H-pyrazol-3-yl]-amine (P-0169),

[5-(5-Chloro-1H-pyrrolo[2,3-b]pyridin-3-ylmethyl)-1-methyl-1H-pyrazol-3-yl]-(4-fluoro-benzyl)-amine (P-0170), (4-Fluoro-benzyl)-{1-methyl-5-[5-(1-methyl-1H-pyrazol-4-yl)-1H-pyrrolo[2,3-b]pyridin-3-ylmethyl]-1H-pyrazol-3-yl}-amine (P-0180), (5-Chloro-1H-pyrrolo[2,3-b]pyridin-3-yl)-[2-ethyl-5-(4-fluoro-benzylamino)-2H-pyrazol-3-yl]-methanone (P-0184),

[5-(5-Chloro-1H-pyrrolo[2,3-b]pyridin-3-ylmethyl)-1-ethyl-1H-pyrazol-3-yl]-(4-fluoro-benzyl)-amine (P-0185), 3-[5-(4-Fluoro-benzylamino)-2-methyl-2H-pyrazol-3-ylmethyl]-1H-pyrrolo[2,3-b]pyridine-5-carbonitrile (P-0191), (3-Chloro-benzyl)-[5-(5-chloro-1H-pyrrolo[2,3-b]pyridin-3-ylmethyl)-1-methyl-1H-pyrazol-3-yl]-amine (P-0410),

[5-(5-Chloro-1H-pyrrolo[2,3-b]pyridin-3-ylmethyl)-1-methyl-1H-pyrazol-3-yl]-(2,5-difluoro-benzyl)-amine (P-0411),

[5-(5-Chloro-1H-pyrrolo[2,3-b]pyridin-3-ylmethyl)-1-methyl-1H-pyrazol-3-yl]-(2-fluoro-benzyl)-amine (P-0413), and all salts, prodrugs, tautomers, and isomers thereof.

In one embodiment, a compound of Formula II has a structure according to the following sub-generic structure, Formula IIh,

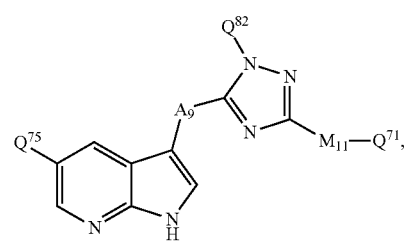

Formula IIh all salts, prodrugs, tautomers, and isomers thereof, wherein:

$A_9$ is selected from the group consisting of —$CR^{19}R^{20}$—, —$C(O)$—, —$C(S)$—, —$S$—, —$S(O)$—, —$S(O)_2$—, —$NR^{21}$—, and —$O$—;

$Q^{75}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —$NH_2$, —$NO_2$, —CN, —NHC(O)$NH_2$, —NHC(S)$NH_2$, —NHS(O)$_2$$NH_2$, —$C(O)NH_2$, —$C(S)NH_2$, —$S(O)NH_2$, —$S(O)_2NH_2$, —$NR^{24}R^{25}$, —$NHR^{23}$, —$OR^{23}$, —$SR^{23}$, —$C(O)R^{23}$, —$C(S)R^{23}$, —$S(O)R^{23}$, —$S(O)_2R^{23}$, —$C(O)NHR^{23}$, —$C(O)NR^{23}R^{23}$, —$C(S)NHR^{23}$, —$C(S)NR^{23}R^{23}$, —$S(O)_2NHR^{23}$, —$S(O)_2NR^{23}R^{23}$, —$NHC(O)R^{23}$, —$NR^{23}C(O)R^{23}$, —$NHC(S)R^{23}$, —$NR^{23}C(S)R^{23}$, —$NHS(O)_2R^{23}$, —$NR^{23}S(O)_2R^{23}$, —$NHC(O)NHR^{23}$, —$NR^{23}C(O)NH_2$, —$NR^{23}C(O)NHR^{23}$, —$NHC(O)NR^{23}R^{23}$, —$NR^{23}C(O)NR^{23}R^{23}$, —$NHC(S)NHR^{23}$, —$NR^{23}C(S)NH_2$, —$NR^{23}C(S)NHR^{23}$, —$NHC(S)NR^{23}R^{23}$, —$NR^{23}C(S)NR^{23}R^{23}$, —$NHS(O)_2NHR^{23}$, —$NR^{23}S(O)_2NH_2$, —$NR^{23}S(O)_2NHR^{23}$, —$NHS(O)_2NR^{23}R^{23}$, and —$NR^{23}S(O)_2NR^{23}R^{23}$;

$M_{11}$, $Q^{71}$, and $Q^{82}$ are as defined for Formula II; and $R^{19}$, $R^{20}$, $R^{21}$, $R^{23}$, $R^{24}$, and $R^{25}$ are as defined for Formula Ib.

In one embodiment of compounds of Formula IIh, $M_{11}$ is —$(CR^{19}R^{20})_t$—$NR^{26}$—$(CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$— or —$NR^{39}(CR^{80}R^{80})_2$—, wherein $R^{39}$ is hydrogen or lower alkyl and $R^{80}$ is hydrogen, lower alkyl or fluoro substituted lower alkyl, preferably hydrogen. In one embodiment, $A_9$ is —$CR^{19}R^{20}$— or —$C(O)$—, preferably —$CH_2$— or —$C(O)$—. In one embodiment, $Q^{71}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$ and $Q^{75}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$.

In one embodiment of compounds of Formula IIh, $M_{11}$ is —$(CR^{19}R^{20})_t$—$NR^{26}$—$(CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$— or —$NR^{39}(CR^{80}R^{80})_2$—, and $A_9$ is —$CR^{19}R^{20}$— or —$C(O)$—, preferably —$CH_2$— or —$C(O)$—. In one embodiment, $M_{11}$ is —$(CR^{19}R^{20})_t$—

—NR²⁶—(CR¹⁹R²⁰)ₛ— or —(CR¹⁹R²⁰)ₜ—NR²⁶C(O)—(CR¹⁹R²⁰)ₛ—, preferably —NR²⁶—(CR¹⁹R²⁰)ₛ— or —NR²⁶C(O)—(CR¹⁹R²⁰)ₛ—, more preferably —NR³⁹CR⁸⁰R⁸⁰— or —NR³⁹(CR⁸⁰R⁸⁰)₂—; A₉ is —CR¹⁹R²⁰— or —C(O)—, preferably —CH₂— or —C(O)—; Q⁷¹ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR²³, —NR²³R²³, —OR²³ and —S(O)₂R²³; and Q⁷⁵ is hydrogen, —OR²³, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR²³, —NR²³R²³, —OR²³ and —S(O)₂R²³.

In one embodiment of compounds of Formula IIh, M₁₁ is —NR³⁹CH₂— or —NR³⁹—(CH₂)₂—; A₉ is —CH₂— or —C(O)—, preferably —CH₂—; Q⁷¹ is aryl or heteroaryl, wherein aryl or heteroaryl are optionally substituted with one or more substituents selected from the group consisting of halogen, lower alkyl, fluoro substituted lower alkyl, —NHR⁴¹, —NR⁴¹R⁴¹, —OR⁴¹ and —S(O)₂R⁴¹; Q⁷⁵ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR⁴¹, —NR⁴¹R⁴¹, —OR⁴¹ and —S(O)₂R⁴¹, wherein R⁴¹ is as defined for Formula Ig.

In one embodiment of compounds of Formula IIh, A₉ is —CH₂— or —C(O)—, preferably —CH₂—; Q⁷¹ is aryl or heteroaryl, wherein aryl or heteroaryl are optionally substituted with one or more substituents selected from the group consisting of —OR⁴¹, —SR⁴¹, —S(O)R⁴¹, —S(O)₂R⁴¹, —NHR⁴¹, —NR⁴¹R⁴¹, —NR³⁹C(O)R⁴¹, —NR³⁹S(O)₂R⁴¹, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of Q⁷¹, or as a substituent of lower alkyl are optionally substituted with one or more substituents selected from the group consisting of —OH, —NH₂, —CN, —NO₂, —S(O)₂NH₂, —C(O)NH₂, —OR⁴², —SR⁴², —NHR⁴², —NR⁴²R⁴², —NR³⁹C(O)R⁴², —NR³⁹S(O)₂R⁴², —S(O)₂R⁴², halogen, lower alkyl, fluoro substituted lower alkyl, and cycloalkylamino; Q⁷⁵ is hydrogen, —CN, —OR⁴¹, —SR⁴¹, —S(O)R⁴¹, —S(O)₂R⁴¹, —NHR⁴¹, —NR⁴¹R⁴¹, —NR³⁹C(O)R⁴¹, —NR³⁹S(O)₂R⁴¹, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —NHR⁴¹, —NR⁴¹R⁴¹, and —OR⁴¹; M₁₁ is a bond, —NR³⁹—, —S—, —O—, —NR³⁹CH₂—, —NR³⁹CH₂CH₂—, —NR³⁹CH(R⁴⁰)—, —SCH₂—, —OCH₂—, —C(O)NR³⁹—, —S(O)₂NR³⁹—, —CH₂NR³⁹—, —CH(R⁴⁰)NR³⁹—, —NR³⁹C(O)—, or —NR³⁹S(O)₂—; and Q⁸² is hydrogen, lower alkyl, or fluoro substituted lower alkyl, wherein R³⁹, R⁴⁰, R⁴¹, R⁴² and R⁴⁴ are as defined for Formula II.

In one embodiment of compounds of Formula IIh, A₉ is —CH₂—; Q⁷¹ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; Q⁷⁵ is hydrogen, —CN, fluoro, chloro, lower alkyl, fluoro substituted lower alkyl, lower alkoxy, or fluoro substituted lower alkoxy; M₁₁ is —NR³⁹CH₂—, —NR³⁹CH₂CH₂—, or —NR³⁹CH(R⁴⁰)—; and Q⁸² is hydrogen, lower alkyl, or fluoro substituted lower alkyl.

In one embodiment, further to any of the embodiments of Formula IIh above, each occurrence of R⁴¹ is R⁴² as defined for Formula Ig.

In one embodiment, a compound of Formula II has a structure according to the following sub-generic structure, Formula IIi,

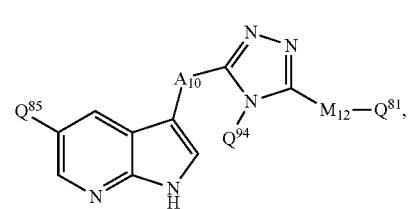

Formula IIi all salts, prodrugs, tautomers, and isomers thereof,
wherein:
A₁₀ is selected from the group consisting of —CR¹⁹R²⁰—, —C(O)—, —C(S)—, —S—, —S(O)—, —S(O)₂—, —NR²¹—, and —O—;

Q⁸⁵ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —NH₂, —NO₂, —CN, —NHC(O)NH₂, —NHC(S)NH₂, —NHS(O)₂NH₂, —C(O)NH₂, —C(S)NH₂, —S(O)₂NH₂, —NR²⁴R²⁵, —NHR²³, —OR²³, —SR²³, —C(O)R²³, —C(S)R²³, —S(O)R²³, —S(O)₂R²³, —C(O)NHR²³, —C(O)NR²³R²³, —C(S)NHR²³, —C(S)NR²³R²³, —S(O)₂NHR²³, —S(O)₂NR²³R²³, —NHC(O)R²³, —NR²³C(O)R²³, —NHC(S)R²³, —NR²³C(S)R²³, —NHS(O)₂R²³, —NR²³S(O)₂R²³, —NHC(O)NHR²³, —NR²³C(O)NH₂, —NR²³C(O)NHR²³, —NHC(O)NR²³R²³, —NR²³C(O)NR²³R²³, —NHC(S)NHR²³, —NR²³C(S)NH₂, —NR²³C(S)NHR²³, —NHC(S)NR²³R²³, —NR²³C(S)NR²³R²³, —NHS(O)₂NHR²³, —NR²³S(O)₂NH₂, —NR²³S(O)₂NHR²³, —NHS(O)₂NR²³R²³, and —NR²³S(O)₂NR²³R²³;

M₁₂, Q⁸¹, and Q⁹⁴ are as defined for Formula II; and
R¹⁹, R²⁰, R²¹, R²³, R²⁴, and R²⁵ are as defined for Formula Ib.

In one embodiment of compounds of Formula IIi, M₁₂ is —(CR¹⁹R²⁰)ₜ—NR²⁶—(CR¹⁹R²⁰)ₛ— or —(CR¹⁹R²⁰)ₜ—NR²⁶C(O)—(CR¹⁹R²⁰)ₛ—, preferably —NR²⁶—(CR¹⁹R²⁰)ₛ— or —NR²⁶C(O)—(CR¹⁹R²⁰)ₛ—, more preferably —NR³⁹CR⁸⁰R⁸⁰— or —NR³⁹(CR⁸⁰R⁸⁰)₂—, wherein R³⁹ is hydrogen or lower alkyl and R⁸⁰ is hydrogen, lower alkyl or fluoro substituted lower alkyl, preferably hydrogen. In one embodiment, A₁₀ is —CR¹⁹R²⁰— or —C(O)—, preferably —CH₂— or —C(O)—. In one embodiment, Q⁸¹ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$ and Q$^{85}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$.

In one embodiment of compounds of Formula IIi, M$_{12}$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CR$^{80}$R$^{80}$— or —NR$^{39}$(CR$^{80}$R$^{80}$)$_2$—, and A$_{10}$ is —CR$^{19}$R$^{20}$— or —C(O)—, preferably —CH$_2$— or —C(O)—. In one embodiment, M$_{12}$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CR$^{80}$R$^{80}$— or —NR$^{39}$(CR$^{80}$R$^{80}$)$_2$—; A$_{10}$ is —CR$^{19}$R$^{20}$— or —C(O)—, preferably —CH$_2$— or —C(O)—; Q$^{81}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and Q$^{85}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$.

In one embodiment of compounds of Formula IIi, M$_{12}$ is —NR$^{39}$CH$_2$— or —NR$^{39}$—(CH$_2$)$_2$—; A$_{10}$ is —CH$_2$— or —C(O)—, preferably —CH$_2$—; Q$^{81}$ is aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; Q$^{85}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$, wherein R$^{41}$ is as defined for Formula Ig.

In one embodiment of compounds of Formula IIi, A$_{10}$ is —CH$_2$— or —C(O)—, preferably —CH$_2$—; Q$^{81}$ is aryl or heteroaryl, wherein aryl or heteroaryl are optionally substituted with one or more substituents selected from the group consisting of —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of Q$^{81}$, or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino; Q$^{85}$ is hydrogen, —CN, —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, and —OR$^{41}$; M$_{12}$ is a bond, —NR$^{39}$—, —S—, —O—, —NR$^{39}$CH$_2$—, —NR$^{39}$CH$_2$CH$_2$—, —NR$^{39}$CH(R$^{40}$)—, —SCH$_2$—, —OCH$_2$—, —C(O)NR$^{39}$—, —S(O)$_2$NR$^{39}$—, —CH$_2$NR$^{39}$—, —CH(R$^{40}$)NR$^{39}$—, —NR$^{39}$C(O)—, or —NR$^{39}$S(O)$_2$—; and Q$^{94}$ is hydrogen, lower alkyl, or fluoro substituted lower alkyl, wherein R$^{39}$, R$^{40}$, R$^{41}$, R$^{42}$ and R$^{44}$ are as defined for Formula II.

In one embodiment of compounds of Formula IIi, A$_{10}$ is —CH$_2$—; Q$^{81}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; Q$^{85}$ is hydrogen, —CN, fluoro, chloro, lower alkyl, fluoro substituted lower alkyl, lower alkoxy, or fluoro substituted lower alkoxy; M$_{12}$ is —NR$^{39}$CH$_2$—, —NR$^{39}$CH$_2$CH$_2$—, or —NR$^{39}$CH(R$^{40}$)—; and Q$^{94}$ is hydrogen, lower alkyl, or fluoro substituted lower alkyl.

In one embodiment, further to any of the embodiments of Formula IIi above, each occurrence of R$^{41}$ is R$^{42}$ as defined for Formula Ig.

In one embodiment, a compound of Formula II has a structure according to the following sub-generic structure, Formula IIj,

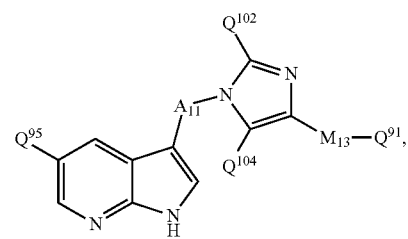

Formula IIj all salts, prodrugs, tautomers, and isomers thereof,
wherein:
A$_{11}$ is selected from the group consisting of —CR$^{19}$R$^{20}$—, —C(O)—, —C(S)—, —S(O)—, and —S(O)$_2$—;
Q$^{95}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —NH$_2$, —NO$_2$, —CN, —NHC(O)NH$_2$, —NHC(S)NH$_2$, —NHS(O)$_2$NH$_2$, —C(O)NH$_2$, —C(S)NH$_2$, —S(O)$_2$NH$_2$, —NR$^{24}$R$^{25}$, —NHR$^{23}$, —OR$^{23}$, —SR$^{23}$, —C(O)R$^{23}$, —C(S)R$^{23}$, —S(O)R$^{23}$, —S(O)$_2$R$^{23}$, —C(O)NHR$^{23}$, —C(O)NR$^{23}$R$^{23}$, —C(S)NHR$^{23}$, —C(S)NR$^{23}$R$^{23}$, —S(O)$_2$NHR$^{23}$, —S(O)$_2$NR$^{23}$R$^{23}$, —NHC(O)R$^{23}$, —NR$^{23}$C(O)R$^{23}$, —NHC(S)R$^{23}$, —NR$^{23}$C(S)R$^{23}$, —NHS(O)$_2$R$^{23}$, —NR$^{23}$S(O)$_2$R$^{23}$, —NHC(O)NHR$^{23}$, —NR$^{23}$C(O)NH$_2$, —NHC(O)NHR$^{23}$, —NHC(O)NR$^{23}$R$^{23}$, —NR$^{23}$C(O)NR$^{23}$R$^{23}$, —NHC(S)NHR$^{23}$, —NR$^{23}$C(S)NH$_2$, —NR$^{23}$C(S)NHR$^{23}$, —NHC(S)NR$^{23}$R$^{23}$, —NR$^{23}$C(S)NR$^{23}$R$^{23}$, —NHS(O)$_2$NHR$^{23}$, —$NR^{23}S(O)_2NH_2$, —$NR^{23}S(O)_2NHR^{23}$, —$NHS(O)_2NR^{23}R^{23}$, and —$NR^{23}S(O)_2NR^{23}R^{23}$; $M_{13}$, $Q^{91}$, $Q^{102}$ and $Q^{104}$ are as defined for Formula II; and $R^{19}$, $R^{20}$, $R^{23}$, $R^{24}$, and $R^{25}$ are as defined for Formula Ib.

In one embodiment of compounds of Formula IIj, $M_{13}$ is —$(CR^{19}R^{20})_t$—$NR^{26}$—$(CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$— or —$NR^{39}(CR^{80}R^{80})_2$—, wherein $R^{39}$ is hydrogen or lower alkyl and $R^{80}$ is hydrogen, lower alkyl or fluoro substituted lower alkyl, preferably hydrogen. In one embodiment, $A_{11}$ is —$CR^{19}R^{20}$— or —$C(O)$—, preferably —$CH_2$— or —$C(O)$—. In one embodiment, $Q^{91}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$ and $Q^{95}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$. Further to any of the above embodiments, $Q^{102}$ and $Q^{104}$ are independently hydrogen, fluoro, chloro, methyl, or —$CF_3$.

In one embodiment of compounds of Formula IIj, $M_{13}$ is —$(CR^{19}R^{20})_t$—$NR^{26}$—$(CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$— or —$NR^{39}(CR^{80}R^{80})_2$—, and $A_{11}$ is —$CR^{19}R^{20}$— or —$C(O)$—, preferably —$CH_2$— or —$C(O)$—. In one embodiment, $M_{13}$ is —$(CR^{19}R^{20})_t$—$NR^{26}$—$(CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NRC(O)$—$(CR^{19}R^{20})_s$—, more preferably —$NR^{39}CR^{80}R^{80}$— or —$NR^{39}(CR^{80}R^{80})_2$—; $A_{11}$ is —$CR^{19}R^{20}$— or —$C(O)$—, preferably —$CH_2$— or —$C(O)$—; $Q^{91}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$; and $Q^{95}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$. In one embodiment, $M_{13}$ is —$(CR^{19}R^{20})_t$—$NR^{26}$—$(CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$— or —$NR^{39}(CR^{80}R^{80})_2$—; $A_{11}$ is —$CR^{19}R^{20}$— or —$C(O)$—, preferably —$CH_2$— or —$C(O)$—; $Q^{91}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$; $Q^{95}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$; and $Q^{102}$ and $Q^{104}$ are independently hydrogen, fluoro, chloro, methyl, or —$CF_3$.

In one embodiment of compounds of Formula IIj, $M_{13}$ is —$NR^{39}CH_2$— or —$NR^{39}$—$(CH_2)_2$—; $A_{11}$ is —$CH_2$— or —$C(O)$—, preferably —$CH_2$—; $Q^{91}$ is aryl or heteroaryl, wherein aryl or heteroaryl are optionally substituted with one or more substituents selected from the group consisting of halogen, lower alkyl, fluoro substituted lower alkyl, —$NHR^{41}$, —$NR^{41}R^{41}$, —$OR^{41}$ and —$S(O)_2R^{41}$; $Q^{95}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{41}$, —$NR^{41}R^{41}$, —$OR^{41}$ and —$S(O)_2R^{41}$; and $Q^{102}$ and $Q^{104}$ are independently hydrogen, fluoro, chloro, lower alkyl, or fluoro substituted lower alkyl, preferably $Q^{102}$ and $Q^{104}$ are independently hydrogen, fluoro, chloro, methyl, or —$CF_3$, wherein $R^{41}$ is as defined for Formula Ig.

In one embodiment of compounds of Formula IIj, $A_{11}$ is —$CH_2$— or —$C(O)$—, preferably —$CH_2$—; $Q^{91}$ is aryl or heteroaryl, wherein aryl or heteroaryl are optionally substituted with one or more substituents selected from the group consisting of —$OR^{41}$, —$SR^{41}$, —$S(O)R^{41}$, —$S(O)_2R^{41}$, —$NHR^{41}$, —$NR^{41}R^{41}$, —$NR^{39}C(O)R^{41}$, —$NR^{39}S(O)_2R^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of $Q^{91}$, or as a substituent of lower alkyl are optionally substituted with one or more substituents selected from the group consisting of —OH, —$NH_2$, —CN, —$NO_2$, —$S(O)_2NH_2$, —$C(O)NH_2$, —$OR^{42}$, —$SR^{42}$, —$NHR^{42}$, —$NR^{42}R^{42}$, —$NR^{39}C(O)R^{42}$, —$NR^{39}S(O)_2R^{42}$, —$S(O)_2R^{42}$, halogen, lower alkyl, fluoro substituted lower alkyl, and cycloalkylamino; $Q^{95}$ is hydrogen, —CN, —$OR^{41}$, —$SR^{41}$, —$S(O)R^{41}$, —$S(O)_2R^{41}$, —$NHR^{41}$, —$NR^{41}R^{41}$, —$NR^{39}C(O)R^{41}$, —$NR^{39}S(O)_2R^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —$NHR^{41}$, —$NR^{41}R^{41}$, and —$OR^{41}$; $M_{13}$ is a bond, —$NR^{39}$—, —S—, —O—, —$NR^{39}CH_2$—, —$NR^{39}CH_2CH_2$—, —$NR^{39}CH(R^{40})$—, —$SCH_2$—, —$OCH_2$—, —$C(O)NR^{39}$—, —$S(O)_2NR^{39}$—, —$CH_2NR^{39}$—, —$CH(R^{40})NR^{39}$—, —$NR^{39}C(O)$—, or —$NR^{39}S(O)_2$—; and $Q^{102}$ and $Q^{104}$ are independently hydrogen, halogen, lower alkyl, fluoro substituted lower alkyl, —$NR^{44}R^{44}$, —$OR^{44}$, or —$SR^{44}$, provided, however, that at least one of $Q^{102}$ and $Q^{104}$ is hydrogen, fluoro, chloro, lower alkyl or fluoro substituted lower alkyl, wherein $R^{39}$, $R^{40}$, $R^{41}$, $R^{42}$ and $R^{44}$ are as defined for Formula II.

In one embodiment of compounds of Formula IIj, $A_{11}$ is —$CH_2$—; $Q^{91}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; $Q^{95}$ is hydrogen, —CN, fluoro, chloro, lower alkyl, fluoro substituted lower alkyl, lower alkoxy, or fluoro substituted lower alkoxy; $M_{13}$ is —$NR^{39}CH_2$—, —$NR^{39}CH_2CH_2$—, or —$NR^{39}CH(R^{40})$—;

and $Q^{102}$ and $Q^{104}$ are independently hydrogen, halogen, lower alkyl, fluoro substituted lower alkyl, lower alkoxy, or fluoro substituted lower alkoxy, provided, however, that at least one of $Q^{102}$ and $Q^{104}$ is hydrogen, fluoro, chloro, lower alkyl or fluoro substituted lower alkyl.

In one embodiment, further to any of the embodiments of Formula IIj above, each occurrence of $R^{41}$ is $R^{42}$ as defined for Formula Ig.

In one embodiment, a compound of Formula II has a structure according to the following sub-generic structure, Formula IIk,

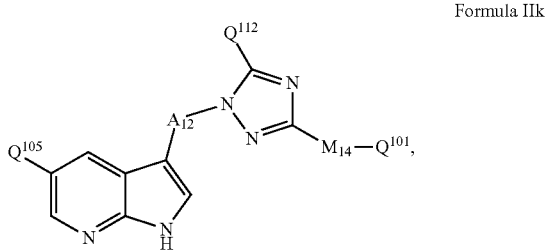

Formula IIk all salts, prodrugs, tautomers, and isomers thereof, wherein:
  $A_{12}$ is selected from the group consisting of —$CR^{19}R^{20}$—, —C(O)—, —C(S)—, S(O)—, and —$S(O)_2$—;
  $Q^{105}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —$NH_2$, —$NO_2$, —CN, —NHC(O)$NH_2$, —NHC(S)$NH_2$, —NHS(O)$_2NH_2$, —C(O)$NH_2$, —C(S)$NH_2$, —S(O)$_2NH_2$, —$NR^{24}R^{25}$, —$NHR^{23}$, —$OR^{23}$, —$SR^{23}$, —C(O)$R^{23}$, —C(S)$R^{23}$, —S(O)$R^{23}$, —S(O)$_2R^{23}$, —C(O)$NHR^{23}$, —C(O)$NR^{23}R^{23}$, —C(S)$NHR^{23}$, —C(S)$NR^{23}R^{23}$, —S(O)$_2NHR^{23}$, —S(O)$_2NR^{23}R^{23}$, —NHC(O)$R^{23}$, —$NR^{23}$C(O)$R^{23}$, —NHC(S)$R^{23}$, —$NR^{23}$C(S)$R^{23}$, —NHS(O)$_2R^{23}$, —$NR^{23}$S(O)$_2R^{23}$, —NHC(O)$NHR^{23}$, —$NR^{23}$C(O)$NH_2$, —$NR^{23}$C(O)$NHR^{23}$, —NHC(O)$NR^{23}R^{23}$, —$NR^{23}$C(O)$NR^{23}R^{23}$, —NHC(S)$NHR^{23}$, —$NR^{23}$C(S)$NH_2$, —$NR^{23}$C(S)$NHR^{23}$, —NHC(S)$NR^{23}R^{23}$, —$NR^{23}$C(S)$NR^{23}R^{23}$, —NHS(O)$_2NHR^{23}$, —$NR^{23}$S(O)$_2NH_2$, —$NR^{23}$S(O)$_2NHR^{23}$, —NHS(O)$_2NR^{23}R^{23}$, and —$NR^{23}$S(O)$_2NR^{23}R^{23}$;
  $M_{14}$, $Q^{101}$, and $Q^{112}$ are as defined for Formula II; and $R^{19}$, $R^{20}$, $R^{23}$, $R^{24}$, and $R^{25}$ are as defined for Formula Ib.

In one embodiment of compounds of Formula IIk, $M_{14}$ is —$(CR^{19}R^{20})_t$—$NR^{26}$—$(CR^{19}R^{20})_s$— or —$(CR^{19}R^{20})_t$—$NR^{26}$C(O)—$(CR^{19}R^{20})_s$—, preferably —$NR^{26}$—$(CR^{19}R^{20})_s$— or —$NR^{26}$C(O)—$(CR^{19}R^{20})_s$—, more preferably —$NR^{39}CR^{80}R^{80}$— or —$NR^{39}(CR^{80}R^{80})_2$—, wherein $R^{39}$ is hydrogen or lower alkyl and $R^{80}$ is hydrogen, lower alkyl or fluoro substituted lower alkyl, preferably hydrogen. In one embodiment, $A_{12}$ is —$CR^{19}R^{20}$— or —C(O)—, preferably —$CH_2$— or —C(O)—. In one embodiment, $Q^{101}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$ and $Q^{105}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$. Further to any of the above embodiments, $Q^{112}$ is hydrogen, fluoro, chloro, lower alkyl or fluoro substituted lower alkyl.

In one embodiment of compounds of Formula IIk, $M_{14}$ is —$(CR^{19}R^{20})_t$—$NR^{26}$—$(CR^{19}R^{20})_s$— or —$(CR^{19}R^{20})_t$—$NR^{26}$C(O)—$(CR^{19}R^{20})_s$—, preferably —$NR^{26}$—$(CR^{19}R^{20})_s$— or —$NR^{26}$C(O)—$(CR^{19}R^{20})_s$—, more preferably —$NR^{39}CR^{80}R^{80}$— or —$NR^{39}(CR^{80}R^{80})_2$—, and $A_{12}$ is —$CR^{19}R^{20}$— or —C(O)—, preferably —$CH_2$— or —C(O)—. In one embodiment, $M_{14}$ is —$(CR^{19}R^{20})_t$—$NR^{26}$—$(CR^{19}R^{20})_s$— or —$(CR^{19}R^{20})_t$—$NR^{26}$C(O)—$(CR^{19}R^{20})_s$—, preferably —$NR^{26}$—$(CR^{19}R^{20})_s$— or —$NR^{26}$C(O)—$(CR^{19}R^{20})_s$—, more preferably —$NR^{39}CR^{80}R^{80}$— or —$NR^{39}(CR^{80}R^{80})_2$—; $A_{12}$ is —$CR^{19}R^{20}$— or —C(O)—, preferably —$CH_2$— or —C(O)—; $Q^{101}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$; and $Q^{105}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and $S(O)_2R^{23}$; and $Q^{112}$ is hydrogen, fluoro, chloro, lower alkyl or fluoro substituted lower alkyl.

In one embodiment of compounds of Formula IIk, $M_{14}$ is —$NR^{39}CH_2$— or —$NR^{39}$—$(CH_2)_2$—; $A_{12}$ is —$CH_2$— or —C(O)—, preferably —$CH_2$—; $Q^{101}$ is aryl or heteroaryl, wherein aryl or heteroaryl are optionally substituted with one or more substituents selected from the group consisting of halogen, lower alkyl, fluoro substituted lower alkyl, —$NHR^{41}$, —$NR^{41}R^{41}$, —$OR^{41}$ and —$S(O)_2R^{41}$; $Q^{105}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{41}$, —$NR^{41}R^{41}$, —$OR^{41}$ and —$S(O)_2R^{41}$; and $Q^{112}$ is hydrogen, fluoro, chloro, lower alkyl or fluoro substituted lower alkyl, wherein $R^{41}$ is as defined for Formula Ig.

In one embodiment of compounds of Formula IIk, $A_{12}$ is —$CH_2$— or —C(O)—, preferably —$CH_2$—; $Q^{101}$ is aryl or heteroaryl, wherein aryl or heteroaryl are optionally substituted with one or more substituents selected from the group consisting of —$OR^{41}$, —$SR^{41}$, —$S(O)R^{41}$, —$S(O)_2R^{41}$, —$NHR^{41}$, —$NR^{41}R^{41}$, —$NR^{39}C(O)R^{41}$, —$NR^{39}S(O)_2R^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of $Q^{101}$, or as a substituent of lower alkyl are optionally substituted with one or more substituents selected from the group consisting of —OH, —$NH_2$, —CN, —$NO_2$, —$S(O)_2NH_2$, —$C(O)NH_2$, —$OR^{42}$, —$SR^{42}$, —$NHR^{42}$, —$NR^{42}R^{42}$, —$NR^{39}C(O)R^{42}$, —$NR^{39}S(O)_2R^{42}$, —$S(O)_2R^{42}$, halogen, lower alkyl, fluoro substituted lower alkyl, and cycloalkylamino; $Q^{105}$ is hydrogen, —CN, —$OR^{41}$, —$SR^{41}$, —$S(O)R^{41}$, —$S(O)_2R^{41}$, —$NHR^{41}$, —$NR^{41}R^{41}$, —$NR^{39}C(O)R^{41}$, —$NR^{39}S(O)_2R^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —$NHR^{41}$, —$NR^{41}R^{41}$, and —$OR^{41}$; $M_{14}$ is a bond, —$NR^{39}$—, —S—, —O—, —$NR^{39}CH_2$—, —$NR^{39}CH_2CH_2$—, —$NR^{39}CH(R^{40})$—, —$SCH_2$—, —$OCH_2$—, —$C(O)NR^{39}$—, —$S(O)_2NR^{39}$—, —$CH_2NR^{39}$—, —$CH(R^{40})NR^{39}$—, —$NR^{39}C(O)$—, or —$NR^{39}S(O)_2$—; and $Q^{112}$ is hydrogen, fluoro, chloro, lower alkyl, fluoro substituted lower alkyl, —$NR^{44}R^{44}$, —$OR^{44}$, or —$SR^{44}$, wherein $R^{39}$, $R^{40}$, $R^{41}$, $R^{42}$ and $R^{44}$ are as defined for Formula II.

In one embodiment of compounds of Formula IIk, $A_{12}$ is —$CH_2$—; $Q^{101}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; $Q^{105}$ is hydrogen, —CN, fluoro, chloro, lower alkyl, fluoro substituted lower alkyl, lower alkoxy, or fluoro substituted lower alkoxy; $M_{14}$ is —$NR^{39}CH_2$—, —$NR^{39}CH_2CH_2$—, or —$NR^{39}CH(R^{40})$—; and $Q^{112}$ is hydrogen, fluoro, chloro, lower alkyl, fluoro substituted lower alkyl, lower alkoxy, or fluoro substituted lower alkoxy.

In one embodiment, further to any of the embodiments of Formula IIk above, each occurrence of $R^{41}$ is $R^{42}$ as defined for Formula Ig.

In one embodiment, a compound of Formula II has a structure according to the following sub-generic structure, Formula IIm,

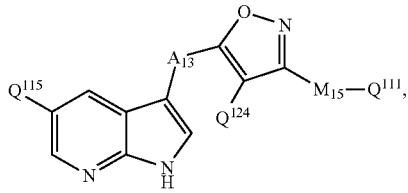

Formula IIm all salts, prodrugs, tautomers, and isomers thereof, wherein:

$A_{13}$ is selected from the group consisting of —$CR^{19}R^{20}$—, —C(O)—, —C(S)—, —S—, —S(O)—, —$S(O)_2$—, —$NR^{21}$—, and —O—;

$Q^{115}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —$NH_2$, —$NO_2$, —CN, —NHC(O)$NH_2$, —NHC(S)$NH_2$, —NHS(O)$_2NH_2$, —C(O)$NH_2$, —C(S)$NH_2$, —S(O)$_2NH_2$, —$NR^{24}R^{25}$, —$NHR^{23}$, —$OR^{23}$, —$SR^{23}$, —$C(O)R^{23}$, —$C(S)R^{23}$, —$S(O)R^{23}$, —$S(O)_2R^{23}$, —$C(O)NHR^{23}$, —$C(O)NR^{23}R^{23}$, —$C(S)NHR^{23}$, —$C(S)NR^{23}R^{23}$, —$S(O)_2NHR^{23}$, —$S(O)_2NR^{23}R^{23}$, —$NHC(O)R^{23}$, —$NR^{23}C(O)R^{23}$, —$NHC(S)R^{23}$, —$NR^{23}C(S)R^{23}$, —$NHS(O)_2R^{23}$, —$NR^{23}S(O)_2R^{23}$, —$NHC(O)NHR^{23}$, —$NR^{23}C(O)NH_2$, —$NR^{23}C(O)NHR^{23}$, —$NHC(O)NR^{23}R^{23}$, —$NR^{23}C(O)NR^{23}R^{23}$, —$NHC(S)NHR^{23}$, —$NR^{23}C(S)NH_2$, —$NR^{23}C(S)NHR^{23}$, —$NHC(S)NR^{23}R^{23}$, —$NR^{23}C(S)NR^{23}R^{23}$, —$NHS(O)_2NHR^{23}$, —$NR^{23}S(O)_2NH_2$, —$NR^{23}S(O)_2NHR^{23}$, —$NHS(O)_2NR^{23}R^{23}$, and —$NR^{23}S(O)_2NR^{23}R^{23}$;

$M_{15}$, $Q^{111}$, and $Q^{124}$ are as defined for Formula II; and $R^{19}$, $R^{20}$, $R^{21}$, $R^{23}$, $R^{24}$, and $R^{25}$ are as defined for Formula Ib.

In one embodiment of compounds of Formula IIm, $M_{15}$ is —$(CR^{19}R^{20})_t$—$NR^{26}$—$(CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$— or —$NR^{39}(CR^{80}R^{80})_2$—, wherein $R^{39}$ is hydrogen or lower alkyl and $R^{80}$ is hydrogen, lower alkyl or fluoro substituted lower alkyl, preferably hydrogen. In one embodiment, $A_{13}$ is —$CR^{19}R^{20}$— or —C(O)—, preferably —$CH_2$— or —C(O)—. In one embodiment, $Q^{111}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$ and $Q^{115}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$. Further to any of the above embodiments, $Q^{124}$ is hydrogen, fluoro, chloro, lower alkyl or fluoro substituted lower alkyl.

In one embodiment of compounds of Formula IIm, $M_{15}$ is —$(CR^{19}R^{20})_t$—$NR^{26}$—$(CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$— or —$NR^{39}(CR^{80}R^{80})_2$—, and $A_{13}$ is —$CR^{19}R^{20}$— or —C(O)—, preferably —$CH_2$— or —C(O)—. In one embodiment, $M_{15}$ is —$(CR^{19}R^{20})_t$—$NR^{26}$—$(CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$— or —$NR^{39}(CR^{80}R^{80})_2$—; $A_{13}$ is —$CR^{19}R^{20}$— or —C(O)—, preferably —$CH_2$— or —C(O)—; $Q^{111}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$; and $Q^{115}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$. In one embodiment, M$_{15}$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CR$^{80}$R$^{80}$— or —NR$^{39}$(CR$^{80}$R$^{80}$)$_2$—; A$_{13}$ is —CR$^{19}$R$^{20}$— or —C(O)—, preferably —CH$_2$— or —C(O)—; Q$^{111}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; Q$^{115}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and Q$^{124}$ is hydrogen, fluoro, chloro, lower alkyl or fluoro substituted lower alkyl.

In one embodiment of compounds of Formula IIm, M$_{15}$ is —NR$^{39}$CH$_2$— or —NR$^{39}$—(CH$_2$)$_2$—; A$_{13}$ is —CH$_2$— or —C(O)—, preferably —CH$_2$—; Q$^{111}$ is aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; Q$^{115}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{42}$, —NR$^{42}$R$^{42}$, —OR$^{42}$ and —S(O)$_2$R$^{42}$; and Q$^{124}$ is hydrogen, fluoro, chloro, lower alkyl or fluoro substituted lower alkyl, wherein R$^{41}$ is as defined for Formula Ig.

In one embodiment of compounds of Formula IIm, A$_{13}$ is —CH$_2$— or —C(O)—, preferably —CH$_2$—; Q$^{111}$ is aryl or heteroaryl, wherein aryl or heteroaryl are optionally substituted with one or more substituents selected from the group consisting of —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of Q$^{111}$, or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino; Q$^{115}$ is hydrogen, —CN, —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, and —OR$^{41}$; M$_{15}$ is a bond, —NR$^{39}$—, —S—, —O—, —NR$^{39}$CH$_2$—, —NR$^{39}$CH$_2$CH$_2$—, —NR$^{39}$CH(R$^{40}$)—, —SCH$_2$—, —OCH$_2$—, —C(O)NR$^{39}$—, —S(O)$_2$NR$^{39}$—, —CH$_2$NR$^{39}$—, —CH(R$^{40}$)NR$^{39}$—, —NR$^{39}$C(O)—, or —NR$^{39}$S(O)$_2$—; and Q$^{124}$ is hydrogen, fluoro, chloro, lower alkyl, fluoro substituted lower alkyl, —NR$^{44}$R$^{44}$, —OR$^{44}$, or —SR$^{44}$, wherein R$^{39}$, R$^{40}$, R$^{41}$, R$^{42}$ and R$^{44}$ are as defined for Formula II.

In one embodiment of compounds of Formula IIm, A$_{13}$ is —CH$_2$—; Q$^{111}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; Q$^{115}$ is hydrogen, —CN, fluoro, chloro, lower alkyl, fluoro substituted lower alkyl, lower alkoxy, or fluoro substituted lower alkoxy; M$_{15}$ is —NR$^{39}$CH$_2$—, —NR$^{39}$CH$_2$CH$_2$—, or —NR$^{39}$CH(R$^{40}$)—; and Q$^{124}$ is hydrogen, fluoro, chloro, lower alkyl, fluoro substituted lower alkyl, lower alkoxy, or fluoro substituted lower alkoxy.

In one embodiment, further to any of the embodiments of Formula IIm above, each occurrence of R$^{41}$ is R$^{42}$ as defined for Formula Ig.

In one embodiment, a compound of Formula II has a structure according to the following sub-generic structure, Formula IIn,

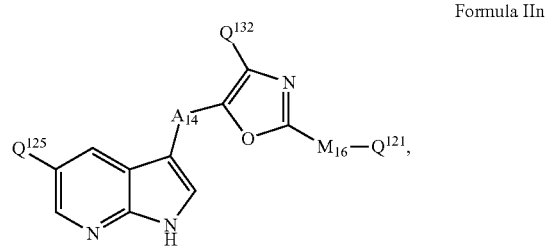

Formula IIn all salts, prodrugs, tautomers, and isomers thereof, wherein:

A$_{14}$ is selected from the group consisting of —CR$^{19}$R$^{20}$—, —C(O)—, —C(S)—, —S—, —S(O)—, —S(O)$_2$—, —NR$^{21}$—, and —O—;

Q$^{125}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —NH$_2$, —NO$_2$, —CN, —NHC(O)NH$_2$, —NHC(S)NH$_2$, —NHS(O)$_2$NH$_2$, —C(O)NH$_2$, —C(S)NH$_2$, —S(O)$_2$NH$_2$, —NR$^{24}$R$^{25}$, —NHR$^{23}$, —OR$^{23}$, —SR$^{23}$, —C(O)R$^{23}$, —C(S)R$^{23}$, —S(O)R$^{23}$, —S(O)$_2$R$^{23}$, —C(O)NHR$^{23}$, —C(O)NR$^{23}$R$^{23}$, —C(S)NHR$^{23}$, —C(S)NR$^{23}$R$^{23}$, —S(O)$_2$NHR$^{23}$, —S(O)$_2$NR$^{23}$R$^{23}$, —NHC(O)R$^{23}$, —NR$^{23}$C(O)R$^{23}$, —NHC(S)R$^{23}$, —NR$^{23}$C(S)R$^{23}$, —NHS(O)$_2$R$^{23}$, —NR$^{23}$S(O)$_2$R$^{23}$, —NHC(O)NHR$^{23}$, —NR$^{23}$C(O)NH$_2$, —NR$^{23}$C(O)NHR$^{23}$, —NHC(O)NR$^{23}$R$^{23}$, —NR$^{23}$C(O)NR$^{23}$R$^{23}$, —NHC(S)NHR$^{23}$, —NR$^{23}$C(S)NH$_2$, —NR$^{23}$C(S)NHR$^{23}$, —NHC(S)NR$^{23}$R$^{23}$, —NR$^{23}$C(S)NR$^{23}$R$^{23}$, —NHS(O)$_2$NHR$^{23}$, —NR$^{23}$S(O)$_2$NH$_2$, —NR$^{23}$S(O)$_2$NHR$^{23}$, —NHS(O)$_2$NR$^{23}$R$^{23}$, and —NR$^{23}$S(O)$_2$NR$^{23}$R$^{23}$;

M$_{16}$, Q$^{121}$, and Q$^{132}$ are as defined for Formula II; and R$^{19}$, R$^{20}$, R$^{21}$, R$^{23}$, R$^{24}$, and R$^{25}$ are as defined for Formula Ib.

In one embodiment of compounds of Formula IIn, $M_{16}$ is —$(CR^{19}R^{20})_t$—$NR^{26}$—$(CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$— or —$NR^{39}(CR^{80}R^{80})_2$—, wherein $R^{39}$ is hydrogen or lower alkyl and $R^{80}$ is hydrogen, lower alkyl or fluoro substituted lower alkyl, preferably hydrogen. In one embodiment, $A_{14}$ is —$CR^{19}R^{20}$— or —$C(O)$—, preferably —$CH_2$— or —$C(O)$—. In one embodiment, $Q^{121}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$ and $Q^{125}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$. Further to any of the above embodiments, $Q^{132}$ is hydrogen, fluoro, chloro, lower alkyl or fluoro substituted lower alkyl.

In one embodiment of compounds of Formula IIn, $M_{16}$ is —$(CR^{19}R^{20})_t$—$NR^{26}$—$(CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$— or —$NR^{39}(CR^{80}R^{80})_2$—, and $A_{14}$ is —$CR^{19}R^{20}$— or —$C(O)$—, preferably —$CH_2$— or —$C(O)$—. In one embodiment, $M_{16}$ is —$(CR^{19}R^{20})_t$—$NR^{26}$—$(CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$— or —$NR^{39}(CR^{80}R^{80})_2$—; $A_{14}$ is —$CR^{19}R^{20}$— or —$C(O)$—, preferably —$CH_2$— or —$C(O)$—; $Q^{121}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$; and $Q^{125}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$. In one embodiment, $M_{16}$ is —$(CR^{19}R^{20})_t$—$NR^{26}$—$(CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$— or —$NR^{39}(CR^{80}R^{80})_2$—; $A_{14}$ is —$CR^{19}R^{20}$— or —$C(O)$—, preferably —$CH_2$— or —$C(O)$—; $Q^{121}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$; $Q^{125}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$; and $Q^{132}$ is hydrogen, fluoro, chloro, lower alkyl or fluoro substituted lower alkyl.

In one embodiment of compounds of Formula IIn, $M_{16}$ is —$NR^{39}CH_2$— or —$NR^{39}$—$(CH_2)_2$—; $A_{14}$ is —$CH_2$— or —$C(O)$—, preferably —$CH_2$—; $Q^{121}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{42}$, —$NR^{42}R^{42}$, —$OR^{42}$ and —$S(O)_2R^{42}$; $Q^{25}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{41}$, —$NR^{41}R^{41}$, —$OR^{41}$ and —$S(O)_2R^{41}$; and $Q^{132}$ is hydrogen, fluoro, chloro, lower alkyl or fluoro substituted lower alkyl, wherein $R^{41}$ is as defined for Formula Ig.

In one embodiment of compounds of Formula IIn, $A_{14}$ is —$CH_2$— or —$C(O)$—, preferably —$CH_2$—; $Q^{121}$ is aryl or heteroaryl, wherein aryl or heteroaryl are optionally substituted with one or more substituents selected from the group consisting of —$OR^{41}$, —$SR^{41}$, —$S(O)R^{41}$, —$S(O)_2R^{41}$, —$NHR^{41}$, —$NR^{41}R^{41}$, —$NR^{39}C(O)R^{41}$, —$NR^{39}S(O)_2R^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of $Q^{121}$, or as a substituent of lower alkyl are optionally substituted with one or more substituents selected from the group consisting of —OH, —$NH_2$, —CN, —$NO_2$, —$S(O)_2NH_2$, —$C(O)NH_2$, —$OR^{42}$, —$SR^{42}$, —$NHR^{42}$, —$NR^{42}R^{42}$, —$NR^{39}C(O)R^{42}$, —$NR^{39}S(O)_2R^{42}$, —$S(O)_2R^{42}$, halogen, lower alkyl, fluoro substituted lower alkyl, and cycloalkylamino; $Q^{125}$ is hydrogen, —CN, —$OR^{41}$, —$SR^{41}$, —$S(O)R^{41}$, —$S(O)_2R^{41}$, —$NHR^{41}$, —$NR^{41}R^{41}$, —$NR^{39}C(O)R^{41}$, —$NR^{39}S(O)_2R^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —$NHR^{41}$, —$NR^{41}R^{41}$, and —$OR^{41}$; $M_{16}$ is a bond, —$NR^{39}$—, —S—, —O—, —$NR^{39}CH_2$—, —$NR^{39}CH_2CH_2$—, —$NR^{39}CH(R^{40})$—, —$SCH_2$—, —$OCH_2$—, —$C(O)NR^{39}$—, —$S(O)_2NR^{39}$—, —$CH_2NR^{39}$—, —$CH(R^{40})NR^{39}$—, —$NR^{39}C(O)$—, or —$NR^{39}S(O)_2$—; and $Q^{132}$ is hydrogen, fluoro, chloro, lower alkyl, fluoro substituted lower alkyl, —$NR^{44}R^{44}$, —$OR^{44}$, or —$SR^{44}$, wherein $R^{39}$, $R^{40}$, $R^{41}$, $R^{42}$ and $R^{44}$ are as defined for Formula II.

In one embodiment of compounds of Formula IIn, $A_{14}$ is —$CH_2$—; $Q^{121}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; $Q^{125}$ is hydrogen, —CN, fluoro, chloro, lower alkyl, fluoro substituted lower alkyl, lower alkoxy, or fluoro substituted lower alkoxy; $M_{16}$ is —$NR^{39}CH_2$—, —$NR^{39}CH_2CH_2$—, or —$NR^{39}CH(R^{40})$—; and $Q^{132}$ is hydrogen, fluoro, chloro, lower alkyl, fluoro substituted lower alkyl, lower alkoxy, or fluoro substituted lower alkoxy.

In one embodiment, further to any of the embodiments of Formula IIn above, each occurrence of $R^{41}$ is $R^{42}$ as defined for Formula Ig.

In one embodiment, a compound of Formula II has a structure according to the following sub-generic structure, Formula IIo,

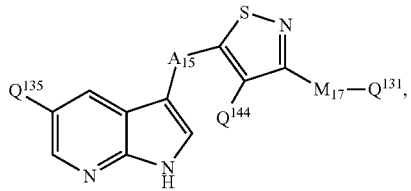

Formula IIo all salts, prodrugs, tautomers, and isomers thereof,
wherein:
$A_{15}$ is selected from the group consisting of —$CR^{19}R^{20}$—, —C(O)—, —C(S)—, —S—, —S(O)—, —$S(O)_2$—, —$NR^2$—, and —O—;
$Q^{135}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —$NH_2$, —$NO_2$, —CN, —NHC(O)$NH_2$, —NHC(S)$NH_2$, —NHS(O)$_2NH_2$, —C(O)$NH_2$, —C(S)$NH_2$, —S(O)$_2NH_2$, —$NR^{24}R^{25}$, —$NHR^{23}$, —$OR^{23}$, —$SR^{23}$, —C(O)$R^{23}$, —C(S)$R^{23}$, —S(O)$R^{23}$, —$S(O)_2R^{23}$, —C(O)$NHR^{23}$, —C(O)$NR^{23}R^{23}$, —C(S)$NHR^{23}$, —C(S)$NR^{23}R^{23}$, —S(O)$NHR^{23}$, —$S(O)_2NR^{23}R^{23}$, —NHC(O)$R^{23}$, —$NR^{23}$C(O)$R^{23}$, —NHC(S)$R^{23}$, —$NR^{23}$C(S)$R^{23}$, —NHS(O)$_2R^{23}$, —$NR^{23}S(O)_2R^{23}$, —NHC(O)$NHR^{23}$, —$NR^{23}$C(O)$NH_2$, —$NR^{23}$C(O)$NHR^{23}$, —NHC(O)$NR^{23}R^{23}$, —$NR^{23}$C(O)$NR^{23}R^{23}$, —NHC(S)$NHR^{23}$, —$NR^{23}$C(S)$NH_2$, —$NR^{23}$C(S)$NHR^{23}$, —NHC(S)$NR^{23}R^{23}$, —$NR^{23}$C(S)$NR^{23}R^{23}$, —NHS(O)$_2NHR^{23}$, —$NR^{23}S(O)_2NH_2$, —$NR^{23}S(O)_2NHR^{23}$, —NHS(O)$_2NR^{23}R^{23}$, and —$NR^{23}S(O)_2NR^{23}R^{23}$;
$M_{17}$, $Q^{131}$, and $Q^{144}$ are as defined for Formula II; and $R^{19}$, $R^{20}$, $R^{21}$, $R^{23}$, $R^{24}$, and $R^{25}$ are as defined for Formula Ib.

In one embodiment of compounds of Formula IIo, $M_{17}$ is —$(CR^{19}R^{20})_t$—$NR^{26}$—$(CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$— or —$NR^{39}(CR^{80}R^{80})_2$—, wherein $R^{39}$ is hydrogen or lower alkyl and $R^{80}$ is hydrogen, lower alkyl or fluoro substituted lower alkyl, preferably hydrogen. In one embodiment, $A_{15}$ is —$CR^{19}R^{20}$— or —C(O)—, preferably —$CH_2$— or —C(O)—. In one embodiment, $Q^{131}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$ and $Q^{135}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$. Further to any of the above embodiments, $Q^{144}$ is hydrogen, fluoro, chloro, lower alkyl, or fluoro substituted lower alkyl.

In one embodiment of compounds of Formula IIo, $M_{17}$ is —$(CR^{19}R^{20})_t$—$NR^{26}$—$(CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$—, —$NR^{39}(CR^{80}R^{80})_2$—, and $A_{15}$ is —$CR^{19}R^{20}$— or —C(O)—, preferably —$CH_2$— or —C(O)—. In one embodiment, $M_{17}$ is —$(CR^{19}R^{20})_t$—$NR^{26}$—$(CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$—, —$NR^{39}(CR^{80}R^{80})_2$—; $A_{15}$ is —$CR^{19}R^{20}$— or —C(O)—, preferably —$CH_2$— or —C(O)—; $Q^{131}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$; and $Q^{135}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$; and $Q^{144}$ is hydrogen, fluoro, chloro, lower alkyl, or fluoro substituted lower alkyl.

In one embodiment of compounds of Formula IIo, $M_{17}$ is —$NR^{39}CH_2$— or —$NR^{39}$—$(CH_2)_2$—; $A_{15}$ is —$CH_2$— or —C(O)—, preferably —$CH_2$—; $Q^{131}$ is aryl or heteroaryl, wherein aryl or heteroaryl are optionally substituted with one or more substituents selected from the group consisting of halogen, lower alkyl, fluoro substituted lower alkyl, —$NHR^{42}$, —$NR^{42}R^{42}$, —$OR^{42}$ and —$S(O)_2R^{42}$; $Q^{135}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{41}$, —$NR^{41}R^{41}$, —$OR^{41}$ and —$S(O)_2R^{41}$; and $Q^{144}$ is hydrogen, fluoro, chloro, lower alkyl, or fluoro substituted lower alkyl, wherein $R^{41}$ is as defined for Formula Ig.

In one embodiment of compounds of Formula IIo, $A_{15}$ is —$CH_2$— or —C(O)—, preferably —$CH_2$—; $Q^{131}$ is aryl or heteroaryl, wherein aryl or heteroaryl are optionally substituted with one or more substituents selected from the group consisting of —$OR^{41}$, —$SR^{41}$, —$S(O)R^{41}$, —$S(O)_2R^{41}$, —$NHR^{41}$, —$NR^{41}R^{41}$, —$NR^{39}C(O)R^{41}$, —$NR^{39}S(O)_2R^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of $Q^{131}$, or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino; $Q^{35}$ is hydrogen, —CN, —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, and —OR$^{41}$; $M_{15}$ is a bond, —NR$^{39}$—, —S—, —O—, —NR$^{39}$CH$_2$—, —NR$^{39}$CH$_2$CH$_2$—, —NR$^{39}$CH(R$^{40}$)—, —SCH$_2$—, —OCH$_2$—, —C(O)NR$^{39}$—, —S(O)$_2$NR$^{39}$—, —CH$_2$NR$^{39}$—, —CH(R$^{40}$)NR$^{39}$—, —NR$^{39}$C(O)—, or —NR$^{39}$S(O)$_2$—; and $Q^{144}$ is hydrogen, fluoro, chloro, lower alkyl, fluoro substituted lower alkyl, —NR$^{44}$R$^{44}$, —OR$^{44}$, or —SR$^{44}$, wherein R$^{39}$, R$^{40}$, R$^{41}$, R$^{42}$ and R$^{44}$ are as defined for Formula II.

In one embodiment of compounds of Formula IIo, $A_{15}$ is —CH$_2$—; $Q^{131}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; Q is hydrogen, —CN, fluoro, chloro, lower alkyl, fluoro substituted lower alkyl, lower alkoxy, or fluoro substituted lower alkoxy; $M_{15}$ is —NR$^{39}$CH$_2$—, —NR$^{39}$CH$_2$CH$_2$—, or —NR$^{39}$CH(R$^{40}$)—; and $Q^{144}$ is hydrogen, fluoro, chloro, lower alkyl, fluoro substituted lower alkyl, lower alkoxy, or fluoro substituted lower alkoxy.

In one embodiment, further to any of the embodiments of Formula IIo above, each occurrence of R$^{41}$ is R$^{42}$ as defined for Formula Ig.

In one embodiment, a compound of Formula II has a structure according to the following sub-generic structure, Formula IIp,

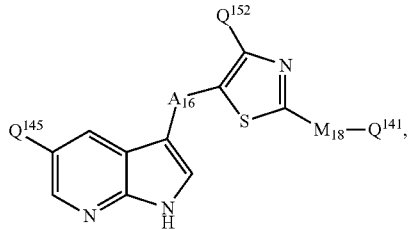

Formula IIp all salts, prodrugs, tautomers, and isomers thereof, wherein:
$A_{16}$ is selected from the group consisting of —CR$^{19}$R$^{20}$—, —C(O)—, —C(S)—, —S—, —S(O)—, —S(O)$_2$—, —NR$^{21}$—, and —O—;
$Q^{145}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —NH$_2$, —NO$_2$, —CN, —NHC(O)NH$_2$, —NHC(S)NH$_2$, —NHS(O)$_2$NH$_2$, —C(O)NH$_2$, —C(S)NH$_2$, —S(O)$_2$NH$_2$, —NR$^{24}$R$^{25}$, —NHR$^{23}$, —OR$^{23}$, —SR$^{23}$, —C(O)R$^{23}$, —C(S)R$^{23}$, —S(O)R$^{23}$, —S(O)$_2$R$^{23}$, —C(O)NHR$^{23}$, —C(O)NR$^{23}$R$^{23}$, —C(S)NHR$^{23}$, —C(S)NR$^{23}$R$^{23}$, —S(O)$_2$NHR$^{23}$, —S(O)$_2$NR$^{23}$R$^{23}$, —NHC(O)R$^{23}$, —NR$^{23}$C(O)R$^{23}$, —NHC(S)R$^{23}$, —NR$^{23}$C(S)R$^{23}$, —NHS(O)$_2$R$^{23}$, —NR$^{23}$S(O)$_2$R$^{23}$, —NHC(O)NHR$^{23}$, —NR$^{23}$C(O)NH$_2$, —NR$^{23}$C(O)NHR$^{23}$, —NHC(O)NR$^{23}$R$^{23}$, —NR$^{23}$C(O)NR$^{23}$R$^{23}$, —NHC(S)NHR$^{23}$, —NR$^{23}$C(S)NH$_2$, —NR$^{23}$C(S)NHR$^{23}$, —NHC(S)NR$^{23}$R$^{23}$, —NR$^{23}$C(S)NR$^{23}$R$^{23}$, —NHS(O)$_2$NHR$^{23}$, —NR$^{23}$S(O)$_2$NH$_2$, —NR$^{23}$S(O)$_2$NHR$^{23}$, —NHS(O)$_2$NR$^{23}$R$^{23}$, and —NR$^{23}$S(O)$_2$NR$^{23}$R$^{23}$;
$M_{18}$, $Q^{141}$, and $Q^{152}$ are as defined for Formula II; and
$R^{19}$, $R^{20}$, $R^{21}$, $R^{23}$, $R^{24}$, and $R^{25}$ are as defined for Formula Ib;
provided, however, that the compound is not

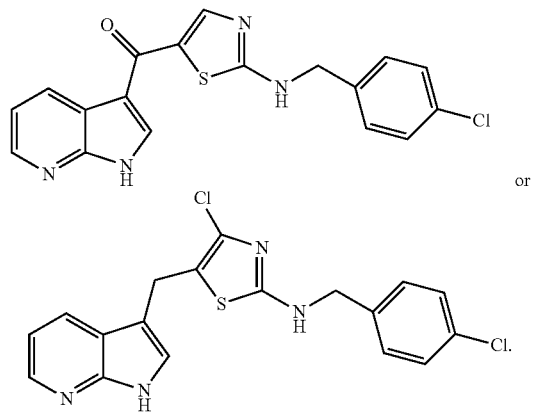

or

In one embodiment of compounds of Formula IIp, $M_{18}$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CR$^{80}$R$^{80}$— or —NR$^{39}$(CR$^{80}$R$^{80}$)$_2$—, wherein R$^{39}$ is hydrogen or lower alkyl and R$^{80}$ is hydrogen, lower alkyl or fluoro substituted lower alkyl, preferably hydrogen. In one embodiment, $A_{16}$ is —CR$^{19}$R$^{20}$— or —C(O)—, preferably —CH$_2$— or —C(O)—. In one embodiment, $Q^{141}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$ and $Q^{145}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$. Further to any of the above embodiments, $Q^{152}$ is hydrogen, fluoro, chloro, lower alkyl, or fluoro substituted lower alkyl.

In one embodiment of compounds of Formula IIp, $M_{18}$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CR$^{80}$R$^{80}$— or —NR$^{39}$(CR$^{80}$R$^{80}$)$_2$—, and $A_{16}$ is —CR$^{19}$R$^{20}$— or —C(O)—, preferably —CH$_2$— or —C(O)—. In one embodiment, $M_{18}$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—

$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$— or —$NR^{39}$ $(CR^{80}R^{80})_2$—; $A_{16}$ is —$CR^{19}R^{20}$— or —$C(O)$—, preferably —$CH_2$— or —$C(O)$—; $Q^{141}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$; and $Q^{145}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$. In one embodiment, $M_{18}$ is —$(CR^{19}R^{20})_t$—$NR^{26}$—$(CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$— or —$NR^{39}(CR^{80}R^{80})_2$—; $A_{16}$ is —$CR^{19}R^{20}$— or —$C(O)$—, preferably —$CH_2$— or —$C(O)$—; $Q^{141}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$; $Q^{145}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$; and $Q^{152}$ is hydrogen, fluoro, chloro, lower alkyl, or fluoro substituted lower alkyl.

In one embodiment of compounds of Formula IIp, $M_{18}$ is —$NR^{39}CH_2$— or —$NR^{39}$—$(CH_2)_2$—; $A_{16}$ is —$CH_2$— or —$C(O)$—, preferably —$CH_2$—; $Q^{141}$ is aryl or heteroaryl, wherein aryl or heteroaryl are optionally substituted with one or more substituents selected from the group consisting of halogen, lower alkyl, fluoro substituted lower alkyl, —$NHR^{41}$, —$NR^{41}R^{41}$, —$OR^{41}$ and —$S(O)_2R^{41}$; $Q^{145}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{41}$, —$NR^{41}R^{41}$, —$OR^{41}$ and —$S(O)_2R^{41}$; and $Q^{152}$ is hydrogen, fluoro, chloro, lower alkyl, or fluoro substituted lower alkyl, wherein $R^{41}$ is as defined for Formula Ig.

In one embodiment of compounds of Formula IIp, $A_{16}$ is —$CH_2$— or —$C(O)$—, preferably —$CH_2$—; $Q^{141}$ is aryl or heteroaryl, wherein aryl or heteroaryl are optionally substituted with one or more substituents selected from the group consisting of —$OR^{41}$, —$SR^{41}$, —$S(O)R^{41}$, —$S(O)_2R^{41}$, —$NHR^{41}$, —$NR^{41}R^{41}$, —$NR^{39}C(O)R^{41}$, —$NR^{39}S(O)_2R^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of $Q^{141}$, or as a substituent of lower alkyl are optionally substituted with one or more substituents selected from the group consisting of —OH, —$NH_2$, —CN, —$NO_2$, —$S(O)_2NH_2$, —$C(O)NH_2$, —$OR^{42}$, —$SR^{42}$, —$NHR^{42}$, —$NR^{42}R^{42}$, —$NR^{39}C(O)R^{42}$, —$NR^{39}S(O)_2R^{42}$, —$S(O)_2R^{42}$, halogen, lower alkyl, fluoro substituted lower alkyl, and cycloalkylamino; $Q^{145}$ is hydrogen, —CN, —$OR^{41}$, —$SR^{41}$, —$S(O)R^{41}$, —$S(O)_2R^{41}$, —$NHR^{41}$, —$NR^{41}R^{41}$, —$NR^{39}C(O)R^{41}$, —$NR^{39}S(O)_2R^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —$NHR^{41}$, —$NR^{41}R^{41}$, and —$OR^{41}$; $M_{18}$ is a bond, —$NR^{39}$—, —S—, —O—, —$NR^{39}CH_2$—, —$NR^{39}CH_2CH_2$—, —$NR^{39}CH(R^{40})$—, —$SCH_2$—, —$OCH_2$—, —$C(O)NR^{39}$, —$S(O)_2NR^{39}$—, —$CH_2NR^{39}$—, —$CH(R^{40})NR^{39}$—, —$NR^{39}C(O)$—, or —$NR^{39}S(O)_2$—; and $Q^{152}$ is hydrogen, fluoro, chloro, lower alkyl, fluoro substituted lower alkyl, —$NR^{44}R^{44}$, —$OR^{44}$, or —$SR^{44}$, wherein $R^{39}$, $R^{40}$, $R^{41}$, $R^{42}$ and $R^{44}$ are as defined for Formula II.

In one embodiment of compounds of Formula IIp, $A_{16}$ is —$CH_2$—; $Q^{141}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; $Q^{145}$ is hydrogen, —CN, fluoro, chloro, lower alkyl, fluoro substituted lower alkyl, lower alkoxy, or fluoro substituted lower alkoxy; $M_{18}$ is —$NR^{39}CH_2$—, —$NR^{39}CH_2CH_2$—, or —$NR^{39}CH(R^{40})$—; and $Q^{152}$ is hydrogen, fluoro, chloro, lower alkyl, fluoro substituted lower alkyl, lower alkoxy, or fluoro substituted lower alkoxy.

In one embodiment, further to any of the embodiments of Formula IIp above, each occurrence of $R^{41}$ is $R^{42}$ as defined for Formula Ig.

In one embodiment of compounds of Formula IIp, $M_{18}$ is —NH—$CH_2$— or —NH—$(CH_2)_2$—, preferably —NH—$CH_2$—; $A_{16}$ is —$CH_2$— or —$C(O)$—, preferably —$CH_2$—; $Q^{141}$ is aryl or heteroaryl, wherein aryl or heteroaryl are optionally substituted with 1 or 2 substituents selected from the group consisting of fluoro, chloro, lower alkyl, fluoro substituted lower alkyl, lower alkoxy, fluoro substituted lower alkoxy, and heterocycloalkyl; $Q^{145}$ is hydrogen, —CN, fluoro, chloro, lower alkyl, fluoro substituted lower alkyl, lower alkoxy, or fluoro substituted lower alkoxy, preferably hydrogen, —CN, or chloro; and $Q^{152}$ is hydrogen, fluoro, chloro, lower alkyl, or fluoro substituted lower alkyl, preferably hydrogen or chloro, more preferably chloro.

In one embodiment, the compound of Formula Ih is selected from the group consisting of

[4-Chloro-5-(1H-pyrrolo[2,3-b]pyridin-3-ylmethyl)-thiazol-2-yl]-(4-fluoro-benzyl)-amine (P-0156),

[4-Ethyl-5-(1H-pyrrolo[2,3-b]pyridin-3-ylmethyl)-thiazol-2-yl]-(4-fluoro-benzyl)-amine (P-0162), (4-Fluoro-benzyl)-[4-methyl-5-(1H-pyrrolo[2,3-b]pyridin-3-ylmethyl)-thiazol-2-yl]-amine (P-0163),

[4-Chloro-5-(1H-pyrrolo[2,3-b]pyridin-3-ylmethyl)-thiazol-2-yl]-pyridin-3-ylmethyl-amine (P-0164),

[4-Chloro-5-(1H-pyrrolo[2,3-b]pyridin-3-ylmethyl)-thiazol-2-yl]-pyridin-2-ylmethyl-amine (P-0167),

[4-Chloro-5-(1H-pyrrolo[2,3-b]pyridin-3-ylmethyl)-thiazol-2-yl]-pyridin-4-ylmethyl-amine (P-0168),

[4-Chloro-5-(1H-pyrrolo[2,3-b]pyridin-3-ylmethyl)-thiazol-2-yl]-(6-methyl-pyridin-2-ylmethyl)-amine (P-0171),

[4-Chloro-5-(1H-pyrrolo[2,3-b]pyridin-3-ylmethyl)-thiazol-2-yl]-(1,5-dimethyl-1H-pyrazol-3-ylmethyl)-amine (P-0172),

[4-Chloro-5-(1H-pyrrolo[2,3-b]pyridin-3-ylmethyl)-thiazol-2-yl]-(6-trifluoromethyl-pyridin-3-ylmethyl)-amine (P-0173),

[4-Chloro-5-(1H-pyrrolo[2,3-b]pyridin-3-ylmethyl)-thiazol-2-yl]-(2,5-dimethyl-2H-pyrazol-3-ylmethyl)-amine (P-0175),

[2-(4-Fluoro-benzylamino)-thiazol-5-yl]-(1H-pyrrolo[2,3-b]pyridin-3-yl)-methanone (P-0177), {2-[(4-Chloro-benzyl)-methyl-amino]-thiazol-5-yl}-(1H-pyrrolo[2,3-b]pyridin-3-yl)-methanone (P-0178),

[4-Chloro-5-(5-chloro-1H-pyrrolo[2,3-b]pyridin-3-ylmethyl)-thiazol-2-yl]-thiazol-2-ylmethyl-amine (P-0189),

[4-Chloro-5-(5-chloro-1H-pyrrolo[2,3-b]pyridin-3-ylmethyl)-thiazol-2-yl]-(6-methoxy-pyridin-3-ylmethyl)-amine (P-0190), Benzyl-[4-chloro-5-(5-chloro-1H-pyrrolo[2,3-b]pyridin-3-ylmethyl)-thiazol-2-yl]-amine (P-0192),

[4-Chloro-5-(5-chloro-1H-pyrrolo[2,3-b]pyridin-3-ylmethyl)-thiazol-2-yl]-(3-methoxy-benzyl)-amine (P-0193), (4-Chloro-benzyl)-[4-chloro-5-(5-chloro-1H-pyrrolo[2,3-b]pyridin-3-ylmethyl)-thiazol-2-yl]-amine (P-0194),

[4-Chloro-5-(5-chloro-1H-pyrrolo[2,3-b]pyridin-3-ylmethyl)-thiazol-2-yl]-(4-fluoro-benzyl)-amine (P-0195),

[4-Chloro-5-(5-chloro-1H-pyrrolo[2,3-b]pyridin-3-ylmethyl)-thiazol-2-yl]-(2,4-dimethyl-thiazol-5-ylmethyl)-amine (P-0196),

[4-Chloro-5-(5-chloro-1H-pyrrolo[2,3-b]pyridin-3-ylmethyl)-thiazol-2-yl]-(2-ethyl-5-methyl-3H-imidazol-4-ylmethyl)-amine (P-0197),

[4-Chloro-5-(5-chloro-1H-pyrrolo[2,3-b]pyridin-3-ylmethyl)-thiazol-2-yl]-(2-ethyl-2H-pyrazol-3-ylmethyl)-amine (P-0198),

[4-Chloro-5-(5-chloro-1H-pyrrolo[2,3-b]pyridin-3-ylmethyl)-thiazol-2-yl]-(6-methoxy-pyridin-2-ylmethyl)-amine (P-0199),

[4-Chloro-5-(5-chloro-1H-pyrrolo[2,3-b]pyridin-3-ylmethyl)-thiazol-2-yl]-(3-fluoro-pyridin-4-ylmethyl)-amine (P-0200),

[4-Chloro-5-(5-chloro-1H-pyrrolo[2,3-b]pyridin-3-ylmethyl)-thiazol-2-yl]-(2-methyl-thiazol-4-ylmethyl)-amine (P-0201),

[4-Chloro-5-(5-chloro-1H-pyrrolo[2,3-b]pyridin-3-ylmethyl)-thiazol-2-yl]-(4-methyl-thiazol-5-ylmethyl)-amine (P-0202),

[4-Chloro-5-(5-chloro-1H-pyrrolo[2,3-b]pyridin-3-ylmethyl)-thiazol-2-yl]-(5-chloro-pyridin-2-ylmethyl)-amine (P-0203),

[4-Chloro-5-(1H-pyrrolo[2,3-b]pyridin-3-ylmethyl)-thiazol-2-yl]-(2,4-dimethyl-thiazol-5-ylmethyl)-amine (P-0204),

[4-Chloro-5-(1H-pyrrolo[2,3-b]pyridin-3-ylmethyl)-thiazol-2-yl]-(2-ethyl-5-methyl-3H-imidazol-4-ylmethyl)-amine (P-0205),

[4-Chloro-5-(1H-pyrrolo[2,3-b]pyridin-3-ylmethyl)-thiazol-2-yl]-(5-fluoro-pyridin-2-ylmethyl)-amine (P-0206),

[4-Chloro-5-(1H-pyrrolo[2,3-b]pyridin-3-ylmethyl)-thiazol-2-yl]-(5-methoxy-pyridin-3-ylmethyl)-amine (P-0207),

[4-Chloro-5-(1H-pyrrolo[2,3-b]pyridin-3-ylmethyl)-thiazol-2-yl]-(4,5-dimethyl-thiophen-2-ylmethyl)-amine (P-0208),

[4-Chloro-5-(1H-pyrrolo[2,3-b]pyridin-3-ylmethyl)-thiazol-2-yl]-(2,5-dimethyl-thiophen-3-ylmethyl)-amine (P-0209),

[4-Chloro-5-(5-chloro-1H-pyrrolo[2,3-b]pyridin-3-ylmethyl)-thiazol-2-yl]-(5-fluoro-pyridin-3-ylmethyl)-amine (P-0231),

[4-Chloro-5-(5-chloro-1H-pyrrolo[2,3-b]pyridin-3-ylmethyl)-thiazol-2-yl]-pyridin-3-ylmethyl-amine (P-0236),

[4-Chloro-5-(5-chloro-1H-pyrrolo[2,3-b]pyridin-3-ylmethyl)-thiazol-2-yl]-pyridin-4-ylmethyl-amine (P-0237),

[4-Chloro-5-(5-chloro-1H-pyrrolo[2,3-b]pyridin-3-ylmethyl)-thiazol-2-yl]-(3-chloro-pyridin-4-ylmethyl)-amine (P-0238),

[4-Chloro-5-(5-chloro-1H-pyrrolo[2,3-b]pyridin-3-ylmethyl)-thiazol-2-yl]-(1-ethyl-1H-pyrazol-4-ylmethyl)-amine (P-0239),

[4-Chloro-5-(5-chloro-1H-pyrrolo[2,3-b]pyridin-3-ylmethyl)-thiazol-2-yl]-(5-fluoro-pyridin-2-ylmethyl)-amine (P-0240),

[4-Chloro-5-(5-chloro-1H-pyrrolo[2,3-b]pyridin-3-ylmethyl)-thiazol-2-yl]-(5-methoxy-pyridin-3-ylmethyl)-amine (P-0241),

[4-Chloro-5-(5-chloro-1H-pyrrolo[2,3-b]pyridin-3-ylmethyl)-thiazol-2-yl]-(6-trifluoromethyl-pyridin-3-ylmethyl)-amine (P-0242),

[4-Chloro-5-(5-chloro-1H-pyrrolo[2,3-b]pyridin-3-ylmethyl)-thiazol-2-yl]-(2-chloro-6-fluoro-benzyl)-amine (P-0243),

[4-Chloro-5-(5-chloro-1H-pyrrolo[2,3-b]pyridin-3-ylmethyl)-thiazol-2-yl]-phenethyl-amine (P-0244),

[4-Chloro-5-(5-chloro-1H-pyrrolo[2,3-b]pyridin-3-ylmethyl)-thiazol-2-yl]-(2,4-difluoro-benzyl)-amine (P-0245),

[4-Chloro-5-(5-chloro-1H-pyrrolo[2,3-b]pyridin-3-ylmethyl)-thiazol-2-yl]-(2-fluoro-benzyl)-amine (P-0246),

[4-Chloro-5-(5-chloro-1H-pyrrolo[2,3-b]pyridin-3-ylmethyl)-thiazol-2-yl]-(2-methoxy-pyridin-3-ylmethyl)-amine (P-0247), (2-Chloro-benzyl)-[4-chloro-5-(5-chloro-1H-pyrrolo[2,3-b]pyridin-3-ylmethyl)-thiazol-2-yl]-amine (P-0248),

[4-Chloro-5-(5-chloro-1H-pyrrolo[2,3-b]pyridin-3-ylmethyl)-thiazol-2-yl]-(2-methyl-benzyl)-amine (P-0249),

[4-Chloro-5-(5-chloro-1H-pyrrolo[2,3-b]pyridin-3-ylmethyl)-thiazol-2-yl]-(2-chloro-4-fluoro-benzyl)-amine (P-0250),

[4-Chloro-5-(5-chloro-1H-pyrrolo[2,3-b]pyridin-3-ylmethyl)-thiazol-2-yl]-(3-fluoro-pyridin-2-ylmethyl)-amine (P-0251),

[4-Chloro-5-(5-chloro-1H-pyrrolo[2,3-b]pyridin-3-ylmethyl)-thiazol-2-yl]-(6-morpholin-4-yl-pyridin-2-ylmethyl)-amine (P-0252),

[4-Chloro-5-(5-chloro-1H-pyrrolo[2,3-b]pyridin-3-ylmethyl)-thiazol-2-yl]-(3,5-dichloro-pyridin-4-ylmethyl)-amine (P-0253),

[4-Chloro-5-(5-chloro-1H-pyrrolo[2,3-b]pyridin-3-ylmethyl)-thiazol-2-yl]-(2-trifluoromethyl-benzyl)-amine (P-0254),

[4-Chloro-5-(5-chloro-1H-pyrrolo[2,3-b]pyridin-3-ylmethyl)-thiazol-2-yl]-(6-methyl-pyridin-2-ylmethyl)-amine (P-0255),

[5-(5-Chloro-1H-pyrrolo[2,3-b]pyridin-3-ylmethyl)-thiazol-2-yl]-(4-fluoro-benzyl)-amine (P-0290), and all salts, prodrugs, tautomers, and isomers thereof.

In one embodiment, a compound of Formula I has a structure according to the following sub-generic structure, Formula III,

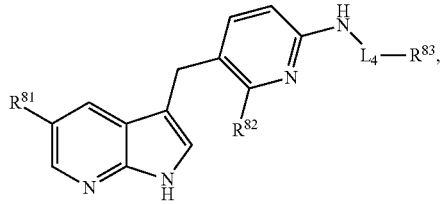

Formula III all salts, prodrugs, tautomers, and isomers thereof,
wherein:

$L_4$ is —CH$_2$—, —CH$_2$CH$_2$—, —CH(R$^{40}$)—, —C(O)—, or —C(O)NH—;

$R^{81}$ is selected from the group consisting of hydrogen, —OR$^{41}$, —CN, fluoro, chloro, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$;

$R^{82}$ is selected from the group consisting of hydrogen, C$_{1-3}$ alkyl, fluoro substituted C$_{2-3}$ alkyl, OH, C$_{1-3}$ alkoxy, and fluoro substituted C$_{1-3}$ alkoxy;

$R^{83}$ is heterocycloalkyl, heteroaryl, or

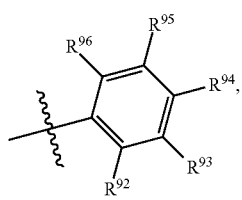

in which

indicates the attachment point of $R^{83}$ to $L_4$ of Formula III, wherein heterocycloalkyl or heteroaryl are optionally substituted with one or more substituents selected from the group consisting of halogen, lower alkyl, fluoro substituted lower alkyl, cycloalkylamino, —NHR$^{41}$, —NR$^{41}$R$^{41}$, —OR$^{41}$ and —S(O)$_2$R$^{41}$;

$R^{92}$, $R^{93}$, $R^{94}$, $R^{95}$, and $R^{96}$ are independently selected from the group consisting of hydrogen, halogen, lower alkyl, fluoro substituted lower alkyl, cycloalkylamino, —NHS(O)$_2$R$^{41}$, —NHC(O)R$^{41}$, —NHR$^{41}$, —NR$^{41}$R$^{41}$, —OR$^{41}$ and —S(O)$_2$R$^{41}$; and $R^{40}$ and $R^{41}$ are as defined for Formula Ig;
provided, however, that the compound is not

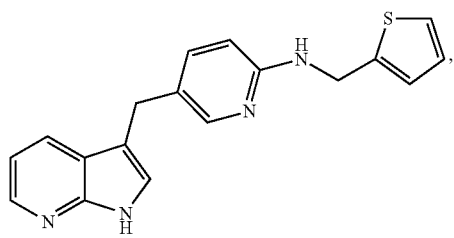

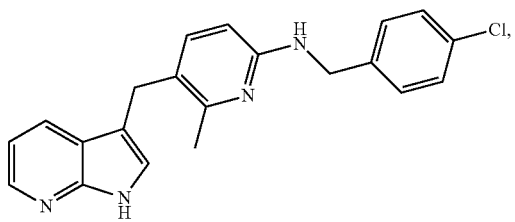

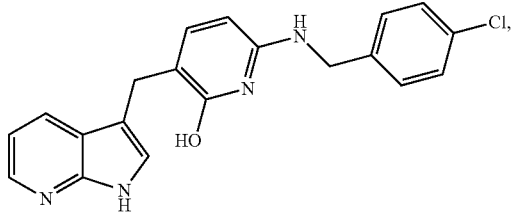

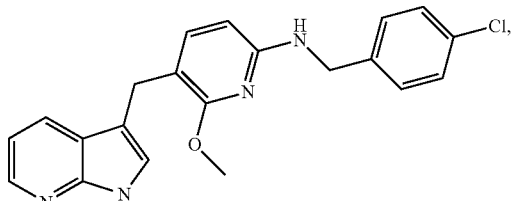

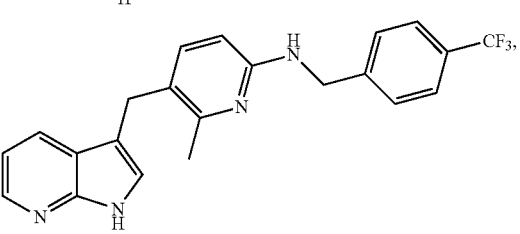

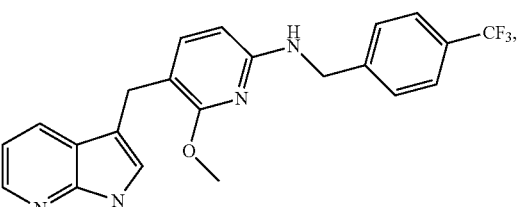

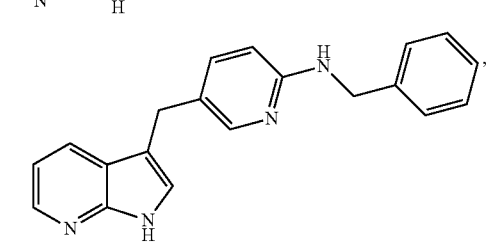

-continued
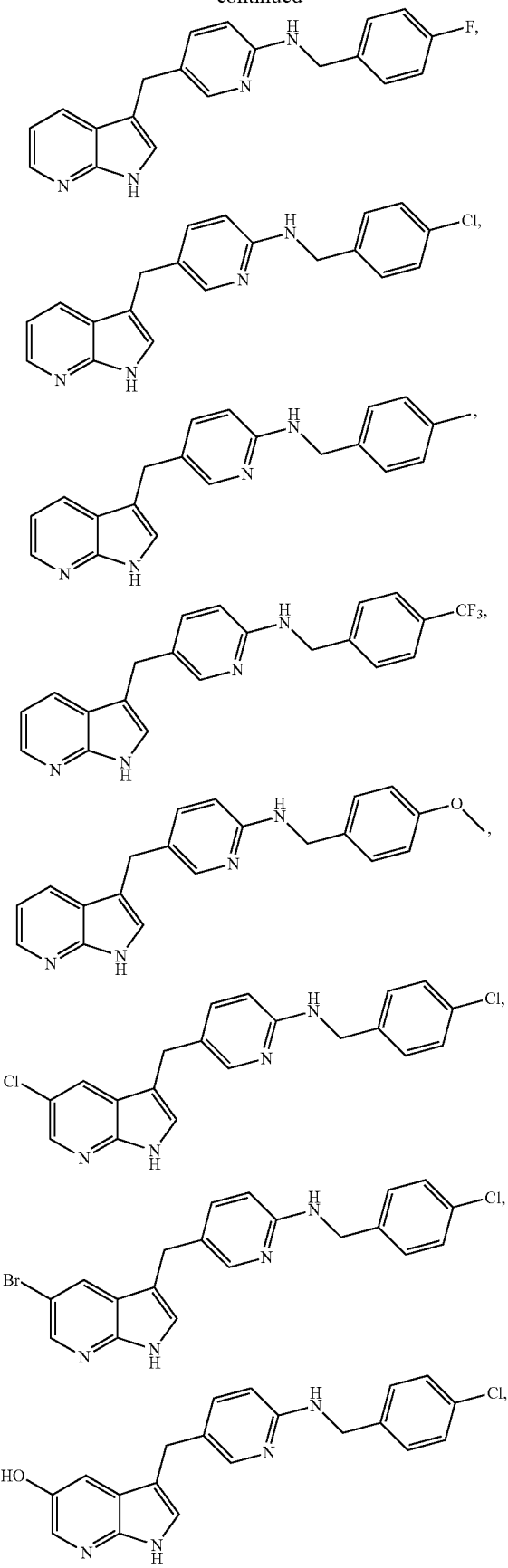
-continued
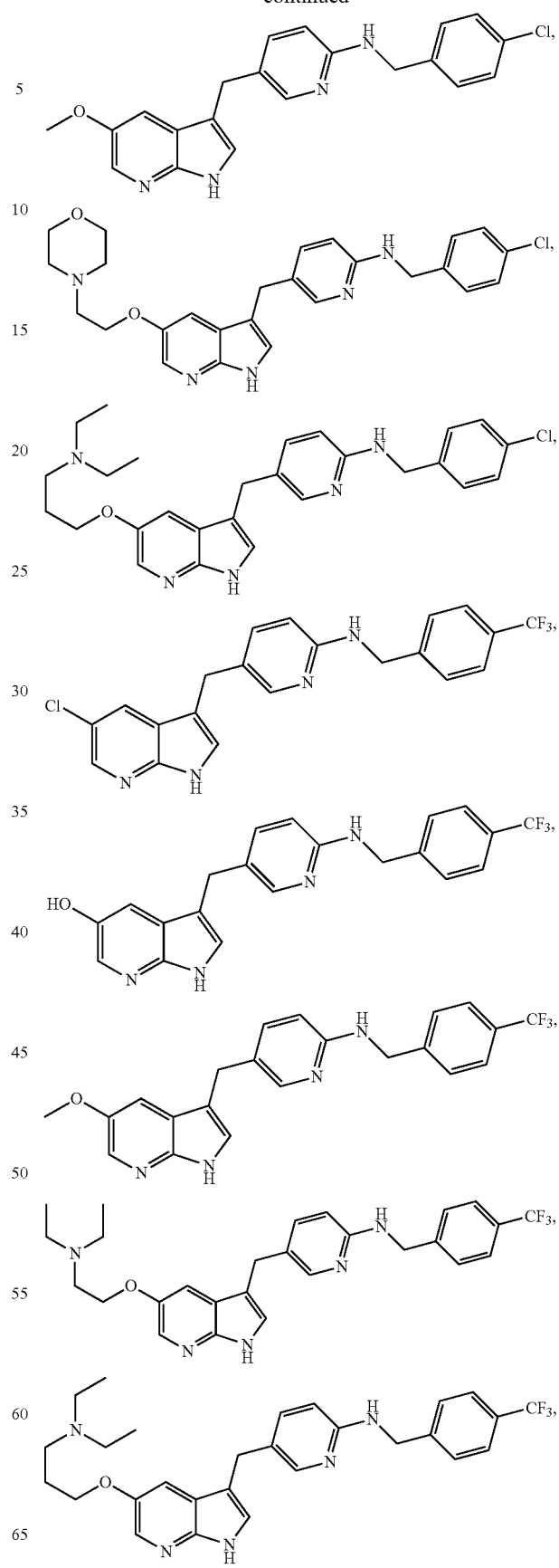

-continued

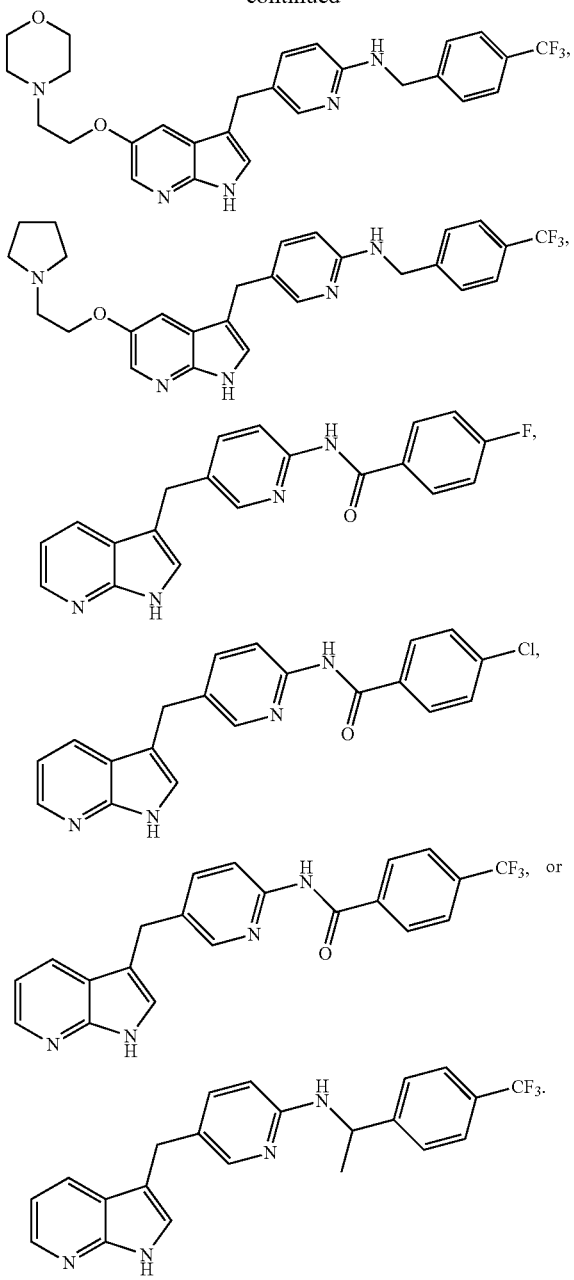

In one embodiment of compounds of Formula III, $L_4$ is —CH$_2$—, —CH$_2$CH$_2$—, —CH(CH$_3$)— or —C(O)—, $R^{81}$ is hydrogen, fluoro, chloro, —CN, lower alkyl, fluoro substituted lower alkyl, lower alkoxy, or fluoro substituted lower alkoxy, $R^{82}$ is hydrogen, $R^{83}$ is

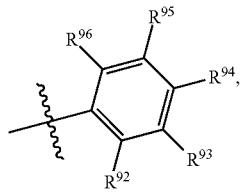

wherein $R^{92}$, $R^{93}$, $R^{94}$, $R^{95}$, and $R^{96}$ are independently hydrogen, fluoro, chloro, lower alkyl, fluoro substituted lower alkyl, lower alkoxy, or fluoro substituted lower alkoxy, provided, however, that when $R^{94}$ is fluoro, chloro, lower alkyl, fluoro substituted lower alkyl, lower alkoxy, or fluoro substituted lower alkoxy, at least one of $R^{92}$, $R^{93}$, $R^{95}$, and $R^{96}$ is fluoro, chloro, lower alkyl, fluoro substituted lower alkyl, lower alkoxy, or fluoro substituted lower alkoxy.

In one embodiment of compounds of Formula III, $L_4$ is —CH$_2$—, —CH$_2$CH$_2$—, —CH(CH$_3$)— or —C(O)—, $R^{81}$ is hydrogen, fluoro, chloro, —CN, methyl, or methoxy, preferably hydrogen, chloro, —CN, or methyl, $R^{82}$ is hydrogen, $R^{83}$ is

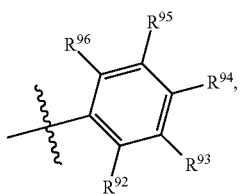

wherein $R^{92}$, $R^{93}$, $R^{94}$, $R^{95}$, and $R^{96}$ are independently hydrogen, fluoro, chloro, methyl, ethyl, trifluoromethyl, methoxy, ethoxy, difluoromethoxy or trifluoromethoxy, preferably hydrogen, chloro, methyl, trifluoromethyl, methoxy, ethoxy, or trifluoromethoxy, provided, however, that when $R^{94}$ is fluoro, chloro, methyl, ethyl, trifluoromethyl, methoxy, ethoxy, difluoromethoxy or trifluoromethoxy, at least one of $R^{92}$, $R^{93}$, $R^{95}$, and $R^{96}$ is fluoro, chloro, methyl, ethyl, trifluoromethyl, methoxy, ethoxy, difluoromethoxy or trifluoromethoxy.

In one embodiment of compounds of Formula III, $L_4$ is —CH$_2$—, $R^{81}$ is fluoro, chloro, —CN, methyl, or methoxy, preferably chloro, —CN, or methyl, $R^{82}$ is hydrogen, $R^{83}$ is

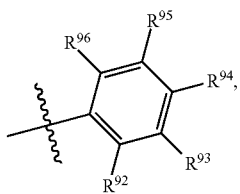

wherein $R^{94}$ is hydrogen and $R^{92}$, $R^{93}$, $R^{95}$, and $R^{96}$ are independently hydrogen, fluoro, chloro, methyl, trifluoromethyl, methoxy, ethoxy, difluoromethoxy or trifluoromethoxy.

In one embodiment of compounds of Formula III, $L_4$ is —CH$_2$—, —CH$_2$CH$_2$—, —C(O)—, or —CH(CH$_3$)—, preferably —CH$_2$— or —C(O)—, $R^{81}$ is hydrogen, fluoro, $R^{82}$ is hydrogen, $R^{83}$ is

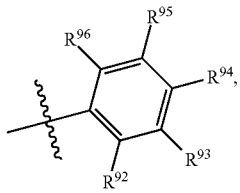

wherein $R^{92}$ is fluoro, chloro, methyl, ethyl, trifluoromethyl, methoxy, ethoxy, difluoromethoxy, or trifluoromethoxy, preferably fluoro, chloro, methyl, or trifluoromethyl, and $R^{93}$, $R^{94}$, $R^{95}$, and $R^{96}$ are independently hydrogen, fluoro, chloro, methyl, trifluoromethyl, methoxy, difluoromethoxy, or trifluoromethoxy, preferably hydrogen or fluoro. In one embodiment, $L_4$ is —CH$_2$—, —C(O)—, or —CH(CH$_3$)—, $R^{81}$ is hydrogen, $R^{82}$ is hydrogen, $R^{92}$ is fluoro, chloro, methyl, ethyl, trifluoromethyl, methoxy, ethoxy, difluoromethoxy, or trifluoromethoxy, preferably fluoro, methyl, or trifluoromethyl, and $R^{93}$, $R^{94}$, $R^{95}$, and $R^{96}$ are hydrogen. In one embodiment, $L_4$ is —CH$_2$—, —C(O)—, or —CH(CH$_3$)—, $R^{81}$ is hydrogen, $R^{82}$ is hydrogen, $R^{92}$ is fluoro, chloro, methyl, ethyl, trifluoromethyl, methoxy, ethoxy, difluoromethoxy, or trifluoromethoxy, preferably fluoro, methyl, or trifluoromethyl, $R^{94}$, $R^{95}$, and $R^{96}$ are hydrogen, and $R^{93}$ is fluoro, chloro, methyl, ethyl, trifluoromethyl, methoxy, ethoxy, difluoromethoxy, or trifluoromethoxy, preferably fluoro, chloro, trifluoromethyl or methoxy, more preferably fluoro. In one embodiment, $L_4$ is —CH$_2$—, —C(O)—, or —CH(CH$_3$)—, $R^{81}$ is hydrogen, $R^{82}$ is hydrogen, $R^{92}$ is fluoro, chloro, methyl, ethyl, trifluoromethyl, methoxy, ethoxy, difluoromethoxy, or trifluoromethoxy, preferably fluoro, methyl, or trifluoromethyl, $R^{93}$, $R^{95}$, and $R^{96}$ are hydrogen, and $R^{94}$ is fluoro, chloro, methyl, ethyl, trifluoromethyl, methoxy, ethoxy, difluoromethoxy, or trifluoromethoxy, preferably fluoro, chloro, methyl or trifluoromethyl, more preferably fluoro. In one embodiment, $L_4$ is —CH$_2$CH$_2$— or —C(O)—, $R^{81}$ is hydrogen, $R^{82}$ is hydrogen, $R^{92}$, $R^{95}$, and $R^{96}$ are hydrogen, $R^{93}$ is hydrogen, fluoro, chloro, methyl, ethyl, trifluoromethyl, methoxy, ethoxy, difluoromethoxy, or trifluoromethoxy, preferably hydrogen, fluoro, chloro, methyl, trifluoromethyl, methoxy, or trifluoromethoxy, more preferably fluoro, chloro, trifluoromethyl or methoxy, and $R^{94}$ is hydrogen, fluoro, or chloro, provided, however, that when $L_4$ is —C(O)— and $R^{94}$ is fluoro or chloro, $R^{93}$ is not hydrogen. In one embodiment, $L_4$ is —CH$_2$CH$_2$—, $R^{81}$ is hydrogen, $R^{82}$ is hydrogen, $R^{92}$, $R^{94}$, $R^{95}$, and $R^{96}$ are hydrogen, and $R^{93}$ is hydrogen, fluoro, chloro, methyl, ethyl, trifluoromethyl, methoxy, ethoxy, difluoromethoxy, or trifluoromethoxy, preferably hydrogen or fluoro. In one embodiment, $L_4$ is —C(O)—, $R^{81}$ is hydrogen, $R^{82}$ is hydrogen, $R^{92}$, $R^{95}$, and $R^{96}$ are hydrogen, $R^{93}$ is fluoro, chloro, methyl, ethyl, trifluoromethyl, methoxy, ethoxy, difluoromethoxy, or trifluoromethoxy, preferably fluoro, chloro, trifluoromethyl or methoxy, and $R^{94}$ is hydrogen, fluoro, or chloro.

In one embodiment of compounds of Formula III, $R^{83}$ is pyrrolidine, morpholine, pyridine, pyrimidine, pyrazine, pyrazole, isoxazole, imidazol, or benzimidazole, wherein $R^{83}$ is optionally substituted with one or more substituents independently selected from the group consisting of halogen, lower alkyl, fluoro substituted lower alkyl, cycloalkylamino, —NHR$^{41}$, —NR$^{41}$R$^{41}$, —OR$^{41}$ and —S(O)$_2$R$^{41}$, preferably wherein $R^{83}$ is optionally substituted with 1 or 2 substituents independently selected from fluoro, chloro, lower alkyl, fluoro substituted lower alkyl, lower alkoxy, fluoro substituted lower alkoxy, or cycloalkylamino, more preferably fluoro, chloro, methyl, trifluoromethyl, methoxy or morpholine.

In one embodiment of compounds of Formula III, $L_4$ is —CH$_2$—, —CH$_2$CH$_2$—, —CH(CH$_3$)— or —C(O)—, preferably —CH$_2$—, —CH$_2$CH$_2$—, or —C(O)—, $R^{81}$ is hydrogen, fluoro, chloro, —CN, lower alkyl, fluoro substituted lower alkyl, lower alkoxy, or fluoro substituted lower alkoxy, preferably hydrogen, chloro, methyl or —CN, $R^{82}$ is hydrogen, and $R^{83}$ is pyrrolidine, morpholine, pyridine, pyrimidine, pyrazine, pyrazole, isoxazole, imidazole, or benzimidazole, wherein $R^{83}$ is optionally substituted with 1 or 2 substituents independently selected from fluoro, chloro, lower alkyl, fluoro substituted lower alkyl, lower alkoxy, fluoro substituted lower alkoxy, or cycloalkylamino, preferably fluoro, chloro, methyl, trifluoromethyl, methoxy or morpholine.

In one embodiment of compounds of Formula III, the compound is selected from the group consisting of:
Pyridin-3-ylmethyl-[5-(1H-pyrrolo[2,3-b]pyridin-3-ylmethyl)-pyridin-2-yl]-amine (P-0094),
(5-Methyl-isoxazol-3-ylmethyl)-[5-(1H-pyrrolo[2,3-b]pyridin-3-ylmethyl)-pyridin-2-yl]-amine (P-0095),
(2-Pyrrolidin-1-yl-ethyl)-[5-(1H-pyrrolo[2,3-b]pyridin-3-ylmethyl)-pyridin-2-yl]-amine (P-0096),
[1-(4-Methanesulfonyl-phenyl)-ethyl]-[5-(1H-pyrrolo[2,3-b]pyridin-3-ylmethyl)-pyridin-2-yl]-amine (P-0097),
(2-Morpholin-4-yl-ethyl)-[5-(1H-pyrrolo[2,3-b]pyridin-3-ylmethyl)-pyridin-2-yl]-amine (P-0099),
3,4-Dichloro-N-[5-(1H-pyrrolo[2,3-b]pyridin-3-ylmethyl)-pyridin-2-yl]-benzamide (P-0100),
2-Chloro-4-fluoro-N-[5-(1H-pyrrolo[2,3-b]pyridin-3-ylmethyl)-pyridin-2-yl]-benzamide (P-0101),
2,5-Dimethyl-2H-pyrazole-3-carboxylic acid [5-(1H-pyrrolo[2,3-b]pyridin-3-ylmethyl)-pyridin-2-yl]-amide (P-0102),
Thiophene-2-carboxylic acid [5-(1H-pyrrolo[2,3-b]pyridin-3-ylmethyl)-pyridin-2-yl]-amide (P-0103),
2-Methoxy-N-[5-(1H-pyrrolo[2,3-b]pyridin-3-ylmethyl)-pyridin-2-yl]-isonicotinamide (P-0104),
N-[5-(1H-Pyrrolo[2,3-b]pyridin-3-ylmethyl)-pyridin-2-yl]-isonicotinamide (P-0105),
Pyrazine-2-carboxylic acid [5-(1H-pyrrolo[2,3-b]pyridin-3-ylmethyl)-pyridin-2-yl]-amide (P-0106),
Pyridine-2-carboxylic acid [5-(1H-pyrrolo[2,3-b]pyridin-3-ylmethyl)-pyridin-2-yl]-amide (P-0107),
6-Methyl-N-[5-(1H-pyrrolo[2,3-b]pyridin-3-ylmethyl)-pyridin-2-yl]-nicotinamide (P-0108),
4-Fluoro-3-methyl-N-[5-(1H-pyrrolo[2,3-b]pyridin-3-ylmethyl)-pyridin-2-yl]-benzamide (P-0109),
5-Methyl-pyrazine-2-carboxylic acid [5-(1H-pyrrolo[2,3-b]pyridin-3-ylmethyl)-pyridin-2-yl]-amide (P-0110),
3-Chloro-N-[5-(1H-pyrrolo[2,3-b]pyridin-3-ylmethyl)-pyridin-2-yl]-benzamide (P-0111),
4-Fluoro-N-[5-(1H-pyrrolo[2,3-b]pyridin-3-ylmethyl)-pyridin-2-yl]-3-trifluoromethyl-benzamide (P-0112),
N-[5-(1H-Pyrrolo[2,3-b]pyridin-3-ylmethyl)-pyridin-2-yl]-3-trifluoromethoxy-benzamide (P-0113),
N-[5-(1H-Pyrrolo[2,3-b]pyridin-3-ylmethyl)-pyridin-2-yl]-3-trifluoromethyl-benzamide (P-0114),
3-Chloro-4-fluoro-N-[5-(1H-pyrrolo[2,3-b]pyridin-3-ylmethyl)-pyridin-2-yl]-benzamide (P-0115),
3,4-Difluoro-N-[5-(1H-pyrrolo[2,3-b]pyridin-3-ylmethyl)-pyridin-2-yl]-benzamide (P-0116),
2-Chloro-N-[5-(1H-pyrrolo[2,3-b]pyridin-3-ylmethyl)-pyridin-2-yl]-benzamide (P-0117),
5-Fluoro-2-methyl-N-[5-(1H-pyrrolo[2,3-b]pyridin-3-ylmethyl)-pyridin-2-yl]-benzamide (P-0118),
2-Fluoro-N-[5-(1H-pyrrolo[2,3-b]pyridin-3-ylmethyl)-pyridin-2-yl]-benzamide (P-0119),
3-Methoxy-N-[5-(1H-pyrrolo[2,3-b]pyridin-3-ylmethyl)-pyridin-2-yl]-benzamide (P-0120),
3-Fluoro-N-[5-(1H-pyrrolo[2,3-b]pyridin-3-ylmethyl)-pyridin-2-yl]-benzamide (P-0121),
3-Methyl-N-[5-(1H-pyrrolo[2,3-b]pyridin-3-ylmethyl)-pyridin-2-yl]-benzamide (P-0122), 2-Chloro-N-[5-(1H-pyrrolo[2,3-b]pyridin-3-ylmethyl)-pyridin-2-yl]-isonicotinamide (P-0123),
((R)-1-Phenyl-ethyl)-[5-(1H-pyrrolo[2,3-b]pyridin-3-ylmethyl)-pyridin-2-yl]-amine (P-0125),
(3-Morpholin-4-yl-benzyl)-[5-(1H-pyrrolo[2,3-b]pyridin-3-ylmethyl)-pyridin-2-yl]-amine (P-0126),
[1-(2-Fluoro-phenyl)-ethyl]-[5-(1H-pyrrolo[2,3-b]pyridin-3-ylmethyl)-pyridin-2-yl]-amine (P-0127),
[2-(3-Fluoro-phenyl)-ethyl]-[5-(1H-pyrrolo[2,3-b]pyridin-3-ylmethyl)-pyridin-2-yl]-amine (P-0128),
(3-Chloro-benzyl)-[5-(1H-pyrrolo[2,3-b]pyridin-3-ylmethyl)-pyridin-2-yl]-amine (P-0129),
(1-Methyl-1H-imidazol-4-ylmethyl)-[5-(1H-pyrrolo[2,3-b]pyridin-3-ylmethyl)-pyridin-2-yl]-amine (P-0130),
(1,5-Dimethyl-1H-pyrazol-3-ylmethyl)-[5-(1H-pyrrolo[2,3-b]pyridin-3-ylmethyl)-pyridin-2-yl]-amine (P-0131),
[5-(5-Chloro-1H-pyrrolo[2,3-b]pyridin-3-ylmethyl)-pyridin-2-yl]-(6-trifluoromethyl-pyridin-3-ylmethyl)-amine (P-0181),
[5-(1H-Pyrrolo[2,3-b]pyridin-3-ylmethyl)-pyridin-2-yl]-(6-trifluoromethyl-pyridin-3-ylmethyl)-amine (P-0182),
(3-Chloro-pyridin-4-ylmethyl)-[5-(1H-pyrrolo[2,3-b]pyridin-3-ylmethyl)-pyridin-2-yl]-amine (P-0183),
(2-Chloro-6-fluoro-benzyl)-[5-(1H-pyrrolo[2,3-b]pyridin-3-ylmethyl)-pyridin-2-yl]-amine (P-0210),
Phenethyl-[5-(1H-pyrrolo[2,3-b]pyridin-3-ylmethyl)-pyridin-2-yl]-amine (P-0211),
(2,4-Difluoro-benzyl)-[5-(1H-pyrrolo[2,3-b]pyridin-3-ylmethyl)-pyridin-2-yl]-amine (P-0212),
(2-Fluoro-benzyl)-[5-(1H-pyrrolo[2,3-b]pyridin-3-ylmethyl)-pyridin-2-yl]-amine (P-0213),
(3-Bromo-pyridin-4-ylmethyl)-[5-(1H-pyrrolo[2,3-b]pyridin-3-ylmethyl)-pyridin-2-yl]-amine (P-0214),
(2-M ethoxy-pyridin-3-ylmethyl)-[5-(1H-pyrrolo[2,3-b]pyridin-3-ylmethyl)-pyridin-2-yl]-amine (P-0215),
(2-Chloro-benzyl)-[5-(1H-pyrrolo[2,3-b]pyridin-3-ylmethyl)-pyridin-2-yl]-amine (P-0216),
(2-Methyl-benzyl)-[5-(1H-pyrrolo[2,3-b]pyridin-3-ylmethyl)-pyridin-2-yl]-amine (P-0217),
(1-Methyl-1H-benzoimidazol-2-ylmethyl)-[5-(1H-pyrrolo[2,3-b]pyridin-3-ylmethyl)-pyridin-2-yl]-amine (P-0218),
(6-M ethoxy-pyridin-3-ylmethyl)-[5-(1H-pyrrolo[2,3-b]pyridin-3-ylmethyl)-pyridin-2-yl]-amine (P-0219),
(1H-Benzoimidazol-2-ylmethyl)-[5-(1H-pyrrolo[2,3-b]pyridin-3-ylmethyl)-pyridin-2-yl]-amine (P-0220),
(2-Chloro-4-fluoro-benzyl)-[5-(1H-pyrrolo[2,3-b]pyridin-3-ylmethyl)-pyridin-2-yl]-amine (P-0221),
(5-Methoxy-pyridin-3-ylmethyl)-[5-(1H-pyrrolo[2,3-b]pyridin-3-ylmethyl)-pyridin-2-yl]-amine (P-0222),
(3-Fluoro-pyridin-4-ylmethyl)-[5-(1H-pyrrolo[2,3-b]pyridin-3-ylmethyl)-pyridin-2-yl]-amine (P-0223),
(6-Methoxy-pyridin-2-ylmethyl)-[5-(1H-pyrrolo[2,3-b]pyridin-3-ylmethyl)-pyridin-2-yl]-amine (P-0224),
(4-Fluoro-2-trifluoromethyl-benzyl)-[5-(1H-pyrrolo[2,3-b]pyridin-3-ylmethyl)-pyridin-2-yl]-amine (P-0225),
[5-(1H-Pyrrolo[2,3-b]pyridin-3-ylmethyl)-pyridin-2-yl]-(2-trifluoromethyl-benzyl)-amine (P-0226),
(3,5-Dichloro-pyridin-4-ylmethyl)-[5-(1H-pyrrolo[2,3-b]pyridin-3-ylmethyl)-pyridin-2-yl]-amine (P-0227),
(6-Morpholin-4-yl-pyridin-2-ylmethyl)-[5-(1H-pyrrolo[2,3-b]pyridin-3-ylmethyl)-pyridin-2-yl]-amine (P-0228),
(3-Fluoro-pyridin-2-ylmethyl)-[5-(1H-pyrrolo[2,3-b]pyridin-3-ylmethyl)-pyridin-2-yl]-amine (P-0229),
(5-Fluoro-pyridin-3-ylmethyl)-[5-(1H-pyrrolo[2,3-b]pyridin-3-ylmethyl)-pyridin-2-yl]-amine (P-0230),
(3-Chloro-pyridin-4-ylmethyl)-[5-(5-chloro-1H-pyrrolo[2,3-b]pyridin-3-ylmethyl)-pyridin-2-yl]-amine (P-0235),
3-{6-[(3-Chloro-pyridin-4-ylmethyl)-amino]-pyridin-3-ylmethyl}-1H-pyrrolo[2,3-b]pyridine-5-carbonitrile (P-0256),
3-[6-(4-Chloro-benzylamino)-pyridin-3-ylmethyl]-1H-pyrrolo[2,3-b]pyridine-5-carbonitrile (P-0257),
Propane-1-sulfonic acid (2,4-difluoro-3-{[5-(1H-pyrrolo[2,3-b]pyridin-3-ylmethyl)-pyridin-2-ylamino]-methyl}-phenyl)-amide (P-0258),
Propane-1-sulfonic acid (3-{[5-(5-chloro-1H-pyrrolo[2,3-b]pyridin-3-ylmethyl)-pyridin-2-ylamino]-methyl}-2,4-difluoro-phenyl)-amide (P-0259),
3-[6-(4-Trifluoromethyl-benzylamino)-pyridin-3-ylmethyl]-1H-pyrrolo[2,3-b]pyridine-5-carbonitrile (P-0269),
[5-(5-Chloro-1H-pyrrolo[2,3-b]pyridin-3-ylmethyl)-pyridin-2-yl]-(2-fluoro-benzyl)-amine (P-0270),
3-[6-(2-Fluoro-benzylamino)-pyridin-3-ylmethyl]-1H-pyrrolo[2,3-b]pyridine-5-carbonitrile (P-0271),
(2-Fluoro-benzyl)-[5-(5-methyl-1H-pyrrolo[2,3-b]pyridin-3-ylmethyl)-pyridin-2-yl]-amine (P-0272),
3-{6-[(6-Trifluoromethyl-pyridin-3-ylmethyl)-amino]-pyridin-3-ylmethyl}-1H-pyrrolo[2,3-b]pyridine-5-carbonitrile (P-0273),
3-[6-(2-Trifluoromethyl-benzylamino)-pyridin-3-ylmethyl]-1H-pyrrolo[2,3-b]pyridine-5-carbonitrile (P-0274),
[5-(5-Chloro-1H-pyrrolo[2,3-b]pyridin-3-ylmethyl)-pyridin-2-yl]-(2-trifluoromethyl-benzyl)-amine (P-0275),
[5-(5-Methyl-1H-pyrrolo[2,3-b]pyridin-3-ylmethyl)-pyridin-2-yl]-(2-trifluoromethyl-benzyl)-amine (P-0276),
3-[6-(2,6-Difluoro-benzylamino)-pyridin-3-ylmethyl]-1H-pyrrolo[2,3-b]pyridine-5-carbonitrile (P-0277),
[5-(5-Chloro-1H-pyrrolo[2,3-b]pyridin-3-ylmethyl)-pyridin-2-yl]-(2,6-difluoro-benzyl)-amine (P-0278),
(2-Chloro-benzyl)-[5-(5-methyl-1-pyrrolo[2,3-b]pyridin-3-ylmethyl)-pyridin-2-yl]-amine (P-0279),
(2-Chloro-benzyl)-[5-(5-chloro-1H-pyrrolo[2,3-b]pyridin-3-ylmethyl)-pyridin-2-yl]-amine (P-0280),
3-[6-(2-Chloro-benzylamino)-pyridin-3-ylmethyl]-1H-pyrrolo[2,3-b]pyridine-5-carbonitrile (P-0281),
(6-M ethoxy-pyridin-3-ylmethyl)-[5-(5-methyl-1H-pyrrolo[2,3-b]pyridin-3-ylmethyl)-pyridin-2-yl]-amine (P-0282),
[5-(5-Chloro-1H-pyrrolo[2,3-b]pyridin-3-ylmethyl)-pyridin-2-yl]-(6-methoxy-pyridin-3-ylmethyl)-amine (P-0283),
3-{6-[(6-Methoxy-pyridin-3-ylmethyl)-amino]-pyridin-3-ylmethyl}-1H-pyrrolo[2,3-b]pyridine-5-carbonitrile (P-0284),
(2-Methoxy-pyridin-3-ylmethyl)-[5-(5-methyl-1H-pyrrolo[2,3-b]pyridin-3-ylmethyl)-pyridin-2-yl]-amine (P-0285),
[5-(5-Chloro-1H-pyrrolo[2,3-b]pyridin-3-ylmethyl)-pyridin-2-yl]-(2-methoxy-pyridin-3-ylmethyl)-amine (P-0286),
3-{6-[(2-Methoxy-pyridin-3-ylmethyl)-amino]-pyridin-3-ylmethyl}-1H-pyrrolo[2,3-b]pyridine-5-carbonitrile (P-0287),
(2-Ethoxy-benzyl)-[5-(1H-pyrrolo[2,3-b]pyridin-3-ylmethyl)-pyridin-2-yl]-amine (P-0288),
(2,5-Difluoro-benzyl)-[5-(1H-pyrrolo[2,3-b]pyridin-3-ylmethyl)-pyridin-2-yl]-amine (P-0296),
(2,5-Difluoro-benzyl)-[5-(5-methyl-1H-pyrrolo[2,3-b]pyridin-3-ylmethyl)-pyridin-2-yl]-amine (P-0297),
[5-(5-Chloro-1H-pyrrolo[2,3-b]pyridin-3-ylmethyl)-pyridin-2-yl]-(2,5-difluoro-benzyl)-amine (P-0298),
3-[6-(2,5-Difluoro-benzylamino)-pyridin-3-ylmethyl]-1H-pyrrolo[2,3-b]pyridine-5-carbonitrile (P-0299),
3-[6-(2-Trifluoromethoxy-benzylamino)-pyridin-3-ylmethyl]-1H-pyrrolo[2,3-b]pyridine-5-carbonitrile (P-0321),

[5-(1H-Pyrrolo[2,3-b]pyridin-3-ylmethyl)-pyridin-2-yl]-(2-trifluoromethoxy-benzyl)-amine (P-0322),
3-[6-(2-Ethoxy-benzylamino)-pyridin-3-ylmethyl]-1H-pyrrolo[2,3-b]pyridine-5-carbonitrile (P-0323),
[5-(5-Chloro-1H-pyrrolo[2,3-b]pyridin-3-ylmethyl)-pyridin-2-yl]-(5-fluoro-pyridin-3-ylmethyl)-amine (P-0324),
[5-(5-Fluoro-1H-pyrrolo[2,3-b]pyridin-3-ylmethyl)-pyridin-2-yl]-(2-trifluoromethyl-benzyl)-amine (P-0325),
[5-(5-Methoxy-1H-pyrrolo[2,3-b]pyridin-3-ylmethyl)-pyridin-2-yl]-(2-trifluoromethyl-benzyl)-amine (P-0326),
(2-Chloro-benzyl)-[5-(5-fluoro-1H-pyrrolo[2,3-b]pyridin-3-ylmethyl)-pyridin-2-yl]-amine (P-0327),
(2-Chloro-benzyl)-[5-(5-methoxy-1H-pyrrolo[2,3-b]pyridin-3-ylmethyl)-pyridin-2-yl]-amine (P-0328),
(2,5-Difluoro-benzyl)-[5-(5-fluoro-1H-pyrrolo[2,3-b]pyridin-3-ylmethyl)-pyridin-2-yl]-amine (P-0329),
(2,5-Difluoro-benzyl)-[5-(5-methoxy-1H-pyrrolo[2,3-b]pyridin-3-ylmethyl)-pyridin-2-yl]-amine (P-0330),
[5-(5-Fluoro-1H-pyrrolo[2,3-b]pyridin-3-ylmethyl)-pyridin-2-yl]-(6-methoxy-pyridin-3-ylmethyl)-amine (P-0331),
(6-Methoxy-pyridin-3-ylmethyl)-[5-(5-methoxy-1H-pyrrolo[2,3-b]pyridin-3-ylmethyl)-pyridin-2-yl]-amine (P-0332),
(2,6-Difluoro-benzyl)-[5-(5-fluoro-1H-pyrrolo[2,3-b]pyridin-3-ylmethyl)-pyridin-2-yl]-amine (P-0333),
(2,6-Difluoro-benzyl)-[5-(5-methoxy-1H-pyrrolo[2,3-b]pyridin-3-ylmethyl)-pyridin-2-yl]-amine (P-0334),
(2-Methoxy-benzyl)-[5-(1H-pyrrolo[2,3-b]pyridin-3-ylmethyl)-pyridin-2-yl]-amine (P-0336),
3-[6-(2-Methoxy-benzylamino)-pyridin-3-ylmethyl]-1H-pyrrolo[2,3-b]pyridine-5-carbonitrile (P-0337),
[5-(5-Chloro-1H-pyrrolo[2,3-b]pyridin-3-ylmethyl)-pyridin-2-yl]-(2-difluoromethoxy-benzyl)-amine (P-0338),
3-[6-(2-Difluoromethoxy-benzylamino)-pyridin-3-ylmethyl]-1H-pyrrolo[2,3-b]pyridine-5-carbonitrile (P-0339),
(2,6-Difluoro-benzyl)-[5-(1H-pyrrolo[2,3-b]pyridin-3-ylmethyl)-pyridin-2-yl]-amine (P-0340),
(2,6-Difluoro-benzyl)-[5-(5-methyl-1H-pyrrolo[2,3-b]pyridin-3-ylmethyl)-pyridin-2-yl]-amine (P-0341),
(2,4-Dichloro-benzyl)-[5-(1H-pyrrolo[2,3-b]pyridin-3-ylmethyl)-pyridin-2-yl]-amine (P-0342),
(3-Fluoro-benzyl)-[5-(1H-pyrrolo[2,3-b]pyridin-3-ylmethyl)-pyridin-2-yl]-amine (P-0343),
(2-Fluoro-4-trifluoromethyl-benzyl)-[5-(1H-pyrrolo[2,3-b]pyridin-3-ylmethyl)-pyridin-2-yl]-amine (P-0344),
(4-Chloro-2-fluoro-benzyl)-[5-(1H-pyrrolo[2,3-b]pyridin-3-ylmethyl)-pyridin-2-yl]-amine (P-0345),
(3-Fluoro-5-trifluoromethyl-benzyl)-[5-(1H-pyrrolo[2,3-b]pyridin-3-ylmethyl)-pyridin-2-yl]-amine (P-0346),
(2-Morpholin-4-yl-pyridin-3-ylmethyl)-[5-(1H-pyrrolo[2,3-b]pyridin-3-ylmethyl)-pyridin-2-yl]-amine (P-0347),
(4-Chloro-3-trifluoromethyl-benzyl)-[5-(1H-pyrrolo[2,3-b]pyridin-3-ylmethyl)-pyridin-2-yl]-amine (P-0348),
(2-Chloro-5-trifluoromethyl-benzyl)-[5-(1H-pyrrolo[2,3-b]pyridin-3-ylmethyl)-pyridin-2-yl]-amine (P-0349),
(2-Fluoro-5-trifluoromethyl-benzyl)-[5-(1H-pyrrolo[2,3-b]pyridin-3-ylmethyl)-pyridin-2-yl]-amine (P-0350),
(2,3-Dichloro-benzyl)-[5-(1H-pyrrolo[2,3-b]pyridin-3-ylmethyl)-pyridin-2-yl]-amine (P-0351),
(2-Fluoro-3-methoxy-benzyl)-[5-(1H-pyrrolo[2,3-b]pyridin-3-ylmethyl)-pyridin-2-yl]-amine (P-0352),
Dimethyl-(5-{[5-(1H-pyrrolo[2,3-b]pyridin-3-ylmethyl)-pyridin-2-ylamino]-methyl}-pyrimidin-2-yl)-amine (P-0353),
(3-Chloro-2-fluoro-benzyl)-[5-(1H-pyrrolo[2,3-b]pyridin-3-ylmethyl)-pyridin-2-yl]-amine (P-0354),
(5-Fluoro-pyridin-2-ylmethyl)-[5-(1H-pyrrolo[2,3-b]pyridin-3-ylmethyl)-pyridin-2-yl]-amine (P-0355),
(3,5-Difluoro-benzyl)-[5-(1H-pyrrolo[2,3-b]pyridin-3-ylmethyl)-pyridin-2-yl]-amine (P-0356),
(2-Propoxy-benzyl)-[5-(1H-pyrrolo[2,3-b]pyridin-3-ylmethyl)-pyridin-2-yl]-amine (P-0357),
(2-Morpholin-4-yl-benzyl)-[5-(1H-pyrrolo[2,3-b]pyridin-3-ylmethyl)-pyridin-2-yl]-amine (P-0358),
(2-Chloro-3-methoxy-benzyl)-[5-(1H-pyrrolo[2,3-b]pyridin-3-ylmethyl)-pyridin-2-yl]-amine (P-0359),
(2-Fluoro-6-trifluoromethyl-benzyl)-[5-(1H-pyrrolo[2,3-b]pyridin-3-ylmethyl)-pyridin-2-yl]-amine (P-0360),
[2-(2-Morpholin-4-yl-ethoxy)-benzyl]-[5-(1H-pyrrolo[2,3-b]pyridin-3-ylmethyl)-pyridin-2-yl]-amine (P-0361),
(2,3-Difluoro-benzyl)-[5-(1H-pyrrolo[2,3-b]pyridin-3-ylmethyl)-pyridin-2-yl]-amine (P-0362),
(2-Chloro-3-trifluoromethyl-benzyl)-[5-(1H-pyrrolo[2,3-b]pyridin-3-ylmethyl)-pyridin-2-yl]-amine (P-0363),
(2-Chloro-5-fluoro-benzyl)-[5-(1H-pyrrolo[2,3-b]pyridin-3-ylmethyl)-pyridin-2-yl]-amine (P-0364),
(2-Fluoro-3-trifluoromethyl-benzyl)-[5-(1H-pyrrolo[2,3-b]pyridin-3-ylmethyl)-pyridin-2-yl]-amine (P-0365),
(5-Fluoro-2-methoxy-benzyl)-[5-(1H-pyrrolo[2,3-b]pyridin-3-ylmethyl)-pyridin-2-yl]-amine (P-0366),
(2-Difluoromethoxy-benzyl)-[5-(1H-pyrrolo[2,3-b]pyridin-3-ylmethyl)-pyridin-2-yl]-amine (P-0367),
(2-Fluoro-4-methyl-benzyl)-[5-(1H-pyrrolo[2,3-b]pyridin-3-ylmethyl)-pyridin-2-yl]-amine (P-0368),
[2-(3-Dimethylamino-propoxy)-benzyl]-[5-(1H-pyrrolo[2,3-b]pyridin-3-ylmethyl)-pyridin-2-yl]-amine (P-0369),
(2,6-Dimethoxy-pyridin-3-ylmethyl)-[5-(1H-pyrrolo[2,3-b]pyridin-3-ylmethyl)-pyridin-2-yl]-amine (P-0370),
(2-Fluoro-5-methoxy-benzyl)-[5-(1H-pyrrolo[2,3-b]pyridin-3-ylmethyl)-pyridin-2-yl]-amine (P-0371),
(4-Fluoro-2-methyl-benzyl)-[5-(1H-pyrrolo[2,3-b]pyridin-3-ylmethyl)-pyridin-2-yl]-amine (P-0372),
(3-Chloro-5-fluoro-benzyl)-[5-(1H-pyrrolo[2,3-b]pyridin-3-ylmethyl)-pyridin-2-yl]-amine (P-0373),
(6-Cyclopentyloxy-pyridin-3-ylmethyl)-[5-(1H-pyrrolo[2,3-b]pyridin-3-ylmethyl)-pyridin-2-yl]-amine (P-0374),
(5-Fluoro-2-trifluoromethyl-benzyl)-[5-(1H-pyrrolo[2,3-b]pyridin-3-ylmethyl)-pyridin-2-yl]-amine (P-0375),
[5-(1H-Pyrrolo[2,3-b]pyridin-3-ylmethyl)-pyridin-2-yl]-[2-(2,2,2-trifluoro-ethoxy)-pyridin-3-ylmethyl]-amine (P-0376),
Propane-1-sulfonic acid (2-fluoro-3-{[5-(1H-pyrrolo[2,3-b]pyridin-3-ylmethyl)-pyridin-2-ylamino]-methyl}-phenyl)-amide (P-0377),
(2,5-Dichloro-benzyl)-[5-(1H-pyrrolo[2,3-b]pyridin-3-ylmethyl)-pyridin-2-yl]-amine (P-0380),
Pyrimidin-5-ylmethyl-[5-(1H-pyrrolo[2,3-b]pyridin-3-ylmethyl)-pyridin-2-yl]-amine (P-0381),
(5-Chloro-2-fluoro-benzyl)-[5-(1H-pyrrolo[2,3-b]pyridin-3-ylmethyl)-pyridin-2-yl]-amine (P-0382),
(2-Ethyl-benzyl)-[5-(1H-pyrrolo[2,3-b]pyridin-3-ylmethyl)-pyridin-2-yl]-amine (P-0383),
2,2-Dimethyl-N-(3-{[5-(1H-pyrrolo[2,3-b]pyridin-3-ylmethyl)-pyridin-2-ylamino]-methyl}-pyridin-2-yl)-propionamide (P-0384),
Methyl-(3-{[5-(1H-pyrrolo[2,3-b]pyridin-3-ylmethyl)-pyridin-2-ylamino]-methyl}-pyridin-2-yl)-amine (P-0385),
Methyl-(5-{[5-(1H-pyrrolo[2,3-b]pyridin-3-ylmethyl)-pyridin-2-ylamino]-methyl}-pyrimidin-2-yl)-amine (P-0386),
(2-Chloro-4-methanesulfonyl-benzyl)-[5-(1H-pyrrolo[2,3-b]pyridin-3-ylmethyl)-pyridin-2-yl]-amine (P-0387),
{5-[1-(1H-Pyrrolo[2,3-b]pyridin-3-yl)-ethyl]-pyridin-2-yl}-(4-trifluoromethyl-benzyl)-amine (P-0388), (5-Fluoro-2-methyl-benzyl)-[5-(1-pyrrolo[2,3-b]pyridin-3-ylmethyl)-pyridin-2-yl]-amine (P-0397),
Dimethyl-(3-{[5-(1H-pyrrolo[2,3-b]pyridin-3-ylmethyl)-pyridin-2-ylamino]-methyl}-pyridin-2-yl)-amine (P-0399),
(5-Chloro-pyridin-3-ylmethyl)-[5-(1H-pyrrolo[2,3-b]pyridin-3-ylmethyl)-pyridin-2-yl]-amine (P-0400),
(2-M ethoxy-pyrimidin-5-ylmethyl)-[5-(1H-pyrrolo[2,3-b]pyridin-3-ylmethyl)-pyridin-2-yl]-amine (P-0401),
[5-(5-Chloro-1H-pyrrolo[2,3-b]pyridin-3-ylmethyl)-pyridin-2-yl]-[6-(2,2,2-trifluoro-ethoxy)-pyridin-3-ylmethyl]-amine (P-0409),
1-(3-Fluoro-phenyl)-3-[5-(1H-pyrrolo[2,3-b]pyridin-3-ylmethyl)-pyridin-2-yl]-urea (P-0412), and
all salts, prodrugs, tautomers, and isomers thereof.

In one embodiment, a compound of the invention is:
(4-Chloro-benzyl)-[6-(1H-pyrrolo[2,3-b]pyridin-3-ylmethyl)-pyridazin-3-yl]-amine (P-0092),
(4-Morpholin-4-ylmethyl-benzyl)-[5-(1H-pyrrolo[2,3-b]pyridin-3-ylmethyl)-pyridin-2-yl]-amine (P-0093),
(2-Methoxy-ethyl)-[5-(1H-pyrrolo[2,3-b]pyridin-3-ylmethyl)-pyridin-2-yl]-amine (P-0098),
[4-Chloro-1-ethyl-5-(1H-pyrrolo[2,3-b]pyridin-3-ylmethyl)-1H-pyrazol-3-yl]-[1-(4-fluoro-phenyl)-meth-(E)-ylidene]-amine (P-0166),
((2,2-Difluoro-benzo[1,3]dioxol-4-ylmethyl)-[5-(1H-pyrrolo[2,3-b]pyridin-3-ylmethyl)-pyridin-2-yl]-amine (P-0398); or
all salts, prodrugs, tautomers, and isomers thereof.

In certain embodiments of the above compounds, compounds are excluded where N (except where N is a heteroaryl ring atom), O, or S is bound to a carbon that is also bound to N (except where N is a heteroaryl ring atom), O, or S, except where the carbon forms a double bond with one of the heteroatoms, such as in an amide, carboxylic acid, and the like; or where N (except where N is a heteroaryl ring atom), O, C(S), C(O), or S(O)$_n$ (n is 0-2) is bound to an alkene carbon of an alkenyl group or bound to an alkyne carbon of an alkynyl group; accordingly, in certain embodiments compounds which include linkages such as the following are excluded from the present invention: —NR—CH$_2$—NR—, —O—CH$_2$—NR—, —S—CH$_2$—NR—, —NR—CH$_2$—O—, O—CH$_2$—O—, —S—CH$_2$—O—, —NR—CH$_2$—S—, —O—CH$_2$—S—, S—CH$_2$—S—, —NR—CH=CH—, —CH=CH—NR—, —NR—C≡C—, —C≡C—NR—, —O—CH=CH—, —CH=CH—O—, —O—C≡C—, —C≡C—O—, —S(O)$_{0-2}$—CH=CH—, —CH=CH—S(O)$_{0-2}$—, S(O)$_{0-2}$—C≡C—, —C≡C—S(O)$_{0-2}$—, C(O)—CH=CH—, CH=CH—C(O)—, —C≡C—C(O)—, or —C(O)—C≡C—, —C(S)—CH=CH—, —CH=CH—C(S)—, —C≡C—C(S)—, or —C(S)—C≡C—.

In reference to compounds herein, specification of a compound or group of compounds includes pharmaceutically acceptable salts of such compound(s), prodrug(s), and all stereoisomers, unless clearly indicated to the contrary. In reference to compounds of Formula II, unless clearly indicated to the contrary, it is understood that such reference includes compounds of Formulae IIa, IIb, IIc, IId, IIe, IIi; IIg, IIh, IIi, IIj, IIk, IIm, IIn, and IIp, and all sub-embodiments thereof.

In another aspect, the invention provides methods for treating a c-kit-mediated disease or condition in an animal subject (e.g. a mammal such as a human, other primates, sports animals, animals of commercial interest such as cattle, farm animals such as horses, or pets such as dogs and cats), e.g., a disease or condition characterized by abnormal c-kit activity (e.g. kinase activity). Invention methods involve administering to the subject suffering from or at risk of a c-kit-mediated disease or condition an effective amount of a compound of Formula II or Formula III, and all sub-embodiments thereof. In one embodiment, the c-kit mediated disease is selected from the group consisting of malignancies, including, but not limited to, mast cell tumors, small cell lung cancer, testicular cancer, gastrointestinal stromal tumors (GISTs), glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myelocytic leukemia, acute lymphocytic leukemia, chronic myelogenous leukemia, mastocytosis, melanoma, and canine mast cell tumors, and inflammatory diseases, including, but not limited to, asthma, rheumatoid arthritis, allergic rhinitis, multiple sclerosis, inflammatory bowel syndrome, transplant rejection, and hypereosinophilia.

In a related aspect, compounds of Formula II or Formula III, and all sub-embodiments thereof, can be used in the preparation of a medicament for the treatment of a c-kit-mediated disease or condition selected from the group consisting of malignancies, including, but not limited to, mast cell tumors, small cell lung cancer, testicular cancer, gastrointestinal stromal tumors (GISTs), glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myelocytic leukemia, acute lymphocytic leukemia, chronic myelogenous leukemia, mastocytosis, melanoma, and canine mast cell tumors, and inflammatory diseases, including, but not limited to, asthma, rheumatoid arthritis, allergic rhinitis, multiple sclerosis, inflammatory bowel syndrome, transplant rejection, and hypereosinophilia.

In a further aspect, the invention provides methods for treating a c-fms-mediated disease or condition in an animal subject (e.g. a mammal such as a human, other primates, sports animals, animals of commercial interest such as cattle, farm animals such as horses, or pets such as dogs and cats), e.g., a disease or condition characterized by abnormal c-fms activity (e.g. kinase activity). Invention methods involve administering to the subject suffering from or at risk of a c-fms-mediated disease or condition an effective amount of compound of Formula II or Formula III, and all sub-embodiments thereof. In one embodiment, the c-fms mediated disease is selected from the group consisting of immune disorders, including, but not limited to, rheumatoid arthritis, systemic lupus erythematosis (SLE), and transplant rejection; inflammatory diseases including, but not limited to, osteoarthritis, inflammatory bowel syndrome, ulcerative colitis, Crohn's disease, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, increased risk of fracture, Paget's disease, hypercalcemia, infection-mediated osteolysis (e.g. osteomyelitis), peri-prosthetic or wear-debris-mediated osteolysis, and metastasis of cancer to bone; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the central nervous system, including, but not limited to, multiple sclerosis, stroke, Alzheimer's disease and Parkinson's disease; inflammatory and chronic pain, including, but not limited to, bone pain; and cancers, including, but not limited to, multiple myeloma, acute myeloid leukemia (AML), chronic myeloid leukemia (CML), prostate cancer, breast cancer, ovarian cancer, melanoma, glioblastoma multiforme, metastasis of tumors to other tissues, and other chronic myeloproliferative diseases such as myelofibrosis.

In a related aspect, compounds of Formula II or Formula III, and all sub-embodiments thereof, can be used in the preparation of a medicament for the treatment of a c-fms-mediated disease or condition selected from the group consisting of immune disorders, including, but not limited to, rheumatoid arthritis, systemic lupus erythematosis (SLE), and transplant rejection; inflammatory diseases including, but not limited to, osteoarthritis, inflammatory bowel syndrome, ulcerative colitis, Crohn's disease, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, increased risk of fracture, Paget's disease, hypercalcemia, infection-mediated osteolysis (e.g. osteomyelitis), peri-prosthetic or wear-debris-mediated osteolysis, and metastasis of cancer to bone; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the central nervous system, including, but not limited to, multiple sclerosis, stroke, Alzheimer's disease and Parkinson's disease; inflammatory and chronic pain, including, but not limited to, bone pain; and cancers, including, but not limited to, multiple myeloma, acute myeloid leukemia (AML), chronic myeloid leukemia (CML), prostate cancer, breast cancer, ovarian cancer, melanoma, glioblastoma multiforme, metastasis of tumors to other tissues, and other chronic myeloproliferative diseases such as myelofibrosis.

In a further aspect, the invention provides methods for treating a c-fms-mediated disease or condition in an animal subject (e.g. a mammal such as a human, other primates, sports animals, animals of commercial interest such as cattle, farm animals such as horses, or pets such as dogs and cats), e.g., a disease or condition characterized by abnormal c-fms activity (e.g. kinase activity). Invention methods involve administering to the subject suffering from or at risk of a c-fms-mediated disease or condition an effective amount of compound of Formula I, Formula Ia, Formula Ib, or Formula Ig, and all sub-embodiments thereof. In one embodiment, the c-fms mediated disease is selected from the group consisting of osteoarthritis, inflammatory bowel syndrome, ulcerative colitis, Crohn's disease, Kawasaki's Disease, hemophagocytic syndrome (macrophage activation syndrome), multicentric reticulohistiocytosis, Type I diabetes, Type II diabetes, obesity, Paget's disease, infection-mediated osteolysis (e.g. osteomyelitis), peri-prosthetic or wear-debris-mediated osteolysis, endometriosis, diabetic nephropathy, multiple sclerosis, stroke, Alzheimer's disease and Parkinson's disease, inflammatory pain, chronic pain, bone pain, prostate cancer, melanoma, glioblastoma multiforme, and metastasis of tumors to tissues other than bone, preferably the c-fms mediated disease is selected from the group consisting of inflammatory bowel syndrome, ulcerative colitis, Crohn's disease, Type I diabetes, Type II diabetes, Paget's disease, diabetic nephropathy, multiple sclerosis, stroke, Alzheimer's disease and Parkinson's disease, inflammatory pain, chronic pain, bone pain, prostate cancer, metastasis of tumors to tissues other than bone, and other chronic myeloproliferative diseases such as myelofibrosis.

In a related aspect, compounds of Formula I, Formula Ia, Formula Ib, or Formula Ig, and all sub-embodiments thereof, can be used in the preparation of a medicament for the treatment of a c-fms-mediated disease or condition selected from the group consisting of osteoarthritis, inflammatory bowel syndrome, ulcerative colitis, Crohn's disease, Kawasaki's Disease, hemophagocytic syndrome (macrophage activation syndrome), multicentric reticulohistiocytosis, Type I diabetes, Type II diabetes, obesity, Paget's disease, infection-mediated osteolysis (e.g. osteomyelitis), peri-prosthetic or wear-debris-mediated osteolysis, endometriosis, diabetic nephropathy, multiple sclerosis, stroke, Alzheimer's disease and Parkinson's disease, inflammatory pain, chronic pain, bone pain, prostate cancer, melanoma, glioblastoma multiforme, and metastasis of tumors to tissues other than bone, preferably the c-fms mediated disease is selected from the group consisting of inflammatory bowel syndrome, ulcerative colitis, Crohn's disease, Type I diabetes, Type II diabetes, Paget's disease, diabetic nephropathy, multiple sclerosis, stroke, Alzheimer's disease and Parkinson's disease, inflammatory pain, chronic pain, bone pain, prostate cancer, metastasis of tumors to tissues other than bone, and other chronic myeloproliferative diseases such as myelofibrosis.

In a further aspect, the invention provides methods for treating, in an animal subject (e.g. a mammal such as a human, other primates, sports animals, animals of commercial interest such as cattle, farm animals such as horses, or pets such as dogs and cats), a disease or condition mediated by c-fms and c-kit, e.g., a disease or condition characterized by abnormal c-fms activity and/or c-kit activity (e.g. kinase activity). Invention methods involve administering to the subject suffering from or at risk of a disease or condition mediated by c-fms and c-kit an effective amount of compound of Formula II or Formula III, and all sub-embodiments thereof. In one embodiment, the condition mediated by c-fms and c-kit is selected from the group consisting of mast cell tumors, small cell lung cancer, testicular cancer, gastrointestinal stromal tumors, glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myeloid leukemia, acute lymphocytic leukemia, chronic myelogenous leukemia, multiple myeloma, mastocytosis, melanoma, breast cancer, ovarian cancer, prostate cancer, canine mast cell tumors, metastasis of cancer to bone or other tissues, chronic myeloproliferative diseases such as myelofibrosis, renal hypertrophy, asthma, rheumatoid arthritis, allergic rhinitis, multiple sclerosis, osteoarthritis, inflammatory bowel syndrome, transplant rejection, systemic lupus erythematosis, ulcerative colitis, Crohn's disease, chronic obstructive pulmonary disease, emphysema, Kawasaki's Disease, hemophagocytic syndrome (macrophage activation syndrome), multicentric reticulohistiocytosis, atherosclerosis, Type I diabetes, Type II diabetes, insulin resistance, hyperglycemia, obesity, lipolysis, hypereosinophilia, osteoporosis, increased risk of fracture, Paget's disease, hypercalcemia, infection-mediated osteolysis (e.g. osteomyelitis), peri-prosthetic or wear-debris-mediated osteolysis, endometriosis, glomerulonephritis, interstitial nephritis, Lupus nephritis, tubular necrosis, diabetic nephropathy, stroke, Alzheimer's disease, Parkinson's disease, inflammatory pain, chronic pain, and bone pain.

In a related aspect, compounds of Formula II or Formula III, and all sub-embodiments thereof, can be used in the preparation of a medicament for the treatment of a c-fms-mediated and/or c-kit mediated disease or condition selected from the group consisting of mast cell tumors, small cell lung cancer, testicular cancer, gastrointestinal stromal tumors, glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myeloid leukemia, acute lymphocytic leukemia, chronic myelogenous leukemia, multiple myeloma, mastocytosis, melanoma, breast cancer, ovarian cancer, prostate cancer, canine mast cell tumors, metastasis of cancer to bone or other tissues, chronic myeloproliferative diseases such as myelofibrosis, renal hypertrophy, asthma, rheumatoid arthritis, allergic rhinitis, multiple sclerosis, osteoarthritis, inflammatory bowel syndrome, transplant rejection, systemic lupus erythematosis, ulcerative colitis, Crohn's disease, chronic obstructive pulmonary disease, emphysema, Kawasaki's Disease, hemophagocytic syndrome (macrophage activation syndrome), multicentric reticulohistiocytosis, atherosclerosis, Type I diabetes, Type II diabetes, insulin resistance, hyperglycemia, obesity, lipolysis, hypereosinophilia, osteoporosis, increased risk of fracture, Paget's disease, hypercalcemia, infection-mediated osteolysis (e.g. osteomyelitis), peri-prosthetic or wear-debris-mediated osteolysis, endometriosis, glomerulonephritis, interstitial nephritis, Lupus nephritis, tubular necrosis, diabetic nephropathy, stroke, Alzheimer's disease, Parkinson's disease, inflammatory pain, chronic pain, and bone pain.

In particular embodiments, the compound has an $IC_{50}$ of less than 100 nM, less than 50 nM, less than 20 nM, less than 10 nM, or less than 5 nM as determined in a generally accepted kinase activity assay. In certain embodiments, the selectivity of the compound is such that the compound is at least 2-fold, 5-fold, 10-fold, or 100-fold more active on c-kit than on Ret, PDGF, or both Ret and PDGF. In certain embodiments, the selectivity of the compound is such that the compound is at least 2-fold, 5-fold, 10-fold, or 100-fold more active on c-kit than on c-fms. In certain embodiments, the selectivity of the compound is such that the compound is at least 2-fold, 5-fold, 10-fold, or 100-fold more active on c-fms than on c-kit. In certain embodiments, the compound has in combination each pairing of activity (e.g. $IC_{50}$) and/or selectivity as specified in this paragraph.

In particular embodiments, the compound has an $IC_{50}$ of less than 100 nM, less than 50 nM, less than 20 nM, less than 10 nM, or less than 5 nM as determined in a generally accepted kinase activity assay for c-kit, c-fms, or both c-kit and c-fms kinase activity. In certain embodiments, the selectivity of the compound is such that the compound is at least 2-fold, 5-fold, 10-fold, or 100-fold more active on c-kit, c-fms, or both c-kit and c-fms than on Ret, PDGF, or both Ret and PDGF.

In particular embodiments, the compound has an $IC_{50}$ of less than 100 nM, less than 50 nM, less than 20 nM, less than 10 nM, or less than 5 nM as determined in a generally accepted kinase activity assay for c-kit, c-fms, or both c-kit and c-fms kinase activity, and further has an $IC_{50}$ of less than 100 nM, less than 50 nM, less than 20 nM, less than 10 nM, or less than 5 nM as determined in a generally accepted kinase activity assay for at least one of HGK, TrkA, or TrkB kinase activity.

An additional aspect of this invention relates to compositions that include a therapeutically effective amount of a compound of Formula II or Formula III and all sub-embodiments thereof and at least one pharmaceutically acceptable carrier, excipient, and/or diluent, including combinations of any two or more compounds of Formula II or Formula III. The composition can further include one or more different pharmacologically active compounds, which can include one or more compounds of Formula I (including Formula Ia, Ib, and Ig, and all sub-embodiments thereof), Formula II or Formula III.

In one aspect, the invention provides a method of treating a cancer by administering to the subject an effective amount of a composition including a compound of Formula II or Formula III, in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one aspect, the one or more suitable anticancer therapies or medical procedures is selected from treatment with a chemotherapeutic agent (e.g. chemotherapeutic drug), radiation treatment (e.g. x-ray, γ-ray, or electron, proton, neutron, or a particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), surgery, and bone marrow and stem cell transplantation.

In one aspect, the invention provides a method of treating a cancer by administering to the subject an effective amount of a composition including a compound of Formula II or Formula III, in combination with one or more suitable chemotherapeutic agents. In one aspect, the one or more suitable chemotherapeutic agents is selected from an alkylating agent, including, but not limited to, adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; an antibiotic, including, but not limited to, bleomycin, dactinomycin, daunorubicin, doxorubicin, epirubicin, idarubicin, menogaril, mitomycin, mitoxantrone, neocarzinostatin, pentostatin, and plicamycin; an antimetabolite, including, but not limited to, azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; an immunotherapy, including, but not limited to, alemtuzumab, bevacizumab, cetuximab, galiximab, gemtuzumab, panitumumab, pertuzumab, rituximab, tositumomab, trastuzumab, and 90 Y ibritumomab tiuxetan; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, paclitaxel and DHA-paclitaxel; a retinoid, including, but not limited to, alitretinoin, bexarotene, fenretinide, isotretinoin, and tretinoin; an alkaloid, including, but not limited to, etoposide, homoharringtonine, teniposide, vinblastine, vincristine, vindesine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, edotecarin, exatecan, irinotecan (also active metabolite SN-38 (7-ethyl-10-hydroxy-camptothecin)), rubitecan, topotecan, and 9-aminocamptothecin; a kinase inhibitor, including, but not limited to, erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), and vatalanib; a targeted signal transduction inhibitor including, but not limited to bortezomib, geldanamycin, and rapamycin; a biological response modifier, including, but not limited to, imiquimod, interferon-α, and interleukin-2; and other chemotherapeutics, including, but not limited to 3-AP (3-amino-2-carboxyaldehyde thiosemicarbazone), aminoglutethimide, asparaginase, bryostatin-1, cilengitide, E7389, ixabepilone, procarbazine, sulindac, temsirolimus, tipifarnib. Preferably, the method of treating a cancer involves administering to the subject an effective amount of a composition of Formula II, Formula III or Formula IV in combination with a chemotherapeutic agent selected from 5-fluorouracil, carboplatin, dacarbazine, gefitinib, oxaliplatin, paclitaxel, SN-38, temozolomide, vinblastine, bevacizumab, cetuximab, or erlotinib.

In another aspect, the invention provides a method of treating or prophylaxis of a disease or condition in a mammal, by administering to the mammal a therapeutically effective amount of a compound of Formula II or Formula III, a prodrug of such compound, or a pharmaceutically acceptable salt of such compound or prodrug. The compound can be alone or can be part of a composition.

In a related aspect, the invention provides kits that include a composition as described herein. In particular embodiments, the composition is packaged, e.g., in a vial, bottle, flask, which may be further packaged, e.g., within a box, envelope, or bag; the composition is approved by the U.S. Food and Drug Administration or similar regulatory agency for administration to a mammal, e.g., a human; the composition is approved for administration to a mammal, e.g., a human, for a c-kit- and/or c-fms-mediated disease or condition; the kit of the invention includes written instructions on use and/or other indication that the composition is suitable or approved for administration to a mammal, e.g., a human, for a c-kit- and/or c-fms-mediated disease or condition; the composition is packaged in unit dose or single dose form, e.g., single dose pills, capsules, or the like.

In another aspect, the present invention also provides a method for modulating c-kit or c-fms activity by contacting c-kit or c-fms with an effective amount of a compound of Formula II or Formula III and all sub-embodiments thereof active on c-kit and/or c-fms (such as compounds developed using methods described herein). The compound is preferably provided at a level sufficient to modulate the activity of the c-kit or c-fms by at least 10%, more preferably at least 20%, 30%, 40%, 50%, 60%, 70%, 80%, 90%, or greater than 90%. In many embodiments, the compound will be at a concentration of about 1 μM, 100 μM, or 1 mM, or in a range of 1-100 nM, 100-500 nM, 500-1000 nM, 1-100 μM, 100-500 μM, or 500-1000 μM. In particular embodiments, the contacting is carried out in vitro.

Additional aspects and embodiments will be apparent from the following Detailed Description and from the claims.

DETAILED DESCRIPTION OF THE PREFERRED EMBODIMENTS

As used herein the following definitions apply:

"Halo" and "halogen" refer to all halogens, that is, chloro (Cl), fluoro (F), bromo (Br), or iodo (I).

"Hydroxyl" and "hydroxy" refer to the group —OH.

"Thiol" refers to the group —SH.

"Lower alkyl" alone or in combination means an alkane-derived radical containing from 1 to 6 carbon atoms (unless specifically defined) that includes a straight chain alkyl or branched alkyl. The straight chain or branched alkyl group is attached at any available point to produce a stable compound. In many embodiments, a lower alkyl is a straight or branched alkyl group containing from 1-6, 1-4, or 1-2, carbon atoms, such as methyl, ethyl, propyl, isopropyl, butyl, t-butyl, and the like. "Optionally substituted lower alkyl" denotes lower alkyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O)NHR$^a$, —C(S)NHR$^a$, —C(O)NR$^a$R$^a$, —C(S)NR$^a$R$^a$, —S(O)$_2$NHR$^a$, —S(O)$_2$NR$^a$R$^a$, —C(NH)NHR$^a$, —C(NH)NR$^b$R$^c$, —NHC(O)R$^a$, —NHC(S)R$^a$, —NR$^a$C(O)R$^a$, —NR$^a$C(S)R$^a$, —NHS(O)$_2$R$^a$, —NR$^a$S(O)$_2$R$^a$, —NHC(O)NHR$^a$, —NHC(S)NHR$^a$, —NR$^a$C(O)NH$_2$, —NR$^a$C(S)NH$_2$, —NR$^a$C(O)NHR$^a$, —NR$^a$C(S)NHR$^a$, —NHC(O)NR$^a$R$^a$, —NHC(S)NR$^a$R$^a$, —NR$^a$C(O)NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$, —NR$^a$R$^a$, —R$^e$, —R$^f$, and —R$^g$. Further, possible substitutions include subsets of these substitutions, such as are indicated herein, for example, in the description of compounds of Formula I (including Formulae Ia, Ib, Ig and all sub-embodiments thereof), attached at any available atom to produce a stable compound. For example "fluoro substituted lower alkyl" denotes a lower alkyl group substituted with one or more fluoro atoms, such as perfluoroalkyl, where preferably the lower alkyl is substituted with 1, 2, 3, 4 or 5 fluoro atoms, also 1, 2, or 3 fluoro atoms. While it is understood that substitutions are attached at any available atom to produce a stable compound, when optionally substituted alkyl is an R group of a moiety such as —OR, —NHR, —C(O)NHR, and the like, substitution of the alkyl R group is such that substitution of the alkyl carbon bound to any —O—, —S—, or —N— of the moiety (except where —N— is a heteroaryl ring atom) excludes substituents that would result in any —O—, —S—, or —N— of the substituent (except where —N— is a heteroaryl ring atom) being bound to the alkyl carbon bound to any —O—, —S—, or —N— of the moiety.

"Lower alkylene" refers to a divalent alkane-derived radical containing 1-6 carbon atoms, straight chain or branched, from which two hydrogen atoms are taken from the same carbon atom or from different carbon atoms. Examples of lower alkylene include, but are not limited to, methylene —CH$_2$—, ethylene —CH$_2$CH$_2$—, propylene —CH$_2$CH$_2$CH$_2$—, isopropylene —CH(CH$_3$)CH—, and the like. "Optionally substituted lower alkylene" denotes lower alkylene that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O)R$^a$, —OC(S)R$^a$, —C(O)R$^a$, —C(S)R$^a$, —C(O)OR$^a$, —C(S)

$-OR^a$, $-S(O)R^a$, $-S(O)_2R^a$, $-C(O)NHR^a$, $-C(S)NHR^a$, $-C(O)NR^aR^a$, $-C(S)NR^aR^a$, $-S(O)_2NHR^a$, $-S(O)_2NR^aR^a$, $-C(NH)NHR^a$, $-C(NH)NR^bR^c$, $-NHC(O)R^a$, $-NHC(S)R^a$, $-NR^aC(O)R^a$, $-NR^aC(S)R^a$, $-NHS(O)_2R^a$, $-NR^aS(O)_2R^a$, $-NHC(O)NHR^a$, $-NHC(S)NHR^a$, $-NR^aC(O)NHR^a$, $-NR^aC(O)NH_2$, $-NR^aC(S)NH_2$, $-NR^aC(S)NHR^a$, $-NHC(O)NR^aR^a$, $-NHC(S)NR^aR^a$, $-NR^aC(O)NR^aR^a$, $-NR^aC(S)NR^aR^a$, $-NHS(O)_2NHR^a$, $-NR^aS(O)_2NH_2$, $-NR^aS(O)_2NHR^a$, $-NHS(O)_2NR^aR^a$, $-NR^aS(O)_2NR^aR^a$, $-NHR^a$, $-NR^aR^a$, $-R^e$, $-R^f$, and $-R^g$, or two substituents on any one carbon or a substituent on each of any two carbons in the alkylene chain may join to form a 3-7 membered monocyclic cycloalkyl or 5-7 membered monocyclic heterocycloalkyl wherein the monocyclic cycloalkyl or monocyclic heterocycloalkyl are optionally substituted with one or more substituents selected from the group consisting of halogen, $-OH$, $-NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino.

"Lower alkenyl" alone or in combination means a straight or branched hydrocarbon containing 2-6 carbon atoms (unless specifically defined) and at least one, preferably 1-3, more preferably 1-2, most preferably one, carbon to carbon double bond. Carbon to carbon double bonds may be either contained within a straight chain or branched portion. Examples of lower alkenyl groups include ethenyl, propenyl, isopropenyl, butenyl, and the like. "Substituted lower alkenyl" denotes lower alkenyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of $-F$, $-OH$, $-NH_2$, $-NO_2$, $-CN$, $-C(O)OH$, $-C(S)OH$, $-C(O)NH_2$, $-C(S)NH_2$, $-S(O)_2NH_2$, $-NHC(O)NH_2$, $-NHC(S)NH_2$, $-NHS(O)_2NH_2$, $-C(NH)NH_2$, $-OR^a$, $-SR^a$, $-OC(O)R^a$, $-OC(S)R^a$, $-C(O)R^a$, $-C(S)R^a$, $-C(O)OR^a$, $-C(S)OR^a$, $-S(O)R^a$, $-S(O)_2R^a$, $-C(O)NHR^a$, $-C(S)NHR^a$, $-C(O)NR^aR^a$, $-C(S)NR^aR^a$, $-S(O)_2NHR^a$, $-S(O)_2NR^aR^a$, $-C(NH)NHR^a$, $-C(NH)NR^bR^c$, $-NHC(O)R^a$, $-NHC(S)R^a$, $-NR^aC(O)R^a$, $-NR^aC(S)R^a$, $-NHS(O)_2R^a$, $-NR^aS(O)_2R^a$, $-NHC(O)NHR^a$, $-NHC(S)NHR^a$, $-NR^aC(O)NH_2$, $-NR^aC(S)NH_2$, $-NR^aC(O)NHR^a$, $-NR^aC(S)NHR^a$, $-NHC(O)NR^aR^a$, $-NHC(S)NR^aR^a$, $-NR^aC(O)NR^aR^a$, $-NR^aC(S)NR^aR^a$, $-NHS(O)_2NHR^a$, $-NR^aS(O)_2NH_2$, $-NR^aS(O)_2NHR^a$, $-NHS(O)_2NR^aR^a$, $-NR^aS(O)_2NR^aR^a$, $-NHR^a$, $-NR^aR^a$, $-R^d$, $-R^f$, and $-R^g$. Further, possible possible substitutions include subsets of these substitutions, such as are indicated herein, for example, in the description of compounds of Formula I (including Formulae Ia, Ib, Ig and all sub-embodiments thereof), attached at any available atom to produce a stable compound. For example "fluoro substituted lower alkenyl" denotes a lower alkenyl group substituted with one or more fluoro atoms, where preferably the lower alkenyl is substituted with 1, 2, 3, 4 or 5 fluoro atoms, also 1, 2, or 3 fluoro atoms. While it is understood that substitutions are attached at any available atom to produce a stable compound, substitution of alkenyl groups are such that $-F$, $-C(O)-$, $-C(S)-$, $-C(NH)-$, $-S(O)-$, $-S(O)_2-$, $-O-$, $-S-$, or $-N-$(except where $-N-$ is a heteroaryl ring atom), are not bound to an alkene carbon thereof. Further, where alkenyl is a substituent of another moiety or an R group of a moiety such as $-OR$, $-NHR$, $-C(O)R$, and the like, substitution of the moiety is such that any $-C(O)-$, $-C(S)-$, $-S(O)-$, $-S(O)_2-$, $-O-$, $-S-$, or $-N-$ thereof (except where $-N-$ is a heteroaryl ring atom) are not bound to an alkene carbon of the alkenyl substituent or R group. Further, where alkenyl is a substituent of another moiety or an R group of a moiety such as $-OR$, $-NHR$, $-C(O)NHR$, and the like, substitution of the alkenyl R group is such that substitution of the alkenyl carbon bound to any $-O-$, $-S-$, or $-N-$ of the moiety (except where $-N-$ is a heteroaryl ring atom) excludes substituents that would result in any $-O-$, $-S-$, or $-N-$ of the substituent (except where $-N-$ is a heteroaryl ring atom) being bound to the alkenyl carbon bound to any $-O-$, $-S-$, or $-N-$ of the moiety. An "alkenyl carbon" refers to any carbon within an alkenyl group, whether saturated or part of the carbon to carbon double bond. An "alkene carbon" refers to a carbon within an alkenyl group that is part of a carbon to carbon double bond.

"Lower alkynyl" alone or in combination means a straight or branched hydrocarbon containing 2-6 carbon atoms (unless specifically defined) containing at least one, preferably one, carbon to carbon triple bond. Examples of alkynyl groups include ethynyl, propynyl, butyryl, and the like. "Substituted lower alkynyl" denotes lower alkynyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of $-F$, $-OH$, $-NH_2$, $-NO_2$, $-CN$, $-C(O)OH$, $-C(S)OH$, $-C(O)NH_2$, $-C(S)NH_2$, $-S(O)_2NH_2$, $-NHC(O)NH_2$, $-NHC(S)NH_2$, $-NHS(O)_2NH_2$, $-C(NH)NH_2$, $-OR^a$, $-SR^a$, $-OC(O)R^a$, $-OC(S)R^a$, $-C(O)R^a$, $-C(S)R^a$, $-C(O)OR^a$, $-C(S)OR^a$, $-S(O)R^a$, $-S(O)_2R^a$, $-C(O)NHR^a$, $-C(S)NHR^a$, $-C(O)NR^aR^a$, $-C(S)NR^aR^a$, $-S(O)_2NHR^a$, $-S(O)_2NR^aR^a$, $-C(NH)NHR^a$, $-C(NH)NR^bR^c$, $-NHC(O)R^a$, $-NHC(S)R^a$, $-NR^aC(O)R^a$, $-NR^aC(S)R^a$, $-NHS(O)_2R^a$, $-NR^aS(O)_2R^a$, $-NHC(O)NHR^a$, $-NHC(S)NHR^a$, $-NR^aC(O)NH_2$, $-NR^aC(S)NH_2$, $-NR^aC(O)NHR^a$, $-NR^aC(S)NHR^a$, $-NHC(O)NR^aR^a$, $-NHC(S)NR^aR^a$, $-NR^aC(O)NR^aR^a$, $-NR^aC(S)NR^aR^a$, $-NHS(O)_2NHR^a$, $-NR^aS(O)_2NH_2$, $-NR^aS(O)_2NHR^a$, $-NHS(O)_2NR^aR^a$, $-NR^aS(O)_2NR^aR^a$, $-NHR^a$, $-NR^aR^a$, $-R^d$, $-R^e$, and $-R^g$. Further, possible substitutions include subsets of these substitutions, such as are indicated herein, for example, in the description of compounds of Formula I (including Formulae Ia, Ib, Ig and all sub-embodiments thereof), attached at any available atom to produce a stable compound. For example "fluoro substituted lower alkynyl" denotes a lower alkynyl group substituted with one or more fluoro atoms, where preferably the lower alkynyl is substituted with 1, 2, 3, 4 or 5 fluoro atoms, also 1, 2, or 3 fluoro atoms. While it is understood that substitutions are attached at any available atom to produce a stable compound, substitution of alkynyl groups are such that $-F$, $-C(O)-$, $-C(S)-$, $-C(NH)-$, $-S(O)-$, $-S(O)_2-$, $-O-$, $-S-$, or $-N-$ (except where $-N-$ is a heteroaryl ring atom), are not bound to an alkyne carbon thereof. Further, where alkynyl is a substituent of another moiety or an R group of a moiety such as $-OR$, $-NHR$, $-C(O)R$, and the like, substitution of the moiety is such that any $-C(O)-$, $-C(S)-$, $-S(O)-$, $-S(O)_2-$, $-O-$, $-S-$, or $-N-$ thereof (except where $-N-$ is a heteroaryl ring atom) are not bound to an alkyne carbon of the alkynyl substituent or R group. Further, where alkynyl is a substituent of another moiety or an R group of a moiety such as $-OR$, $-NHR$, $-C(O)NHR$, and the like, substitution of the alkynyl R group is such that substitution of the alkynyl carbon bound to any $-O-$, $-S-$, or $-N-$ of the moiety (except where $-N-$ is a heteroaryl ring atom) excludes substituents that would result in any $-O-$, $-S-$, or $-N-$ of the substituent (except where —N— is a heteroaryl ring atom) being bound to the alkynyl carbon bound to any —O—, —S—, or —N— of the moiety. An "alkynyl carbon" refers to any carbon within an alkynyl group, whether saturated or part of the carbon to carbon triple bond. An "alkyne carbon" refers to a carbon within an alkynyl group that is part of a carbon to carbon triple bond.

"Cycloalkyl" refers to saturated or unsaturated, non-aromatic monocyclic, bicyclic or tricyclic carbon ring systems of 3-10, also 3-8, more preferably 3-6, ring members per ring, such as cyclopropyl, cyclopentyl, cyclohexyl, adamantyl, and the like. "Cycloalkylene" is a divalent cycloalkyl. A "substituted cycloalkyl" is a cycloalkyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O)NHR$^a$, —C(S)NHR$^a$, —C(O)NR$^a$R$^a$, —C(S)NR$^a$R$^a$, —S(O)$_2$NHR$^a$, —S(O)$_2$NR$^a$R$^a$, —C(NH)NHR$^a$, —C(NH)NR$^b$R$^c$, —NHC(O)R$^a$, —NHC(S)R$^a$, —NR$^a$C(O)R$^a$, —NR$^a$C(S)R$^a$, —NHS(O)$_2$R$^a$, —NR$^a$S(O)$_2$R$^a$, —NHC(O)NHR$^a$, —NHC(S)NHR$^a$, —NR$^a$C(O)NH$_2$, —NR$^a$C(S)NH$_2$, —NR$^a$C(O)NHR$^a$, —NR$^a$C(S)NHR$^a$, —NHC(O)NR$^a$R$^a$, —NHC(S)NR$^a$R$^a$, —NR$^a$C(O)NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$, —NR$^a$R$^a$, —R$^d$, —R$^e$, —R$^f$, and —R$^g$. "Substituted cycloalkylene" is a divalent substituted cycloalkyl.

"Heterocycloalkyl" refers to a saturated or unsaturated non-aromatic cycloalkyl group having from 5 to 10 atoms in which from 1 to 3 carbon atoms in the ring are replaced by heteroatoms of O, S or N, and are optionally fused with benzo or heteroaryl of 5-6 ring members. Heterocycloalkyl is also intended to include oxidized S or N, such as sulfinyl, sulfonyl and N-oxide of a tertiary ring nitrogen. Heterocycloalkyl is also intended to include compounds in which one of the ring carbons is oxo substituted, i.e. the ring carbon is a carbonyl group, such as lactones and lactams. The point of attachment of the heterocycloalkyl ring is at a carbon or nitrogen atom such that a stable ring is retained. Examples of heterocycloalkyl groups include, but are not limited to, morpholino, tetrahydrofuranyl, dihydropyridinyl, piperidinyl, pyrrolidinyl, pyrrolidonyl, piperazinyl, dihydrobenzofuryl, and dihydroindolyl. "Heterocycloalkylene" is a divalent heterocycloalkyl. A "substituted heterocycloalkyl" is a heterocycloalkyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O)NHR$^a$, —C(S)NHR$^a$, —C(O)NR$^a$R$^a$, —C(S)NR$^a$R$^a$, —S(O)$_2$NHR$^a$, —S(O)$_2$NR$^a$R$^a$, —C(NH)NHR$^a$, —C(NH)NR$^b$R$^c$, —NHC(O)R$^a$, —NHC(S)R$^a$, —NR$^a$C(O)R$^a$, —NR$^a$C(S)R$^a$, —NHS(O)$_2$R$^a$, —NR$^a$S(O)$_2$R$^a$, —NHC(O)NHR$^a$, —NHC(S)NHR$^a$, —NR$^a$C(O)NH$_2$, —NR$^a$C(S)NH$_2$, —NR$^a$C(O)NHR$^a$, —NR$^a$C(S)NHR$^a$, —NHC(O)NR$^a$R$^a$, —NHC(S)NR$^a$R$^a$, —NR$^a$C(O)NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$, —NR$^a$R$^a$, —R$^d$, —R$^e$, —R$^f$, and —R$^g$. "Substituted heterocycloalkylene" is a divalent substituted heterocycloalkyl.

"Aryl" alone or in combination refers to a monocyclic or bicyclic ring system containing aromatic hydrocarbons such as phenyl or naphthyl, which may be optionally fused with a cycloalkyl of preferably 5-7, more preferably 5-6, ring members. "Arylene" is a divalent aryl. A "substituted aryl" is an aryl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O)NHR$^a$, —C(S)NHR$^a$, —C(O)NR$^a$R$^a$, —C(S)NR$^a$R$^a$, —S(O)$_2$NHR$^a$, —S(O)$_2$NR$^a$R$^a$, —C(NH)NHR$^a$, —C(NH)NR$^b$R$^c$, —NHC(O)R$^a$, —NHC(S)R$^a$, —NR$^a$C(O)R$^a$, —NR$^a$C(S)R$^a$, —NHS(O)$_2$R$^a$, —NR$^a$S(O)$_2$R$^a$, —NHC(O)NHR$^a$, —NHC(S)NHR$^a$, —NR$^a$C(O)NH$_2$, —NR$^a$C(S)NH$_2$, —NR$^a$C(O)NHR$^a$, —NR$^a$C(S)NHR$^a$, —NHC(O)NR$^a$R$^a$, —NHC(S)NR$^a$R$^a$, —NR$^a$C(O)NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$, —NR$^a$R$^a$, —R$^d$, —R$^e$, —R$^f$, and —R$^g$. A "substituted arylene" is a divalent substituted aryl.

"Heteroaryl" alone or in combination refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfonyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, and indolyl. "Nitrogen containing heteroaryl" refers to heteroaryl wherein any heteroatoms are N. "Heteroarylene" is a divalent heteroaryl. A "substituted heteroaryl" is a heteroaryl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O)NHR$^a$, —C(S)NHR$^a$, —C(O)NR$^a$R$^a$, —C(S)NR$^a$R$^a$, —S(O)$_2$NHR$^a$, —S(O)$_2$NR$^a$R$^a$, —C(NH)NHR$^a$, —C(NH)NR$^b$R$^c$, —NHC(O)R$^a$, —NHC(S)R$^a$, —NR$^a$C(O)R$^a$, —NR$^a$C(S)R$^a$, —NHS(O)$_2$R$^a$, —NR$^a$S(O)$_2$R$^a$, —NHC(O)NHR$^a$, —NHC(S)NHR$^a$, —NR$^a$C(O)NH$_2$, —NR$^a$C(S)NH$_2$, —NR$^a$C(O)NHR$^a$, —NR$^a$C(S)NHR$^a$, —NHC(O)NR$^a$R$^a$, —NHC(S)NR$^a$R$^a$, —NR$^a$C(O)NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$, —NR$^a$R$^a$, —R$^d$, —R$^e$, R$^f$, and —R$^g$. "Substituted heteroarylene" is a divalent substituted heteroaryl.

The variables R$^a$, R$^b$, R$^c$, —R$^d$, —R$^e$, —R$^f$ and —R$^g$ as used in the description of optional substituents for alkyl, alkylene, alkenyl, alkynyl, cycloalkyl, heterocycloalkyl, aryl and heteroaryl are defined as follows:

each R$^a$, R$^b$, and R$^c$ are independently selected from the group consisting of —R$^d$, —R$^e$, —R$^f$, and —R$^g$, or R$^b$ and R$^c$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, —OR$^u$, —SR$^u$, —NHR$^u$, —NR$^u$R$^u$, —R$^x$, and —R$^y$;

each —R$^d$ is independently lower alkyl, wherein lower alkyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^k$, —SR$^k$, —OC(O)R$^k$, —OC(S)R$^k$, —C(O)R$^k$, —C(S)R$^k$, —C(O)OR$^k$, —C(S)OR$^k$, —S(O)R$^k$, —S(O)$_2$R$^k$, —C(O)NHR$^k$, —C(S)NHR$^k$, —C(O)NR$^k$R$^k$, —C(S)NR$^k$R$^k$, —S(O)$_2$NHR$^k$, —S(O)$_2$NR$^k$R$^k$, —C(NH)NHR$^k$, —C(NH)NR$^m$R$^n$, —NHC(O)R$^k$, —NHC(S)R$^k$, —NR$^k$C(O)R$^k$, —NR$^k$C(S)R$^k$, —NHS(O)$_2$R$^k$, —NR$^k$S(O)$_2$R$^k$, —NHC(O)NHR$^k$, —NHC(S)NHR$^k$, —NR$^k$C(O)NH$_2$, —NR$^k$C(S)NH$_2$, —NR$^k$C(O)NHR$^k$, —NR$^k$C(S)NHR$^k$, —NHC(O)NR$^k$R$^k$, —NHC(S)NR$^k$R$^k$, —NR$^k$C(O)NR$^k$R$^k$, —NR$^k$C(S)NR$^k$R$^k$, —NHS(O)$_2$NHR$^k$, —NR$^k$S(O)$_2$NH$_2$, —NR$^k$S(O)$_2$NHR$^k$, —NHS(O)$_2$NR$^k$R$^k$, —NR$^k$S(O)$_2$NR$^k$R$^k$, —NHR$^k$, —NR$^k$R$^k$, —R$^i$, and —R$^j$;

each —R$^e$ is independently lower alkenyl, wherein lower alkenyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^k$, —SR$^k$, —OC(O)R$^k$, —OC(S)R$^k$, —C(O)R$^k$, —C(S)R$^k$, —C(O)OR$^k$, —C(S)OR$^k$, —S(O)R$^k$, —S(O)$_2$R$^k$, —C(O)NHR$^k$, —C(S)NHR$^k$, —C(O)NR$^k$R$^k$, —C(S)NR$^k$R$^k$, —S(O)$_2$NHR$^k$, —S(O)$_2$NR$^k$R$^k$, —C(NH)NHR$^k$, —C(NH)NR$^m$R$^n$, —NHC(O)R$^k$, —NHC(S)R$^k$, —NR$^k$C(O)R$^k$, —NR$^k$C(S)R$^k$, —NHS(O)$_2$R$^k$, —NR$^k$S(O)$_2$R$^k$, —NHC(O)NHR$^k$, —NHC(S)NHR$^k$, —NR$^k$C(O)NH$_2$, —NR$^k$C(S)NH$_2$, —NR$^k$C(O)NHR$^k$, —NR$^k$C(S)NHR$^k$, —NHC(O)NR$^k$R$^k$, —NHC(S)NR$^k$R$^k$, —NR$^k$C(O)NR$^k$R$^k$, —NR$^k$C(S)NR$^k$R$^k$, —NHS(O)$_2$NHR$^k$, —NR$^k$S(O)$_2$NH$_2$, —NR$^k$S(O)$_2$NHR$^k$, —NHS(O)$_2$NR$^k$R$^k$, —NR$^k$S(O)$_2$NR$^k$R$^k$, —NHR$^k$, —NR$^k$R$^k$, —R$^h$, and —R$^j$;

each —R$^f$ is independently lower alkynyl, wherein lower alkynyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^k$, —SR$^k$, —OC(O)R$^k$, —OC(S)R$^k$, —C(O)R$^k$, —C(S)R$^k$, —C(O)OR$^k$, —C(S)OR$^k$, —S(O)R$^k$, —S(O)$_2$R$^k$, —C(O)NHR$^k$, —C(S)NHR$^k$, —C(O)NR$^k$R$^k$, —C(S)NR$^k$R$^k$, —S(O)$_2$NHR$^k$, —S(O)$_2$NR$^k$R$^k$, —C(NH)NHR$^k$, —C(NH)NR$^m$R$^n$, —NHC(O)R$^k$, —NHC(S)R$^k$, —NR$^k$C(O)R$^k$, —NR$^k$C(S)R$^k$, —NHS(O)$_2$R$^k$, —NR$^k$S(O)$_2$R$^k$, —NHC(O)NHR$^k$, —NHC(S)NHR$^k$, —NR$^k$C(O)NH$_2$, —NR$^k$C(S)NH$_2$, —NR$^k$C(O)NHR$^k$, —NR$^k$C(S)NHR$^k$, —NHC(O)NR$^k$R$^k$, —NHC(S)NR$^k$R$^k$, —NR$^k$C(O)NR$^k$R$^k$, —NR$^k$C(S)NR$^k$R$^k$, —NHS(O)$_2$NHR$^k$, —NR$^k$S(O)$_2$NH$_2$, —NR$^k$S(O)$_2$NHR$^k$, —NHS(O)$_2$NR$^k$R$^k$, —NR$^k$S(O)$_2$NR$^k$R$^k$, —NHR$^k$, —NR$^k$R$^k$, —R$^h$, —R$^h$, and —R$^j$;

each —R$^g$ is independently selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2 or 3 substituents selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^k$, —SR$^k$, —OC(O)R$^k$, —OC(S)R$^k$, —C(O)R$^k$, —C(S)R$^k$, —C(O)OR$^k$, —C(S)OR$^k$, —S(O)R$^k$, —S(O)$_2$R$^k$, —C(O)NHR$^k$, —C(S)NHR$^k$, —C(O)NR$^k$R$^k$, —C(S)NR$^k$R$^k$, —S(O)$_2$NHR$^k$, —S(O)$_2$NR$^k$R$^k$, —C(NH)NHR$^k$, —C(NH)NR$^m$R$^n$, —NHC(O)R$^k$, —NHC(S)R$^k$, —NR$^k$C(O)R$^k$, —NR$^k$C(S)R$^k$, —NHS(O)$_2$R$^k$, —NR$^k$S(O)$_2$R$^k$, —NHC(O)NHR$^k$, —NHC(S)NHR$^k$, —NR$^k$C(O)NH$_2$, —NR$^k$C(S)NH$_2$, —NR$^k$C(O)NHR$^k$, —NR$^k$C(S)NHR$^k$, —NHC(O)NR$^k$R$^k$, —NHC(S)NR$^k$R$^k$, —NR$^k$C(O)NR$^k$R$^k$, —NR$^k$C(S)NR$^k$R$^k$, —NHS(O)$_2$NHR$^k$, —NR$^k$S(O)$_2$NH$_2$, —NR$^k$S(O)$_2$NHR$^k$, —NHS(O)$_2$NR$^k$R$^k$, —NR$^k$S(O)$_2$NR$^k$R$^k$, —NHR$^k$, —NR$^k$R$^k$, —R$^h$, —R$^h$, and —R$^j$;

wherein R$^k$, R$^m$, and R$^n$ at each occurrence are independently selected from the group consisting of —R$^h$, —R$^i$, and —R$^j$, or R$^m$ and R$^n$ combine with the nitrogen to which they are attached form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, OR$^u$, —SR$^u$, —NHR$^u$, —NR$^u$R$^u$, —R$^x$, and —R$^y$;

wherein each —R$^h$ is independently lower alkyl optionally substituted with one or more, preferably 1, 2, 3, 4 or 5, also 1, 2, or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^r$, —SR$^r$, —OC(O)R$^r$, —OC(S)R$^r$, —C(O)R$^r$, —C(S)R$^r$, —C(O)OR$^r$, —C(S)OR$^r$, —S(O)R$^r$, —S(O)$_2$R$^r$, —C(O)NHR$^r$, —C(S)NHR$^r$, —C(O)NR$^r$R$^r$, —C(S)NR$^r$R$^r$, —S(O)$_2$NHR$^r$, —S(O)$_2$NR$^r$R$^r$, —C(NH)NHR$^r$, —C(NH)NR$^s$R$^t$, —NHC(O)R$^r$, —NHC(S)R$^r$, —NR$^r$C(O)R$^r$, —NR$^r$C(S)R$^r$, —NHS(O)$_2$R$^r$, —NR$^r$S(O)$_2$R$^r$, —NHC(O)NHR$^r$, —NHC(S)NHR$^r$, —NR$^r$C(O)NH$_2$, —NR$^r$C(S)NH$_2$, —NR$^r$C(O)NHR$^r$, —NR$^r$C(S)NHR$^r$, —NHC(O)NR$^r$R$^r$, —NHC(S)NR$^r$R$^r$, —NR$^r$C(O)NR$^r$R$^r$, —NR$^r$C(S)NR$^r$R$^r$, —NHS(O)$_2$NHR$^r$, —NR$^r$S(O)$_2$NH$_2$, —NR$^r$S(O)$_2$NHR$^r$, —NHS(O)$_2$NR$^r$R$^r$, —NR$^r$S(O)$_2$NR$^r$R$^r$, —NHR$^r$, —NR$^r$R$^r$, —R$^i$, and —R$^j$;

wherein each —R$^i$ is independently selected from the group consisting of lower alkenyl and lower alkynyl, wherein lower alkenyl or lower alkynyl are optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^r$, —SR$^r$, —OC(O)R$^r$, —OC(S)R$^r$, —C(O)R$^r$, —C(S)R$^r$, —C(O)OR$^r$, —C(S)OR$^r$, —S(O)R$^r$, —S(O)$_2$R$^r$, —C(O)NHR$^r$, —C(S)NHR$^r$, —C(O)NR$^r$R$^r$, —C(S)NR$^r$R$^r$, —S(O)$_2$NHR$^r$, —S(O)$_2$NR$^r$R$^r$, —C(NH)NHR$^r$, —C(NH)NR$^s$R$^t$, —NHC(O)R$^r$, —NHC(S)R$^r$, —NR'C(O)R$^r$, —NR'C(S)R$^r$, —NHS(O)$_2$R$^r$, —NR'S(O)$_2$R$^r$, —NHC(O)NHR$^r$, —NHC(S)NHR$^r$, —NR'C(O)NH$_2$, —NR'C(S)NH$_2$, —NR'C(O)NHR$^r$, —NR'C(S)NHR$^r$, —NHC(O)NR'R$^r$, —NHC(S)NR'R$^r$, —NR'C(O)NR'R$^r$, —NR'C(S)NR'R$^r$, —NHS(O)$_2$NHR$^r$, —NR'S(O)$_2$NH$_2$, —NR'S(O)$_2$NHR$^r$, —NHS(O)$_2$NR'R$^r$, —NR'S(O)$_2$NR'R$^r$, —NHR$^r$, —NR'R$^r$, and —R$^j$;

wherein each —R$^j$ is independently selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2 or 3 substituents selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^r$, —SR$^r$, —OC(O)R$^r$, —OC(S)R$^r$, —C(O)R$^r$, —C(S)R$^r$, —C(O)OR$^r$, —C(S)OR$^r$, —S(O)R$^r$, —S(O)$_2$R$^r$, —C(O)NHR$^r$, —C(S)NHR$^r$, —C(O)NR'R$^r$, —C(S)NR'R$^r$, —S(O)$_2$NHR$^r$, —S(O)$_2$NR'R$^r$, —C(NH)NHR$^r$, —C(NH)NR$^s$R$^t$, —NHC(O)R$^r$, —NHC(S)R$^r$, —NR'C(O)R$^r$, —NR'C(S)R$^r$, —NHS(O)$_2$R$^r$, —NR'S(O)$_2$R$^r$, —NHC(O)NHR$^r$, —NHC(S)NHR$^r$, —NR'C(O)NH$_2$, —NR'C(S)NH$_2$, —NR'C(O)NHR$^r$, —NR'C(S)NHR$^r$, —NHC(O)NR'R$^r$, —NHC(S)NR'R$^r$, —NR'C(O)NR'R$^r$, —NR'C(S)NR'R$^r$, —NHS(O)$_2$NHR$^r$, —NR'S(O)$_2$NH$_2$, —NR'S(O)$_2$NHR$^r$, —NHS(O)$_2$NR'R$^r$, —NR'S(O)$_2$NR'R$^r$, —NHR$^r$, —NR'R$^r$, cycloalkylamino, and —R$^x$;

wherein each R$^r$, R$^s$, and R$^t$ at each occurrence are independently selected from the group consisting of lower alkyl, C$_{3-6}$ alkenyl, C$_{3-6}$ alkynyl, cycloalkyl, heterocycloalkyl, aryl and heteroaryl, wherein lower alkyl is optionally substituted with one or more, preferably 1, 2, 3, 4 or 5, also 1, 2, or 3 substituents selected from the group consisting of —R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided that any substitution of the lower alkyl carbon bound to any —O—, —S—, or —N— of —OR$^r$, —SR$^r$, —C(O)OR$^r$, —C(S)OR$^r$, —C(O)NHR$^r$, —C(S)NHR$^r$, —C(O)NR'R$^r$, —C(S)NR'R$^r$, —S(O)$_2$NHR$^r$, —S(O)$_2$NR'R$^r$, —C(NH)NHR$^r$, —NR'C(O)R$^r$, —NR'C(S)R$^r$, —NR'S(O)$_2$R$^r$, —NHC(O)NHR$^r$, —NHC(S)NHR$^r$, —NR'C(O)NH$_2$, —NR'C(S)NH$_2$, —NR'C(O)NHR$^r$, —NR'C(S)NHR$^r$, —NHC(O)NR'R$^r$, —NHC(S)NR'R$^r$, —NR'C(O)NR'R$^r$, —NR'C(S)NR'R$^r$, —NHS(O)$_2$NHR$^r$, —NR'S(O)$_2$NH$_2$, —NR'S(O)$_2$NHR$^r$, —NHS(O)$_2$NR'R$^r$, —NR'S(O)$_2$NR'R$^r$, —NHR$^r$, or —NR'R$^r$ is selected from the group consisting of fluoro and —R$^y$, and wherein C$_{3-6}$ alkenyl or C$_{3-6}$ alkynyl are optionally substituted with one or more, preferably 1, 2, 3, 4 or 5, also 1, 2, or 3 substituents selected from the group consisting of —R$^y$, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, provided that any substitution of the C$_{3-6}$ alkenyl or C$_{3-6}$ alkynyl carbon bound to any —O—, —S—, or —N— of —OR$^r$, —SR$^r$, —C(O)OR$^r$, —C(S)OR$^r$, —C(O)NHR$^r$, —C(S)NHR$^r$, —C(O)NR'R$^r$, —C(S)NR'R$^r$, —S(O)$_2$NHR$^r$, —S(O)$_2$NR'R$^r$, —C(NH)NHR$^r$, —NR'C(O)R$^r$, —NR'C(S)R$^r$, —NR'S(O)$_2$R$^r$, —NHC(O)NHR$^r$, —NHC(S)NHR$^r$, —NR'C(O)NH$_2$, —NR'C(S)NH$_2$, —NR'C(O)NHR$^r$, —NR'C(S)NHR$^r$, —NHC(O)NR'R$^r$, —NHC(S)NR'R$^r$, —NR'C(O)NR'R$^r$, —NR'C(S)NR'R$^r$, —NHS(O)$_2$NHR$^r$, —NR'S(O)$_2$NH$_2$, —NR'S(O)$_2$NHR$^r$, —NHS(O)$_2$NR'R$^r$, —NR'S(O)$_2$NR'R$^r$, —NHR$^r$, or —NR'R$^r$ is selected from the group consisting of fluoro, lower alkyl, fluoro substituted lower alkyl, or —R$^y$, and wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkyl amino, di-alkyl amino, and cycloalkylamino, or R$^s$ and R$^t$ combine with the nitrogen to which they are attached form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, OR$^u$, —SR$^u$, —NHR$^u$, —NR$^u$R$^u$, —R$^x$, and —R$^y$;

wherein each R$^u$ is independently selected from the group consisting of lower alkyl, C$_{3-6}$ alkenyl, C$_{3-6}$ alkynyl, cycloalkyl, heterocycloalkyl, aryl, and heteroaryl, wherein lower alkyl is optionally substituted with one or more, preferably 1, 2, 3, 4 or 5, also 1, 2, or 3 substituents selected from the group consisting of —R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided that any substitution of the lower alkyl carbon bound to the —O— of —OR$^u$, —S— of —SR$^u$, or —N— of —NHR$^u$ is fluoro or —R$^y$, and wherein C$_{3-6}$ alkenyl or C$_{3-6}$ alkynyl are optionally substituted with one or more, preferably 1, 2, 3, 4 or 5, also 1, 2, or 3 substituents selected from the group consisting of —R$^y$, fluoro, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, provided that any substitution of the C$_{3-6}$ alkenyl or C$_{3-6}$ alkynyl carbon bound to the —O— of OR$^u$, —S— of SR$^u$, or —N— of NHR$^u$ is fluoro, lower alkyl, fluoro substituted lower alkyl, or R$^y$, and wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkyl amino, di-alkyl amino, and cycloalkylamino;

wherein each —R$^x$ is selected from the group consisting of lower alkyl, lower alkenyl and lower alkynyl, wherein lower alkyl is optionally substituted with one or more, preferably 1, 2, 3, 4 or 5, also 1, 2, or 3 substituents selected from the group consisting of R$^y$, fluoro, —OH, —NH$_2$, lower alkoxy, fluoro substituted lower alkoxy, lower alkylthio, fluoro substituted lower alkylthio, mono-alkyl amino, di-alkyl amino, and cycloalkylamino, and wherein lower alkenyl or lower alkynyl are optionally substituted with one or more, preferably 1, 2, 3, 4 or 5, also 1, 2, or 3 substituents selected from the group consisting of $R^y$, fluoro, —OH, —NH$_2$, lower alkyl, fluoro substituted lower alkyl, lower alkoxy, fluoro substituted lower alkoxy, lower alkylthio, fluoro substituted lower alkylthio, mono-alkyl amino, di-alkyl amino, and cycloalkylamino;

wherein each —$R^y$ is selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkyl amino, di-alkyl amino, and cycloalkylamino.

"Lower alkoxy" denotes the group —$OR^z$, where $R^z$ is lower alkyl. "Substituted lower alkoxy" denotes lower alkoxy in which $R^z$ is lower alkyl substituted with one or more substituents as indicated herein, for example, in the description of compounds of Formula I (including Formulae Ia, Ib, Ig and all sub-embodiments thereof), including descriptions of substituted cycloalkyl, cycloheteroalkyl, aryl and heteroaryl, attached at any available atom to produce a stable compound. Preferably, substitution of lower alkoxy is with 1, 2, 3, 4, or 5 substituents, also 1, 2, or 3 substituents. For example "fluoro substituted lower alkoxy" denotes lower alkoxy in which the lower alkyl is substituted with one or more fluoro atoms, where preferably the lower alkoxy is substituted with 1, 2, 3, 4 or 5 fluoro atoms, also 1, 2, or 3 fluoro atoms. While it is understood that substitutions on alkoxy are attached at any available atom to produce a stable compound, substitution of alkoxy is such that —O—, —S—, or —N— (except where N is a heteroaryl ring atom), are not bound to the alkyl carbon bound to the alkoxy —O—. Further, where alkoxy is described as a substituent of another moiety, the alkoxy oxygen is not bound to a carbon atom that is bound to an —O—, —S—, or —N— of the other moiety (except where N is a heteroaryl ring atom), or to an alkene or alkyne carbon of the other moiety.

"Lower alkylthio" denotes the group —$SR^{aa}$, where $R^{aa}$ is lower alkyl. "Substituted lower alkylthio" denotes lower alkylthio in which $R^{aa}$ is lower alkyl substituted with one or more substituents as indicated herein, for example, in the description of compounds of Formula I (including Formulae Ia, Ib, Ig and all sub-embodiments thereof), including descriptions of substituted cycloalkyl, cycloheteroalkyl, aryl and heteroaryl, attached at any available atom to produce a stable compound. Preferably, substitution of lower alkylthio is with 1, 2, 3, 4, or 5 substituents, also 1, 2, or 3 substituents. For example "fluoro substituted lower alkylthio" denotes lower alkylthio in which the lower alkyl is substituted with one or more fluoro atoms, where preferably the lower alkylthio is substituted with 1, 2, 3, 4 or 5 fluoro atoms, also 1, 2, or 3 fluoro atoms. While it is understood that substitutions on alkylthio are attached at any available atom to produce a stable compound, substitution of alkylthio is such that —O—, —S—, or —N— (except where N is a heteroaryl ring atom), are not bound to the alkyl carbon bound to the alkylthio —S—. Further, where alkylthio is described as a substituent of another moiety, the alkylthio sulfur is not bound to a carbon atom that is bound to an —O—, —S—, or —N— of the other moiety (except where N is a heteroaryl ring atom), or to an alkene or alkyne carbon of the other moiety.

"Amino" or "amine" denotes the group NH$_2$. "Mono-alkylamino" denotes the group —$NHR^{bb}$ where $R^{bb}$ is lower alkyl. "Di-alkylamino" denotes the group $NR^{bb}R^{cc}$, where $R^{bb}$ and $R^{cc}$ are independently lower alkyl. "Cycloalkylamino" denotes the group —$NR^{dd}R^{ee}$, where $R^{dd}$ and $R^{ee}$ combine with the nitrogen to form a 5-7 membered heterocycloalkyl, where the heterocycloalkyl may contain an additional heteroatom within the ring, such as —O—, —N—, or S—, and may also be further substituted with lower alkyl. Examples of 5-7 membered heterocycloalkyl include, but are not limited to, piperidine, piperazine, 4-methylpiperazine, morpholine, and thiomorpholine. While it is understood that when mono-alkylamino, di-alkylamino, or cycloalkylamino are substituents on other moieties that are attached at any available atom to produce a stable compound, the nitrogen of mono-alkylamino, di-alkylamino, or cycloalkylamino as substituents is not bound to a carbon atom that is bound to an —O—, —S—, or —N— of the other moiety.

As used herein, the term c-kit-mediated disease or condition refers to a disease or condition in which the biological function of c-kit affects the development and/or course of the disease or condition, and/or in which modulation of c-kit alters the development, course, and/or symptoms. For example, mutations in the c-kit gene such as the W42, Wv, and W41 mutations reported by Herbst et al (J. Biol. Chem., 1992, 267: 13210-13216) confer severe, intermediate, and mild phenotypic characteristics, respectively. These mutations attenuate the intrinsic tyrosine kinase activity of the receptor to different degrees and are models for the effect of modulation of c-kit activity. A c-kit mediated disease or condition includes a disease or condition for which c-kit inhibition provides a therapeutic benefit, e.g. wherein treatment with c-kit inhibitors, including compounds described herein, provides a therapeutic benefit to the subject suffering from or at risk of the disease or condition.

As used herein, the term c-fms-mediated disease or condition refers to a disease or condition in which the biological function of c-fms affects the development and/or course of the disease or condition, and/or in which modulation of c-fms alters the development, course, and/or symptoms. For example, the Csf1r$^-$/Csf1r$^-$ mutant mouse of Dai et al (Blood, 2002, 99: 111-120) which lacks c-fms is an animal model for diseases or conditions wherein c-fms activity has been abolished. A c-fms mediated disease or condition includes a disease or condition for which c-fms inhibition provides a therapeutic benefit, e.g. wherein treatment with c-fms inhibitors, including compounds described herein, provides a therapeutic benefit to the subject suffering from or at risk of the disease or condition.

As used herein, the term "composition" refers to a formulation suitable for administration to an intended animal subject for therapeutic purposes that contains at least one pharmaceutically active compound and at least one pharmaceutically acceptable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

In the present context, the terms "therapeutically effective" and "effective amount" indicate that the materials or amount of material is effective to prevent, alleviate, or ameliorate one or more symptoms of a disease or medical condition, and/or to prolong the survival of the subject being treated.

Reference to particular amino acid residues in human c-kit polypeptide is defined by the numbering corresponding to the Kit sequence in GenBank NP_000213 (SEQ ID NO:1). Reference to particular nucleotide positions in a nucleotide sequence encoding all or a portion of c-kit is defined by the numbering corresponding to the sequence provided in GenBank NM_000222 (SEQ ID NO:2). Reference to particular amino acid residues in human c-fms polypeptide is defined by the numbering corresponding to the FMS precursor sequence in GenBank NP 005202 (SEQ ID NO:3). Reference to particular nucleotide positions in a nucleotide sequence encoding all or a portion of c-fms is defined by the numbering corresponding to the sequence provided in GenBank NM 005211 (SEQ ID NO:4).

The terms "kit", "c-kit", and "c-Kit" mean an enzymatically active kinase that contains a portion with greater than 90% amino acid sequence identity to amino acid residues including the ATP binding site of full-length c-kit (e.g., human c-kit, e.g., the sequence NP_000213, SEQ ID NO:1), for a maximal alignment over an equal length segment; or that contains a portion with greater than 90% amino acid sequence identity to at least 200 contiguous amino acids of native c-kit and retains kinase activity. Preferably the sequence identity is at least 95, 97, 98, 99, or even 100%. Preferably the specified level of sequence identity is over a sequence at least 100-500, at least 200-400, or at least 300 contiguous amino acid residues in length. Unless indicated to the contrary, the term includes reference to wild-type c-kit, allelic variants, and mutated forms (e.g., having activating mutations).

The terms "fms", "c-fms", "FMS", and "c-Fms" mean an enzymatically active kinase that contains a portion with greater than 90% amino acid sequence identity to amino acid residues including the ATP binding site of full-length c-fms (e.g. human c-fms, e.g. residues 20-972 of GenBank sequence NP 005202, SEQ ID NO:3), for a maximal alignment over an equal length segment; or that contains a portion with greater than 90% amino acid sequence identity to at least 200 contiguous amino acids of native c-fms and retains kinase activity. Preferably the sequence identity is at least 95, 97, 98, 99, or 100%. Preferably the specified level of sequence identity is over a sequence at least 100-150, at least 200-400, or at least 300 contiguous amino acid residues in length. Unless indicated to the contrary, the term includes wild-type c-fms, allelic variants, and mutated forms (e.g. having activating mutations). The term "pFMS" refers to phosphorylated c-fms. The term "c-fms activity" refers to a biological activity of c-fms, particularly including kinase activity. The abbreviation "M-CSF" refers to the ligand for the c-fms RPTK, and the abbreviation "SCF" refers to the ligand for the c-Kit RPTK.

The term "c-kit kinase domain" refers to a reduced length c-kit (i.e., shorter than a full-length c-kit by at least 100 amino acids) that includes the kinase catalytic region in c-kit. The term "c-fms kinase domain" refers to a c-fms of reduced length (i.e., shorter than a full-length c-fms by at least 100 amino acids) that includes the kinase catalytic region of c-fms. Highly preferably for use in this invention, the kinase domain retains kinase activity, preferably at least 60, 70, 80, 90, or 100% of the native c-fms kinase activity. The term "the kinase" or terms of similar import relate to either c-kit or c-fms.

As used herein, the terms "ligand" and "modulator" are used equivalently to refer to a compound that changes (i.e., increases or decreases) the activity of a target biomolecule, e.g., an enzyme such as a kinase or kinase. Generally a ligand or modulator will be a small molecule, where "small molecule" refers to a compound with a molecular weight of 1500 daltons or less, or preferably 1000 daltons or less, 800 daltons or less, or 600 daltons or less.

In the context of compounds binding to a target, the term "greater affinity" indicates that the compound binds more tightly than a reference compound, or than the same compound in a reference condition, i.e., with a lower dissociation constant. In particular embodiments, the greater affinity is at least 2, 3, 4, 5, 8, 10, 50, 100, 200, 400, 500, 1000, or 10,000-fold greater affinity.

Also in the context of compounds binding to a biomolecular target, the term "greater specificity" indicates that a compound binds to a specified target to a greater extent than to another biomolecule or biomolecules that may be present under relevant binding conditions, where binding to such other biomolecules produces a different biological activity than binding to the specified target. Typically, the specificity is with reference to a limited set of other biomolecules, e.g., in the case of c-kit or c-fms, other tyrosine kinases or even other type of enzymes. In particular embodiments, the greater specificity is at least 2, 3, 4, 5, 8, 10, 50, 100, 200, 400, 500, or 1000-fold greater specificity.

As used herein in connection with binding compounds or ligands, the term "specific for c-kit kinase", "specific for c-kit", and terms of like import mean that a particular compound binds to c-kit to a statistically greater extent than to other kinases that may be present in a particular sample. Also, where biological activity other than binding is indicated, the term "specific for c-kit" indicates that a particular compound has greater biological effect associated with binding c-kit than to other tyrosine kinases, e.g., kinase activity inhibition. Preferably, the specificity is also with respect to other biomolecules (not limited to tyrosine kinases) that may be present in a particular sample. The term "specific for c-fms kinase", "specific for c-fms", and terms of like import mean that a particular compound binds to c-fms to a statistically greater extent than to other kinases that may be present in a particular sample. Also, where biological activity other than binding is indicated, the term "specific for c-fms" indicates that a particular compound has greater biological effect associated with binding c-fms than to other tyrosine kinases, e.g., kinase activity inhibition. Preferably, the specificity is also with respect to other biomolecules (not limited to tyrosine kinases) that may be present in a particular sample.

As used herein in connection with test compounds, binding compounds, and modulators (ligands), the term "synthesizing" and like terms means chemical synthesis from one or more precursor materials.

By "assaying" is meant the creation of experimental conditions and the gathering of data regarding a particular result of the experimental conditions. For example, enzymes can be assayed based on their ability to act upon a detectable substrate. A compound or ligand can be assayed based on its ability to bind to a particular target molecule or molecules.

As used herein, the term "modulating" or "modulate" refers to an effect of altering a biological activity, especially a biological activity associated with a particular biomolecule such as c-kit or c-fms. For example, an agonist or antagonist of a particular biomolecule modulates the activity of that biomolecule, e.g., an enzyme.

The term "c-kit activity" refers to a biological activity of c-kit, particularly including kinase activity. The term "c-fms activity" refers to a biological activity of c-fms, particularly including kinase activity.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

As used herein in connection with amino acid or nucleic acid sequence, the term "isolate" indicates that the sequence is separated from at least a portion of the amino acid and/or nucleic acid sequences with which it would normally be associated.

In connection with amino acid or nucleic sequences, the term "purified" indicates that the particular molecule constitutes a significantly greater proportion of the biomolecules in a composition than in a prior composition, e.g., in a cell culture. The greater proportion can be 2-fold, 5-fold, 10-fold or more greater.

I. General

In one aspect, the present invention concerns compounds of Formula I, Formula Ia, Formula Ib, Formula Ig, Formula II, Formula IIa, Formula IIb, Formula IIc, Formula IId, Formula IIe, Formula IIf, Formula IIg, Formula IIh, Formula IIi, Formula IIj, Formula IIk, Formula IIm, Formula IIn, Formula IIo, Formula IIp, or Formula III, and all sub-embodiments thereof, that are inhibitors of c-kit, c-fms, or both c-kit and c-fms, and the use of the compounds in treating diseases that are mediated by c-kit, c-fms, or both c-kit and c-fms.

Exemplary Diseases Associated with c-Kit.

The compounds described herein are useful for treating disorders related to c-kit e.g., diseases related to unregulated kinase signal transduction, including cell proliferative disorders, fibrotic disorders and metabolic disorders, among others. As described in more detail below and in Lipson et al., U.S. 20040002534 (U.S. application 10600, 868, filed Jun. 23, 2003) which is incorporated herein by reference in its entirety, cell proliferative disorders which can be treated by the present invention include cancers, and mast cell proliferative disorders.

The presence of c-kit has also been associated with a number of different types of cancers, as described below. In addition, the association between abnormalities in c-kit and disease are not restricted to cancer. As such, c-kit has been associated with malignancies, including mast cell tumors, small cell lung cancer, testicular cancer, gastrointestinal stromal tumors (GISTs), glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myelocytic leukemia, acute lymphocytic leukemia, chronic myelogenous leukemia, mastocytosis, melanoma, and canine mast cell tumors, and inflammatory diseases, including asthma, rheumatoid arthritis, allergic rhinitis, multiple sclerosis, inflammatory bowel syndrome, transplant rejection, and hypereosinophilia.

Exemplary Malignant Diseases Associated with c-Kit

Aberrant expression and/or activation of c-kit has been implicated in a variety of cancers. Evidence for a contribution of c-kit to neoplastic pathology includes its association with leukemias and mast cell tumors, small cell lung cancer, testicular cancer, and some cancers of the gastrointestinal tract and central nervous system. In addition, c-kit has been implicated in playing a role in carcinogenesis of the female genital tract (Inoue, et al., 1994, Cancer Res. 54(11):3049-3053), sarcomas of neuroectodermal origin (Ricotti, et al., 1998, Blood 91:2397-2405), and Schwann cell neoplasia associated with neurofibromatosis (Ryan, et al., 1994, J. Neuro. Res. 37:415-432). It was found that mast cells are involved in modifying the tumor microenvironment and enhancing tumor growth (Yang et al., 2003, J Clin Invest. 112:1851-1861; Viskochil, 2003, J Clin Invest. 112:1791-1793). Thus, c-kit is a useful target in treating neurofibromatosis as well as malignant tumors.

Small cell lung carcinoma: c-kit kinase receptor has been found to be aberrantly expressed in many cases of small cell lung carcinoma (SCLC) cells (Hibi, et al., 1991, Oncogene 6:2291-2296). Thus, as an example, inhibition of c-kit kinase can be beneficial in treatment of SCLC, e.g., to improve the long term survival of patients with SCLC.

Leukemias: SCF binding to the c-kit protects hematopoietic stem and progenitor cells from apoptosis (Lee, et al., 1997, J. Immunol. 159:3211-3219), thereby contributing to colony formation and hematopoiesis. Expression of c-kit is frequently observed in acute myelocytic leukemia (AML), and in some cases of acute lymphocytic leukemia (ALL) (for reviews, see Sperling, et al., 1997, Haemat 82:617-621; Escribano, et al., 1998, Leuk. Lymph. 30:459-466). Although c-kit is expressed in the majority of AML cells, its expression does not appear to be prognostic of disease progression (Sperling, et al, 1997, Haemat 82:617-621). However, SCF protected AML cells from apoptosis induced by chemotherapeutic agents (Hassan, et al., 1996, Acta. Hem. 95:257-262). Inhibition of c-kit by the present invention will enhance the efficacy of these agents and can induce apoptosis of AML cells.

The clonal growth of cells from patients with myelodysplastic syndrome (Sawada, et al., 1996, Blood 88:319-327) or chronic myelogenous leukemia (CML) (Sawai, et al., 1996, Exp. Hem. 2:116-122) was found to be significantly enhanced by SCF in combination with other cytokines CML is characterized by expansion of Philadelphia chromosome positive cells of the marrow (Verfaillie, et al., Leuk. 1998, 12:136-138), which appears to primarily result from inhibition of apoptotic death (Jones, Curr. Opin. One. 1997, 9:3-7). The product of the Philadelphia chromosome, $p210^{BCR-ABL}$, has been reported to mediate inhibition of apoptosis (Bedi, et al., Blood 1995, 86:1148-1158). Since $p210^{BCR-ABL}$ and c-kit both inhibit apoptosis and $p62^{dok}$ has been suggested as a substrate (Carpino, et al., Cell 1997, 88:197-204), clonal expansion mediated by these kinases may occur through a common signaling pathway. However, c-kit has also been reported to interact directly with $p210^{BCR-ABL}$ (Hallek, et al., Brit. J Haem. 1996, 94:5-16), which suggests that c-kit has a more causative role in CML pathology. Therefore, inhibition of c-kit will be useful in the treatment of the above disorders.

Gastrointestinal cancers: Normal colorectal mucosa does not express c-kit (Bellone, et al., 1997, J. Cell Physiol. 172:1-11). However, c-kit is frequently expressed in colorectal carcinoma (Bellone, et al., 1997, J. Cell Physiol. 172: 1-11), and autocrine loops of SCF and c-kit have been observed in several colon carcinoma cell lines (Toyota, et al., 1993, Turn Biol 14:295-302; Lahm, et al., 1995, Cell Growth & Differ 6:1111-1118; Bellone, et al., 1997, J. Cell Physiol. 172:1-11). Furthermore, disruption of the autocrine loop by the use of neutralizing antibodies (Lahm, et al., 1995, Cell Growth & Differ. 6:1111-1118) and downregulation of c-kit and/or SCF significantly inhibits cell proliferation (Lahm, et al., 1995, Cell Growth & Differ 6:1111-1118; Bellone, et al., 1997, J. Cell Physiol. 172:1-11).

SCF/c-kit autocrine loops have been observed in gastric carcinoma cell lines (Turner, et al., 1992, Blood 80:374-381; Hassan, et al., 1998, Digest. Dis. Science 43:8-14), and constitutive c-kit activation also appears to be important for gastrointestinal stromal tumors (GISTs). GISTs are the most common mesenchymal tumor of the digestive system. More than 90% of GISTs express c-kit, which is consistent with the putative origin of these tumor cells from interstitial cells of Cajal (ICCs) (Hirota, et al., 1998, Science 279:577-580). ICCs are thought to regulate contraction of the gastrointestinal tract, and patients lacking c-kit in their ICCs exhibited a myopathic form of chronic idiopathic intestinal pseudo-obstruction (Isozaki, et al., 1997, Amer. J. of Gast. 9 332-334). The c-kit expressed in GISTs from several different patients was observed to have mutations in the intracellular juxtamembrane domain leading to constitutive activation of c-kit (Hirota, et al., 1998, Science 279:577-580). Hence, inhibition of c-kit kinase will be an efficacious means for the treatment of these cancers.

Testicular cancers: Male germ cell tumors have been histologically categorized into seminomas, which retain germ cell characteristics, and nonseminomas which can display characteristics of embryonal differentiation. Both seminomas and nonseminomas are thought to initiate from a preinvasive stage designated carcinoma in situ (CIS) (Murty, et al., 1998, Sem. Oncol. 25:133-144). Both c-kit and SCF have been reported to be essential for normal gonadal development during embryogenesis (Loveland, et al., 1997, J. Endocrinol 153:337-344). Loss of either the receptor or the ligand resulted in animals devoid of germ cells. In postnatal testes, c-kit has been found to be expressed in Leydig cells and spermatogonia, while SCF was expressed in Sertoli cells (Loveland, et al., 1997, J. Endocrinol 153:337-344). Testicular tumors develop from Leydig cells with high frequency in transgenic mice expressing human papilloma virus 16 (HPV16) E6 and E7 oncogenes (Kondoh, et al., 1991, J. Virol. 65:3335-3339; Kondoh, et al., 1994, J. Urol. 152:2151-2154). These tumors express both c-kit and SCF, and an autocrine loop may contribute to the tumorigenesis (Kondoh, et al., 1995, Oncogene 10:341-347) associated with cellular loss of functional p53 and the retinoblastoma gene product by association with E6 and E7 (Dyson, et al., 1989, Science 243:934-937; Werness, et al., 1990, Science 248:76-79; Scheffner, et al., 1990, Cell 63:1129-1136). Defective signaling mutants of SCF (Kondoh, et al., 1995, Oncogene 10:341-347) or c-kit (Li, et al., 1996, Canc. Res. 56:4343-4346) inhibited formation of testicular tumors in mice expressing HPV16 E6 and E7. The c-kit kinase activation is pivotal to tumorigenesis in these animals and thus modulation of the c-kit kinase pathway by the present invention will prevent or treat such disorders.

Expression of c-kit in germ cell tumors shows that the receptor is expressed by the majority of carcinomas in situ and seminomas, but c-kit is expressed in only a minority of nonseminomas (Strohmeyer, et al., 1991, Canc. Res. 51:1811-1816; Rajpert-de Meyts, et al., 1994, Int. J. Androl. 17:85-92; Izquierdo, et al., 1995, J. Pathol. 177:253-258; Strohmeyer, et al., 1995, J. Urol. 153:511-515; Bokenmeyer, et al., 1996, J. Cancer Res. Clin. Oncol. 122:301-306; Sandlow, et al., 1996, J. Androl. 17:403-408). Therefore, inhibition of c-kit kinase provides a means for treating these disorders.

CNS cancers: SCF and c-kit are expressed throughout the CNS of developing rodents, and the pattern of expression indicates a role in growth, migration and differentiation of neuroectodermal cells. Expression of both receptor and ligand have also been reported in the adult brain (Hamel, et al., 1997, J. Neuro-One. 35:327-333). Expression of c-kit has also been observed in normal human brain tissue (Tada, et al. 1994, J. Neuro 80:1063-1073). Glioblastoma and astrocytoma, which define the majority of intracranial tumors, arise from neoplastic transformation of astrocytes (Levin, et al., 1997, Principles & Practice of Oncology: 2022-2082). Expression of c-kit has been observed in glioblastoma cell lines and tissues (Berdel, et al., 1992, Canc. Res. 52:3498-3502; Tada, et al. 1994, J. Neuro 80:1063-1073; Stanulla, et al., 1995, Act Neuropath 89:158-165).

Cohen, et al., 1994, Blood 84:3465-3472 reported that all 14 neuroblastoma cell lines examined contained c-kit/SCF autocrine loops, and expression of both the receptor and ligand were observed in 45% of tumor samples examined. In two cell lines, anti-c-kit antibodies inhibited cell proliferation, suggesting that the SCF/c-kit autocrine loop contributed to growth (will Cohen, et al., 1994, Blood 84:3465-3472). Hence, c-kit kinase inhibitors can be used to treat these cancers.

Exemplary Mast Cell Diseases Involving c-Kit

Excessive activation of c-kit is also associated with diseases resulting from an over-abundance of mast cells. Mastocytosis is the term used to describe a heterogeneous group of disorders characterized by excessive mast cell proliferation (Metcalfe, 1991, J. Invest. Derm 93:2 S-4S; Golkar, et al., 1997, Lancet 349:1379-1385). Elevated c-kit expression was reported on mast cells from patients with aggressive mastocytosis (Nagata, et al., 1998, Leukemia 12:175-181).

Additionally, mast cells and eosinophils represent key cells involved in allergy, inflammation and asthma (Thomas, et al., 1996, Gen. Pharmacol 27:593-597; Metcalfe, et al., 1997, Physiol Rev 77:1033-1079; Naclerio, et al., 1997, JAMA 278:1842-1848; Costa, et al., 1997, JAMA 278:1815-1822). SCF, and hence c-kit, directly and indirectly regulates activation of both mast cells and eosinophils, thereby influencing the primary cells involved in allergy and asthma through multiple mechanisms. Because of this mutual regulation of mast cell and eosinophil function, and the role that SCF can play in this regulation, inhibition of c-kit can be used to treat allergy-associated chronic rhinitis, inflammation and asthma.

Mastocytosis: SCF (also known as mast cell growth factor) stimulation of c-kit has been reported to be essential for the growth and development of mast cells (Hamel, et al., 1997, J. Neuro-One. 35:327-333; Kitamura, et al., 1995, Int. Arch. Aller. Immunol. 107:54-56). Mice with mutations of c-kit that attenuate its signaling activity have exhibited significantly fewer mast cells in their skin (Tsujimura, 1996, Pathol Int 46:933-938). Excessive activation of c-kit can be associated with diseases resulting from an over abundance of mast cells.

Mastocytosis is limited to the skin in the majority of patients, but can involve other organs in 15-20% of patients (Valent, 1996, Wein/Klin Wochenschr 108:385-397; Golkar, et al., 1997, Lancet 349:1379-1385). Even among patients with systemic mastocytosis, the disease can range from having a relatively benign prognosis to aggressive mastocytosis and mast cell leukemia. (Valent, 1996, Wein/Klin Wochenschr 108:385-397; Golkar, et al., 1997, Lancet 349:1379-1385). c-kit has been observed on malignant mast cells from canine mast cell tumors (London, et al., 1996, J. Compar. Pathol. 115:399-414), as well as on mast cells from patients with aggressive systemic mastocytosis (Baghestanian, et al., 1996, Leuk.: 116-122; Castells, et al., 1996, J. Aller. Clin. Immunol. 98:831-840).

SCF has been shown to be expressed on stromal cells as a membrane-bound protein, and its expression can be induced by fibrogenic growth factors such as PDGF. It has also been shown to be expressed on keratinocytes as a membrane-bound protein in normal skin. However, in the skin of patients with mastocytosis, an increased amount of soluble SCF has been observed (Longley, et al., 1993, New Engl. J. Med. 328:1302-1307).

Mast cell chymase has been reported to cleave membrane-associated SCF to a soluble and biologically active form. This mast cell-mediated process can generate a feedback loop to enhance mast cell proliferation and function (Longley, et al., 1997, Proc. Natl. Acad. Sci. 94:9017-9021), and may be important for the etiology of mastocytosis. Transgenic mice overexpressing a form of SCF that could not be proteolytically released from keratinocytes did not develop mastocytosis, while similar animals expressing normal SCF in keratinocytes exhibited a phenotype resembling human cutaneous mastocytosis (Kunisada, et al., 1998, J. Exp. Med. 187:1565-1573). Formation of large amounts of soluble SCF can contribute to the pathology associated with mastocytosis in some patients and the present invention can treat or prevent such disorders by modulating the interaction between SCF and c-kit kinase. Several different mutations of c-kit that resulted in constitutive kinase activity have been found in human and rodent mast cell tumor cell lines (Furitsu, et al., 1993, J. Clin. Invest. 92:1736-1744; Tsujimura, et al., 1994, Blood 9:2619-2626; Tsujimura, et al., 1995, Int. Arch. Aller. Immunol 106: 377-385; Tsujimura, 1996, Pathol Int 46:933-938). In addition, activating mutations of the c-kit gene have been observed in peripheral mononuclear cells isolated from patients with mastocytosis and associated hematologic disorders (Nagata, et al., 1998, Mastocytosis Leuk 12:175-181), and in mast cells from a patient with urticaria pigmentosa and aggressive mastocytosis (Longley, et al., 1996, Nat. Gen. 12:312-314). Inhibition of c-kit kinase will therefore prove to have an excellent therapeutic role in the treatment of these disorders.

In some patients, activating mutations of c-kit may be responsible for the pathogenesis of the disease and these patients can be treated, or their diseases prevented, by modulation of the SCF interaction with c-kit kinase. SCF activation of c-kit as been shown to prevent mast cell apoptosis which may be critical for maintaining cutaneous mast cell homeostasis (Iemura, et al., 1994, Amer. J. Pathol 144:321-328; Yee, et al., 1994, J. Exp. Med. 179:1777-1787; Mekori, et al., 1994, J. Immunol 153:2194-2203; Mekori, et al., 1995, Int. Arch. Allergy Immunol. 107:137-138). Inhibition of mast cell apoptosis can lead to the mast cell accumulation associated with mastocytosis. Thus, observation of c-kit activation resulting from overexpression of the receptor, excessive formation of soluble SCF, or mutations of the c-kit gene that constitutively activate its kinase, provides a rationale that inhibition of the kinase activity of c-kit will decrease the number of mast cells and provide benefit for patients with mastocytosis.

For cells with activating c-kit mutations, it was found that inhibitors of c-kit inhibit or even kill the cells (Ma et al., 2000, J Invest Dermatol. 114:392-394), particularly for mutations in the regulatory region (Ma et al., 2002, Blood 99:1741-1744). Ma et al., 2002, also showed that for mutations in the catalytic region, inhibitors STI571 (Gleevec) and SU9529 did not inhibit the cells, such that additional types of c-kit inhibitors are useful. Thus, c-kit inhibitors can be used against both wild-type c-kit as well as c-kit having mutations, e.g., activating mutations in the regulatory region and/or catalytic region.

Asthma & Allergy: Mast cells and eosinophils represent key cells in parasitic infection, allergy, inflammation, and asthma (Thomas, et al., 1996, Gen. Pharmacol 27:593-597; Metcalfe, et al., 1997, Physiol Rev 77:1033-1079; Holgate, 1997, CIBA Found. Symp.; Naclerio, et al., 1997, JAMA 278:1842-1848; Costa, et al., 1997, JAMA 778:1815-1822). SCF has been shown to be essential for mast cell development, survival and growth (Kitamura, et al., 1995, Int. Arch. Aller. Immunol. 107:54-56; Metcalfe, et al., 1997, Physiol Rev 77:1033-1079). In addition, SCF cooperates with the eosinophil-specific regulator, IL-5, to increase the development of eosinophil progenitors (Metcalf, et al., 1998, Proc. Natl. Acad. Sci., USA 95:6408-6412). SCF has also been reported to induce mast cells to secrete factors (Okayama, et al., 1997, Int. Arch. Aller. Immunol. 114:75-77; Okayama, et al., 1998, Eur. J. Immunol. 28:708-715) that promote the survival of eosinophils (Kay, et al., 1997, Int. Arch. Aller. Immunol. 113:196-199), which may contribute to chronic, eosinophil-mediated inflammation (Okayama, et al., 1997, Int. Arch. Aller. Immunol. 114:75-77; Okayama, et al., 1998, Eur. J. Immunol. 28:708-715). In this regard, SCF directly and indirectly regulates activation of both mast cells and eosinophils.

SCF induces mediator release from mast cells, as well as priming these cells for IgE-induced degranulation (Columbo, et al., 1992, J. Immunol 149:599-602) and sensitizing their responsiveness to eosinophil-derived granule major basic protein (Furuta, et al., 1998, Blood 92:1055-1061). Among the factors released by activated mast cells are IL-5, GM-CSF and TNF-α, which influence eosinophil protein secretion (Okayama, et al., 1997, Int. Arch. Aller. Immunol. 114:75-77; Okayama, et al., 1998, Eur. J. Immunol. 28:708-715). In addition to inducing histamine release from mast cells (Luckacs, et al., 1996, J. Immunol. 156:3945-3951; Hogaboam, et al., 1998, J. Immunol. 160:6166-6171), SCF promotes the mast cell production of the eosinophil chemotactic factor, eotaxin (Hogaboam, et al., 1998, J. Immunol. 160:6166-6171), and eosinophil infiltration (Luckacs, et al., 1996, J. Immunol. 156:3945-3951).

SCF also directly influences the adhesion of both mast cells (Dastych, et al., 1994, J. Immunol. 152:213-219; Kinashi, et al., 1994, Blood 83:1033-1038) and eosinophils (Yuan, et al., 1997, J. Exp. Med. 186:313-323), which in turn, regulates tissue infiltration. Thus, SCF can influence the primary cells involved in allergy and asthma through multiple mechanisms. Currently, corticosteroids are the most effective treatment for chronic rhinitis and inflammation associated with allergy (Naclerio, et al., 1997, JAMA 278:1842-1848; Meltzer, 1997, Aller. 52:33-40). These agents work through multiple mechanisms including reduction of circulating and infiltrating mast cells and eosinophils, and diminished survival of eosinophils associated with inhibition of cytokine production (Meltzer, 1997, Aller. 52:33-40). Steroids have also been reported to inhibit the expression of SCF by fibroblasts and resident connective tissue cells, which leads to diminished mast cell survival (Finotto, et al., 1997, J. Clin. Invest. 99 1721-1728). Because of the mutual regulation of mast cell and eosinophil function, and the role that SCF can play in this regulation, inhibition of c-kit kinase will provide a means to treat allergy-associated chronic rhinitis, inflammation and asthma.

Inflammatory arthritis (e.g. rheumatoid arthritis): Due to the association of mast cells with the arthritic process (Lee et al., 2002, Science 297:1689-1692), c-kit provides a useful target for prevention, delay, and/or treatment of inflammatory arthritis, such as rheumatoid arthritis.

Multiple sclerosis: Mast cells have been shown to play an extensive role in autoimmune diseases, as demonstrated in the mouse model of multiple sclerosis (MS), experimental allergic encephalomyelitis (EAE). Mast cells were indicated to be required for full manifestation of the disease. Secor et al., 2000, J Exp Med 191:813-821. Thus, c-kit also provides a useful target for the prevention, delay, and/or treatment of multiple sclerosis.

Exemplary Diseases Associated with c-Fms

The presence of c-fms has been associated with a number of different types of diseases. As such, c-fms has been associated with immune disorders, including rheumatoid arthritis, systemic lupus erythematosis (SLE), and transplant rejection; inflammatory diseases including, but not limited to, osteoarthritis, inflammatory bowel syndrome, ulcerative colitis, Crohn's disease, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, increased risk of fracture, Paget's disease, hypercalcemia, infection-mediated osteolysis (e.g., osteomyelitis), peri-prosthetic or wear-debris-mediated osteolysis, and metastasis of cancer to bone; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the central nervous system, including, but not limited to, multiple sclerosis, stroke, Alzheimer's disease and Parkinson's disease; inflammatory and chronic pain, including, but not limited to bone pain; and cancers, including, but not limited to, multiple myeloma, acute myeloid leukemia (AML), chronic myeloid leukemia (CML), prostate cancer, breast cancer, ovarian cancer, melanoma, glioblastoma multiforme, metastasis of tumors to other tissues, and other chronic myeloproliferative diseases such as myelofibrosis.

Aberrant expression and/or activation of c-fms has been implicated in acute myeloid leukemia, AML (Ridge et al, Proc. Nat. Acad. Sci., 1990, 87:1377-1380). Mutations at codon 301 are believed to lead to neoplastic transformation by ligand independence and constitutive tyrosine kinase activity of the receptor. The tyrosine residue at codon 969 has been shown to be involved in a negative regulatory activity, which is disrupted by amino acid substitutions. Accordingly, c-fms mutations are most prevalent (20%) in chronic myelomonocytic leukemia and AML type M4 (23%), both of which are characterized by monocytic differentiation.

A condition related to AML is chronic myeloid leukemia (CML). During the myeloid blast crisis (BC) of CML, non-random additional chromosome abnormalities occur in over 80% of patients. However, these cytogenetic changes have been reported to precede the clinical signs of CML-BC by several months to years suggesting that other biological events may participate in the multistep process of acute transformation of CML. The autocrine production of growth factors has been shown to occur in several hematological malignancies and particularly in AML. Specchia et al [Br J Haematol. 1992 March; 80(3):310-6] have demonstrated that IL-1 beta gene is expressed in almost all cases of CML in myeloid blast crisis, and that a high proportion of cases showed constitutive expression of the M-CSF gene. Many of the same patients in the Specchia et al study demonstrated simultaneous co-expression of c-fms. After exposure of leukemic cells to phorbol myristate acetate (PMA), release of M-CSF protein was documented in three of five patients studied; however, no significant interleukin-3 (IL-3), granulocyte-macrophage colony-stimulating factor (GM-CSF) or granulocyte colony-stimulating factor (G-CSF), was detected in these patients. This demonstrates that different patterns of growth factors secretion exist in AML and CML, and that distinct molecular events are likely involved in the control of leukemic proliferation.

The observation that production of M-CSF, the major macrophage growth factor, is increased in tissues during inflammation (Le Meur et al, J. Leukocyte Biology. 2002; 72:530-537) provides a role for c-fms in certain diseases. For example, COPD is characterized by airflow limitation that is not fully reversible. The airflow limitation is usually progressive and associated with an abnormal inflammatory response of the lungs to noxious particles or gases. The chronic inflammation of COPD is observed through the airways, parenchyma, and pulmonary vasculature. The inflammatory cell population consists of neutrophils, macrophages, and T lymphocytes, along with eosinophils in some patients. Macrophages are postulated to play an orchestrating role in COPD inflammation by releasing mediators such as TNF-α, IL-8 and LTB4, which are capable of damaging lung structures and/or sustaining neutrophilic inflammation.

Further, M-CSF/Fms signaling is critical to osteoclast formation and survival of osteoclast precursors. For example, estrogen loss in menopause results in increased M-CSF and thus increased osteoclast number and bone resorption which leads to increased risk of fracture and osteoporosis. Accordingly, blockage of this signal is a target for the inhibition of bone resorption (Teitelbaum, Science. 2000; 289:1504; Rohan, Science. 2000; 289:1508.)

Atherosclerosis, an inflammatory disease of the vessel walls, is associated with significant morbidity and mortality. A effect for c-fms inhibition in the treatment and prevention of atherosclerosis depends on several observations (Libby, Nature. 2002; 420:868-874.) First, monocytes resident in the arterial intima increase expression of scavenger receptors and internalize modified lipoproteins. The resulting lipid-laden macrophages develop into foam cells characteristic of the atherosclerotic lesion. Macrophages in atheroma secrete cytokines and growth factors involved in lesion progression. Additionally, macrophages replicate within the intima. Through c-fms, M-CSF activates the transition from monocyte to lipid-laden macrophage and augments expression of scavenger receptor A. Indeed, atherosclerotic plaques overexpress M-CSF which is critical for atherosclerotic progression. Mice deficient in M-CSF have been found to experience less severe atherosclerosis than mice with normal M-CSF (Rajavashisth, et. al., J. Clin. Invest. 1998; 101:2702-2710; Qiao, et. al., Am. J. Path. 1997; 150:1687-1699). Accordingly, inhibitors of c-fms disrupt M-CSF signaling, compromising monocyte to macrophage foam cell progression, macrophage survival and replication, and cytokine signaling that participates in lesion progression.

The role of M-CSF and c-fms in emphysema appears to involve the regulation of elastin metabolism through control of matrix metalloproteins. M-CSF has a role in the modulation of the accumulation and function of alveolar macrophages (AMs) in vivo (Shibata et al, Blood 2001, 98: pp. 2845-2852). Osteopetrotic (Op/Op) mice have no detectable M-CSF and show variable tissue-specific reductions in macrophage numbers. Accordingly, it was hypothesized that AMs would be decreased in number and have altered function in Op/Op mice because of the absence of M-CSF. Shibata et al found that lung macrophages identified in lung sections were decreased in number in 20-day-old Op/Op mice but not Op/Op mice older than 4 months compared with findings in age-matched littermate controls. The numbers of AMs recovered by bronchoalveolar lavage (BAL) were also reduced in young but not adult Op/Op mice compared with controls. Importantly, AMs of Op/Op mice spontaneously release higher levels of matrix metalloproteinases (MMPs) than AMs of controls. Consistent with an increased release of MMP, Op/Op mice have abnormal elastin deposition and spontaneously develop emphysema in the absence of molecular or cellular evidence of lung inflammation. Accordingly, the modulation of metalloelastase activity in macrophages by M-CSF may control the degradation of elastin fibers in lungs or blood vessels.

Metastatic cancer cells cause bone destruction, with associated fracture, pain, deformation, and hypercalcaemia, due to production of osteoclasticogenic factors including M-CSF by tumor cells (Clohisy et al, Clin. Orthop. 2000, 373: 104-14). Binding of M-CSF to the c-fms product stimulates formation of osteoclasts and osteolytic activity (Kodama et al, J. Exp. Med. 1991, 173: 269-72; Feng et al, Endocrinology 2002, 143: 4868-74). Accordingly, inhibition of osteoclast activity at the level of c-fms offers a compelling target for amelioration of bone metastasis.

Macrophage accumulation is a prominent feature in many forms of glomerulonephritis. Local proliferation of macrophages within the kidney has been described in human and experimental glomerulonephritis and may have an important role in augmenting the inflammatory response. Isbel et al (Nephrol Dial Transplant 2001, 16: 1638-1647) examined the relationship between local macrophage proliferation and renal expression of M-CSF. Glomerular and tubulointerstitial M-CSF expression was found to be up-regulated in human glomerulonephritis, being most prominent in proliferative forms of disease. Because this correlates with local macrophage proliferation, it suggests that increased renal M-CSF production plays an important role in regulating local macrophage proliferation in human glomerulonephritis. In a model of renal inflammation (UUO—unilateral ureteric obstruction) anti-c-fms antibody treatment reduced macrophage accumulation (Le Meur et. al., J Leukocyte Biology, 2002, 72: 530-537). Accordingly, inhibition of c-fms offers a target for therapeutic intervention in glomerulonephritis.

Insulin resistance and obesity are hallmark of type II diabetes and there is a strong correlation between insulin resistance and abdominal visceral fat accumulation (Bjorntrop, Diabetes Metab. Res. Rev., 1999, 15: 427-441). Current evidence indicates that macrophages accumulating in adipose tissue release TNF-a and other factors that cause adipocyte changes (hypertrophy, lipolysis, reduced insulin sensitivity) and also promote insulin resistance in surrounding tissues. Therefore, macrophage accumulation in type 2 diabetes is important for disease progression. Accordingly, inhibition of c-fms has potential in preventing the development of insulin resistance and hyperglycemia.

Dewar et al. have recently demonstrated that the kinase inhibitor imatinib also specifically targets the macrophage colony stimulating factor receptor, c-fms, at therapeutic concentrations. Although this finding has important implications with regard to potential side effects in patients currently receiving imatinib therapy, these results suggest that imatinib may also be useful in the treatment of diseases where c-fms is implicated. This includes breast and ovarian cancer and inflammatory conditions such as rheumatoid arthritis. Dewar et al. also speculate that imatinib may be used in diseases where bone destruction occurs due to excessive osteoclast activity, such as in the hematological malignancy, multiple myeloma (Dewar et al., Cell Cycle 2005, 4(7):851-3).

To determine the importance of M-CSF in driving macrophage proliferation during acute rejection, Jose et al. blocked the M-CSF receptor, c-fms, in a mouse model of acute renal allograft rejection. They observed that the severity of tubulointerstitial rejection was reduced in the treatment group as shown by decreased tubulitis and tubular cell proliferation. Macrophage proliferation during acute allograft rejection is dependent on the interaction of M-CSF with its receptor c-fms. They indicate that this pathway plays a significant and specific role in the accumulation of macrophages within a rejecting renal allograft (Jose et al., Am J Transplant 2003, 3(3):294-300).

Further, modulators of both c-fms and c-kit function can be used against diseases such as those indicated above, where in some instances, the dual activity of the modulator for both c-fms and c-kit provides distinct advantages in treating such diseases. The complementary activities provided by a single compound would provide added benefits over compounds targeting one or the other activity, or separate compounds targeting these activities. For example, by attenuating release of macrophage chemo-attractants by mast cells or mast cell chemoattractants by macrophages, these anti-inflammatory effects would synergize with the concomitant inhibition of intrinsic cellular function. Limitations in co-administration are absent in a dual inhibitor. Further, the dual activity may result in much lower effective doses for treatment.

Exemplary Diseases Associated with TrkA and TrkB

TrkA:

Target kinase TrkA (i.e., neurotrophic tyrosine kinase, receptor, type 1) is a 140 kDa tyrosine kinase encoded by chromosome 1q21-q22 (symbol: NTRK1). TrkA inhibitors may be useful in treating pain (e.g. chronic pain, neuropathic pain), cancer (e.g. prostate cancer, lung cancer, myeloid leukemia, pancreatic cancer), allergic disorders (e.g. asthma), arthritis, diabetic retinopathy, macular degeneration and psoriasis.

TrkA is a plasma member receptor composed of an extracellular domain (responsible for high affinity binding to nerve growth factor, NGF), a transmembrane segment and an intracellular protein tyrosine kinase domain (responsible to transmit the NGF signal to initiate and coordinate neuronal responses). NGF binding induces TrkA clustering on the membrane and activates the kinase. The kinase initiates a cascade of protein phosphorylation events through multiple pathways including SHC/Ras/MAPK, PI3K and PLCg1. A TrkA kinase inhibitor would not prevent NGF/TrkA binding, but could prevent down-stream signal transduction.

Nerve Growth Factor (NGF) is produced by a number of tissues and inflammatory cells during tissue injury and host immune response. It initiates and maintains hypersensitivity to incoming stimulus (hyperalgesia) and the perception of non-noxious stimuli (allodynia). Through its high-affinity receptor TrkA, NGF increases the excitation state of sensory neurons leading to the central nervous system (peripheral sensitization), and increases transmitter release from the dorsal spinal cord (central sensitization). In clinical trials, a single NGF subcutaneous injection generated local hyperalgesia persisting up to 7 weeks. At doses above 0.1 microgram/kg, NGF caused muscle pain that varied from mild to moderate, primarily in the bulbar and truncal musculature. Intravenous NGF produced earlier and more pronounced systemic effects (Petty et al, 1994, Ann Neurol. 36: 244-6). Conversely, TrkA kinase inhibitors could be used to treat diseases of enhanced states of nociception.

In Complete Freund's Adjuvant (CFA)-induced hind-paw inflammation, spinal nerve ligation and streptozoticin-induced neuropathic pain models, a single intraperitoneal injection of anti-NGF reversed established tactile allodynia from day 3 to day 7 following treatment. In the mouse CCI model, anti-NGF reversed tactile allodynia when administered 2 weeks after surgery. Repeated administration of this antibody to CCI mice for 3 weeks produced a sustained reversal of tactile allodynia (Wild et al, 2007, J. Pharmacol. Exp. Ther. 322:282-287).

Prostate tumors that have metastasized to bone frequently induce bone pain which can be difficult to fully control as it seems to be driven simultaneously by inflammatory, neuropathic, and tumorigenic mechanisms. Anti-NGF produced a significant reduction in both early and late stage bone cancer pain-related behaviors. This therapy did not influence tumor-induced bone remodeling, osteoblast proliferation, osteoclastogenesis, tumor growth, or markers of sensory or sympathetic innervation in the skin or bone. All nerve fibers that innervate the bone express TrkA and p75, and these are the receptors through which NGF sensitizes and/or activates nociceptors (Halvorson et al, 2005, Cancer Res. 65:9426-35).

In patients with mild asthma due to exposure to cat allergen, NGF expression was strongly induced in epithelial cells, fibroblasts, blood vessels, and a few infiltrating cells. TrkA mRNA and protein levels in bronchial biopsies were increased significantly after allergen exposure in infiltrating mast cells before the onset of symptoms (Kassel et al, 2001, Clin Exp Allergy 31:1432-40).

The late phase reaction in asthma following allergen provocation is dominated by an influx of activated eosinophils into the bronchial lumen, which correlates with the release of eosinophilic products into the airways to increase disease severity. The viability and activation of eosinophils from patients with mild asthma were significantly enhanced after NGF stimulation. Addition of neutralizing anti-NGF antibodies ex vivo abrogated the effects (Nassentein et al, 2003, J Exp Med 198:455-467). TrkA kinase inhibitors could decrease this paracrine loop between the respiratory tract and infiltrating mast cells as well as endobronchial eosinophils, and thus be useful for the treatment of asthma and other allergic disorders.

TrkB:

Target kinase TrkB (i.e., neurotrophic tyrosine kinase, receptor, type 2) is a 145 kDa tyrosine kinase encoded by chromosome 9q22.1 (symbol: NTRK2). TrkB inhibitors may be useful in treating various cancers and their metastases (e.g. prostate cancer, lung cancer, Wilms tumors, neuroblastoma, and pancreatic cancer), and various neuropathies (e.g. stroke, multiple sclerosis, transverse myelitis, and encephalitis).

In clinical trials with recombinant BDNF, paresthesia was developed at the site of subcutaneous injection (Coulie et al, 2000, Gastroenterology 119:41-50). Intrathecal infusion of BDNF in humans also induced paresthesia and warmth as side effects (Ochs et al, 2000, Amyotroph Lateral Scler Other Motor Neuron Disord. 1:201-6). Chronic paresthesia is often a symptom of an underlying neurological disease or traumatic nerve damage. Paresthesia can be caused by disorders affecting the central nervous system, such as stroke and transient ischemic attacks (mini-strokes), multiple sclerosis, transverse myelitis, and encephalitis. Since BDNF binds to TrkB specifically with high affinity these neuropath effects are mediated through TrkB signaling. Thus Trkb kinase inhibitors could be used to treat certain patients with neuropathy.

BDNF is known to act at the synapses between primary sensory and spinal dorsal horn neurons to affect pain transmission during inflammation. The primary afferent is the only source of BDNF in the spinal cord, and it is up-regulated in the dorsal root ganglion (DRG) by peripheral NGF a few days after inflammation, and is transported and released into the superficial dorsal horn in an activity-dependent manner. TrkB expression in the dorsal horn also increases for a few days after inflammation. These findings suggest that BDNF may act during the restricted period in the early phase of inflammation. Through TrkB, BDNF activates two distinct channels: (1) transient receptor potential canonicals (TRPC3), which produces a slow response by opening of a non-selective cation channel; and (2) Na+ channel, which mediates a rapid depolarization in the hippocampus. These channels have been strongly associated with inflammatory pain. Anti-BDNF significantly increased the withdrawal threshold in CFA-treated rats, a model of inflammatory pain. Since the swelling at the site of CFA injection was not affected by antiserum, the residual component might be due to peripheral sensitization (Matayoshi et al, 2005, J Physiol. 569:685-95).

In patients with neuroblastomas, co-expression of TrkB and BDNF, co-expression of TrkB with N-Myc amplification, and expression of truncated TrkB are found to be associated with poorer clinical outcome (Nakagawara et al, 1994, Mol Cell Biol. 14:759-767). Co-expression of TrkB with its ligand BDNF could generate a positive feedback loop through autocrine and paracrine loops. Also TrkB truncations found in these tumors generate activated forms of the intracellular protein tyrosine kinase. The constitutively active TrkB signals through multiple pathways to promote cancer initiation, progression and metastasis. These truncated TrkB kinases were also found in hepatocellular carcinoma (Yang et al, 2005, Cancer. Res 65:219-225). Thus TrkB inhibitors could be used to treat a sub-population of cancer patients with an activated TrkB pathway.

In patients with pancreatic cancer, TrkB expression is correlated with perineural invasion, positive retroperitoneal margin, and shorter latency to development of liver metastasis (Sclabas et al, 2005, Clin. Cancer. Res V11:440-449). Mechanistically, TrkB activates the PI3K pathway to suppress anoikis (apoptosis resulting from loss of cell-matrix interactions) which is one of the physiological barriers to metastasis. TrkB kinase inhibition could break down resistance to anoikis of metastasizing tumors (Douma et al, 2004, Nature 430: 1034-9). Therefore, TrkB inhibitors could have utility in a broad range of tumor types.

Exemplary Diseases Associated with HGK

HGK:

Target kinase HGK (i.e., Hematopoietic progenitor kinase/ Germinal center kinase-like Kinase, aka mitogen-activated protein kinase kinase kinase kinase 4) is a 130 kDa serine/ threonine kinase encoded by chromosome 2q11.2-q12 (symbol: MAP4K4). It is a member of the human STE20/mitogen-activated protein kinase kinase kinase kinase (MAP4K) family of serine/threonine kinases and is the human ortholog of mouse NIK (Nck-interacting kinase). The N-terminus of the mature HGK protein has a catalytic kinase domain that shares 47% and 48% amino acid sequence identity to the catalytic domain of Hematopoietic progenitor kinase 1 (HPK1) and Germinal center kinase (GCK), respectively. Yao et al. (J. Biol. Chem. 274: 2118-2125, 1999) identified 2 HGK isoforms, one of which has no proline-rich domains, and another, longer variant that contains such domains and appears to be expressed in brain only. Northern blot analysis revealed expression of 3 HGK transcripts of approximately 4.6, 6.5, and 8.5 kb in heart, brain, skeletal muscle, pancreas, placenta, liver, lung, and kidney. By Western blot analysis with a polyclonal antibody, Yao et al. (J. Biol. Chem. 274: 2118-2125, 1999) found that the 130-kD protein is expressed in multiple cell lines.

Expression of HGK in transfected cell lines resulted in strong JNK activation and, in turn, c-jun transcriptional activity (Yao et al. J. Biol. Chem. 274: 2118-2125, 1999). HGK-induced JNK activation was inhibited by dominant-negative MAP2K4, MAP2K7, and TAK1 mutants. TNF-alpha also stimulated HGK kinase activity. HGK was identified as a putative effect of Rap2 to activate JNK (Machida et al. J. Biol. Chem. 279: 15711-15714, 2004). This link establishes HGK as a potential target for a range of metabolic indications, since the JNK pathway clearly antagonizes insulin signaling. An HGK inhibitor could re-sensitize fat and muscle cells to insulin.

HGK is found to be broadly expressed in human tumor cells and can modulate cellular transformation, invasion, and adhesion (Wright et al. Mol. Cell. Biol. 23: 2068-2082, 2003). Wright et al showed HGK to be highly expressed in most tumor cell lines relative to normal tissue. An active role for this kinase in transformation was suggested by an inhibition of H-Ras(V12)-induced focus formation by expression of inactive, dominant-negative mutants of HGK in both fibroblast and epithelial cell lines. Expression of an inactive mutant of HGK also inhibited the anchorage-independent growth of cells yet had no effect on proliferation in monolayer culture. Expression of HGK mutants modulated integrin receptor expression and had a striking effect on hepatocyte growth factor-stimulated epithelial cell invasion. Together, these results suggest an important role for HGK in cell transformation and invasiveness. More recently, a small interfering RNA screen for modulators of tumor cell motility identifies MAP4K4 as a promigratory kinase (Collins et al. Proc. Natl. Acad. Sci. USA, 103: 3775-3780, 2006). Collins et al. showed that the knockdown of the HGK transcript inhibited the migration of multiple carcinoma cell lines, indicating a broad role in cell motility, and potently suppressed the invasion of SKOV-3 cells in vitro. The effect of HGK on cellular migration was found to be mediated through JNK kinase, independent of AP1 activation and downstream transcription. Accordingly, small molecule inhibition of c-Jun N-terminal kinase suppressed SKOV-3 cell migration, underscoring the potential therapeutic utility of mitogen-activated protein kinase pathway inhibition in cancer progression (Collins et al. Proc. Natl. Acad. Sci. USA, 103: 3775-3780, 2006). These studies strongly support HGK as a target in a broad range of oncology indications. In particular, an HGK inhibitor could have utility in blocking the migration, invasion and metastasis in many different tumor types.

Activation of T-cells by antigens initiates a complex series of signal-transduction events that are critical for immune responses. Mack et al. (Immunol. Lett. 96, 129-145, 2005) developed a genetic screen to survey the functional roles of kinases in antigen mediated T-cell activation and identified 19 protein kinases that were previously implicated in T-cell signaling processes and 12 kinases that were not previously linked to T-cell activation, including HGK. siRNA studies showed a role for HGK in antigen mediated T-cell responses in Jurkat and primary T-cells. In addition, by analyzing multiple promoter elements using reporter assays, Mack et al. have shown that MAP4K4 is implicated in the activation of the TNF-alpha promoter. Therefore, inhibition of HGK could have broad therapeutic utility for T-cell-mediated autoimmune diseases.

Insulin-regulated glucose transporter GLUT4 is a key modulator of whole body glucose homeostasis, and its selective loss in adipose tissue or skeletal muscle causes insulin resistance and diabetes. Using an RNA interference-based screen, Tang et al. (Proc Natl Acad Sci USA. 103:2087-2092, 2006) found 4 negative regulators of insulin-responsive glucose transport in mouse adipocytes: Pctk1, Pftk1, Ikbka (CHUK), and HGK. HGK suppressed expression of adipogenic transcription factors, C/EBPA, C/EBPB, and PPARG, and it suppressed surface expression of GLUT4 (SLC2A4), resulting in attenuated membrane hexose transport activity. RNA interference-mediated depletion of HGK early in differentiation enhanced adipogenesis and triglyceride deposition; in fully differentiated adipocytes, loss of HGK upregulated GLUT4 expression. Conversely, conditions that inhibited adipogenesis, such as TNF-alpha treatment or PPARG depletion, markedly upregulated HGK. Tang et al. (Proc Natl Acad Sci USA. 103:2087-2092, 2006) concluded that MAP4K4-dependent signaling inhibited PPARG-responsive gene expression, adipogenesis, and insulin-stimulated glucose transport. Furthermore, TNF-alpha signaling to down-regulate GLUT4 is impaired in the absence of HGK, indicating that HGK expression is required for optimal TNF-alpha action. This study further supports HGK as a target in metabolic disease, and suggests a role for HGK inhibition in ameliorating the pathology in adipocytes.

In a separate study (Bouzakri and Zierath J. Biol. Chem. 282:7783-7789, 2007), using small interfering RNA (siRNA) to suppress the expression of HGK protein 85% in primary human skeletal muscle cells, TNF-alpha-induced insulin resistance on glucose uptake was completely prevented. HGK silencing inhibited TNF-alpha-induced negative signaling inputs by preventing excessive JNK and ERK-12 phosphorylation, as well as IRS-1 serine phosphorylation. These results highlight the HGK/JNK/ERK/IRS module in the negative regulation of insulin signaling to glucose transport in response to TNF-alpha. Depletion of HGK also prevented TNF-alpha-induced insulin resistance on AKT and the AKT substrate 160 (AS160), providing evidence that appropriate insulin signaling inputs for glucose metabolism were rescued. The authors suggested that strategies to inhibit HGK may be efficacious in the prevention of TNF-alpha-induced inhibitory signals that cause skeletal muscle insulin resistance on glucose metabolism in humans. Moreover, in myotubes from insulin-resistant type II diabetic patients, siRNA against HGK restored insulin action on glucose uptake to levels observed in healthy subjects. This study further supports HGK as a target in metabolic diseases such as type II diabetes, and suggests a role for HGK inhibition in ameliorating the pathology in muscle cells.

HGK inhibitors may be useful in treating metabolic indications, including re-sensitizing fat and muscle cells to insulin, ameliorating the pathology in adipocytes, ameliorating the pathology in muscle cells, and type II diabetes; a broad range of oncology indications, including blocking the migration, invasion and metastasis in many different tumor types; and T-cell mediated autoimmune diseases.

II. Production of c-Kit and c-Fms Related Polypeptides

The native and mutated kinase polypeptides described herein may be chemically synthesized in whole or part using techniques that are well-known in the art (see, e.g., Creighton (1983) Biopolymers 22(1):49-58).

Alternatively, methods which are well known to those skilled in the art can be used to construct expression vectors containing the native or mutated kinase polypeptide coding sequence and appropriate transcriptional/translational control signals. These methods include in vitro recombinant DNA techniques, synthetic techniques and in vivo recombination/genetic recombination. See, for example, the techniques described in Maniatis, T (1989). *Molecular cloning: A laboratory Manual*. Cold Spring Harbor Laboratory, New York. Cold Spring Harbor Laboratory Press; and Ausubel, F. M. et al. (1994) *Current Protocols in Molecular Biology*. John Wiley & Sons, Secaucus, N.J.

A variety of host-expression vector systems may be utilized to express the kinase coding sequence. These include but are not limited to microorganisms such as bacteria transformed with recombinant bacteriophage DNA, plasmid DNA or cosmid DNA expression vectors containing the kinase domain coding sequence; yeast transformed with recombinant yeast expression vectors containing the kinase domain coding sequence; insect cell systems infected with recombinant virus expression vectors (e.g. baculovirus) containing the kinase domain coding sequence; plant cell systems infected with recombinant virus expression vectors (e.g. cauliflower mosaic virus, CaMV; tobacco mosaic virus, TMV) or transformed with recombinant plasmid expression vectors (e.g. Ti plasmid) containing the kinase domain coding sequence; or animal cell systems. The expression elements of these systems vary in their strength and specificities.

Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g. heat shock promoters; the promoter for the small subunit of RUBISCO; the promoter for the chlorophyll a/b binding protein) or from plant viruses (e.g. the 35S RNA promoter of CaMV; the coat protein promoter of TMV) may be used; when cloning in mammalian cell systems, promoters derived from the genome of mammalian cells (e.g. metallothionein promoter) or from mammalian viruses (e.g. the adenovirus late promoter; the vaccinia virus 7.5K promoter) may be used; when generating cell lines that contain multiple copies of the kinase domain DNA, SV4O-, BPV- and EBV-based vectors may be used with an appropriate selectable marker.

Exemplary methods describing methods of DNA manipulation, vectors, various types of cells used, methods of incorporating the vectors into the cells, expression techniques, protein purification and isolation methods, and protein concentration methods are disclosed in detail in PCT publication WO 96/18738. This publication is incorporated herein by reference in its entirety, including any drawings. Those skilled in the art will appreciate that such descriptions are applicable to the present invention and can be easily adapted to it.

III. Binding Assays

The methods of the present invention can involve assays that are able to detect the binding of compounds to a target molecule. Such binding is at a statistically significant level, preferably with a confidence level of at least 90%, more preferably at least 95, 97, 98, 99% or greater confidence level that the assay signal represents binding to the target molecule, i.e., is distinguished from background. Preferably controls are used to distinguish target binding from non-specific binding. A large variety of assays indicative of binding are known for different target types and can be used for this invention.

Binding compounds can be characterized by their effect on the activity of the target molecule. Thus, a "low activity" compound has an inhibitory concentration ($IC_{50}$) or effective concentration ($EC_{50}$) of greater than 1 µM under standard conditions. By "very low activity" is meant an $IC_{50}$ or $EC_{50}$ of above 100 µM under standard conditions. By "extremely low activity" is meant an $IC_{50}$ or $EC_{50}$ of above 1 mM under standard conditions. By "moderate activity" is meant an $IC_{50}$ or $EC_{50}$ of 200 nM to 1 µM under standard conditions. By "moderately high activity" is meant an $IC_{50}$ or $EC_{50}$ of 1 nM to 200 nM. By "high activity" is meant an $IC_{50}$ or $EC_{50}$ of below 1 nM under standard conditions. The $IC_{50}$ or $EC_{50}$ is defined as the concentration of compound at which 50% of the activity of the target molecule (e.g. enzyme or other protein) activity being measured is lost or gained relative to the range of activity observed when no compound is present. Activity can be measured using methods known to those of ordinary skill in the art, e.g., by measuring any detectable product or signal produced by occurrence of an enzymatic reaction, or other activity by a protein being measured.

By "background signal" in reference to a binding assay is meant the signal that is recorded under standard conditions for the particular assay in the absence of a test compound, molecular scaffold, or ligand that binds to the target molecule. Persons of ordinary skill in the art will realize that accepted methods exist and are widely available for determining background signal.

By "standard deviation" is meant the square root of the variance. The variance is a measure of how spread out a distribution is. It is computed as the average squared deviation of each number from its mean. For example, for the numbers 1, 2, and 3, the mean is 2 and the variance is:

$$\sigma^2 = \frac{(1-2)^2 + (2-2)^2 + (3-2)^2}{3} = 0.667.$$

Surface Plasmon Resonance

Binding parameters can be measured using surface plasmon resonance, for example, with a BIAcore® chip (Biacore, Japan) coated with immobilized binding components. Surface plasmon resonance is used to characterize the microscopic association and dissociation constants of reaction between an sFv or other ligand directed against target molecules. Such methods are generally described in the following references which are incorporated herein by reference. Vely F. et al., (2000) BIAcore® analysis to test phosphopeptide-SH2 domain interactions, Methods in Molecular Biology. 121: 313-21; Liparoto et al., (1999) Biosensor analysis of the interleukin-2 receptor complex, Journal of Molecular Recognition. 12:316-21; Lipschultz et al., (2000) Experimental design for analysis of complex kinetics using surface plasmon resonance, Methods. 20(3):310-8; Malmqvist., (1999) BIACORE: an affinity biosensor system for characterization of biomolecular interactions, Biochemical Society Transactions 27:335-40; Alfthan, (1998) Surface plasmon resonance biosensors as a tool in antibody engineering, Biosensors & Bioelectronics. 13:653-63; Fivash et al., (1998) BIAcore for macromolecular interaction, Current Opinion in Biotechnology. 9:97-101; Price et al.; (1998) Summary report on the ISOBM TD-4 Workshop: analysis of 56 monoclonal antibodies against the MUC1 mucin. Tumour Biology 19 Suppl 1:1-20; Malmqvist et al, (1997) Biomolecular interaction analysis: affinity biosensor technologies for functional analysis of proteins, Current Opinion in Chemical Biology. 1:378-83; O'Shannessy et al., (1996) Interpretation of deviations from pseudo-first-order kinetic behavior in the characterization of ligand binding by biosensor technology, Analytical Biochemistry. 236:275-83; Malmborg et al., (1995) BIAcore as a tool in antibody engineering, Journal of Immunological Methods. 183:7-13; Van Regenmortel, (1994) Use of biosensors to characterize recombinant proteins, Developments in Biological Standardization. 83:143-51; and O'Shannessy, (1994) Determination of kinetic rate and equilibrium binding constants for macromolecular interactions: a critique of the surface plasmon resonance literature, Current Opinions in Biotechnology. 5:65-71.

BIAcore® uses the optical properties of surface plasmon resonance (SPR) to detect alterations in protein concentration bound to a dextran matrix lying on the surface of a gold/glass sensor chip interface, a dextran biosensor matrix. In brief, proteins are covalently bound to the dextran matrix at a known concentration and a ligand for the protein is injected through the dextran matrix. Near infrared light, directed onto the opposite side of the sensor chip surface is reflected and also induces an evanescent wave in the gold film, which in turn, causes an intensity dip in the reflected light at a particular angle known as the resonance angle. If the refractive index of the sensor chip surface is altered (e.g. by ligand binding to the bound protein) a shift occurs in the resonance angle. This angle shift can be measured and is expressed as resonance units (RUs) such that 1000 RUs is equivalent to a change in surface protein concentration of 1 ng/mm$^2$. These changes are displayed with respect to time along the y-axis of a sensorgram, which depicts the association and dissociation of any biological reaction.

High Throughput Screening (HTS) Assays

HTS typically uses automated assays to search through large numbers of compounds for a desired activity. Typically HTS assays are used to find new drugs by screening for chemicals that act on a particular enzyme or molecule. For example, if a chemical inactivates an enzyme it might prove to be effective in preventing a process in a cell which causes a disease. High throughput methods enable researchers to assay thousands of different chemicals against each target molecule very quickly using robotic handling systems and automated analysis of results.

As used herein, "high throughput screening" or "HTS" refers to the rapid in vitro screening of large numbers of compounds (libraries); generally tens to hundreds of thousands of compounds, using robotic screening assays. Ultra high-throughput Screening (uHTS) generally refers to the high-throughput screening accelerated to greater than 100,000 tests per day.

To achieve high-throughput screening, it is advantageous to house samples on a multicontainer carrier or platform. A multicontainer carrier facilitates measuring reactions of a plurality of candidate compounds simultaneously. Multi-well microplates may be used as the carrier. Such multi-well microplates, and methods for their use in numerous assays, are both known in the art and commercially available.

Screening assays may include controls for purposes of calibration and confirmation of proper manipulation of the components of the assay. Blank wells that contain all of the reactants but no member of the chemical library are usually included. As another example, a known inhibitor (or activator) of an enzyme for which modulators are sought, can be incubated with one sample of the assay, and the resulting decrease (or increase) in the enzyme activity used as a comparator or control. It will be appreciated that modulators can also be combined with the enzyme activators or inhibitors to find modulators which inhibit the enzyme activation or repression that is otherwise caused by the presence of the known the enzyme modulator.

Measuring Enzymatic and Binding Reactions During Screening Assays

Techniques for measuring the progression of enzymatic and binding reactions, e.g., in multicontainer carriers, are known in the art and include, but are not limited to, the following.

Spectrophotometric and spectrofluorometric assays are well known in the art. Examples of such assays include the use of colorimetric assays for the detection of peroxides, as described in Gordon, A. J. and Ford, R. A., (1972) *The Chemist's Companion: A Handbook Of Practical Data, Techniques, And References*, John Wiley and Sons, N.Y., Page 437.

Fluorescence spectrometry may be used to monitor the generation of reaction products. Fluorescence methodology is generally more sensitive than the absorption methodology. The use of fluorescent probes is well known to those skilled in the art. For reviews, see Bashford et al., (1987) *Spectrophotometry and Spectrofluorometry: A Practical Approach*, pp. 91-114, IRL Press Ltd.; and Bell, (1981) *Spectroscopy In Biochemistry*, Vol. I, pp. 155-194, CRC Press.

In spectrofluorometric methods, enzymes are exposed to substrates that change their intrinsic fluorescence when processed by the target enzyme. Typically, the substrate is non-fluorescent and is converted to a fluorophore through one or more reactions. As a non-limiting example, SMase activity can be detected using the Amplex® Red reagent (Molecular Probes, Eugene, Oreg.). In order to measure sphingomyelinase activity using Amplex® Red, the following reactions occur. First, SMase hydrolyzes sphingomyelin to yield ceramide and phosphorylcholine. Second, alkaline phosphatase hydrolyzes phosphorylcholine to yield choline. Third, choline is oxidized by choline oxidase to betaine. Finally, $H_2O_2$, in the presence of horseradish peroxidase, reacts with Amplex® Red to produce the fluorescent product, Resorufin, and the signal therefrom is detected using spectrofluorometry.

Fluorescence polarization (FP) is based on a decrease in the speed of molecular rotation of a fluorophore that occurs upon binding to a larger molecule, such as a receptor protein, allowing for polarized fluorescent emission by the bound ligand. FP is empirically determined by measuring the vertical and horizontal components of fluorophore emission following excitation with plane polarized light. Polarized emission is increased when the molecular rotation of a fluorophore is reduced. A fluorophore produces a larger polarized signal when it is bound to a larger molecule (i.e. a receptor), slowing molecular rotation of the fluorophore. The magnitude of the polarized signal relates quantitatively to the extent of fluorescent ligand binding. Accordingly, polarization of the "bound" signal depends on maintenance of high affinity binding.

FP is a homogeneous technology and reactions are very rapid, taking seconds to minutes to reach equilibrium. The reagents are stable, and large batches may be prepared, resulting in high reproducibility. Because of these properties, FP has proven to be highly automatable, often performed with a single incubation with a single, premixed, tracer-receptor reagent. For a review, see Owicki et al., (1997), Application of Fluorescence Polarization Assays in High-Throughput Screening, Genetic Engineering News, 17:27.

FP is particularly desirable since its readout is independent of the emission intensity (Checovich, W. J., et al., (1995) Nature 375:254-256; Dandliker, W. B., et al., (1981) Methods in Enzymology 74:3-28) and is thus insensitive to the presence of colored compounds that quench fluorescence emission. FP and FRET (see below) are well-suited for identifying compounds that block interactions between sphingolipid receptors and their ligands. See, for example, Parker et al., (2000) Development of high throughput screening assays using fluorescence polarization: nuclear receptor-ligand-binding and kinase/phosphatase assays, J Biomol Screen 5:77-88.

Fluorophores derived from sphingolipids that may be used in FP assays are commercially available. For example, Molecular Probes (Eugene, Oreg.) currently sells sphingomyelin and one ceramide fluorophores. These are, respectively, N-(4,4-difluoro-5,7-dimethyl-4-bora-3a,4a-diaza-s-indacene-3-pentanoyl)sphingosyl phosphocholine (BODIPY® FL C5-sphingomyelin); N-(4,4-difluoro-5,7-dimethyl-4-bora-3a,4a-diaza-s-indacene-3-dodecanoyl)sphingosyl phosphocholine (BODIPY® FL C12-sphingomyelin); and N-(4,4-difluoro-5,7-dimethyl-4-bora-3a,4a-diaza-s-indacene-3-pentanoyl)sphingosine (BODIPY® FL C5-ceramide). U.S. Pat. No. 4,150,949, (Immunoassay for gentamicin), discloses fluorescein-labelled gentamicins, including fluoresceinthiocarbanyl gentamicin. Additional fluorophores may be prepared using methods well known to the skilled artisan.

Exemplary normal-and-polarized fluorescence readers include the POLARION® fluorescence polarization system (Tecan AG, Hombrechtikon, Switzerland). General multiwell plate readers for other assays are available, such as the VERSAMAX® reader and the SPECTRAMAX® multiwell plate spectrophotometer (both from Molecular Devices).

Fluorescence resonance energy transfer (FRET) is another useful assay for detecting interaction and has been described. See, e.g., Heim et al., (1996) Curr. Biol. 6:178-182; Mitra et al., (1996) Gene 173:13-17; and Selvin et al., (1995) Meth. Enzymol. 246:300-345. FRET detects the transfer of energy between two fluorescent substances in close proximity, having known excitation and emission wavelengths. As an example, a protein can be expressed as a fusion protein with green fluorescent protein (GFP). When two fluorescent proteins are in proximity, such as when a protein specifically interacts with a target molecule, the resonance energy can be transferred from one excited molecule to the other. As a result, the emission spectrum of the sample shifts, which can be measured by a fluorometer, such as a fMAX multiwell fluorometer (Molecular Devices, Sunnyvale Calif.).

Scintillation proximity assay (SPA) is a particularly useful assay for detecting an interaction with the target molecule. SPA is widely used in the pharmaceutical industry and has been described (Hanselman et al., (1997) J. Lipid Res. 38:2365-2373; Kahl et al., (1996) Anal. Biochem. 243:282-283; Undenfriend et al., (1987) Anal. Biochem. 161:494-500). See also U.S. Pat. Nos. 4,626,513 and 4,568,649, and European Patent No. 0,154,734. One commercially available system uses FLASHPLATE® scintillant-coated plates (NEN Life Science Products, Boston, Mass.).

The target molecule can be bound to the scintillator plates by a variety of well known means. Scintillant plates are available that are derivatized to bind to fusion proteins such as GST, His6 or Flag fusion proteins. Where the target molecule is a protein complex or a multimer, one protein or subunit can be attached to the plate first, then the other components of the complex added later under binding conditions, resulting in a bound complex.

In a typical SPA assay, the gene products in the expression pool will have been radiolabeled and added to the wells, and allowed to interact with the solid phase, which is the immobilized target molecule and scintillant coating in the wells. The assay can be measured immediately or allowed to reach equilibrium. Either way, when a radiolabel becomes sufficiently close to the scintillant coating, it produces a signal detectable by a device such as a TOPCOUNT NXT® microplate scintillation counter (Packard BioScience Co., Meriden Conn.). If a radiolabeled expression product binds to the target molecule, the radiolabel remains in proximity to the scintillant long enough to produce a detectable signal.

In contrast, the labeled proteins that do not bind to the target molecule, or bind only briefly, will not remain near the scintillant long enough to produce a signal above background. Any time spent near the scintillant caused by random Brownian motion will also not result in a significant amount of signal. Likewise, residual unincorporated radiolabel used during the expression step may be present, but will not generate significant signal because it will be in solution rather than interacting with the target molecule. These non-binding interactions will therefore cause a certain level of background signal that can be mathematically removed. If too many signals are obtained, salt or other modifiers can be added directly to the assay plates until the desired specificity is obtained (Nichols et al., (1998) Anal. Biochem. 257:112-119).

IV. Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases described assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phospho-specific antibody.

V. Organic Synthetic Techniques

A wide array of organic synthetic techniques exist in the art to meet the challenge of constructing potential modulators. Many of these organic synthetic methods are described in detail in standard reference sources utilized by those skilled in the art. One example of suh a reference is March, 1994, *Advanced Organic Chemistry; Reactions, Mechanisms and Structure*, New York, McGraw Hill. Thus, the techniques useful to synthesize a potential modulator of kinase function are readily available to those skilled in the art of organic chemical synthesis.

Regarding the synthetic examples described herein, solvents include polar and non-polar solvents known to those of skill in the art, including polar aprotic and polar protic solvents. Polar solvents include, without limitation, protic solvents such as methanol, ethanol, isopropyl alcohol, t-butanol, n-butanol, acetic acid, formic acid or water, or aprotic solvents such as tetrahydrofuran (THF), acetonitrile, dioxane, methylene chloride, dimethylsulfoxide (DMSO), acetone, N,N-dimethylformamide (DMF), N,N-dimethylacetamide (DMA), ethyl acetate, 1,2-dimethoxyethane, 1,2-dichloroethane, chloroform, 1,2-dichloroethane, or pyridine. Polar solvents include a mixture of water with any of the above, or a mixture of any two or more of the above. Apolar solvents include, without limitation, toluene, benzene, chlorobenzene, xylenes and hexanes.

Regarding the synthetic examples described herein, reducing agent includes, without limitation, a reducing agent such as catalytic reducing agents using hydrogen and transition metal catalysts such as palladium, platinum, rhodium, etc. (e.g. Pt/acetic acid/$H_2$); a mixture of trifluoroacetic acid and triethylsilane, borane tetrahydrofuran complex, diborane, borane dimethylsulfide complex, and a combination of sodium borohydride and boron trifluoride; metals such as reduced iron, zinc powder, magnesium etc.; metal hydrogen complex compounds such as alkali metal borohydrides (for example, potassium borohydride, sodium borohydride, lithium borohydride, zinc borohydride, sodium triacetoxyborohydride, etc.), aluminum lithium hydride, etc.; metal hydrides such as sodium hydride, etc.; organic tin compounds (triphenyltin hydride, etc.); and metal salts such as nickel compounds, zinc compounds, tin compounds (for example tin(II) chloride), and samarium iodide/pivalic acid/hexamethylphorphoric triamide.

Regarding the synthetic examples described herein, oxidizing agent includes, without limitation, an oxidizing agent such as Dess-Martin reagent, TEMPO (2,2,6,6-tetramethylpiperidine-N-oxide), DDQ (2,3-Dichloro-5,6-dicyano-1,4-benzoquinone), PDC (pyridinium dichromate), PCC (pyridinium chlorochromate), Pyridine.SO3, Chromium trioxide, p-nitroperbenzoic acid, magnesium monoperoxyphthalate, sodium periodate, potassium periodate, hydrogen peroxide, urea peroxide, alkali metal bromates, cumene hydroperoxide, tert-butyl peroxide, peracids such as performic acid, peracetic acid, pertrifluoroacetic acid, perbenzoic acid, m-chloroperbenzoic acid, o-carboxyperbenzoic acid and the like; sodium metaperiodate, bichromic acid; bichromates such as sodium bichromate, potassium bichromate; permanganic acid; permanganates such as potassium permanganate, sodium permanganate; and lead salts such as lead tetraacetate.

VI. Alternative Compound Forms or Derivatives (a) Isomers, Prodrugs, and Active Metabolites Compounds contemplated herein are described with reference to both generic formulae and specific compounds. In addition, the invention compounds may exist in a number of different forms or derivatives, all within the scope of the present invention. These include, for example, tautomers, stereoisomers, racemic mixtures, regioisomers, salts, prodrugs (e.g. carboxylic acid esters), solvated forms, different crystal forms or polymorphs, and active metabolites.

(b) Tautomers, Stereoisomers, Regioisomers, and Solvated Forms

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds according to the present invention may exist as stereoisomers, i.e. having the same atomic connectivity of covalently bonded atoms yet differing in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent carbons of a double bond. All such single stereoisomers, racemates and mixtures thereof are intended to be within the scope of the present invention. Unless specified to the contrary, all such stereoisomeric forms are included within the formulae provided herein.

In some embodiments, a chiral compound of the present invention is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form.

For compounds in which synthesis involves addition of a single group at a double bond, particularly a carbon-carbon double bond, the addition may occur at either of the double bond-linked atoms. For such compounds, the present invention includes both such regioisomers.

Additionally, the formulae are intended to cover solvated as well as unsolvated forms of the identified structures. For example, the indicated structures include both hydrated and non-hydrated forms. Other examples of solvates include the structures in combination with a suitable solvent such as isopropanol, ethanol, methanol, DMSO, ethyl acetate, acetic acid, or ethanolamine.

(c) Prodrugs and Metabolites

In addition to the present formulae and compounds described herein, the invention also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more of advantageous handling, administration, and/or metabolic properties. For example, some prodrugs are esters of the active compound; during metabolysis, the ester group is cleaved to yield the active drug. Also, some prodrugs are activated enzymatically to yield the active compound, or a compound which, upon further chemical reaction, yields the active compound.

In this context, a common example of a prodrug is an alkyl ester of a carboxylic acid. Relative to compounds of Formula I, Formula Ia, Formula Ib, Formula Ig, Formula II, Formula IIa, Formula IIb, Formula IIc, Formula IId, Formula IIe, Formula IIf, Formula IIg, Formula IIh, Formula IIi, Formula IIj, Formula IIk, Formula IIm, Formula IIn, Formula IIo, Formula IIp, or Formula III, further examples include, without limitation, an amide or carbamate derivative at the pyrrole nitrogen (i.e. N1) of the azaindole core.

As described in *The Practice of Medicinal Chemistry*, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the follow types:

Oxidative Reactions:

Oxidative reactions are exemplified without limitation to reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive Reactions:

Reductive reactions are exemplified without limitation to reactions such as reduction of carbonyl functionalities, reduction of alcohol functionalities and carbon-carbon double bonds, reduction of nitrogen-containing functional groups, and other reduction reactions.

Reactions without Change in the Oxidation State:

Reactions without change in the state of oxidation are exemplified without limitation to reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 20040077595, application Ser. No. 10/656,838, incorporated herein by reference.) Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g. stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, supra.

Prodrugs may proceed from prodrug form to active form in a single step or may have one or more intermediate forms which may themselves have activity or may be inactive.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic process in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug.

Prodrugs and active metabolites may be identified using routine techniques known in the art. See, e.g., Bertolini et al., 1997, *J. Med. Chem.*, 40:2011-2016; Shan et al., 1997, *J Pharm Sci* 86(7):756-757; Bagshawe, 1995, *Drug Dev. Res.*, 34:220-230; Wermuth, supra.

(d) Pharmaceutically Acceptable Salts

Compounds can be formulated as or be in the form of pharmaceutically acceptable salts. Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug.

Pharmaceutically acceptable salts include acid addition salts such as those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethanolamine, t-butylamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see *Remington's Pharmaceutical Sciences*, 19$^{th}$ ed., Mack Publishing Co., Easton, Pa., Vol. 2, p. 1457, 1995. Such salts can be prepared using the appropriate corresponding bases.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent.

Thus, for example, if the particular compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Similarly, if the particular compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as L-glycine, L-lysine, and L-arginine, ammonia, primary, secondary, and tertiary amines, and cyclic amines, such as hydroxyethylpyrrolidine, piperidine, morpholine or piperazine, and inorganic salts derived from sodium, calcium, potassium, magnesium, manganese, iron, copper, zinc, aluminum and lithium.

The pharmaceutically acceptable salt of the different compounds may be present as a complex. Examples of complexes include 8-chlorotheophylline complex (analogous to, e.g., dimenhydrinate: diphenhydramine 8-chlorotheophylline (1:1) complex; Dramamine) and various cyclodextrin inclusion complexes.

Unless specified to the contrary, specification of a compound herein includes pharmaceutically acceptable salts of such compound.

(e) Polymorphic Forms

In the case of agents that are solids, it is understood by those skilled in the art that the compounds and salts may exist in different crystal or polymorphic forms, all of which are intended to be within the scope of the present invention and specified formulae.

VII. Administration

The methods and compounds will typically be used in therapy for human subjects. However, they may also be used to treat similar or identical indications in other animal subjects. In this context, the terms "subject," "animal subject," and the like refer to human and non-human vertebrates, e.g. mammals, such as non-human primates, sports and commercial animals, e.g., equines, bovines, porcines, ovines, rodents, and pets, e.g., canines and felines.

Suitable dosage forms, in part, depend upon the use or the route of administration, for example, oral, transdermal, transmucosal, inhalant, or by injection (parenteral). Such dosage forms should allow the compound to reach target cells. Other factors are well known in the art, and include considerations such as toxicity and dosage forms that retard the compound or composition from exerting its effects. Techniques and formulations generally may be found in The Science and Practice of Pharmacy, 21$^{st}$ edition, Lippincott, Williams and Wilkins, Philadelphia, Pa., 2005 (hereby incorporated by reference herein).

Compounds of the present invention (i.e. Formula I, Formula Ia, Formula Ib, Formula Ig, Formula II, Formula IIa, Formula IIb, Formula IIc, Formula IId, Formula IIe, Formula IIf, Formula IIg, Formula IIh, Formula IIi, Formula IIj, Formula IIk, Formula IIm, Formula IIn, Formula IIo, Formula IIp, or Formula III, and all sub-embodiments disclosed herein) can be formulated as pharmaceutically acceptable salts.

Carriers or excipients can be used to produce compositions. The carriers or excipients can be chosen to facilitate administration of the compound. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

The compounds can be administered by different routes including intravenous, intraperitoneal, subcutaneous, intramuscular, oral, transmucosal, rectal, transdermal, or inhalant. In some embodiments, oral administration is preferred. For oral administration, for example, the compounds can be formulated into conventional oral dosage forms such as capsules, tablets, and liquid preparations such as syrups, elixirs, and concentrated drops.

For inhalants, compounds of the invention may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds of the invention may also be used in combination with other inhaled therapies, for example corticosteroids such as fluticasone propionate, beclomethasone dipropionate, triamcinolone acetonide, budesonide, and mometasone furoate; beta agonists such as albuterol, salmeterol, and formoterol; anticholinergic agents such as ipratropium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

Pharmaceutical preparations for oral use can be obtained, for example, by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid, or a salt thereof such as sodium alginate.

Dragee cores are provided with suitable coatings. For this purpose, concentrated sugar solutions may be used, which may optionally contain, for example, gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Alternatively, injection (parenteral administration) may be used, e.g., intramuscular, intravenous, intraperitoneal, and/or subcutaneous. For injection, the compounds of the invention are formulated in sterile liquid solutions, preferably in physiologically compatible buffers or solutions, such as saline solution, Hank's solution, or Ringer's solution. In addition, the compounds may be formulated in solid form and redissolved or suspended immediately prior to use. Lyophilized forms can also be produced.

Administration can also be by transmucosal, topical, transdermal, or inhalant means. For transmucosal, topical or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal).

The topical compositions of this invention are formulated preferably as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount solvent (e.g. an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will, of course, be continuous rather than intermittent throughout the dosage regimen.

The amounts of various compounds to be administered can be determined by standard procedures taking into account factors such as the compound $IC_{50}$, the biological half-life of the compound, the age, size, and weight of the subject, and the indication being treated. The importance of these and other factors are well known to those of ordinary skill in the art. Generally, a dose will be between about 0.01 and 50 mg/kg, preferably 0.1 and 20 mg/kg of the subject being treated. Multiple doses may be used.

The compounds of the invention may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the invention or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound of the present invention, or at the same time as a compound of the invention. Use in combination also includes use with a therapy or medical procedure that is administered once or infrequently, such as surgery, along with a compound of the invention administered within a short time or longer time before or after the other therapy or procedure. In some embodiments, the present invention provides for delivery of compounds of the invention and one or more other drug therapeutics delivered by a different route of administration or by the same route of administration. The use in combination for any route of administration includes delivery of compounds of the invention and one or more other drug therapeutics delivered by the same route of administration together in any formulation, including formulations where the two compounds are chemically linked in such a way that they maintain their therapeutic activity when administered. In one aspect, the other drug therapy may be co-administered with one or more compounds of the invention. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of compounds of the invention and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

VIII. Manipulation of c-Kit and c-Fms

As the full-length coding sequence and amino acid sequence of c-kit and c-fms from various mammals including human is known, cloning, construction of recombinant c-kit and c-fms, production and purification of recombinant protein, introduction of c-kit or c-fms into other organisms, and other molecular biological manipulations of c-kit and c-fms are readily performed.

Techniques for the manipulation of nucleic acids, such as, e.g., subcloning, labeling probes (e.g. random-primer labeling using Klenow polymerase, nick translation, amplification), sequencing, hybridization and the like are well disclosed in the scientific and patent literature, see, e.g., Sambrook, ed., Molecular Cloning: a Laboratory Manual (2nd ed.), Vols. 1-3, Cold Spring Harbor Laboratory, (1989); Current Protocols in Molecular Biology, Ausubel, ed. John Wiley & Sons, Inc., New York (1997); Laboratory Techniques in Biochemistry and Molecular Biology: Hybridization With Nucleic Acid Probes, Part I. Theory and Nucleic Acid Preparation, Tijssen, ed. Elsevier, N.Y. (1993).

Nucleic acid sequences can be amplified as necessary for further use using amplification methods, such as PCR, isothermal methods, rolling circle methods, etc., are well known to the skilled artisan. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1; 29(11):E54-E54; Hafner et al., Biotechniques 2001 April; 30(4):852-6, 858, 860 passim; Zhong et al., Biotechniques 2001 April; 30(4):852-6, 858, 860 passim.

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immuno-electrophoresis, radioimmunoassays (RIAs), enzyme-linked immunosorbent assays (ELISAs), immuno-fluorescent assays, Southern analysis, Northern analysis, dot-blot analysis, gel electrophoresis (e.g. SDS-PAGE), nucleic acid or target or signal amplification methods, radiolabeling, scintillation counting, and affinity chromatography.

Obtaining and manipulating nucleic acids used to practice the methods of the invention can be performed by cloning from genomic samples, and, if desired, screening and re-cloning inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

The nucleic acids used to practice the methods of the invention can be operatively linked to a promoter. A promoter can be one motif or an array of nucleic acid control sequences which direct transcription of a nucleic acid. A promoter can include necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The nucleic acids used to practice the methods of the invention can also be provided in expression vectors and cloning vehicles, e.g., sequences encoding the polypeptides used to practice the methods of the invention. Expression vectors and cloning vehicles used to practice the methods of the invention can comprise viral particles, baculovirus, phage, plasmids, phagemids, cosmids, fosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors used to practice the methods of the invention can include chromosomal, non-chromosomal and synthetic DNA sequences. Large numbers of suitable vectors are known to those of skill in the art, and are commercially available.

The nucleic acids used to practice the methods of the invention can be cloned, if desired, into any of a variety of vectors using routine molecular biological methods; methods for cloning in vitro amplified nucleic acids are disclosed, e.g., U.S. Pat. No. 5,426,039. To facilitate cloning of amplified sequences, restriction enzyme sites can be "built into" a PCR primer pair. Vectors may be introduced into a genome or into the cytoplasm or a nucleus of a cell and expressed by a variety of conventional techniques, well described in the scientific and patent literature. See, e.g., Roberts (1987) Nature 328: 731; Schneider (1995) Protein Expr. Purif. 6435:10; Sambrook, Tijssen or Ausubel. The vectors can be isolated from natural sources, obtained from such sources as ATCC or GenBank libraries, or prepared by synthetic or recombinant methods. For example, the nucleic acids used to practice the methods of the invention can be expressed in expression cassettes, vectors or viruses which are stably or transiently expressed in cells (e.g. episomal expression systems). Selection markers can be incorporated into expression cassettes and vectors to confer a selectable phenotype on transformed cells and sequences. For example, selection markers can code for episomal maintenance and replication such that integration into the host genome is not required.

In one aspect, the nucleic acids used to practice the methods of the invention are administered in vivo for in situ expression of the peptides or polypeptides used to practice the methods of the invention. The nucleic acids can be administered as "naked DNA" (see, e.g., U.S. Pat. No. 5,580,859) or in the form of an expression vector, e.g., a recombinant virus. The nucleic acids can be administered by any route, including peri- or intra-tumorally, as described below. Vectors administered in vivo can be derived from viral genomes, including recombinantly modified enveloped or non-enveloped DNA and RNA viruses, preferably selected from baculoviridiae, parvoviridiae, picornoviridiae, herpesveridiae, poxyiridiae, adenoviridiae, or picornnaviridiae. Chimeric vectors may also be employed which exploit advantageous merits of each of the parent vector properties (See e.g., Feng (1997) Nature Biotechnology 15:866-870). Such viral genomes may be modified by recombinant DNA techniques to include the nucleic acids used to practice the methods of the invention; and may be further engineered to be replication deficient, conditionally replicating or replication competent. In alternative aspects, vectors are derived from the adenoviral (e.g. replication incompetent vectors derived from the human adenovirus genome, see, e.g., U.S. Pat. Nos. 6,096,718; 6,110,458; 6,113,913; 5,631,236); adeno-associated viral and retroviral genomes. Retroviral vectors can include those based upon murine leukemia virus (MuLV), gibbon ape leukemia virus (GaLV), Simian Immuno deficiency virus (SIV), human immuno deficiency virus (HIV), and combinations thereof; see, e.g., U.S. Pat. Nos. 6,117,681; 6,107,478; 5,658, 775; 5,449,614; Buchscher (1992) J. Virol. 66:2731-2739; Johann (1992) *J. Virol.* 66:1635-1640). Adeno-associated virus (AAV)-based vectors can be used to transduce cells with target nucleic acids, e.g., in the in vitro production of nucleic acids and peptides, and in in vivo and ex vivo gene therapy procedures; see, e.g., U.S. Pat. Nos. 6,110,456; 5,474,935; Okada (1996) *Gene Ther.* 3:957-964.

The present invention also relates to use of fusion proteins, and nucleic acids encoding them. A polypeptide used to practice the methods of the invention can be fused to a heterologous peptide or polypeptide, such as N-terminal identification peptides which impart desired characteristics, such as increased stability or simplified purification. Peptides and polypeptides used to practice the methods of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. In one aspect, a nucleic acid encoding a polypeptide used to practice the methods of the invention is assembled in appropriate phase with a leader sequence capable of directing secretion of the translated polypeptide or fragment thereof. Technology pertaining to vectors encoding fusion proteins and application of fusion proteins are well disclosed in the scientific and patent literature, see e.g., Kroll (1993) DNA Cell. Biol. 12:441-53.

The nucleic acids and polypeptides used to practice the methods of the invention can be bound to a solid support, e.g., for use in screening and diagnostic methods. Solid supports can include, e.g., membranes (e.g. nitrocellulose or nylon), a microtiter dish (e.g. PVC, polypropylene, or polystyrene), a test tube (glass or plastic), a dip stick (e.g. glass, PVC, polypropylene, polystyrene, latex and the like), a microfuge tube, or a glass, silica, plastic, metallic or polymer bead or other substrate such as paper. One solid support uses a metal (e.g. cobalt or nickel)-comprising column which binds with specificity to a histidine tag engineered onto a peptide.

Adhesion of molecules to a solid support can be direct (i.e., the molecule contacts the solid support) or indirect (a "linker" is bound to the support and the molecule of interest binds to this linker). Molecules can be immobilized either covalently (e.g. utilizing single reactive thiol groups of cysteine residues (see, e.g., Colloid (1993) Bioconjugate Chem. 4:528-536) or non-covalently but specifically (e.g. via immobilized antibodies (see, e.g., Schuhmann (1991) Adv. Mater. 3:388-391; Lu (1995) Anal. Chem. 67:83-87; the biotin/strepavidin system (see, e.g., Iwane (1997) Biophys. Biochem. Res. Comm. 230:76-80); metal chelating, e.g., Langmuir-Blodgett films (see, e.g., Ng (1995) Langmuir 11:4048-55); metal-chelating self-assembled monolayers (see, e.g., Sigal (1996) Anal. Chem. 68:490-497) for binding of polyhistidine fusions.

Indirect binding can be achieved using a variety of linkers which are commercially available. The reactive ends can be any of a variety of functionalities including, but not limited to: amino reacting ends such as N-hydroxysuccinimide (NHS) active esters, imidoesters, aldehydes, epoxides, sulfonyl halides, isocyanate, isothiocyanate, and nitroaryl halides; and thiol reacting ends such as pyridyl disulfides, maleimides, thiophthalimides, and active halogens. The heterobifunctional crosslinking reagents have two different reactive ends, e.g., an amino-reactive end and a thiol-reactive end, while homobifunctional reagents have two similar reactive ends, e.g., bismaleimidohexane (BMH) which permits the crosslinking of sulfhydryl-containing compounds. The spacer can be of varying length and be aliphatic or aromatic. Examples of commercially available homobifunctional cross-linking reagents include, but are not limited to, the imidoesters such as dimethyl adipimidate dihydrochloride (DMA); dimethyl pimelimidate dihydrochloride (DMP); and dimethyl suberimidate dihydrochloride (DMS). Heterobifunctional reagents include commercially available active halogen-NHS active esters coupling agents such as N-succinimidyl bromoacetate and N-succinimidyl (4-iodoacetyl)aminobenzoate (SIAB) and the sulfosuccinimidyl derivatives such as sulfosuccinimidyl(4-iodoacetyl)aminobenzoate (sulfo-SIAB) (Pierce). Another group of coupling agents is the heterobifunctional and thiol cleavable agents such as N-succinimidyl 3-(2-pyridyldithio)propionate (SPDP) (Pierce Chemicals, Rockford, Ill.).

Antibodies can also be used for binding polypeptides and peptides used to practice the methods of the invention to a solid support. This can be done directly by binding peptide-specific antibodies to the column or it can be done by creating fusion protein chimeras comprising motif-containing peptides linked to, e.g., a known epitope (e.g. a tag (e.g. FLAG, myc) or an appropriate immunoglobulin constant domain sequence (an "immunoadhesin," see, e.g., Capon (1989) Nature 377:525-531 (1989).

Nucleic acids or polypeptides used to practice the methods of the invention can be immobilized to or applied to an array. Arrays can be used to screen for or monitor libraries of compositions (e.g. small molecules, antibodies, nucleic acids, etc.) for their ability to bind to or modulate the activity of a nucleic acid or a polypeptide used to practice the methods of the invention. For example, in one aspect of the invention, a monitored parameter is transcript expression of a gene comprising a nucleic acid used to practice the methods of the invention. One or more, or all the transcripts of a cell can be measured by hybridization of a sample comprising transcripts of the cell, or nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. Polypeptide arrays" can also be used to simultaneously quantify a plurality of proteins.

The terms "array" or "microarray" or "biochip" or "chip" as used herein is a plurality of target elements, each target element comprising a defined amount of one or more polypeptides (including antibodies) or nucleic acids immobilized onto a defined area of a substrate surface. In practicing the methods of the invention, any known array and/or method of making and using arrays can be incorporated in whole or in part, or variations thereof, as disclosed, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent application Nos. 20010018642; 20010019827; 20010016322; 20010014449; 20010014448; 20010012537; 20010008765.

Host Cells and Transformed Cells

The invention also provides a transformed cell comprising a nucleic acid sequence used to practice the methods of the invention, e.g., a sequence encoding a polypeptide used to practice the methods of the invention, or a vector used to practice the methods of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Salmonella typhimurium* and various species within the genera *Pseudomonas, Streptomyces*, and *Staphylococcus*. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

Vectors may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation.

Engineered host cells can be cultured in conventional nutrient media modified as appropriate for activating promoters, selecting transformants or amplifying the genes used to practice the methods of the invention. Following transformation of a suitable host strain and growth of the host strain to an appropriate cell density, the selected promoter may be induced by appropriate means (e.g. temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides used to practice the methods of the invention may or may not also include an initial methionine amino acid residue.

Cell-free translation systems can also be employed to produce a polypeptide used to practice the methods of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

For transient expression in mammalian cells, cDNA encoding a polypeptide of interest may be incorporated into a mammalian expression vector, e.g. pcDNA1, which is available commercially from Invitrogen Corporation (San Diego, Calif., U.S.A.; catalogue number V490-20). This is a multi-functional 4.2 kb plasmid vector designed for cDNA expression in eukaryotic systems, and cDNA analysis in prokaryotes, incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and anti-sense RNA transcripts and a Col El-like high copy plasmid origin. A polylinker is located appropriately downstream of the CMV promoter (and 3' of the T7 promoter).

The cDNA insert may be first released from the above phagemid incorporated at appropriate restriction sites in the pcDNAI polylinker. Sequencing across the junctions may be performed to confirm proper insert orientation in pcDNAI. The resulting plasmid may then be introduced for transient expression into a selected mammalian cell host, for example, the monkey-derived, fibroblast like cells of the COS-1 lineage (available from the American Type Culture Collection, Rockville, Md. as ATCC CRL 1650).

For transient expression of the protein-encoding DNA, for example, COS-1 cells may be transfected with approximately 8 µg DNA per $10^6$ COS cells, by DEAE-mediated DNA transfection and treated with chloroquine according to the procedures described by Sambrook et al, Molecular Cloning: A Laboratory Manual, 1989, Cold Spring Harbor Laboratory Press, Cold Spring Harbor N.Y., pp. 16.30-16.37. An exemplary method is as follows. Briefly, COS-1 cells are plated at a density of $5 \times 10^6$ cells/dish and then grown for 24 hours in FBS-supplemented DMEM/F12 medium. Medium is then removed and cells are washed in PBS and then in medium. A transfection solution containing DEAE dextran (0.4 mg/ml), 100 µM chloroquine, 10% NuSerum, DNA (0.4 mg/ml) in DMEM/F12 medium is then applied on the cells 10 ml volume. After incubation for 3 hours at 37° C., cells are washed in PBS and medium as just described and then shocked for 1 minute with 10% DMSO in DMEM/F12 medium. Cells are allowed to grow for 2-3 days in 10% FBS-supplemented medium, and at the end of incubation dishes are placed on ice, washed with ice cold PBS and then removed by scraping. Cells are then harvested by centrifugation at 1000 rpm for 10 minutes and the cellular pellet is frozen in liquid nitrogen, for subsequent use in protein expression. Northern blot analysis of a thawed aliquot of frozen cells may be used to confirm expression of receptor-encoding cDNA in cells under storage.

In a like manner, stably transfected cell lines can also prepared, for example, using two different cell types as host: CHO K1 and CHO Pro5. To construct these cell lines, cDNA coding for the relevant protein may be incorporated into the mammalian expression vector pRC/CMV (Invitrogen), which enables stable expression. Insertion at this site places the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

An exemplary protocol to introduce plasmids constructed as described above is as follows. The host CHO cells are first seeded at a density of $5 \times 10^5$ in 10% FBS-supplemented MEM medium. After growth for 24 hours, fresh medium is added to the plates and three hours later, the cells are transfected using the calcium phosphate-DNA co-precipitation procedure (Sambrook et al, supra). Briefly, 3 µg of DNA is mixed and incubated with buffered calcium solution for 10 minutes at room temperature. An equal volume of buffered phosphate solution is added and the suspension is incubated for 15 minutes at room temperature. Next, the incubated suspension is applied to the cells for 4 hours, removed and cells were shocked with medium containing 15% glycerol. Three minutes later, cells are washed with medium and incubated for 24 hours at normal growth conditions. Cells resistant to neomycin are selected in 10% FBS-supplemented alpha-MEM medium containing G418 (1 mg/ml). Individual colonies of G418-resistant cells are isolated about 2-3 weeks later, clonally selected and then propagated for assay purposes.

EXAMPLES

A number of examples illustrative of the present invention are described below. In most cases, alternative techniques could also be used. The examples are intended to be illustrative and are not limiting or restrictive to the scope of the invention. Unless specifically noted to the contrary, in cases where a compound number is not preceded by a "P-" (e.g., "P-0001") in the Examples section, compound naming and/or enumeration is not related to naming and/or enumeration employed in other sections of this application. Similarly, structure and substituent naming and enumeration within the Examples are independent of structure and substituent naming and enumeration in above sections of this application unless clearly indicated otherwise.

In the following Examples, it is understood that the solvents and reagents used or suggested are not limiting, and can be substituted appropriately with solvents and reagents known to those of skill in the art. Reaction products may be isolated by means known in the art, such as extraction with a suitable solvent, precipitation from a suitable solvent, chromatography using a suitable solvent system, including silica gel column chromatography, HPLC, preparative TLC, and the like. Exemplary methods for synthesis of compounds of the present invention may be found in US Patent Application Publication number US 20070032519, the disclosure of which is hereby incorporated by reference. The 1H-pyrrolo[2,3-b]pyridine core of compounds described in the examples may also be referred to as 7-azaindole in the examples.

Example 1

Synthesis of Compound of Formula I, where $X_1$, $X_2$, $Y_1$ and $Y_2$ are CH and $L^1$ is —$CH_2$—

Compounds of Formula I, as described in paragraph [0011], where $X_1$, $X_2$, $Y_1$ and $Y_2$ are CH and $L^1$ is —$CH_2$— or —CO— may be synthesized from 7-azaindole according to one of the following Schemes 1-3, where $R^{24}$ is consistent with $Ar_1$, which can be further substituted to provide compounds where $R^{24}$ is $Ar_1$-$L^2$-$R^1$ as described for Formula I.

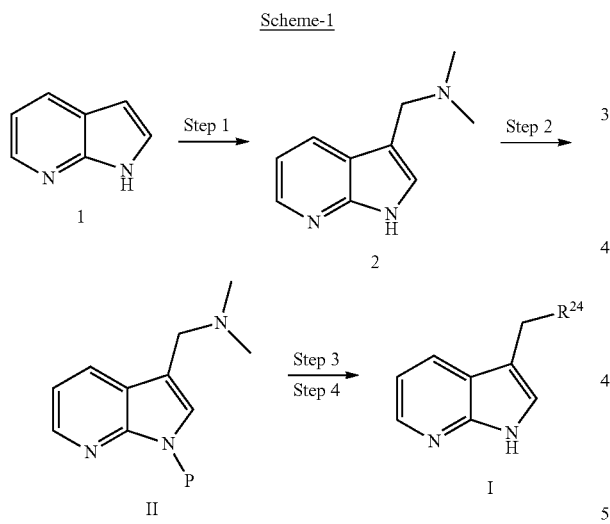

Step-1—Synthesis of Compound 2

Compound 2 is synthesized from commercially available 7-azaindole following the literature procedure (Robinson, *J. Am. Chem. Soc.*, 1955, 77, p. 457).

Step-2—Synthesis of Compound of Formula II

Compound of Formula II, where P is a protecting group, is synthesized by deprotonation using base (e.g. BuLi, NaH) in aprotic solvent like tetrahydrofuran or ether and reacting the anion with a silyl chloride (e.g. TIPS) or an anhydride (e.g. Boc anhydride). The compound is isolated by following standard procedure (quenching with ice-cold brine, work up, and purification by flash silica gel chromatography).

Steps-3 and 4—Synthesis of Compound of Formula I

Compounds of Formula I, wherein $R^{24}$ is $Ar_1$ as defined in Formula I, is synthesized through the reaction of compounds of Formula II with isopropyl chloroformate (or ethyl chloroformate) at room temperature in toluene to give a 3-chloromethyl intermediate. This intermediate is cooled to 78° C. and immediately reacted with an organocopper reagent, which is generated from the reaction between a Grignard reagent (or organolithium reagent) and a solution of copper cyanide and LiCl. The mixture is stirred at 78° C. for one hour and allowed to warm to room temperature. The reaction is quenched with a solution of 4:1 ammonium chloride:ammonium hydroxide. The reaction is worked up in the usual manner and purified by flash silica gel chromatography to give the nitrogen-protected compound. The final compound can be realized through the deprotection of the protecting group (Boc, TIPS) using standard conditions (TFA or $NH_4F$) at room temperature.

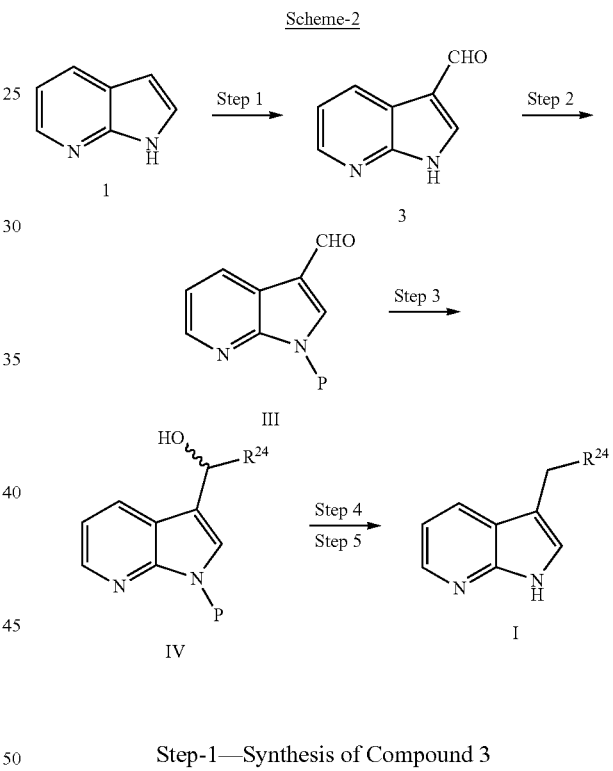

Step-1—Synthesis of Compound 3

Compound 3 is synthesized by reacting commercially available 7-azaindole, compound 1, with hexamethyltetramine and acetic acid in water with heating to reflux for two hours. After cooling, the desired compound is precipitated and collected by filtration.

Step-2—Synthesis of Compound of Formula III

Compound of Formula III, where P is a protecting group, is synthesized by reacting compound 3 with an appropriate reagent to introduce a protecting group (e.g. tert-butyloxycarbonyl di anhydride) and a base (e.g. sodium hydride) in an appropriate solvent (e.g. tetrahydrofuran) typically at room temperature for 12-18 hours. The compound can be isolated by conventional means (e.g. extraction).

Step-3—Synthesis of Compound of Formula IV

Compound of Formula IV, wherein $R^{24}$ is $Ar_1$, is synthesized by reacting compound of Formula III in an appropriate solvent (e.g. 1,2-dimethoxyethane) with a Grignard reagent of the formula $R^{24}MgCl$ or $R^{24}MgBr$ (e.g. pyridinyl magnesium bromide) or an equivalent nucleophile in an appropriate solvent (e.g. tetrahydrofuran) under inert atmosphere cooled typically to 10° C. The reaction is typically allowed to warm to room temperature and stirred for 12-18 hours. The desired compound is purified by reverse phase high pressure liquid chromatography.

Steps-4 and 5—Synthesis of an Intermediate of Compound of Formula I

An intermediate of compound of Formula I is synthesized by reacting compound of Formula IV with a reducing agent (e.g. sodium borohydride) in a polar solvent (e.g. ethanol) typically with heating to 80° C. for 1-4 hours. The reaction is quenched with the addition of methanol and concentrated and purified by reverse phase high performance liquid chromatography. Compound of Formula I where $R^{24}$ is $Ar_1$ is synthesized by reacting this intermediate with an appropriate reagent to remove the protecting group, P, (e.g. hydrochloric acid) in an apolar solvent (e.g. dioxane). The final compound is isolated by standard procedures (e.g. reverse phase preparative high pressure liquid chromatography).

Scheme-3

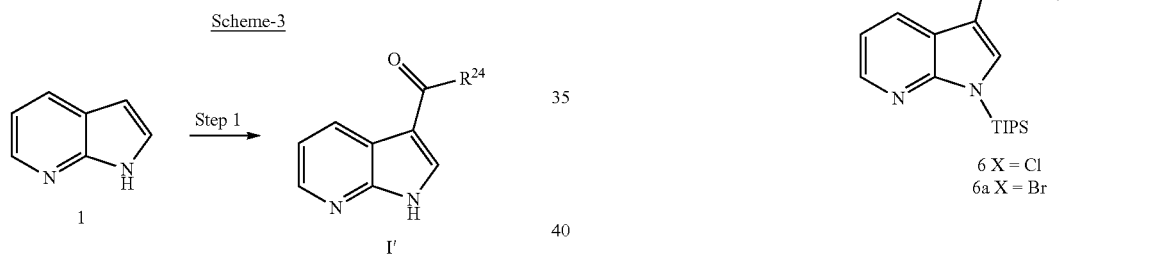

Step-1—Synthesis of Compound of Formula I'

Compound of Formula I' where $R^{24}$ is $Ar_1$, is synthesized by reacting compound 1 with an activating agent (e.g. methyl magnesium bromide and zinc dichloride or anhydrous aluminum chloride) and a heteroaryl acid chloride (e.g. nicotinic acid chloride) in a non-reactive solvent (e.g. dichloromethane), under inert atmosphere (e.g. argon), at room temperature or with heating up to reflux for 18-24 hours. The compound is isolated by standard procedures (e.g. extraction and silica-gel chromatography).

Example 2

Synthesis of intermediate 3-(6-Chloro-pyridin-3-ylmethyl)-1-triisopropylsilanyl-1H-pyrrolo[2,3-b]pyridine (6) and (3-(6-Bromo-pyridin-3-ylmethyl)-1-triisopropylsilanyl-1H-pyrrolo[2,3-b]pyridine) (6a)

Compound 6, an intermediate to compounds of Formula I, as described in paragraph [0011], where $X_1, X_2, Y_1$ and $Y_2$ are CH, n is 1, P, Q and T are CH and $L^1$ is —$CH_2$—, may be synthesized in four steps from 7-azaindole according to the following Scheme 4.

Scheme-4

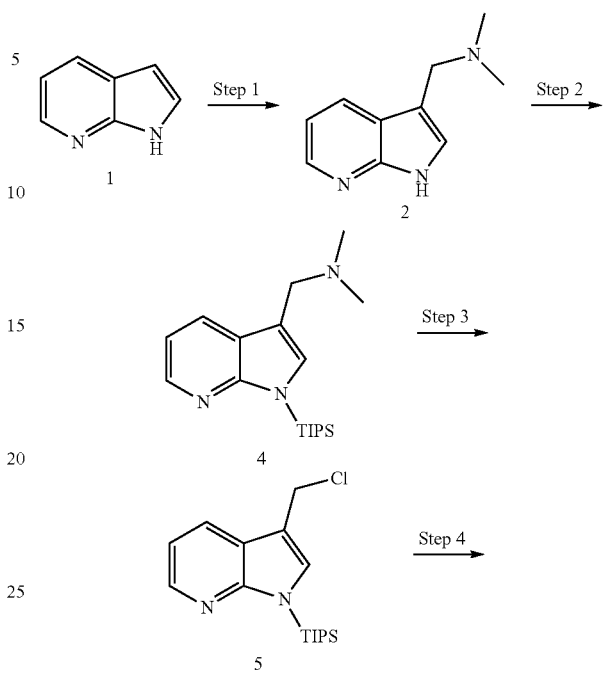

Step-1—Synthesis of dimethyl-(1H-pyrrolo[2,3-h]pyridin-3-ylmethyl)-amine (2)

Into a 3-neck round bottom flask was added Isopropyl alcohol (320.0 mL) followed by the addition of 1H-pyrrolo[2,3-b]pyridine 1 (7.10 g, 60.1 mmol), dimethylamine hydrochloride (5.4 g, 0.066 mol), and formaldehyde (2.0 g, 0.066 mol). The reaction mixture was stirred at room temperature for 12 hours, and then refluxed for 30 minutes. The suspension solution was evaporated to dryness in vacuo. To the residue was added water (60.0 mL, 3.33 mol) and concentrated hydrochloric acid (6.0 mL, 0.20 mol). The water layer was extracted with ether and the aqueous layer was neutralized with potassium carbonate. The aqueous layer was extracted with dichloromethane, dried over sodium sulfate and concentrated to give the compound, which was then further washed with ether and dried to afford compound 2 (7.1 g, yield=67.4%), as a white solid.

Step-2—Synthesis of dimethyl-(1-triisopropylsilanyl-1H-pyrrolo[2,3-h]pyridin-3-ylmethyl)-amine (4)

Into a round bottom flask 7-Azagramine 2 (5.38 g, 30.7 mmol), N,N-dimethylformamide (25.0 mL), and sodium hydride (1.35 g, 33.8 mol) were combined. Into the reaction was added triisopropylsilyl chloride (6.8 mL, 0.032 mol). The reaction was stirred at 20° C. for 12 hours. The reaction mixture was poured into water and extracted with ethyl acetate. The organic layer was washed with brine, dried over sodium sulfate, concentrated and purified with biotage to give compound 4 (6.0 g, yield=58.8%) as a colorless oil.

Step-3—Synthesis of 3-chloromethyl-1-triisopropyl-silanyl-1H-pyrrolo[2,3-b]pyridine (5)

Into a round bottom flask was added compound 4 (500.0 mg, 1.51 mmol) and toluene (5.0 mL, 0.047 mol) under an atmosphere of nitrogen. Into the reaction mixture 1.0 M isopropyl chloroformate in toluene (1.6 mL) was added slowly at room temperature. The reaction mixture was stirred for another 2 hours to give desired compound 5 used for next step without purification.

Step-4—Synthesis of 3-(6-Chloro-pyridin-3-ylmethyl)-1-triisopropylsilanyl-1H-pyrrolo[2,3-b]pyridine (6)

Into a round bottom flask was added 5-iodo-2-chloro-pyridine (315.0 mg, 1.32 mmol) and tetrahydrofuran (12.0 mL, 0.15 mol) at −40° C. under an atmosphere of nitrogen. Into the reaction 2.0 M of isopropylmagnesium chloride in tetrahydrofuran (0.72 mL, 1.44 mmol) was added. The reaction mixture was stirred for 40 minutes at 40° C. TLC (hexane/ethyl acetate 2:1) indicated no starting material. Into the reaction mixture 0.6 M of CuCN.2LiCl in tetrahydrofuran (2.4 mL, 1.44 mmol) was added. The reaction mixture was allowed to come to room temperature for 5 minutes and trimethyl phosphite (0.29 mL, 2.4 mmol) was added. After 10 minutes, this solution was added into a round bottom flask containing compound 5 (315.0 mg) and toluene (8.0 mL). The reaction was stirred at 20° C. for 40 hours. The reaction mixture was poured into water and the compound extracted with ethyl acetate. The organic layer was washed with brine, dried over sodium sulfate, concentrated and purified with biotage (dichloromethane/methanol 1:10) to give compound 6 (230 mg, yield=59.0%) as a white solid. Compound 6a (3-(6-Bromo-pyridin-3-ylmethyl)-1-triisopropylsilanyl-1H-pyrrolo[2,3-b]pyridine) (MS (ESI) [M+H$^+$]$^+$=288.1, 290.1) was prepared substituting 5-iodo-2-chloro-pyridine with 5-iodo-2-bromo-pyridine in Step 4, with reaction conditions and work up procedure the same as that for the synthesis of compound 6.

Example 3

Synthesis of intermediate (6-Chloro-pyridin-3-yl)-(1H-pyrrolo[2,3-b]pyridin-3-yl)-methanone (7)

Compound 7, an intermediate to compounds of Formula I, as described in paragraph [0011], where $X_1$, $X_2$, $Y_1$ and $Y_2$ are CH, n is 1, P, Q and T are CH and $L^1$ is —CO—, may be synthesized in one step from 7-azaindole according to the following Scheme 5.

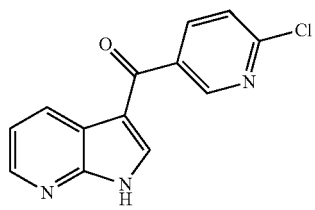

Into a round bottom flask was added aluminum trichloride (16.0 g, 0.12 mol) and dichloromethane (100.0 mL) under an atmosphere of nitrogen. Into the reaction mixture 1H-Pyrrolo[2,3-b]pyridine 1 (3.2 g, 0.027 mol) in dichloromethane (20.0 mL) was added. The reaction was stirred at room temperature for 70.0 minutes and 6-Chloropyridine-3-carbonyl chloride 8 (5.4 g, 0.031 mol) in dichloromethane (10.0 mL) was added. The reaction mixture was stirred at room temperature for 3 hours. Methanol (10 mL) was added to the reaction mixture and the solvent was evaporated in vacuo. The residue was poured into water and the precipitated compound was removed by filtration. The aqueous layer was extracted with ethyl acetate and the organic layer was dried and concentrated and combined with the solid isolated by filtration to give 7 (6.2 g, yield=88.6%) as a white solid. MS (ESI) [M+H$^+$]$^+$=258.

Example 4

Synthesis of benzyl-[5-(1H-pyrrolo[2,3-b]pyridin-3-ylmethyl)-pyridin-2-yl]-amine (P-0001)

Benzyl-[5-(1H-pyrrolo[2, 3-1)]pyridin-3-ylmethyl)-pyridin-2-yl]-amine (P-0001) was prepared in two steps from 3-(6-Chloro-pyridin-3-ylmethyl)-1-triisopropylsilanyl-1H-pyrrolo[2,3-b]pyridine (6) according to Scheme 6.

Scheme-6

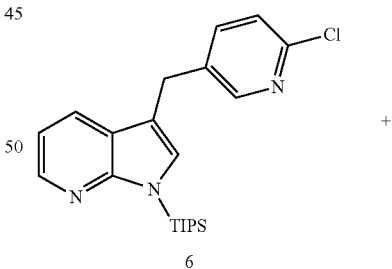

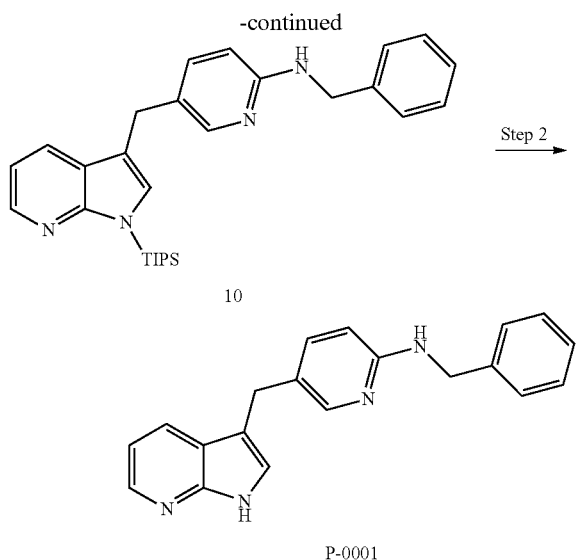

10

P-0001

Step-1—Synthesis of benzyl-[5-(1-triisopropylsilanyl-1H-pyrrolo[2,3-b]pyridin-3-ylmethyl)-pyridin-2-yl]-amine (10)

Into a round bottom flask was added 3-(6-Chloro-pyridin-3-ylmethyl)-1-triisopropylsilanyl-1H-pyrrolo[2,3-b]pyridine 6 (160.0 mg, 0.40 mmol, prepared as described in Example 2), benzylamine (32, 0.1 mL, 0.90 mmol), palladium acetate (17.0 mg, 0.076 mmol), toluene (10.0 mL), potassium tert-butoxide (80.0 mg, 0.71 mmol) and 2-(di-t-butylphosphino)biphenyl (31.4 mg, 0.11 mmol) under an atmosphere of nitrogen. The reaction was stirred under reflux for 3 hours. TLC and MS indicated no starting material. The reaction mixture was poured into water and extracted with ethyl acetate. The organic layer was washed with brine, dried over sodium sulfate, concentrated and purified with biotage (dichloromethane/methanol 1:20) to give compound 10 (110 mg, yield=58.5%) as a white solid. MS (ESI) [M+H$^+$]$^+$=471.

Step-2—Synthesis of benzyl-[5-(1H-pyrrolo[2,3-b]pyridin-3-ylmethyl)-pyridin-2-yl]-amine (P-0001)

Into a round bottom flask was added benzyl-[5-(1-triisopropylsilanyl-1H-pyrrolo[2,3-b]pyridin-3-ylmethyl)-pyridin-2-yl]-amine 10 (400.0 mg, 0.85 mmol), tetrahydrofuran (20.0 mL) and tetra-n-butylammonium fluoride (240 mg, 0.93 mmol). The reaction mixture was stirred at 20° C. for 30 minutes. TLC indicated no starting material. The reaction mixture was poured into water and extracted with ethyl acetate. The organic layer was washed with brine, dried over sodium sulfate, concentrated and purified with biotage (dichloromethane/methanol 1:10) to give compound P-0001 (220 mg, Yield=82.4%) as a white solid. MS (ESI) [M+H$^+$]$^+$=315.

Additional compounds were prepared following the protocol of Scheme 6, substituting benzyl amine with a suitable amine in Step 1, and using either 3-(6-Chloro-pyridin-3-ylmethyl)-1-triisopropylsilanyl-1H-pyrrolo[2,3-b]pyridine 6 or 3-(6-Bromo-pyridin-3-ylmethyl)-1-triisopropylsilanyl-1H-pyrrolo[2,3-b]pyridine 6a, in Step 1. The following compounds were made following this procedure:
Dimethyl-[5-(1H-pyrrolo[2,3-b]pyridin-3-ylmethyl)-pyridin-2-yl]-amine (P-0021),
(4-methoxy-benzyl)-[5-(1H-pyrrolo[2,3-b]pyridin-3-ylmethyl)-pyridin-2-yl]-amine (P-0004),
(4-chloro-benzyl)-[5-(1H-pyrrolo[2,3-b]pyridin-3-ylmethyl)-pyridin-2-yl]-amine (P-0005),
(4-fluoro-benzyl)-[5-(1H-pyrrolo[2,3-b]pyridin-3-ylmethyl)-pyridin-2-yl]-amine (P-0006),
(4-methyl-benzyl)-[5-(1H-pyrrolo[2,3-b]pyridin-3-ylmethyl)-pyridin-2-yl]-amine (P-0007), and
[5-(1H-pyrrolo[2,3-b]pyridin-3-ylmethyl)-pyridin-2-yl]-thiophen-2-ylmethyl-amine (P-0008).

The following table indicates the amine used in Step 1 in place of benzyl amine in Column 3, and whether 3-(6-Chloro-pyridin-3-ylmethyl)-1-triisopropylsilanyl-1H-pyrrolo[2,3-b]pyridine or 3-(6-Bromo-pyridin-3-ylmethyl)-1-triisopropylsilanyl-1H-pyrrolo[2,3-b]pyridine was used in Step 1 in Column 2 (Cl or Br, respectively), with the compound structure in Column 4, experimental mass spectrometry result in Column 5, and compound number in Column 1.

| | Starting azaindole | Amine | Compound | MS(ESI) [M + H$^+$]$^+$ observed |
|---|---|---|---|---|
| P-0021 | Cl |  |  | 253 |
| P-0004 | Br | 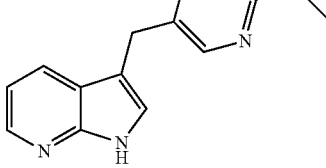 | 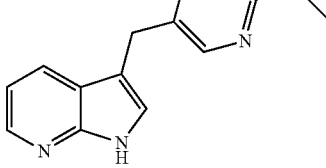 | 344.4 |

-continued

| Starting azaindole | Amine | Compound | MS(ESI) [M + H+]+ observed |
|---|---|---|---|
| P-0005 | Br, 4-chlorobenzylamine | 5-((1H-pyrrolo[2,3-b]pyridin-3-yl)methyl)-N-(4-chlorobenzyl)pyridin-2-amine | 348.8 |
| P-0006 | Br, 4-fluorobenzylamine | 5-((1H-pyrrolo[2,3-b]pyridin-3-yl)methyl)-N-(4-fluorobenzyl)pyridin-2-amine | 332.4 |
| P-0007 | Br, 4-methylbenzylamine | 5-((1H-pyrrolo[2,3-b]pyridin-3-yl)methyl)-N-(4-methylbenzyl)pyridin-2-amine | 328.4 |
| P-0008 | Br, 2-thienylmethylamine | 5-((1H-pyrrolo[2,3-b]pyridin-3-yl)methyl)-N-(thiophen-2-ylmethyl)pyridin-2-amine | 330.4 |

Example 5

Synthesis of (6-Benzylamino-pyridin-3-yl)-(1H-pyrrolo[2,3-b]pyridin-3-yl)-methanone (P-0002)

(6-Benzylamino-pyridin-3-yl)-(1H-pyrrolo[2,3-b]pyridin-3-yl)-methanone (P-0002) was prepared in one step from (6-Chloro-pyridin-3-yl)-(1H-pyrrolo[2,3-b]pyridin-3-yl)-methanone (7) according to Scheme 7.

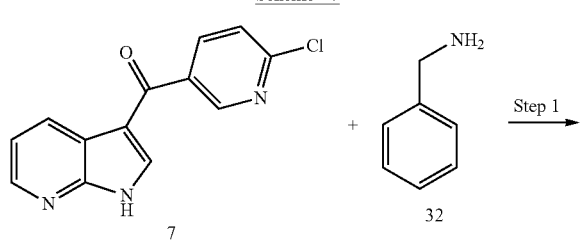

Scheme - 7

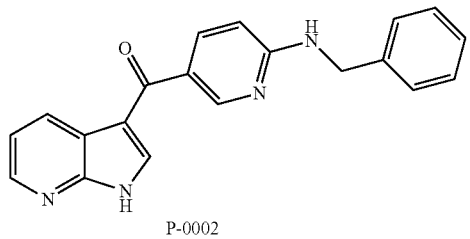

P-0002

Into a pressure tube was added (6-Chloro-pyridin-3-yl)-(1H-pyrrolo[2,3-b]pyridin-3-yl)-methanone 7 (270.0 mg, 1.05 mmol, prepared as described in Example 3), and benzylamine (32, 0.7 mL, 0.006 mol) and tetrahydrofuran (25.0 mL) under an atmosphere of nitrogen. The reaction mixture was heated to 185° C. for 60 hours. The reaction mixture was concentrated to remove most of the solvent and the residue was poured into water and extracted with ethyl acetate. The organic layer was dried over sodium sulfate, concentrated and purified with biotage (dichloromethane/methanol 1:20) to give compound P-0002 (30 mg, yield=8.7%) as a white solid. MS (ESI) [M+H+]+=329.

Additional compounds were prepared following the protocol of Scheme 7, replacing benzylamine with a suitable amine. The following compounds were made following this procedure:
[6-(4-Fluoro-benzylamino)-pyridin-3-yl]-(1H-pyrrolo[2,3-b]pyridin-3-yl)-methanone (P-0015),
[6-(3-Fluoro-benzylamino)-pyridin-3-yl]-(1H-pyrrolo[2,3-b]pyridin-3-yl)-methanone (P-0016),
(1H-Pyrrolo[2,3-b]pyridin-3-yl)-[6-(4-trifluoromethyl-benzylamino)-pyridin-3-yl]-methanone (P-0017),
(1H-Pyrrolo[2,3-b]pyridin-3-yl)-{6-[(thiophen-2-ylmethyl)-amino]-pyridin-3-yl}-methanone (P-0018),
(6-Phenylamino-pyridin-3-yl)-(1H-pyrrolo[2,3-b]pyridin-3-yl)-methanone (P-0023),
(6-Isopropylamino-pyridin-3-yl)-(1H-pyrrolo[2,3-b]pyridin-3-yl)-methanone (P-0024),
(6-Isobutylamino-pyridin-3-yl)-(1H-pyrrolo[2,3-b]pyridin-3-yl)-methanone (P-0025),
[6-(3-Benzyloxy-phenylamino)-pyridin-3-yl]-(1H-pyrrolo[2,3-b]pyridin-3-yl)-methanone (P-0026),
[6-(Cyclopropylmethyl-amino)-pyridin-3-yl]-(1H-pyrrolo[2,3-b]pyridin-3-yl)-methanone (P-0030),
[6-(Cyclohexylmethyl-amino)-pyridin-3-yl]-(1H-pyrrolo[2,3-b]pyridin-3-yl)-methanone (P-0031), The following table indicates the amine substituted in place of benzylamine in column 2, to provide these compounds, shown by structure in column 3. Column 1 provides the compound number and column 4 gives the experimental mass spectrometry result.

| Amine | Compound | | MS(ESI) [M + H⁺]⁺ observed |
|---|---|---|---|
| P-0015 | | | 347.0 |
| P-0016 | | | 347.1 |
| P-0017 | | | 396.9 |
| P-0018 | | | 335.0 |
| P-0023 | | | 315.1 |

-continued

| Amine | Compound | MS(ESI) [M + H⁺]⁺ observed |
|---|---|---|
| P-0024 (isopropylamine) | | 279 [M − H⁺]⁻ |
| P-0025 (isobutylamine) | | 293 [M − H⁺]⁻ |
| P-0026 (3-OBn-aniline) | | 419 [M − H⁺]⁻ |
| P-0030 (cyclopropylmethylamine) | | 293.1 |
| P-0031 (cyclohexylmethylamine) | | 335.2 |

Example 6

Synthesis of Isobutyl-[5-(1H-pyrrolo[2,3-b]pyridin-3-ylmethyl)-pyridin-2-yl]-amine P-0028

Compound P-0028 was synthesized in 1 step from 6-Isobutylamino-pyridin-3-yl)-(1H-pyrrolo[2,3-b]pyridin-3-yl)-methanone P-0025 as shown in Scheme 8.

Scheme 8

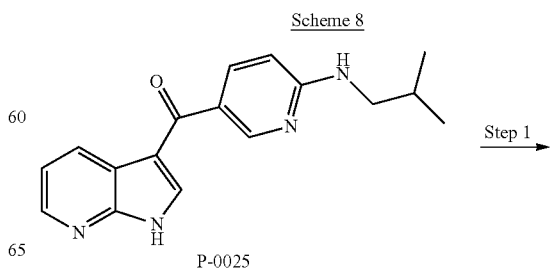

P-0025 → Step 1

-continued

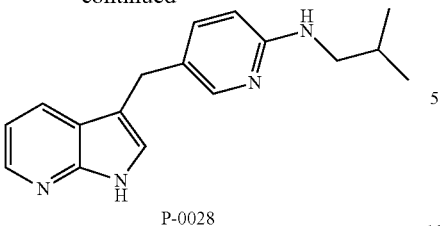

P-0028

Step-1—Synthesis of Isobutyl-[5-(1H-pyrrolo[2,3-b]pyridin-3-ylmethyl)-pyridin-2-yl]-amine (P-0028)

To (6-Isobutylamino-pyridin-3-yl)-(1H-pyrrolo[2,3-b]pyridin-3-yl)-methanone (P-0025, 60.0 mg, 0.20 mmol, prepared as described in Example 5) in 1,2-ethanediol (5.0 mL) was added hydrazine (1.0 mL, 0.032 mol) and potassium hydroxide (200.0 mg, 3.56 mmol). The reaction mixture was heated to 180° C. overnight. The reaction mixture was poured into water and extracted with ethyl acetate. The organic layer was washed with brine, dried over sodium sulfate, concentrated and purified by silica gel column chromatography eluting with 10% methanol in dichloromethane to give compound (P-0028, 10 mg, 16.7%). MS (ESI) [M+H$^+$]$^+$=281.

Cyclopropylmethyl-[5-(1H-pyrrolo[2,3-b]pyridin-3-ylmethyl)-pyridin-2-yl]-amine (P-0032)

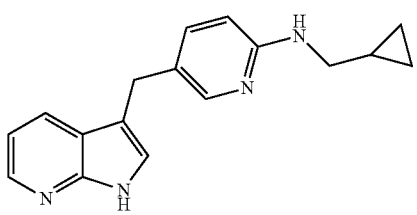 [SMILES: c1cnc2[nH]cc(Cc3ccc(NCC4CC4)nc3)c2c1]

was prepared following the protocol of Scheme 8, substituting (6-Isobutylamino-pyridin-3-yl)-(1H-pyrrolo[2,3-b]pyridin-3-yl)-methanone P-0025 with [6-(Cyclopropylmethyl-amino)-pyridin-3-yl]-(1H-pyrrolo[2,3-b]pyridin-3-yl)-methanone P-0030 (prepared as described in Example 5). MS (ESI) [M+H$^+$]$^+$=279.

Cyclohexylmethyl-[5-(1H-pyrrolo[2,3-b]pyridin-3-ylmethyl)-pyridin-2-yl]-amine (P-0033)

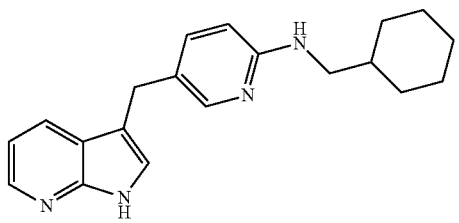 [SMILES: c1cnc2[nH]cc(Cc3ccc(NCC4CCCCC4)nc3)c2c1]

was prepared following the protocol of Scheme 8, substituting (6-Isobutylamino-pyridin-3-yl)-(1H-pyrrolo[2,3-b]pyridin-3-yl)-methanone P-0025 with [6-(Cyclohexylmethyl-amino)-pyridin-3-yl]-(1H-pyrrolo[2,3-b]pyridin-3-yl)-methanone P-0031, (prepared as described in Example 5). MS (ESI) [M+H$^+$]$^+$=321.

Example 7

3-(6-Isopropyl-pyridin-3-ylmethyl)-1H-pyrrolo[2,3-b]pyridine P-0019

3-(6-Isopropyl-pyridin-3-ylmethyl)-1H-pyrrolo[2,3-b]pyridine P-0019 was synthesized in 2 steps from 3-(6-Chloro-pyridin-3-ylmethyl)-1-triisopropylsilanyl-1H-pyrrolo[2,3-b]pyridine 6 as shown in Scheme 9.

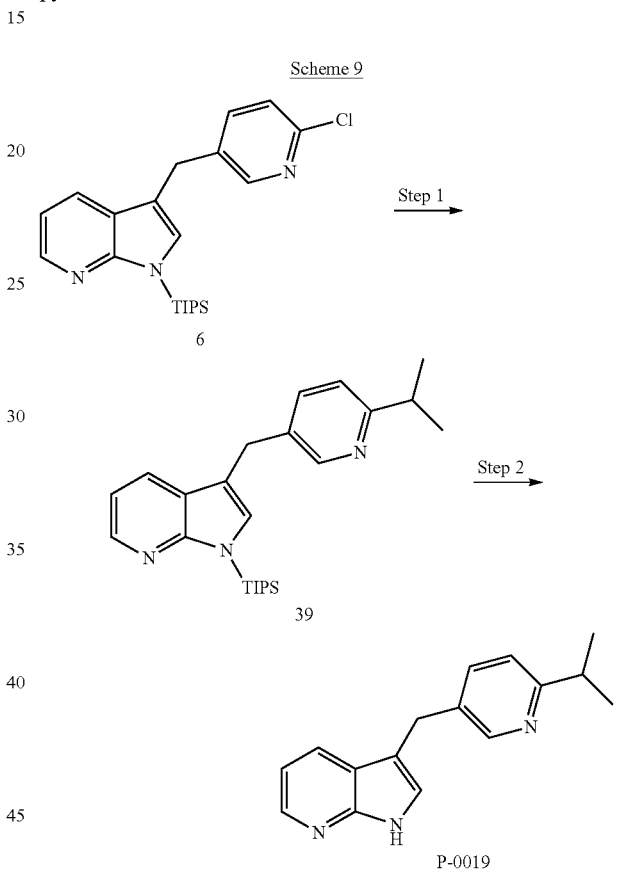

Step-1—Synthesis of 3-(6-Isopropyl-pyridin-3-ylmethyl)-1-triisopropylsilanyl-1H-pyrrolo[2,3-b]pyridine (39)

To 3-(6-Chloro-pyridin-3-ylmethyl)-1-triisopropylsilanyl-1H-pyrrolo[2,3-b]pyridine (6, 54.0 mg, 0.000135 mol, prepared as described in Example 2) in Tetrahydrofuran (4.0 mL) were added [1,1'-bis(diphenylphosphino)ferrocene]-dichloropalladium(II) (23.0 mg) and Isopropylmagnesium Chloride (0.15 mL, 2.0 M in Tetrahydrofuran). The reaction was stirred at 20° C. under an atmosphere of Nitrogen for 3 hours. The reaction mixture was poured into water and extracted with ethyl acetate. The organic layer was washed with brine, dried over sodium sulfate, concentrated and purified by silica gel column chromatography eluting with 10% methanol in dichloromethane to give compound 39 (38 mg, 70.4%).

Step-2—Synthesis of 3-(6-Isopropyl-pyridin-3-ylmethyl)-1H-pyrrolo[2,3-b]pyridine (P-0019)

To 3-(6-Isopropyl-pyridin-3-ylmethyl)-1-triisopropylsilanyl-1H-pyrrolo[2,3-b]pyridine (39, 35.0 mg, 0.086 mmol) in tetrahydrofuran (3.0 mL) was added tetra-n-butylammonium fluoride (29 mg, 0.11 mmol). The reaction was stirred at 20° C. for 30 minutes. The reaction mixture was poured into water and extracted with ethyl acetate. The organic layer was washed with brine, dried over sodium sulfate, concentrated and purified by silica gel column chromatography eluting with 10% methanol in dichloromethane to give compound (P-0019, 18.0 mg, 81.9%). MS (ESI) [M+H$^+$]$^+$=252.

Example 8

Synthesis of [5-(1H-Pyrrolo[2,3-b]pyridin-3-ylmethyl)-pyridin-2-yl]-(4-trifluoromethyl-benzyl)-amine (P-0003)

[5-(1H-Pyrrolo[2,3-b]pyridin-3-ylmethyl)-pyridin-2-yl]-(4-trifluoromethyl-benzyl)-amine (P-0003) was prepared in three steps from (6-Chloro-pyridin-3-yl)-(1H-pyrrolo[2,3-b]pyridin-3-yl)-methanone (7) according to Scheme 10.

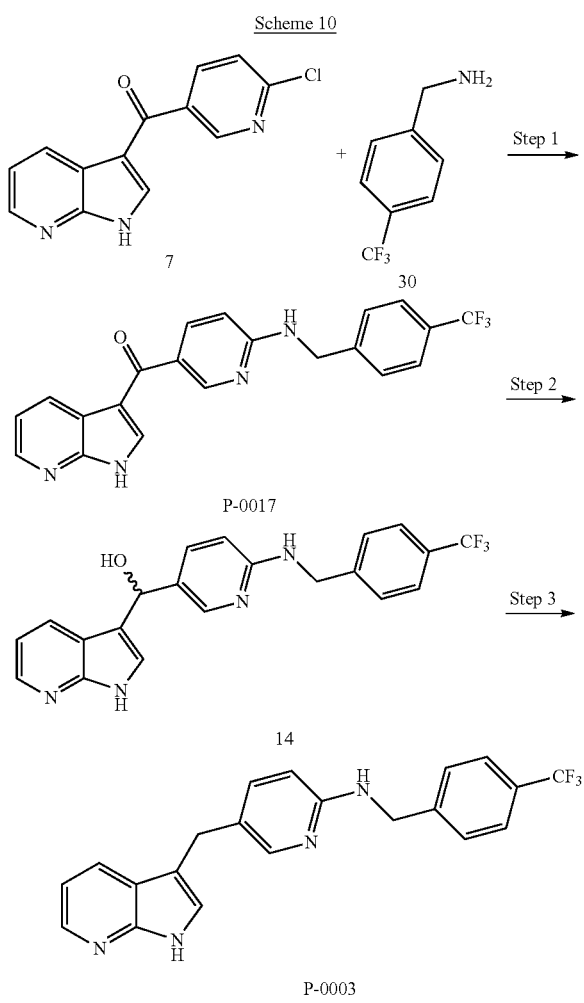

Scheme 10

Step-1—Synthesis of (1H-Pyrrolo[2,3-b]pyridin-3-yl)-[6-(4-trifluoromethyl-benzylamino)-pyridin-3-yl]-methanone (P-0017)

Into a pressure flask was added (6-Chloro-pyridin-3-yl)-(1H-pyrrolo[2,3-b]pyridin-3-yl)-methanone 7 (3.5 g, 0.014 mol, prepared as described in Example 3), 4-(trifluoromethyl)benzylamine (30, 9.0 g, 0.051 mol), tetrahydrofuran (30.0 mL, 0.37 mol), palladium acetate (200.0 mg, 0.890 mmol) and 2-(di-t-butylphosphino)biphenyl (200.0 mg, 0.67 mmol). The reaction mixture was stirred at 180° C. overnight, poured into water and extracted with ethyl acetate. The organic layer was washed with brine, dried over sodium sulfate and concentrated. To the residue was added acetic acid (15.0 mL) and H$_2$O (5.0 mL). The reaction mixture was stirred at 100° C. for 5 hours and concentrated to remove the acetic acid. The residue was then treated with aqueous Na$_2$HCO$_3$ and extracted with ethyl acetate. The organic layer was washed, dried, concentrated and purified to give compound P-0017 (1.0 g, yield=18.5%) as a light yellow solid. MS (ESI) [M+H$^+$]$^+$=397.

Step-2—Synthesis of (1H-Pyrrolo[2,3-b]pyridin-3-yl)-[6-(4-trifluoromethyl-benzylamino)-pyridin-3-yl]-methanol (14)

Into a round bottom flask was added (1H-Pyrrolo[2,3-b]pyridin-3-yl)-[6-(4-trifluoromethyl-benzylamino)-pyridin-3-yl]-methanone P-0017 (210.0 mg, 0.53 mmol) and sodium tetrahydroborate (80.0 mg, 2.11 mmol), dissolved in N,N-dimethylformamide (5.0 mL) and ethanol (20.0 mL). The reaction was stirred at room temperature overnight, poured into water and extracted with ethyl acetate. The organic layer was washed with brine, dried over sodium sulfate, concentrated and purified with biotage (dichloromethane/methanol 1:20) to give compound 14 (63 mg, yield=30%) as a white solid. MS (ESI) [M+H$^+$]$^+$=399.

Step-3—Synthesis of [5-(1H-Pyrrolo[2,3-h]pyridin-3-ylmethyl)-pyridin-2-yl]-(4-trifluoromethyl-benzyl)-amine (P-0003)

Into a round bottom flask was added (1H-Pyrrolo[2,3-b]pyridin-3-yl)-[6-(4-trifluoromethyl-benzylamino)-pyridin-3-yl]-methanol 14 (200.0 mg, 0.50 mmol), trifluoroacetic acid (5.0 mL, 0.065 mol) and triethylsilane (3.0 mL, 0.019 mol). The reaction was stirred at room temperature for 30 min, poured into aqueous sodium bicarbonate, and extracted with ethyl acetate. The organic layer was washed with brine, dried over sodium sulfate, concentrated and purified to give pure compound P-0003 (120.0 mg, yield=62.8%) as a white solid. MS (ESI) [M+H$^+$]$^+$=383.

Example 9

Synthesis of Compounds of Formula I where n is 1, P, Q and T are CH X$_1$, X$_2$ and Y$_2$ are CH, Y$_1$ is CR$^4$, L$^1$ is —CH2-, L$^2$ is NHCH$_2$—, and R$^1$ is 4 Substituted Phenyl (Formula Ic)

Compounds of Formula Ic, where R$^4$ is as defined for Formula I (paragraph [0011]) and Z is a substituent as defined for optionally substituted aryl, can be synthesized in five Steps from 2-amino-5-bromopyridines as shown in the following general Scheme 11.

Scheme 11

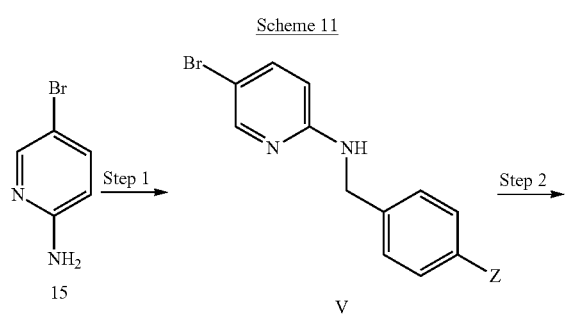

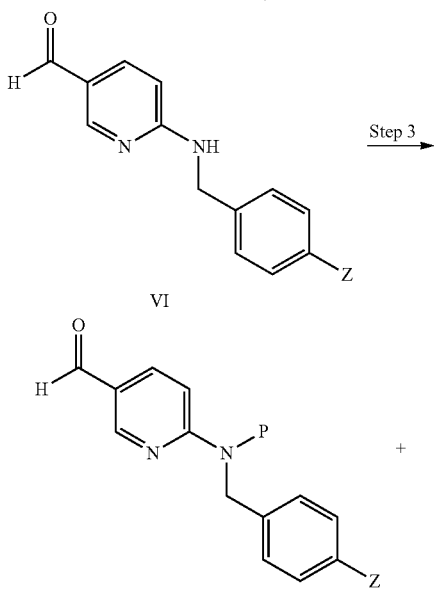

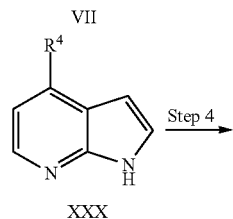

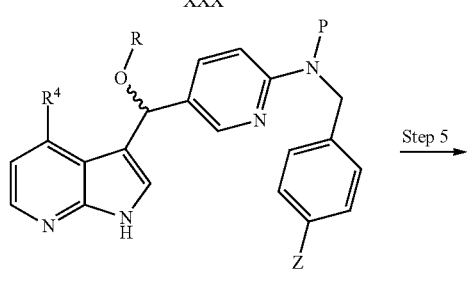

VIII R = H   IX R = CH₃

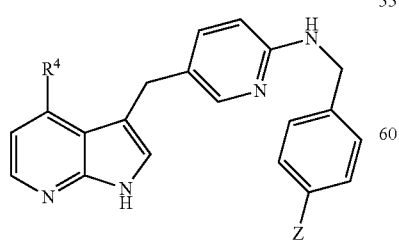

Ic

Step-1—Preparation of Compounds of Formula V

To a solution of an appropriately substituted benzaldehyde (e.g. p-trifluoromethyl benzaldehyde) in a non-reactive solvent (e.g. tetrahydrofuran) is added an appropriate 2-amino-5-bromo-pyridine 15, followed by appropriate reagents to effect the reduction (e.g. dibutyltin dichloride and phenylsilane). Typically the reaction is heated (e.g. 50° C.) overnight. The solvent is removed at reduced pressure after heating to 50° C. overnight. Isolation by conventional means (e.g. extraction) affords compounds of Formula V.

Step-2—Preparation of Compounds of Formula VI

Compound of Formula V is dissolved in a non-reactive solvent (e.g. tetrahydrofuran) and typically cooled at −78° C. under an inert atmosphere. To this mixture is added an organo lithium reagent (e.g. methyl lithium). The reaction mixture is typically stirred at −78° C. for several hours. To this mixture is added an organo lithium reagent (e.g. tert-butyl lithium), and the mixture is stirred for several hours. The reaction mixture is maintained at −78° C., and an appropriate formylating reagent (e.g. 1-piperidine carboxaldehyde) is added. Typically, the reaction is allowed to stir at −78° C. for an additional several hours and slowly warmed to room temperature. Isolation by conventional means (e.g. extraction) affords compounds of Formula VI.

Step-3—Preparation of Compounds of Formula VII

Compound of Formula VI is dissolved in a non-reactive solvent (e.g. tetrahydrofuran) and stirred under an inert atmosphere. To this solution is added a base (e.g. triethylamine) and typically a catalyst (e.g. 4-dimethylaminopyridine). Typically, the mixture is stirred for a few minutes and then a reagent appropriate for the introduction of a protecting group (e.g. di-tert-butyldicarbonate) is added. Typically, the reaction is stirred overnight. Isolation by conventional means (e.g. extraction) affords compounds of Formula VII.

Step-4—Preparation of Compounds of Formula VIII and IX

4-Substituted 1H-pyrrolo[2,3-b]pyridine XXX is added to a stirring solution of base (e.g. potassium hydroxide) in an appropriate polar protic solvent (e.g. methanol). Compound of Formula VII is added, and the mixture is typically stirred at room temperature for several days. The solvent is evaporated, and 1 M HCl is added to the residue. Isolation by conventional means (e.g. extraction, silica gel chromatography) affords compounds of Formula VIII and IX.

Step-5—Preparation of Compounds of Formula Ic

Typically, compounds of Formula VIII and IX is combined and dissolved in an appropriate polar aprotic solvent (e.g. acetonitrile). Reagents appropriate to effect the reduction (e.g. triethylsilane and trifluoroacetic acid) are added. Typically, the reactions are stirred at room temperature for several days. Isolation by conventional means (e.g. extraction, silica gel chromatography) affords compounds of Formula Ic.

Example 10

Synthesis of [5-(4-Methoxy-1H-pyrrolo[2,3-b]pyridin-3-ylmethyl)-pyridin-2-yl]-(4-trifluoromethyl-benzyl)-amine (P-0011)

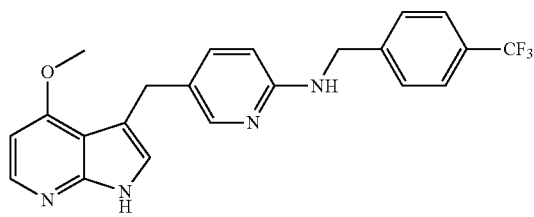 [SMILES: COc1ccnc2[nH]cc(Cc3ccc(NCc4ccc(C(F)(F)F)cc4)nc3)c12]

[5-(4-Methoxy-1H-pyrrolo[2,3-b]pyridin-3-ylmethyl)-pyridin-2-yl]-(4-trifluoromethyl-benzyl)-amine P-0011 was synthesized as shown in Scheme 12:

Scheme 12

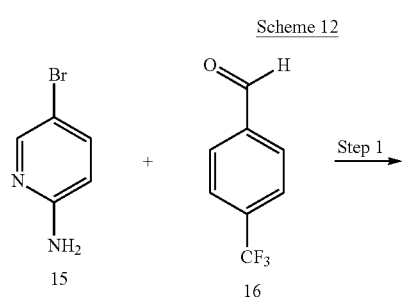

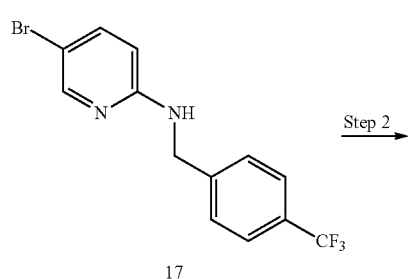

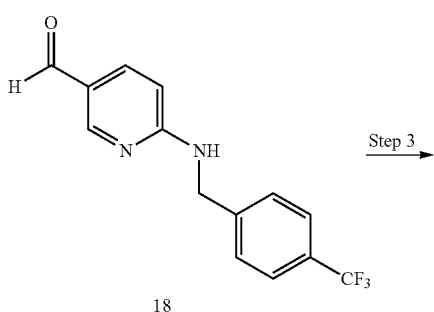

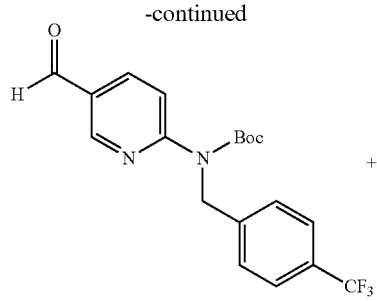

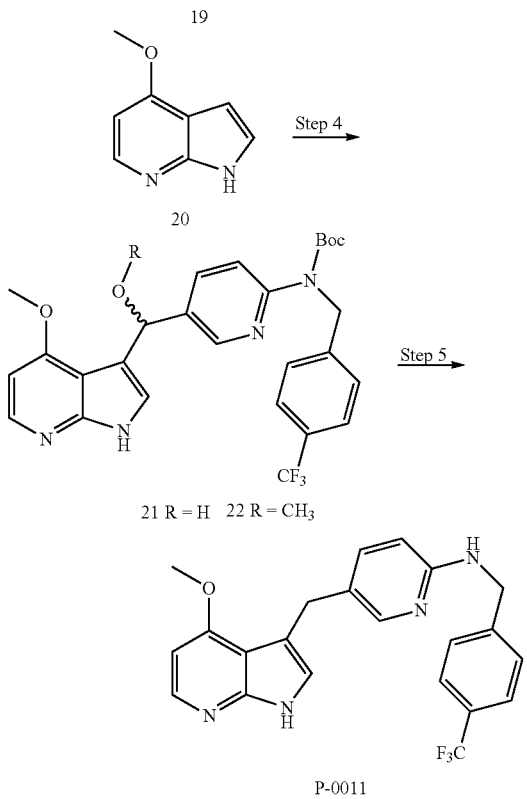

Step 1: Preparation of (5-Bromo-pyridin-2-yl)-(4-trifluoromethyl-benzyl)-amine (17)

Into a round bottom flask fitted with stirrer and reflux condenser was added 2-amino-5-bromopyridine (15, 1.73 mol, 300 g) and p-trifluoromethylbenzaldehyde (16, 1.723 mol, 300 g) to a solution of trifluoroacetic acid (400 mL), triethylsilane (825 mL) and acetonitrile (7500 mL). The reaction was heated to reflux overnight (24 hours). Solvents were removed and the residue was poured into aqueous $K_2CO_3$ and extracted with ethyl acetate. The organic layer was washed with brine, dried over sodium sulfate, and concentrated. The crude compound was crystallized with diethyl ether/hexane to afford compound 17, 420 g (73.6%) as off white solid. MS (ESI) [M+H$^+$]$^+$=331.1 and 333.1 (1:1 ratio).

Step 2: Preparation of 6-(4-Trifluoromethyl-benzylamino)-pyridine-3-carbaldehyde (18)

Into a 5 L round bottom flask was added compound 17 (0.6 mol, 198.6 g,) and tetrahydrofuran (2.5 L) under an atmosphere of argon at −78° C. Into the reaction mixture was added 1.7 M tert-butyllithium in pentane (800 mL) over 60 mins. Two hours after the addition of tert-butyllithium, N,N-dimethylformamide (100 mL) was added. The reaction mixture was stirred at −78° C. for 2 hours, then allowed to stand at room temperature for another 1 hour. The reaction mixture was poured into saturated ammonium chloride solution and extracted with ethyl acetate. The organic layer was washed with brine, dried over sodium sulfate, concentrated and triturated with hexane/isopropyl ether (1:1) to give aldehyde compound 18.

Step 3: Preparation of (5-Formyl-pyridin-2-yl)-(4-trifluoromethyl-benzyl)-carbamic acid tert-butyl ester (19)

Into a 2 L round bottom flask was added di-tert-butyldicarbonate (90 g), aldehyde 18 (75 g), diisopropyl ethyl amine (60 g), 4-dimethylaminopyridine (2.0 g) and dichloromethane (1000.0 mL). The reaction was stirred at room temperature overnight (18 hours) and the solvent was evaporated to give compound 19 (94 g).

Steps 4 and 5: Preparation of [5-(4-Methoxy-1H-pyrrolo[2,3-b]pyridin-3-ylmethyl)-pyridin-2-yl]-(4-trifluoromethyl-benzyl)-amine (P-0011)

Step 4: Into a solution of methanol (20 mL, 0.5 mol) was added sodium hydroxide (0.62 g, 0.016 mol), followed by 4-methoxy-7-azaindole (20, 600 mg, 4 mmol, prepared as described in Example 12). Once the mixture was homogeneous, compound 19 (1.7 g, 4.46 mmol) was added and the mixture was stirred at room temperature for 48 hours. The solvent was evaporated and dilute HCl was added to the residue. The residue was extracted with ethyl acetate and washed with 10% sodium bicarbonate, followed by brine. The organic layer was dried over MgSO₄, filtered and evaporated to give a mixture of crude compounds 21 and 22, which was used in the next step.

Step 5: The mixture of 21 and 22 from Step 4 (2.36 g, 4.46 mmol) was dissolved in dichloromethane (60 mL, 0.9 mol) to which triethylsilane (3.6 mL, 0.022 mol) and trifluoroacetic Acid (2.1 mL, 0.027 mol) were added. The resulting mixture was stirred for 48 hours at room temperature. The solvent was evaporated and the mixture was extracted with dichloromethane:methanol (3:1). The organic layer was washed with saturated bicarbonate followed by brine. The organic layer was dried over MgSO₄, filtered and evaporated to give crude compound as a residue. The residue was purified by flash silica gel chromatography to give 1.15 g of solid P-0011 for a 60% yield.

MS (ESI) [M+H⁺]⁺=413.24.

[5-(4-Methoxy-1H-pyrrolo[2,3-b]pyridin-3-ylmethyl)-pyridin-2-yl]-(4-chloro-benzyl)-amine P-0010

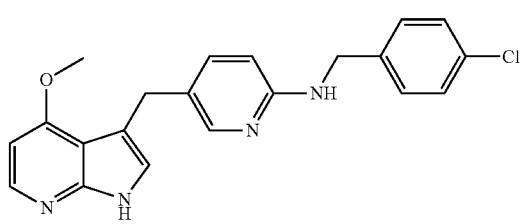 [SMILES: COc1ccnc2[nH]cc(Cc3ccc(NCc4ccc(Cl)cc4)nc3)c12]

was prepared following the protocol of Scheme 12, substituting 4-trifluoro-benzylamine with 4-chloro-benzylamine in Step 1. MS (ESI) [M+H⁺]⁺=379.2 and 381.2 (3:1 ratio).

[5-(4-chloro-1H-pyrrolo[2,3-b]pyridin-3-ylmethyl)-pyridin-2-yl]-(4-chloro-benzyl)-amine P-0009

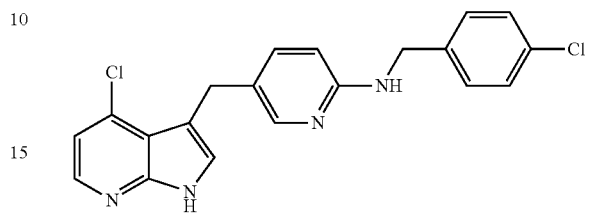

was prepared following the protocol of Scheme 12, substituting 4-trifluoro-benzylamine with 4-chloro-benzylamine in Step 1 and 4-methoxy-7-azaindole with 4-chloro-7-azaindole (24, prepared as described in Example 11) in Step 4. MS (ESI) [M+H⁺]⁺=381.1 and 383.0.

Example 11

Synthesis of 4-chloro-7-azaindole (24)

4-chloro-7-azaindole 24 was synthesized in two Steps from 7-azaindole according to the protocol of Scheme 13.

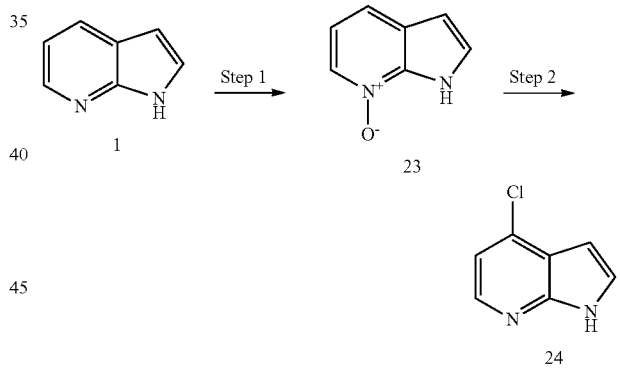

Step-1—Synthesis of 1H-Pyrrolo[2,3-b]pyridine 7-oxide (23)

1H-Pyrrolo[2,3-b]pyridine 7-oxide 23 was synthesized by reacting commercially available 7-azaindole 1 with an oxidizing agent (e.g. m-CPBA) in a non-reactive solvent (e.g. dimethoxyethane) as described by Schneller, S. W.; Luo, Jiann-Kuan. J. Org. Chem. 1980, 45:4045-4048. The compound was isolated by filtration of the resulting solid that forms upon standing at 5° C. for typically 1-3 h.

Step-2—Synthesis of 4-chloro-7-azaindole (24)

4-chloro-7-azaindole 24 was synthesized by reacting 1H-Pyrrolo[2,3-b]pyridine 7-oxide 23 with a chlorinating agent (e.g. POCl₃) neat as described by Schneller, S. W.; Luo, Jiann-Kuan. J. Org. Chem. 1980, 45:4045-4048. The resulting solution after heating for 3-5 h at elevated temperatures (100-150° C.) was neutralized with a base (e.g. NH$_4$OH) until a solid precipitated. The solid was isolated by filtration.

Example 12

Synthesis of 4-methoxy-7-azaindole (20)

4-methoxy-7-azaindole 20 was synthesized in one Step from 4-chloro-7-azaindole according to the protocol of Scheme 14.

Scheme 14

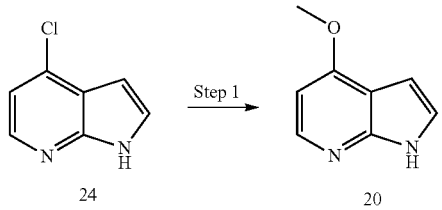

4-methoxy-7-azaindole 20 was prepared by reacting 4-chloro-7-azaindole 24 (prepared as described in Example 9) with sodium hydroxide in methanol as described by Girgis, N. et. al., J. Heterocyclic. Chem. 1989, 26:317-325.

Example 13

Synthesis of Compounds of Formula I where n is 1, P is CR$^{30}$, Q, T, X$_1$, X$_2$, Y$_1$ and Y$_2$ are CH, L$^1$ is —CH2-, L$^2$ is NHCH$_2$—, and R$^1$ is Substituted Phenyl (Formula Id)

Compounds of Formula Id, where R$^{30}$ is a substituent as defined for optionally substituted heteroarylene (further defined in Scheme 13 below) and R$^{31}$ is a substituent as defined for optionally substituted aryl, can be synthesized in six Steps from appropriately substituted 2-halopyridines as shown in the following general Scheme 15.

Scheme 15

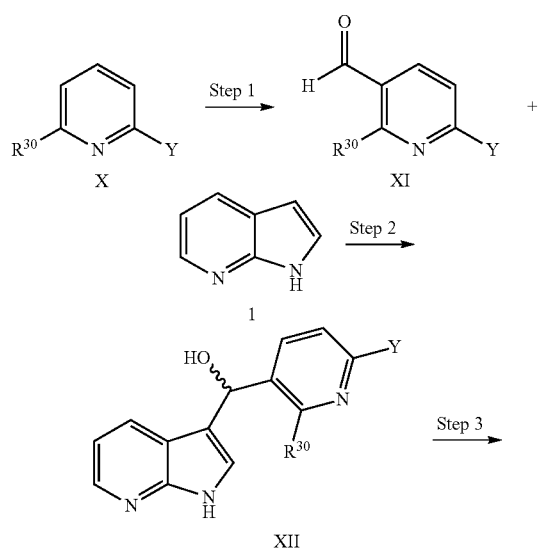

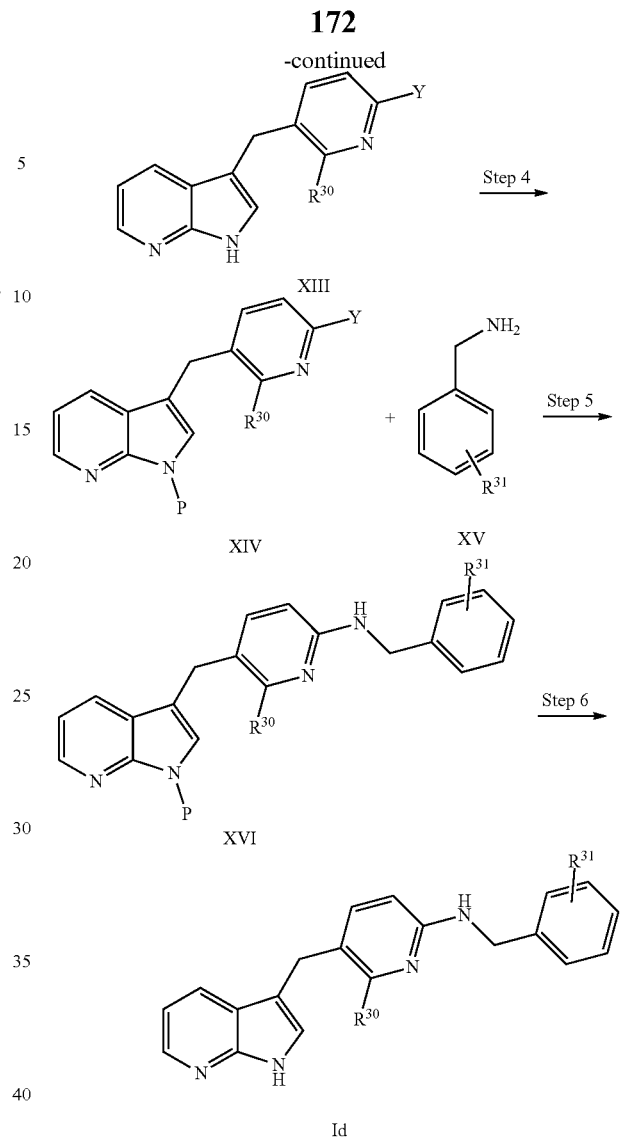

Step 1—Preparation of Compounds of Formula XI

To an appropriately substituted 2-halopyridine X (e.g. 2-chloro-6-methoxypyridine), where Y is a halogen, preferably chlorine or bromine, and R$^{30}$ is a group appropriate to direct the following lithiation to the 5-position (e.g. R$^{30}$=methoxy), in a non-reactive solvent (e.g. tetrahydrofuran) typically cooled in a −78° C. acetone/dry ice bath is added a solution of organolithium reagent (e.g. tert-butyllithium). The reaction is allowed to stir for a period, typically 1 hour. An appropriate formylating agent (e.g. dimethylformamide) is added and the reaction is allowed to stir cooled for a period and then warmed to room temperature for a period, typically 30 minutes. The reaction can be placed back in the dry-ice bath and quenched with 6 N HCl (1.5 mL) followed by water and allowed to warm to room temperature. Isolation by conventional means (e.g. extraction) provides compounds of Formula XI.

Step 2—Preparation of Compounds of Formula XII

To 1H-pyrrolo[2,3-b]pyridine 1 and a compound of Formula XI is added an appropriate polar solvent (e.g. methanol)

followed by an appropriate base (e.g. potassium hydroxide). The reaction is typically allowed to stir at room temperature overnight. Isolation by convention means (e.g. extraction, washing and filtering) affords compounds of Formula XII.

Step 3—Preparation of Compounds of Formula XIII

To a compound of Formula XII in an appropriate polar solvent (e.g. acetonitrile) is added a reducing agent (e.g. trifluoroacetic acid and triethylsilane). Typically, the reaction is allowed to stir at room temperature overnight. Isolation by conventional means (e.g. extraction and silica gel chromatography) affords compounds of Formula XIII.

Step 4—Preparation of Compounds of Formula XIV

To a solution of compound of Formula XIII in an appropriate polar solvent (e.g. dimethylformamide) is added a base (e.g. sodium hydride). Typically, the reaction is stirred at room temperature for 30 minutes, and then an appropriate reagent to introduce a protecting group ("P") is added (e.g. triisopropylsilyl chloride). The reaction typically is stirred at room temperature for several hours. Isolation by conventional means (e.g. extraction and silica gel chromatography) affords compounds of Formula XIV.

Step 5—Preparation of Compounds of Formula XVI

To a compound of Formula XIV, an appropriately substituted benzylamine XV (e.g. 4-(trifluoromethyl)benzylamine), a base (e.g. sodium tert-butoxide), a catalyst (e.g. tris(dibenzylideneacetone)dipalladium(0)), and ligand (e.g. 2,2'-Bis(diphenylphosphino)-1,1'-binaphthyl) are added a non-reactive solvent (e.g. toluene) under an inert atmosphere. Typically, the reaction is heated (e.g. 80° C.) for several hours. Isolation by conventional means (e.g. extraction and silica gel chromatography) affords compounds of Formula XVI.

Step 6—Preparation of Compounds of Formula Id

To compound of Formula XVI is added an appropriate polar solvent (e.g. tetrahydrofuran) followed by an appropriate reagent to remove the protecting group (e.g. tetra-n-butylammonium fluoride). Typically, the reaction is allowed to stir at room temperature for several hours. Isolation by conventional means (e.g. extraction and silica gel chromatography) affords compounds of Formula Id.

Example 14

Synthesis of Compounds of Formula I where n is 1, P is $CR^{32}$, Q, T, $X_1$, $X_2$, $Y_1$ and $Y_2$ are CH, $L^1$ is —CH2—, $L^2$ is NHCH$_2$—, and $R^1$ is Substituted Phenyl (Formula Ie)

Compounds of Formula Id, where $R^{32}$ is a substituent as defined for optionally substituted heteroarylene and $R^{33}$ is a substituent as defined for optionally substituted aryl, can be synthesized in five Steps from appropriately substituted 2-amino-5-bromopyridines as shown in the following general Scheme 16.

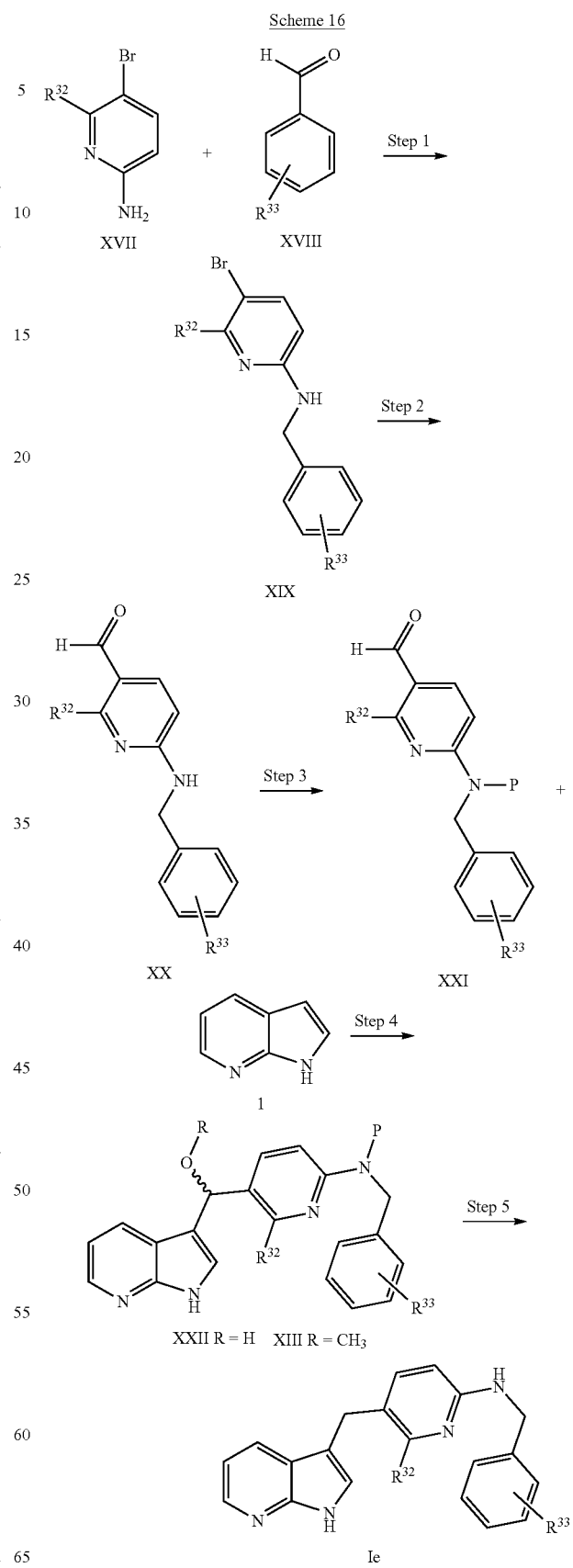

Step-1—Preparation of Compounds of Formula XIX

To a solution of an appropriately substituted benzaldehyde XVIII (e.g. p-trifluoromethyl benzaldehyde) in a non-reactive solvent (e.g. tetrahydrofuran) can be added an appropriate 2-amino-5-bromo-pyridine XVII (e.g. 2-amino-5-bromo-6-methylpyridine), followed by appropriate reagents to effect the reduction (e.g. dibutyltin dichloride and phenylsilane). Typically the reaction is heated (e.g. 50° C.) overnight. Isolation by conventional means (e.g. extraction) affords compounds of Formula XIX.

Step-2—Preparation of Compounds of Formula XX

Compound of Formula XIX is dissolved in a non-reactive solvent (e.g. tetrahydrofuran) and typically cooled at −78° C. under an inert atmosphere. To this mixture is added an organolithium reagent (e.g. methyllithium). The reaction mixture is typically stirred at −78° C. for several hours. To this mixture is added an organolithium reagent (e.g. tert-butyllithium) and the mixture is stirred for several hours. The reaction mixture is maintained at −78° C., and an appropriate formylating reagent (e.g. 1-piperidine carboxaldehyde) is added. Typically, the reaction is allowed to stir at −78° C. for an additional several hours and slowly warmed to room temperature. Isolation by conventional means (e.g. extraction) affords compounds of Formula XX.

Step-3—Preparation of Compounds of Formula XXI

Compound of Formula XX is dissolved in a non-reactive solvent (e.g. tetrahydrofuran) and stirred under an inert atmosphere. To this solution is added a base (e.g. triethylamine) and typically a catalyst (e.g. 4-dimethylaminopyridine). Typically, the mixture is stirred for a few minutes, and then a reagent appropriate for the introduction of a protecting group (e.g. di-tert-butyldicarbonate) is added. Typically, the reaction is stirred overnight. Isolation by conventional means (e.g. extraction) affords compounds of Formula XXI.

Step-4—Preparation of Compounds of Formula XXII and XXIII

1H-Pyrrolo[2,3-b]pyridine 1 is added to a stirred solution of base (e.g. potassium hydroxide) in an appropriate polar solvent (e.g. methanol). Compound of Formula XXI is added, and the mixture is typically stirred at room temperature for several days. The solvent is evaporated and 1 M HCl is added to the residue. Isolation by conventional means (e.g. extraction, silica gel chromatography) affords compounds of Formula XXII and XXIII.

Step-5—Preparation of Compounds of Formula Ie

Typically, compounds of Formula XII and XIII are combined and dissolved in an appropriate polar aprotic solvent (e.g. acetonitrile). Reagents appropriate to effect the reduction (e.g. triethylsilane and trifluoroacetic acid) are added. Typically, the reaction is stirred at room temperature for several days. Isolation by conventional means (e.g. extraction, silica gel chromatography) affords compounds of Formula Ie.

Example 15

Synthesis of [6-Methoxy-5-(1H-pyrrolo[2,3-b]pyridin-3-ylmethyl)-pyridin-2-yl]-(4-trifluoromethyl-benzyl)-amine (P-0012)

[6-Methoxy-5-(1H-pyrrolo[2,3-b]pyridin-3-ylmethyl)-pyridin-2-yl]-(4-trifluoromethyl-benzyl)-amine P-0012 was synthesized in five steps from commercially available 2-chloro-6-methoxypyridine and 7-azaindole as shown in Scheme 17.

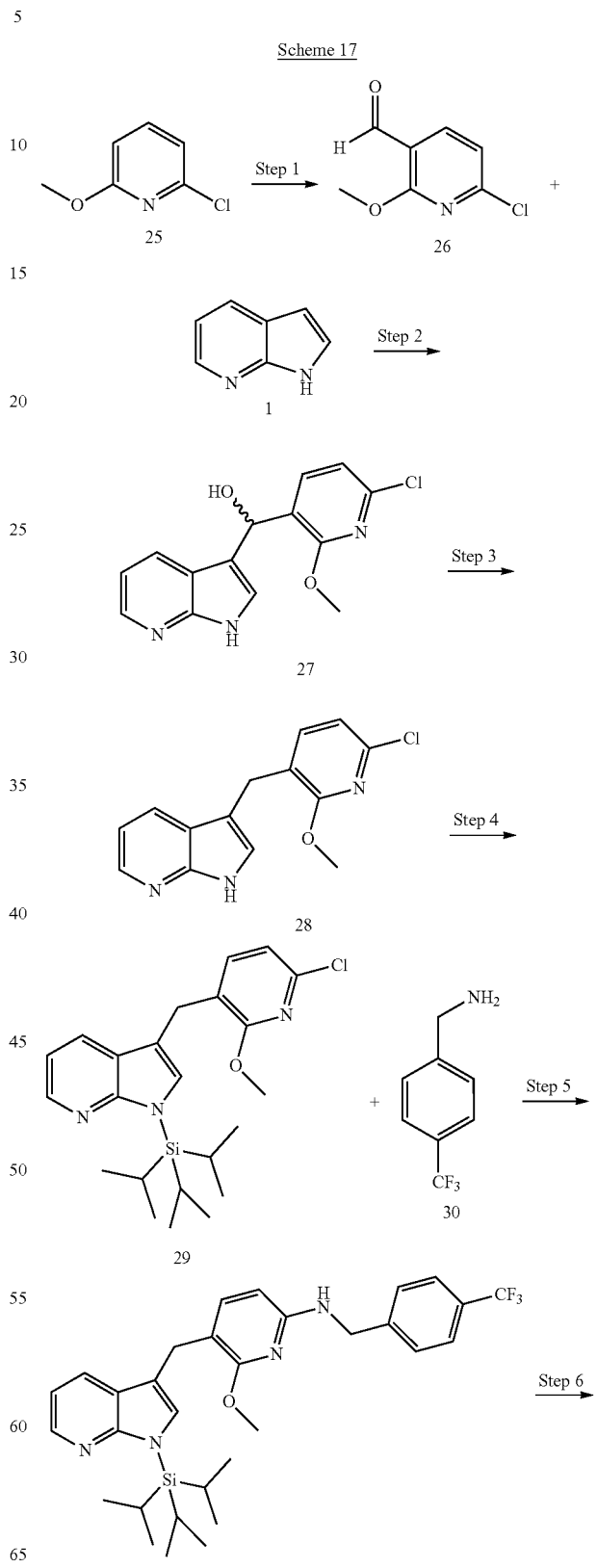

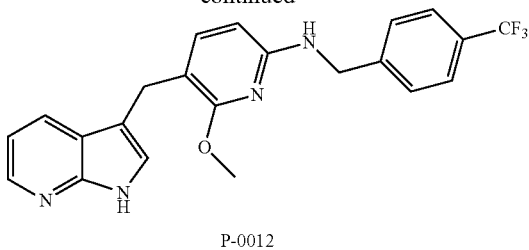

P-0012

Step 1—Preparation of 6-chloro-2-methoxypyridine-3-carbaldehyde (26)

To 2-Chloro-6-methoxypyridine (25, 0.511 g, 3.56 mmol) in tetrahydrofuran (10 mL) cooled in a −78° C. acetone/dry ice bath was added tert-butyllithium (1.7 M in pentane, 5.0 mL, 7.66 mmol). The reaction was allowed to stir for 1 hour. Dimethylformamide (0.673 mL, 17.4 mmol) was added and the reaction was allowed to continue for an additional 30 minutes at −78° C., then stirred for 30 minutes outside of the dry-ice bath. The reaction was placed back in the dry-ice bath and quenched with 6 N HCl (1.5 mL) followed by water and allowed to warm to room temperature. The reaction was extracted with diethyl ether and aqueous (1M) sodium bicarbonate. The organic layer was separated, dried with anhydrous magnesium sulfate, filtered and volatiles removed by rotary evaporation, and the resulting yellow solid was dried under vacuum to provide 561 mg of compound 26 (3.27 mmol, 92% yield). MS (ESI) $[M+H^+]^+=172.0$.

Step 2—Preparation of (6-chloro-2-methoxypyridin-3-yl)(1H-pyrrolo[2,3-b]pyridin-3-yl)methanol (27)

To 1H-Pyrrolo[2,3-b]pyridine (1, 0.455 g, 3.85 mmol) and 6-chloro-2-methoxypyridine-3-carbaldehyde (26, 0.661 g, 3.85 mmol) was added methanol (10 mL) followed by potassium hydroxide (0.310 g, 5.52 mmol). The reaction was allowed to stir at room temperature overnight. The reaction was extracted with diethyl ether/ethyl acetate and water. The organic layer was separated, dried over anhydrous magnesium sulfate, filtered and volatiles were removed by rotary evaporation to provide a solid that was treated with dichloromethane and stored in a freezer overnight. The white solid was collected by vacuum filtration and dried in vacuo to give 613 mg of compound 27 (2.12 mmol, 55%). MS (ESI) $[M+H^+]^+=290.1$.

Step 3—Preparation 3-(6-chloro-2-methoxypyridin-3-ylmethyl)-1H-pyrrolo[2,3-b]pyridine (28)

To (6-chloro-2-methoxypyridin-3-yl)(1H-pyrrolo[2,3-b]pyridin-3-yl)methanol (27, 0.613 g, 2.12 mmol) in acetonitrile (10 mL) was added trifluoroacetic acid (0.82 mL, 10.0 mmol) followed by triethylsilane (1.69 mL, 10.6 mmol). The reaction was allowed to stir at room temperature for 2 days, then 60° C. for 4 hours. The reaction was extracted with diethyl ether and aqueous sodium bicarbonate. The organic layer was dried over anhydrous magnesium sulfate and filtered. The desired material was isolated from the filtrate by silica gel column chromatography eluting with 1% methanol in dichloromethane to give 516 mg of a white solid compound 28 (1.88 mmol, 89%). MS (ESI) $[M+H^+]^+=274.1$.

Step 4—Preparation 3-(6-chloro-2-methoxypyridin-3-ylmethyl)-1-(triisopropylsilyl)-1H-pyrrolo[2,3-b]pyridine (29)

To a clear solution of 3-(6-chloro-2-methoxypyridin-3-ylmethyl)-1H-pyrrolo[2,3-b]pyridine (28, 0.516 g, 1.88 mmol) in dimethylformamide (10 mL) was added sodium hydride (60% dispersion, 0.113 g, 2.82 mmol). After stirring at room temperature for 30 minutes, triisopropylsilyl chloride (600 µL, 2.83 mmol) was added. The reaction was stirred at room temperature for 2 hours, then poured into aqueous (1M) sodium bicarbonate and extracted with ethyl acetate. The organic layer was separated, dried (magnesium sulfate), filtered and volatiles were removed by rotary evaporation to give a crude solid. The compound was purified by silica gel column chromatography eluting with 2% ethyl acetate in hexanes. This provided 732 mg of the desired compound as a white, crystalline solid (29, 1.70 mmol, 90%). MS (ESI) $[M+H^+]^+=430.2$.

Step 5—Preparation of [6-Methoxy-5-(1-triisopropylsilanyl-1H-pyrrolo[2,3-b]pyridin-3-ylmethyl)-pyridin-2-yl]-(4-trifluoromethyl-benzyl)-amine (31)

3-(6-chloro-2-methoxypyridin-3-ylmethyl)-1-(triisopropylsilyl)-1H-pyrrolo[2,3-b]pyridine (29, 0.104 g, 0.242 mmol), 4-(Trifluoromethyl)benzylamine (30, 0.047 g, 0.266 mmol), sodium tert-butoxide (0.0325 g, 0.338 mmol), Tris(dibenzylideneacetone)-dipalladium (0) (0.00062 g, 0.0006 mmol), and 2,2'-Bis(diphenylphosphino)-1,1'-binaphthyl (0.0011 g, 0.0018 mmol) were added to toluene (2 mL) under nitrogen. The reaction vial was placed in an oil bath at 80° C. for 3 hours. The reaction was poured into water and extracted with ethyl acetate. The organic layer was dried (magnesium sulfate), filtered, and volatiles were removed by rotary evaporation. The residue was purified by silica gel column chromatography eluting with 2% ethyl acetate in hexanes. This provided 34 mg of the desired compound 31 (0.060 mmol, 25%). MS (ESI) $[M+H^+]^+=569.3$.

Step 6—Preparation of [6-Methoxy-5-(1H-pyrrolo[2,3-b]pyridin-3-ylmethyl)-pyridin-2-yl]-(4-trifluoromethyl-benzyl)-amine (P-0012)

To [6-Methoxy-5-(1-triisopropylsilanyl-1H-pyrrolo[2,3-b]pyridin-3-ylmethyl)-pyridin-2-yl]-(4-trifluoromethyl-benzyl)-amine (31, 0.0340 g, 0.0598 mmol) was added tetrahydrofuran (5 mL) followed by tetra-n-butylammonium fluoride (1M solution in tetrahydrofuran, 66 µL, 0.0658 mmol). The reaction was allowed to stir at room temperature for 2 hours, then poured into 1:1 water:saturated sodium bicarbonate and extracted with ethyl acetate. The organic layer was separated, dried over magnesium sulfate, filtered and the volatiles were removed by rotary evaporation. The resulting residue was purified by silica gel column chromatography, eluting with dichloromethane followed by 1% methanol in dichloromethane and finally 3% methanol in dichloromethane. This provided 20 mg of the desired compound as a white solid (P-0012, 0.048 mmol, 81%). MS (ESI) $[M+H^+]^+=413.2$.

Example 16

Synthesis of [6-Methyl-5-(1H-pyrrolo[2,3-b]pyridin-3-ylmethyl)-pyridin-2-yl]-(4-trifluoromethyl-benzyl)-amine (P-0013)

[6-Methyl-5-(1H-pyrrolo[2,3-b]pyridin-3-ylmethyl)-pyridin-2-yl]-(4-trifluoromethyl-benzyl)-amine (P-0013) was synthesized in five steps from commercially available 2-amino-5-bromo-6-methylpyridine and 7-azaindole as shown in Scheme 18.

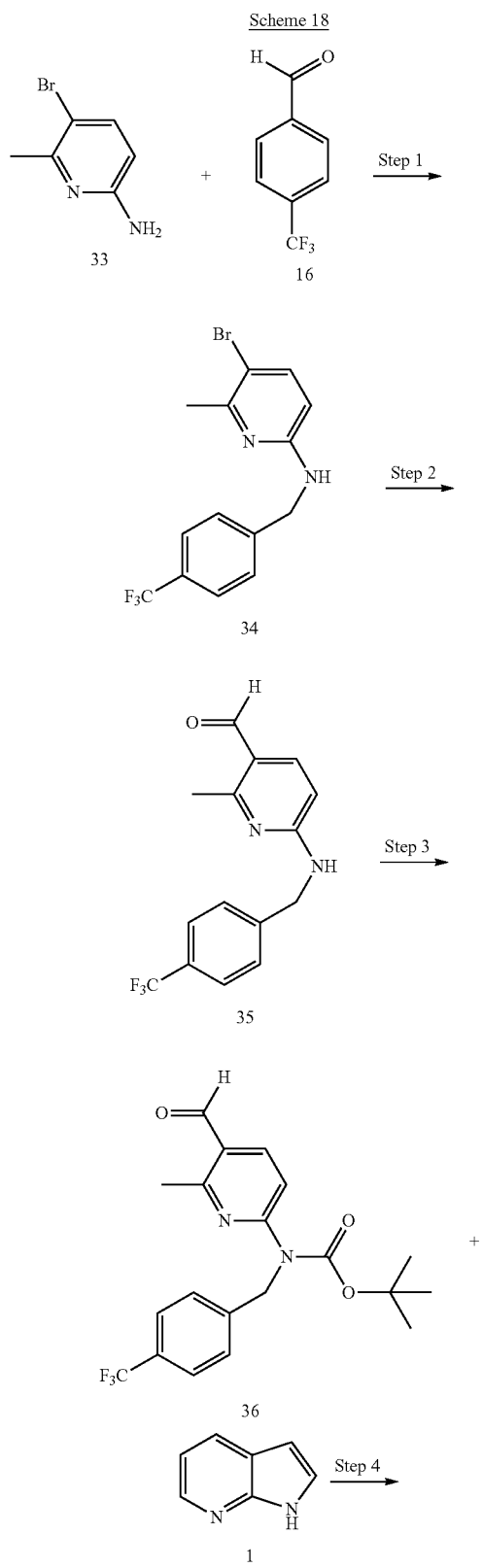

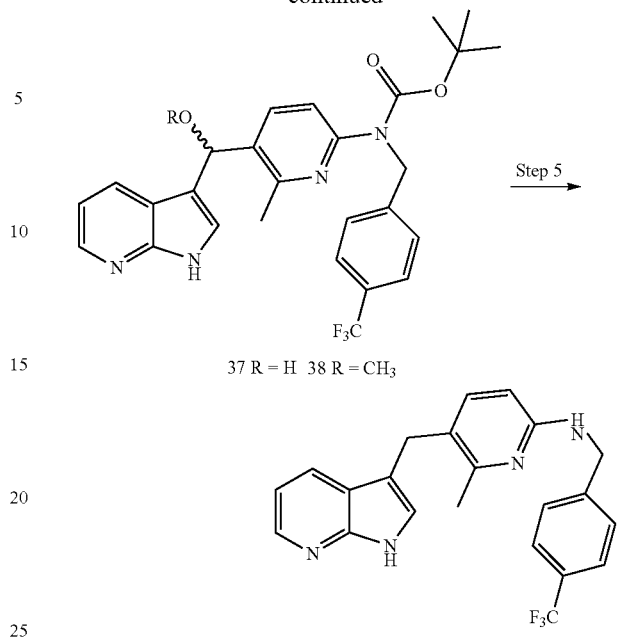

Step-1—Preparation of (5-Bromo-6-methyl-pyridin-2-yl)-(4-trifluoromethyl-benzyl)-amine (34)

To a solution of p-trifluoromethylbenzaldehyde (16, 1.00 g, 5.74 mmol) in tetrahydrofuran (9 mL) was added 2-amino-5-bromo-6-methylpyridine (33, 1.08 g, 5.77 mmol), followed by dibutyltin dichloride (40 mg, 0.13 mmol). The mixture was stirred for 5 minutes at 25° C. and phenylsilane (0.69 g, 6.4 mmol) was added. The reaction was heated at 50° C. overnight, then the solvent was removed at reduced pressure. Ethyl acetate was added to the resulting solid which was washed with saturated sodium carbonate, dried over magnesium sulfate and filtered. Concentration under reduced pressure afforded a light yellow solid (34, 1.7 g, 4.93 mmol). MS (ESI) [M+H$^+$]$^+$=345.1.

Step-2—Preparation of 2-Methyl-6-(4-trifluoromethyl-benzylamino)-pyridine-3-carbaldehyde (35)

(5-Bromo-6-methyl-pyridin-2-yl)-(4-trifluoromethyl-benzyl)-amine (34, 1.7 g, 4.93 mmol) was dissolved in tetrahydrofuran (40 mL) and cooled at 78° C. under a nitrogen atmosphere. To this mixture was added methyllithium (1.6 M in diethyl ether, 5.91 mmol) dropwise over 20 minutes. After the addition of methyllithium was completed, the reaction mixture was stirred at −78° C. for 2 hours. To this mixture was added tert-butyllithium (1.7 M in pentane, 10.85 mmol) and the mixture was stirred for 4 hours. The reaction mixture was maintained at −78° C., and 1-piperidinecarboxaldehyde (0.60 mL, 5.42 mmol) was added dropwise. The reaction was allowed to stir at −78° C. for an additional 2 hours and warming to 25° C. was achieved from the slow evaporation of the dry ice/acetone cooling bath. The reaction was quenched with ice cold saturated sodium chloride and the resulting mixture was extracted with ethyl acetate. The organic layer was dried over magnesium sulfate and filtered. Concentration under reduced pressure afforded an orange oil (35, 1.4 g, 4.93 mmol).
MS (ESI) [M+H$^+$]$^+$=295.1.

Step-3—Preparation of (5-Formyl-6-methyl-pyridin-2-yl)-(4-trifluoromethyl-benzyl)-carbamic acid tert-butyl ester (36)

2-Methyl-6-(4-trifluoromethyl-benzylamino)-pyridine-3-carbaldehyde (35, 1.4 g, 4.9 mmol) was dissolved in tetrahydrofuran (22 mL) and was stirred under an atmosphere of nitrogen. To this solution was added 4-dimethylaminopyridine (150 mg, 1.23 mmol) and triethylamine (0.66 mL, 4.9 mmol). The mixture was stirred for 5 minutes before solid di-tert-butyldicarbonate (1.0 g, 4.9 mmol) was added directly to the reaction mixture. The mixture was stirred overnight at 25° C. and was diluted with ethyl acetate and washed with sodium bicarbonate, followed by washing with saturated sodium chloride. The resulting organic layer was dried over magnesium sulfate, filtered and evaporated to give a beige solid (36, 1.8 g, 4.6 mmol). MS (ESI) [M+H$^+$]$^+$=395.2.

Step-4—Preparation of {5-[Hydroxy-(1H-pyrrolo[2,3-b]pyridin-3-yl)-methyl]-6-methyl-pyridin-2-yl}-(4-trifluoromethyl-benzyl)-carbamic acid tert-butyl ester (37) and {5-[Methoxy-(1H-pyrrolo[2,3-b]pyridin-3-yl)-methyl]-6-methyl-pyridin-2-yl}-(4-trifluoromethyl-benzyl)-carbamic acid tert-butyl ester (38)

1H-Pyrrolo[2,3-b]pyridine (1, 540 mg, 4.57 mmol) was added to a stirring solution of potassium hydroxide (868 mg, 10.08 mmol) in methanol (33 mL). Once the mixture was homogeneous, (5-formyl-6-methyl-pyridin-2-yl)-(4-trifluoromethyl-benzyl)-carbamic acid tert-butyl ester (36, 1.8 g, 4.6 mmol) was added and the mixture was stirred at 25° C. for 72 hours. The solvent was evaporated and 1 M HCl was added to the residue. The organic material was extracted with ethyl acetate and washed with 10% sodium bicarbonate, followed by washing with saturated sodium chloride. The organic layer was dried over magnesium sulfate. Concentration under reduced pressure afforded the crude material, which was purified by silica gel column chromatography (0-5% methanol in dichloromethane) to yield the desired compounds as a light yellow solid (37 and 38 as a mixture, 294 mg; 13% yield). MS (ESI) [M+H$^+$]$^+$=511.2 for 37 and MS (ESI) [M+H$^+$]$^+$=525.2 for 38.

Step-5 Preparation of [6-Methyl-5-(1H-pyrrolo[2,3-b]bipyridin-3-ylmethyl)-pyridin-2-yl]-(4-trifluoromethyl-benzyl)-amine (P-0013)

The combined materials of {5-[Hydroxy-(1H-pyrrolo[2,3-b]pyridin-3-yl)-methyl]-6-methyl-pyridin-2-yl}-(4-trifluoromethyl-benzyl)-carbamic acid tert-butyl ester (37) and {5-[Methoxy-(1H-pyrrolo[2,3-b]pyridin-3-yl)-methyl]-6-methyl-pyridin-2-yl}-(4-trifluoromethyl-benzyl)-carbamic acid tert-butyl ester (38) (194 mg, 0.378 mmol) were dissolved in acetonitrile (3 mL) and triethylsilane (0.30 mL, 1.9 mmol) and trifluoroacetic acid (0.17 mL, 2.3 mmol) were added. After stirring at 25° C. for overnight, TLC analysis indicated that the reaction was about 50% complete. To the reaction mixture was added triethylsilane (0.30 mL, 1.9 mmol), and trifluoroacetic acid (0.17 mL, 2.3 mmol). The mixture was allowed to stir for another 48 hours at 25° C. and the solvent, excess triethylsilane and trifluoroacetic acid were removed by evaporation. Ethyl acetate was added and washed with saturated sodium bicarbonate. The organic layer was dried over magnesium sulfate, filtered and concentrated at reduced pressure to afford a brown oil. Purification of 80 mg of the crude material was carried out using preparatory chromatography (50% ethyl acetate in hexanes) to afford the compound as an off-white solid (P-0013, 10 mg, 0.025 mmol).

MS (ESI) [M+H$^+$]$^+$=397.2.

(4-Chloro-benzyl)-[6-methyl-5-(1H-pyrrolo[2,3-b]pyridin-3-ylmethyl)-pyridin-2-yl]-amine P-0014

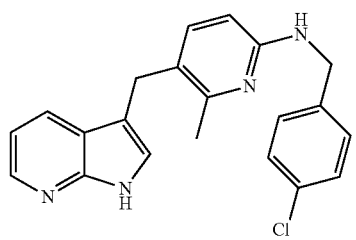 [SMILES: Cc1nc(NCc2ccc(Cl)cc2)ccc1Cc1c[nH]c2ncccc12]

was prepared following the protocol of Scheme 18, substituting 4-trifluoromethyl benzaldehyde with 4-chlorobenzaldehyde (40) in Step 1. MS (ESI) [M+H$^+$]$^+$=363.1.

Example 17

Synthesis of [5-(5-Bromo-1H-pyrrolo[2,3-b]pyridin-3-ylmethyl)-pyridin-2-yl]-(4-chloro-benzyl)-amine (P-0038)

[5-(5-Bromo-1H-pyrrolo[2,3-b]pyridin-3-ylmethyl)-pyridin-2-yl]-(4-chloro-benzyl)-amine P-0038 was synthesized in 5 steps from commercially available 2-Amino-5-bromopyridine 15 as shown in Scheme 19.

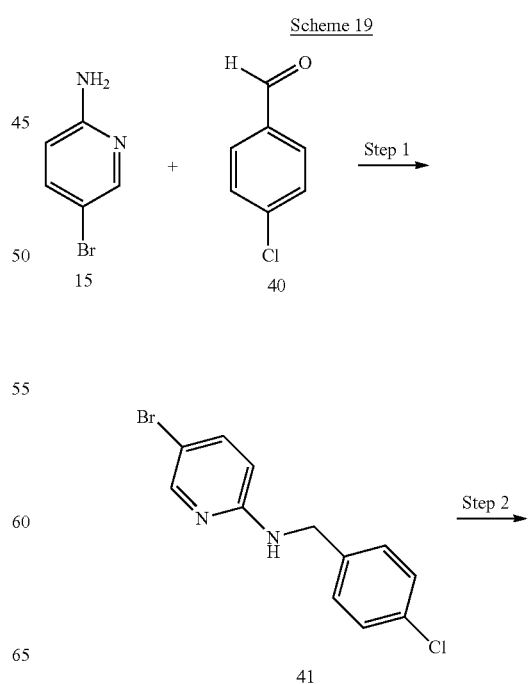

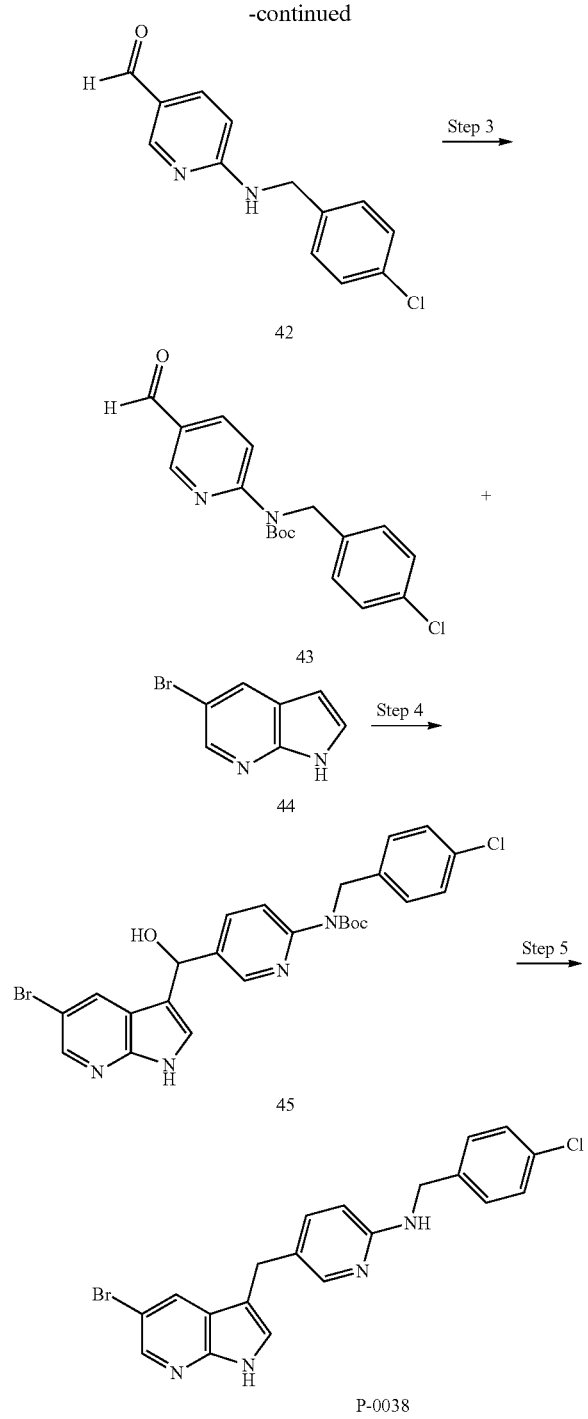

Step 1—Synthesis of (5-Bromo-pyridin-2-yl)-(4-chlorobenzyl)-amine (41)

To 2-Amino-5-bromopyridine (15, 6.10 g, 0.0352 mol) in toluene (90.0 mL) were added 4-chlorobenzaldehyde (40, 5.00 g, 0.0356 mol), trifluoroacetic acid (8.0 mL, 0.10 mol) and triethylsilane (16.5 mL, 0.103 mol). The reaction was heated to reflux for 48 hours. The reaction was concentrated, poured into aqueous potassium carbonate and extracted with ethyl acetate. The organic layer was washed with brine, dried over sodium sulfate and concentrated. The crude residue was crystallized with ethyl acetate to give compound (41, 6.8 g, 65.4%).

Step 2—Synthesis of 6-(4-Chloro-benzylamino)-pyridine-3-carbaldehyde (42)

To (5-Bromo-pyridin-2-yl)-(4-chloro-benzyl)-amine (41, 10.00 g, 0.03360 mol) in tetrahydrofuran (400.0 mL) under an atmosphere of nitrogen at −78° C. was added n-butyllithium (17.5 mL, 2.00 M in cyclohexane). After 90 minutes, tert-butyllithium (42.00 mL, 1.70 M in hexane) was added to the reaction. After 80 minutes, N,N-dimethylformamide (6.9 mL, 0.089 mol) was added to the reaction. The reaction mixture was stirred at −78° C. for 2 hours, then allowed to warm to room temperature for 1 hour. The reaction mixture was poured into water and extracted with ethyl acetate. The organic layer was washed with brine, dried over sodium sulfate and concentrated to give the crude compound, which was crystallized from tert-butoxyl methyl ether to provide compound (42, 7.66 g, 92.2%).

Step 3—Synthesis of (4-Chloro-benzyl)-(5-formyl-pyridin-2-yl)-carbamic acid tert-butyl ester (43)

To 6-(4-Chloro-benzylamino)-pyridine-3-carbaldehyde (42, 2.00 g, 8.11 mmol) in dichloromethane (20.0 mL) were added triethylamine (1.70 mL, 12.2 mmol), di-tert-butyldicarbonate (2.00 g, 9.16 mmol) and 4-dimethylaminopyridine (52.3 mg, 0.43 mmol). The reaction was stirred at room temperature for 48 hours. The reaction was concentrated and purified by silica gel column chromatography eluting with 20% ethyl acetate in hexane to give compound (43, 2.50 g, 89.3%).

Step 4—Synthesis of {5-[(5-Bromo-1H-pyrrolo[2,3-b]pyridin-3-yl)-hydroxy-methyl]-pyridin-2-yl}-(4-chloro-benzyl)-carbamic acid tert-butyl ester (45)

To 5-bromo-7-azaindole (44, 198.0 mg, 1.01 mmol) in methanol (30.0 mL, 0.741 mol) were added (4-Chloro-benzyl)-(5-formyl-pyridin-2-yl)-carbamic acid tert-butyl ester (43, 355.0 mg, 1.02 mmol) and potassium hydroxide (80.0 mg, 1.42 mmol). The reaction was stirred at room temperature 48 hours. The reaction mixture was poured into water and extracted with ethyl acetate. The organic layer was washed with brine, dried over sodium sulfate, concentrated and purified by silica gel column chromatography eluting with 8% methanol in dichloromethane to give compound (45, 200.0 mg, 36.8%).

Step 5—Synthesis of [5-(5-Bromo-1H-pyrrolo[2,3-b]pyridin-3-ylmethyl)-pyridin-2-yl]-(4-chloro-benzyl)-amine (P-0038)

To {5-[(5-Bromo-1H-pyrrolo[2,3-b]pyridin-3-yl)-hydroxy-methyl]-pyridin-2-yl}-(4-chloro-benzyl)-carbamic acid tert-butyl ester (45, 180.0 mg, 0.33 mmol) in acetonitrile (30.0 mL) were added trifluoroacetic acid (2.0 mL, 0.026 mol) and triethylsilane (4.0 mL, 0.025 mol). The reaction was heated to reflux for 4 hours. The reaction mixture was poured into water and extracted with ethyl acetate. The organic layer was washed with brine, dried over sodium sulfate, concentrated and purified by silica gel column chromatography eluting with 10% methanol in dichloromethane to give compound (P-0038, 120 mg, 85.2%).

MS (ESI)[M+H$^+$]$^+$=427.2, 429.2.

Additional compounds were prepared following the protocol of Scheme 19, optionally replacing 4-chlorobenzaldehyde 40 with an appropriate aldehyde in Step 1 and optionally replacing 5-bromo-7-azaindole 44 with an appropriate azaindole in Step 4. The following compounds were made following this procedure:

[5-(5-Chloro-1H-pyrrolo[2,3-b]pyridin-3-ylmethyl)-pyridin-2-yl]-(6-trifluoromethyl-pyridin-3-ylmethyl)-amine (P-0181),

[5-(1H-Pyrrolo[2,3-b]pyridin-3-ylmethyl)-pyridin-2-yl]-(6-trifluoromethyl-pyridin-3-ylmethyl)-amine (P-0182), 3-[6-(4-Chloro-benzylamino)-pyridin-3-ylmethyl]-1H-pyrrolo[2,3-b]pyridine-5-carbonitrile (P-0257), 3-[6-(4-Trifluoromethyl-benzylamino)-pyridin-3-ylmethyl]-1H-pyrrolo[2,3-b]pyridine-5-carbonitrile (P-0269),

[5-(5-Chloro-1H-pyrrolo[2,3-b]pyridin-3-ylmethyl)-pyridin-2-yl]-(2-fluoro-benzyl)-amine (P-0270), 3-[6-(2-Fluoro-benzylamino)-pyridin-3-ylmethyl]-1H-pyrrolo[2,3-b]pyridine-5-carbonitrile (P-0271), (2-Fluoro-benzyl)-[5-(5-methyl-1H-pyrrolo[2,3-b]pyridin-3-ylmethyl)-pyridin-2-yl]-amine (P-0272), 3-{6-[(6-Trifluoromethyl-pyridin-3-ylmethyl)-amino]-pyridin-3-ylmethyl}-1H-pyrrolo[2,3-b]pyridine-5-carbonitrile (P-0273), 3-[6-(2-Trifluoromethyl-benzylamino)-pyridin-3-ylmethyl]-1H-pyrrolo[2,3-b]pyridine-5-carbonitrile (P-0274),

[5-(5-Chloro-1H-pyrrolo[2,3-b]pyridin-3-ylmethyl)-pyridin-2-yl]-(2-trifluoromethyl-benzyl)-amine (P-0275),

[5-(5-Methyl-1H-pyrrolo[2,3-b]pyridin-3-ylmethyl)-pyridin-2-yl]-(2-trifluoromethyl-benzyl)-amine (P-0276), 3-[6-(2,6-Difluoro-benzylamino)-pyridin-3-ylmethyl]-1H-pyrrolo[2,3-b]pyridine-5-carbonitrile (P-0277),

[5-(5-Chloro-1H-pyrrolo[2,3-b]pyridin-3-ylmethyl)-pyridin-2-yl]-(2,6-difluoro-benzyl)-amine (P-0278), (2-Chloro-benzyl)-[5-(5-methyl-1H-pyrrolo[2,3-b]pyridin-3-ylmethyl)-pyridin-2-yl]-amine (P-0279), (2-Chloro-benzyl)-[5-(5-chloro-1H-pyrrolo[2,3-b]pyridin-3-ylmethyl)-pyridin-2-yl]-amine (P-0280), 3-[6-(2-Chloro-benzylamino)-pyridin-3-ylmethyl]-1H-pyrrolo[2,3-b]pyridine-5-carbonitrile (P-0281), (6-M ethoxy-pyridin-3-ylmethyl)-[5-(5-methyl-1H-pyrrolo[2,3-b]pyridin-3-ylmethyl)-pyridin-2-yl]-amine (P-0282),

[5-(5-Chloro-1H-pyrrolo[2,3-b]pyridin-3-ylmethyl)-pyridin-2-yl]-(6-methoxy-pyridin-3-ylmethyl)-amine (P-0283), 3-{6-[(6-M ethoxy-pyridin-3-ylmethyl)-amino]-pyridin-3-ylmethyl}-1H-pyrrolo[2,3-b]pyridine-5-carbonitrile (P-0284), (2-M ethoxy-pyridin-3-ylmethyl)-[5-(5-methyl-1H-pyrrolo[2,3-b]pyridin-3-ylmethyl)-pyridin-2-yl]-amine (P-0285),

[5-(5-Chloro-1H-pyrrolo[2,3-b]pyridin-3-ylmethyl)-pyridin-2-yl]-(2-methoxy-pyridin-3-ylmethyl)-amine (P-0286), 3-{6-[(2-M ethoxy-pyridin-3-ylmethyl)-amino]-pyridin-3-ylmethyl}-1H-pyrrolo[2,3-b]pyridine-5-carbonitrile (P-0287), (2-Ethoxy-benzyl)-[5-(1H-pyrrolo[2,3-b]pyridin-3-ylmethyl)-pyridin-2-yl]-amine (P-0288), (2,5-Difluoro-benzyl)-[5-(1H-pyrrolo[2,3-b]pyridin-3-ylmethyl)-pyridin-2-yl]-amine (P-0296), (2,5-Difluoro-benzyl)-[5-(5-methyl-1H-pyrrolo[2,3-b]pyridin-3-ylmethyl)-pyridin-2-yl]-amine (P-0297),

[5-(5-Chloro-1H-pyrrolo[2,3-b]pyridin-3-ylmethyl)-pyridin-2-yl]-(2,5-difluoro-benzyl)-amine (P-0298), 3-[6-(2,5-Difluoro-benzylamino)-pyridin-3-ylmethyl]-1H-pyrrolo[2,3-b]pyridine-5-carbonitrile (P-0299), 3-[6-(2-Trifluoromethoxy-benzylamino)-pyridin-3-ylmethyl]-1H-pyrrolo[2,3-b]pyridine-5-carbonitrile (P-0321),

[5-(1H-Pyrrolo[2,3-b]pyridin-3-ylmethyl)-pyridin-2-yl]-(2-trifluoromethoxy-benzyl)-amine (P-0322), 3-[6-(2-Ethoxy-benzylamino)-pyridin-3-ylmethyl]-1H-pyrrolo[2,3-b]pyridine-5-carbonitrile (P-0323),

[5-(5-Fluoro-1H-pyrrolo[2,3-b]pyridin-3-ylmethyl)-pyridin-2-yl]-(2-trifluoromethyl-benzyl)-amine (P-0325),

[5-(5-Methoxy-1H-pyrrolo[2,3-b]pyridin-3-ylmethyl)-pyridin-2-yl]-(2-trifluoromethyl-benzyl)-amine (P-0326), (2-Chloro-benzyl)-[5-(5-fluoro-1H-pyrrolo[2,3-b]pyridin-3-ylmethyl)-pyridin-2-yl]-amine (P-0327), (2-Chloro-benzyl)-[5-(5-methoxy-1H-pyrrolo[2,3-b]pyridin-3-ylmethyl)-pyridin-2-yl]-amine (P-0328), (2,5-Difluoro-benzyl)-[5-(5-fluoro-1H-pyrrolo[2,3-b]pyridin-3-ylmethyl)-pyridin-2-yl]-amine (P-0329), (2,5-Difluoro-benzyl)-[5-(5-methoxy-1H-pyrrolo[2,3-b]pyridin-3-ylmethyl)-pyridin-2-yl]-amine (P-0330),

[5-(5-Fluoro-1H-pyrrolo[2,3-b]pyridin-3-ylmethyl)-pyridin-2-yl]-(6-methoxy-pyridin-3-ylmethyl)-amine (P-0331), (6-Methoxy-pyridin-3-ylmethyl)-[5-(5-methoxy-1H-pyrrolo[2,3-b]pyridin-3-ylmethyl)-pyridin-2-yl]-amine (P-0332), (2,6-Difluoro-benzyl)-[5-(5-fluoro-1H-pyrrolo[2,3-b]pyridin-3-ylmethyl)-pyridin-2-yl]-amine (P-0333), (2,6-Difluoro-benzyl)-[5-(5-methoxy-1H-pyrrolo[2,3-b]pyridin-3-ylmethyl)-pyridin-2-yl]-amine (P-0334), (2-Methoxy-benzyl)-[5-(1H-pyrrolo[2,3-b]pyridin-3-ylmethyl)-pyridin-2-yl]-amine (P-0336), 3-[6-(2-Methoxy-benzylamino)-pyridin-3-ylmethyl]-1H-pyrrolo[2,3-b]pyridine-5-carbonitrile (P-0337), (2,6-Difluoro-benzyl)-[5-(1H-pyrrolo[2,3-b]pyridin-3-ylmethyl)-pyridin-2-yl]-amine (P-0340), and (2,6-Difluoro-benzyl)-[5-(5-methyl-1H-pyrrolo[2,3-b]pyridin-3-ylmethyl)-pyridin-2-yl]-amine (P-0341).

The following table indicates the aldehyde used in Step 1 in Column 3 and the azaindole used in Step 4 in Column 2 to provide the compound of Column 4. Column 1 provides the compound number and Column 5 the measured mass spectrometry result.

| Compound number | Azaindole in Step 4 | Aldehyde in Step 1 | Compound structure | MS [M + H+]+ |
|---|---|---|---|---|
| P-0181 | 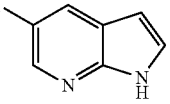 | 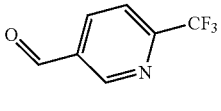 [SMILES: O=Cc1ccc(C(F)(F)F)nc1] | 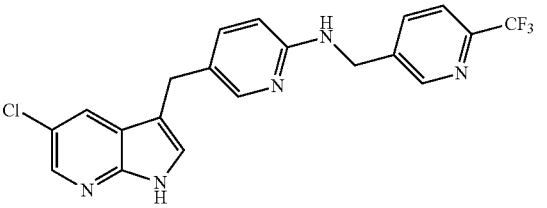 [SMILES: FC(F)(F)c1ccc(CNc2ccc(Cc3c[nH]c4ncc(Cl)cc34)cn2)cn1] | 418.2 |
| P-0182 | 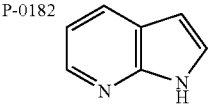 | 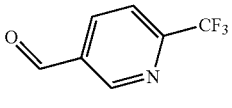 [SMILES: O=Cc1ccc(C(F)(F)F)nc1] | 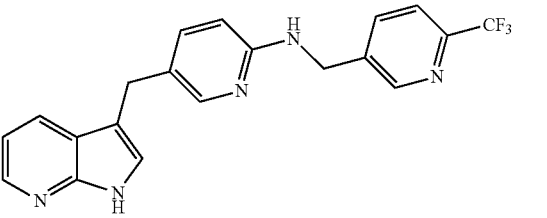 [SMILES: FC(F)(F)c1ccc(CNc2ccc(Cc3c[nH]c4ncccc34)cn2)cn1] | 384.2 |
| P-0257 | 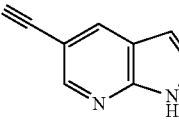 | 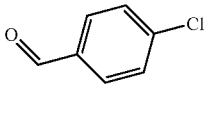 | 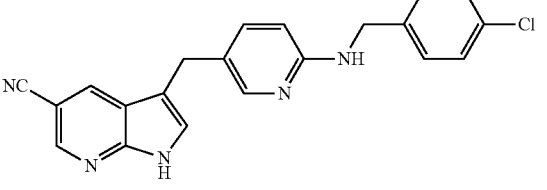 | 374.2 |
| P-0269 | 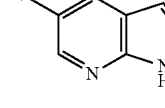 | 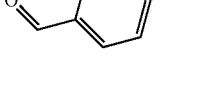 | 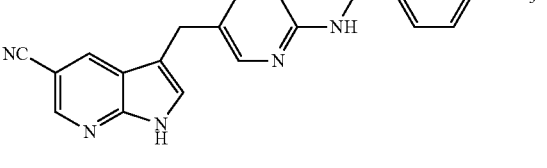 | 408.7 |
| P-0270 | 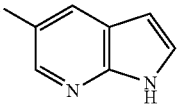 | 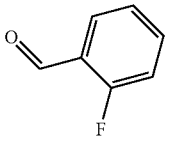 | 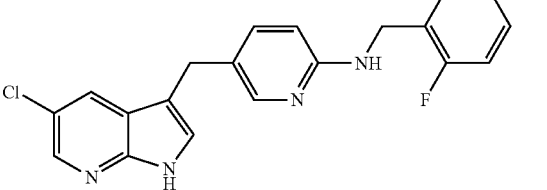 | 367.0 |
| P-0271 | 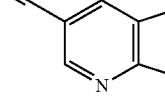 | 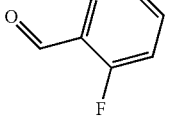 | 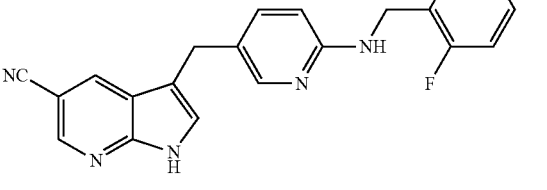 | 358.0 |
| P-0272 | 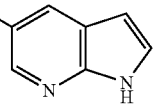 | 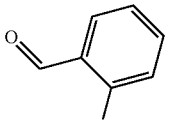 | 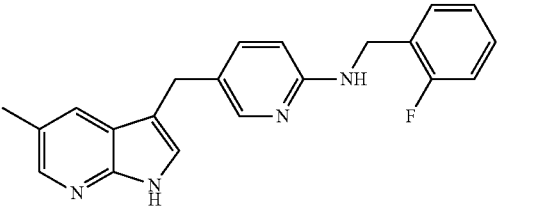 [SMILES: Cc1cnc2[nH]cc(Cc3ccc(NCc4ccccc4F)nc3)c2c1] | 347.0 |

-continued

| Compound number | Azaindole in Step 4 | Aldehyde in Step 1 | Compound structure | MS [M + H+]+ |
|---|---|---|---|---|
| P-0273 | 5-cyano-7-azaindole | 6-(trifluoromethyl)pyridine-3-carbaldehyde | 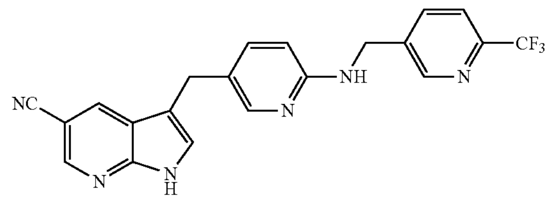 [SMILES: N#Cc1cnc2[nH]cc(Cc3ccc(NCc4ccc(C(F)(F)F)nc4)nc3)c2c1] | 409.4 |
| P-0274 | 5-cyano-7-azaindole | 2-(trifluoromethyl)benzaldehyde | 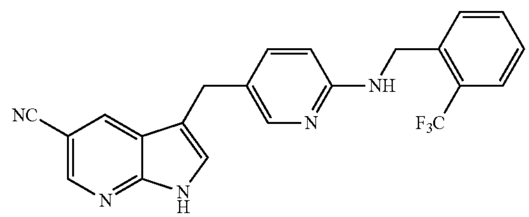 | 408.5 |
| P-0275 | 5-chloro-7-azaindole | 2-(trifluoromethyl)benzaldehyde | 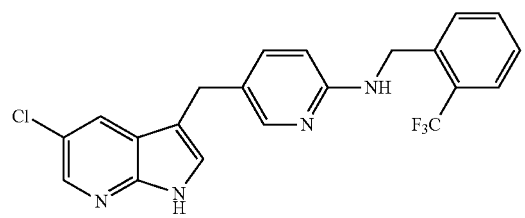 [SMILES: FC(F)(F)c1ccccc1CNc1ccc(Cc2c[nH]c3ncc(Cl)cc23)cn1] | 417.0 |
| P-0276 | 5-methyl-7-azaindole | 2-(trifluoromethyl)benzaldehyde | 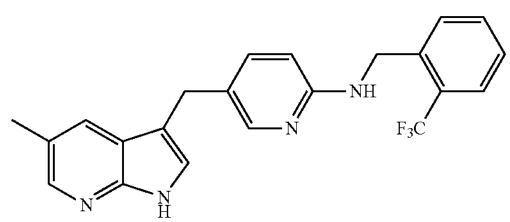 [SMILES: Cc1cnc2[nH]cc(Cc3ccc(NCc4ccccc4C(F)(F)F)nc3)c2c1] | 397.6 |
| P-0277 | 5-cyano-7-azaindole | 2,6-difluorobenzaldehyde | 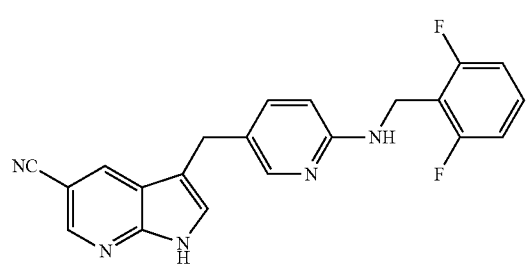 [SMILES: N#Cc1cnc2[nH]cc(Cc3ccc(NCc4c(F)cccc4F)nc3)c2c1] | 376.5 |
| P-0278 | 5-chloro-7-azaindole | 2,6-difluorobenzaldehyde | 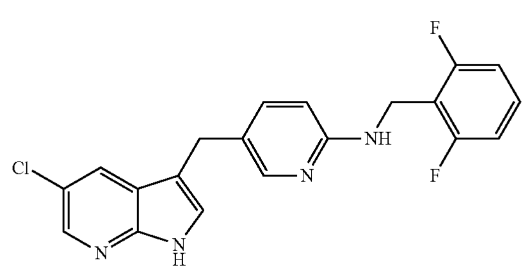 [SMILES: Fc1cccc(F)c1CNc1ccc(Cc2c[nH]c3ncc(Cl)cc23)cn1] | 385.0 |

-continued

| Compound number | Azaindole in Step 4 | Aldehyde in Step 1 | Compound structure | MS [M+H+]+ |
|---|---|---|---|---|
| P-0279 | | | 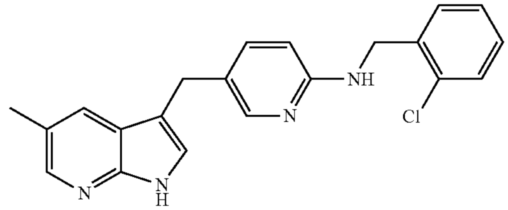 | 363.0 |
| P-0280 | | | 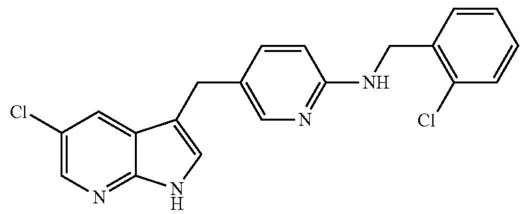 [SMILES: Clc1cnc2[nH]cc(Cc3ccc(NCc4ccccc4Cl)nc3)c2c1] | 383.3 |
| P-0281 | | | 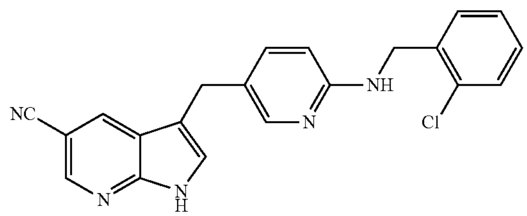 [SMILES: N#Cc1cnc2[nH]cc(Cc3ccc(NCc4ccccc4Cl)nc3)c2c1] | 374.0 |
| P-0282 | | | 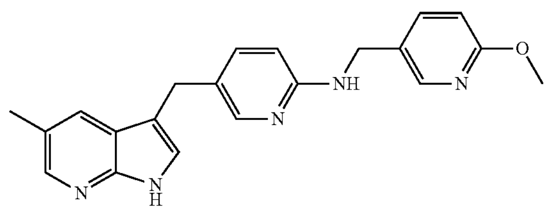 | 360.8 |
| P-0283 | | | 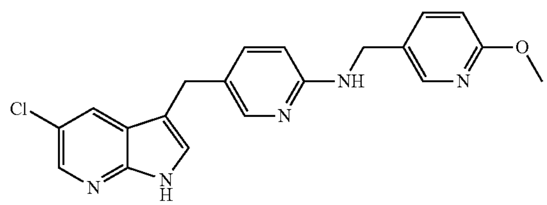 [SMILES: COc1ccc(CNc2ccc(Cc3c[nH]c4ncc(Cl)cc34)cn2)cn1] | 380.0 |
| P-0284 | | | 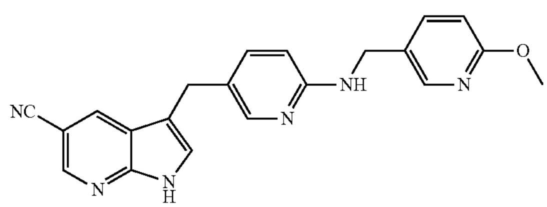 | 371.5 |
| P-0285 | | | 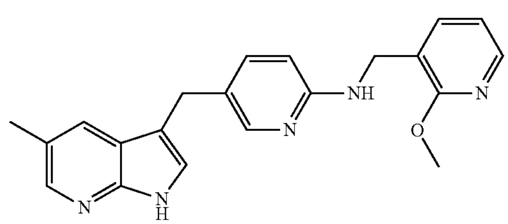 [SMILES: COc1ncccc1CNc1ccc(Cc2c[nH]c3ncc(C)cc23)cn1] | 360.1 |

| Compound number | Azaindole in Step 4 | Aldehyde in Step 1 | Compound structure | MS [M + H+]+ |
|---|---|---|---|---|
| P-0286 | 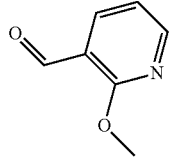 | 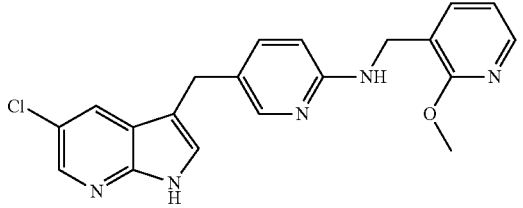 | 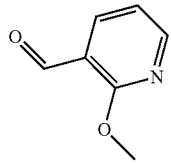 | 380.0 |
| P-0287 | 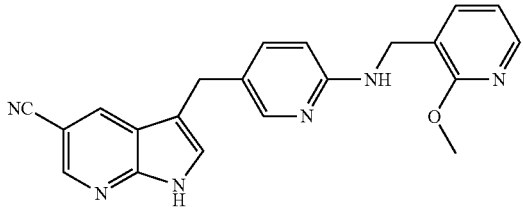 [SMILES: COc1ncccc1CNc1ccc(Cc2c[nH]c3ncc(C#N)cc23)cn1] | 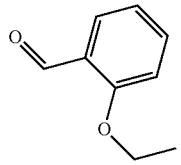 | 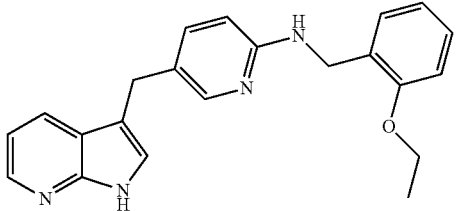 [SMILES: CCOc1ccccc1CNc1ccc(Cc2c[nH]c3ncccc23)cn1] | 371.0 |
| P-0288 | 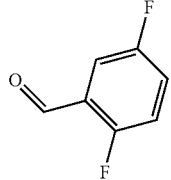 | 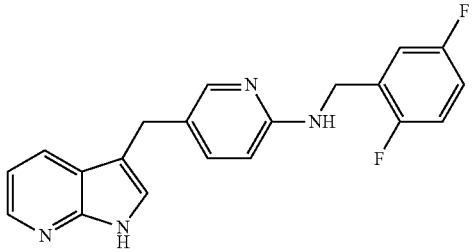 | 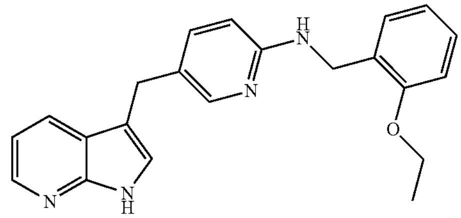 | 359.6 |
| P-0296 | 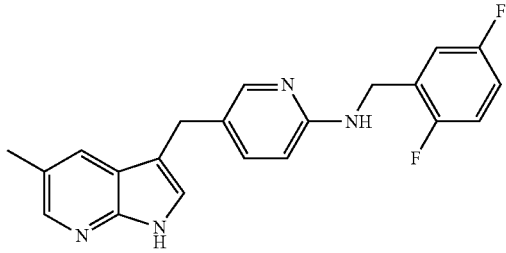 | 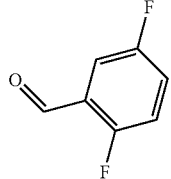 | 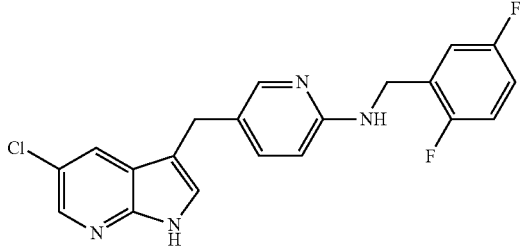 | 351.6 |
| P-0297 | | | 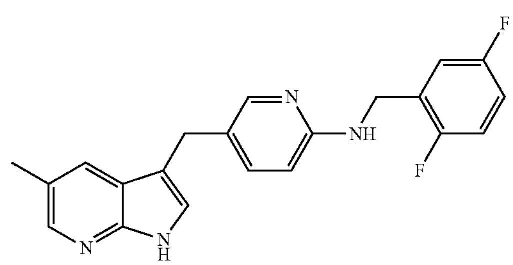 [SMILES: Cc1cnc2[nH]cc(Cc3ccc(NCc4cc(F)ccc4F)nc3)c2c1] | 365.5 |
| P-0298 | | | 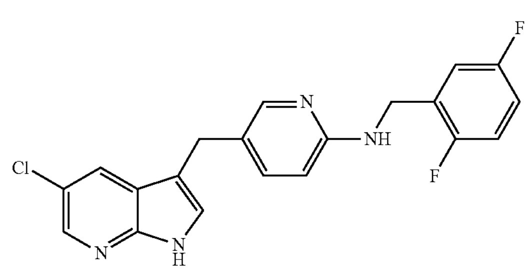 [SMILES: Fc1ccc(F)c(CNc2ccc(Cc3c[nH]c4ncc(Cl)cc34)cn2)c1] | 385.9 |

-continued

| Compound number | Azaindole in Step 4 | Aldehyde in Step 1 | Compound structure | MS [M + H⁺]⁺ |
|---|---|---|---|---|
| P-0299 | | | 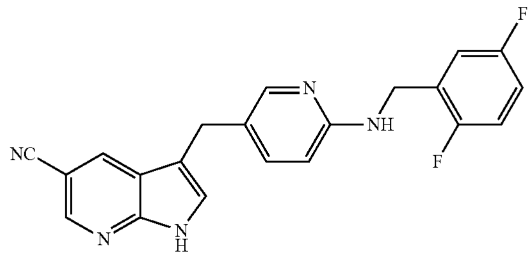 [SMILES: N#Cc1cnc2[nH]cc(Cc3ccc(NCc4cc(F)ccc4F)nc3)c2c1] | 376.4 |
| P-0321 | | | 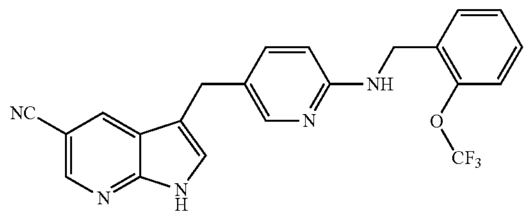 [SMILES: N#Cc1cnc2[nH]cc(Cc3ccc(NCc4ccccc4OC(F)(F)F)nc3)c2c1] | 424.6 |
| P-0322 | | | 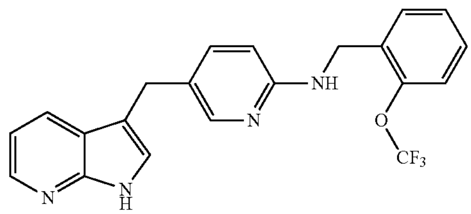 | 399.5 |
| P-0323 | | | 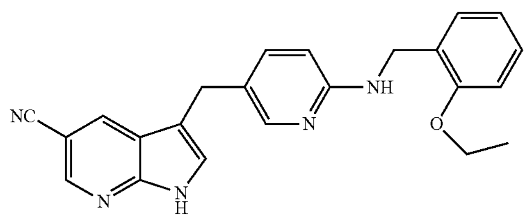 [SMILES: CCOc1ccccc1CNc1ccc(Cc2c[nH]c3ncc(C#N)cc23)cn1] | 384.7 |
| P-0325 | | | 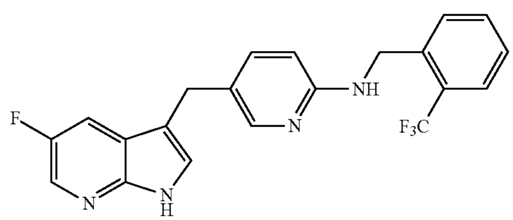 | 401.5 |
| P-0326 | | | 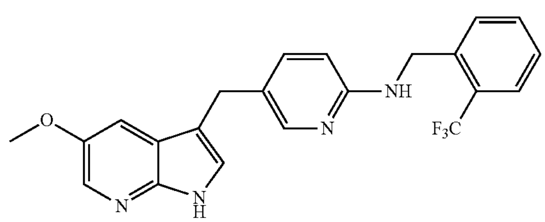 [SMILES: COc1cnc2[nH]cc(Cc3ccc(NCc4ccccc4C(F)(F)F)nc3)c2c1] | 413.4 |

| Compound number | Azaindole in Step 4 | Aldehyde in Step 1 | Compound structure | MS [M + H⁺]⁺ |
|---|---|---|---|---|
| P-0327 | 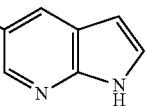 | 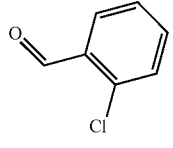 | 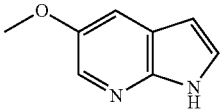 | 367.2 |
| P-0328 | 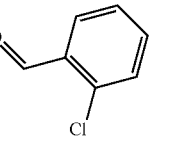 | 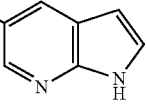 | 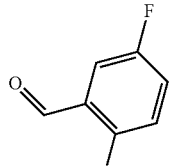 | 379.0 |
| P-0329 | 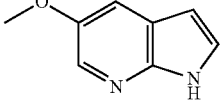 |  | 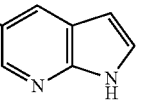 | 369.7 |
| P-0330 | 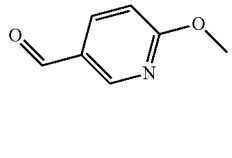 | 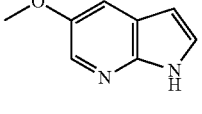 | 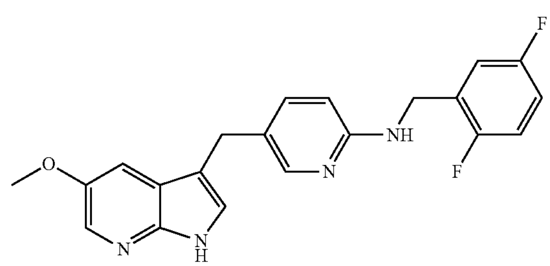 [SMILES: COc1cnc2[nH]cc(Cc3ccc(NCc4cc(F)ccc4F)nc3)c2c1] | 381.6 |
| P-0331 | | | 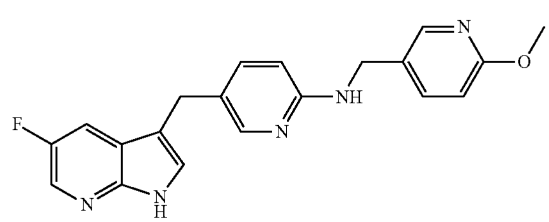 [SMILES: COc1ccc(CNc2ccc(Cc3c[nH]c4ncc(F)cc34)cn2)cn1] | 364.5 |
| P-0332 | | | 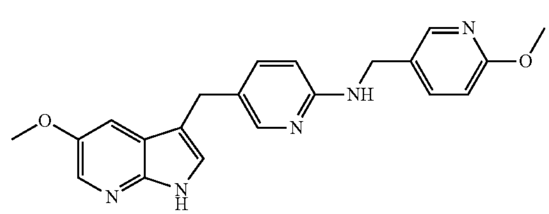 | 376.4 |

-continued

| Compound number | Azaindole in Step 4 | Aldehyde in Step 1 | Compound structure | MS [M + H⁺]⁺ |
|---|---|---|---|---|
| P-0333 | | | 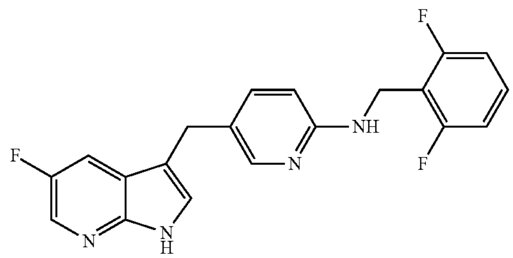 [SMILES: Fc1cnc2[nH]cc(Cc3ccc(NCc4c(F)cccc4F)nc3)c2c1] | 369.6 |
| P-0334 | | | 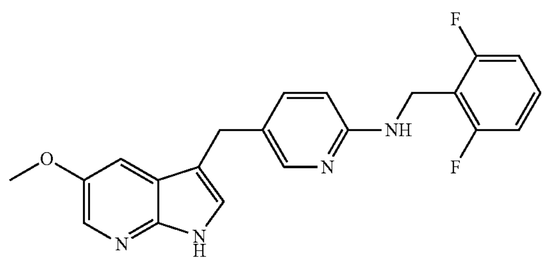 [SMILES: COc1cnc2[nH]cc(Cc3ccc(NCc4c(F)cccc4F)nc3)c2c1] | 381.6 |
| P-0336 | | | 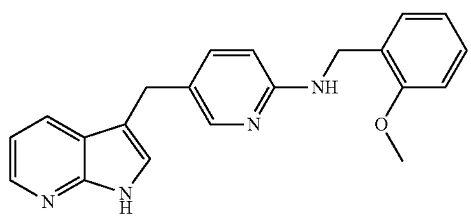 [SMILES: COc1ccccc1CNc1ccc(Cc2c[nH]c3ncccc23)cn1] | 345.7 |
| P-0337 | | | 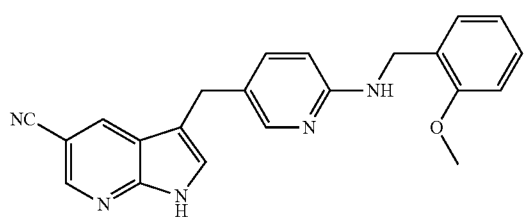 | 370.7 |
| P-0340 | | | 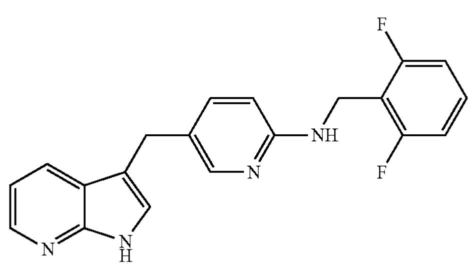 [SMILES: Fc1cccc(F)c1CNc1ccc(Cc2c[nH]c3ncccc23)cn1] | 351.5 |
| P-0341 | | | 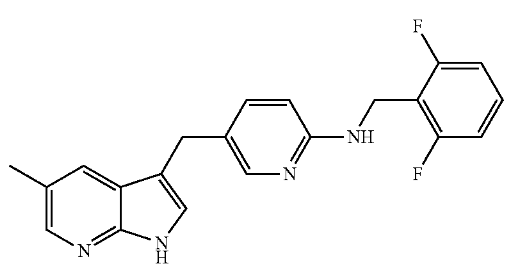 [SMILES: Cc1cnc2[nH]cc(Cc3ccc(NCc4c(F)cccc4F)nc3)c2c1] | 365.5 |

Additional compounds were prepared following the protocol of Scheme 19, Steps 4 and 5, replacing (4-Chloro-benzyl)-(5-formyl-pyridin-2-yl)-carbamic acid tert-butyl ester 43 with an appropriate protected aldehyde and 5-bromo-7-azaindole 44 with an appropriate azaindole in Step 4. Aldehydes were prepared as described in Example 60. The following compounds were made following this procedure:

3-{2-Chloro-6-[(6-trifluoromethyl-pyridin-3-ylmethyl)-amino]-pyridin-3-ylmethyl}-1H-pyrrolo[2,3-b]pyridine-5-carbonitrile (P-0232),

[6-Chloro-5-(5-methyl-1H-pyrrolo[2,3-b]pyridin-3-ylmethyl)-pyridin-2-yl]-(6-trifluoromethyl-pyridin-3-ylmethyl)-amine (P-0233),

[6-Chloro-5-(5-methyl-1H-pyrrolo[2,3-b]pyridin-3-ylmethyl)-pyridin-2-yl]-(6-trifluoromethyl-pyridin-3-ylmethyl)-amine (P-0234), (3-Chloro-pyridin-4-ylmethyl)-[5-(5-chloro-1H-pyrrolo[2,3-b]pyridin-3-ylmethyl)-pyridin-2-yl]-amine (P-0235), 3-{6-[(3-Chloro-pyridin-4-ylmethyl)-amino]-pyridin-3-ylmethyl}-1H-pyrrolo[2,3-b]pyridine-5-carbonitrile (P-0256),

[5-(5-Chloro-1H-pyrrolo[2,3-b]pyridin-3-ylmethyl)-pyridin-2-yl]-(2-difluoromethoxy-benzyl)-amine (P-0338), 3-[6-(2-Difluoromethoxy-benzylamino)-pyridin-3-ylmethyl]-1H-pyrrolo[2,3-b]pyridine-5-carbonitrile (P-0339), The following table indicates the aldehyde used in Column 2 and the azaindole used in Column 3 to provide the compound of Column 4. Column 1 provides the compound number and Column 5 the measured mass spectrometry result.

| Compound number | Aldehyde | Azaindole |
|---|---|---|
| P-0232 | | |
| P-0233 | | |
| P-0234 | | |
| P-0235 | | |
| P-0256 | | |
| P-0338 | | |

-continued
| | | |
|---|---|---|
| P-0339 | 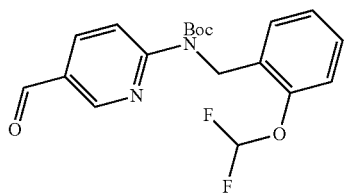 [SMILES: CC(C)(C)OC(=O)N(Cc1ccccc1OC(F)F)c1ccc(C=O)cn1] | 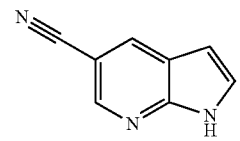 [SMILES: N#Cc1cnc2[nH]ccc2c1] |
| Compound number | Compound | MS [M + H⁺]⁺ |
|---|---|---|
| P-0232 | | 443.0 |
| P-0233 | | [M − H⁺]⁻ = 446.1 |
| P-0234 | | 430.1 |
| P-0235 | | 383.9 |
| P-0256 | | 375.2 |
| P-0338 | | 415.0 |

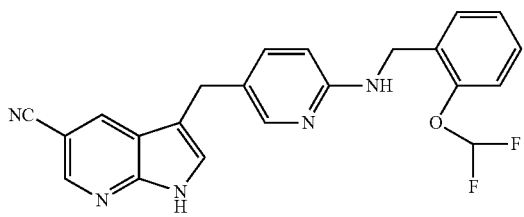 [SMILES: N#Cc1cnc2[nH]cc(Cc3ccc(NCc4ccccc4OC(F)F)nc3)c2c1]

| P-0339 | | 406.6 |

Example 18

Synthesis of 1-triisopropylsilanyl-1H-pyrrolo[2,3-b]pyridine-3-carbaldehyde 47

Compound 47 was synthesized in 2 steps from 7-azaindole 1 as described in Scheme 20.

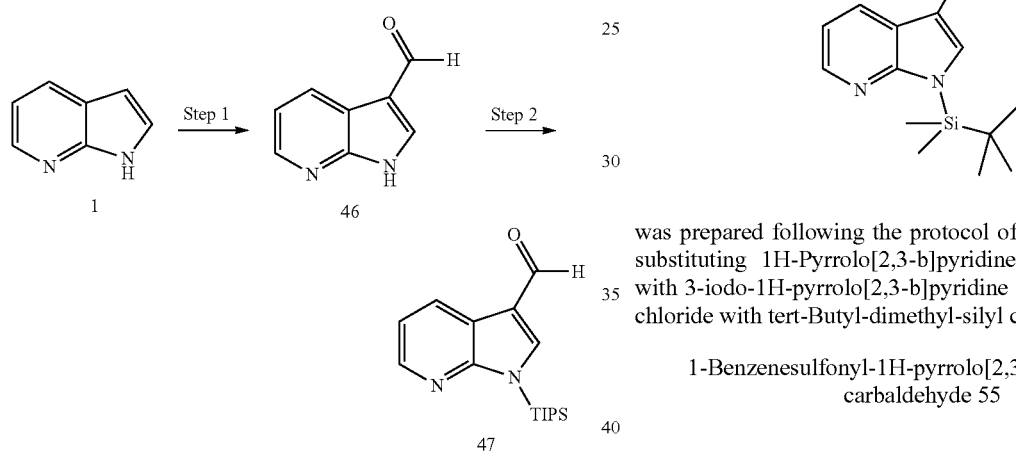

Scheme 20

Step 1—Preparation of 1H-pyrrolo[2,3-b]pyridine-3-carbaldehyde (46)

To 1H-Pyrrolo[2,3-b]pyridine (1, 16.0 g, 135 mmol) in water (110 mL), were added hexamethylenetetramine (26.0 g, 185 mmol), and acetic acid (55.0 mL, 967 mmol). The reaction was refluxed for 12 hours. Water (329 mL) was added and the reaction was cooled to room temperature. The reaction was filtered and washed with water to give compound (46, 15.0 g, 76%). MS (ESI)[M+H$^+$]$^+$=147.

Step 2—Preparation of 1-triisopropylsilanyl-1H-pyrrolo[2,3-b]pyridine-3-carbaldehyde (47)

To 1H-Pyrrolo[2,3-b]pyridine-3-carbaldehyde (46, 4.05 g, 27.71 mmol) in tetrahydrofuran (30.0 mL) were added sodium hydride (60% in mineral oil, 1.5 g, 38 mmol) and triisopropylsilyl chloride (8.0 mL, 38 mmol) under an atmosphere of nitrogen. The reaction was stirred for 2 hours at room temperature. The reaction was poured into water and extracted with ethyl acetate. The organic layer was washed with brine, dried over anhydrous sodium sulfate and filtered. The filtrate was concentrated and purified by silica gel column chromatography eluting with 10% ethyl acetate in hexane to give compound (47, 3.0 g, 36%). MS (ESI) [M+H$^+$]$^+$=303.

1-(tert-Butyl-dimethyl-silanyl)-3-iodo-1H-pyrrolo[2,3-b]pyridine 66

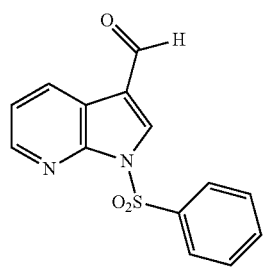 [SMILES: O=Cc1cn(S(=O)(=O)c2ccccc2)c2ncccc12]

was prepared following the protocol of Scheme 20 Step 2, substituting 1H-Pyrrolo[2,3-b]pyridine-3-carbaldehyde 46 with 3-iodo-1H-pyrrolo[2,3-b]pyridine and triisopropylsilyl chloride with tert-Butyl-dimethyl-silyl chloride.

1-Benzenesulfonyl-1H-pyrrolo[2,3-b]pyridine-3-carbaldehyde 55 was prepared following the protocol of Scheme 20, substituting triisopropylsilyl chloride with benzenesulfonyl chloride in Step 2.

Example 19

Synthesis of N-[5-(1H-Pyrrolo[2,3-b]pyridin-3-ylmethyl)-pyridin-2-yl]-4-trifluoromethyl-benzenesulfonamide (P-0071)

N-[5-(1H-Pyrrolo[2,3-b]pyridin-3-ylmethyl)-pyridin-2-yl]-4-trifluoromethyl-benzenesulfonamide P-0071 was synthesized in 3 steps from 2-Amino-5-bromopyridine 15 as shown in Scheme 21.

Scheme 21

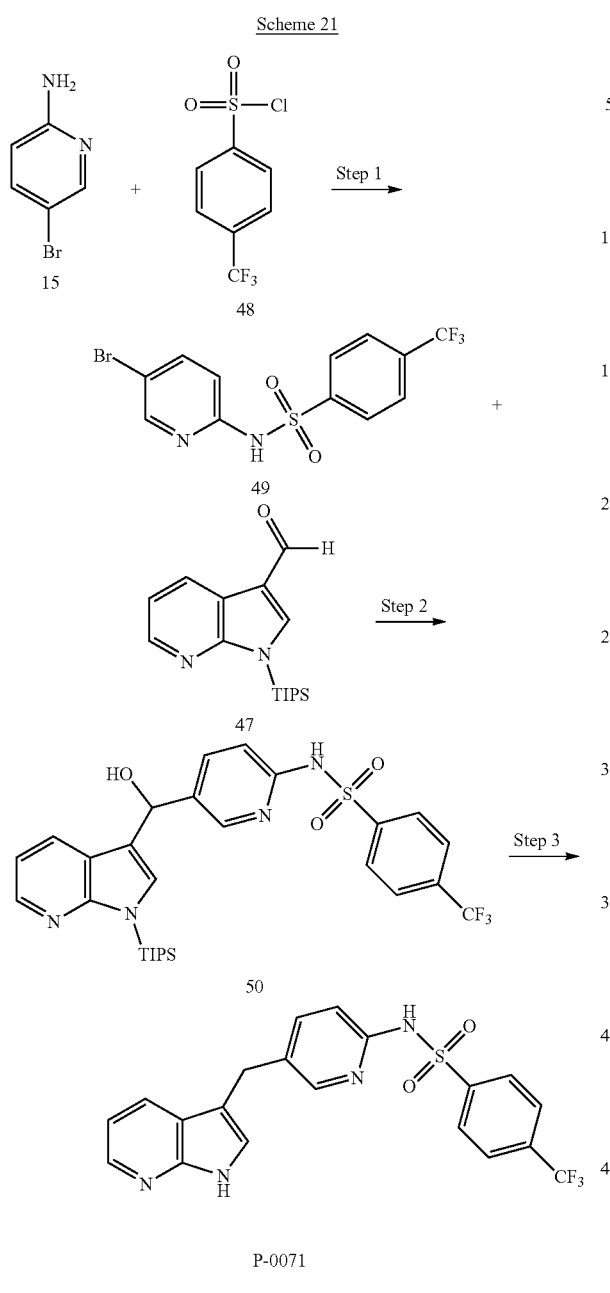

Step 1—Synthesis of N-(5-Bromo-pyridin-2-yl)-4-trifluoromethyl-benzenesulfonamide (49)

To 2-Amino-5-bromopyridine (15, 1.50 g, 8.67 mmol) in acetonitrile (20.0 mL) were added pyridine (6.0 mL, 0.074 mol), 4-dimethylaminopyridine (0.10 g, 0.82 mmol) and 4-trifluoromethyl-benzenesulfonyl chloride (48, 2.14 g, 8.75 mmol). The reaction mixture was stirred at room temperature overnight. The reaction was concentrated, poured into water, acidified with 1N HCl to pH=2, and extracted with ethyl acetate. The organic layer was washed with brine, dried over anhydrous sodium sulfate and concentrated. The residue was washed with ethyl acetate to give a white solid as desired compound (49, 2.80 g, 84.8%). MS (ESI) [M+H$^+$]$^+$=381.0, 383.0.

Step 2—Synthesis of N-5-[Hydroxy-(1-triisopropyl-silanyl-1H-pyrrolo[2,3-b]pyridin-3-yl)-methyl]-pyridin-2-yl-4-trifluoromethyl-benzenesulfonamide (50)

To N-(5-Bromo-pyridin-2-yl)-4-trifluoromethyl-benzenesulfonamide (49, 0.96 g, 2.5 mmol) in tetrahydrofuran (50.0 mL) under an atmosphere of nitrogen at −78° C., tert-butyllithium (4.62 mL, 1.70 M in hexane) was added slowly. After 15 minutes, 1-triisopropylsilanyl-1H-pyrrolo[2,3-b]pyridine-3-carbaldehyde (47, 0.30 g, 0.99 mmol, prepared as described in Example 18) in tetrahydrofuran (15.0 mL) was added to the reaction. After 30 minutes, the reaction was allowed to come to room temperature for 10 minutes. The reaction was poured into water, acidified with 1N HCl to pH around 2, and extracted with ethyl acetate. The organic layer was dried over anhydrous sodium sulfate and filtered. The filtrate was concentrated and purified by silica gel column chromatography eluting with 20% ethyl acetate in hexane to give a white solid compound (50, 0.55 g, 90.1%). MS (ESI) [M+H$^+$]$^+$=605.3.

Step 3—Synthesis of N-[5-(1H-Pyrrolo[2,3-b]pyridin-3-ylmethyl)-pyridin-2-yl]-4-trifluoromethyl-benzenesulfonamide (P-0071)

To N-5-[Hydroxy-(1-triisopropylsilanyl-1H-pyrrolo[2,3-b]pyridin-3-yl)-methyl]-pyridin-2-yl-4-trifluoromethyl-benzenesulfonamide (50, 0.27 g, 0.45 mmol) in acetonitrile (15.0 mL) were added trifluoroacetic acid (1.0 mL, 0.013 mol) and triethylsilane (2.0 mL, 0.012 mol). The reaction was heated to 85° C. for 1 hour. The reaction was concentrated, poured into water and extracted with ethyl acetate. The organic layer was purified with silica gel column chromatography eluting with 50% ethyl acetate in hexane to give a white solid compound (P-0071, 28.5 mg, 14.7%). MS (ESI) [M+H$^+$]$^+$=433.2.

4-Chloro-N-[5-(1H-pyrrolo[2,3-b]pyridin-3-ylmethyl)-pyridin-2-yl]-benzamide P-0074

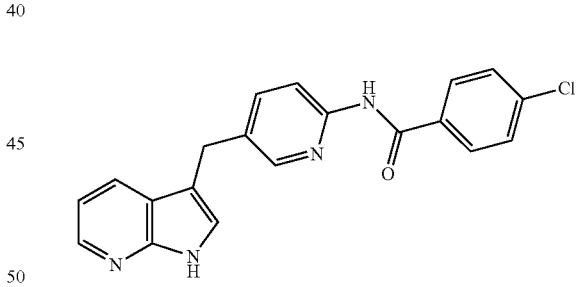

was prepared following the protocol of Scheme 21, substituting 4-trifluoromethyl-benzenesulfonyl chloride 48 with 4-chloro-benzoyl chloride in step 1. MS (ESI) [M+H$^+$]$^+$=363.2.

Example 20

Synthesis of N-[5-(1H-Pyrrolo[2,3-b]pyridin-3-ylmethyl)-pyridin-2-yl]-4-trifluoromethyl-benzamide (P-0072)

N-[5-(1H-Pyrrolo[2,3-b]pyridin-3-ylmethyl)-pyridin-2-yl]-4-trifluoromethyl-benzamide P-0072 was synthesized in one step from (3-(6-Bromo-pyridin-3-ylmethyl)-1-triisopropylsilanyl-1H-pyrrolo[2,3-b]pyridine 6a as shown in Scheme 22.

Scheme 22

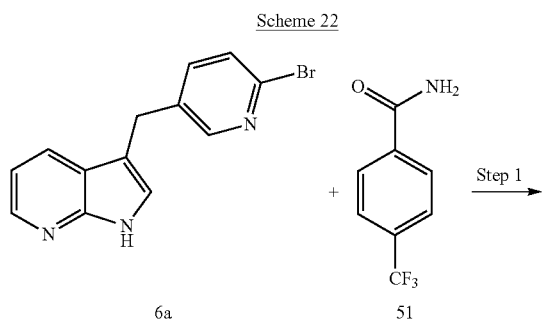

Step 1—Synthesis of N-[5-(1H-Pyrrolo[2,3-b]pyridin-3-ylmethyl)-pyridin-2-yl]-4-trifluoromethyl-benzamide (P-0072)

To 3-(6-Bromo-pyridin-3-ylmethyl)-1H-pyrrolo[2,3-b]pyridine (6a, 50.0 mg, 0.000174 mol, prepared as described in Example 2) in 1,4-dioxane (4.0 mL) were added 4-trifluoromethyl-benzamide (51, 70.0 mg, 0.37 mmol), Xanthphos (15.0 mg, 0.026 mmol), cesium carbonate (130.0 mg, 0.40 mmol) and Tris(dibenzylideneacetone)-dipalladium(0) (25.0 mg, 0.024 mmol) under an atmosphere of nitrogen. The reaction was heated to 120° C. for 10 minutes in a CEM Discover microwave instrument. The reaction was poured into water and extracted with ethyl acetate. The organic layer was dried over anhydrous sodium sulfate and filtered. The filtrate was concentrated and purified by silica gel column chromatography eluting with 50% ethyl acetate in hexane to give a white solid (P-0072, 4.7 mg, 6.8%). MS (ESI) [M+H$^+$]$^+$=397.2.

4-Fluoro-N-[5-(1H-pyrrolo[2,3-b]pyridin-3-ylmethyl)-pyridin-2-yl]-benzamide P-0073

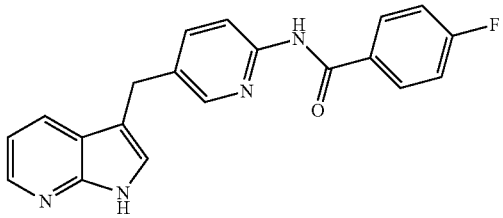 [SMILES: O=C(Nc1ccc(Cc2c[nH]c3ncccc23)cn1)c1ccc(F)cc1]

was prepared following the protocol of Scheme 22, substituting 4-trifluoromethyl-benzamide with 4-fluoromethyl-benzamide. MS (ESI) [M+H$^+$]$^+$=347.2.

Example 21

Synthesis of (4-Chloro-phenyl)-[5-(1H-pyrrolo[2,3-b]pyridin-3-ylmethyl)-pyridin-2-ylmethyl]-amine (P-0078)

(4-Chloro-phenyl)-[5-(1H-pyrrolo[2,3-b]pyridin-3-ylmethyl)-pyridin-2-ylmethyl]-amine P-0078 was synthesized in 3 steps from 5-Bromo-pyridine-2-carbaldehyde 52 as shown in Scheme 23.

Scheme 23

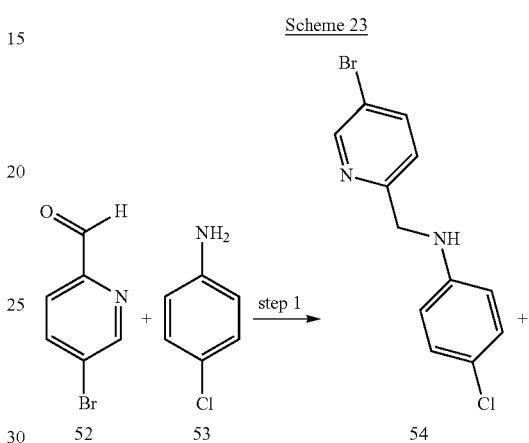

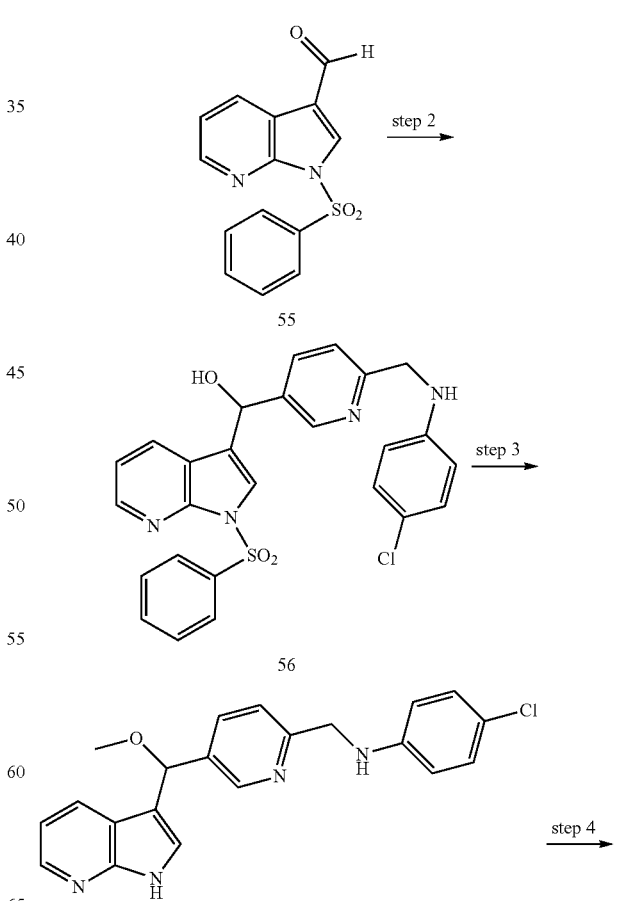

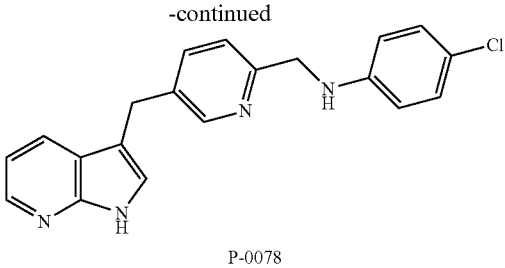

P-0078

Step 1—Synthesis of (5-Bromo-pyridin-2-ylmethyl)-(4-chloro-phenyl)-amine (54)

To 5-Bromo-pyridine-2-carbaldehyde (52, 1.00 g, 5.38 mmol) in acetonitrile (50.0 mL) were added p-chloroaniline (53, 0.686 g, 5.38 mmol), triethylsilane (6.00 mL, 0.0376 mol) and trifluoroacetic acid (3.00 mL, 0.0389 mol). The reaction was heated to reflux for 3 hours. The reaction was concentrated, poured into water and then extracted with ethyl acetate. The organic layer was dried over anhydrous sodium sulfate and filtered. The filtrate was concentrated and purified by silica gel column chromatography eluting with 20% ethyl acetate in hexane to give a white solid (54, 0.75 g, 47.0%).

Step 2—Synthesis of (1-Benzenesulfonyl-1H-pyrrolo[2,3-b]pyridin-3-yl)-6-[(4-chloro-phenylamino)-methyl]-pyridin-3-yl-methanol (56)

To (5-Bromo-pyridin-2-ylmethyl)-(4-chloro-phenyl)-amine (54, 0.380 g, 1.28 mmol) in tetrahydrofuran (15.0 mL) under an atmosphere of nitrogen at −78° C. was added n-butyllithium (0.850 mL, 1.60 M in hexane). After 10 minutes, 1,2-bis-(chloro-dimethyl-silanyl)-ethane (0.135 g, 0.627 mmol) in tetrahydrofuran (5.0 mL) was added to the reaction. The reaction was allowed to warm to room temperature for 40 minutes. The reaction was cooled to −78° C., followed by addition of 1.70 M tert-butyllithium in hexane (1.58 mL). After 30 minutes, 1-benzenesulfonyl-1H-pyrrolo[2,3-b]pyridine-3-carbaldehyde (55, 0.380 g, 1.33 mmol, prepared as described in Example 18) in tetrahydrofuran (10.0 mL) was added to the reaction. After 20 minutes, the reaction was allowed to warm to room temperature. The reaction was poured into water and extracted with ethyl acetate. The organic layer was dried over anhydrous sodium sulfate and filtered. The filtrate was concentrated and purified by silica gel column chromatography eluting with 50% ethyl acetate in hexane to give compound (56, 0.30 g, 46.0%). MS (ESI) [M+H$^+$]$^+$=505.3.

Step 3—(4-Chloro-phenyl)-5-[methoxy-(1H-pyrrolo[2,3-b]pyridin-3-yl)-methyl]-pyridin-2-ylmethyl-amine (57)

To (1-Benzenesulfonyl-1H-pyrrolo[2,3-b]pyridin-3-yl)-6-[(4-chloro-phenylamino)-methyl]-pyridin-3-yl-methanol (56, 120.0 mg, 0.24 mmol) in methanol (20.0 mL) were added potassium hydroxide (0.400 g, 7.13 mmol) and water (5.0 mL, 0.28 mol). The reaction was heated to 50° C. for 10 hours. The reaction was poured into water and extracted with ethyl acetate. The organic layer was dried over anhydrous sodium sulfate and filtered. The filtrate was concentrated and purified by silica gel column chromatography eluting with 20% ethyl acetate in hexane to give compound (57, 30 mg, 33.0%). MS (ESI) [M+H$^+$]$^+$=379.4.

Step 4—Synthesis of (4-Chloro-phenyl)-[5-(1H-pyrrolo[2,3-b]pyridin-3-ylmethyl)-pyridin-2-ylmethyl]-amine (P-0078)

To (4-Chloro-phenyl)-5-[methoxy-(1H-pyrrolo[2,3-b]pyridin-3-yl)-methyl]-pyridin-2-ylmethyl-amine (57, 20.8 mg, 0.055 mmol) in acetonitrile (10.0 mL) were added trifluoroacetic acid (0.50 mL, 6.5 mmol) and triethylsilane (1.00 mL, 6.26 mmol). The reaction was heated to reflux for 3 hours, then poured into water and extracted with ethyl acetate. The organic layer was dried over anhydrous sodium sulfate and filtered. The filtrate was concentrated and purified by silica gel column chromatography eluting with 10% methanol in dichloromethane to give compound (P-0078, 6.1 mg, 32.0%). MS (ESI) [M+H$^+$]$^+$=349.4.

Example 22

Synthesis of (4-Chloro-benzyl)-[6-fluoro-5-(1H-pyrrolo[2,3-b]pyridin-3-ylmethyl)-pyridin-2-yl]-amine (P-0082)

(4-Chloro-benzyl)-[6-fluoro-5-(1H-pyrrolo[2,3-b]pyridin-3-ylmethyl)-pyridin-2-yl]-amine P-0082 was synthesized in 8 steps from 2,6-Difluoropyridine 58 as shown in Scheme 24.

Scheme 24

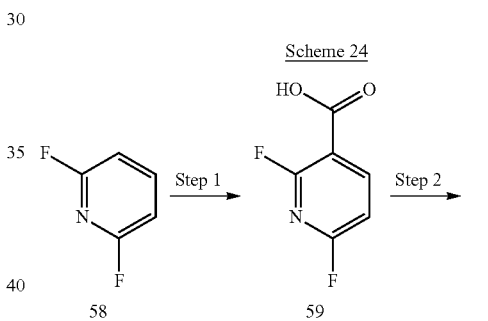

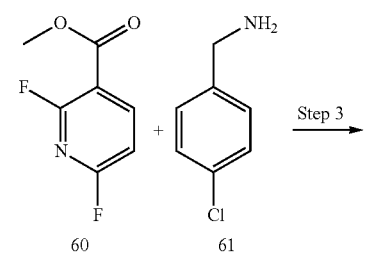

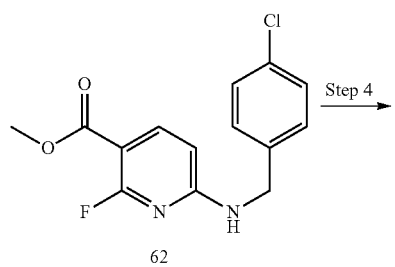

213

-continued

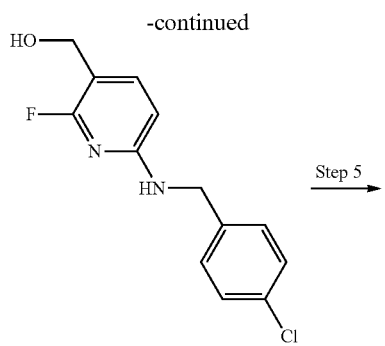

63

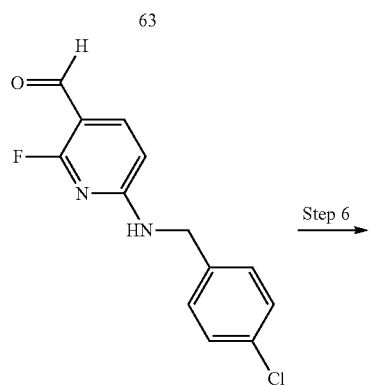

64

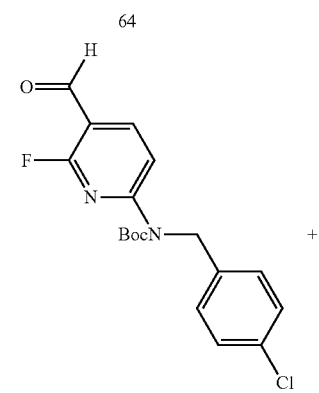

65

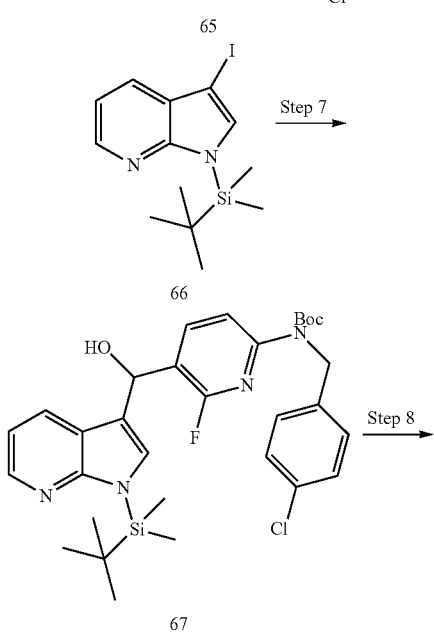

66

67

214

-continued

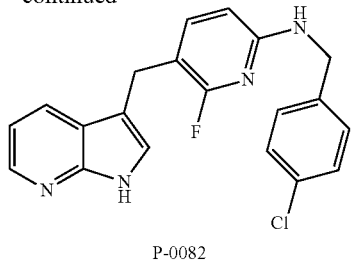

P-0082

Step 1—Synthesis of 2,6-Difluoro-nicotinic acid (59)

To 2,6-difluoropyridine (58, 7.10 g, 0.0617 mol) in tetrahydrofuran (150.0 mL) under an atmosphere of nitrogen at −78° C., n-butyllithium (26.0 mL, 2.50 M in hexane) was added slowly. After 30 minutes, dry ice (3.0 g) was added to the reaction. After 1 hour, the reaction was allowed to warm to room temperature, then poured into water and extracted with ethyl acetate. The aqueous layer was acidified with 1 N HCl to pH=4-5 and extracted with ethyl acetate. The organic layer was dried over anyhydrous sodium sulfate, filtered and concentrated to give the crude compound as a light yellow solid (59, 5.6 g, 57.0%).

Step 2—Synthesis of 2,6-Difluoro-nicotinic acid methyl ester (60)

To 2,6-difluoro-nicotinic acid (59, 5.60 g, 0.0352 mol) in methanol (60.0 mL) was added concentrated sulfuric acid (1.0 mL, 0.019 mol). The reaction was heated to reflux overnight, then poured into water, basified with 1M potassium carbonate to pH around 9, and extracted with ethyl acetate. The organic layer was dried over anhydrous sodium sulfate and concentrated to give a yellow oil (60, 3.5 g, 57.0%).

Step 3—Synthesis of 6-(4-Chloro-benzylamino)-2-fluoro-nicotinic acid methyl ester (62)

To 2,6-difluoro-nicotinic acid methyl ester (60, 2.00 g, 0.0116 mol) in N,N-dimethylformamide (20.0 mL), under an atmosphere of nitrogen at −40° C., was added p-chlorobenzylamine (61, 2.60 mL, 0.0214 mol). The reaction was stirred at −40° C. to −20° C. for 2 hours, then poured into water and extracted with ethyl acetate. The organic layer was dried over anhydrous sodium sulfate and filtered. The filtrate was concentrated and purified by silica gel column chromatography eluting with 25% ethyl acetate in hexane to give compound (62, 2.0 g, 58.7%).

Step 4—Synthesis of [6-(4-Chloro-benzylamino)-2-fluoro-pyridin-3-yl]-methanol (63)

To 6-(4-Chloro-benzylamino)-2-fluoro-nicotinic acid methyl ester (62, 2.00 g, 6.79 mmol) in tetrahydrofuran (100.0 mL) was added lithium tetrahydroaluminate (13.6 mL, 1.00 M in Tetrahydrofuran) under an atmosphere of nitrogen. The reaction was stirred at room temperature overnight. To the reaction was added an excessive amount of $NaSO_4 \cdot 10H_2O$, and then stirred for 1 hour. Filtration, concentration and purification with silica gel column chromatography eluting with 30% ethyl acetate in hexane provided compound 63 (1.0 g, 55.0%).

Step 5—Synthesis of 6-(4-Chloro-benzylamino)-2-fluoro-pyridine-3-carbaldehyde (64)

To [6-(4-Chloro-benzylamino)-2-fluoro-pyridin-3-yl]-methanol (63, 1.0 g, 3.7 mmol) in tetrahydrofuran (50.0 mL) was added Dess-Martin periodinane (1.75 g, 4.12 mmol). The reaction was stirred at room temperature for 10 minutes, then poured into water and extracted with ethyl acetate. The organic layer was dried over anhydrous sodium sulfate and filtered. The filtrate was concentrated and purified by silica gel column chromatography eluting with 20% ethyl acetate in hexane to give a white solid (64, 0.67 g, 68.0%).

Step 6—Synthesis of (4-Chloro-benzyl)-(6-fluoro-5-formyl-pyridin-2-yl)-carbamic acid tert-butyl ester (65)

To 6-(4-Chloro-benzylamino)-2-fluoro-pyridine-3-carbaldehyde (64, 670.0 mg, 2.53 mmol) in dichloromethane (16.2 mL) were added di-tert-butyldicarbonate (1.23 g, 5.65 mmol) and 4-dimethylaminopyridine (16.2 mg, 0.133 mmol). The reaction was stirred at room temperature overnight. The reaction was concentrated and purified by silica gel column chromatography eluting with 30% ethyl acetate in hexane to give a white solid (65, 0.63 g, 68.0%).

Step 7—Synthesis of (5-[1-(tert-Butyl-dimethyl-silanyl)-1H-pyrrolo[2,3-b]pyridin-3-yl]-hydroxy-methyl-6-fluoro-pyridin-2-yl)-(4-chloro-benzyl)-carbamic acid tert-butyl ester (67)

To 1-(tert-butyl-dimethyl-silanyl)-3-iodo-1H-pyrrolo[2,3-b]pyridine (66, 0.53 g, 0.0015 mol) and tetrahydrofuran (15.0 mL), under an atmosphere of nitrogen at −20° C., was added isopropylmagnesium chloride (0.78 mL, 2.0 M in tetrahydrofuran). The reaction was allowed to warm to 0° C. (around 80 minutes), then cooled to −20° C., followed by addition of (4-Chloro-benzyl)-(6-fluoro-5-formyl-pyridin-2-yl)-carbamic acid tert-butyl ester (65, 0.200 g, 0.55 mmol) in tetrahydrofuran (6.0 mL). The reaction was allowed to warm to room temperature in 1 hour, then poured into water and extracted with ethyl acetate. The organic layer was dried over anhydrous sodium sulfate, and filtered. The filtrate was concentrated and purified by silica gel column chromatography eluting with 20% ethyl acetate in hexane to give a yellow solid (67, 0.20 g, 61.1%). MS (ESI) [M+H$^+$]$^+$=597.4.

Step 8—Synthesis of (4-Chloro-benzyl)-[6-fluoro-5-(1H-pyrrolo[2,3-b]pyridin-3-ylmethyl)-pyridin-2-yl]-amine (P-0082)

To (5-[1-(tert-Butyl-dimethyl-silanyl)-1H-pyrrolo[2,3-b]pyridin-3-yl]-hydroxy-methyl-6-fluoro-pyridin-2-yl)-(4-chloro-benzyl)-carbamic acid tert-butyl ester (67, 0.10 g, 0.17 mmol) in acetonitrile (10.0 mL) were added triethylsilane (1.00 mL, 6.26 mmol) and trifluoroacetic acid (0.50 mL, 6.5 mmol). The reaction was heated to reflux for 2 hours, then poured into aqueous potassium carbonate, and extracted with ethyl acetate. The organic layer was dried over anhydrous sodium sulfate, and filtered. The filtrate was concentrated and purified by silica gel column chromatography eluting with 30% ethyl acetate in hexane to give a white solid (P-0082, 43.2 mg, 70.0%). MS (ESI) [M+H$^+$]$^+$=367.4.

Example 23

Synthesis of (4-Chloro-benzyl)-[6-methoxy-5-(1H-pyrrolo[2,3-b]pyridin-3-ylmethyl)-pyridin-2-yl]-amine (P-0081)

(4-Chloro-benzyl)-[6-methoxy-5-(1H-pyrrolo[2,3-b]pyridin-3-ylmethyl)-pyridin-2-yl]-amine P-0081 was synthesized in 2 steps from (4-Chloro-benzyl)-(6-fluoro-5-formyl-pyridin-2-yl)-carbamic acid tert-butyl ester 65 as shown in Scheme 25.

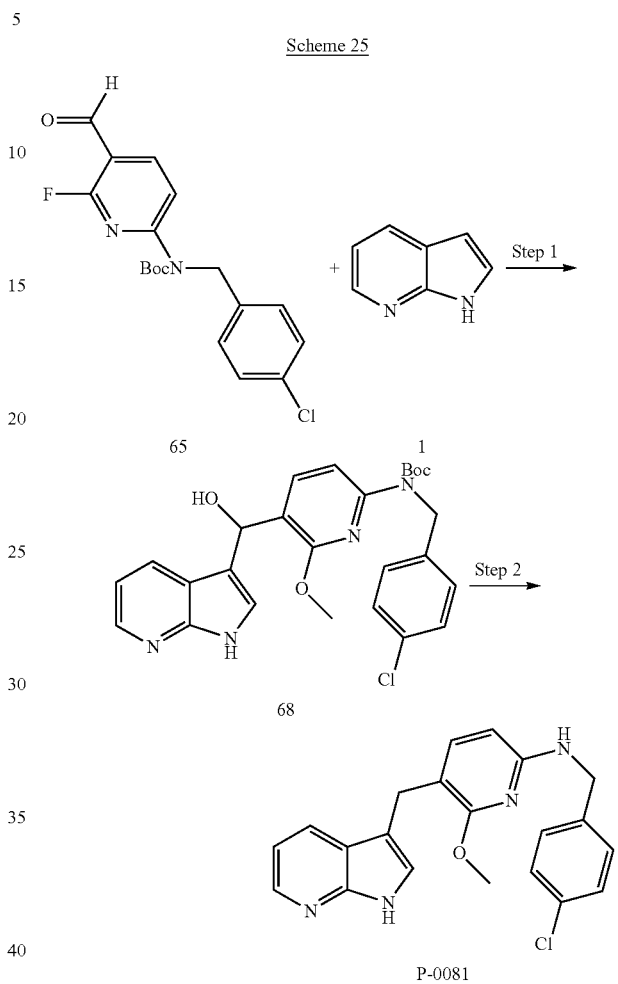

Scheme 25

Step 1—Synthesis of (4-Chloro-benzyl)-5-[hydroxy-(1H-pyrrolo[2,3-b]pyridin-3-yl)-methyl]-6-methoxy-pyridin-2-yl-carbamic acid tert-butyl ester (68)

To 1H-Pyrrolo[2,3-b]pyridine (1, 90.0 mg, 0.76 mmol) in methanol (30.0 mL) were added (4-chloro-benzyl)-(6-fluoro-5-formyl-pyridin-2-yl)-carbamic acid tert-butyl ester (65, 300.0 mg, 0.82 mmol) and potassium hydroxide (720.0 mg, 12.83 mmol) under an atmosphere of nitrogen. The reaction was stirred at room temperature for 2 hours, then poured into water and extracted with ethyl acetate. The organic layer was dried over anhydrous sodium sulfate and filtered. The filtrate was concentrated and purified by silica gel column chromatography eluting with 20% ethyl acetate in hexane to give the compound (68, 60 mg, 15.9%). MS (ESI) [M+H$^+$]$^+$=495.3.

Step 2—Synthesis of (4-Chloro-benzyl)-[6-methoxy-5-(1H-pyrrolo[2,3-b]pyridin-3-ylmethyl)-pyridin-2-yl]-amine (P-0081)

To (4-Chloro-benzyl)-5-[hydroxy-(1H-pyrrolo[2,3-b]pyridin-3-yl)-methyl]-6-methoxy-pyridin-2-yl-carbamic acid tert-butyl ester (68, 40.0 mg, 0.081 mmol) in acetonitrile (10.0 mL) were added trifluoroacetic acid (0.30 mL, 0.0039 mol) and triethylsilane (0.60 mL, 0.0038 mol). The reaction was heated to reflux for 3 hours. The reaction was concentrated to remove the solvents, then purified with silica gel column chromatography eluting with 40% ethyl acetate in hexane to give compound (P-0081, 10 mg, 32.7%). MS (ESI) [M+H$^+$]$^+$=379.4.

Example 24

Synthesis of 5-(1H-Pyrrolo[2,3-b]pyridin-3-ylmethyl)-pyridine-2-carboxylic acid (4-chloro-phenyl)-amide (P-0076)

5-(1H-Pyrrolo[2,3-b]pyridin-3-ylmethyl)-pyridine-2-carboxylic acid (4-chloro-phenyl)-amide P-0076 was synthesized in 3 Steps from 5-Bromo-pyridine-2-carbonyl chloride 69 as shown in Scheme 26.

Scheme 26

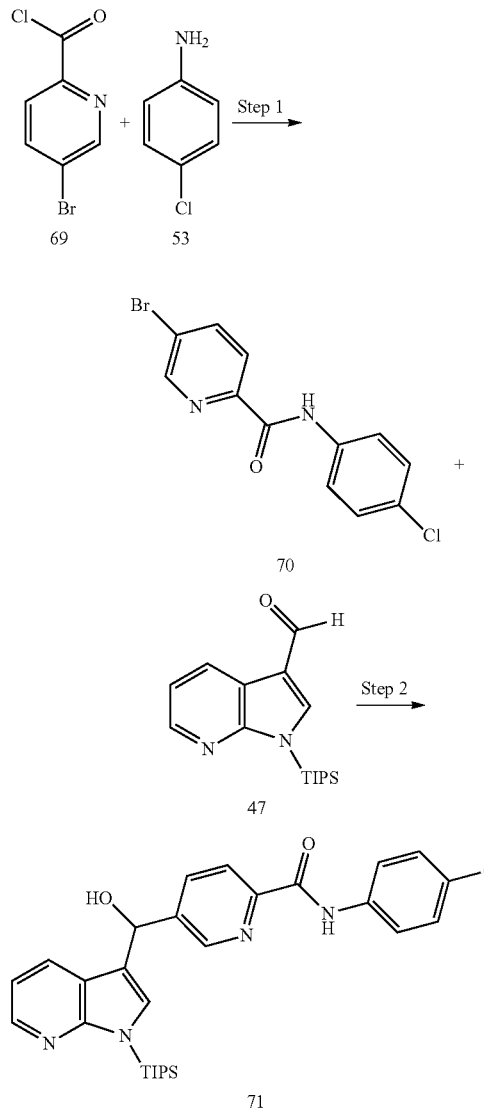

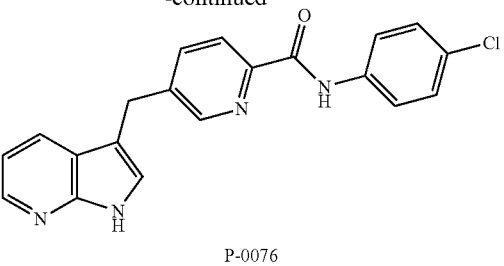

P-0076

Step 1—Synthesis of 5-Bromo-pyridine-2-carboxylic acid (4-chloro-phenyl)-amide (70)

To 5-Bromo-pyridine-2-carbonyl chloride (69, 0.76 g, 3.4 mmol) in acetonitrile (29.0 mL) were added p-chloroaniline (53, 0.702 g, 5.50 mmol), 4-dimethylamino-pyridine (0.12 g, 0.96 mmol) and pyridine (2.9 mL, 0.036 mol). The reaction was stirred at 68° C. overnight, then poured into water, acidified with 1 N HCl to pH around 1 and extracted with ethyl acetate. The organic layer was dried over anhydrous sodium sulfate and filtered. The filtrate was concentrated and purified by silica gel column chromatography eluting with dichloromethane to give a white solid (70, 0.75 g, 70.0%).

Step 2—Synthesis of 5-[Hydroxy-(1-triisopropylsilanyl-1H-pyrrolo[2,3-b]pyridin-3-yl)-methyl]-pyridine-2-carboxylic acid (4-chloro-phenyl)-amide (71)

To 5-Bromo-pyridine-2-carboxylic acid (4-chloro-phenyl)-amide (70, 0.50 g, 1.60 mmol) in tetrahydrofuran (20.0 mL), under an atmosphere of nitrogen at −78° C., tert-butyl-lithium (3.02 mL, 1.70 M in Hexane) was added. After 20 minutes, 1-triisopropylsilanyl-1H-pyrrolo[2,3-b]pyridine-3-carbaldehyde (47, 0.39 g, 1.3 mmol, prepared as described in Example 18) in tetrahydrofuran (10.0 mL) was added to the reaction. The reaction was stirred at −78° C. for 1 hour, then allowed to warm to room temperature for 10 minutes. The reaction was poured into water and extracted with ethyl acetate. The organic layer was dried over anhydrous sodium sulfate and filtered. The filtrate was concentrated and purified by silica gel column chromatography eluting with 20% ethyl acetate in hexane to give the compound as colorless oil (71, 100 mg, 14%). MS (ESI) [M+H$^+$]$^+$=535.3.

Step 3—Synthesis of 5-(1H-Pyrrolo[2,3-b]pyridin-3-ylmethyl)-pyridine-2-carboxylic acid (4-chloro-phenyl)-amide (P-0076)

To 5-[Hydroxy-(1-triisopropylsilanyl-1H-pyrrolo[2,3-b]pyridin-3-yl)-methyl]-pyridine-2-carboxylic acid (4-chlorophenyl)-amide (71, 100.0 mg, 0.19 mmol) in acetonitrile (10.0 mL) were added trifluoroacetic acid (0.20 mL, 2.6 mmol) and triethylsilane (0.40 mL, 2.5 mmol). The reaction was stirred at 80° C. for 2 hours. The reaction was concentrated and purified by silica gel column chromatography eluting with 20% ethyl acetate in hexane to give a yellow solid compound (P-0076, 5.5 mg, 8.1%).
MS (ESI) [M−H$^+$]$^-$=361.1.

Example 25

Synthesis of [6-(3-Hydroxy-phenylamino)-pyridin-3-yl]-(1H-pyrrolo[2,3-b]pyridin-3-yl)-methanone (P-0027)

[6-(3-Hydroxy-phenylamino)-pyridin-3-yl]-(1H-pyrrolo[2,3-b]pyridin-3-yl)-methanone P-0027 was synthesized in 1

Step from [6-(3-Benzyloxy-phenylamino)-pyridin-3-yl]-(1H-pyrrolo[2,3-b]pyridin-3-yl)-methanone P-0026 as shown in Scheme 27.

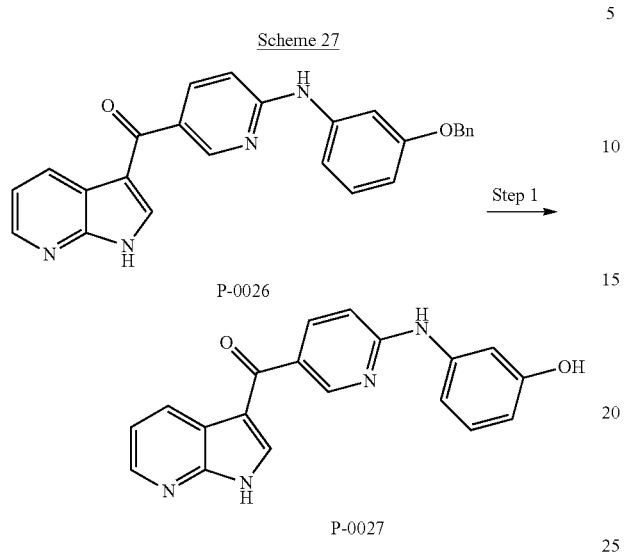

To [6-(3-Benzyloxy-phenylamino)-pyridin-3-yl]-(1H-pyrrolo[2,3-b]pyridin-3-yl)-methanone (P-0026, 12.0 mg, 0.0285 mmol) in methanol (5.0 mL) was added 20% palladium hydroxide on carbon (10.0 mg) under an atmosphere of hydrogen. The reaction was stirred at room temperature for 5 hours. Filtration and concentration gave compound (P-0027, 3.5 mg, 37%). MS (ESI) [M+H$^+$]$^+$=331.

Example 26

Synthesis of 3-[6-(3-Trifluoromethyl-benzyloxy)-pyridin-3-ylmethyl]-1H-pyrrolo[2,3-b]pyridine P-0057

3-[6-(3-Trifluoromethyl-benzyloxy)-pyridin-3-ylmethyl]-1H-pyrrolo[2,3-b]pyridine P-0057 was synthesized in 4 steps from commercially available 7-azaindole as shown in Scheme 28.

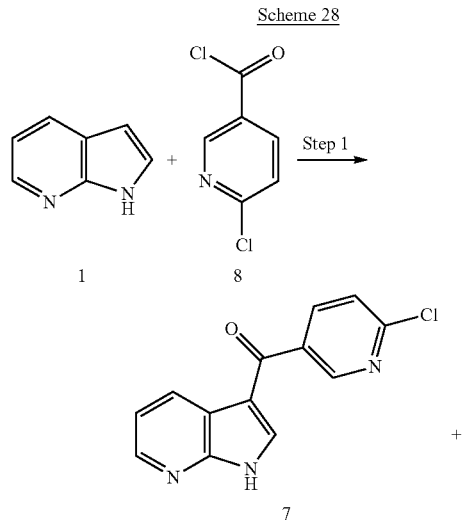

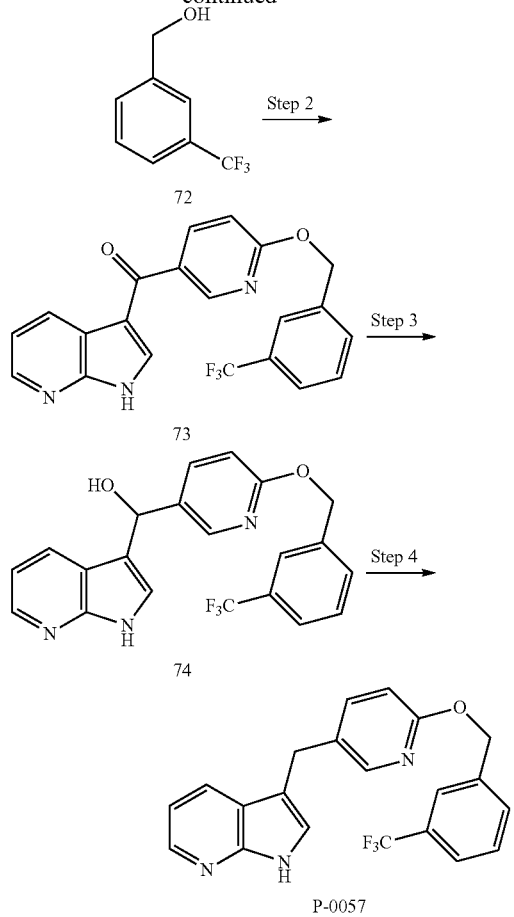

Step 1—Preparation of (6-Chloro-pyridin-3-yl)-(1H-pyrrolo[2,3-b]pyridin-3-yl)-methanone (7)

To 7-azaindole 1 in dichloromethane was added 6-chloronicotinoyl chloride 8, followed by aluminum chloride, under an atmosphere of nitrogen at −10° C. The reaction was stirred and allowed to warm to room temperature overnight. The reaction was quenched with 3 N hydrochloric acid and concentrated hydrochloric acid was added until all solids dissolved. The mixture was extracted with dichloromethane and the combined organic portions were dried with magnesium sulfate, filtered, and the filtrate was concentrated. The resulting solid material was recrystallized from chloroform/hexane to provide (6-Chloro-pyridin-3-yl)-(1H-pyrrolo[2,3-b]pyridin-3-yl)-methanone 7 and used in the next step without further purification.

Step 2—Preparation of (1H-pyrrolo[2,3-b]pyridin-3-yl)-[6-(3-trifluoromethyl-benzyloxy)-pyridin-3-yl]-methanone (73)

To (6-Chloro-pyridin-3-yl)-(1H-pyrrolo[2,3-b]pyridin-3-yl)-methanone 7 in DMSO was added (3-trifluoromethyl-phenyl)-methanol 72. Sodium hydride was added and the reaction was heated to 60° C. for two hours. The reaction was quenched with water and extracted with ethyl acetate. The organic portion was dried with magnesium sulfate and concentrated to provide (1H-pyrrolo[2,3-b]pyridin-3-yl)-[6-(3- trifluoromethyl-benzyloxy)-pyridin-3-yl]-methanone 73, which was used in the next step without additional purification.

Step 3—Preparation (1H-Pyrrolo[2,3-b]pyridin-3-yl)-[6-(3-trifluoromethyl-benzyloxy)-pyridin-3-yl]-methanol (74)

To (1H-pyrrolo[2,3-b]pyridin-3-yl)-[6-(3-trifluoromethyl-benzyloxy)-pyridin-3-yl]-methanone 73 in ethanol was added sodium borohydride. After one hour, the reaction was quenched with water and extracted with ethyl acetate. The organic portion was dried with magnesium sulfate and concentrated to provide (1H-Pyrrolo[2,3-b]pyridin-3-yl)-[6-(3-trifluoromethyl-benzyloxy)-pyridin-3-yl]-methanol 74, which was used in the next step without additional purification.

Step 4—Preparation of 3-[6-(3-Trifluoromethyl-benzyloxy)-pyridin-3-ylmethyl]-1H-pyrrolo[2,3-b]pyridine, P-0057

(1H-Pyrrolo[2,3-b]pyridin-3-yl)-[6-(3-trifluoromethyl-benzyloxy)-pyridin-3-yl]-methanol 74 was dissolved in 9:1 trifluoroacetic acid: triethylsilane. The reaction was stirred at room temperature for 15 hours. The reaction was diluted with water and extracted with ethyl acetate and concentrated. The crude material was purified by reverse phase HPLC to provide 3-[6-(3-Trifluoromethyl-benzyloxy)-pyridin-3-ylmethyl]-1H-pyrrolo[2,3-b]pyridine P-0057. MS (ESI) [M+H$^+$]$^+$ =384.3.

Additional compounds may be prepared using steps 2-4 of Scheme 28, replacing (3-trifluoromethyl-phenyl)-methanol with an appropriate benzyl alcohol. The following compounds were made following this procedure:
3-[6-(4-Chloro-benzyloxy)-pyridin-3-ylmethyl]-1H-pyrrolo[2,3-b]pyridine (P-0056)
3-[6-(3-Chloro-benzyloxy)-pyridin-3-ylmethyl]-1H-pyrrolo[2,3-b]pyridine (P-0055)
The benzyl alcohols used in step 2 of this procedure are indicated in column 2 of the following table, with the compound structure indicated in column 3. Column 1 provides the compound number and Column 4 the measured mass spectrometry result.

Example 27

Synthesis of [2-Chloro-6-(4-chloro-benzylamino)-pyridin-3-yl]-(1H-pyrrolo[2,3-b]pyridin-3-yl)-methanone P-0048

[2-Chloro-6-(4-chloro-benzylamino)-pyridin-3-yl]-(1H-pyrrolo[2,3-b]pyridin-3-yl)-methanone P-0048 was synthesized in 3 steps from commercially available 2,6-dichloropyridine-3-carboxylic acid 75 as shown in Scheme 29.

Scheme 29

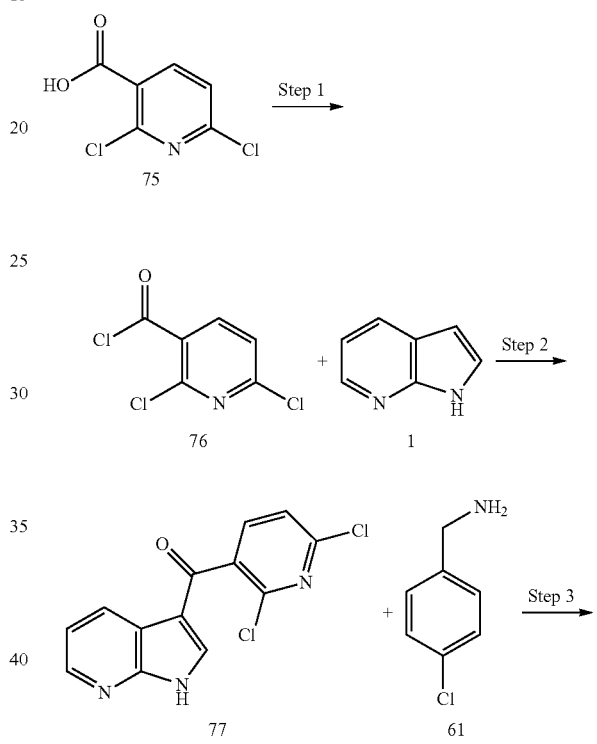

| | Benzyl alcohol | Compound | MS(ESI) [M + H$^+$]$^+$ observed |
|---|---|---|---|
| P-0056 | HO-CH$_2$-C$_6$H$_4$-Cl (4-Cl) | structure | 350.3 |
| P-0055 | HO-CH$_2$-C$_6$H$_4$-Cl (3-Cl) | structure | 350.3 |

223
-continued

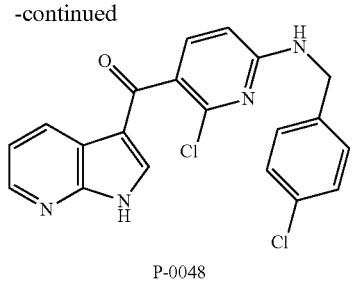

P-0048

Step 1—Preparation of 2,6-dichloropyridine-3-carbonyl chloride (76)

To 2,6-dichloropyridine-3-carboxylic acid (75, 1.00 g, 0.00521 mol) in dichloromethane (75 mL) was added 2 M Oxalyl chloride (2.61 mL, 0.727 g, 0.00573 mol). The solution began to show vigorous gas evolution, which slowed but continued for about 2 hours. The reaction was allowed to continue at room temperature for an additional 3 hours. The reaction was concentrated to give the compound as a brown oil that crystallized on standing (76, 1.09 g, 99%).

Step 2—Preparation of (2,6-dichloropyridin-3-yl)(1H-pyrrolo[2,3-b]pyridin-3-yl)methanone (77)

To Aluminum trichloride (4.18 g, 0.0314 mol) and dichloromethane (97.5 mL, 1.52 mol) under an atmosphere of nitrogen was added 1H-Pyrrolo[2,3-b]pyridine (1, 828.5 mg, 0.0070 mol) in dichloromethane (5.0 mL). The reaction was stirred at room temperature for 60 minutes, then added 2,6-dichloropyridine-3-carbonyl chloride (76, 1.09 g, 0.00523 mol) in dichloromethane (6.0 mL). The reaction was stirred at room temperature for 2 hours. A precipitate formed, and nitromethane was added in 1 mL portions until almost all solid dissolved (8 mL). After an additional 60 minutes at room temperature, the reaction was slowly poured into water and extracted with ethyl acetate. The organic layer was dried over anhydrous magnesium sulfate and filtered. The filtrate was concentrated to give 1.54 g of solid, which turned dark purple on sitting overnight. The solid was treated with dichloromethane, and the insoluble material was collected by vacuum filtration to give compound (77, 863 mg, 57%). MS (ESI) $[M+H^+]^+$=292.2.

Step 3—Preparation of [2-Chloro-6-(4-chloro-benzylamino)-pyridin-3-yl]-(1H-pyrrolo[2,3-b]pyridin-3-yl)-methanone (P-0048)

To (2,6-dichloropyridin-3-yl)(1H-pyrrolo[2,3-b]pyridin-3-yl)methanone (77, 0.0570 g, 0.195 mmol) was added 2-propanol (1.5 mL) followed by p-chlorobenzylamine (61, 49.8 µL, 0.410 mmol). The reaction was microwaved at 300 watts, 100° C. for 10 minutes, at 120° C. for 10 minutes, and finally at 150° C. for 10 minutes. Additional p-chlorobenzylamine (50 µL, 0.410 mmol) was added and the reaction continued at 150° C. for 20 minutes. The reaction was extracted with ethyl acetate and 1 M sodium bicarbonate. The organic layer was dried over anhydrous magnesium sulfate and filtered. The filtrate was concentrated and purified by silica gel column chromatography eluting with dichloromethane followed by 1% methanol to give compound (P-0048, 47 mg, 61%). MS (ESI) $[M+H^+]^+$=397.3.

224

Additional compounds may be prepared according to Scheme 29, replacing 2,6-dichloropyridine-3-carboxylic acid with an appropriate carboxylic acid. (6-(4-chlorobenzylamino)-2-(trifluoromethyl)pyridin-3-yl)(1H-pyrrolo[2,3-b]pyridin-3-yl)methanone P-0070

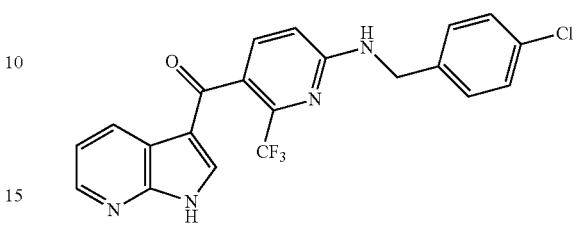

was made following this protocol, using 6-Chloro-2-trifluoromethyl-nicotinic acid as the carboxylic acid (prepared in two steps from commercially available 2-chloro-6-(trifluoromethyl)pyridine according to Cottet, F. and Schlosser, M. Eur. J. Org. Chem. 2004, 3793-3798). MS (ESI) $[M+H^+]^+$=431.2.

Example 28

Synthesis of 3-((1H-pyrrolo[2,3-b]pyridin-3-yl)methyl)-6-(4-chlorobenzylamino)pyridin-2-ol P-0051

3-((1H-pyrrolo[2,3-b]pyridin-3-yl)methyl)-6-(4-chlorobenzylamino)pyridin-2-ol P-0051 was synthesized in 2 steps from [2-Chloro-6-(4-chloro-benzylamino)-pyridin-3-yl]-(1H-pyrrolo[2,3-b]pyridin-3-yl)-methanone P-0048 as shown in Scheme 30.

Scheme 30

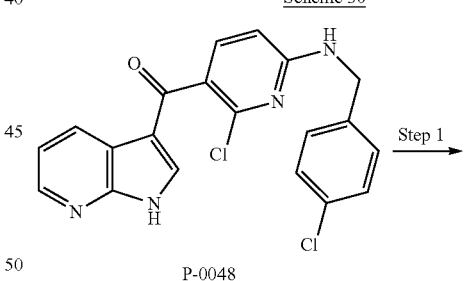

P-0048

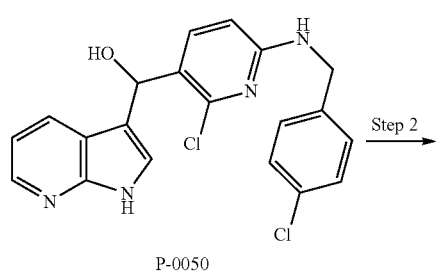

P-0050

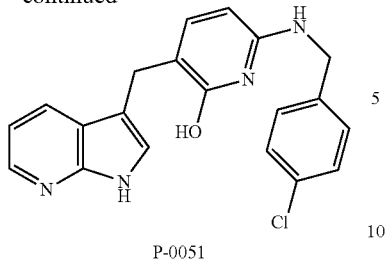

P-0051

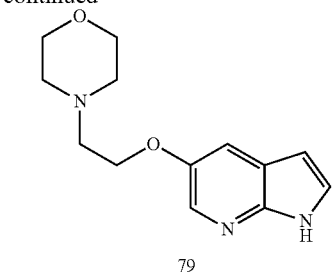

79

Step 1—Preparation of (6-(4-chlorobenzylamino)-2-chloropyridin-3-yl)(1H-pyrrolo[2,3-b]pyridin-3-yl)methanol (P-0050)

To [2-Chloro-6-(4-chloro-benzylamino)-pyridin-3-yl]-(1H-pyrrolo[2,3-b]pyridin-3-yl)-methanone (P-0048, 0.045 g, 0.00011 mol, prepared as described in Example 27) was added methanol (10 mL) and sodium borohydride (0.00428 g, 0.000113 mol). The reaction was allowed to stir at 50° C. overnight. The volatiles were removed from the reaction, and the resulting material was extracted with ethyl acetate and 1M aqueous sodium bicarbonate. The organic layer was dried over magnesium sulfate and filtered. The filtrate was concentrated and purified by silica gel column chromatography eluting with dichloromethane followed by 1% methanol in dichloromethane to give the compound (P-0050, 31 mg, 68%). MS (ESI) [M+H$^+$]$^+$=399.2.

Step 2—Preparation of 3-((1H-pyrrolo[2,3-b]pyridin-3-yl)methyl)-6-(4-chlorobenzylamino)pyridin-2-ol (P-0051)

To (6-(4-chlorobenzylamino)-2-chloropyridin-3-yl)(1H-pyrrolo[2,3-b]pyridin-3-yl)methanol (P-0050, 0.028 g, 0.000070 mol) dissolved in acetonitrile (1 mL) was added triethylsilane (42.6 uL, 0.000266 mol) and trifluoroacetic acid (28.4 uL, 0.000368 mol). The reaction was heated at 85° C. overnight. The reaction was extracted with ethyl acetate and saturated sodium bicarbonate. The organic layer was separated, dried over magnesium sulfate and filtered. The filtrate was concentrated and purified by silica gel column chromatography eluting with dichloromethane, 3%, 5% and finally 10% methanol in dichloromethane to give the compound as a white solid (P-0051, 20 mg, 78%). MS (ESI) [M+H$^+$]$^+$=365.3.

Example 29

Synthesis of 5 substituted 7-azaindole intermediates 5-(2-Morpholin-4-yl-ethoxy)-1H-pyrrolo[2,3-b]pyridine 79 was synthesized in 1 Step from commercially available 5-bromo-azaindole as shown in Scheme 31.

Scheme 31

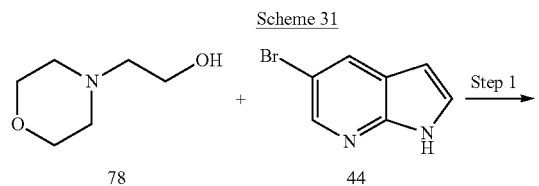

Step 1—5-(2-Morpholin-4-yl-ethoxy)-1H-pyrrolo[2,3-b]pyridine (79)

To 4-morpholineethanol (30 mL, 0.2 mol) in N,N-dimethylformamide (30 mL) was slowly added sodium hydride (7 g, 60% dispersion in mineral oil, 0.2 mol). After the solution turned clear, a solution of 5-bromo-7-azaindole (44, 1.0 g, 0.0051 mol) in N,N-dimethylformamide (5 mL) and copper (I) bromide (1.4 g, 0.0098 mol) were added. The reaction mixture was stirred at 120° C. under nitrogen for 2 hours. The reaction mixture was concentrated and the residue was dissolved in ethyl acetate and water. The organic layer was collected, washed with a solution of ammonium chloride and ammonium hydroxide (4:1), brine, and dried over magnesium sulfate. After removal of solvent, the residue was purified by silica gel column chromatography eluting with ethyl acetate in hexane to provide the compound as an off-white solid (79, 0.62 g, 50%). MS (ESI) [M+H$^+$]$^+$=248.25.

Additional 5-substituted 7-azaindoles were prepared following the protocol of Scheme 31, replacing 4-morpholineethanol with either 2-diethylamino-ethanol, 3-diethylamino-propan-1-ol, 2-piperidin-1-yl-ethanol, or 2-pyrrolidin-1-yl-ethanol to provide diethyl-[2-(1H-pyrrolo[2,3-b]pyridin-5-yloxy)-ethyl]-amine, Diethyl-[3-(1H-pyrrolo[2,3-b]pyridin-5-yloxy)-propyl]-amine, 5-(2-piperidin-1-yl-ethoxy)-1H-pyrrolo[2,3-b]pyridine, and 5-(2-pyrrolidin-1-yl-ethoxy)-1H-pyrrolo[2,3-b]pyridine, respectively.

Example 30

Synthesis of {5-[5-(2-Morpholin-4-yl-ethoxy)-1H-pyrrolo[2,3-b]pyridin-3-ylmethyl]-pyridin-2-yl}-(4-trifluoromethyl-benzyl)-amine P-0065

{5-[5-(2-Morpholin-4-yl-ethoxy)-1H-pyrrolo[2,3-b]pyridin-3-ylmethyl]-pyridin-2-yl}-(4-trifluoromethyl-benzyl)-amine P-0065 was synthesized in 4 Steps from (5-bromo-pyridin-2-yl)-(4-trifluoromethylbenzyl)-amine 17 as shown in Scheme 32.

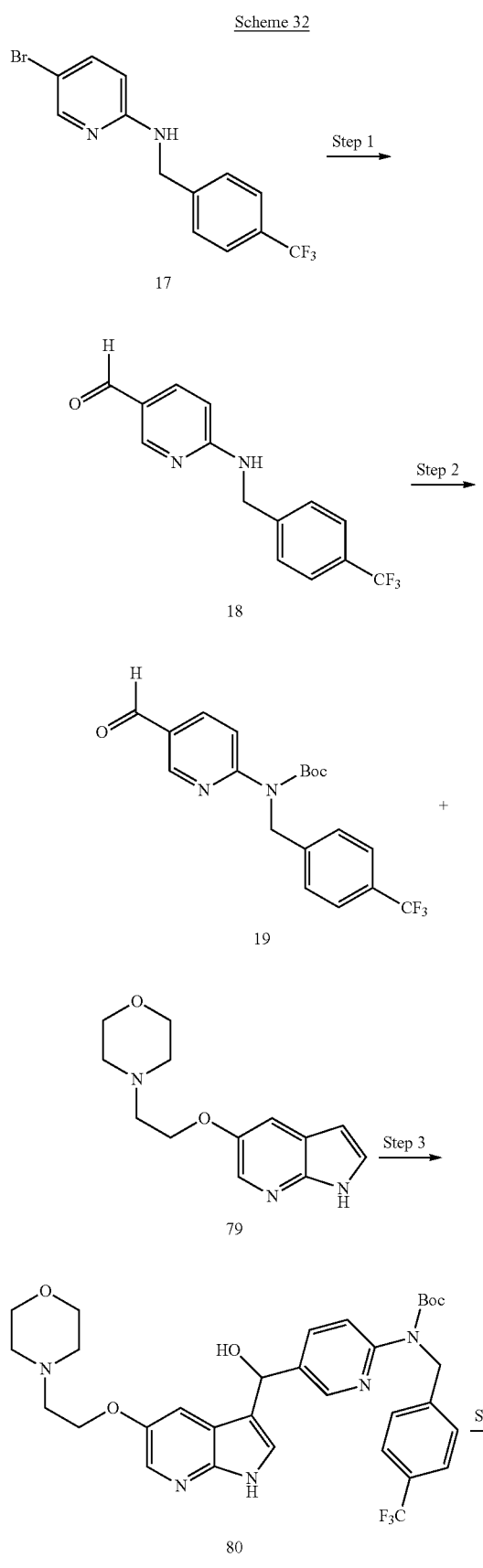

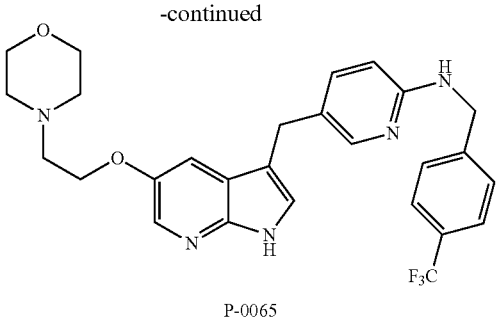

P-0065

Step 1—Preparation of 6-(4-Trifluoromethyl-benzylamino)-pyridine-3-carbaldehyde (18)

To a solution of (5-bromo-pyridin-2-yl)-(4-trifluoromethyl-benzyl)-amine (17, 3.55 g, 0.0107 mol, commercially available, or prepared as described in Example 10) in tetrahydrofuran (150 mL) was added tert-butyllithium (13.2 mL, 1.70 M in pentane, 0.0224 mol) slowly under an atmosphere of nitrogen at −78° C. over 10 minutes. The reaction mixture was stirred at −78° C. for 90 minutes. N,N-Dimethylformamide (2.2 mL, 0.028 mol) was added slowly into the reaction mixture. The reaction mixture was stirred at −78° C. for 2 hours, then allowed to warm to room temperature. After stirring at room temperature for 2 hours, the reaction mixture was poured into ice water and extracted with ethyl acetate. The organic phase was washed with saturated sodium bicarbonate, brine, and dried over magnesium sulfate. After removal of solvent, the residue was purified by silica gel column chromatography eluting with ethyl acetate in hexane to provide the compound as a light yellow solid (18, 1.67 g, 56%).

Step 2—Preparation of (5-Formyl-pyridin-2-yl)-(4-trifluoromethyl-benzyl)-carbamic acid tert-butyl ester (19)

To a solution of 6-(4-trifluoromethyl-benzylamino)-pyridine-3-carbaldehyde (18, 3.7 g, 0.013 mol) and di-tert-butyl-dicarbonate (3.4 g, 0.016 mol) in dichloromethane (100 mL) was added N,N-diisopropylethylamine (4.6 mL, 0.026 mol) and 4-diethylaminopyridine (0.2 g, 0.002 mol). The reaction mixture was stirred at room temperature overnight. The reaction mixture was concentrated and then dissolved in ethyl acetate. The solution was washed with hydrochloric acid (10%), saturated sodium bicarbonate, brine, and dried over magnesium sulfate. After removal of solvent, the residue was purified by silica gel column chromatography eluting with ethyl acetate in hexane to provide the compound as a white solid (19, 4.38 g, 87%).

Step 4—Preparation of (5-{Hydroxy-[5-(2-morpholin-4-yl-ethoxy)-1H-pyrrolo[2,3-b]pyridin-3-yl]-methyl}-pyridin-2-yl)-(4-trifluoromethyl-benzyl)-carbamic acid tert-butyl ester (80)

A mixture of (5-Formyl-pyridin-2-yl)-(4-trifluoromethyl-benzyl)-carbamic acid tert-butyl ester (19, 315 mg, 0.828 mmol), 5-(2-morpholin-4-yl-ethoxy)-1H-pyrrolo[2,3-b]pyridine (79, 205 mg, 0.829 mmol, prepared as described in Example 29), and potassium hydroxide (70 mg, 1 mmol) in methanol (25 mL) was stirred at room temperature overnight. The reaction mixture was poured into ice water, extracted with ethyl acetate, washed with brine, and dried over sodium sulfate. After removal of solvent, the residue was purified by silica gel column chromatography eluting with methanol in dichloromethane to provide the compound as a yellow solid (80, 0.2 g, 40%). MS (ESI) [M+H$^+$]$^+$=628.42.

Step 5—Preparation of {5-[5-(2-Morpholin-4-yl-ethoxy)-1H-pyrrolo[2,3-b]pyridin-3-ylmethyl]-pyridin-2-yl}-(4-trifluorom ethyl-benzyl)-amine (P-0065)

A mixture of (5-{Hydroxy-[5-(2-morpholin-4-yl-ethoxy)-1H-pyrrolo[2,3-b]pyridin-3-yl]-methyl}-pyridin-2-yl)-(4-trifluoromethyl-benzyl)-carbamic acid tert-butyl ester (80, 0.2 g, 0.3 mmol), triethylsilane (4 mL, 0.02 mol), and trifluoroacetic acid (2 mL, 0.02 mol) in acetonitrile (30 mL) was refluxed for 2 hours. After removal of solvent, the residue was dissolved in ethyl acetate, washed with saturated sodium bicarbonate, brine, and dried over magnesium sulfate. After removal of solvent, the residue was purified by silica gel column chromatography eluting with methanol in dichloromethane to provide the compound as a light yellow solid (P-0065, 17 mg, 10%). MS (ESI) [M+H$^+$]$^+$=512.42.

Additional compounds may be prepared using steps 3 and 4 of Scheme 32, using (5-Formyl-pyridin-2-yl)-(4-trifluoromethyl-benzyl)-carbamic acid tert-butyl ester 19 or replacing it with (5-Formyl-pyridin-2-yl)-(4-chloro-benzyl)-carbamic acid tert-butyl ester (43, prepared as described in Example 17) and replacing 5-(2-Morpholin-4-yl-ethoxy)-1H-pyrrolo[2,3-b]pyridine 79 with an appropriate azaindole, prepared as in Example 29 or 5-methoxy-7-azaindole (prepared as described in Example 31) or with commercially available 5-chloro-7-azaindole. The following compounds were made following this procedure:

[5-(5-Methoxy-1H-pyrrolo[2,3-b]pyridin-3-ylmethyl)-pyridin-2-yl]-(4-trifluoromethyl-benzyl)-amine (P-0053),
[5-(5-Chloro-1H-pyrrolo[2,3-b]pyridin-3-ylmethyl)-pyridin-2-yl]-(4-trifluoromethyl-benzyl)-amine (P-0054),
(4-Chloro-benzyl)-[5-(5-methoxy-1H-pyrrolo[2,3-b]pyridin-3-ylmethyl)-pyridin-2-yl]-amine (P-0058),
(4-Chloro-benzyl)-[5-(5-chloro-1H-pyrrolo[2,3-b]pyridin-3-ylmethyl)-pyridin-2-yl]-amine (P-0059),
{5-[5-(2-Diethylamino-ethoxy)-1H-pyrrolo[2,3-b]pyridin-3-ylmethyl]-pyridin-2-yl}-(4-trifluoromethyl-benzyl)-amine (P-0060),
(4-Chloro-benzyl)-{5-[5-(2-morpholin-4-yl-ethoxy)-1H-pyrrolo[2,3-b]pyridin-3-ylmethyl]-pyridin-2-yl}-amine (P-0063),
{5-[5-(2-Pyrrolidin-1-yl-ethoxy)-1H-pyrrolo[2,3-b]pyridin-3-ylmethyl]-pyridin-2-yl}-(4-trifluoromethyl-benzyl)-amine (P-0064),
{5-[5-(3-Diethylamino-propoxy)-1H-pyrrolo[2,3-b]pyridin-3-ylmethyl]-pyridin-2-yl}-(4-trifluoromethyl-benzyl)-amine (P-0066),
(4-Chloro-benzyl)-{5-[5-(3-diethylamino-propoxy)-1H-pyrrolo[2,3-b]pyridin-3-ylmethyl]-pyridin-2-yl}-amine (P-0069), The aldehyde and azaindole used in step 4 of this procedure are indicated in columns 2 and 3 of the following table, respectively, with the compound structure indicated in column 4. Column 1 provides the compound reference number and Column 5 the experimental mass spectrometry result.

| | Aldehyde | Azaindole | Compound | MS (ESI) [M + H$^+$]$^+$ observed |
|---|---|---|---|---|
| P-0053 | | | | 413.2 |
| P-0054 | | | | 417.2 |

-continued
| | Aldehyde | Azaindole | Compound | MS (ESI) [M + H⁺]⁺ observed |
|---|---|---|---|---|
| P-0058 | 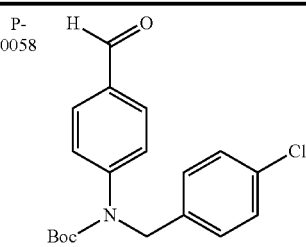 | 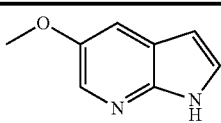 | 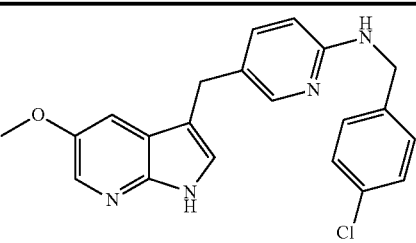 | 379.2 |
| P-0059 | 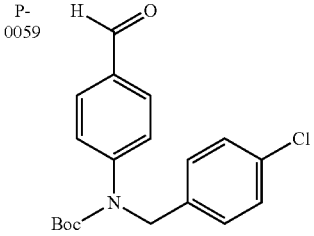 | 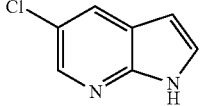 | 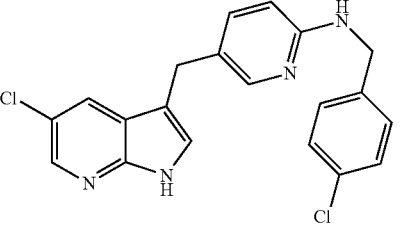 [SMILES: Clc1ccc(CNc2ccc(Cc3c[nH]c4ncc(Cl)cc34)cn2)cc1] | 383.2 |
| P-0060 | 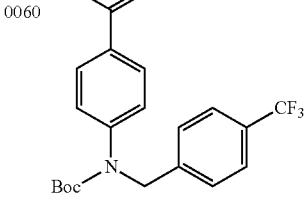 | 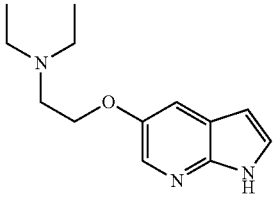 [SMILES: CCN(CC)CCOc1cnc2[nH]ccc2c1] | 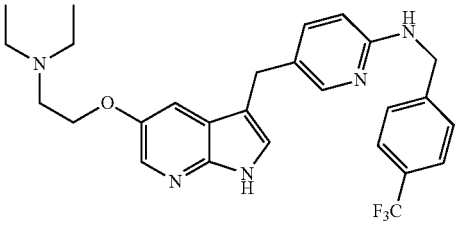 [SMILES: CCN(CC)CCOc1cnc2[nH]cc(Cc3ccc(NCc4ccc(C(F)(F)F)cc4)nc3)c2c1] | 498.4 |
| P-0063 | 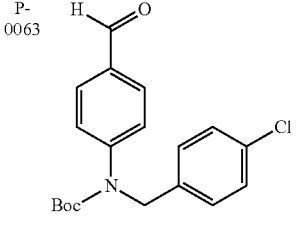 | 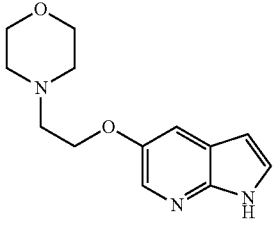 [SMILES: c1cc2cc(OCCN3CCOCC3)cnc2[nH]1] | 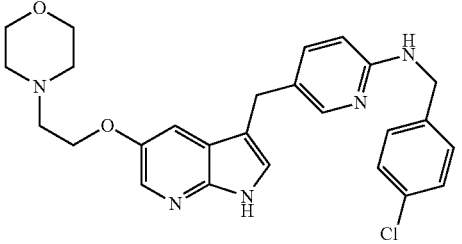 [SMILES: Clc1ccc(CNc2ccc(Cc3c[nH]c4ncc(OCCN5CCOCC5)cc34)cn2)cc1] | 478.3 |
| P-0064 | 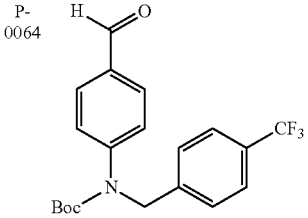 | 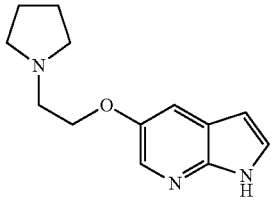 [SMILES: c1cc2cc(OCCN3CCCC3)cnc2[nH]1] | 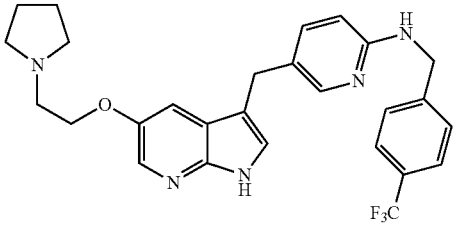 [SMILES: FC(F)(F)c1ccc(CNc2ccc(Cc3c[nH]c4ncc(OCCN5CCCC5)cc34)cn2)cc1] | 496.3 |
| P-0066 | 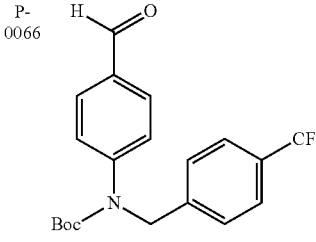 | 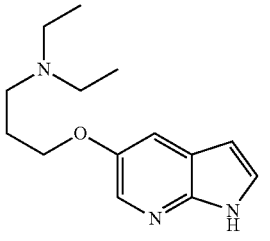 [SMILES: CCN(CC)CCCOc1cnc2[nH]ccc2c1] | 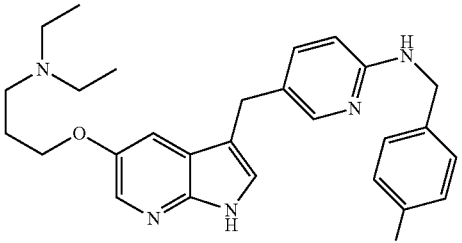 | 512.3 |

| Aldehyde | Azaindole | Compound | MS (ESI) [M + H⁺]⁺ observed |
|---|---|---|---|
| P-0069 | | | 478.3 |

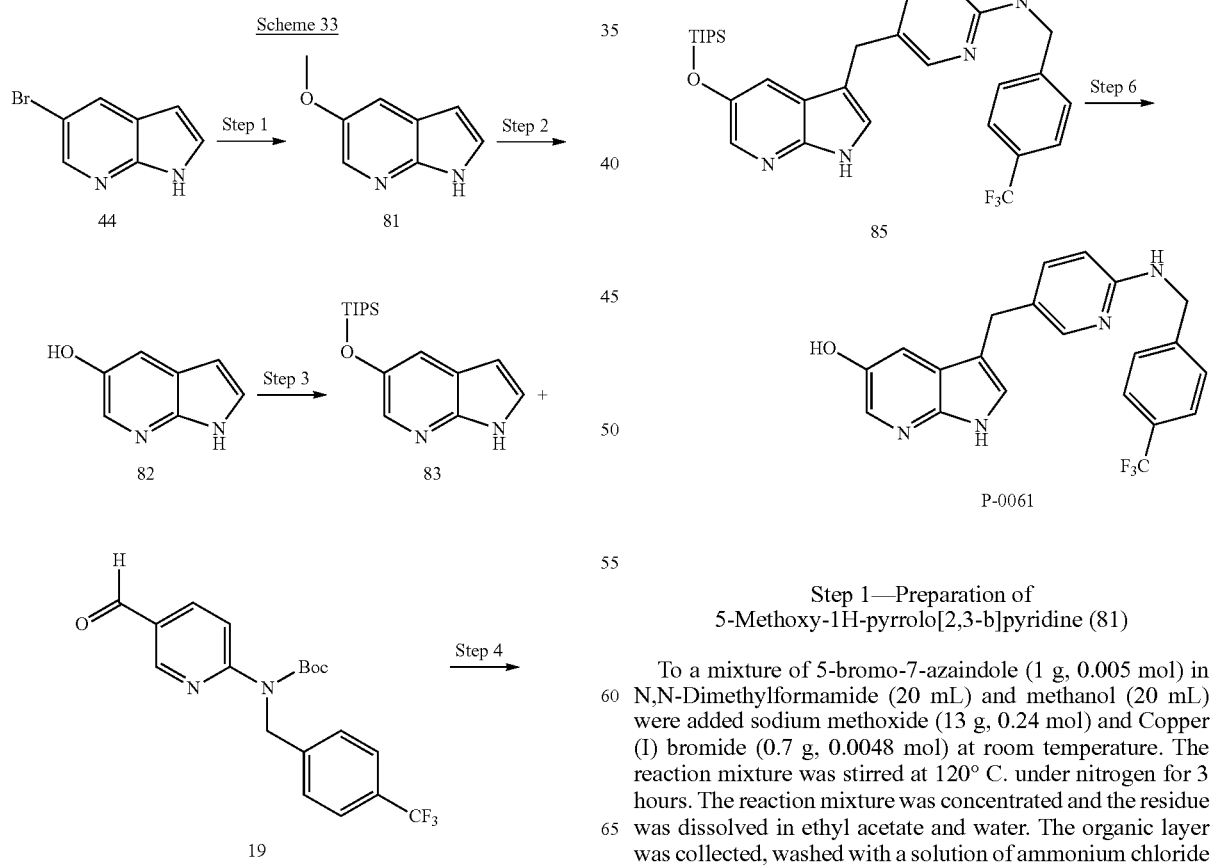

Example 31

Synthesis of 3-[6-(4-Trifluoromethyl-benzylamino)-pyridin-3-ylmethyl]-1H-pyrrolo[2,3-b]pyridin-5-ol P-0061

3-[6-(4-Trifluoromethyl-benzylamino)-pyridin-3-ylmethyl]-1H-pyrrolo[2,3-b]pyridin-5-ol P-0061 was synthesized in 6 Steps from 5-bromo-7-azaindole 44 as described in Scheme 33.

Step 1—Preparation of 5-Methoxy-1H-pyrrolo[2,3-b]pyridine (81)

To a mixture of 5-bromo-7-azaindole (1 g, 0.005 mol) in N,N-Dimethylformamide (20 mL) and methanol (20 mL) were added sodium methoxide (13 g, 0.24 mol) and Copper (I) bromide (0.7 g, 0.0048 mol) at room temperature. The reaction mixture was stirred at 120° C. under nitrogen for 3 hours. The reaction mixture was concentrated and the residue was dissolved in ethyl acetate and water. The organic layer was collected, washed with a solution of ammonium chloride and ammonium hydroxide (4:1), brine, and dried over magnesium sulfate. After removal of solvent, the residue was purified by silica gel column chromatography eluting with ethyl acetate in hexane to provide the compound as a white solid (81, 0.4 g, 50%). MS (ESI) [M+H$^+$]$^+$=149.09.

Step 2—Preparation of 1H-Pyrrolo[2,3-b]pyridin-5-ol (82)

To a solution of 5-methoxy-1H-pyrrolo[2,3-b]pyridine (81, 0.5 g, 3 mmol) in tetrahydrofuran (20 mL) was added boron tribromide (1.5 g, 6.0 mmol) at 0° C. The reaction mixture was allowed to warm to room temperature, then stirred at room temperature for 3 hours. The reaction mixture was quenched by methanol. After repeated addition of methanol and removal of solvent, the concentrated reaction mixture was dissolved in ethyl acetate and water. The organic layer was collected, washed with brine, and dried over magnesium sulfate. After removal of solvent, the residue was purified by silica gel column chromatography eluting with ethyl acetate in hexane to provide the compound as an off-white solid (82, 0.18 g, 40%).

Step 3—Preparation of 5-Triisopropylsilanyloxy-1H-pyrrolo[2,3-b]pyridine (83)

To a solution of 1H-Pyrrolo[2,3-b]pyridin-5-ol (0.5 g, 0.004 mol) and 1H-imidazole (0.98 g, 0.014 mol) in N,N-dimethylformamide (5 mL) was added triisopropylsilyl chloride (1 mL, 0.005 mol). The reaction mixture was stirred at room temperature overnight. Dichloromethane (10 mL) was added and the solution was washed with brine and dried over sodium sulfate. After removal of solvent, the residue was purified by silica gel column chromatography eluting with ethyl acetate in hexane to provide the compound as a viscous liquid (83, 0.4 g, 40%).

Step 4—Preparation of {5-[Hydroxy-(5-triisopropyl-silanyloxy-1H-pyrrolo[2,3-b]pyridin-3-yl)-methyl]-pyridin-2-yl}-(4-trifluoromethyl-benzyl)-carbamic acid tert-butyl ester (84)

A mixture of (5-Formyl-pyridin-2-yl)-(4-trifluoromethyl-benzyl)-carbamic acid tert-butyl ester (19, 41 mg, 0.11 mmol, prepared as described in Example 30), 5-triisopropylsilanyloxy-1H-pyrrolo[2,3-b]pyridine (83, 34 mg, 0.12 mmol) and potassium hydroxide (9.8 mg, 0.17 mmol) in methanol (10 mL) was stirred at room temperature overnight. The reaction mixture was poured into water, extracted with ethyl acetate, washed with brine and dried over sodium sulfate. After removal of solvent, the residue was purified by silica gel column chromatography eluting with ethyl acetate in hexane to provide the compound as a viscous liquid (84, 0.05 g, 70%). MS (ESI) [M+H$^+$]$^+$=671.38.

Step 5—Preparation of (4-Trifluoromethyl-benzyl)-[5-(5-triisopropylsilanyloxy-1H-pyrrolo[2,3-b]pyridin-3-ylmethyl)-pyridin-2-yl]-amine (85)

A mixture of {5-[hydroxy-(5-triisopropylsilanyloxy-1H-pyrrolo[2,3-b]pyridin-3-yl)-methyl]-pyridin-2-yl}-(4-trifluoromethyl-benzyl)-carbamic acid tert-butyl ester (84, 0.05 g, 0.07 mmol), trifluoroacetic acid (0.5 mL, 0.006 mol), and triethylsilane (1 mL, 0.006 mol) in acetonitrile (10 mL) was refluxed for 2 hours. The reaction mixture was poured into ice water, extracted with ethyl acetate, washed with saturated sodium bicarbonate, brine, and dried over sodium sulfate. After removal of solvent, the residue was purified by silica gel column chromatography eluting with ethyl acetate in hexane to provide the compound as a viscous liquid (85, 0.04 g, 97%). MS (ESI) [M+H$^+$]$^+$=555.38.

Step 6—Preparation of 3-[6-(4-Trifluoromethyl-benzylamino)-pyridin-3-ylmethyl]-1H-pyrrolo[2,3-b]pyridin-5-ol (P-0061)

To (4-Trifluoromethyl-benzyl)-[5-(5-triisopropylsilanyloxy-1H-pyrrolo[2,3-b]pyridin-3-ylmethyl)-pyridin-2-yl]-amine (85, 0.13 g, 0.23 mmol) in tetrahydrofuran (10 mL) was added tetrabutylammonium fluoride (3 mL, 1.0 M in tetrahydrofuran, 3 mmol). The reaction mixture was stirred at room temperature overnight, and then was stirred at 65° C. for 48 hours. The reaction mixture was concentrated and purified by silica gel column chromatography eluting with ethyl acetate in hexane to provide the compound as a viscous liquid (P-0061, 0.062 g, 66%). MS (ESI) [M+H$^+$]$^+$=399.19.

3-[6-(4-Chloro-benzylamino)-pyridin-3-ylmethyl]-1H-pyrrolo[2,3-b]pyridin-5-ol P-0062

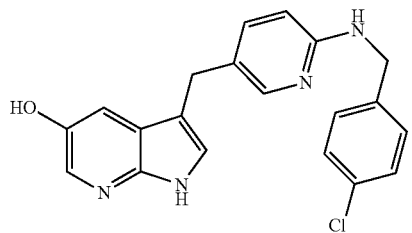 [SMILES: Oc1cnc2[nH]cc(Cc3ccc(NCc4ccc(Cl)cc4)nc3)c2c1]

was prepared following the protocol of Scheme 33, replacing (5-Formyl-pyridin-2-yl)-(4-trifluoromethyl-benzyl)-carbamic acid tert-butyl ester 19 with (5-Formyl-pyridin-2-yl)-(4-chloro-benzyl)-carbamic acid tert-butyl ester (43, prepared as described in Example 17). MS (ESI) [M+H$^+$]$^+$=365.2.

Example 32

Synthesis of N-[5-(1H-Pyrrolo[2,3-b]pyridine-3-carbonyl)-pyridin-2-yl]-4-trifluoromethyl-benzamide P-0067

N-[5-(1H-Pyrrolo[2,3-b]pyridine-3-carbonyl)-pyridin-2-yl]-4-trifluoromethyl-benzamide P-0067 was synthesized in 2 Steps from 7-azaindole 1 as described in Scheme 34.

Scheme 34

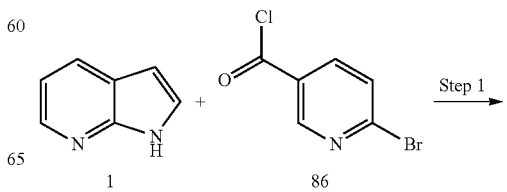

237

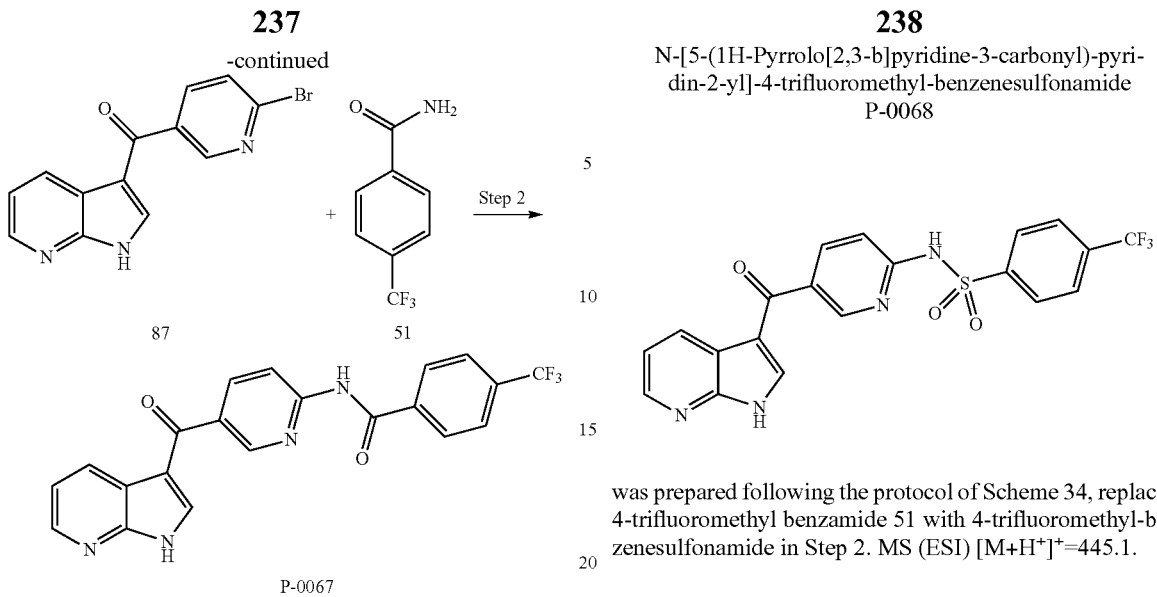

Step 1—Preparation of (6-Bromo-pyridin-3-yl)-(1H-pyrrolo[2,3-b]pyridin-3-yl)-methanone (87)

To a solution of 1H-Pyrrolo[2,3-b]pyridine (1, 1.2 g, 0.010 mol) in dichloromethane (50 mL) was added 6-bromo-nicotinoyl chloride (86, 2.6 g, 0.012 mol) at −10° C. After the solution turned clear, aluminum trichloride (10.2 g, 0.0765 mol) was added in one portion with vigorous stirring. The reaction mixture was stirred at −10° C. for 30 minutes, then was allowed to warm to room temperature and stirred at room temperature overnight. The reaction was quenched with ice water and neutralized with sodium bicarbonate. The solution was extracted with dichloromethane, washed with brine, and dried over sodium sulfate. After removal of solvent, the residue was purified by silica gel column chromatography eluting with methanol in dichloromethane to provide the compound as a white solid (87, 0.35 g, 11%).

Step 2—Preparation of N-[5-(1H-Pyrrolo[2,3-b]pyridine-3-carbonyl)-pyridin-2-yl]-4-trifluoromethyl-benzamide (P-0067)

A mixture of (6-bromo-pyridin-3-yl)-(1H-pyrrolo[2,3-b]pyridin-3-yl)-methanone (87, 160 mg, 0.53 mmol), 4-trifluoromethyl benzamide (51, 130 mg, 0.69 mmol), xanthphos (9 mg, 0.02 mmol), cesium carbonate (245 mg, 0.752 mmol), and tris(dibenzylideneacetone)dipalladium (0) (5 mg, 0.005 mmol) in toluene (2 mL) in a sealed tube was stirred at 110° C. for 1 hour. The reaction was quenched with water and extracted with dichloromethane. The organic layer was collected, washed with brine and dried over sodium sulfate. After removal of the solvent, the residue was purified with silica gel column chromatography eluting with ethyl acetate in hexane to provide the compound as an off-white solid (P-0067, 0.42 mg, 19%). MS (ESI) [M+H⁺]⁺=411.17.

238

N-[5-(1H-Pyrrolo[2,3-b]pyridine-3-carbonyl)-pyridin-2-yl]-4-trifluoromethyl-benzenesulfonamide P-0068 was prepared following the protocol of Scheme 34, replacing 4-trifluoromethyl benzamide 51 with 4-trifluoromethyl-benzenesulfonamide in Step 2. MS (ESI) [M+H⁺]⁺=445.1.

Example 33

Synthesis of [(S)-1-(4-Chloro-phenyl)-ethyl]-[5-(1H-pyrrolo[2,3-b]pyridin-3-ylmethyl)-pyridin-2-yl]-amine P-0075

[(S)-1-(4-Chloro-phenyl)-ethyl]-[5-(1H-pyrrolo[2,3-b]pyridin-3-ylmethyl)-pyridin-2-yl]-amine P-0075 was synthesized in 3 Steps from 7-azaindole 1 as described in Scheme 35.

Scheme 35

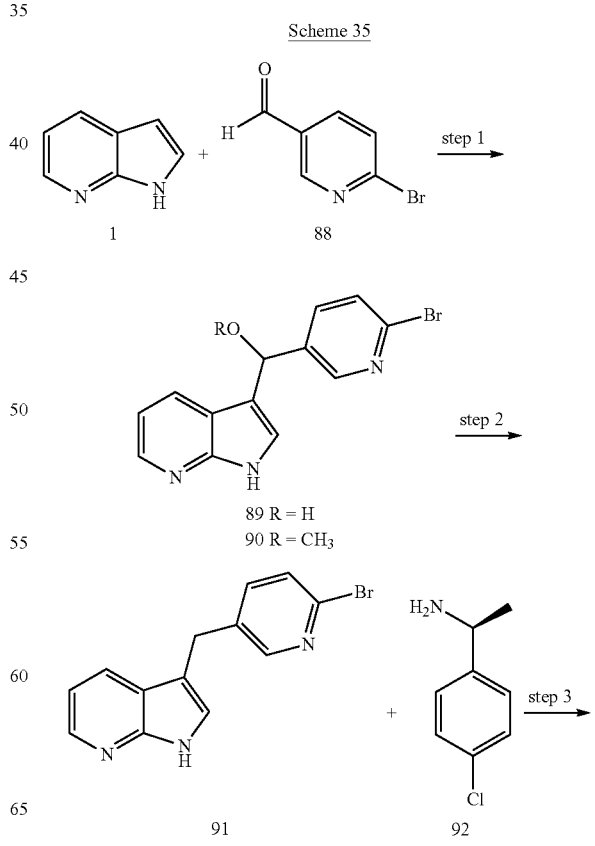

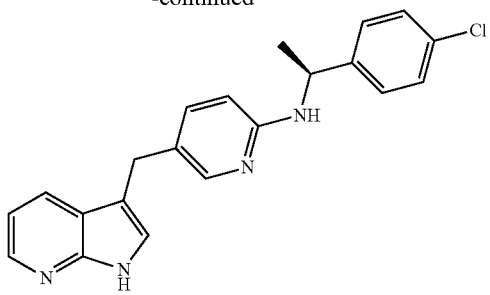

P-0075

Scheme 36

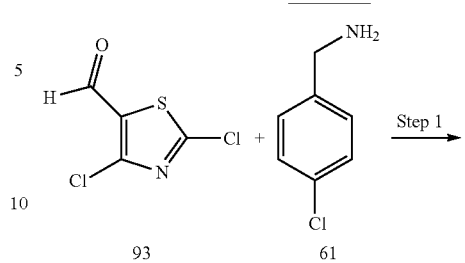

Step 1—Preparation of (6-Bromo-pyridin-3-yl)-(1H-pyrrolo[2,3-b]pyridin-3-yl)-methanol (89)

A mixture of 1H-Pyrrolo[2,3-b]pyridine (1, 1.2 g, 0.010 mol), 6-bromo-pyridine-3-carbaldehyde (88, 1.8 g, 0.0097 mol), and potassium hydroxide (1.8 g, 0.032 mol) in methanol (25 mL) was stirred at room temperature overnight. The reaction mixture was poured into ice water, extracted with ethyl acetate, washed with brine, and dried over sodium sulfate. After removal of solvent, the residue was purified by silica gel column chromatography eluting with methanol in dichloromethane to provide the compound as a white solid (89, 1.4 g, 45%), or may be used as mixture of 89 and 90 in Step 2.

Step 2—Preparation of 3-(6-Bromo-pyridin-3-ylmethyl)-1H-pyrrolo[2,3-b]pyridine (91)

A mixture of (6-bromo-pyridin-3-yl)-(1H-pyrrolo[2,3-b]pyridin-3-yl)-methanol (89, 1 g, 0.003 mol) and 3-[(6-bromo-pyridin-3-yl)-methoxy-methyl]-1H-pyrrolo[2,3-b]pyridine (90, 2 g, 0.006 mol), triethylsilane (1 mL, 0.006 mol), and trifluoroacetic acid (0.5 mL, 0.006 mol) in acetonitrile (25 mL) was refluxed for 2 hours. The reaction mixture was concentrated and the residue was dissolved in ethyl acetate and water. The organic layer was collected, washed with saturated sodium bicarbonate, brine, and dried over sodium sulfate. After removal of the solvent, the residue was purified with silica gel column chromatography eluting with ethyl acetate in hexane to provide the compound as an off-white solid (91, 0.75 g, 60%). MS (ESI) [M+H$^+$]$^+$=288.06, 290.00.

Step 3—Preparation of [(S)-1-(4-Chloro phenyl)-ethyl]-[5-(1H-pyrrolo[2,3-b]pyridin-3-ylmethyl)-pyridin-2-yl]-amine P-0075

A mixture of 3-(6-bromo-pyridin-3-ylmethyl)-1H-pyrrolo[2,3-b]pyridine (91, 100 mg, 0.0003 mol) and (S)-1-(4-chloro-phenyl)-ethylamine (92, 0.5 g, 0.003 mol) in N-methylpyrrolidine (3 mL) was stirred at 150° C. in microwave for 100 minutes. The reaction mixture was concentrated under vacuum and the residue was purified with silica gel column chromatography eluting with ethyl acetate in hexane to provide the compound as a white solid (P-0075, 0.03 g, 20%). MS (ESI) [M+H$^+$]$^+$=363.18.

Example 34

Synthesis of (4-Chloro-benzyl)-[4-chloro-5-(1H-pyrrolo[2,3-b]pyridin-3-ylmethyl)-thiazol-2-yl]-amine P-0083

(4-Chloro-benzyl)-[4-chloro-5-(1H-pyrrolo[2,3-b]pyridin-3-ylmethyl)-thiazol-2-yl]-amine P-0083 was synthesized in 4 steps from 2,4-Dichloro-thiazole-5-carbaldehyde 93 as described in Scheme 36.

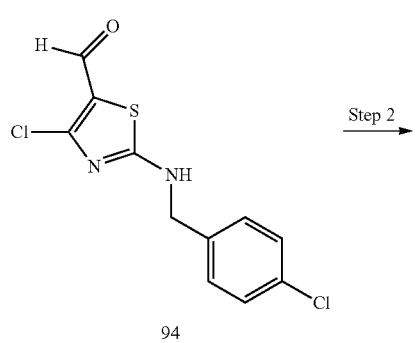

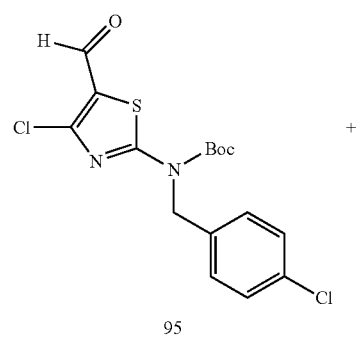

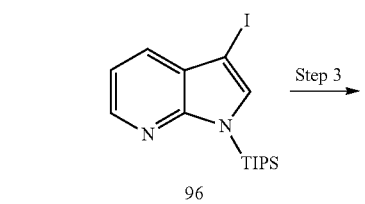

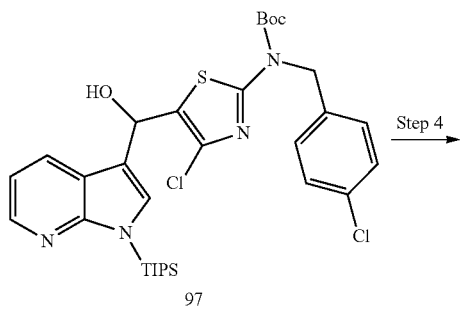

-continued

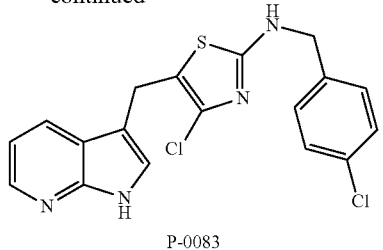

P-0083

Step 1—Preparation of 4-Chloro-2-(4-chloro-benzylamino)-thiazole-5-carbaldehyde (94)

To a solution of p-chlorobenzylamine (61, 283 mg, 2.00 mmol) and N,N-Diisopropylethylamine (0.697 mL) in tetrahydrofuran (20 mL) was slowly added 2,4-Dichloro-thiazole-5-carbaldehyde (93, 364 mg, 2.00 mmol) in tetrahydrofuran (10 mL) at room temperature. The reaction was stirred at room temperature overnight. The reaction mixture was poured into iced water, extracted with ethyl acetate, washed with brine, and dried over sodium sulfate. After removal of solvent, the residue was purified by silica gel column chromatography eluting with ethyl acetate in hexane to provide the compound as a yellow solid (94, 0.3 g, 50%). MS (ESI) [M−H+]=286.97.

Step 2—Preparation of (4-Chloro-benzyl)-(4-chloro-5-formyl-thiazol-2-yl)-carbamic acid tert-butyl ester (95)

To a solution of 4-Chloro-2-(4-chloro-benzylamino)-thiazole-5-carbaldehyde (94, 0.32 g, 0.0011 mol) in dichloromethane (20 mL) was slowly added N,N-diisopropylethylamine (0.4 mL, 0.002 mol), 4-dimethylaminopyridine (27 mg, 0.22 mmol), and a solution of di-tert-butyldicarbonate (290 mg, 0.0013 mol) in dichloromethane (5 mL) at room temperature. The reaction mixture was stirred at room temperature overnight, then poured into iced water, extracted with dichloromethane, washed with brine, and dried over sodium sulfate. After removal of solvent, the residue was purified by silica gel column chromatography eluting with ethyl acetate in hexane to provide the compound as a light brown solid (95, 0.32 g, 74%). MS (ESI) [M+H+]=387.26.

Step 3—Preparation of (4-Chloro-benzyl)-{4-chloro-5-[hydroxy-(1-triisopropylsilanyl-1H-pyrrolo[2,3-b]pyridin-3-yl)-methyl]-thiazol-2-yl}-carbamic acid tert-butyl ester (97)

To a solution of 3-Iodo-1-triisopropylsilanyl-1H-pyrrolo[2,3-b]pyridine (96, 99 mg, 0.25 mmol) in tetrahydrofuran (5 ml) at −20° C. under nitrogen was added 2.0 M solution isopropylmagnesium chloride in tetrahydrofuran (0.2 ml, 0.31 mmol). The reaction mixture was stirred for 1.5 hours, then allowed to warm to 5° C. After the reaction mixture was cooled down to −20° C., a solution of (4-Chloro-benzyl)-(4-chloro-5-formyl-thiazol-2-yl)-carbamic acid tert-butyl ester (95, 80 mg, 0.2 mmol) in tetrahydrofuran (5 mL) was slowly added. The reaction mixture was stirred for 2.5 hrs, then allowed to warm to 5° C. The reaction mixture was poured into iced water, extracted with ethyl acetate, washed with brine, and dried over magnesium sulfate. After removal of solvent, the residue was purified by silica gel column chromatography eluting with ethyl acetate in hexane to provide the compound as an off-white solid (97, 76 mg, 50%). MS (ESI) [M+H+]=661.32, 663.32.

Step 4—Preparation of (4-Chloro-benzyl)-[4-chloro-5-(1H-pyrrolo[2,3-b]pyridin-3-ylmethyl)-thiazol-2-yl]-amine (P-0083)

A mixture of (4-Chloro-benzyl)-{4-chloro-5-[hydroxy-(1-triisopropylsilanyl-1H-pyrrolo[2,3-b]pyridin-3-yl)-methyl]-thiazol-2-yl}-carbamic acid tert-butyl ester (97, 76 mg, 0.11 mmol), triethylsilane (0.5 mL, 3 mmol), and trifluoroacetic acid (0.25 mL, 3.2 mmol) in acetonitrile (5 mL) was refluxed for 3 hours. The reaction mixture was poured into iced water, extracted with ethyl acetate, washed with sodium bicarbonate, brine, and dried over sodium sulfate. After removal of solvent, the residue was purified by silica gel column chromatography eluting with ethyl acetate in hexane to provide the compound as a yellow solid (P-0083, 5.6 mg, 14%). MS (ESI) [M+H+]=389.35, 390.36.

Example 35

Synthesis of [2-(4-Chloro-benzylamino)-thiazol-5-yl]-(1H-pyrrolo[2,3-b]pyridin-3-yl)-methanone P-0077

[2-(4-Chloro-benzylamino)-thiazol-5-yl]-(1H-pyrrolo[2,3-b]pyridin-3-yl)-methanone P-0077 was synthesized in 2 steps from 2-Bromo-thiazole-5-carboxylic acid 98 and 1H-pyrrolo[2,3-b]pyridine 1 as shown in Scheme 37.

Scheme 37

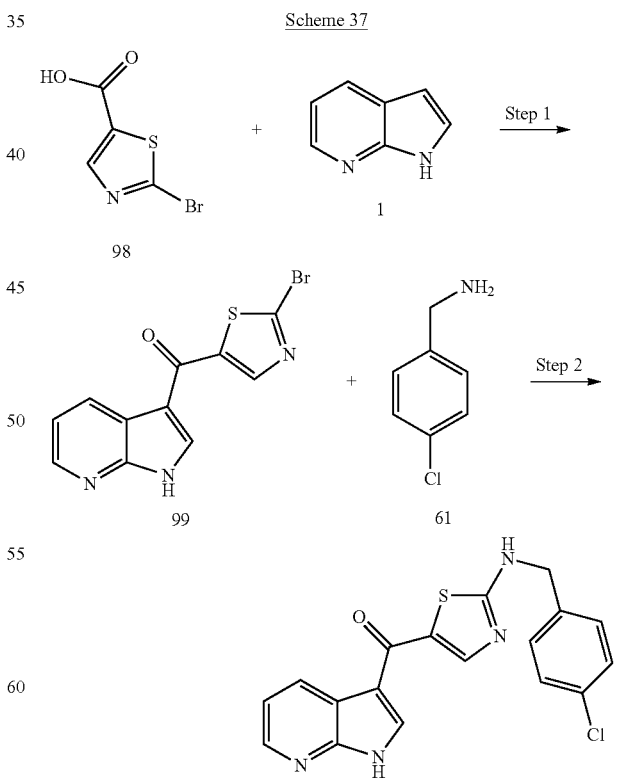

P-0077

Step 1—Preparation of (2-Bromo-thiazol-5-yl)-(1H-pyrrolo[2,3-b]pyridin-3-yl)-methanone (99)

A suspension of 2-Bromo-thiazole-5-carboxylic acid (98, 0.5 g, 0.002 mol) in oxalyl chloride (3 mL) was stirred at room temperature until it turned into a clear solution. Solvent was removed and the residue was dried over vacuum. A light yellow solid was obtained and was dissolved in dichloromethane (10 mL) and slowly added to a solution of 1H-Pyrrolo[2,3-b]pyridine (1, 0.34 g, 0.0029 mol) in dichloromethane (30 mL) at −10° C. To the mixture was then added aluminum trichloride (2.6 g, 0.019 mol) in one portion with vigorous stirring. The reaction was held at −10° C. for 30 minutes, then allowed to warm to room temperature. The reaction mixture was stirred at ambient temperature overnight. The reaction was quenched with ice-water and acidified with hydrochloric acid (10%) to pH 4. The solution was then extracted with dichloromethane. The organic layer was collected, washed with brine, and dried over magnesium sulfate. After removal of solvent, the residue was purified by silica gel column chromatography eluting with ethyl acetate in hexane to provide the compound as a white solid (99, 12 mg, 2%). MS (ESI) [M−H+]=369.09.

Step 2—Preparation of [2-(4-Chloro-benzylamino)-thiazol-5-yl]-(1H-pyrrolo[2,3-b]pyridin-3-yl)-methanone (P-0077)

A mixture of (2-Bromo-thiazol-5-yl)-(1H-pyrrolo[2,3-b]pyridin-3-yl)-methanone (99, 5 mg, 0.02 mmol), p-chlorobenzylamine (61, 10 mg, 0.08 mmol), and N,N-Diisopropylethylamine (10 µL, 0.08 mmol) in tetrahydrofuran (10 mL), in a sealed reaction vessel, was stirred room temperature overnight. The reaction mixture was poured into iced water, extracted with ethyl acetate, washed with brine, and dried over magnesium sulfate. After removal of solvent, the residue was purified by silica gel column chromatography eluting with ethyl acetate in hexane to provide the compound as a light yellow solid (P-0077, 2 mg, 30%). MS (ESI) [M+H+]=305.90, 307.88.

Example 36

Synthesis of 3-((5-chloro-3-methyl-1-phenyl-1H-pyrazol-4-yl)methyl)-1H-pyrrolo[2,3-b]pyridine P-0080

3-((5-chloro-3-methyl-1-phenyl-1H-pyrazol-4-yl)methyl)-1H-pyrrolo[2,3-b]pyridine P-0080 was synthesized in 2 steps from 5-chloro-3-methyl-1-phenyl-1H-pyrazole-4-carbaldehyde 100 and 7-azaindole 1 as shown in Scheme 38.

Scheme 38

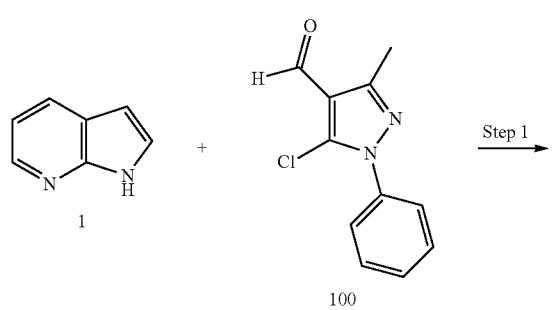

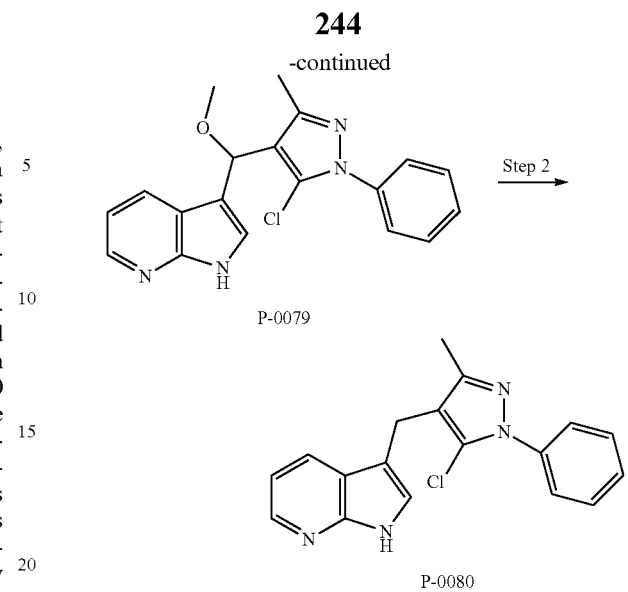

Step 1—Preparation of 3-((5-chloro-3-methyl-1-phenyl-1H-pyrazol-4-yl)(methoxy)methyl)-1H-pyrrolo[2,3-b]pyridine (P-0079)

To 1H-Pyrrolo[2,3-b]pyridine (1, 0.100 g, 0.846 mmol) and 5-chloro-3-methyl-1-phenyl-1H-pyrazole-4-carbaldehyde (100, 0.205 g, 0.931 mmol) was added 2 mL of methanol to give a solution. Potassium hydroxide (0.0475 g, 0.846 mmol) was added and the reaction was allowed to stir at room temperature for 48 hours. The reaction was extracted with ethyl acetate and water. The organic layer was dried over anhydrous magnesium sulfate and filtered. The filtrate was concentrated and purified by silica gel column chromatography eluting with a gradient of 0-5% methanol in dichloromethane to give the compound (P-0079, 32 mg, 11%). MS (ESI) [M+H+]+=353.2.

Step 2—Preparation of 3-((5-chloro-3-methyl-1-phenyl-1H-pyrazol-4-yl)methyl)-1H-pyrrolo[2,3-b]pyridine (P-0080)

To 3-((5-chloro-3-methyl-1-phenyl-1H-pyrazol-4-yl)(methoxy)methyl)-1H-pyrrolo[2,3-b]pyridine (P-0079, 0.030 g, 0.085 mmol) was added acetonitrile (10 mL, 0.2 mol). Trifluoroacetic acid (500 uL, 0.006 mol) and triethylsilane (500 uL, 0.003 mol) were added and the reaction allowed to stir at room temperature for 16 hours. The reaction was extracted with ethyl acetate and water. The organic layer was dried over anhydrous magnesium sulfate and filtered. The filtrate was concentrated and purified by silica gel column chromatography eluting with dichloromethane followed 5% methanol in dichloromethane to give the compound as a yellowish foam (P-0080, 29 mg, 98%).
MS (ESI) [M+H+]+=323.2.

Example 37 cKit Kinase Domain and Construction of c-Kit Sequences c-Kit cDNA sequence is available from NCBI, e.g., as GenBank accession number NM_000222. Using this sequence, c-kit DNA sequences can be cloned from commercially available libraries (e.g. cDNA libraries) or can be synthesized by conventional cloning methods.

Using conventional cloning methods, constructs encoding three c-kit polypeptides were prepared, and used to express c-kit kinase domain polypeptides. One such active c-kit kinase domain sequence included residues P551-S948, with the deletion of residues Q694-T753.

Example 38

Expression and Purification of c-Kit Kinase Domain

Purified c-kit kinase domain can be obtained using conventional expression and purification methods. Exemplary methods are described, for example, in Lipson et al., U.S. 20040002534 (U.S. application 10600, 868, filed Jun. 23, 2003), which is incorporated herein by reference in its entirety.

Example 39

Binding Assays

Binding assays can be performed in a variety of ways, including a variety of ways known in the art. For example, as indicated above, binding assays can be performed using fluorescence resonance energy transfer (FRET) format, or using an AlphaScreen.

Alternatively, any method which can measure binding of a ligand to the ATP-binding site can be used. For example, a fluorescent ligand can be used. When bound to c-kit, the emitted fluorescence is polarized. Once displaced by inhibitor binding, the polarization decreases.

Determination of $IC_{50}$ for compounds by competitive binding assays. (Note that $K_I$ is the dissociation constant for inhibitor binding; $K_D$ is the dissociation constant for substrate binding.) For this system, the IC50, inhibitor binding constant and substrate binding constant can be interrelated according to the following Formula:

When using radiolabeled substrate $$K_I = \frac{IC50}{1 + [L^*]/K_D},$$

the $IC_{50} \sim K_I$ when there is a small amount of labeled substrate.

Example 40

Cell-Based Assays of c-Fms Kinase Activity or c-Kit Kinase Activity

M-CSF dependent RAW264.7 cells were seeded on a 12 well plate, $2.5 \times 10^5$ cells/well and the cells were allowed to attach overnight at 37° C., 5% $CO_2$. The cells were then starved in serum-free medium overnight at 37° C., 5% $CO_2$. The cells were treated with compound for 1 hour in serum-free media (1% DMSO final concentration); and then stimulated with 20 ng/ml M-CSF for 5 minutes. After stimulation, the cells were lysed on ice, and the lysates were centrifuged at 13,000 rpm for 1 minute. The amount of protein in the sample was quantitated, sample buffer was added, and the samples were boiled at 95° C. for 10 minutes. The samples were then centrifuged at 13,000 rpm for 1 minute. The samples (15-20 µg/lane) were loaded and run on 4-12% tris-glycine gel at 75V, and then transferred onto a PVDF membrane. The membrane was blocked for 1 hour with 5% BSA in PBS/1% Tween-20 (PBST); or 5% milk, depending on the primary antibody used. Then the blots were incubated with primary antibody overnight at 4 degrees with gentle shaking. After incubation with the capture antibody, the membranes were washed 3×10 minutes with PBST; then incubated with detection antibody Goat Anti-Rabbit-HRP for 1 hour, with gentle shaking. The membranes were washed again 3×10 minutes with PBST. ECL Plus substrate was then added to the blots, the image captured with chemiluminescence camera, and the bands quantitated for pFMS and FMS levels.

The Fms inhibitors may also be assessed using M-NFS-60 mouse myelogenous leukemia cell line (ATCC catalog #CRL-1838). This cell line proliferation is stimulated by M-CSF, which binds and activates the fms tyrosine kinase receptor Inhibitors of fms kinase activity reduce or eliminate the M-CSF stimulated kinase activity, resulting in reduced cell proliferation. This inhibition is measured as a function of compound concentration to assess $IC_{50}$ values. M-NFS-60 cells were seeded at $5 \times 10^4$ cells per well of a 96 well cell culture plate in 50 µl of cell culture medium of RPMI 1640 (CellGro Mediatech catalog #10-040-CV) supplemented with 10% FBS (HyClone catalog #SH30071.03). Compounds were dissolved in DMSO at a concentration of 1 mM and were serially diluted 1:3 for a total of eight points and added to the cells to final concentrations of 10, 3.3, 1.1, 0.37, 0.12, 0.041, 0.014 and 0.0046 µM in 100 µl cell culture medium (final concentration 0.2% DMSO). Cells were also treated with staurosporine as a positive control. The cells were stimulated by adding 20 µl of 372 ng/ml M-CSF to a final concentration of 62 ng/ml (R&D Systems catalog #216-MC). The cells were incubated at 37° C., 5% $CO_2$ for three days. CellTiter-Glo Buffer (Promega Cell Viability Assay catalog #G7573) and substrate were equilibrated to room temperature, and enzyme/substrate Recombinant Firefly Luciferase/Beetle Luciferin was reconstituted. The cell plates were equilibrated to room temperature for 30 minutes, then lysed by addition of an equivalent volume of the Celltiter-Glo Reagent. The plate was mixed for 2 minutes on a plate shaker to lyse the cells, then incubated for 10 minutes at room temperature. The plates were read on a Victor Wallac II using Luminescence protocol modified to read 0.1 s per well. The luminescence reading assesses the ATP content, which correlates directly with cell number such that the reading as a function of compound concentration was used to determine the $IC_{50}$ value.

The c-Kit inhibitors were assessed using M-07e cell line (DSMZ catalog #ACC 104). The M-07e proliferation is stimulated by SCF (Stem Cell Factor), which binds and activates c-Kit tyrosine kinase receptor. Inhibitors of c-Kit kinase reduce or eliminate the SCF mediated kinase activation, resulting in reduced cell proliferation of SCF stimulated cells. This inhibition is measured by the effect of compound concentration on cell growth to assess $IC_{50}$ values. M-07e cells were seeded at $5 \times 10^4$ cells per well of a 96 well cell culture plate in 50 µl of cell culture medium of Iscove's Medium 1× (MOD, CellGro Mediatech catalog #15-016-CV) supplemented with 10% FBS (HyClone catalog #SH30071.03). Compounds were dissolved in DMSO at a concentration of 0.1 mM and were serially diluted 1:3 for a total of eight points and added to the cells to final concentrations of 1, 0.33, 0.11, 0.037, 0.012, 0.0041, 0.0014 and 0.00046 µM in 100 µl cell culture medium (final concentration 0.2% DMSO). Cells were also treated with staurosporine as a positive control. Cells were stimulated by adding 20 µl of 600 ng/ml SCF to a final concentration of 100 ng/ml (Biosource International SCF kit ligand catalog #PHC2115) in cell culture medium. The cells were incubated at 37° C., 5% $CO_2$ for three days. CellTiter-Glo Buffer (Promega Cell Viability Assay catalog #G7573) and substrate were equilibrated to room temperature, and enzyme/substrate Recombinant Firefly Luciferase/ Beetle Luciferin was reconstituted. The cell plates were equilibrated to room temperature for 30 minutes, then lysed by addition of an equivalent volume of the Celltiter-Glo Reagent. The plate was mixed for 2 minutes on a plate shaker to lyse the cells, then incubated for 10 minutes at room temperature. The plates were read on a Victor Wallac II using Luminescence protocol modified to read 0.1 s per well. The luminescence reading assesses the ATP content, which correlates directly with cell number such that the reading as a function of compound concentration is used to determine the $IC_{50}$ value.

This cell based assay was also used to assess phosphorylation. Samples were prepared with compounds as described for the growth inhibition assay only M-07e cells were seeded at $2 \times 10^5$ cells per well in a 96 well filter plate. Cells were incubated for 1 hour at 37° C. with the compounds as described above, and then stimulated by adding SCF to a final concentration of 50 ng/ml and incubated for 10 minutes at 37° C. The culture medium was removed by centrifugation and the cells were lysed by addition of 30 µl lysis buffer (25 mM Tris HCl pH 7.5, 150 mM NaCl, 5 mM EDTA, 1% Triton X100, 5 mM NaF, 1 mM NaVanadate, 10 mM Beta-glycerophosphate, no EDTA (Boehringer-Roche catalog #1873580) and placed on ice for 30 minutes. A 15 µl aliquot of the lysate was taken and assayed according to Biosource Immunoassay Kit: Human c-Kit [pY823] (Catalog #KHO0401) by diluting the aliquot with 85 µl dilution buffer in the assay plate, incubating for 2 hours at room temperature and washing the plate 4 times with wash buffer. Detection antibody (100 µl) was added to the plate and samples incubated for 1 hour at room temperature, then washed 4 times with wash buffer. HRP anti-rabbit antibody (100 µl) was added and samples incubated for 30 minutes at room temperature, then washed 4 times with wash buffer. Stabilized chromogen (100 µl) was added and samples incubated for 15-25 minutes at room temperature, then washed 4 times with wash buffer. Stop solution (100 µl) was added and the samples read on a Wallac Victor reader at 450 nm. The absorbance was plotted against the compound concentration and the $IC_{50}$ concentration was determined.

Additional cell based assays can be correlated to the Fms activity of compounds of the invention. For example, the ability of osteoclast precursor cells (commercially available from Lonza) to differentiate into mature osteoclasts, due to stimulation by M-CSF and RANKL, in the presence of compounds, can be measured using a method analogous to that previously reported (Hudson et al., Journal of Urology, 1947, 58:89-92), where the amount of acid phosphatase in the supernatant (i.e. TRAP5b excreted by mature osteoclasts) is proportional to the number of mature osteoclasts present. In another example, the ability of M-CSF-dependent murine macrophage cells (BAC1.2F5) to proliferate in the presence of compounds can be measured by culturing cells as previously described (Morgan et al., Journal of Cellular Physiology, 1987, 130:420-427) and determining cell viability by analysis of ATP levels in the cell culture (Crouch et al., Journal of Immunological Methods, 1993, 160:81-8).

Example 41 c-Kit, c-Fms, TrkA, and HGK Activity Assays

The effect of potential modulators of kinase activity of c-kit and other kinases can be measured in a variety of different assays known in the art, e.g., biochemical assays, cell-based assays, and in vivo testing (e.g. model system testing). Such in vitro and/or in vivo assays and tests can be used in the present invention. As an exemplary kinase assay, the kinase activity of c-kit or Fms is measured in AlphaScreening (Packard BioScience).

Exemplary c-Kit Biochemical Assay

The c-kit (or kinase domain thereof) is an active kinase in AlphaScreen. $IC_{50}$ values are determined with respect to inhibition of c-Kit kinase activity, where inhibition of phosphorylation of a peptide substrate is measured as a function of compound concentration. Compounds to be tested were dissolved in DMSO to a concentration of 20 mM. These were diluted 30 µl into 120 µl of DMSO (4 mM) and 1 µl was added to an assay plate. These were then serially diluted 1:3 (50 µl to 100 µl DMSO) for a total of 8 points. Plates were prepared such that each kinase reaction is 20 µl in 1× kinase buffer (50 mM HEPES, pH 7.2, 5 mM $MgCl_2$, 5 mM $MnCl_2$, 0.01% NP-40, 0.2% BSA), 5% DMSO and 10 µM ATP. Substrate was 100 nM biotin-$(E4Y)_3$ (Open Source Biotech, Inc.). C-kit kinase was at 0.1 ng per sample. After incubation of the kinase reaction for 1 hour at room temperature, 5 µl of donor beads (Streptavidin coated beads (Perkin Elmer Life Science) final concentration 1 µg/ml) in stop buffer (50 mM EDTA in 1× kinase buffer) was added, the sample was mixed and incubated for 20 minutes at room temperature before adding 5 µl of acceptor beads (PY20 coated beads (Perkin Elmer Life Science) final concentration 1 µg/ml) in stop buffer. The samples were incubated for 60 minutes at room temperature and the signal per well was read on AlphaQuest reader. Phosphorylated substrate results in binding of the PY20 antibody and association of the donor and acceptor beads such that signal correlates with kinase activity. The signal vs. compound concentration was used to determine the $IC_{50}$.

Compounds were also tested using a similar assay with a 10-fold higher ATP concentration. For these samples, compounds to be tested were dissolved in DMSO to a concentration of 20 mM. These were diluted 30 µl into 120 µl of DMSO (4 mM) and 1 µl was added to an assay plate. These were then serially diluted 1:3 (50 µl to 100 µl DMSO) for a total of 8 points. Plates were prepared such that each kinase reaction is 20 µl in 1× kinase buffer (25 mM HEPES, pH 7.5, 2 mM $MgCl_2$, 2 mM $MnCl_2$, 0.01% Tween-20, 1 mM DTT, and 0.001% BSA), 5% DMSO and 100 µM ATP. Substrate was 30 nM biotin-(E4Y) 10 (Upstate Biotech, Cat #12-440). C-kit kinase was at 1 ng per sample. After incubation of the kinase reaction for 1 hour at room temperature, 5 µl of donor beads (Streptavidin coated beads (Perkin Elmer Life Science) final concentration 10 µg/ml) in stop buffer (25 mM HEPES pH 7.5, 100 mM EDTA, 0.3% BSA) was added, the sample was mixed and incubated for 20 minutes at room temperature before adding 5 µl of acceptor beads (PY20 coated beads (Perkin Elmer Life Science) final concentration 10 µg/ml) in stop buffer. The samples were incubated for 60 minutes at room temperature and the signal per well was read on AlphaQuest or Envision reader (Perkin Elmer Life Science). Phosphorylated substrate results in binding of the PY20 antibody and association of the donor and acceptor beads such that signal correlates with kinase activity. The signal vs. compound concentration was used to determine the $IC_{50}$.

The c-kit enzyme used in the above assay was either obtained from Cell Signaling Technology (Cat. #7754) or was prepared as follows: A plasmid encoding kit (DNA and encoded protein sequences shown below) was engineered using common polymerase chain reaction (PCR) methods. Complementary DNA cloned from various human tissues were purchased from Invitrogen, and these were used as substrates in the PCR reactions. Specific custom synthetic oligonucleotide primers were designed to initiate the PCR product, and also to provide the appropriate restriction enzyme cleavage sites for ligation with the plasmids. The entire sequence encoding the enzyme was made through a gene synthesis procedure, using custom synthetic oligonucleotides covering the entire coding sequence (Invitrogen, see below).

The plasmid used for ligation with the kinase-encoding inserts was derivative of pET (Novagen) for expression using E. coli. The Kit kinase was engineered to include a Histidine tag for purification using metal affinity chromatography. The kinase-encoding plasmid was engineered as bicistronic mRNA to co-express a second protein that modifies the kinase protein during its expression in the host cell. Protein tyrosine phosphatase 1B (PTP), was co-expressed for dephosphorylation of the phospho-Tyrosines.

For protein expression, the plasmid containing the Kit gene was transformed into E. coli strains BL21(DE3)RIL and transformants selected for growth on LB agar plates containing appropriate antibiotics. Single colonies were grown overnight at 37° C. in 200 ml TB (Terrific broth) media. 16×1 L of fresh TB media in 2.8 L flasks were inoculated with 10 ml of overnight culture and grown with constant shaking at 37° C. Once cultures reached an absorbance of 1.0 at 600 nm, IPTG was added and cultures were allowed to grow for a further 12 to 18 hrs at temperatures ranging from 12-30° C. Cells were harvested by centrifugation and pellets frozen at −80° C. until ready for lysis.

For protein Purification; frozen E. coli cell pellets were resuspended in lysis buffer and lysed using standard mechanical methods. Protein was purified via poly-Histidine tags using immobilized metal affinity purification IMAC. The Kit kinase was purified using a 3 step purification process utilizing; IMAC, size exclusion chromatography and ion exchange chromatography. The poly-Histidine tag was removed using Thrombin (Calbiochem).

Compounds were assayed using a similar assay to that described above, using in a final reaction volume of 25 µl: c-Kit (h) (5-10 mU) in 8 mM MOPS pH 7.0, 0.2 mM EDTA, 10 mM MnCl$_2$, 0.1 mg/ml poly (Glu, Tyr) 4:1, 10 mM MgAcetate and γ-$^{33}$P-ATP (approximately 500 cpm/pmol), with appropriate concentrations of compound. Incubated for 40 minutes at room temperature and stopped by addition of 5 µl of 3% phosphoric acid. Spotted 10 µl of each sample onto Filtermat A and washed 3× with 75 mM phosphoric acid, once with methanol, dried and measured on scintillation counter (performed at Upstate USA, Charlottesville, Va.).

Compounds P-0001, P-0002, P-0003, P-0004, P-0005, P-0006, P-0007, P-0008, P-0009, P-0010, P-0011, P-0012, P-0013, P-0014, P-0015, P-0016, P-0017, P-0018, P-0020, P-0022, P-0024, P-0025, P-0026, P-0027, P-0028, P-0030, P-0031, P-0032, P-0033, P-0038, P-0053, P-0054, P-0055, P-0056, P-0057, P-0058, P-0059, P-0060, P-0061, P-0062, P-0063, P-0064, P-0065, P-0066, P-0069, P-0071, P-0072, P-0073, P-0074, P-0075, P-0078, P-0082, P-0092, P-0093, P-0094, P-0095, P-0096, P-0097, P-0098, P-0099, P-0100, P-0101, P-0102, P-0103, P-0104, P-0105, P-0107, P-0108, P-0109, P-0111, P-0112, P-0113, P-0114, P-0115, P-0116, P-0118, P-0120, P-0121, P-0122, P-0123, P-0125, P-0126, P-0127, P-0128, P-0129, P-0131, P-0132, P-0138, P-0143, P-0144, P-0145, P-0148, P-0154, P-0156, P-0157, P-0159, P-0161, P-0163, P-0170, P-0171, P-0173, P-0174, P-0176, P-0177, P-0179, P-0180, P-0181, P-0182, P-0186, P-0187, P-0188, P-0190, P-0192, P-0193, P-0194, P-0195, P-0197, P-0199, P-0201, P-0203, P-0205, P-0206, P-0208, P-0211, P-0212, P-0213, P-0214, P-0215, P-0216, P-0217, P-0218, P-0219, P-0221, P-0222, P-0224, P-0225, P-0226, P-0228, P-0234, P-0237, P-0239, P-0240, P-0242, P-0243, P-0244, P-0245, P-0246, P-0252, P-0253, P-0255, P-0257, P-0258, P-0259, P-0260, P-0262, P-0263, P-0264, P-0265, P-0266, P-0267, P-0268, P-0269, P-0270, P-0271, P-0272, P-0273, P-0274, P-0275, P-0276, P-0277, P-0278, P-0279, P-0280, P-0281, P-0282, P-0283, P-0284, P-0285, P-0286, P-0287, P-0288, P-0289, P-0290, P-0291, P-0294, P-0297, P-0298, P-0301, P-0302, P-0303, P-0305, P-0306, P-0307, P-0308, P-0309, P-0311, P-0312, P-0313, P-0314, P-0316, P-0319, P-0320, P-0321, P-0322, P-0323, P-0324, P-0325, P-0326, P-0327, P-0328, P-0329, P-0330, P-0331, P-0332, P-0334, P-0336, P-0337, P-0338, P-0339, P-0340, P-0341, P-0342, P-0343, P-0344, P-0345, P-0346, P-0347, P-0348, P-0350, P-0351, P-0352, P-0354, P-0355, P-0356, P-0357, P-0358, P-0359, P-0361, P-0362, P-0363, P-0365, P-0366, P-0367, P-0368, P-0369, P-0370, P-0371, P-0372, P-0373, P-0375, P-0376, P-0377, P-0378, P-0379, P-0382, P-0383, P-0385, P-0387, P-0390, P-0392, P-0393, P-0394, P-0395, P-0396, P-0402, P-0404, P-0406, P-0407, P-0408, P-0409, and P-0412 had IC$_{50}$ of less than 1 µM in at least one of the c-kit assays described above in Examples 40 and 41.

Kit

| | PCR primers | |
|---|---|---|
| KIT 8K1A | ATGTACGAAGTTCAGTGGAAAGTTGTTGAAGAAATCAACGG (SEQ ID NO: 5) | 1776 |
| 8K1B | GGTCGATGTAAACGTAGTTGTTACCGTTGATTTCTTCAACAACTTT (SEQ ID NO: 6) | 1777 |
| 8K2A | AACAACTACGTTTACATCGACCCGACCCAGCTGCCGTACGAC (SEQ ID NO: 7) | 1779 |
| 8K2B | GTTACGCGGGAACTCCCATTTGTGGTCGTACGGCAGCTGGGTC (SEQ ID NO: 8) | 1781 |
| 8K3A | AAATGGGAGTTCCCGCGTAACCGTCTGTCTTTCGGTAAAACCC (SEQ ID NO: 9) | 1782 |
| 8K3B | ACCGAACGCACCCGCACCCAGGGTTTTACCGAAAGACAGAC (SEQ ID NO: 10) | 1783 |
| 8K4A | GGTGCGGGTGCGTTCGGTAAAGTTGTTGAAGCGACCGCGTACG (SEQ ID NO: 11) | 1784 |

-continued

| | | |
|---|---|---|
| 8K4B | GCCGCGTCAGATTTGATCAGACCGTACGCGGTCGCTTCAAC (SEQ ID NO: 12) | 1785 |
| 8K5A | CTGATCAAATCTGACGCGGCGATGACCGTTGCGGTTAAAATGC (SEQ ID NO: 13) | 1786 |
| 8K5B | GTCAGGTGCGCAGACGGTTTCAGCATTTTAACCGCAACGGTCA (SEQ ID NO: 14) | 1787 |
| 8K6A | AAACCGTCTGCGCACCTGACCGAACGTGAAGCGCTGATGTCTG (SEQ ID NO: 15) | 1788 |
| 8K6B | CCAGGTAAGACAGAACTTTCAGTTCAGACATCAGCGCTTCACGT (SEQ ID NO: 16) | 1789 |
| 8K7A | CTGAAAGTTCTGTCTTACCTGGGTAACCACATGAACATCGTTAA (SEQ ID NO: 17) | 1791 |
| 8K7B | GGTGCACGCACCCAGCAGGTTAACGATGTTCATGTGGTTAC (SEQ ID NO: 18) | 1792 |
| 8K8A | CTGCTGGGTGCGTGCACCATCGGTGGTCCGACCCTGGTTATCA (SEQ ID NO: 19) | 1793 |
| 8K8B | GTCACCGTAGCAGCAGTATTCGGTGATAACCAGGGTCGGACCA (SEQ ID NO: 20) | 1794 |
| 8K9A | GAATACTGCTGCTACGGTGACCTGCTGAACTTCCTGCGTCGTA (SEQ ID NO: 21) | 1795 |
| 8K9B | AGAGCAGATGAAAGAGTCACGTTTACGACGCAGGAAGTTCAGC (SEQ ID NO: 22) | 1796 |
| 8K10A | CGTGACTCTTTCATCTGCTCTAAACAGGAAGACCACGCGGAAG (SEQ ID NO: 23) | 1797 |
| 8K10B | CAGCAGGTTTTTGTACAGCGCCGCTTCCGCGTGGTCTTCCTGT (SEQ ID NO: 24) | 1798 |
| 8K11A | GCGCTGTACAAAAACCTGCTGCACTCTAAAGAATCTTCTTGCTC (SEQ ID NO: 25) | 1799 |
| 8K11B | CCATGTATTCGTTGGTAGAGTCAGAGCAAGAAGATTCTTTAGAGT (SEQ ID NO: 26) | 1811 |
| 8K11A | GACTCTACCAACGAATACATGGACATGAAACCGGGTGTTTCTTA (SEQ ID NO: 27) | 1812 |
| 8K11B | TCCGCTTTGGTCGGAACAACGTAAGAAACACCCGGTTTCATGT (SEQ ID NO: 28) | 1813 |
| 8K12A | GTTGTTCCGACCAAAGCGGACAAACGTCGTTCTGTTCGTATCG (SEQ ID NO: 29) | 1814 |
| 8K12B | TAACGTCACGTTCGATGTAAGAACCGATACGAACAGAACGACGTTT (SEQ ID NO: 30) | 1815 |
| 8K13A | TCTTACATCGAACGTGACGTTACCCCGGCGATCATGGAAGACG (SEQ ID NO: 31) | 1816 |
| 8K13B | CCAGGTCCAGCGCCAGTTCGTCGTCTTCCATGATCGCCGG (SEQ ID NO: 32) | 1817 |
| 8K14A | GAACTGGCGCTGGACCTGGAAGACCTGCTGTCTTTCTCTTACC (SEQ ID NO: 33) | 1818 |
| 8K14B | GAACGCCATACCTTTCGCAACCTGGTAAGAGAAAGACAGCAGGT (SEQ ID NO: 34) | 1819 |
| 8K15A | GTTGCGAAAGGTATGGCGTTCCTGGCGTCTAAAAACTGCATCCA (SEQ ID NO: 35) | 1821 |
| 8K15B | CGCGCCGCCAGGTCACGGTGGATGCAGTTTTTAGACGCC (SEQ ID NO: 36) | 1822 |
| 8K16A | CGTGACCTGGCGGCGCGTAACATCCTGCTGACCCACGGTCG (SEQ ID NO: 37) | 1823 |

-continued

| | | |
|---|---|---|
| 8K16B | ACCGAAGTCGCAGATTTTGGTGATACGACCGTGGGTCAGCAGG (SEQ ID NO: 38) | 1824 |
| 8K17A | ACCAAAATCTGCGACTTCGGTCTGGCGCGTGACATCAAAAACG (SEQ ID NO: 39) | 1825 |
| 8K17B | GTTACCTTTAACAACGTAGTTAGAGTCGTTTTTGATGTCACGCGCC (SEQ ID NO: 40) | 1826 |
| 8K18A | TCTAACTACGTTGTTAAAGGTAACGCGCGTCTGCCGGTTAAATG (SEQ ID NO: 41) | 1827 |
| 8K18B | GAAGATAGATTCCGGCGCCATCCATTTAACCGGCAGACGCGC (SEQ ID NO: 42) | 1829 |
| 8K19A | ATGGCGCCGGAATCTATCTTCAACTGCGTTTACACCTTCGAATC (SEQ ID NO: 43) | 1831 |
| 8K19B | GATACCGTAAGACCAAACGTCAGATTCGAAGGTGTAAACGCAG (SEQ ID NO: 44) | 1832 |
| 8K20A | GACGTTTGGTCTTACGGTATCTTCCTGTGGGAACTGTTCTCTC (SEQ ID NO: 45) | 1833 |
| 8K20B | CCTGTGGGAACTGTTCTCTCTGGGTTCTTCTCCGTACCCGG (SEQ ID NO: 46) | 1834 |
| 8K21A | GGTTCTTCTCCGTACCCGGGTATGCCGGTTGACTCTAAATTCTAT (SEQ ID NO: 47) | 1835 |
| 8K21B | CGGAAACCTTCTTTGATCATTTTGTAGAATTTAGAGTCAACCGGC (SEQ ID NO: 48) | 1836 |
| 8K22A | AAAATGATCAAAGAAGGTTTCCGTATGCTGTCTCCGGAACACG (SEQ ID NO: 49) | 1837 |
| 8K22B | ATGTCGTACATTTCCGCCGGCGCGTGTTCCGGAGACAGCATA (SEQ ID NO: 50) | 1838 |
| 8K23A | CCGGCGGAAATGTACGACATCATGAAAACCTGCTGGGACGCG (SEQ ID NO: 51) | 1839 |
| 8K23B | AAGGTCGGACGTTTCAGCGGGTCCGCGTCCCAGCAGGTTTTC (SEQ ID NO: 52) | 1841 |
| 8K24A | CCGCTGAAACGTCCGACCTTCAAACAGATCGTTCAGCTGATCG (SEQ ID NO: 53) | 1842 |
| 8K24B | TTGGTAGATTCAGAGATCTGTTTTTCGATCAGCTGAACGATCTGTT (SEQ ID NO: 54) | 1843 |
| 8K25A | AAACAGATCTCTGAATCTACCAACCACATCTACTCTAACCTGGC (SEQ ID NO: 55) | 1844 |
| 8K25B | TGACGGTTCGGAGAGCAGTTCGCCAGGTTAGAGTAGATGTGG (SEQ ID NO: 56) | 1845 |
| 8K26A | AACTGCTCTCCGAACCGTCAGAAACCGGTTGTTGACCACTCTG (SEQ ID NO: 57) | 1846 |
| 8K26B | GTAGAACCAACAGAGTTGATACGAACAGAGTGGTCAACAACCGGT (SEQ ID NO: 58) | 1847 |
| 8K27A | CGTATCAACTCTGTTGGTTCTACCGCGTCTTCTTCTCAGCCG (SEQ ID NO: 59) | 1848 |
| 8K27B | AACGTCGTCGTGAACCAGCAGCGGCTGAGAAGAAGACGCG (SEQ ID NO: 60) | 1849 |
| 8K - F | GTTGTTTCATATGTACGAAGTTCAGTGGAAAG (SEQ ID NO: 61) | 1851 |
| 8K - R | GTTGTTTGTCGACTAAACGTCGTCGTGAACCAGCAG (SEQ ID NO: 62) | 1852 |
| KIT COD-K948X | GTTCTTGTCGACTAtttctgacggttcggagagc (SEQ ID NO: 63) | 3411 |

P1332.N6 BI PTP KIT M552-K948-X COD
(Nucleic Acid SEQ ID NO: 64) (Protein SEQ ID NO: 65)

```
taatacgactcactatagggg aattgtgagcggataacaatt ccctctagaaataattt
tgtttaactttaagaaggaga tataccatgggtcaccacatc accatcatatgtacgaa
                                 M  G  H  H  H  H  H  H  M  Y  E gttcagtggaaagttgttgaa gaaatcaacggtaacaactac gtttacatcgacccgacc
 V  Q  W  K  V  V  E  E  I  N  G  N  N  Y  V  V  Y  I  D  P  T cagctgccgtacgaccacaaa tgggagttcccgcgtaaccgt ctgtctttcggtaaaacc
 Q  L  P  Y  D  H  K  W  E  F  P  R  N  R  L  S  F  G  K  T ctgggtgcgggtgcgttcggt aaagttgttgaagcgaccgcg tacggtctgatcaaatct
 L  G  A  G  A  F  G  K  V  V  E  A  T  A  Y  G  L  I  K  S gacgcggcgatgaccgttgcg gttaaaatgctgaaaccgtct gcgcacctgaccgaacgt
 D  A  A  M  T  V  A  V  K  M  L  K  P  S  A  H  L  T  E  R
gaagcgctgatgtctgaactg aaagttctgtcttacctgggt aaccacatgaacatcgtt

E  A  L  M  S  E  L  K  V  L  S  Y  L  G  N  H  M  N  I  V aacctgctgggtgcgtgcacc atcggtggtccgaccctggtt atcaccgaatactgctgc
 N  L  L  G  A  C  T  I  G  G  P  T  L  V  I  T  E  Y  C  C tacggtgacctgctgaacttc ctgcgtcgtaaacgtgactct ttcatctgctctaaacag
 Y  G  D  L  L  N  F  L  R  R  K  R  D  S  F  I  C  S  K  Q gaagaccacgcggaagcggcg ctgtacaaaaaacctgctgca ctctaaagaatcttcttgc
 E  D  H  A  E  A  A  L  Y  K  N  L  L  H  S  K  E  S  S  C tctgactctaccaacgaatac atggacatgaaaccgggtgtt tcttacgttgttccgacc
 S  D  S  T  N  E  Y  M  D  M  K  P  G  V  S  Y  V  V  P  T aaagcggacaaacgtcgttct gttcgtatcggttcttacatc gaacgtgacgttaccccg
 K  A  D  K  R  R  S  V  R  I  G  S  Y  I  E  R  D  V  T  P gcgatcatggaagacgacgaa ctggcgctggacctggaagac ctgctgtctttctcttac
 A  I  M  E  D  D  E  L  A  L  D  L  E  D  L  L  S  F  S  Y caggttgcgaaaggtatggcg ttcctggcgtctaaaaactgc atccaccgtgacctggcg
 Q  V  A  K  G  M  A  F  L  A  S  K  N  C  I  H  R  D  L  A gcgcgtaacatcctgctgacc cacggtcgtatcaccaaaatc tgcgacttcggtctggcg
 A  R  N  I  L  L  T  H  G  R  I  T  K  I  C  D  F  G  L  A cgtgacatcaaaaacgactct aactacgttgttaaaggtaac gcgcgtctgccggttaaa
 R  D  I  K  N  D  S  N  Y  V  V  K  G  N  A  R  L  P  V  K tggatggcgccggaatctatc ttcaactgcgtttacaccttc gaatctgacgtttggtct
 W  M  A  P  E  S  I  F  N  C  V  Y  T  F  E  S  D  V  W  S tacggtatcttcctgtgggaa ctgttctctctgggttcttct ccgtacccgggtatgccg
 Y  G  I  F  L  W  E  L  F  S  L  G  S  S  P  Y  P  G  M  P gttgactctaaattctacaaa atgatcaaagaaggtttccgt atgctgtctccggaacac
 V  D  S  K  F  Y  K  M  I  K  E  G  F  R  M  L  S  P  E  H gcgccggcgaaatgtacgac atcatgaaaacctgctgggac gcggacccgctgaaacgt
 A  P  A  E  M  Y  D  I  M  K  T  C  W  D  A  D  P  L  K  R ccgaccttcaaacagatcgtt cagctgatcgaaaaacagatc tctgaatctaccaaccac
 P  T  F  K  Q  I  V  Q  L  I  E  K  Q  I  S  E  S  T  N  H atctactctaacctggcgaac tgctctccgaaccgtcagaaa tagtcgactgaaaaagga
 I  Y  S  N  L  A  N  C  S  P  N  R  Q  K  - agagt
```

Additional Biochemical and Cell-Based Assays

In general, any protein kinase assay can be adapted for use with c-kit. For example, assays (e.g. biochemical and cell-based assays) as described in Lipson et al., U.S. Patent Publ. 20040002534 (incorporated herein by reference in its entirety) can be used in the present invention.

In Vivo Model System Testing

For in vivo testing, a suitable animal model system can be selected for use. For example, for multiple sclerosis, the rodent experimental allergic encephalomyelitis (EAE) is commonly used. This system is well-known, and is described, for example, in Steinman, 1996, Cell 85:299-302 and Secor et al., 2000, J Exp. Med 5:813-821, which are incorporated herein by reference in their entireties.

Similarly, other model systems can be selected and used in the present invention.

Exemplary Fms Biochemical Assay $IC_{50}$ values were determined with respect to inhibition of Fms kinase activity, where inhibition of phosphorylation of a peptide substrate is measured as a function of compound concentration. Compounds to be tested, dissolved in DMSO (1 µL), were added to a white 384-well plate (Costar #3705). Working stocks of Fms kinase (Upstate Biotech, #14-551), biotin-$(E4Y)_{10}$ substrate (Upstate Biotech, Cat #12-440), and ATP (Sigma, Cat #A-3377) were prepared in 8 mM MOPS pH 7.4, 2 mM $MgCl_2$, 8 mM $MnCl_2$, 2 mM DTT, and 0.01% Tween-20. All components were added to the 384-well plate for a final concentration of 0.5 ng/well Fms, 30 nM biotin-$(E4Y)_{10}$ (Upstate Biotechnology) and 10 µM ATP in a volume of 20 µL. Each sample was at 5% DMSO. The plate was then incubated for 60 minutes at room temperature. Just before use, working stocks of donor and acceptor beads from the AlphaScreen PY20 Detection Kit (PerkinElmer, Cat #676601M) were prepared in 8 mM MOPS, pH 7.4, 100 mM EDTA, 0.3% BSA. To stop the reaction, the plate was uncovered in the dark and 5 µl of Donor Beads solution (Streptavidin beads) was added to each well. The plate was incubated at room temperature for 20 minutes. Five microliters of Acceptor Beads solution (PY20 coated beads) were then added to each well. The final concentration of each bead was 20 µg/mL. The plates were incubated at room temperature for 60 minutes. Fluorescence signal was recorded on the Fusion Alpha reader or AlphaQuest reader. Phosphorylated substrate results in binding of the PY20 antibody and association of the donor and acceptor beads such that signal correlates with kinase activity. The signal vs. compound concentration was used to determine the $IC_{50}$.

Compounds were also tested using a similar assay with a 10-fold higher ATP concentration. Compounds to be tested, dissolved in DMSO (1 µL), were added to a white 384-well plate (Costar #3705). Working stocks of Fms kinase (Upstate Biotech, #14-551), biotin-$(E4Y)_{10}$ substrate (Upstate Biotech, Cat #12-440), and ATP (Sigma, Cat #A-3377) were prepared in 25 mM HEPES pH 7.5, 0.5 mM $MgCl_2$, 2 mM $MnCl_2$, 2 mM DTT, 0.01% BSA, and 0.01% Tween-20. All components were added to the 384-well plate for a final concentration of 0.5 ng/well Fms, 30 nM biotin-$(E4Y)_{10}$ (Upstate Biotechnology) and 100 µM ATP in a volume of 20 µL. Each sample was at 5% DMSO. The plate was then incubated for 30 minutes at room temperature. Just before use, working stocks of donor and acceptor beads from the AlphaScreen PY20 Detection Kit (PerkinElmer, Cat #676601M) were prepared in 25 mM HEPES pH 7.5, 100 mM EDTA, 0.01% BSA. To stop the reaction, the plate was uncovered in the dark and 5 µl of Donor Beads solution (Streptavidin beads) was added to each well. The plate was incubated at room temperature for 20 minutes. Five microliters of Acceptor Beads solution (PY20 coated beads) were then added to each well. The final concentration of each bead was 10 µg/mL. The plates were incubated at room temperature for 60 minutes. Fluorescence signal was recorded on the AlphaQuest or Envision reader. Phosphorylated substrate results in binding of the PY20 antibody and association of the donor and acceptor beads such that signal correlates with kinase activity. The signal vs. compound concentration was used to determine the $IC_{50}$.

Compounds were assayed using a similar assay to that described above, using in a final reaction volume of 25 µl: Fms (h) (5-10 mU) in 8 mM MOPS pH 7.0, 0.2 mM EDTA, 250 mM KKKSPGEYVNIEFG (SEQ ID NO:66), 10 mM MgAcetate and $\gamma$-$^{33}$P-ATP (approximately 500 cpm/pmol), with appropriate concentrations of compound. Samples were incubated for 40 minutes at room temperature and stopped by addition of 5 µl of 3% phosphoric acid. 10 µl of each sample is spotted onto a P30 filtermat and washed 3× with 75 mM phosphoric acid, once with methanol, dried and measured on scintillation counter (Upstate USA, Charlottesville, Va.).

Compounds P-0001, P-0002, P-0003, P-0004, P-0005, P-0006, P-0007, P-0008, P-0009, P-0010, P-0011, P-0013, P-0014, P-0015, P-0016, P-0028, P-0032, P-0033, P-0038, P-0053, P-0054, P-0055, P-0056, P-0057, P-0058, P-0059, P-0060, P-0061, P-0062, P-0063, P-0064, P-0065, P-0066, P-0069, P-0072, P-0073, P-0074, P-0075, P-0076, P-0078, P-0081, P-0082, P-0092, P-0093, P-0094, P-0095, P-0096, P-0097, P-0098, P-0099, P-0100, P-0101, P-0102, P-0103, P-0104, P-0105, P-0106, P-0107, P-0108, P-0109, P-0110, P-0111, P-0112, P-0113, P-0114, P-0115, P-0116, P-0117, P-0118, P-0119, P-0120, P-0121, P-0122, P-0123, P-0125, P-0126, P-0127, P-0128, P-0129, P-0130, P-0131, P-0132, P-0134, P-0135, P-0136, P-0137, P-0140, P-0141, P-0142, P-0143, P-0144, P-0145, P-0146, P-0147, P-0148, P-0149, P-0150, P-0151, P-0152, P-0153, P-0154, P-0156, P-0157, P-0158, P-0159, P-0160, P-0161, P-0163, P-0164, P-0165, P-0167, P-0168, P-0169, P-0170, P-0171, P-0172, P-0173, P-0174, P-0175, P-0176, P-0179, P-0180, P-0181, P-0182, P-0183, P-0185, P-0186, P-0187, P-0188, P-0189, P-0190, P-0191, P-0192, P-0193, P-0194, P-0195, P-0196, P-0197, P-0198, P-0199, P-0200, P-0201, P-0202, P-0203, P-0204, P-0205, P-0206, P-0207, P-0208, P-0209, P-0210, P-0211, P-0212, P-0213, P-0214, P-0215, P-0216, P-0217, P-0218, P-0219, P-0220, P-0221, P-0222, P-0223, P-0224, P-0225, P-0226, P-0227, P-0228, P-0229, P-0230, P-0231, P-0232, P-0233, P-0234, P-0235, P-0236, P-0237, P-0238, P-0239, P-0240, P-0241, P-0242, P-0243, P-0244, P-0245, P-0246, P-0247, P-0248, P-0249, P-0250, P-0251, P-0252, P-0253, P-0254, P-0255, P-0256, P-0257, P-0258, P-0259, P-0260, P-0261, P-0262, P-0263, P-0264, P-0265, P-0266, P-0267, P-0268, P-0269, P-0270, P-0271, P-0272, P-0273, P-0274, P-0275, P-0276, P-0277, P-0278, P-0279, P-0280, P-0281, P-0282, P-0283, P-0284, P-0285, P-0286, P-0287, P-0288, P-0289, P-0290, P-0291, P-0292, P-0293, P-0294, P-0295, P-0296, P-0297, P-0298, P-0299, P-0300, P-0301, P-0302, P-0303, P-0304, P-0305, P-0306, P-0307, P-0308, P-0309, P-0310, P-0311, P-0312, P-0313, P-0314, P-0315, P-0316, P-0317, P-0318, P-0319, P-0320, P-0321, P-0322, P-0323, P-0324, P-0325, P-0326, P-0327, P-0328, P-0329, P-0330, P-0331, P-0332, P-0333, P-0334, P-0335, P-0336, P-0337, P-0338, P-0339, P-0340, P-0341, P-0342, P-0343, P-0344, P-0345, P-0346, P-0347, P-0348, P-0349, P-0350, P-0351, P-0352, P-0353, P-0354, P-0355, P-0356, P-0357, P-0358, P-0359, P-0360, P-0361, P-0362, P-0363, P-0364, P-0365, P-0366, P-0367, P-0368, P-0369, P-0370, P-0371, P-0372, P-0373, P-0374, P-0375, P-0376, P-0377, P-0378, P-0379, P-0380, P-0381, P-0382, P-0383, P-0384, P-0385, P-0386, P-0387, P-0390, P-0391, P-0392, P-0393, P-0394, P-0395, P-0396, P-0402, P-0403, P-0404, P-0405, P-0406, P-0407, P-0408, P-0409, and P-0412 had $IC_{50}$ of less than 1 μM in at least one of the Fms assays described above in Examples 40 or 41.

Exemplary TrkA Biochemical Assay

Compounds were similarly assayed to determine $IC_{50}$ values with respect to inhibition of TrkA kinase activity, where inhibition of phosphorylation of a peptide substrate was measured as a function of compound concentration. Compounds tested were dissolved in DMSO (1 μL) and added to a white 384-well plate (Costar #3705). Working stocks of TrkA kinase (Upstate Biotech, #14-571), biotin-$(E4Y)_{10}$ substrate (Upstate Biotech, Cat #12-440), and ATP (Sigma, Cat #A-3377) were prepared in 25 mM Hepes pH 7.5, 10 mM $MnCl_2$, 1 mM DTT, and 0.01% Tween-20. All components were added to the 384-well plate for a final concentration of 1 ng/well TrkA, 30 nM biotin-$(E4Y)_{10}$ (Upstate Biotechnology) and 100 μM ATP in a volume of 20 μL. Each sample was at 5% DMSO. The plate was then incubated for 40 minutes at room temperature. Just before use, working stocks of donor and acceptor beads from the AlphaScreen PY20 Detection Kit (PerkinElmer, Cat #676601M) were prepared in 25 mM Hepes pH 7.5, 100 mM EDTA, 0.3% BSA. To stop the reaction, the plate was uncovered in the dark and 5 μl of Donor Beads solution (Streptavidin beads) was added to each well. The plate was incubated at room temperature for 20 minutes. Five microliters of Acceptor Beads solution (PY20 coated beads) were then added to each well. The final concentration of each bead was 10 μg/mL. The plates were incubated at room temperature for 60 minutes. Fluorescence signal was recorded on the AlphaQuest or Envision reader. Phosphorylated substrate results in binding of the PY20 antibody and association of the donor and acceptor beads such that signal correlates with kinase activity. The signal vs. compound concentration was used to determine the $IC_{50}$. Compounds P-0157, P-0171, P-0179, P-0180, P-0303, and P-0412 had $IC_{50}$ of less than 1 μM in this TrkA assay.

Exemplary HGK Biochemical Assay

The MAP4K4 (or kinase domain thereof) is an active kinase in AlphaScreen. $IC_{50}$ values are determined with respect to inhibition of MAP4K4 kinase activity, where inhibition of phosphorylation of a peptide substrate is measured as a function of compound concentration. Compounds to be tested were dissolved in DMSO to a concentration of 20 mM. These were diluted 30 μl into 120 μl of DMSO (4 mM) and 1 μl was added to an assay plate. These were then serially diluted 1:3 (50 μl to 100 μl DMSO) for a total of 8 points. Plates were prepared such that each kinase reaction is 20 μl in 1× kinase buffer (20 mM Tris, pH 7.4, 10 mM $MgCl_2$, 1 mM DTT, 0.01% Tween-20), 5% DMSO and 10 μM ATP. Substrate was 10 nM biotin-ERM (T567T564T558, Cell Signaling, Inc., cat #1344). MAP4K4 kinase was at 0.5 ng per sample. After incubation of the kinase reaction for 40 min at room temperature, 5 μl of donor beads and protein A acceptor beads (Perkin Elmer Life Science, cat #67606017) at final concentration 1 μg/ml in stop buffer (20 mM Tris, pH 7.4, 200 mM Nacl, 100 mM EDTA, 0.03% BSA) was added, along with Phospho-ERM Antibody (T567T564T558, Cell Signaling, Inc., cat #3141) at 1:1000 dilution. The samples were incubated for 2 hours at room temperature and the signal per well was read on AlphaQuest reader. Phosphorylated substrate results in binding of the antibody which binds to protein A acceptor bead and association of the donor and acceptor beads is such that the signal correlates with kinase activity. The signal vs. compound concentration was used to determine the $IC_{50}$. Compounds P-0156, P-0177, P-0179, P-0195, P-0201, P-0203, P-0206, P-0207, P-0231, P-0240, P-0241, P-0255, P-0324, P-0341, and P-0403 had $IC_{50}$ of less than 1 μM in this HGK assay.

Example 42

Site-Directed Mutagenesis of c-Kit, c-Fms and Other Kinases

Mutagenesis of c-kit and other kinases (as well as other sequences of interest) can be carried out according to the following procedure as described in Molecular Biology: Current Innovations and Future Trends. Eds. A. M. Griffin and H. G. Griffin. (1995) ISBN 1-898486-01-8, Horizon Scientific Press, PO Box 1, Wymondham, Norfolk, U.K., among others.

In vitro site-directed mutagenesis is an invaluable technique for studying protein structure-function relationships, gene expression and vector modification. Several methods have appeared in the literature, but many of these methods require single-stranded DNA as the template. The reason for this, historically, has been the need for separating the complementary strands to prevent reannealing. Use of PCR in site-directed mutagenesis accomplishes strand separation by using a denaturing step to separate the complementing strands and allowing efficient polymerization of the PCR primers. PCR site-directed methods thus allow site-specific mutations to be incorporated in virtually any double-stranded plasmid; eliminating the need for M13-based vectors or single-stranded rescue.

It is often desirable to reduce the number of cycles during PCR when performing PCR-based site-directed mutagenesis to prevent clonal expansion of any (undesired) second-site mutations. Limited cycling which would result in reduced product yield, is offset by increasing the starting template concentration. A selection is used to reduce the number of parental molecules coming through the reaction. Also, in order to use a single PCR primer set, it is desirable to optimize the long PCR method. Further, because of the extendase activity of some thermostable polymerases it is often necessary to incorporate an end-polishing step into the procedure prior to end-to-end ligation of the PCR-generated product containing the incorporated mutations in one or both PCR primers.

The following protocol provides a facile method for site-directed mutagenesis and accomplishes the above desired features by the incorporation of the following steps: (i) increasing template concentration approximately 1000-fold over conventional PCR conditions; (ii) reducing the number of cycles from 25-30 to 5-10; (iii) adding the restriction endonuclease DpnI (recognition target sequence: 5-Gm6ATC-3, where the A residue is methylated) to select against parental DNA (note: DNA isolated from almost all common strains of E. coli is Dam-methylated at the sequence 5-GATC-3); (iv) using Taq Extender in the PCR mix for increased reliability for PCR to 10 kb; (v) using Pfu DNA polymerase to polish the ends of the PCR product, and (vi) efficient intramolecular ligation in the presence of T4 DNA ligase.

Plasmid template DNA (approximately 0.5 pmole) is added to a PCR cocktail containing, in 25 ul of 1× mutagenesis buffer: (20 mM Tris HCl, pH 7.5; 8 mM MgCl2; 40 ug/ml BSA); 12-20 pmole of each primer (one of which must contain a 5-prime phosphate), 250 uM each dNTP, 2.5 U Taq DNA polymerase, 2.5 U of Taq Extender (Stratagene).

The PCR cycling parameters are 1 cycle of: 4 min at 94 C, 2 min at 50 C and 2 min at 72° C.; followed by 5-10 cycles of 1 min at 94° C., 2 min at 54 C and 1 min at 72° C. (step 1).

The parental template DNA and the linear, mutagenesis-primer incorporating newly synthesized DNA are treated with DpnI (10 U) and Pfu DNA polymerase (2.5 U). This results in the DpnI digestion of the in vivo methylated parental template and hybrid DNA and the removal, by Pfu DNA polymerase, of the Taq DNA polymerase-extended base(s) on the linear PCR product.

The reaction is incubated at 37° C. for 30 min and then transferred to 72° C. for an additional 30 min (step 2).

Mutagenesis buffer (1×, 115 ul, containing 0.5 mM ATP) is added to the DpnI-digested, Pfu DNA polymerase-polished PCR products.

The solution is mixed and 10 ul is removed to a new microfuge tube and T4 DNA ligase (2-4 U) added.

The ligation is incubated for greater than 60 min at 37° C. (step 3).

The treated solution is transformed into competent *E. coli* (step 4).

In addition to the PCR-based site-directed mutagenesis described above, other methods are available. Examples include those described in Kunkel (1985) Proc. Natl. Acad. Sci. 82:488-492; Eckstein et al. (1985) Nucl. Acids Res. 13:8764-8785; and using the GeneEditor™ Site-Directed Mutagenesis System from Promega.

Example 43

Synthesis of 3,5-Dimethyl-4-(1H-pyrrolo[2,3-b]pyridin-3-ylmethyl)-pyrazole-1-carboxylic acid benzylamide P-0084

3,5-Dimethyl-4-(1H-pyrrolo[2,3-b]pyridin-3-ylmethyl)-pyrazole-1-carboxylic acid benzylamide P-0084 was synthesized in 6 steps from dimethyl-(1H-pyrrolo[2,3-b]pyridin-3-ylmethyl)-amine 2 as shown in Scheme 158.

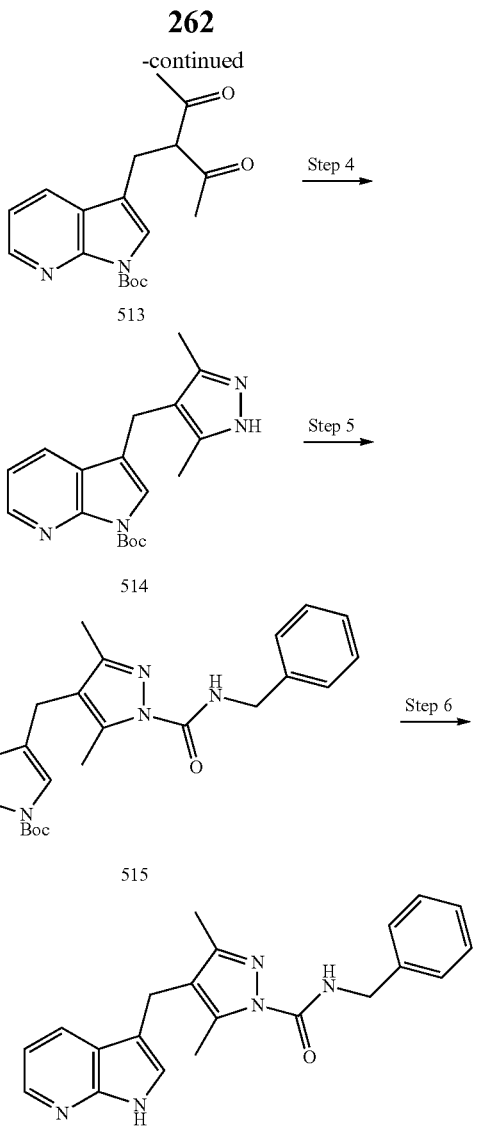

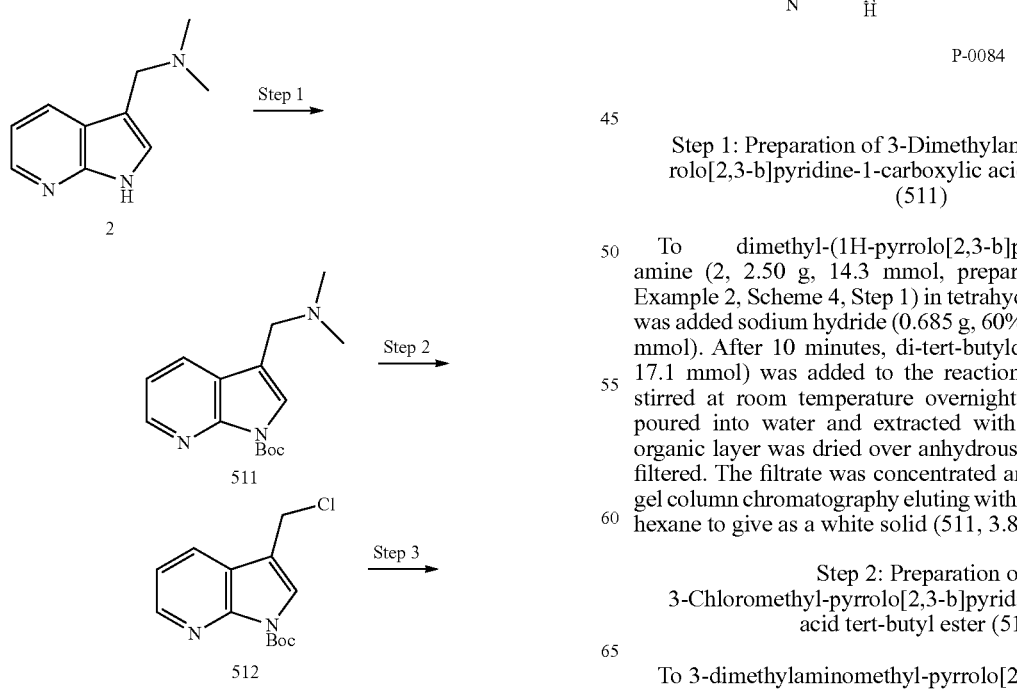

Step 1: Preparation of 3-Dimethylaminomethyl-pyrrolo[2,3-b]pyridine-1-carboxylic acid tert-butyl ester (511)

To dimethyl-(1H-pyrrolo[2,3-b]pyridin-3-ylmethyl)-amine (2, 2.50 g, 14.3 mmol, prepared as described in Example 2, Scheme 4, Step 1) in tetrahydrofuran (200.0 mL) was added sodium hydride (0.685 g, 60% in mineral oil, 17.1 mmol). After 10 minutes, di-tert-butyldicarbonate (3.74 g, 17.1 mmol) was added to the reaction. The reaction was stirred at room temperature overnight. The reaction was poured into water and extracted with ethyl acetate. The organic layer was dried over anhydrous sodium sulfate and filtered. The filtrate was concentrated and purified by silica gel column chromatography eluting with 30% ethyl acetate in hexane to give as a white solid (511, 3.80 g, 96.7%).

Step 2: Preparation of 3-Chloromethyl-pyrrolo[2,3-b]pyridine-1-carboxylic acid tert-butyl ester (512)

To 3-dimethylaminomethyl-pyrrolo[2,3-b]pyridine-1-carboxylic acid tert-butyl ester (511, 2.60 g, 9.44 mmol) in toluene (50.00 mL) was added isopropyl chloroformate (11.3 mL, 1.0 M in toluene) under an atmosphere of nitrogen. The reaction was stirred at room temperature for 3 hours. The reaction was poured into water and extracted with ethyl acetate. The organic layer was dried over anhydrous sodium sulfate and filtered. The filtrate was concentrated and purified by silica gel column chromatography eluting with 20% ethyl acetate in hexane to give a white solid (512, 2.0 g, 79.4%).

Step 3—Preparation of 3-(2-Acetyl-3-oxo-butyl)-pyrrolo[2,3-b]pyridine-1-carboxylic acid tert-butyl ester (513)

To acetylacetone (0.563 g, 5.62 mmol) in dimethyl sulfoxide (29.0 mL) was added sodium hydride (0.225 g, 60% in mineral oil, 5.62 mmol). After 20 minutes, 3-chloromethyl-pyrrolo[2,3-b]pyridine-1-carboxylic acid tert-butyl ester (512, 1.00 g, 3.75 mmol) was added to the reaction. The reaction was stirred at room temperature for 2 hours. The reaction was poured into water and extracted with ethyl acetate. The organic layer was dried over anhydrous sodium sulfate and filtered. The filtrate was concentrated and purified by silica gel column chromatography eluting with 40% ethyl acetate in hexane to give a colorless oil (513, 0.59 g, 48.0%). MS (ESI) [M+H$^+$]$^+$=331.4.

Step 4—Preparation of 3-(3,5-Dimethyl-1H-pyrazol-4-ylmethyl)-pyrrolo[2,3-b]pyridine-1-carboxylic acid tert-butyl ester (514)

To 3-(2-acetyl-3-oxo-butyl)-pyrrolo[2,3-b]pyridine-1-carboxylic acid tert-butyl ester (513, 1.20 g, 3.63 mmol) in methanol (15.0 mL), cooled to −20° C. under an atmosphere of nitrogen, was added hydrazine (0.128 g, 4.00 mmol) in dichloromethane (6.0 mL). The reaction was stirred for 2 hours. The reaction was concentrated to remove the solvents, and the residue was poured into water and extracted with ethyl acetate. The organic layer was dried over anhydrous sodium sulfate and filtered. The filtrate was concentrated and purified by silica gel column chromatography eluting with 60% ethyl acetate in hexane to give a white solid (514, 1.0 g, 84.4%). MS (ESI) [M+H$^+$]$^+$=327.4.

Step 5—Preparation of 3-(1-Benzylcarbamoyl-3,5-dimethyl-1H-pyrazol-4-ylmethyl)-pyrrolo[2,3-b]pyridine-1-carboxylic acid tert-butyl ester (515)

To 3-(3,5-dimethyl-1H-pyrazol-4-ylmethyl)-pyrrolo[2,3-b]pyridine-1-carboxylic acid tert-butyl ester (514, 60.0 mg, 0.18 mmol) in dichloromethane (6.0 mL) were added 1,8-diazabicyclo[5.4.0]undec-7-ene (0.033 mL, 0.220 mmol) and benzyl isocyanate (29.4 mg, 0.220 mmol) under an atmosphere of nitrogen. The reaction was stirred at room temperature for 2 hours. The reaction was concentrated and purified by silica gel column chromatography eluting with 30% ethyl acetate in hexane to give crude compound (515, approx. 50 mg) that was used in the next step directly. MS (ESI) [M+H$^+$]$^+$=460.5.

Step 6—3,5-Dimethyl-4-(1H-pyrrolo[2,3-b]pyridin-3-ylmethyl)-pyrazole-1-carboxylic acid benzylamide (P-0084)

To 3-(1-benzylcarbamoyl-3,5-dimethyl-1H-pyrazol-4-ylmethyl)-pyrrolo[2,3-b]pyridine-1-carboxylic acid tert-butyl ester (515, 50.0 mg, 0.11 mmol) in dichloromethane (6.0 mL) was added trifluoroacetic acid (0.20 mL, 2.6 mmol) under an atmosphere of nitrogen. The reaction was stirred at room temperature for 20 minutes. The reaction was poured into aqueous potassium carbonate and extracted with ethyl acetate. The organic layer was dried over anhydrous sodium sulfate and filtered. The filtrate was concentrated and purified by silica gel column chromatography eluting with 30% ethyl acetate in hexane to give a white solid (P-0084, 11.0 mg, 28.1%). MS (ESI) [M+H$^+$]$^+$=360.5.

3-(3,5-Dimethyl-1H-pyrazol-4-ylmethyl)-pyrrolo[2,3-b]pyridine P-0124

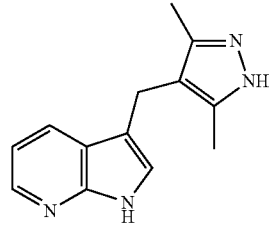 [SMILES: Cc1n[nH]c(C)c1Cc1c[nH]c2ncccc12]

was prepared from 3-(3,5-Dimethyl-1H-pyrazol-4-ylmethyl)-pyrrolo[2,3-b]pyridine-1-carboxylic acid tert-butyl ester (514, 15.0 mg, 0.046 mmol) by dissolving in dichloromethane (10.0 mL) to which trifluoroacetic acid (0.10 mL, 1.3 mmol) was added. The reaction was stirred at room temperature for 1 hour, then poured into aqueous potassium carbonate and extracted with ethyl acetate. The organic layer was dried over anhydrous sodium sulfate and filtered. The filtrate was concentrated and washed with ethyl acetate in hexane to give an off-white solid (P-0124, 7.5 mg, 72.0%). MS (ESI) [M+H$^+$]$^+$=227.3.

Additional compounds were prepared following the protocol of Scheme 158, replacing benzyl isocyanate with an appropriate electrophile in Step 5. The following compounds were made following this procedure:

3,5-Dimethyl-4-(1H-pyrrolo[2,3-b]pyridin-3-ylmethyl)-pyrazole-1-carboxylic acid phenylamide (P-0085),

[3,5-Dimethyl-4-(1H-pyrrolo[2,3-b]pyridin-3-ylmethyl)-pyrazol-1-yl]-phenyl-methanone (P-0086), 1-[3,5-Dimethyl-4-(1H-pyrrolo[2,3-b]pyridin-3-ylmethyl)-pyrazol-1-yl]-3-phenyl-propan-1-one (P-0087), 3-(3,5-Dimethyl-1-phenylmethanesulfonyl-1H-pyrazol-4-ylmethyl)-1H-pyrrolo[2,3-b]pyridine (P-0088), 3-[1-(Butane-1-sulfonyl)-3,5-dimethyl-1H-pyrazol-4-ylmethyl]-1H-pyrrolo[2,3-b]pyridine (P-0089), 3,5-Dimethyl-4-(1H-pyrrolo[2,3-b]pyridin-3-ylmethyl)-pyrazole-1-carboxylic acid butylamide (P-0090), and 3,5-Dimethyl-4-(1H-pyrrolo[2,3-b]pyridin-3-ylmethyl)-pyrazole-1-carboxylic acid phenethyl-amide (P-0091).

The electrophile used in place of benzyl isocyanate in Step 5 is indicated in Column 2 of the following table, with the compound structure given in Column 3. Column 1 provides the compound number and Column 4 the experimental mass spectrometry result.

| Electrophile | Compound | MS(ESI) [M + H⁺]⁺ observed |
|---|---|---|
| P-0085 | | 346.4 |
| P-0086 | | 331.2 |
| P-0087 | | 359.2 |
| P-0088 | | 381.2 |
| P-0089 | | 347.2 |
| P-0090 | | 326.2 |

| Electrophile | Compound | MS(ESI) [M + H⁺]⁺ observed |
|---|---|---|
| P-0091 | | |

Additional compounds were prepared following the protocol of Scheme 158, replacing dimethyl-(1H-pyrrolo[2,3-b]pyridin-3-ylmethyl)-amine 2 with (5-chloro-1H-pyrrolo[2,3-b]pyridin-3-ylmethyl)-dimethyl-amine (prepared as described in Example 107, Scheme 164, isolated after step 1) in Step 1 and replacing benzyl isocyanate with an appropriate electrophile in Step 5. The following compounds were made following this procedure:

4-(5-Chloro-1H-pyrrolo[2,3-b]pyridin-3-ylmethyl)-3,5-dimethyl-pyrazole-1-carboxylic acid [2-(4-fluoro-phenyl)-ethyl]-amide (P-0157), 4-(5-Chloro-1H-pyrrolo[2,3-b]pyridin-3-ylmethyl)-3,5-dimethyl-pyrazole-1-carboxylic acid 4-fluoro-benzylamide (P-0158), 4-(5-Chloro-1H-pyrrolo[2,3-b]pyridin-3-ylmethyl)-3,5-dimethyl-pyrazole-1-carboxylic acid 4-chloro-benzylamide (P-0159), and 4-(5-Chloro-1H-pyrrolo[2,3-b]pyridin-3-ylmethyl)-3,5-dimethyl-pyrazole-1-carboxylic acid [(S)-1-(4-fluorophenyl)-ethyl]-amide (P-0160).

The electrophile used in place of benzyl isocyanate in Step 5 is indicated in Column 2 of the following table, with the compound structure given in Column 3. Column 1 provides the compound number and Column 4 the experimental mass spectrometry result.

| Electrophile | Compound | MS(ESI) [M + H⁺]⁺ observed |
|---|---|---|
| P-0157 | | 426.2 |
| P-0158 | | 412.2 |
| P-0159 | | 428.2 |

| Electrophile | Compound | MS(ESI) [M + H⁺]⁺ observed |
|---|---|---|
| P-0160 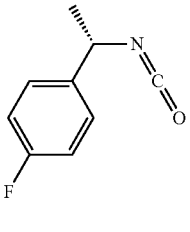 | | 426.2 |
Example 44
Synthesis of [4-chloro-5-(1H-pyrrolo[2,3-b]pyridin-3-ylmethyl)-thiazol-2-yl]-pyridin-4-ylmethyl-amine P-0168
[4-Chloro-5-(1H-pyrrolo[2,3-b]pyridin-3-ylmethyl)-thiazol-2-yl]-pyridin-4-ylmethyl-amine P-0168 was synthesized in 5 steps as shown in Scheme 159.
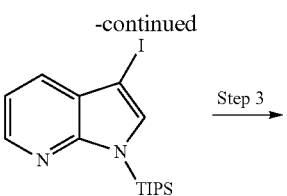
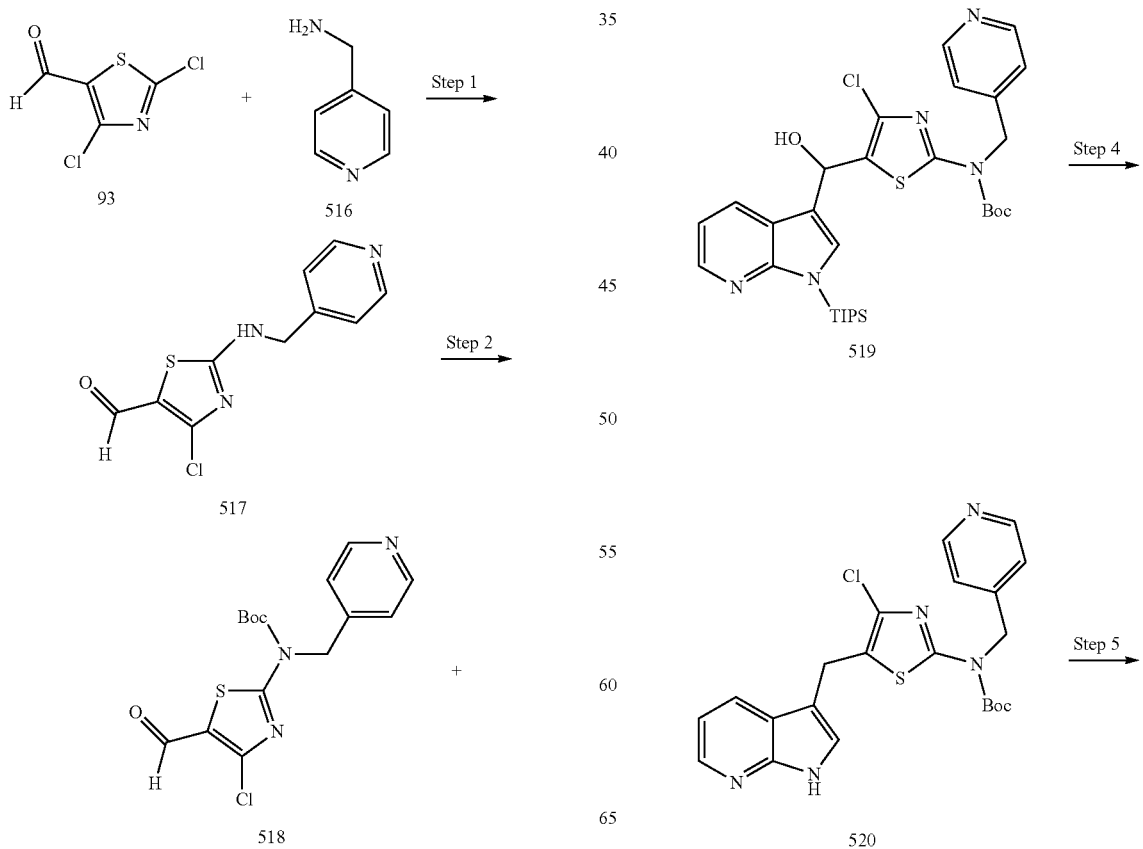

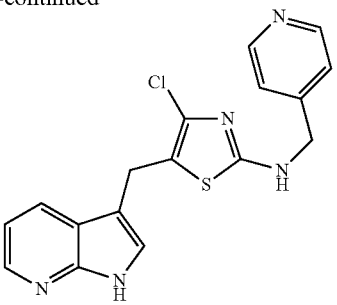

P-0168

Step 1—Preparation of 4-chloro-2-[(pyridin-4-ylmethyl)-amino]-thiazole-5-carbaldehyde (517)

To a solution of 4-(aminomethyl)pyridine (516, 1.16 mL, 11.5 mmol) and N,N-diisopropylethylamine (3.8 mL, 22 mmol) in tetrahydrofuran (50 mL) was added 2,4-dichlorothiazole-5-carbaldehyde (93, 2.0 g, 11.0 mmol) in tetrahydrofuran (5 mL) at room temperature. The reaction mixture was stirred at room temperature overnight. The reaction mixture was poured into ice water, extracted with ethyl acetate, washed with brine, and dried over sodium sulfate. The crude compound 4-chloro-2-[(pyridin-4-ylmethyl)-amino]-thiazole-5-carbaldehyde (517) was used for the next step without purification.

Step 2—Preparation of (4-chloro-5-formyl-thiazol-2-yl)-pyridin-4-ylmethyl-carbamic acid tert-butyl ester (518)

A mixture of 4-chloro-2-[(pyridin-4-ylmethyl)-amino]-thiazole-5-carbaldehyde (517, 3.28 g, 11.0 mmol), di-tert-butyldicarbonate (4.0 g, 18 mol) and triethylamine (10 mL, 74 mmol) in dichloromethane (120 mL) was stirred at room temperature for 6 hours. The reaction mixture was poured into ice water, extracted with ethyl acetate, washed with brine, and dried over sodium sulfate. After removal of solvent, the residue was purified by silica gel column chromatography eluting with ethyl acetate in hexanes to provide the desired compound as a yellow solid (518, 564 mg, 15%). MS (ESI) [M+H$^+$]$^+$=354.1.

Step 3—Preparation of {4-chloro-5-[hydroxy-(1-triisopropylsilanyl-1H-pyrrolo[2,3-b]pyridin-3-yl)-methyl]-thiazol-2-yl}-pyridin-4-ylmethyl-carbamic acid tert-butyl ester (519)

To a solution of 3-iodo-1-triisopropylsilanyl-1H-pyrrolo[2,3-b]pyridine (96, 0.44 g, 1.1 mmol) in tetrahydrofuran (20 mL) at −20° C., isopropylmagnesium chloride (2 M in tetrahydrofuran, 0.6 mL, 1.2 mmol) was added dropwise. The reaction mixture was allowed to warm to 0° C. in 10 minutes. The reaction mixture was then cooled to −40° C. A solution of (4-chloro-5-formyl-thiazol-2-yl)-pyridin-4-ylmethyl-carbamic acid tert-butyl ester (518, 0.26 g, 0.73 mmol) in tetrahydrofuran (4 mL) was added to the reaction mixture. The reaction mixture was allowed to warm to −10° C. over 30 minutes. The reaction mixture was poured into ice water, extracted with ethyl acetate, washed with brine, and dried over sodium sulfate. After removal of solvent, the residue was purified by silica gel column chromatography eluting with ethyl acetate in hexanes to provide the desired compound as a yellow solid (519, 397 mg, 86%). MS (ESI) [M+H$^+$]$^+$=628.3.

Step 4—Preparation of [4-chloro-5-(1H-pyrrolo[2,3-b]pyridin-3-ylmethyl)-thiazol-2-yl]-pyridin-4-ylmethyl-carbamic acid tert-butyl ester (520)

A mixture of {4-chloro-5-[hydroxy-(1-triisopropylsilanyl-1H-pyrrolo[2, 3-1)]pyridin-3-yl)-methyl]-thiazol-2-yl}-pyridin-4-ylmethyl-carbamic acid tert-butyl ester (519, 0.397 g, 0.57 mmol), triethylsilane (1.0 mL, 6.3 mmol), and trifluoroacetic acid (0.5 mL, 6 mmol) in acetonitrile (10 mL) was stirred at 40° C. for 2 hours. The reaction mixture was poured into ice water, extracted with ethyl acetate, washed with sodium bicarbonate, washed with brine, and dried over sodium sulfate. After removal of solvent, the residue was purified by silica gel column chromatography eluting with methanol in dichloromethane to provide the desired compound as a yellow solid (520, 126 mg, 49%). MS (ESI) [M+H$^+$]$^+$=456.2.

Step 5—Preparation of [4-chloro-5-(1H-pyrrolo[2,3-b]pyridin-3-ylmethyl)-thiazol-2-yl]-pyridin-4-ylmethyl-amine (P-0168)

To a solution of [4-chloro-5-(1H-pyrrolo[2,3-b]pyridin-3-ylmethyl)-thiazol-2-yl]-pyridin-4-ylmethyl-carbamic acid tert-butyl ester (520, 126 mg, 0.000276 mol) in dichloromethane (2 mL) was added hydrogen chloride (4 M in 1,4-dioxane, 2 mL). The reaction mixture was stirred at room temperature overnight. The reaction mixture was poured into cold sodium bicarbonate solution, extracted with ethyl acetate, washed with brine and dried over magnesium sulfate. After removal of solvents, the residue was washed with ethyl acetate to provide the desired compound as a light yellow solid (P-0168, 68.4 mg, 70%). MS (ESI) [M+H$^+$]$^+$=356.2.

Additional compounds were prepared following the protocol of Scheme 159, replacing 4-(aminomethyl)pyridine 516 with an appropriate amine. The following compounds were made following this procedure:

[4-Chloro-5-(1H-pyrrolo[2,3-b]pyridin-3-ylmethyl)-thiazol-2-yl]-pyridin-3-ylmethyl-amine (P-0164),

[4-Chloro-5-(1H-pyrrolo[2,3-b]pyridin-3-ylmethyl)-thiazol-2-yl]-pyridin-2-ylmethyl-amine (P-0167),

[4-Chloro-5-(1H-pyrrolo[2,3-b]pyridin-3-ylmethyl)-thiazol-2-yl]-(6-methyl-pyridin-2-ylmethyl)-amine (P-0171),

[4-Chloro-5-(1H-pyrrolo[2,3-b]pyridin-3-ylmethyl)-thiazol-2-yl]-(6-trifluoromethyl-pyridin-3-ylmethyl)-amine (P-0173),

[4-Chloro-5-(1H-pyrrolo[2,3-b]pyridin-3-ylmethyl)-thiazol-2-yl]-(1,5-dimethyl-1H-pyrazol-3-ylmethyl)-amine (P-0172),

[4-Chloro-5-(1H-pyrrolo[2,3-b]pyridin-3-ylmethyl)-thiazol-2-yl]-(2,5-dimethyl-2H-pyrazol-3-ylmethyl)-amine (P-0175), and

[4-Chloro-5-(1H-pyrrolo[2,3-b]pyridin-3-ylmethyl)-thiazol-2-yl]-(4-fluoro-benzyl)-amine (P-0156).

The following table indicates the amine (Column 2) used in Scheme 159 to provide the compounds (Column 3). Column 1 provides the compound number and Column 4 the observed mass.

| Compound number | Amine | Compound | MS(ESI) [M + H+]+ observed |
|---|---|---|---|
| P-0164 | H2N-CH2-(3-pyridyl) | 7-azaindole-CH2-(4-chlorothiazol-5-yl)-2-NH-CH2-(3-pyridyl) | 356.1 |
| P-0167 | H2N-CH2-(2-pyridyl) | 7-azaindole-CH2-(4-chlorothiazol-5-yl)-2-NH-CH2-(2-pyridyl) | 356.1 |
| P-0171 | H2N-CH2-(6-methylpyridin-2-yl) | 7-azaindole-CH2-(4-chlorothiazol-5-yl)-2-NH-CH2-(6-methylpyridin-2-yl) | 370.2 |
| P-0173 | H2N-CH2-(6-trifluoromethylpyridin-3-yl) | 7-azaindole-CH2-(4-chlorothiazol-5-yl)-2-NH-CH2-(6-trifluoromethylpyridin-3-yl) | 424.2 |
| P-0172 | H2N-CH2-(1,5-dimethyl-1H-pyrazol-3-yl) | 7-azaindole-CH2-(4-chlorothiazol-5-yl)-2-NH-CH2-(1,5-dimethyl-1H-pyrazol-3-yl) | 373.2 |
| P-0175 | H2N-CH2-(1,3-dimethyl-1H-pyrazol-5-yl) | 7-azaindole-CH2-(4-chlorothiazol-5-yl)-2-NH-CH2-(1,3-dimethyl-1H-pyrazol-5-yl) | 373.2 |
| P-0156 | H2N-CH2-(4-fluorophenyl) | 7-azaindole-CH2-(4-chlorothiazol-5-yl)-2-NH-CH2-(4-fluorophenyl) | 373.1 |

Example 45

Synthesis of [4-ethyl-5-(1H-pyrrolo[2,3-b]pyridin-3-ylmethyl)-thiazol-2-yl]-(4-fluoro-benzyl)-amine P-0162 and (4-fluoro-benzyl)-[4-methyl-5-(1H-pyrrolo[2,3-b]pyridin-3-ylmethyl)-thiazol-2-yl]-amine P-0162

[4-Ethyl-5-(1H-pyrrolo[2,3-b]pyridin-3-ylmethyl)-thiazol-2-yl]-(4-fluoro-benzyl)-amine P-0162 was synthesized in 1 step from [4-chloro-5-(1H-pyrrolo[2,3-b]pyridin-3-ylmethyl)-thiazol-2-yl]-(4-fluoro-benzyl)-amine P-0156 as shown in Scheme 160.

Scheme 160

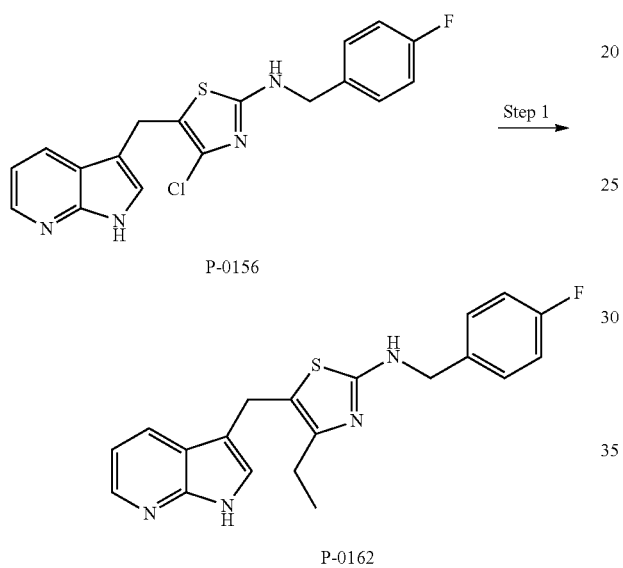

Step 1—Preparation of [4-ethyl-5-(1H-pyrrolo[2,3-b]pyridin-3-ylmethyl)-thiazol-2-yl]-(4-fluoro-benzyl)-amine (P-0162)

Into a round bottom flask, under an atmosphere of nitrogen, [1,1'-bis(diphenyl phosphino)ferrocene]dichloro palladium (II), complex with dichloromethane (1:1), was placed with toluene (15 mL, 140 mmol). [4-Chloro-5-(1H-pyrrolo[2,3-b]pyridin-3-ylmethyl)-thiazol-2-yl]-(4-fluoro-benzyl)-amine (P-0156, 145 mg, 0.4 mmol) was added in 5 ml of toluene at room temperature. The mixture was stirred for 10 minutes. To the stirring reaction, a solution of 3.13 Methyl magnesium bromide in ether (1.86 mL) was added dropwise at room temperature. The opaque solution was heated to 60° C. Tetrahydrofuran (10 mL) was added to the warm solution. The mixture was heated to reflux for an additional two hours. After cooling to 0° C., the reaction was quenched with a solution of citric acid at pH 4-5 in ice-water and stirred to room temperature. The mixture was diluted with ethyl acetate and washed with saturated sodium bicarbonate and brine. The organic layer was dried over anhydrous sodium sulfate and the solvent was removed under reduced pressure. Purification with flash chromatography, eluting with a gradient of ethyl acetate:hexanes (20:100), gave a yellow solid that was further washed with ethyl acetate to give P-0162 (15 mg, 10%) as an off-white solid. MS (ESI) [M+H$^+$]$^+$=367.2.

(4-Fluoro-benzyl)-[4-methyl-5-(1H-pyrrolo[2,3-b]pyridin-3-ylmethyl)-thiazol-2-yl]-amine P-0163

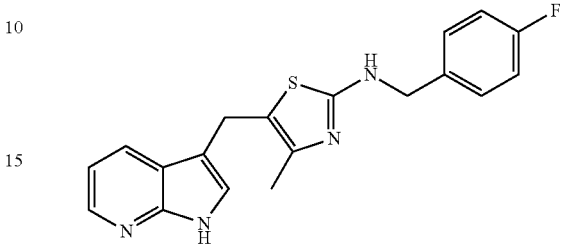

was prepared using the protocol of Scheme 160, substituting the 3.13 M ethyl magnesium bromide in ether solution with 1.4 M of methylmagnesium bromide in tetrahydrofuran. MS (ESI) [M+H$^+$]$^+$=353.2.

Example 46

Synthesis of (4-Chloro-benzyl)-[6-(1H-pyrrolo[2,3-b]pyridin-3-ylmethyl)-pyridazin-3-yl]-amine P-0092

(4-Chloro-benzyl)-[6-(1H-pyrrolo[2,3-b]pyridin-3-ylmethyl)-pyridazin-3-yl]-amine P-0092 was synthesized in 3 steps as shown in Scheme 161.

Scheme 161

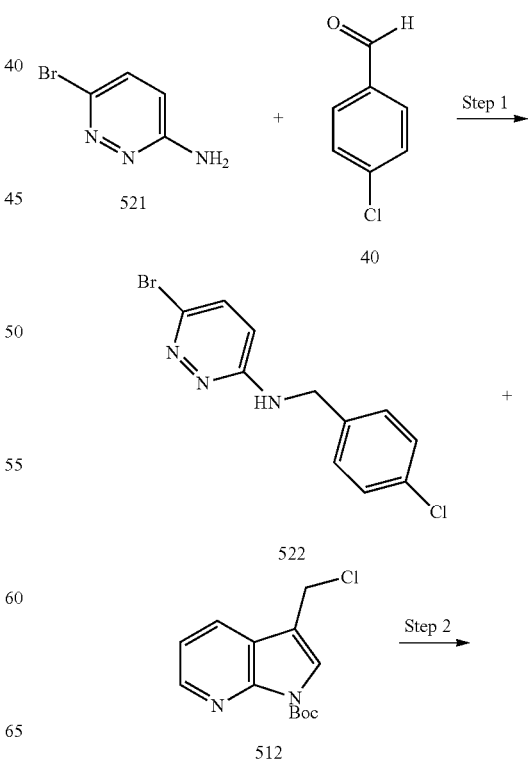

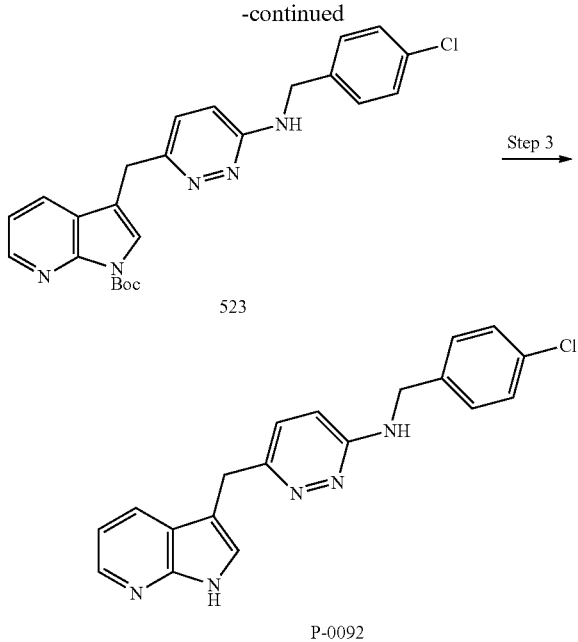

523

P-0092

Step 1—Synthesis of (6-bromo-pyridazin-3-yl)-(4-chloro-benzyl)-amine (522)

To 6-bromo-pyridazin-3-ylamine (521, 0.85 g, 0.0049 mol) in acetonitrile (30.0 mL) were added 4-chlorobenzaldehyde (40, 0.82 g, 0.0058 mol), triethylsilane (4.0 mL, 0.025 mol) and trifluoroacetic acid (2.0 mL, 0.026 mol). The reaction was heated to reflux for 4 hours, then poured into water, and extracted with ethyl acetate. The organic layer was washed with brine, dried over anhydrous sodium sulfate, and filtered. The filtrate was concentrated and washed with ethyl acetate to give a white solid (522, 1.0 g). MS (ESI) [M+H$^+$]$^+$ =298.3, 300.2.

Step 2—Preparation of 3-[6-(4-chloro-benzylamino)-pyridazin-3-ylmethyl]-pyrrolo[2,3-b]pyridine-1-carboxylic acid tert-butyl ester (523)

To (6-bromo-pyridazin-3-yl)-(4-chloro-benzyl)-amine (522, 0.560 g, 1.88 mmol) in tetrahydrofuran (45.0 mL), under an atmosphere of nitrogen at −78° C., was added n-butyllithium (2.50 M in hexane, 0.760 mL) slowly. After 10 minutes, 1,2-bis-(chloro-dimethyl-silanyl)-ethane (0.201 g, 0.94 mmol) in tetrahydrofuran (5.0 mL) was added to the reaction. The reaction mixture was allowed to stir at room temperature for 3 hours. The reaction was cooled to −78° C., followed by addition of 1.70 M of tert-butyllithium in hexane (1.20 mL) slowly. The reaction was stirred for 20 minutes, followed by addition of a solution of CuCN.2LiCl (0.6 M in tetrahydrofuran, 3.00 mL) and 3-chloromethyl-pyrrolo[2,3-b]pyridine-1-carboxylic acid tert-butyl ester (512, 0.47 g, 1.8 mol) in tetrahydrofuran (10.0 mL). After 30 minutes, the reaction was allowed to warm to room temperature for 10 minutes. The reaction was poured into water and extracted with ethyl acetate. The organic layer was dried over anhydrous sodium sulfate and filtered. The filtrate was treated with trifluoroacetic acid (1.0 mL) dissolved in dichloromethane (10.0 mL) for 10 minutes. The reaction was concentrated, poured into aqueous potassium carbonate and extracted with ethyl acetate. The organic layer was dried over anhydrous sodium sulfate and filtered. The filtrate was concentrated and purified with silica gel column chromatography eluting with 60% ethyl acetate in hexane to give the desired compound (523, 0.10 g, 23.8%). MS (ESI) [M+H$^+$]$^+$=450.1.

Step 3—Preparation of (4-chloro-benzyl)-[6-(1H-pyrrolo[2,3-b]pyridin-3-ylmethyl)-pyridazin-3-yl]-amine (P-0092)

To 3-[6-(4-chloro-benzylamino)-pyridazin-3-ylmethyl]-pyrrolo[2,3-b]pyridine-1-carboxylic acid tert-butyl ester (523, 50.0 mg, 0.111 mmol) in dichloromethane (10.0 mL) was added trifluoroacetic acid (0.30 mL, 0.0039 mol). The reaction was stirred at room temperature overnight. The reaction was concentrated, poured into aqueous potassium carbonate and extracted with ethyl acetate. The organic layer was dried over anhydrous sodium sulfate and filtered. The filtrate was concentrated and washed with ethyl acetate and hexane to give an off-white solid (P-0092, 7.3 mg, 19.0%). MS (ESI) [M+H$^+$]$^+$=350.1.

Example 47

Synthesis of [1-ethyl-5-(1H-pyrrolo[2,3-b]pyridin-3-ylmethyl)-1H-pyrazol-3-yl]-(4-fluoro-benzyl)-amine P-0165

[1-Ethyl-5-(1H-pyrrolo[2,3-b]pyridin-3-ylmethyl)-1H-pyrazol-3-yl]-(4-fluoro-benzyl)-amine P-0165 was synthesized in 7 steps as shown in Scheme 162.

Scheme 162

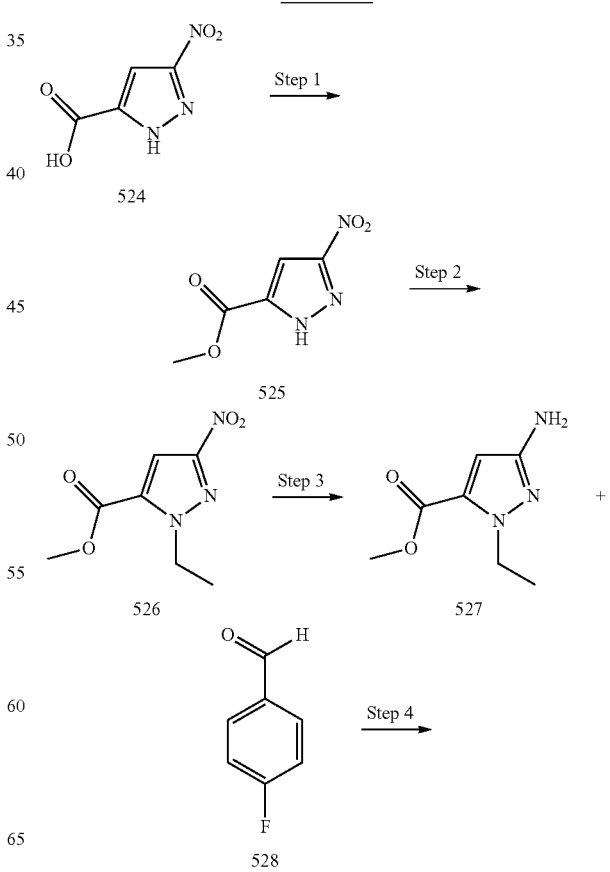

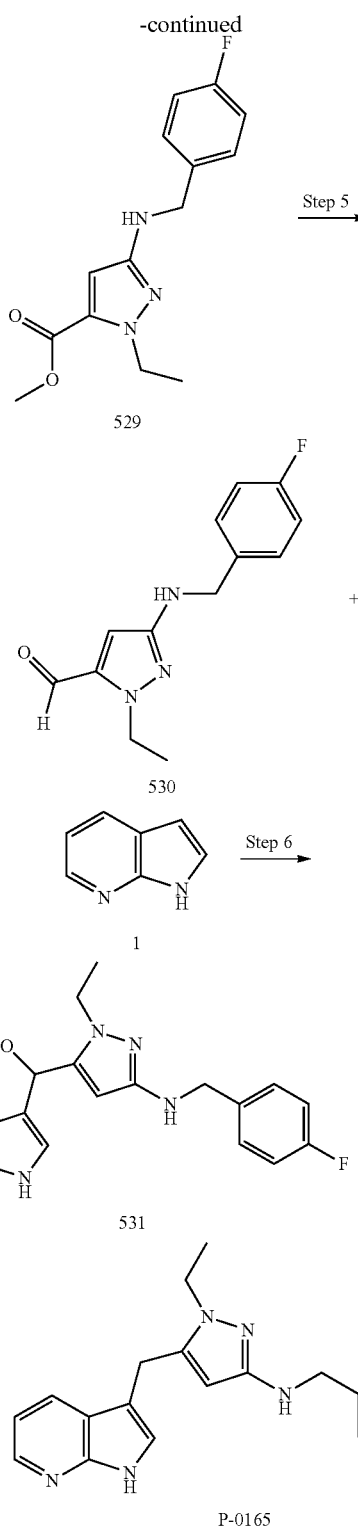

Step 1—Preparation of 5-nitro-2H-pyrazole-3-carboxylic acid methyl ester (525)

To 5-nitro-2H-pyrazole-3-carboxylic acid (524, 10.0 g, 0.0637 mol) in methanol (100.0 mL) was added concentrated sulfuric acid (1.00 mL, 0.0180 mol). The reaction was stirred at room temperature overnight. The reaction was poured into aqueous potassium carbonate and extracted with ethyl acetate. The organic layer was dried over anhydrous sodium sulfate and filtered. The filtrate was concentrated and purified by silica gel column chromatography eluting with 20% ethyl acetate in hexane to give a white solid (525, 1.5 g, 13.8%).

Step 2—Preparation of 2-ethyl-5-nitro-2H-pyrazole-3-carboxylic acid methyl ester (526)

To 5-nitro-2H-pyrazole-3-carboxylic acid methyl ester (525, 2.50 g, 0.0146 mol) in N,N-dimethylformamide (62.5 mL) were added iodoethane (1.2 mL, 0.016 mol) and potassium carbonate (4.17 g, 0.0301 mol) under an atmosphere of nitrogen. The reaction was stirred at room temperature overnight. The reaction was poured into water and extracted with ethyl acetate. The organic layer was dried over anhydrous sodium sulfate and filtered. The filtrate was concentrated and purified by silica gel column chromatography eluting with 20% to 100% ethyl acetate in hexane to give a white solid (526, 1.3 g, 44.7%).

Step 3—Preparation of 5-amino-2-ethyl-2H-pyrazole-3-carboxylic acid methyl ester (527)

To 2-ethyl-5-nitro-2H-pyrazole-3-carboxylic acid methyl ester (526, 1.30 g, 6.53 mmol) in methanol (60.0 mL) was added 20% Pd(OH)$_2$C (0.1 g). The reaction was stirred under an atmosphere of hydrogen overnight. The reaction was filtered and concentrated to give a light yellow solid (527, 1.0 g, 90.6%).

Step 4—Preparation of 2-ethyl-5-(4-fluoro-benzylamino)-2H-pyrazole-3-carboxylic acid methyl ester (529)

To 5-amino-2-ethyl-2H-pyrazole-3-carboxylic acid methyl ester (527, 1.00 g, 5.91 mmol) in acetonitrile (27.5 mL) were added 4-fluorobenzaldehyde (528, 0.660 mL, 6.26 mmol), triethylsilane (4.77 mL, 0.0298 mol) and trifluoroacetic acid (2.38 mL, 0.0310 mol). The reaction was stirred at 80° C. for 4 hours, then concentrated, poured into aqueous potassium carbonate, and extracted with ethyl acetate. The organic layer was dried over anhydrous sodium sulfate and filtered. The filtrate was concentrated and purified by silica gel column chromatography eluting with 20% to 100% ethyl acetate in hexane to give a white solid (529, 1.00 g, 61%).

Step 5—Preparation of 2-ethyl-5-(4-fluoro-benzylamino)-2H-pyrazole-3-carbaldehyde (530)

To 2-ethyl-5-(4-fluoro-benzylamino)-2H-pyrazole-3-carboxylic acid methyl ester (529, 1.00 g, 3.61 mol) in tetrahydrofuran (70.0 mL) under an atmosphere of nitrogen at room temperature, lithium tetrahydroaluminate (1.00 M of in tetrahydrofuran, 10.00 mL) was slowly added. The reaction was stirred at room temperature overnight, followed by slowly adding sodium sulfate decahydrate (15.0 g). After 2 hours, the reaction was filtered, concentrated and purified with silica gel column chromatography eluting with 20% to 100% ethyl acetate in hexane to give a yellow oil (530, 0.16 g, 18%). MS (ESI) [M+H$^+$]$^+$=248.2.

Step 6—Preparation of 1-ethyl-5-[methoxy-(1H-pyrrolo[2,3-b]pyridin-3-yl)-methyl]-1H-pyrazol-3-yl-(4-fluoro-benzyl)-amine (531)

To 1H-Pyrrolo[2,3-b]pyridine (1, 54.0 mg, 0.46 mmol) in methanol (15.0 mL) were added 2-ethyl-5-(4-fluoro-benzylamino)-2H-pyrazole-3-carbaldehyde (530, 110.0 mg, 0.44 mmol) and potassium hydroxide (0.60 g, 0.011 mol) under an atmosphere of nitrogen. The reaction was stirred at room temperature overnight, then poured into water and extracted with ethyl acetate. The organic layer was dried over anhydrous sodium sulfate and filtered. The filtrate was concentrated and purified by silica gel column chromatography eluting with 40% ethyl acetate in hexane to give a white solid (531, 0.12 g, 71.1%). MS (ESI) [M–H$^+$]$^-$=378.2.

Step 7—Preparation of [1-ethyl-5-(1H-pyrrolo[2,3-b]pyridin-3-ylmethyl)-1H-pyrazol-3-yl]-(4-fluoro-benzyl)-amine (P-0165)

To 1-ethyl-5-[methoxy-(1H-pyrrolo[2,3-b]pyridin-3-yl)-methyl]-1H-pyrazol-3-yl-(4-fluoro-benzyl)-amine (531, 0.12 g, 0.32 mmol) in acetonitrile (10.0 mL, 0.191 mol) were added triethylsilane (0.60 mL, 0.0038 mol) and trifluoroacetic acid (0.30 mL, 0.0039 mol). The reaction was stirred at 80° C. for 2 hours. The reaction was poured into aqueous potassium carbonate and extracted with ethyl acetate. The organic layer was dried over anhydrous sodium sulfate and filtered. The filtrate was concentrated and washed with ethyl acetate and hexane to give crude compound. $^1$H NMR indicated that the reaction was incomplete. The crude compound was dissolved in dichloromethane (15.0 mL), trifluoroacetic acid (0.30 mL) and triethylsilane (0.60 mL). The reaction was stirred at 43° C. for 72 hours. The reaction was concentrated, poured into aqueous potassium carbonate and extracted with ethyl acetate. The organic layer was dried over anhydrous sodium sulfate and filtered. The filtrate was concentrated and washed with ethyl acetate and hexane to give an off-white solid (P-0165, 18.7 mg, 17%). MS (ESI) [M+H$^+$]$^+$=350.3.

(4-Fluoro-benzyl)-[1-methyl-5-(1H-pyrrolo[2,3-b]pyridin-3-ylmethyl)-1H-pyrazol-3-yl]-amine P-0169

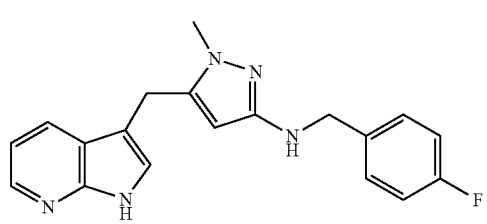 [SMILES: Cn1nc(NCc2ccc(F)cc2)cc1Cc1c[nH]c2ncccc12]

was prepared using the protocol of Scheme 162, substituting iodoethane with iodomethane in Step 2. MS (ESI) [M+H$^+$]$^+$=336.3.

[5-(5-Chloro-1H-pyrrolo[2,3-b]pyridin-3-ylmethyl)-1-methyl-1H-pyrazol-3-yl]-(4-fluoro-benzyl)-amine P-0170

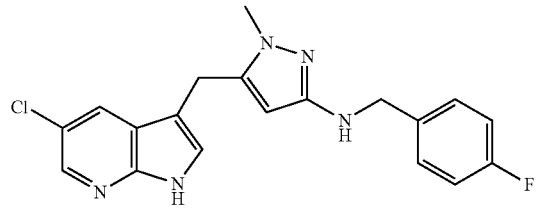 [SMILES: Cn1nc(NCc2ccc(F)cc2)cc1Cc1c[nH]c2ncc(Cl)cc12]

was prepared using the protocol of Scheme 162, substituting iodoethane with iodomethane in step 2 and 1H-pyrrolo[2,3-b]pyridine 1 with 5-chloro-1H-pyrrolo[2,3-b]pyridine in step 6.

MS (ESI) [M+H$^+$]$^+$=370.3

(4-Fluoro-benzyl)-{1-methyl-5-[5-(1-methyl-1H-pyrazol-4-yl)-1H-pyrrolo[2,3-b]pyridin-3-ylmethyl]-1H-pyrazol-3-yl}-amine P-0180

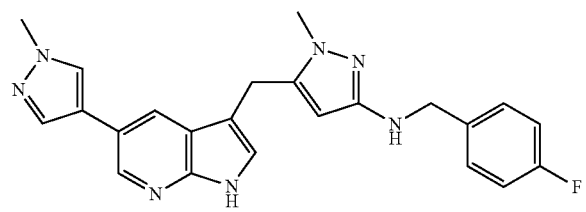 [SMILES: Cn1cc(-c2cnc3[nH]cc(Cc4cc(NCc5ccc(F)cc5)nn4C)c3c2)cn1]

was prepared using the protocol of Scheme 162, substituting iodoethane with iodomethane in step 2 and 1H-Pyrrolo[2,3-b]pyridine 1 with 5-(1-Methyl-1H-pyrazol-4-yl)-1H-pyrrolo[2,3-b]pyridine (prepared as described in Example 115, Scheme 172) in step 6. MS (ESI) [M+H$^+$]$^+$=416.2.

3-[5-(4-Fluoro-benzylamino)-2-methyl-2H-pyrazol-3-ylmethyl]-1H-pyrrolo[2,3-b]pyridine-5-carbonitrile P-0191

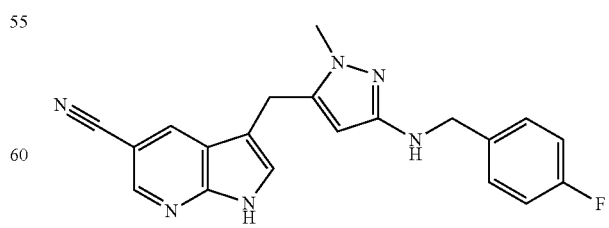

was prepared using the protocol of Scheme 162, substituting 1H-Pyrrolo[2,3-b]pyridine 1 with 1H-Pyrrolo[2,3-b]pyridine-5-carbonitrile in Step 6. MS (ESI) [M+H$^+$]$^+$=361.5.

Example 48

Synthesis of [4-chloro-1-ethyl-5-(1H-pyrrolo[2,3-b]pyridin-3-ylmethyl)-1H-pyrazol-3-yl]-[1-(4-fluoro-phenyl)-meth-(E)-ylidene]-amine P-0166

[4-chloro-1-ethyl-5-(1H-pyrrolo[2,3-b]pyridin-3-ylmethyl)-1H-pyrazol-3-yl]-[1-(4-fluoro-phenyl)-meth-(E)-ylidene]-amine P-0166 was synthesized in 1 step as shown in Scheme 163.

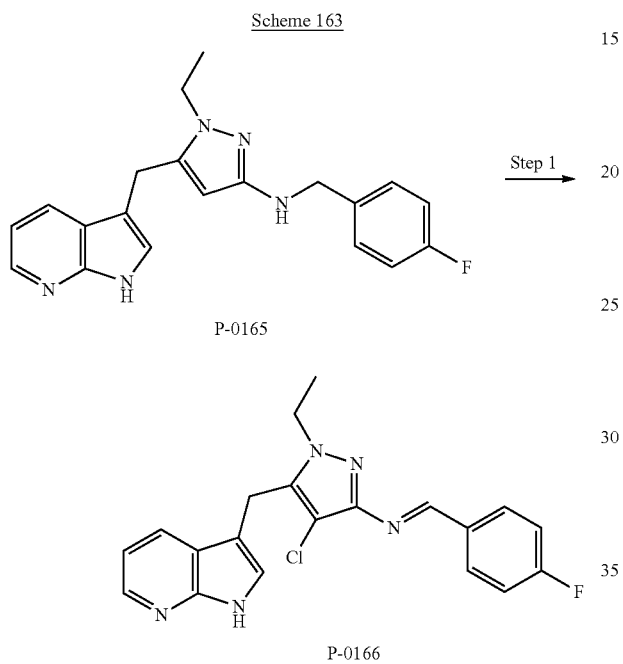

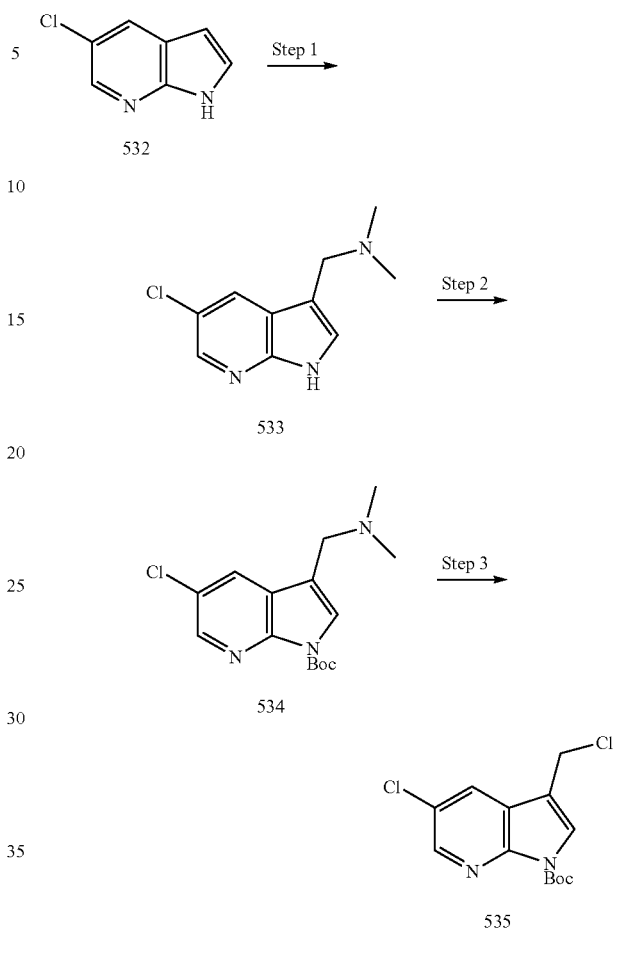

Step 1—Preparation of [4-chloro-1-ethyl-5-(1H-pyrrolo[2,3-b]pyridin-3-ylmethyl)-1H-pyrazol-3-yl]-[1-(4-fluoro-phenyl)-meth-(E)-ylidene]-amine (P-0166)

To [1-ethyl-5-(1H-pyrrolo[2,3-b]pyridin-3-ylmethyl)-1H-pyrazol-3-yl]-(4-fluoro-benzyl)-amine (P-0165, 10.1 mg, 0.0289 mmol, prepared as described in Example 105, Scheme 162) in acetonitrile (8.0 mL) was added N-chloro-succinimide (4.18 mg, 0.0318 mmol). The reaction was stirred at room temperature for 2 hours. The reaction was concentrated and purified by silica gel column chromatography eluting with 20% to 100% ethyl acetate in hexane to give a white solid (P-0166, 1.1 mg). MS (ESI) [M+H$^+$]$^+$=382.1.

Example 49

Synthesis of 5-chloro-3-chloromethyl-pyrrolo[2,3-b]pyridine-1-carboxylic acid tert-butyl ester 5-chloro-3-chloromethyl-pyrrolo[2,3-b]pyridine-1-carboxylic acid tert-butyl ester was synthesized in 3 steps as shown in Scheme 164.

Step 1—Preparation of (5-chloro-1H-pyrrolo[2,3-b]pyridin-3-ylmethyl)-dimethyl-amine (533)

To 5-Chloro-1H-pyrrolo[2,3-b]pyridine (532, 8.00 g, 0.0524 mol) in isopropyl alcohol (250.0 mL) were added dimethylamine hydrochloride (4.79 g, 0.0587 mol) and formaldehyde (1.77 g, 0.0589 mol). The reaction was stirred at room temperature overnight, followed by refluxing for 4 hours. The reaction was concentrated, poured into water, and extracted with ethyl acetate. The organic layer was dried over anhydrous sodium sulfate and filtered. The filtrate was concentrated to give crude compound (533, 10.0 g, 91%), that was used directly in the next step.

Step 2 and 3—Preparation of 5-chloro-3-chloromethyl-pyrrolo[2,3-b]pyridine-1-carboxylic acid tert-butyl ester (535)

5-Chloro-3-chloromethyl-pyrrolo[2,3-b]pyridine-1-carboxylic acid tert-butyl ester 535 was prepared following the protocol of Scheme 158 (Example 101) steps 1 and 2, substituting dimethyl-(1H-pyrrolo[2,3-b]pyridin-3-ylmethyl)-amine 2 with (5-chloro-1H-pyrrolo[2,3-b]pyridin-3-ylmethyl)-dimethyl-amine 533 in step 1.

Example 50

Synthesis of (4-chloro-benzyl)-[5-(5-chloro-1H-pyrrolo[2,3-b]pyridin-3-ylmethyl)-6-fluoro-pyridin-2-yl]-amine P-0132

(4-Chloro-benzyl)-[5-(5-chloro-1H-pyrrolo[2,3-b]pyridin-3-ylmethyl)-6-fluoro-pyridin-2-yl]-amine P-0132 was synthesized in 3 steps as shown in Scheme 165.

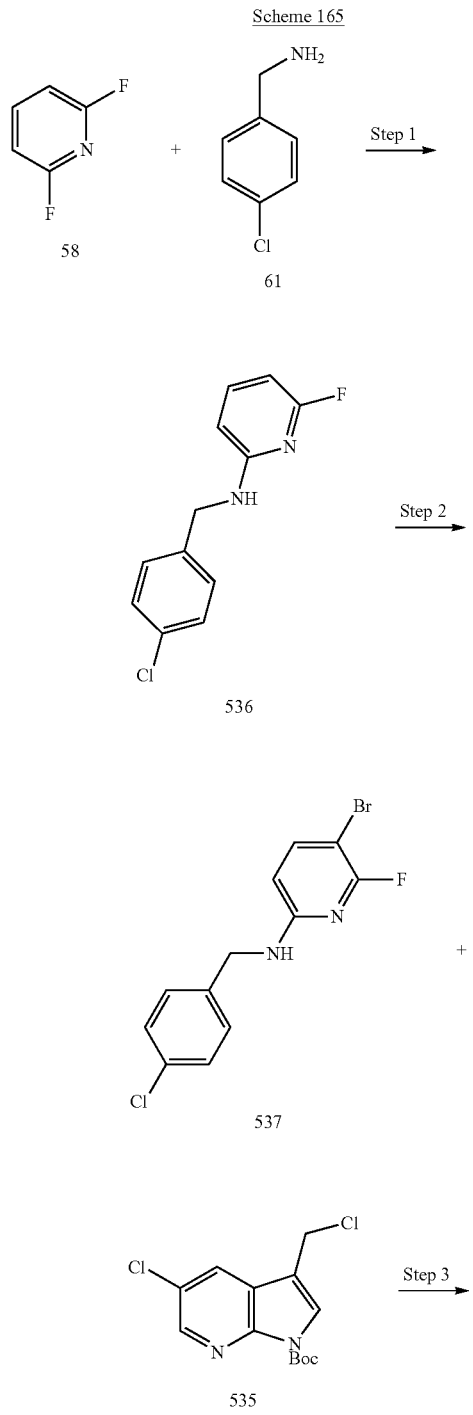

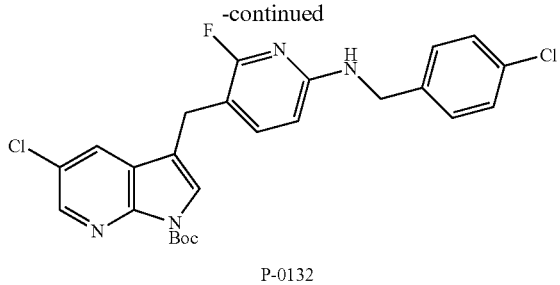

P-0132

Step 1—Preparation of (4-chloro-benzyl)-(6-fluoro-pyridin-2-yl)-amine (536)

To 2,6-difluoropyridine (58, 9.85 g, 0.0856 mol) in N-methylpyrrolidinone (50.0 mL) were added p-chlorobenzylamine (61, 10.5 mL, 8.63 mmol) and N,N-diisopropylethylamine (30.0 mL, 0.172 mol). The reaction was stirred at 90° C. overnight. The reaction was poured into water and extracted with ethyl acetate. The organic layer was dried over anhydrous sodium sulfate and filtered. The filtrate was concentrated and purified by silica gel column chromatography eluting with 25% ethyl acetate in hexane, then washed with ethyl acetatehexane to give a white solid (536, 10 g, 50%).

Step 2—Preparation of (5-bromo-6-fluoro-pyridin-2-yl)-(4-chloro-benzyl)-amine (537)

To (4-chloro-benzyl)-(6-fluoro-pyridin-2-yl)-amine (536, 1.03 g, 4.35 mmol) in acetonitrile (30.0 mL), under an atmosphere of nitrogen, N-bromosuccinimide (0.820 g, 4.61 mol) was added slowly. After 2 hours, the reaction was poured into a solution of sodium thiosulfate and extracted with ethyl acetate. The organic layer was dried over sodium sulfate, concentrated and crystallized with ethyl acetate and hexane to give a white solid (537, 1.10 g, 80.1%).

Step 3—Preparation of (4-chloro-benzyl)-[5-(5-chloro-1H-pyrrolo[2,3-b]pyridin-3-ylmethyl)-6-fluoro-pyridin-2-yl]-amine (P-0132)

To (5-bromo-6-fluoro-pyridin-2-yl)-(4-chloro-benzyl)-amine (537, 2.76 g, 8.75 mol) in tetrahydrofuran (90.0 mL), under an atmosphere of nitrogen at −78° C., n-butyllithium (2.50 M in hexane, 3.64 mL) was added slowly. After 60 minutes, 1,2-bis-(chloro-dimethyl-silanyl)-ethane (0.942 g, 4.38 mol) in tetrahydrofuran (8.0 mL) was added to the reaction. The reaction mixture was allowed to stir at room temperature for 2 hours. The reaction was cooled to −78° C., followed by addition of tert-butyllithium (1.70 M in hexane, 10.50 mL). The reaction was stirred for 30 minutes, followed by addition of 0.65 M of CuCN.2LiCl in tetrahydrofuran (14.0 mL). The reaction was stirred at −35° C. for 10 minutes, followed by addition of 5-chloro-3-chloromethyl-pyrrolo[2,3-b]pyridine-1-carboxylic acid tert-butyl ester (535, 1.70 g, 5.64 mol, prepared as described in Example 49, Scheme 164) in tetrahydrofuran (10.0 mL). The reaction was allowed to warm to room temperature for 1 hour and 2 N HCl (30 mL) was added to the reaction mixture, then stirred for 30 minutes. The reaction was poured into aqueous ammonia and extracted with ethyl acetate. The organic layer was dried over anhydrous sodium sulfate and filtered. The filtrate was concentrated and purified with silica gel column chromatography eluting with 30% ethyl acetate in hexane to give the desired compound (P-0132, 0.75 g, 33.1%). MS (ESI) [M+H⁺]⁺=401.1.

Example 51

Synthesis of 5-chloro-3-(2,6-difluoro-pyridin-3-ylmethyl)-1H-pyrrolo[2,3-b]pyridine P-0155

5-Chloro-3-(2,6-difluoro-pyridin-3-ylmethyl)-1H-pyrrolo[2,3-b]pyridine P-0155 was synthesized in 1 step as shown in Scheme 166.

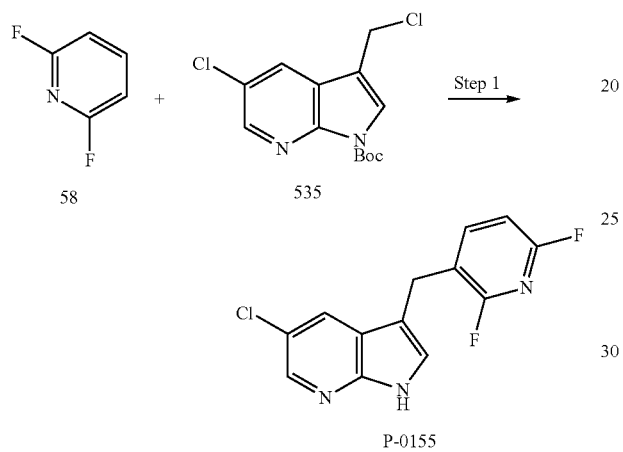

Step 1—Preparation of 5-chloro-3-(2,6-difluoro-pyridin-3-ylmethyl)-1H-pyrrolo[2,3-b]pyridine (P-0155)

To 2,6-Difluoropyridine (58, 3.40 g, 0.0295 mol) in tetrahydrofuran (200.0 mL), under an atmosphere of nitrogen at −78° C., 2.50 M of n-butyllithium in hexane (12.0 mL) was added slowly. After 60 minutes, CuCN.2LiCl (0.75 M in tetrahydrofuran, 40.0 mL) was added to the reaction mixture. After 5 minutes, 5-chloro-3-chloromethyl-pyrrolo[2,3-b]pyridine-1-carboxylic acid tert-butyl ester (535, 4.20 g, 0.0139 mol, prepared as described in Example 49, Scheme 164) in tetrahydrofuran (20 mL) was added to the reaction. The reaction was stirred at −78° C. overnight, then poured into water and ammonia (10 mL), and extracted with ethyl acetate. The organic layer was dried over anhydrous sodium sulfate and filtered. The filtrate was concentrated and purified by silica gel column chromatography eluting with 15% ethyl acetate in hexane to give a white solid (P-0155, 300 mg, 7.7%). MS (ESI) [M−H⁺]⁻=278.1.

Example 52

Synthesis of 3-(2,6-difluoro-pyridin-3-ylmethyl)-1H-pyrrolo[2,3-b]pyridine P-0154

3-(2,6-difluoro-pyridin-3-ylmethyl)-1H-pyrrolo[2,3-b]pyridine P-0154 was synthesized in 1 step as shown in Scheme 167.

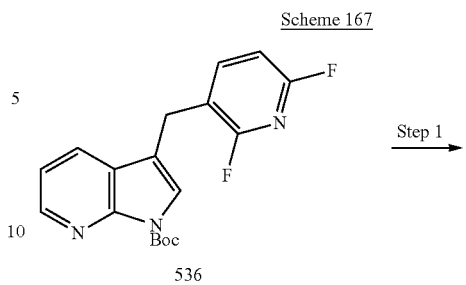

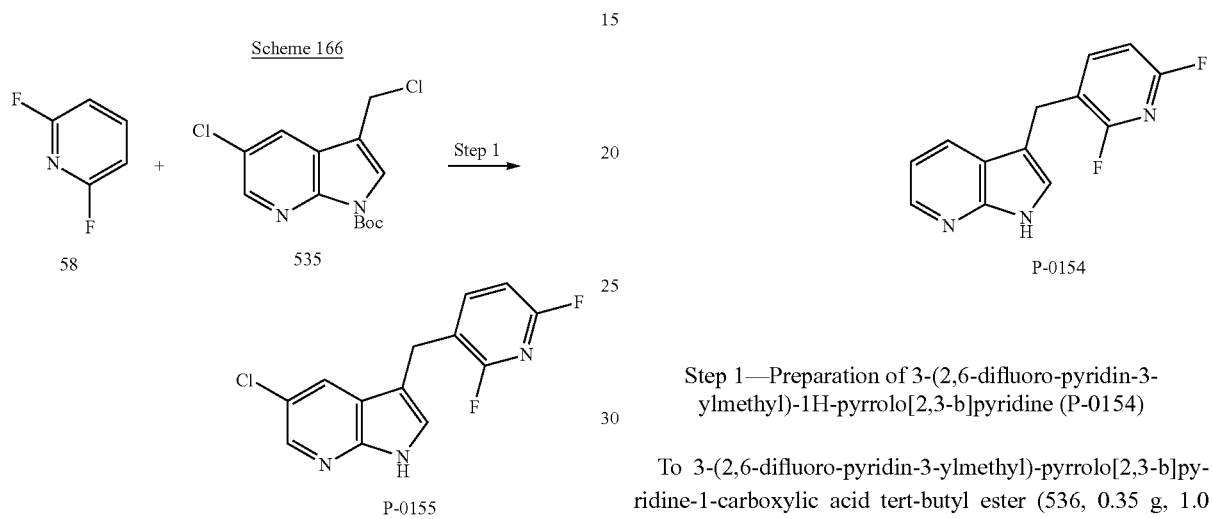

Step 1—Preparation of 3-(2,6-difluoro-pyridin-3-ylmethyl)-1H-pyrrolo[2,3-b]pyridine (P-0154)

To 3-(2,6-difluoro-pyridin-3-ylmethyl)-pyrrolo[2,3-b]pyridine-1-carboxylic acid tert-butyl ester (536, 0.35 g, 1.0 mmol, prepared as described in Example 49, Scheme 164, replacing 5-chloro-1H-pyrrolo[2,3-b]pyridine 532 with 1H-pyrrolo[2,3-b]pyridine in step 1) in N-methylpyrrolidinone (3.00 mL) were added p-chlorobenzylamine (0.20 mL, 1.6 mmol) and N,N-diisopropylethylamine (0.30 mL, 0.0017 mol). The reaction was stirred at 50° C. for 72 hours. The reaction was poured into water and extracted with ethyl acetate. The organic layer was dried over anhydrous sodium sulfate and filtered. The filtrate was concentrated and the crude intermediate was dissolve in dichloromethane (15.0 mL) and trifluoroacetic acid (0.5 mL). The reaction was stirred at room temperature for 2 hours, then concentrated, poured into aqueous potassium carbonate, and extracted with ethyl acetate. The organic layer was dried over anhydrous sodium sulfate and filtered. The filtrate was concentrated and purified by silica gel column chromatography eluting with 35% ethyl acetate in hexane to give a white solid (P-0154, 0.18 g, 72%). MS (ESI) [M+H⁺]⁺=246.2.

Example 53

Synthesis of 5-((1H-pyrrolo[2,3-b]pyridin-3-yl)methyl)-N-(4-chlorobenzyl)-6-chloropyridin-2-amine P-0161

5-((1H-pyrrolo[2,3-b]pyridin-3-yl)methyl)-N-(4-chlorobenzyl)-6-chloropyridin-2-amine P-0161 was synthesized in 6 steps as shown in Scheme 168.

Scheme 168

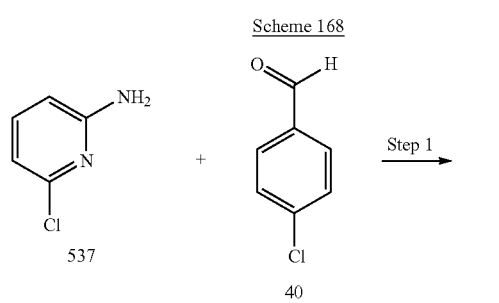

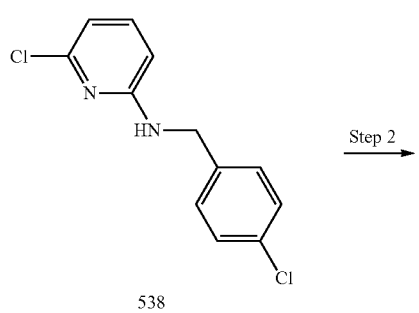

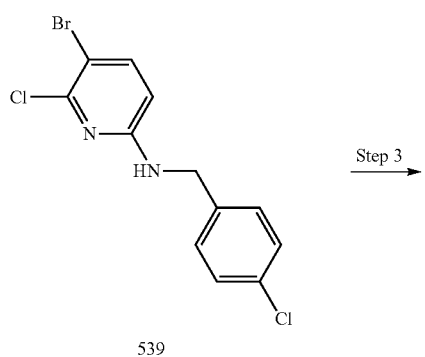

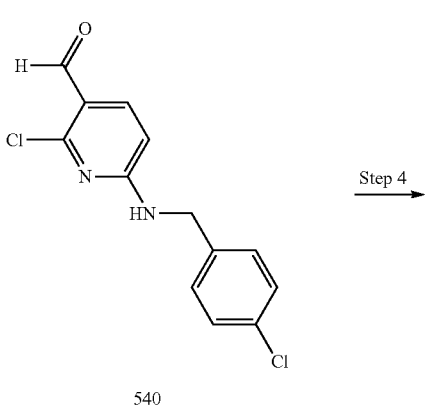

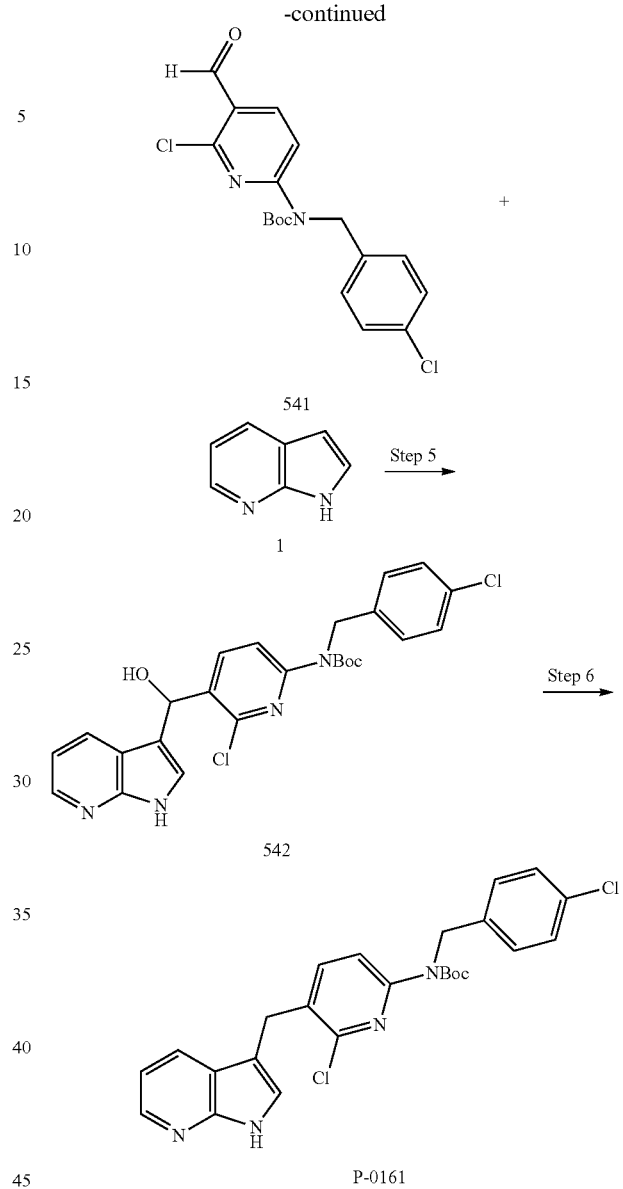

Step 1—Preparation of (4-chloro-benzyl)-(6-chloro-pyridin-2-yl)-amine (538)

To 6-chloro-pyridin-2-ylamine (537, 5.60 g, 0.0436 mol) in acetonitrile (300 mL) were added 4-chlorobenzaldehyde (40, 6.7 g, 0.048 mol), trifluoroacetic acid (13 mL, 0.17 mol) and triethylsilane (21 mL, 0.13 mol). The reaction was heated to reflux for 4 hours, then concentrated, poured into water, extracted with ethyl acetate, and washed with sodium bicarbonate and brine. The organic layer was dried over anhydrous sodium sulfate, filtered and concentrated. The filtrate was purified with silica gel column chromatography eluting with 20% to 100% ethyl acetate in hexane to give a white solid (538, 6.5 g, 59%). MS (ESI) [M+H$^+$]$^+$=255.1.

Step 2—Preparation of (5-bromo-6-chloro-pyridin-2-yl)-(4-chloro-benzyl)-amine (539)

To (4-chloro-benzyl)-(6-chloro-pyridin-2-yl)-amine (538, 4.00 g, 0.0158 mol) in acetonitrile (66.7 mL, 1.28 mol) under an atmosphere of nitrogen, N-bromosuccinimide (2.81 g, 0.0158 mol) in acetonitrile (20 mL) was added slowly. The reaction was stirred at room temperature overnight, then poured into water and extracted with ethyl acetate. The organic layer was dried over sodium sulfate, concentrated and crystallized with ethyl acetate in hexane to give a white solid (539, 2.60 g, 95.3%).

Step 3—Preparation of 2-chloro-6-(4-chloro-benzylamino)-pyridine-3-carbaldehyde (540)

To (5-bromo-6-chloro-pyridin-2-yl)-(4-chloro-benzyl)-amine (539, 2.60 g, 7.83 mmol) in tetrahydrofuran (60.0 mL) under an atmosphere of nitrogen at −78° C., isopropylmagnesium chloride (2.00 M in tetrahydrofuran, 4.20 mL) was added over 10 minutes. The reaction was stirred at −78° C. for 20 minutes, then allowed to warm to room temperature for 10 minutes. The reaction was cooled to −78° C. tert-Butyllithium (1.70 M in hexane, 10.2 mL) was added to the reaction over 10 minutes. After 40 minutes, N,N-dimethylformamide (1.80 mL, 0.0232 mol) was added to the reaction. The reaction was stirred at −78° C. for 40 minutes, then allowed to warm to room temperature for another 30 minutes. The reaction mixture was poured into water and extracted with ethyl acetate. The organic layer was washed with brine, dried over sodium sulfate, concentrated and purified by silica gel column chromatography eluting with 35% to 100% ethyl acetate in hexane to give a light yellow solid (540, 1.0 g, 45.4%). MS (ESI) [M−H+]−=279.0.

Step 4—Preparation of (4-chloro-benzyl)-(6-chloro-5-formyl-pyridin-2-yl)-carbamic acid tert-butyl ester (541)

To 2-chloro-6-(4-chloro-benzylamino)-pyridine-3-carbaldehyde (540, 0.40 g, 1.42 mmol) in dichloromethane (10.0 mL) were added 4-dimethylaminopyridine (10.0 mg, 0.082 mmol), di-tert-butyldicarbonate (0.693 g, 3.17 mmol) and triethylamine (0.50 mL, 0.0036 mol). The reaction was stirred at room temperature overnight, then concentrated and purified by silica gel column chromatography eluting with 20% to 100% ethyl acetate in hexane to give the desired compound (541, 0.45 g, 83.0%).

Step 5—Preparation of (4-chloro-benzyl)-6-chloro-5-[hydroxy-(1H-pyrrolo[2,3-b]pyridin-3-yl)-methyl]-pyridin-2-yl-carbamic acid tert-butyl ester (542)

To 1H-Pyrrolo[2,3-b]pyridine (1, 465 mg, 3.93 mmol) in methanol (50 mL) were added sodium hydroxide (0.630 g, 0.0157 mol) and (4-chloro-benzyl)-(6-chloro-5-formyl-pyridin-2-yl)-carbamic acid tert-butyl ester (541, 1.5 g, 0.0039 mol). The reaction was stirred at room temperature overnight, then poured into water and extracted with ethyl acetate. The organic layer was washed with brine, dried over sodium sulfate, concentrated and purified with silica gel column chromatography eluting with 20% to 100% ethyl acetate in hexane to give the desired compound (542, 1.0 g, 51%). MS (ESI) [M+H+]+=499.1.

Step 6—Preparation of 5-((1H-pyrrolo[2,3-b]pyridin-3-yl)methyl)-N-(4-chlorobenzyl)-6-chloropyridin-2-amine (P-0161)

To (4-chloro-benzyl)-6-chloro-5-[hydroxy-(1H-pyrrolo[2,3-b]pyridin-3-yl)-methyl]-pyridin-2-yl-carbamic acid tert-butyl ester (542, 1.00 g, 2.00 mmol) in acetonitrile (130.0 mL) were added triethylsilane (11.5 mL, 0.0720 mol) and trifluoroacetic acid (5.5 mL, 0.071 mol). The reaction was heated to reflux for 2 hours, then concentrated, poured into aqueous potassium carbonate, and extracted with ethyl acetate. The organic layer was dried over anhydrous sodium sulfate and filtered. The filtrate was concentrated and washed with ethyl acetate and hexane to give a light yellow solid (P-0161, 480 mg, 62%). MS (ESI) [M+H+]+=383.1, 385.1.

[6-Chloro-5-(1H-pyrrolo[2,3-b]pyridin-3-ylmethyl)-pyridin-2-yl]-(6-trifluoromethyl-pyridin-3-ylmethyl)-amine P-0174

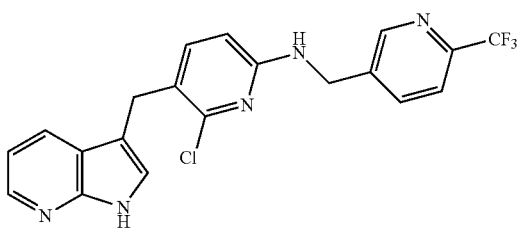 [SMILES: FC(F)(F)c1ccc(CNc2ccc(Cc3c[nH]c4ncccc34)c(Cl)n2)cn1]

was prepared following the protocol of Scheme 168, substituting 4-chloro-benzaldehyde 40 with 6-trifluoromethyl-pyridine-3-carbaldehyde in step 1. MS (ESI) [M+H+]+=418.2.

[6-Chloro-5-(5-chloro-1H-pyrrolo[2,3-b]pyridin-3-ylmethyl)-pyridin-2-yl]-(6-trifluoromethyl-pyridin-3-ylmethyl)-amine P-0176

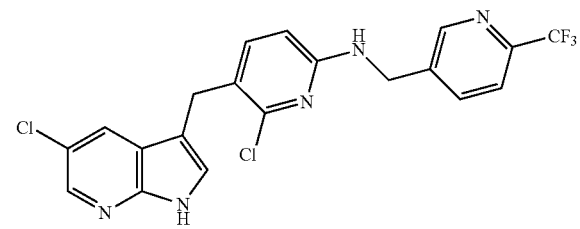 [SMILES: FC(F)(F)c1ccc(CNc2ccc(Cc3c[nH]c4ncc(Cl)cc34)c(Cl)n2)cn1]

was prepared following the protocol of Scheme 168, substituting 4-chloro-benzaldehyde 40 with 6-trifluoromethyl-pyridine-3-carbaldehyde in step 1 and 1H-Pyrrolo[2,3-b]pyridine 1 with 5-chloro-1H-pyrrolo[2,3-b]pyridine in step 5. MS (ESI) [M+H+]+=452.0.

{6-Chloro-5-[5-(1-methyl-1H-pyrazol-4-yl)-1H-pyrrolo[2,3-b]pyridin-3-ylmethyl]-pyridin-2-yl}-(6-trifluoromethyl-pyridin-3-ylmethyl)-amine P-0179

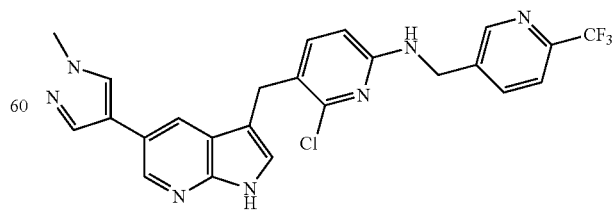

was prepared following the protocol of Scheme 168, substituting 4-chloro-benzaldehyde 40 with 6-trifluoromethyl-pyridine-3-carbaldehyde in step 1 and 1H-Pyrrolo[2,3-b]pyridine 1 with 5-(1-Methyl-1H-pyrazol-4-yl)-1H-pyrrolo[2,3-b]pyridine (prepared as described in Example 57, Scheme 172) in step 5. MS (ESI) [M+H$^+$]$^+$=498.0.

Example 54

Synthesis of (3-chloro-benzyl)-[5-(1H-pyrrolo[2,3-b]pyridin-3-ylmethyl)-pyridin-2-yl]-amine P-0129

(3-Chloro-benzyl)-[5-(1H-pyrrolo[2,3-b]pyridin-3-ylmethyl)-pyridin-2-yl]-amine P-0129 was synthesized in 1 step as shown in Scheme 169.

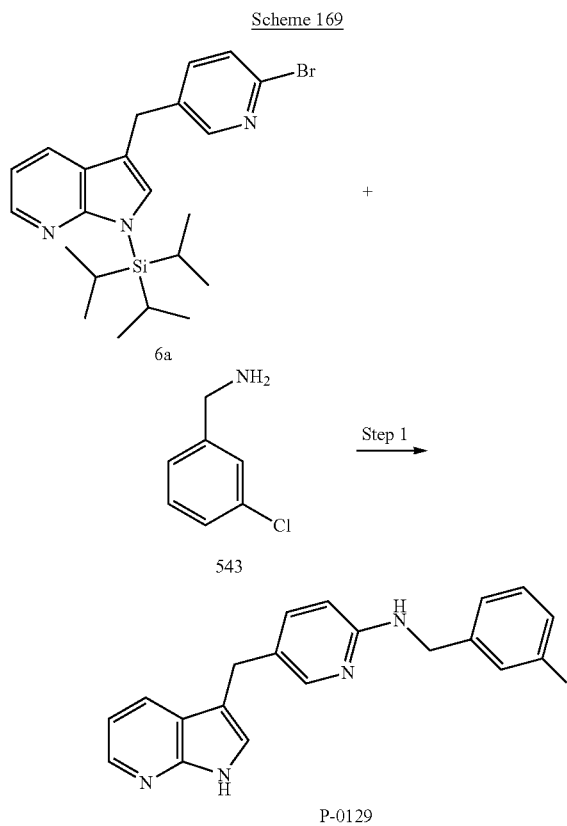

Step 1—Preparation of (3-chloro-benzyl)-[5-(1H-pyrrolo[2,3-b]pyridin-3-ylmethyl)-pyridin-2-yl]-amine (P-0129)

3-(6-bromo-pyridin-3-ylmethyl)-1-triisopropylsilanyl-1H-pyrrolo[2,3-b]pyridine (6a, 10 mg, 0.023 mmol, prepared as described in Example 2, Scheme 4) was combined with 3-chlorobenzyl amine (543, 13 mg, 0.093 mmol) in dioxane (0.3 mL). Tris(dibenzylideneacetone)-dipalladium(0) (3 mg), 4,5-bis(diphenylphosphino)-9,9-dimethylxanthene (Xantphos, 3 mg) and sodium tert-butoxide (15 mg) were added. The mixture was heated at 100° C. overnight. Acetic acid (0.1 mL) was added and the solvents removed under reduced pressure. The remaining residue was dissolved in DMSO and purified by reverse phase HPLC on a YMC-Pack ODS-A C-18 column (50 mm×10 mm ID), eluting with water with 0.1% trifluoroacetic acid and 5-40% acetonitrile with 0.1% trifluoroacetic acid over 13 minutes at a flow rate of 6 mL/minute to provide the desired compound P-0129. MS (ESI) [M+H$^+$]$^+$=349.1.

Additional compounds were prepared following the protocol of Scheme 169, replacing 3-chlorobenzyl amine 543 with an appropriate amine. The following compounds were made following this procedure:

(4-Morpholin-4-ylmethyl-benzyl)-[5-(1H-pyrrolo[2,3-b]pyridin-3-ylmethyl)-pyridin-2-yl]-amine (P-0093), Pyridin-3-ylmethyl-[5-(1H-pyrrolo[2,3-b]pyridin-3-ylmethyl)-pyridin-2-yl]-amine (P-0094), (5-Methyl-isoxazol-3-ylmethyl)-[5-(1H-pyrrolo[2,3-b]pyridin-3-ylmethyl)-pyridin-2-yl]-amine (P-0095), (2-Pyrrolidin-1-yl-ethyl)-[5-(1H-pyrrolo[2,3-b]pyridin-3-ylmethyl)-pyridin-2-yl]-amine (P-0096),

[1-(4-Methanesulfonyl-phenyl)-ethyl]-[5-(1H-pyrrolo[2,3-b]pyridin-3-ylmethyl)-pyridin-2-yl]-amine (P-0097), (2-Methoxy-ethyl)-[5-(1H-pyrrolo[2,3-b]pyridin-3-ylmethyl)-pyridin-2-yl]-amine (P-0098), (2-Morpholin-4-yl-ethyl)-[5-(1H-pyrrolo[2,3-b]pyridin-3-ylmethyl)-pyridin-2-yl]-amine (P-0099), ((R)-1-Phenyl-ethyl)-[5-(1H-pyrrolo[2,3-b]pyridin-3-ylmethyl)-pyridin-2-yl]-amine (P-0125), (3-Morpholin-4-yl-benzyl)-[5-(1H-pyrrolo[2,3-b]pyridin-3-ylmethyl)-pyridin-2-yl]-amine (P-0126),

[1-(2-Fluoro-phenyl)-ethyl]-[5-(1H-pyrrolo[2,3-b]pyridin-3-ylmethyl)-pyridin-2-yl]-amine (P-0127),

[2-(3-Fluoro-phenyl)-ethyl]-[5-(1H-pyrrolo[2,3-b]pyridin-3-ylmethyl)-pyridin-2-yl]-amine (P-0128), (1-Methyl-1H-imidazol-4-ylmethyl)-[5-(1H-pyrrolo[2,3-b]pyridin-3-ylmethyl)-pyridin-2-yl]-amine (P-0130), and (1,5-Dimethyl-1H-pyrazol-3-ylmethyl)-[5-(1H-pyrrolo[2,3-b]pyridin-3-ylmethyl)-pyridin-2-yl]-amine (P-0131).

The following table indicates the amine (Column 2) used in Scheme 169 to provide the compounds (Column 3). Column 1 provides the compound number and column 4 the observed mass.

| Compound number | Amine | Compound | MS(ESI) [M + H$^+$]$^+$ observed |
|---|---|---|---|
| P-0093 | | | 414.3 |

-continued
| Compound number | Amine | Compound | MS(ESI) [M + H⁺]⁺ observed |
|---|---|---|---|
| P-0094 | 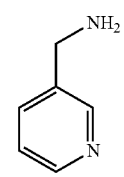 | 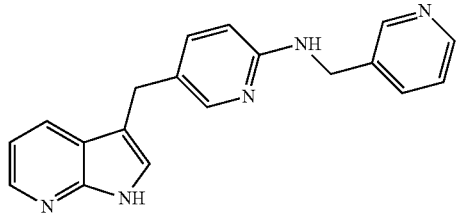 [SMILES: c1cncc(CNc2ccc(Cc3c[nH]c4ncccc34)cn2)c1] | 316.3 |
| P-0095 | 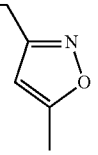 | 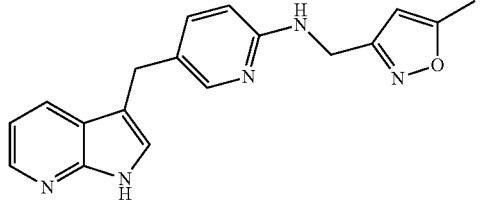 [SMILES: Cc1cc(CNc2ccc(Cc3c[nH]c4ncccc34)cn2)no1] | 319.9 |
| P-0096 | 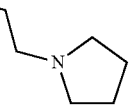 | 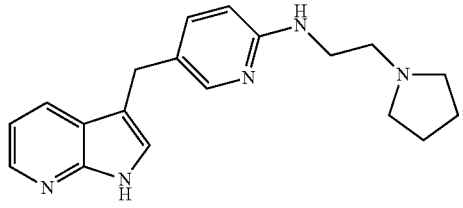 [SMILES: c1cnc2[nH]cc(Cc3ccc(NCCN4CCCC4)nc3)c2c1] | 322.3 |
| P-0097 | 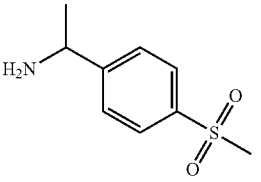 | 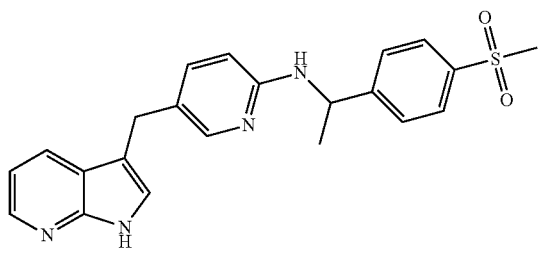 [SMILES: CC(Nc1ccc(Cc2c[nH]c3ncccc23)cn1)c1ccc(S(C)(=O)=O)cc1] | 407.1 |
| P-0098 | 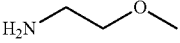 | 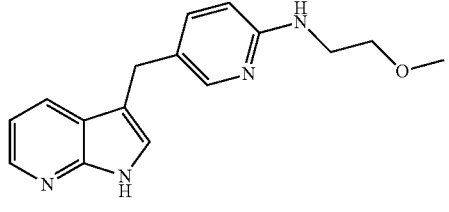 [SMILES: COCCNc1ccc(Cc2c[nH]c3ncccc23)cn1] | 283.5 |
| P-0099 | 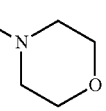 | 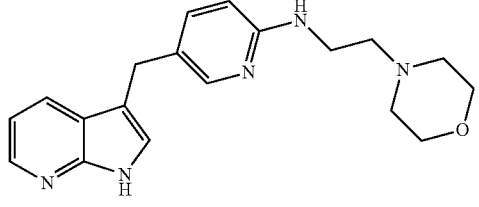 [SMILES: c1cnc2[nH]cc(Cc3ccc(NCCN4CCOCC4)nc3)c2c1] | 338.3 |

-continued
| Compound number | Amine | Compound | MS(ESI) [M + H+]+ observed |
|---|---|---|---|
| P-0125 | 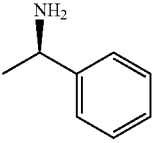 | 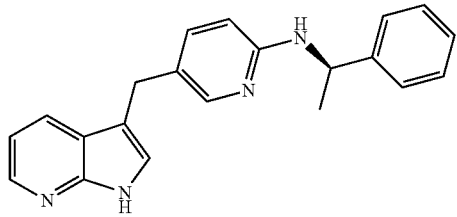 [SMILES: C[C@@H](Nc1ccc(Cc2c[nH]c3ncccc23)cn1)c1ccccc1] | 329.1 |
| P-0126 | 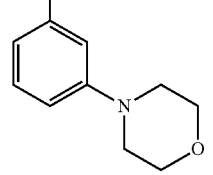 | 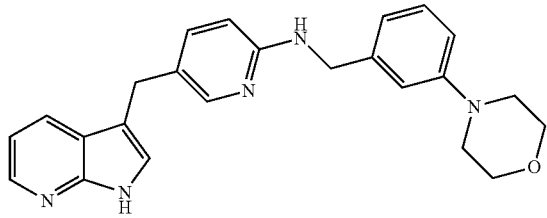 [SMILES: c1cc(CNc2ccc(Cc3c[nH]c4ncccc34)cn2)cc(N2CCOCC2)c1] | 400.3 |
| P-0127 | 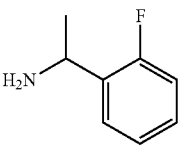 | 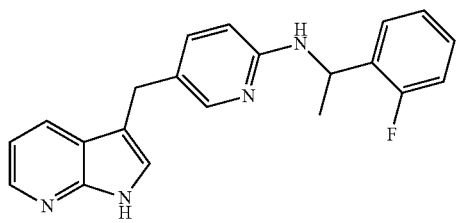 [SMILES: CC(Nc1ccc(Cc2c[nH]c3ncccc23)cn1)c1ccccc1F] | 347.1 |
| P-0128 | 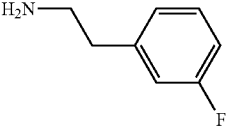 | 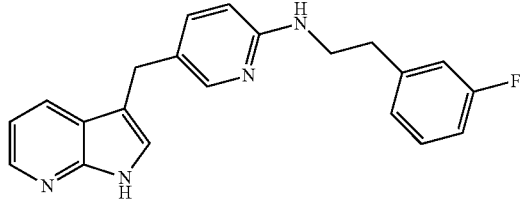 [SMILES: Fc1cccc(CCNc2ccc(Cc3c[nH]c4ncccc34)cn2)c1] | 347.1 |
| P-0130 | 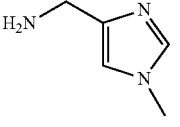 | 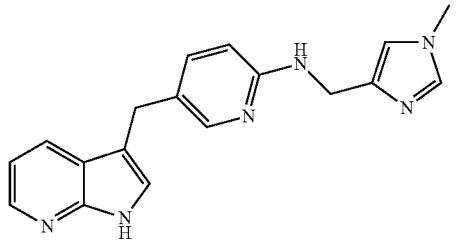 [SMILES: Cn1cnc(CNc2ccc(Cc3c[nH]c4ncccc34)cn2)c1] | 319.1 |
| P-0131 | 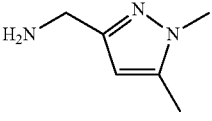 | 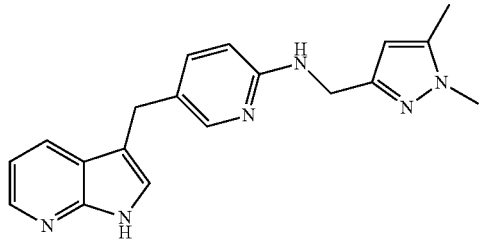 [SMILES: Cc1cc(CNc2ccc(Cc3c[nH]c4ncccc34)cn2)nn1C] | 333.1 |

Example 55

Synthesis of 3-chloro-N-[5-(1H-pyrrolo[2,3-b]pyridin-3-ylmethyl)-pyridin-2-yl]-benzamide P-0111

3-Chloro-N-[5-(1H-pyrrolo[2,3-b]pyridin-3-ylmethyl)-pyridin-2-yl]-benzamide P-0111 was synthesized in 1 step as shown in Scheme 170.

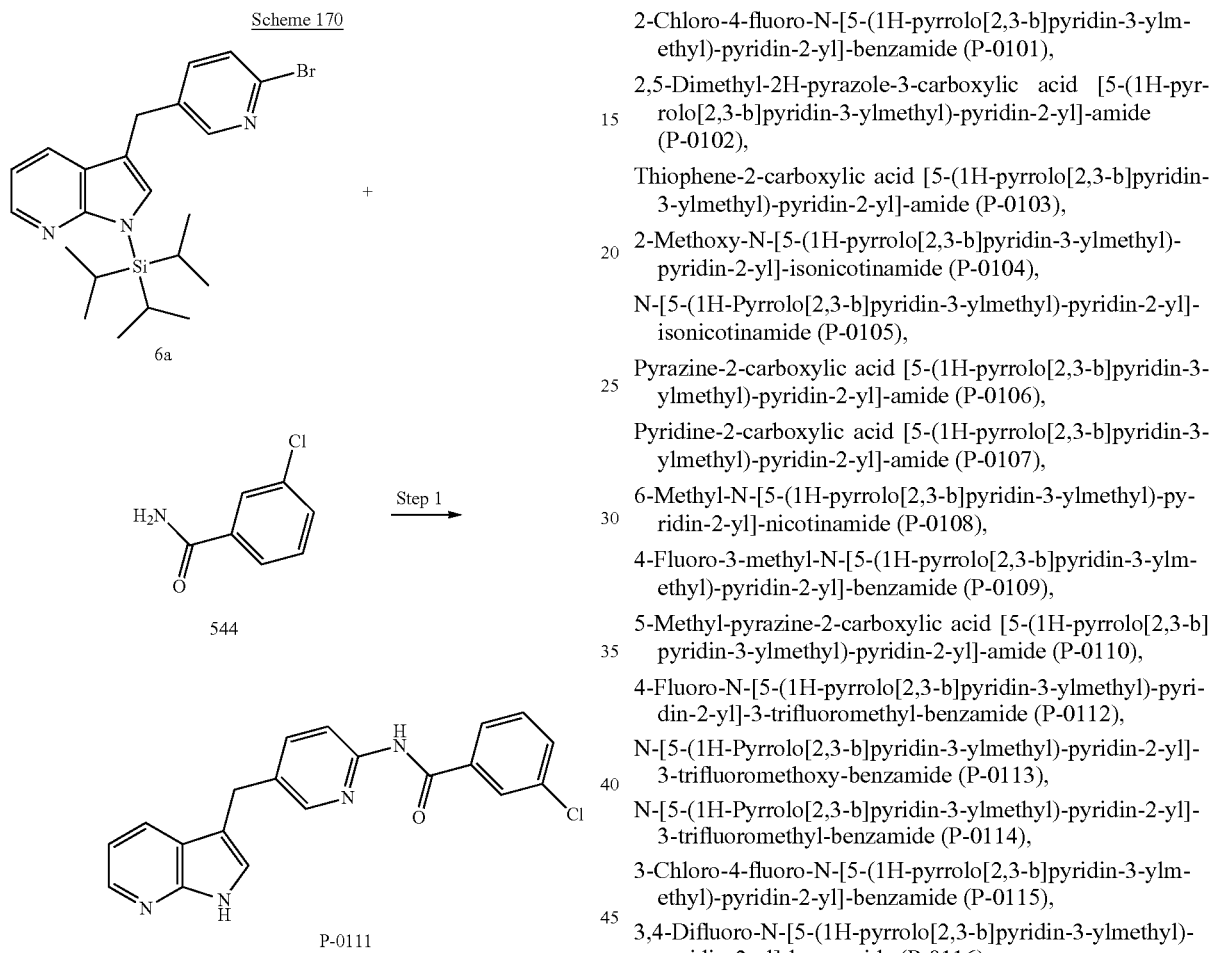

Step 1—Preparation of 3-chloro-N-[5-(1H-pyrrolo[2,3-b]pyridin-3-ylmethyl)-pyridin-2-yl]-benzamide (P-0111)

3-(6-Bromo-pyridin-3-ylmethyl)-1-triisopropylsilanyl-1H-pyrrolo[2,3-b]pyridine (6a, 10 mg, 0.023 mmol, prepared as described in Example 2, Scheme 4) was combined with 3-chloro-benzamide (544, 15 mg, 0.096 mmol) in dioxane (0.4 mL). Tris(dibenzylideneacetone)-dipalladium(0) (3 mg), 4,5-bis(diphenylphosphino)-9,9-dimethylxanthene (Xantphos, 3 mg), and sodium tert-butoxide (15 mg) were added. Cesium carbonate (20 mg) was added and the mixture was heated at 100° C. overnight. Acetic acid (0.1 mL) was added and the solvents removed under reduced pressure. The remaining residue was dissolved in DMSO (0.2 mL) and purified by reverse phase HPLC on a YMC-Pack ODS-A C-18 column (50 mm×10 mm ID), eluting with water with 0.1% trifluoroacetic acid and 5-40% acetonitrile with 0.1% trifluoroacetic acid over 13 minutes at a flow rate of 6 mL/minute to provide the desired compound P-0111. MS (ESI) [M+H$^+$]$^+$=363.1.

Additional compounds were prepared following the protocol of Scheme 170, replacing 3-chloro-benzamide 544 with an appropriate amide. The following compounds were made following this procedure:

3,4-Dichloro-N-[5-(1H-pyrrolo[2,3-b]pyridin-3-ylmethyl)-pyridin-2-yl]-benzamide (P-0100), 2-Chloro-4-fluoro-N-[5-(1H-pyrrolo[2,3-b]pyridin-3-ylmethyl)-pyridin-2-yl]-benzamide (P-0101), 2,5-Dimethyl-2H-pyrazole-3-carboxylic acid [5-(1H-pyrrolo[2,3-b]pyridin-3-ylmethyl)-pyridin-2-yl]-amide (P-0102), Thiophene-2-carboxylic acid [5-(1H-pyrrolo[2,3-b]pyridin-3-ylmethyl)-pyridin-2-yl]-amide (P-0103), 2-Methoxy-N-[5-(1H-pyrrolo[2,3-b]pyridin-3-ylmethyl)-pyridin-2-yl]-isonicotinamide (P-0104), N-[5-(1H-Pyrrolo[2,3-b]pyridin-3-ylmethyl)-pyridin-2-yl]-isonicotinamide (P-0105), Pyrazine-2-carboxylic acid [5-(1H-pyrrolo[2,3-b]pyridin-3-ylmethyl)-pyridin-2-yl]-amide (P-0106), Pyridine-2-carboxylic acid [5-(1H-pyrrolo[2,3-b]pyridin-3-ylmethyl)-pyridin-2-yl]-amide (P-0107), 6-Methyl-N-[5-(1H-pyrrolo[2,3-b]pyridin-3-ylmethyl)-pyridin-2-yl]-nicotinamide (P-0108), 4-Fluoro-3-methyl-N-[5-(1H-pyrrolo[2,3-b]pyridin-3-ylmethyl)-pyridin-2-yl]-benzamide (P-0109), 5-Methyl-pyrazine-2-carboxylic acid [5-(1H-pyrrolo[2,3-b]pyridin-3-ylmethyl)-pyridin-2-yl]-amide (P-0110), 4-Fluoro-N-[5-(1H-pyrrolo[2,3-b]pyridin-3-ylmethyl)-pyridin-2-yl]-3-trifluoromethyl-benzamide (P-0112), N-[5-(1H-Pyrrolo[2,3-b]pyridin-3-ylmethyl)-pyridin-2-yl]-3-trifluoromethoxy-benzamide (P-0113), N-[5-(1H-Pyrrolo[2,3-b]pyridin-3-ylmethyl)-pyridin-2-yl]-3-trifluoromethyl-benzamide (P-0114), 3-Chloro-4-fluoro-N-[5-(1H-pyrrolo[2,3-b]pyridin-3-ylmethyl)-pyridin-2-yl]-benzamide (P-0115), 3,4-Difluoro-N-[5-(1H-pyrrolo[2,3-b]pyridin-3-ylmethyl)-pyridin-2-yl]-benzamide (P-0116), 2-Chloro-N-[5-(1H-pyrrolo[2,3-b]pyridin-3-ylmethyl)-pyridin-2-yl]-benzamide (P-0117), 5-Fluoro-2-methyl-N-[5-(1H-pyrrolo[2,3-b]pyridin-3-ylmethyl)-pyridin-2-yl]-benzamide (P-0118), 2-Fluoro-N-[5-(1H-pyrrolo[2,3-b]pyridin-3-ylmethyl)-pyridin-2-yl]-benzamide (P-0119), 3-Methoxy-N-[5-(1H-pyrrolo[2,3-b]pyridin-3-ylmethyl)-pyridin-2-yl]-benzamide (P-0120), 3-Fluoro-N-[5-(1H-pyrrolo[2,3-b]pyridin-3-ylmethyl)-pyridin-2-yl]-benzamide (P-0121), 3-Methyl-N-[5-(1H-pyrrolo[2,3-b]pyridin-3-ylmethyl)-pyridin-2-yl]-benzamide (P-0122), and 2-Chloro-N-[5-(1H-pyrrolo[2,3-b]pyridin-3-ylmethyl)-pyridin-2-yl]-isonicotinamide (P-0123).

The following table indicates the amide (Column 2) used in Scheme 170 to provide the compounds (Column 3). Column 1 provides the compound number and column 4 the observed mass.

| Compound number | Amide | Compound | MS(ESI) [M + H+]+ observed |
|---|---|---|---|
| P-0100 | 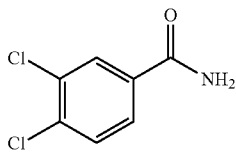 [SMILES: NC(=O)c1ccc(Cl)c(Cl)c1] | 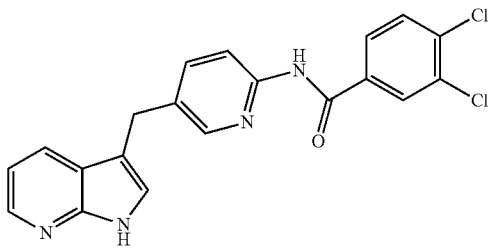 [SMILES: O=C(Nc1ccc(Cc2c[nH]c3ncccc23)cn1)c1ccc(Cl)c(Cl)c1] | 397.1 |
| P-0101 | 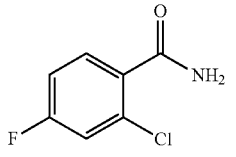 [SMILES: NC(=O)c1ccc(F)cc1Cl] | 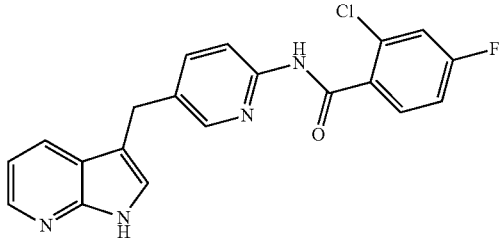 [SMILES: O=C(Nc1ccc(Cc2c[nH]c3ncccc23)cn1)c1ccc(F)cc1Cl] | 381.1 |
| P-0102 | 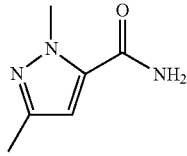 | 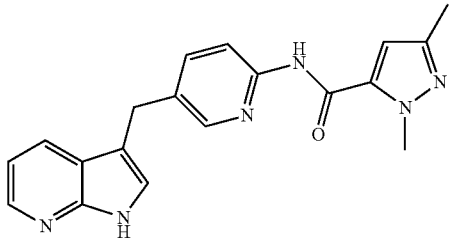 [SMILES: Cc1cc(C(=O)Nc2ccc(Cc3c[nH]c4ncccc34)cn2)n(C)n1] | 347.1 |
| P-0103 | 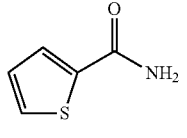 | 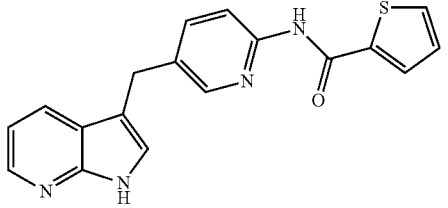 [SMILES: O=C(Nc1ccc(Cc2c[nH]c3ncccc23)cn1)c1cccs1] | 335.1 |
| P-0104 | 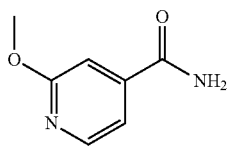 | 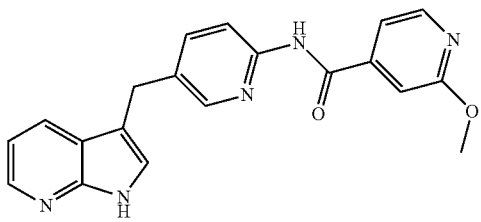 [SMILES: COc1cc(C(=O)Nc2ccc(Cc3c[nH]c4ncccc34)cn2)ccn1] | 360.3 |
| P-0105 | 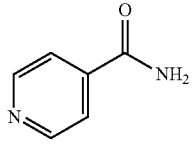 | 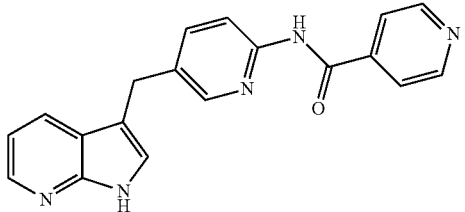 [SMILES: O=C(Nc1ccc(Cc2c[nH]c3ncccc23)cn1)c1ccncc1] | 329.9 |

-continued
| Compound number | Amide | Compound | MS(ESI) [M + H+]+ observed |
|---|---|---|---|
| P-0106 | 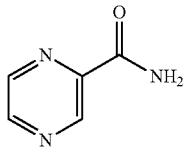 | 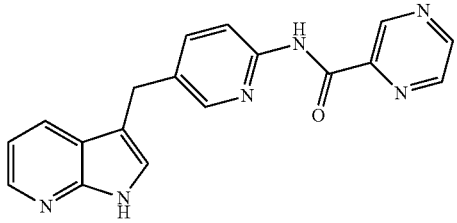 [SMILES: O=C(Nc1ccc(Cc2c[nH]c3ncccc23)cn1)c1cnccn1] | 331.1 |
| P-0107 | 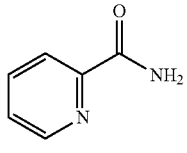 | 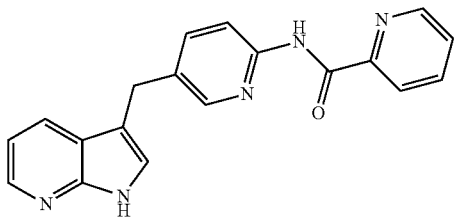 [SMILES: O=C(Nc1ccc(Cc2c[nH]c3ncccc23)cn1)c1ccccn1] | 329.9 |
| P-0108 | 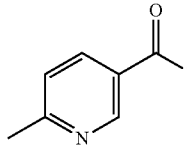 | 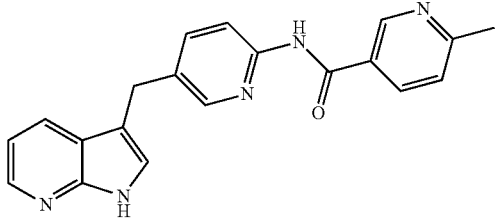 [SMILES: Cc1ccc(C(=O)Nc2ccc(Cc3c[nH]c4ncccc34)cn2)cn1] | 344.3 |
| P-0109 | 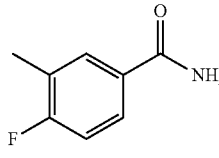 | 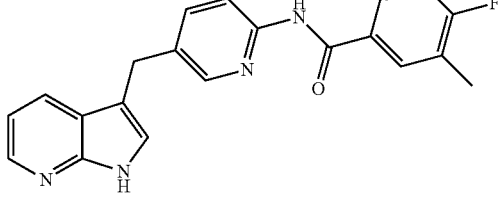 | 361.1 |
| P-0110 | 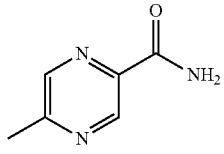 | 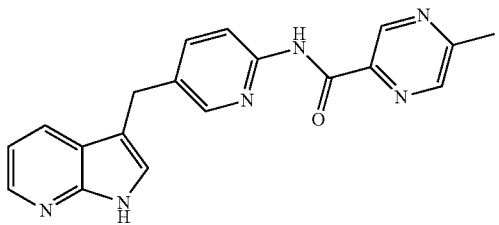 [SMILES: Cc1cnc(C(=O)Nc2ccc(Cc3c[nH]c4ncccc34)cn2)cn1] | 345.1 |
| P-0112 | 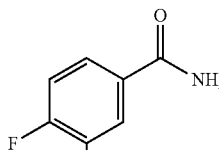 | 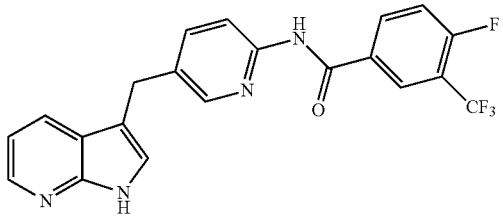 [SMILES: O=C(Nc1ccc(Cc2c[nH]c3ncccc23)cn1)c1ccc(F)c(C(F)(F)F)c1] | 415.1 |

-continued
| Compound number | Amide | Compound | MS(ESI) [M + H+]+ observed |
|---|---|---|---|
| P-0113 | 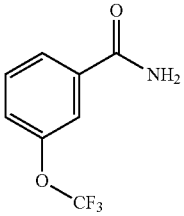 [SMILES: NC(=O)c1cccc(OC(F)(F)F)c1] | 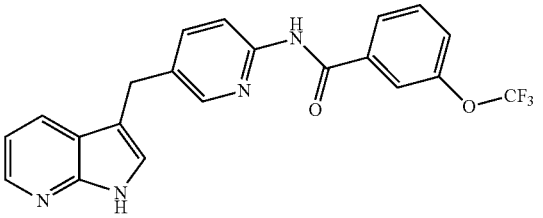 [SMILES: O=C(Nc1ccc(Cc2c[nH]c3ncccc23)cn1)c1cccc(OC(F)(F)F)c1] | 413.1 |
| P-0114 | 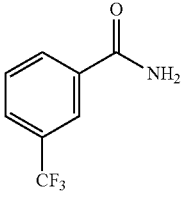 [SMILES: NC(=O)c1cccc(C(F)(F)F)c1] | 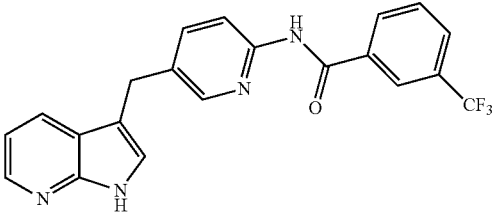 [SMILES: O=C(Nc1ccc(Cc2c[nH]c3ncccc23)cn1)c1cccc(C(F)(F)F)c1] | 397.1 |
| P-0115 | 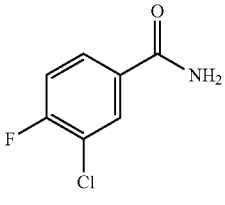 [SMILES: NC(=O)c1ccc(F)c(Cl)c1] | 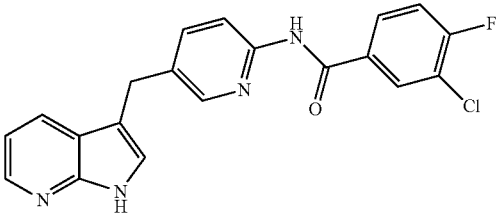 [SMILES: O=C(Nc1ccc(Cc2c[nH]c3ncccc23)cn1)c1ccc(F)c(Cl)c1] | 381.1 |
| P-0116 | 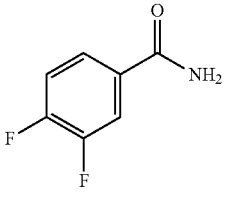 [SMILES: NC(=O)c1ccc(F)c(F)c1] | 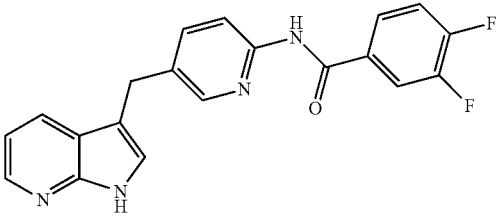 | 365.1 |
| P-0117 | 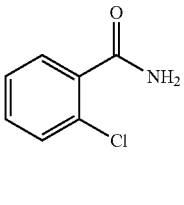 | 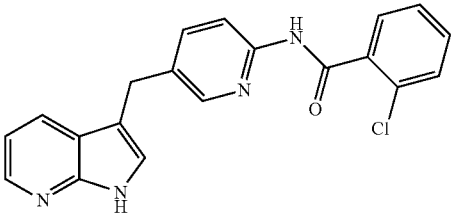 [SMILES: O=C(Nc1ccc(Cc2c[nH]c3ncccc23)cn1)c1ccccc1Cl] | 363.1 |
| P-0118 | 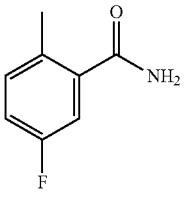 | 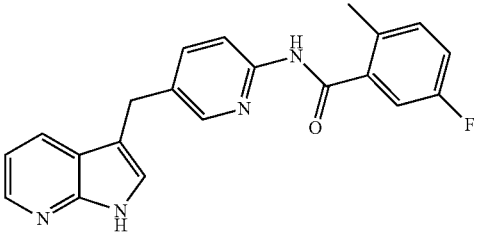 [SMILES: Cc1ccc(F)cc1C(=O)Nc1ccc(Cc2c[nH]c3ncccc23)cn1] | 361.1 |

-continued
| Compound number | Amide | Compound | MS(ESI) [M + H⁺]⁺ observed |
|---|---|---|---|
| P-0119 | 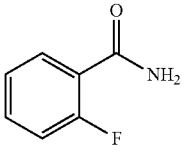 | 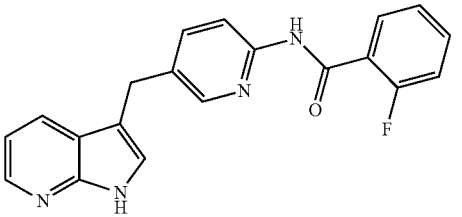 [SMILES: O=C(Nc1ccc(Cc2c[nH]c3ncccc23)cn1)c1ccccc1F] | 347.1 |
| P-0120 | 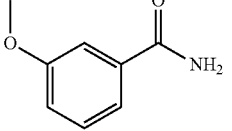 | 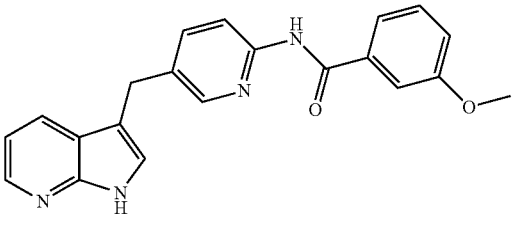 [SMILES: COc1cccc(C(=O)Nc2ccc(Cc3c[nH]c4ncccc34)cn2)c1] | 359.1 |
| P-0121 | 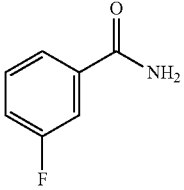 | 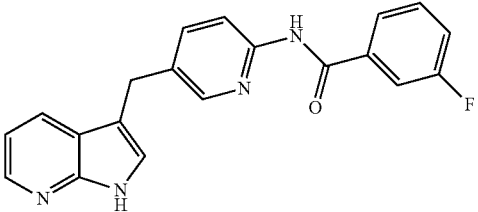 [SMILES: O=C(Nc1ccc(Cc2c[nH]c3ncccc23)cn1)c1cccc(F)c1] | 347.1 |
| P-0122 | 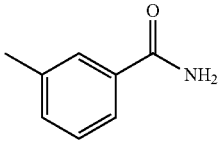 | 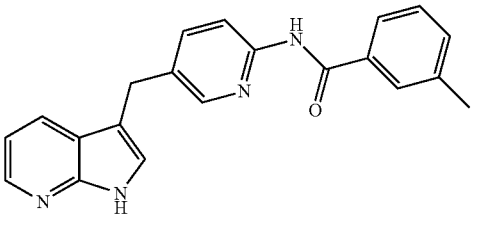 [SMILES: Cc1cccc(C(=O)Nc2ccc(Cc3c[nH]c4ncccc34)cn2)c1] | 343.1 |
| P-0123 | 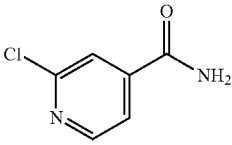 | 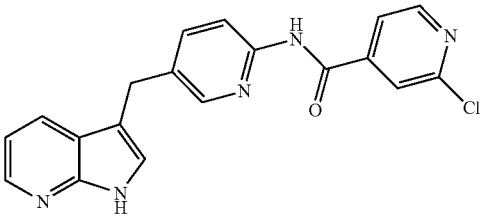 [SMILES: O=C(Nc1ccc(Cc2c[nH]c3ncccc23)cn1)c1ccnc(Cl)c1] | 364.3 |

Example 56

Synthesis of 3,5-dimethyl-4-(1H-pyrrolo[2,3-b]pyridin-3-ylmethyl)-pyrazole-1-carboxylic acid 4-methoxy-benzylamide P-0135

3,5-Dimethyl-4-(1H-pyrrolo[2,3-b]pyridin-3-ylmethyl)-pyrazole-1-carboxylic acid 4-methoxy-benzylamide P-0135 was synthesized in 1 step as shown in Scheme 171.

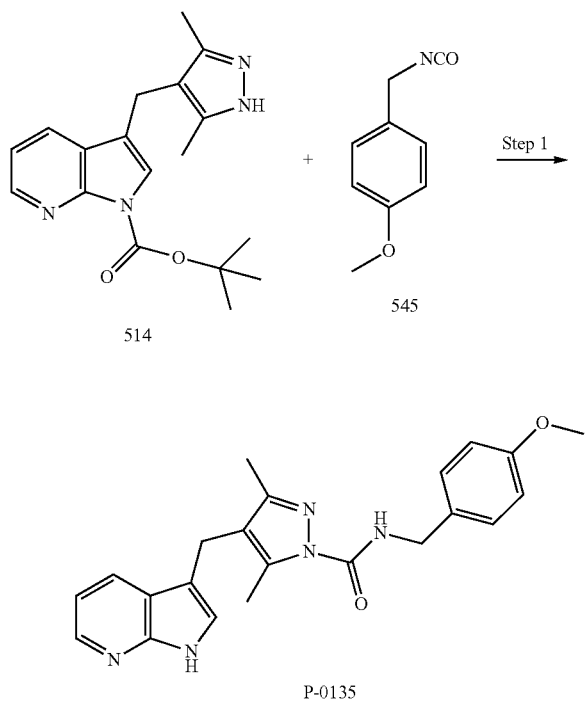

Scheme 171

Step 1—Preparation of 3,5-dimethyl-4-(1H-pyrrolo[2,3-b]pyridin-3-ylmethyl)-pyrazole-1-carboxylic acid 4-methoxy-benzylamide (P-0135)

3-(3,5-dimethyl-1H-pyrazol-4-ylmethyl)-pyrrolo[2,3-b]pyridine-1-carboxylic acid tert-butyl ester (514, 10 mg, 0.03 mmol) was dissolved in dichloromethane (0.5 mL). 1,8-Diazabicylo[5.4.0]unde-7-ene (6 mg, 0.04 mmol) was added. 1-Isocyanatomethyl-4-methoxy-benzene (545, 6.5 mg, 0.04 mmol) was added. The reaction was allowed to proceed at room temperature for 30 minutes. Acetic acid (0.2 mL) was added to the reaction. The solvents were removed under reduced pressure. The residue was dissolved in dimethyl sulfoxide (0.2 mL) and purified by reverse phase HPLC on a Phenomenex column (50 mm×10 mm ID), eluting with water with 0.1% trifluoroacetic acid and 20-100% acetonitrile with 0.1% trifluoroacetic acid over 16 minutes at a flow rate of 6 mL/minute to provide the desired compound P-0135. MS (ESI) $[M+H^+]^+=390.3$.

Additional compounds were prepared following the protocol of Scheme 171, replacing 1-isocyanatomethyl-4-methoxy-benzene 545 with an appropriate isocyanate or bromide. The following compounds were made following this procedure:
3-(1-Benzyl-3,5-dimethyl-1H-pyrazol-4-ylmethyl)-1H-pyrrolo[2,3-b]pyridine (P-0133),
2-[3,5-Dimethyl-4-(1H-pyrrolo[2,3-b]pyridin-3-ylmethyl)-pyrazol-1-yl]-1-phenyl-ethanone (P-0134),
3,5-Dimethyl-4-(1H-pyrrolo[2,3-b]pyridin-3-ylmethyl)-pyrazole-1-carboxylic acid 2-chloro-benzylamide (P-0136),
3,5-Dimethyl-4-(1H-pyrrolo[2,3-b]pyridin-3-ylmethyl)-pyrazole-1-carboxylic acid 2-fluoro-benzylamide (P-0137),
3-[3,5-Dimethyl-1-(5-trifluoromethyl-furan-2-ylmethyl)-1H-pyrazol-4-ylmethyl]-1H-pyrrolo[2,3-b]pyridine (P-0138),
3-[3,5-Dimethyl-1-(5-methyl-isoxazol-3-ylmethyl)-1H-pyrazol-4-ylmethyl]-1H-pyrrolo[2,3-b]pyridine (P-0139),
3,5-Dimethyl-4-(1H-pyrrolo[2,3-b]pyridin-3-ylmethyl)-pyrazole-1-carboxylic acid 4-chloro-benzylamide (P-0140),
3,5-Dimethyl-4-(1H-pyrrolo[2,3-b]pyridin-3-ylmethyl)-pyrazole-1-carboxylic acid [2-(4-ethoxy-phenyl)-ethyl]-amide (P-0141),
3,5-Dimethyl-4-(1H-pyrrolo[2,3-b]pyridin-3-ylmethyl)-pyrazole-1-carboxylic acid 3-methoxy-benzylamide (P-0142),
3-{3,5-Dimethyl-1-[4-methyl-2-(4-trifluoromethyl-phenyl)-thiazol-5-ylmethyl]-1H-pyrazol-4-ylmethyl}-1H-pyrrolo[2,3-b]pyridine (P-0143),
3-[3,5-Dimethyl-1-(4-methyl-2-phenyl-thiazol-5-ylmethyl)-1H-pyrazol-4-ylmethyl]-1H-pyrrolo[2,3-b]pyridine (P-0144),
3,5-Dimethyl-4-(1H-pyrrolo[2,3-b]pyridin-3-ylmethyl)-pyrazole-1-carboxylic acid 2-methoxy-benzylamide (P-0145),
3,5-Dimethyl-4-(1H-pyrrolo[2,3-b]pyridin-3-ylmethyl)-pyrazole-1-carboxylic acid [2-(2,4-dichloro-phenyl)-ethyl]-amide (P-0146),
3,5-Dimethyl-4-(1H-pyrrolo[2,3-b]pyridin-3-ylmethyl)-pyrazole-1-carboxylic acid [2-(4-fluoro-phenyl)-ethyl]-amide (P-0147),
3,5-Dimethyl-4-(1H-pyrrolo[2,3-b]pyridin-3-ylmethyl)-pyrazole-1-carboxylic acid [2-(2-fluoro-phenyl)-ethyl]-amide (P-0148),
3,5-Dimethyl-4-(1H-pyrrolo[2,3-b]pyridin-3-ylmethyl)-pyrazole-1-carboxylic acid ((S)-1-phenyl-ethyl)-amide (P-0149),
3,5-Dimethyl-4-(1H-pyrrolo[2,3-b]pyridin-3-ylmethyl)-pyrazole-1-carboxylic acid 3-fluoro-benzylamide (P-0150),
3,5-Dimethyl-4-(1H-pyrrolo[2,3-b]pyridin-3-ylmethyl)-pyrazole-1-carboxylic acid 4-fluoro-benzylamide (P-0151),
3,5-Dimethyl-4-(1H-pyrrolo[2,3-b]pyridin-3-ylmethyl)-pyrazole-1-carboxylic acid 4-methyl-benzylamide (P-0152), and
3,5-Dimethyl-4-(1H-pyrrolo[2,3-b]pyridin-3-ylmethyl)-pyrazole-1-carboxylic acid 2-methyl-benzylamide (P-0153).

The following table indicates the isocyanate or bromide (Column 2) used in Scheme 171 to provide the compounds (Column 3). Column 1 provides the compound number and Column 4 the observed mass.

| Compound number | Isocyanate or bromide | Compound | MS(ESI) [M + H⁺]⁺ observed |
|---|---|---|---|
| P-0133 | 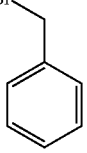 | 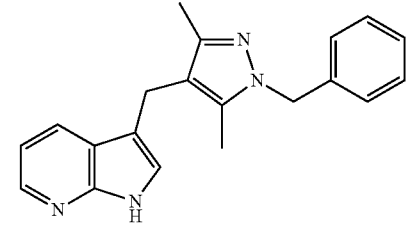 [SMILES: Cc1nn(Cc2ccccc2)c(C)c1Cc1c[nH]c2ncccc12] | 317.1 |
| P-0134 | 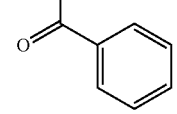 | 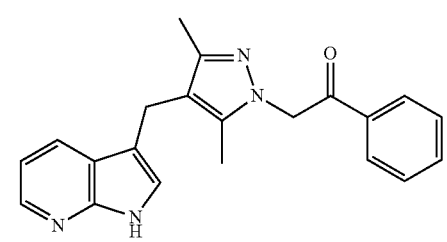 [SMILES: Cc1nn(CC(=O)c2ccccc2)c(C)c1Cc1c[nH]c2ncccc12] | 345.1 |
| P-0136 | 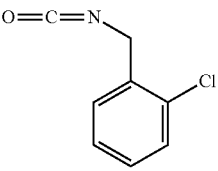 | 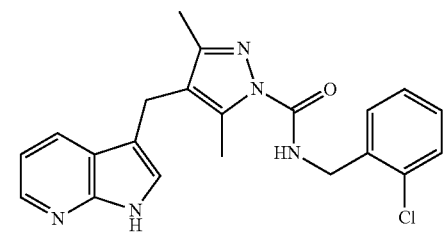 [SMILES: Cc1nn(C(=O)NCc2ccccc2Cl)c(C)c1Cc1c[nH]c2ncccc12] | 394.3 |
| P-0137 | 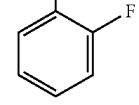 | 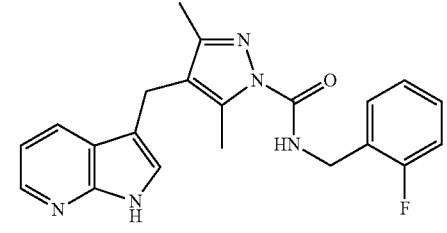 | 378.3 |
| P-0138 | 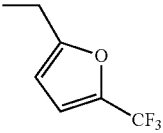 | 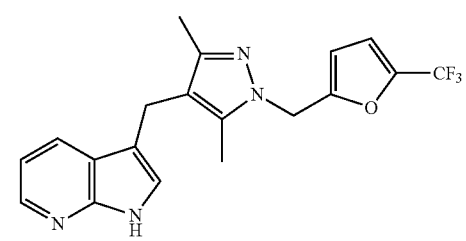 [SMILES: Cc1nn(Cc2ccc(C(F)(F)F)o2)c(C)c1Cc1c[nH]c2ncccc12] | 375.1 |
| P-0139 | 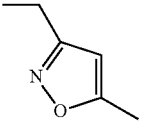 | 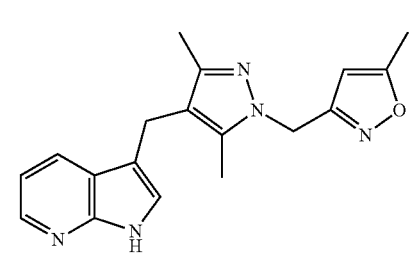 [SMILES: Cc1cc(Cn2nc(C)c(Cc3c[nH]c4ncccc34)c2C)no1] | 322.3 |

-continued
| Compound number | Isocyanate or bromide | Compound | MS(ESI) [M + H+]+ observed |
|---|---|---|---|
| P-0140 | 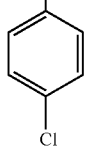 | 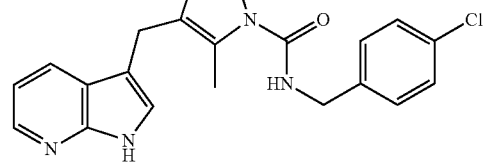 | 393.9 |
| P-0141 | 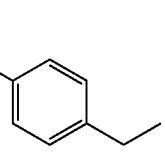 | 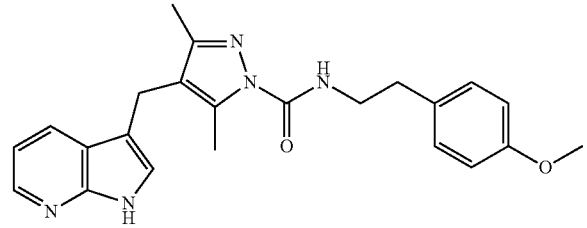 [SMILES: COc1ccc(CCNC(=O)n2nc(C)c(Cc3c[nH]c4ncccc34)c2C)cc1] | 404.3 |
| P-0142 | 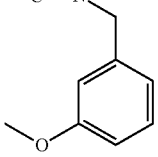 |  | 390.3 |
| P-0143 | 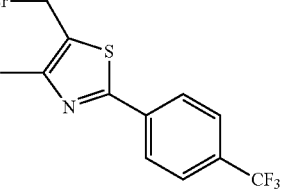 | 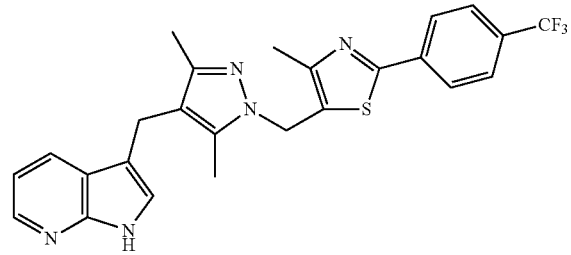 [SMILES: Cc1nc(-c2ccc(C(F)(F)F)cc2)sc1Cn1nc(C)c(Cc2c[nH]c3ncccc23)c1C] | 482.3 |
| P-0144 | 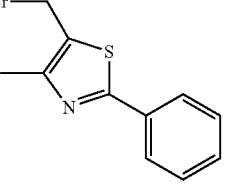 | 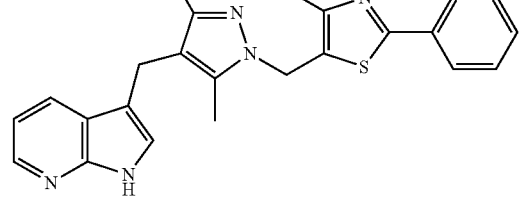 | 414.3 |
| P-0145 | 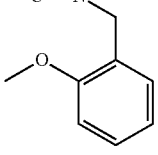 | 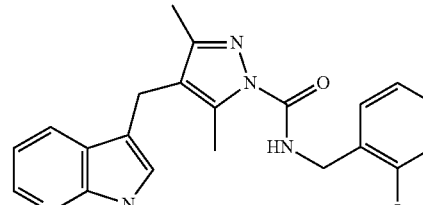 | 390.3 |

-continued
| Compound number | Isocyanate or bromide | Compound | MS(ESI) [M + H⁺]⁺ observed |
|---|---|---|---|
| P-0146 | 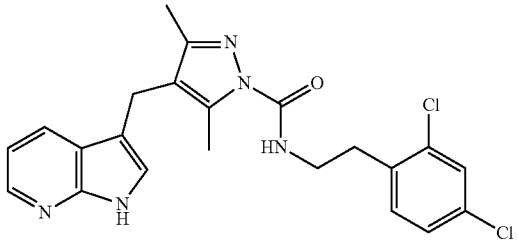 [SMILES: Cc1nn(C(=O)NCCc2ccc(Cl)cc2Cl)c(C)c1Cc1c[nH]c2ncccc12] | | 442.3 |
| P-0147 | 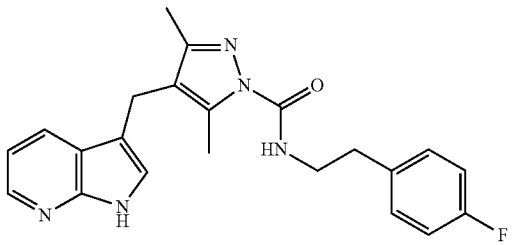 [SMILES: Cc1nn(C(=O)NCCc2ccc(F)cc2)c(C)c1Cc1c[nH]c2ncccc12] | | 392.3 |
| P-0148 | 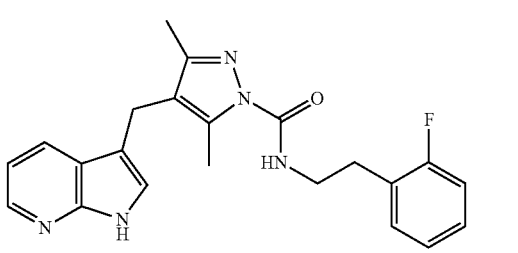 [SMILES: Cc1nn(C(=O)NCCc2ccccc2F)c(C)c1Cc1c[nH]c2ncccc12] | | 392.3 |
| P-0149 | 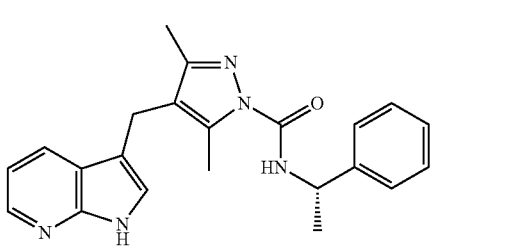 [SMILES: Cc1nn(C(=O)N[C@@H](C)c2ccccc2)c(C)c1Cc1c[nH]c2ncccc12] | | 374.3 |
| P-0150 | 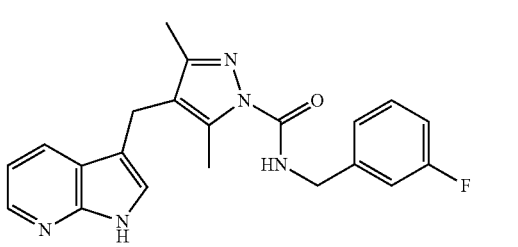 [SMILES: Cc1nn(C(=O)NCc2cccc(F)c2)c(C)c1Cc1c[nH]c2ncccc12] | | 378.3 |
| P-0151 | 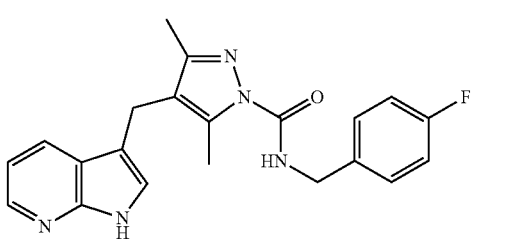 [SMILES: Cc1nn(C(=O)NCc2ccc(F)cc2)c(C)c1Cc1c[nH]c2ncccc12] | | 378.3 |

| Compound number | Isocyanate or bromide | Compound | MS(ESI) [M + H⁺]⁺ observed |
|---|---|---|---|
| P-0152 | O=C=N, 4-methylbenzyl | pyrrolo[2,3-b]pyridine-3-yl methyl dimethylpyrazole-N-carboxamide with 4-methylbenzyl | 374.3 |
| P-0153 | O=C=N, 2-methylbenzyl | pyrrolo[2,3-b]pyridine-3-yl methyl dimethylpyrazole-N-carboxamide with 2-methylbenzyl | 374.3 |

Example 57

Synthesis of 5-(1-methyl-1H-pyrazol-4-yl)-1H-pyrrolo[2,3-b]pyridine 547

5-(1-Methyl-1H-pyrazol-4-yl)-1H-pyrrolo[2,3-b]pyridine 547 was synthesized in 1 step from 5-bromo-1H-pyrrolo[2,3-b]pyridine 44 as shown in Scheme 172.

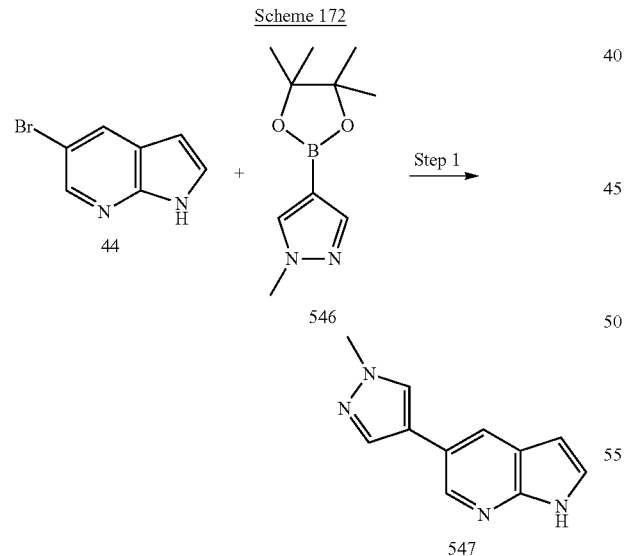

Scheme 172

Step 1—Preparation of 5-(1-Methyl-1H-pyrazol-4-yl)-1H-pyrrolo[2,3-b]pyridine (547)

To 5-bromo-7-azaindole (44, 1.04 g, 5.28 mmol) in 1.00 M potassium carbonate in water (15.8 mL) and tetrahydrofuran (50.0 mL) were added 1-methyl-4-(4,4,5,5-tetramethyl-[1,3,2]dioxaborolan-2-yl)-1H-pyrazole (546, 1.65 g, 7.92 mmol), Tetrakis(triphenylphosphine)palladium(0) (0.305 mg, 0.26 mmol) and tetra-n-butylammonium iodide (0.20 g, 0.53 mmol). The reaction mixture was stirred at 70° C. overnight. The reaction mixture was poured into water and the organic layer was washed with brine, dried over sodium sulfate, and concentrated. The residue was purified with silica gel column chromatography eluting with 25% ethyl acetate in hexane to provide a light yellow solid (547, 670 mg, 64.0%). MS (ESI) [M+H⁺]⁺=199.4.

Example 58

Synthesis of [2-(4-fluoro-benzylamino)-thiazol-5-yl]-(1H-pyrrolo[2,3-b]pyridin-3-yl)-methanone P-0177

[2-(4-Fluoro-benzylamino)-thiazol-5-yl]-(1H-pyrrolo[2,3-b]pyridin-3-yl)-methanone P-0177 was synthesized in 2 steps as shown in Scheme 173.

Scheme 173

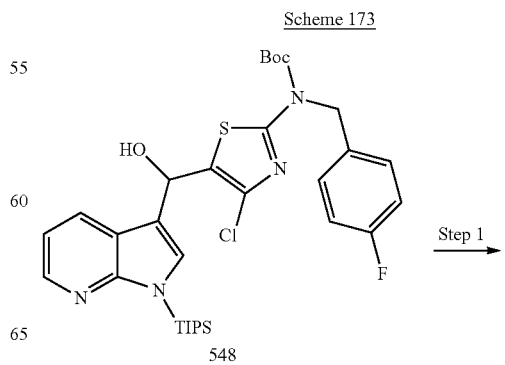

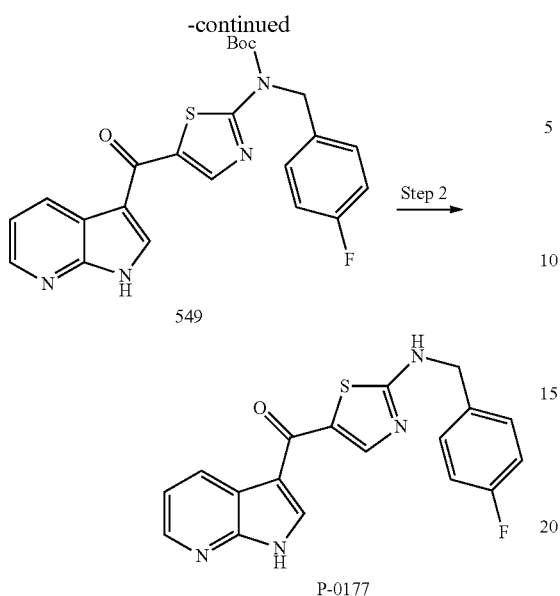

549

P-0177

Step 1—Preparation of (4-fluoro-benzyl)-[5-(1H-pyrrolo[2,3-b]pyridine-3-carbonyl)-thiazol-2-yl]-carbamic acid tert-butyl ester (549)

A mixture of {4-chloro-5-[hydroxy-(1-triisopropylsilanyl-1H-pyrrolo[2,3-b]pyridin-3-yl)-methyl]-thiazol-2-yl}-pyridin-4-ylmethyl-carbamic acid tert-butyl ester (548, 0.397 g, 0.57 mmol, prepared according to the protocol of Scheme 159, Example 44, replacing 4-(aminomethyl)pyridine 516 with 4-fluoro-benzylamine in step 1, isolated after step 3), triethylsilane (1.0 mL, 6.3 mmol), and trifluoroacetic acid (0.5 mL, 6 mmol) in acetonitrile (10 mL) was stirred at 40° C. for 2 hours. The reaction mixture was poured into ice water, extracted with ethyl acetate, washed with sodium bicarbonate and brine, and dried over sodium sulfate. After removal of solvent, the residue was purified by silica gel column chromatography eluting with methanol in dichloromethane to provide the desired compound as a yellow solid (549, 0.11 g, 9%). MS (ESI) [M−H$^+$]$^+$=451.10.

Step 2—Preparation of [2-(4-fluoro-benzylamino)-thiazol-5-yl]-(1H-pyrrolo[2,3-b]pyridin-3-yl)-methanone (P-0177)

To a solution of (4-fluoro-benzyl)-[5-(1H-pyrrolo[2,3-b]pyridine-3-carbonyl)-thiazol-2-yl]-carbamic acid tert-butyl ester (549, 0.11 g, 0.2 mmol) in dichloromethane (2 mL) was added hydrogen chloride (4 M in 1,4-dioxane, 2 mL). The reaction mixture was stirred at room temperature overnight. The reaction mixture was poured into cold sodium bicarbonate solution, extracted with ethyl acetate, washed with brine and dried over magnesium sulfate. After removal of solvents, the residue was washed with ethyl acetate to provide the desired compound as a yellow solid (P-0177, 9 mg, 10%). MS (ESI) [M+H$^+$]$^+$=353.12.

Example 59

Synthesis of {2-[(4-chloro-benzyl)-methyl-amino]-thiazol-5-yl}-(1H-pyrrolo[2,3-b]pyridin-3-yl)-methanone P-0178

{2-[(4-Chloro-benzyl)-methyl-amino]-thiazol-5-yl}-(1H-pyrrolo[2,3-b]pyridin-3-yl)-methanone P-0178 was synthesized in 3 steps as shown in Scheme 174.

Scheme 174

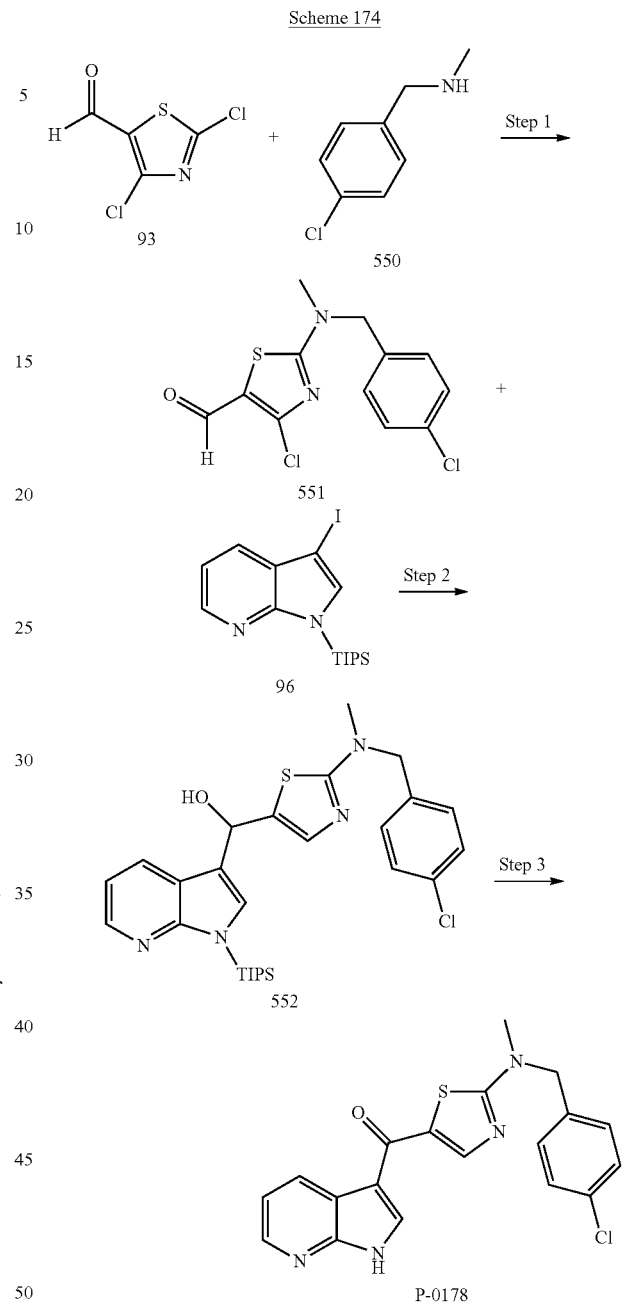

Step 1—Preparation of 4-chloro-2-[(4-chloro-benzyl)-methyl-amino]-thiazole-5-carbaldehyde (551)

To a solution of (4-chloro-benzyl)-methyl-amine (550, 2 g, 0.01 mol) and N,N-diisopropylethylamine (4 mL, 0.03 mol) in tetrahydrofuran (50 mL) was added 2,4-dichloro-thiazole-5-carbaldehyde (93, 3 g, 0.01 mmol) in tetrahydrofuran (20 mL) at room temperature. The reaction mixture was stirred at room temperature overnight. The reaction mixture was poured into ice water, extracted with ethyl acetate, washed with brine, and dried over sodium sulfate. After removal of solvent, the residue was collected by filtration and washed with hexanes to provide the desired compound as a light-yellow solid (551, 3.6 g, 90%).

Step 2—Preparation of {4-chloro-2-[(4-chloro-benzyl)-methyl-amino]-thiazol-5-yl}-(1-triisopropylsilanyl-1H-pyrrolo[2,3-b]pyridin-3-A-methanol (552)

To a solution of 3-iodo-1-triisopropylsilanyl-1H-pyrrolo[2,3-b]pyridine (96, 0.82 g, 2.0 mmol) in tetrahydrofuran (5 mL) at −20° C., isopropylmagnesium chloride (2 M in tetrahydrofuran, 1.1 mL, 2.2 mmol) was added dropwise. The reaction mixture was allowed to warm to 0° C. in 10 minutes. The reaction mixture was then cooled to −40° C. To the reaction mixture was added a solution of 4-chloro-2-[(4-chloro-benzyl)-methyl-amino]-thiazole-5-carbaldehyde (551, 0.41 g, 1.4 mmol) in tetrahydrofuran (10 mL). The reaction mixture was allowed to warm to −10° C. in 30 minutes. The reaction mixture was poured into ice water, extracted with ethyl acetate, washed with brine, and dried over sodium sulfate. After removal of solvent, the residue was purified by silica gel column chromatography eluting with ethyl acetate in hexanes to provide the desired compound as a yellow solid (552, 0.5 g, 60%). MS (ESI) [M+H$^+$]$^+$=575.29.

Step 3—Preparation of {2-[(4-chloro-benzyl)-methyl-amino]-thiazol-5-yl}-(1H-pyrrolo[2,3-b]pyridin-3-yl)-methanone (P-0178)

A mixture of {4-chloro-2-[(4-chloro-benzyl)-methyl-amino]-thiazol-5-yl}-(1-triisopropylsilanyl-1H-pyrrolo[2,3-b]pyridin-3-yl)-methanol (552, 1 g, 2 mmol), triethylsilane (2 mL, 12 mmol), and trifluoroacetic acid (1 mL, 13 mmol) in acetonitrile (10 mL) was stirred at 40° C. for 2 hours. The reaction mixture was poured into ice water, extracted with ethyl acetate, washed with sodium bicarbonate and brine, and dried over sodium sulfate. After removal of solvent, the residue was purified by silica gel column chromatography eluting with methanol in dichloromethane to provide the desired compound as a yellow solid (P-0178, 0.17 g, 30%). MS (ESI) [M+H$^+$]$^+$=383.09.

Example 60

Synthesis of Aldehyde Intermediates (3-Chloro-pyridin-4-ylmethyl)-(5-formyl-pyridin-2-yl)-carbamic acid tert-butyl ester 558 was synthesized in 4 steps from 6-amino-nicotinic acid methyl ester 553 as shown in Scheme 175.

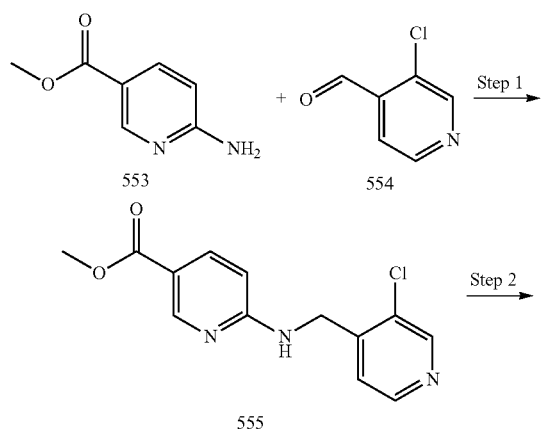

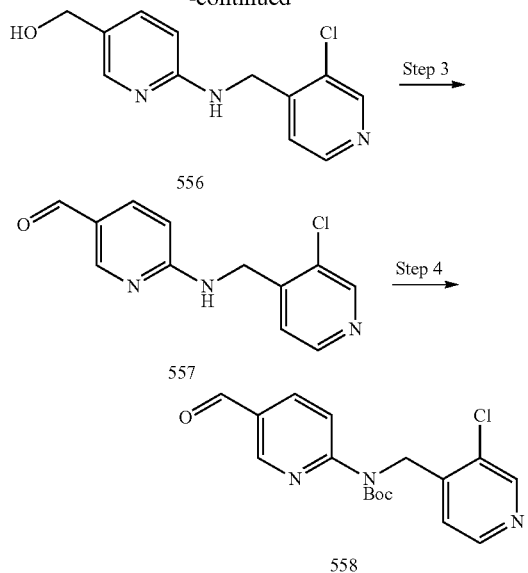

Step 1—Synthesis of 6-[(3-chloro-pyridin-4-ylmethyl)-amino]-nicotinic acid methyl ester (555)

To 6-amino-nicotinic acid methyl ester (553, 2.15 g, 0.014 mol) in acetonitrile (60.0 mL) were added 3-chloro-pyridine-4-carbaldehyde (554, 2.00 g, 0.014 mol), triethylsilane (11.00 mL, 0.069 mol) and trifluoroacetic acid (5.00 mL, 0.065 mol). The reaction was stirred at 80° C. overnight. The reaction was concentrated, poured into aqueous potassium carbonate, and extracted with ethyl acetate. The organic layer was dried over anhydrous sodium sulfate and filtered. The filtrate was concentrated and purified by silica gel column chromatography eluting with 20% to 100% ethyl acetate in hexane to give the desired compound (555, 1.5 g, 38.2%). MS (ESI) [M+H$^+$]$^+$=278.9.

Step 2—Synthesis of 6-[(3-Chloro-pyridin-4-ylmethyl)-amino]pyridin-3-yl-methanol (556)

To 6-[(3-chloro-pyridin-4-ylmethyl)-amino]-nicotinic acid methyl ester (555, 1.00 g, 3.60 mmol) in tetrahydrofuran (120 mL) was added a solution of lithium tetrahydroaluminate (1.00 M in tetrahydrofuran, 5.00 mL) under an atmosphere of nitrogen at room temperature. The reaction was stirred at room temperature overnight, followed with addition of sodium sulfate decahydrate. After 1 hour, the reaction mixture was filtered, concentrated, and purified with silica gel column chromatography eluting with 2% to 20% methanol in dichloromethane to give the desired compound as a white solid (556, 0.5 g, 56%). MS (ESI) [M+H$^+$]$^+$=250.1.

Step 3—Synthesis of 6-[(3-chloro-pyridin-4-ylmethyl)-amino]-pyridine-3-carbaldehyde (557)

To 6-[(3-chloro-pyridin-4-ylmethyl)-amino]-pyridin-3-yl-methanol (556, 0.50 g, 2.00 mmol) in tetrahydrofuran (20.0 mL) was added Dess-Martin periodinane (1.02 g, 2.40 mmol). The reaction was stirred at room temperature for 10 minutes, then poured into aqueous potassium carbonate, and extracted with ethyl acetate. The organic layer was dried over anhydrous sodium sulfate and filtered. The filtrate was concentrated to give crude compound (557, 0.45 g, 91%) that was used in the next step without further purification.

Step 4—Synthesis of (3-chloro-pyridin-4-ylmethyl)-(5-formyl-pyridin-2-yl)-carbamic acid tert-butyl ester (558)

To 6-[(3-chloro-pyridin-4-ylmethyl)-amino]-pyridine-3-carbaldehyde (557, 0.45 g, 1.80 mmol) in dichloromethane (20.0 mL) were added di-tert-butyldicarbonate (0.65 g, 3.00 mmol), 4-dimethylaminopyridine (0.012 g, 0.010 mmol) and triethylamine (0.28 mL, 2.00 mmol). The reaction was stirred at room temperature overnight, then concentrated and purified with silica gel column chromatography eluting with 20% to 100% ethyl acetate in hexane to give the desired compound (558, 250 mg, 40.0%).

(2-Difluoromethoxy-benzyl)-(5-formyl-pyridin-2-yl)-carbamic acid tert-butyl ester 559

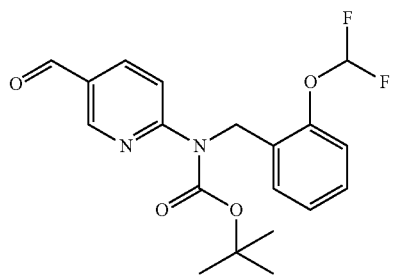 [SMILES: CC(C)(C)OC(=O)N(Cc1ccccc1OC(F)F)c1ccc(C=O)cn1]

was prepared following the protocol of Scheme 175, substituting 3-chloro-pyridine-4-carbaldehyde 554 with 2-difluoromethoxy-benzaldehyde in Step 1.

[2,6-Difluoro-3-(propane-1-sulfonylamino)-benzyl]-(5-formyl-pyridin-2-yl)-carbamic acid tert-butyl ester 560

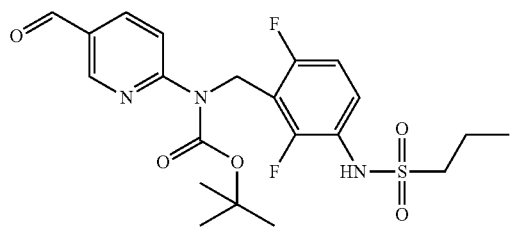 [SMILES: CCCS(=O)(=O)Nc1ccc(F)c(CN(C(=O)OC(C)(C)C)c2ccc(C=O)cn2)c1F]

was prepared following the protocol of Scheme 175, substituting 3-chloro-pyridine-4-carbaldehyde 554 with propane-1-sulfonic acid (2,4-difluoro-3-formyl-phenyl)-amide in Step 1. MS (ESI) [M+H$^+$]$^+$=470.3.

(6-Fluoro-5-formyl-pyridin-2-yl)-(6-trifluoromethyl-pyridin-3-ylmethyl)-carbamic acid tert-butyl ester 565 was synthesized in 4 steps from 2,6-Difluoro-nicotinic acid methyl ester 60 as shown in Scheme 176.

Scheme 176

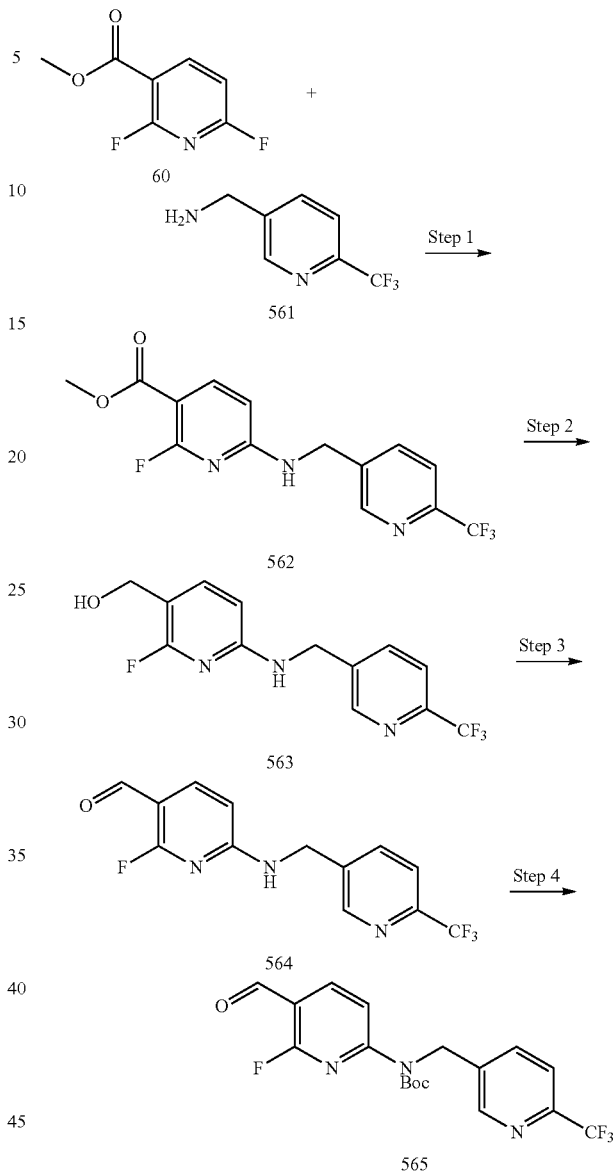

Step 1—Synthesis of 2-fluoro-6-[(6-trifluoromethyl-pyridin-3-ylmethyl)-amino]-nicotinic acid methyl ester (562)

To 2,6-difluoro-nicotinic acid methyl ester (60, 1.82 g, 0.0105 mol, prepared as described in Example 22, Scheme 24, Step 2) in N,N-dimethylformamide (20.0 mL), under an atmosphere of nitrogen at −40° C., C-(6-trifluoromethyl-pyridin-3-yl)-methylamine (561, 1.00 g, 5.68 mmol) was added. The reaction was stirred at −40° C., then allowed to warm to room temperature for 2 hours. The reaction was poured into water and extracted with ethyl acetate. The organic layer was dried over anhydrous sodium sulfate and filtered. The filtrate was concentrated and purified by silica gel column chromatography eluting with 35% to 100% ethyl acetate in hexane to give a white solid (562, 1.40 g, 74.9). MS (ESI) [M+H$^+$]$^+$=330.1.

Step 2—Synthesis of 2-fluoro-6-[(6-trifluoromethyl-pyridin-3-ylmethyl)-amino]-pyridin-3-yl-methanol (563)

To 2-fluoro-6-[(6-trifluoromethyl-pyridin-3-ylmethyl)-amino]-nicotinic acid methyl ester (562, 1.40 g, 4.25 mmol) in tetrahydrofuran (100.0 mL) under an atmosphere of nitrogen at room temperature, a solution of lithium tetrahydroaluminate (1.00 M in tetrahydrofuran, 10.0 mL) was added slowly. The reaction was stirred at room temperature overnight, followed by addition of an appropriate amount of sodium sulfate decahydrate. After 1 hour, the reaction mixture was filtered and concentrated to give crude compound (563, 1.2 g, 93.7%) that was used in the next step without further purification.

Step 3—Synthesis of 2-fluoro-6-[(6-trifluoromethyl-pyridin-3-ylmethyl)-amino]-pyridine-3-carbaldehyde (564)

To 2-fluoro-6-[(6-trifluoromethyl-pyridin-3-ylmethyl)-amino]-pyridin-3-yl-methanol (563, 1.20 g, 3.98 mmol) in dichloromethane (40.0 mL) was added Dess-Martin periodinane (1.86 g, 4.38 mmol). The reaction was stirred at room temperature for 10 minutes, then poured into aqueous sodium thiosulfate and potassium carbonate, and extracted with ethyl acetate. The organic layer was dried over anhydrous sodium sulfate and filtered. The filtrate was concentrated and purified by silica gel column chromatography eluting with 20% to 100% ethyl acetate in hexane to give the desired compound (564, 0.28 g, 23.5%).

Step 4—Synthesis of (6-fluoro-5-formyl-pyridin-2-yl)-(6-trifluoromethyl-pyridin-3-ylmethyl)-carbamic acid tert-butyl ester (565)

To 2-fluoro-6-[(6-trifluoromethyl-pyridin-3-ylmethyl)-amino]-pyridine-3-carbaldehyde (564, 0.28 g, 0.94 mmol) in tetrahydrofuran (10.0 mL) were added di-tert-butyldicarbonate (0.245 g, 1.12 mmol) and 4-dimethylaminopyridine (0.050 g, 0.41 mmol). The reaction was stirred at room temperature overnight, then concentrated and purified with silica gel column chromatography eluting with 20% to 100% ethyl acetate in hexane to give the desired compound (565, 0.22 g, 59%).

(6-Chloro-5-formyl-pyridin-2-yl)-(6-trifluoromethyl-pyridin-3-ylmethyl)-carbamic acid tert-butyl ester 570 was synthesized in 4 steps from 6-chloro-pyridin-2-ylamine 537 as shown in Scheme 177.

Scheme 177

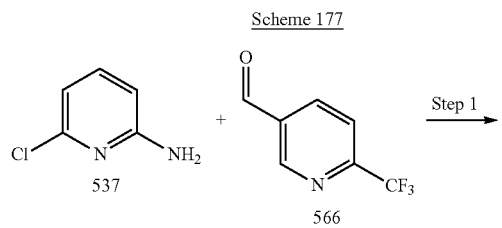

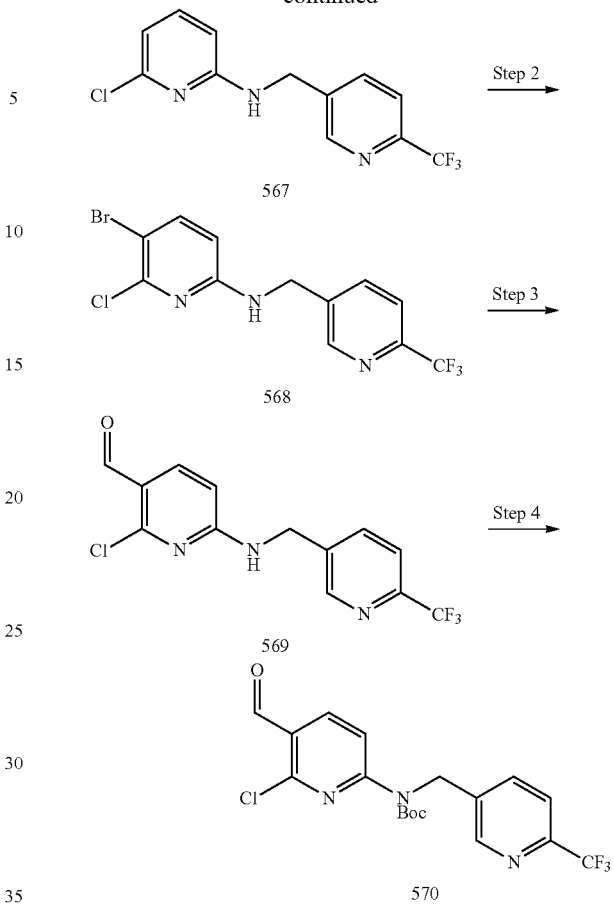

Step 1—Synthesis of (6-chloro-pyridin-2-yl)-(6-trifluoromethyl-pyridin-3-ylmethyl)-amine (567)

To 6-chloro-pyridin-2-ylamine (537, 0.760 g, 5.91 mmol) in acetonitrile (30.0 mL), 6-trifluoromethyl-pyridine-3-carbaldehyde (566, 1.06 g, 6.05 mmol), trifluoroacetic acid (3.00 mL, 0.0389 mol) and triethylsilane (6.00 mL, 0.0376 mol) were added. The reaction was heated to reflux for 4 hours. The reaction was concentrated, poured into aqueous potassium carbonate, and extracted with ethyl acetate. The organic layer was dried over anhydrous sodium sulfate, filtered and concentrated and purified with silica gel column chromatography eluting with 20% to 100% ethyl acetate in hexane to give a white solid (567, 1.60 g, 94.1%).

Step 2—Synthesis of (5-bromo-6-chloro-pyridin-2-yl)-(6-trifluoromethyl-pyridin-3-ylmethyl)-amine (568)

To (6-chloro-pyridin-2-yl)-(6-trifluoromethyl-pyridin-3-ylmethyl)-amine (567, 4.50 g, 0.0156 mol) in acetonitrile (120.0 mL) under an atmosphere of nitrogen, N-bromosuccinimide (3.03 g, 0.0170 mol) in acetonitrile (50 mL) was added slowly. The reaction was stirred at room temperature overnight, then poured into water, and extracted with ethyl acetate. The organic layer was dried over sodium sulfate, concentrated and purified with silica gel column chromatography eluting with 25% to 100% ethyl acetate in hexane to give a white solid (568, 6.20 g, 80.2%).

Step 3—Synthesis of 2-chloro-6-[(6-trifluoromethyl-pyridin-3-ylmethyl)-amino]-pyridine-3-carbaldehyde (569)

To (5-bromo-6-chloro-pyridin-2-yl)-(6-trifluoromethyl-pyridin-3-ylmethyl)-amine (568, 4.60 g, 0.0125 mol) in tetrahydrofuran (60.0 mL) under an atmosphere of nitrogen at −78° C., isopropylmagnesium chloride (2.00 M in tetrahydrofuran, 6.44 mL) was added over 10 minutes. The reaction was stirred at −78° C. for 20 minutes, and then allowed to warm to room temperature for 10 minutes. The reaction was cooled to −78° C., followed by adding tert-butyllithium (1.70 M in hexane, 15.3 mL) over 10 minutes. After 40 minutes, N,N-dimethylformamide (1.23 mL, 0.0158 mol) was added and the reaction was stirred at −78° C. for 40 minutes, then allowed to warm to room temperature for 30 minutes. The reaction mixture was poured into water and extracted with ethyl acetate. The organic layer was washed with brine, dried over sodium sulfate, concentrated and purified by silica gel column chromatography eluting with 35% to 100% ethyl acetate in hexane to give a light yellow solid (569, 2.84 g, 71.7%).

Step 4—Synthesis of (6-chloro-5-formyl-pyridin-2-yl)-(6-trifluoromethyl-pyridin-3-ylmethyl)-carbamic acid tert-butyl ester (570)

To a solution of 2-chloro-6-[(6-trifluoromethyl-pyridin-3-ylmethyl)-amino]-pyridine-3-carbaldehyde (569, 0.545 g, 1.73 mmol) in tetrahydrofuran (10 mL), N,N-diisopropylethylamine (0.60 mL, 3.40 mmol), 4-dimethylaminopyridine (20 mg, 0.10 mmol), and a solution of di-tert-butyldicarbonate (0.41 g, 0.0019 mol) were added. The reaction mixture was stirred at room temperature overnight, then concentrated, poured into water, and extracted with ethyl acetate. The organic layer was washed with brine, dried over sodium sulfate, concentrated and purified by silica gel column chromatography eluting with 20% to 100% ethyl acetate in hexane to give the desired compound (570, 0.60 g, 83.6%).

(5-Bromo-6-fluoro-pyridin-2-yl)-(2-chloro-benzyl)-amine 571

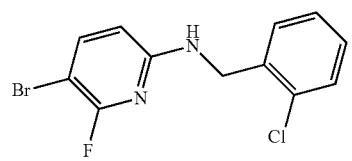 [SMILES: Fc1nc(NCc2ccccc2Cl)ccc1Br]

was prepared following the protocol of Steps 1 and 2 of Scheme 177, substituting 6-chloro-pyridin-2-ylamine 537 and 6-trifluoromethyl-pyridine-3-carbaldehyde 566 with 6-fluoro-pyridin-2-ylamine and 2-chloro-benzaldehyde, respectively in Step 1.

(6-Fluoro-5-formyl-pyridin-2-yl)-(6-methoxy-pyridin-3-ylmethyl)-carbamic acid tert-butyl ester 572

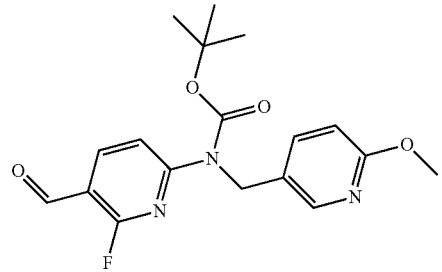 [SMILES: COc1ccc(CN(C(=O)OC(C)(C)C)c2ccc(C=O)c(F)n2)cn1]

was prepared following the protocol of Scheme 177, substituting 6-chloro-pyridin-2-ylamine 537 and 6-trifluoromethyl-pyridine-3-carbaldehyde 566 with 6-fluoro-pyridin-2-ylamine and 6-methoxy-pyridine-3-carbaldehyde, respectively in step 1.

(5-bromo-6-fluoro-pyridin-2-yl)-(5-fluoro-pyridin-3-ylmethyl)-carbamic acid tert-butyl ester 631

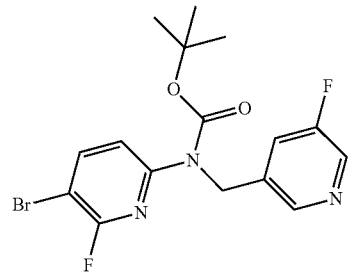 [SMILES: CC(C)(C)OC(=O)N(Cc1cncc(F)c1)c1ccc(Br)c(F)n1]

was prepared following the protocol of Scheme 177, substituting 6-chloro-pyridin-2-ylamine 537 and 6-trifluoromethyl-pyridine-3-carbaldehyde 566 with 6-fluoro-pyridin-2-ylamine and 5-fluoro-pyridine-3-carbaldehyde, respectively in Step 1, without Step 3 (i.e. the product of Step 2 is reacted according to Step 4).

(5-Bromo-6-fluoro-pyridin-2-yl)-(4-chloro-benzyl)-carbamic acid tert-butyl ester 637

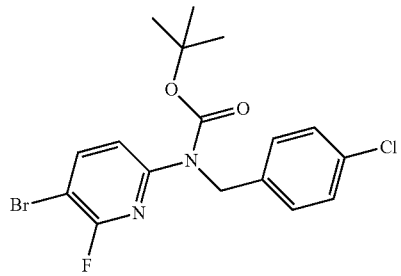 [SMILES: CC(C)(C)OC(=O)N(Cc1ccc(Cl)cc1)c1ccc(Br)c(F)n1]

was prepared following the protocol of Scheme 177, substituting 6-chloro-pyridin-2-ylamine 537 and 6-trifluoromethyl-pyridine-3-carbaldehyde 566 with 6-fluoro-pyridin-2-ylamine and 5-chloro-benzaldehyde, respectively in Step 1, without Step 3 (i.e. the product of Step 2 is reacted according to Step 4).

Example 61

Synthesis of propane-1-sulfonic acid (2,4-difluoro-3-[5-(1H-pyrrolo[2,3-b]pyridin-3-ylmethyl)-pyridin-2-ylamino]-methyl-phenyl)-amide P-0258

Propane-1-sulfonic acid (2,4-difluoro-3-[5-(1H-pyrrolo[2,3-b]pyridin-3-ylmethyl)-pyridin-2-ylamino]-methyl-phenyl)-amide P-0258 was synthesized in 2 steps from 3-Iodo-1-triisopropylsilanyl-1H-pyrrolo[2,3-b]pyridine 96 as shown in Scheme 178.

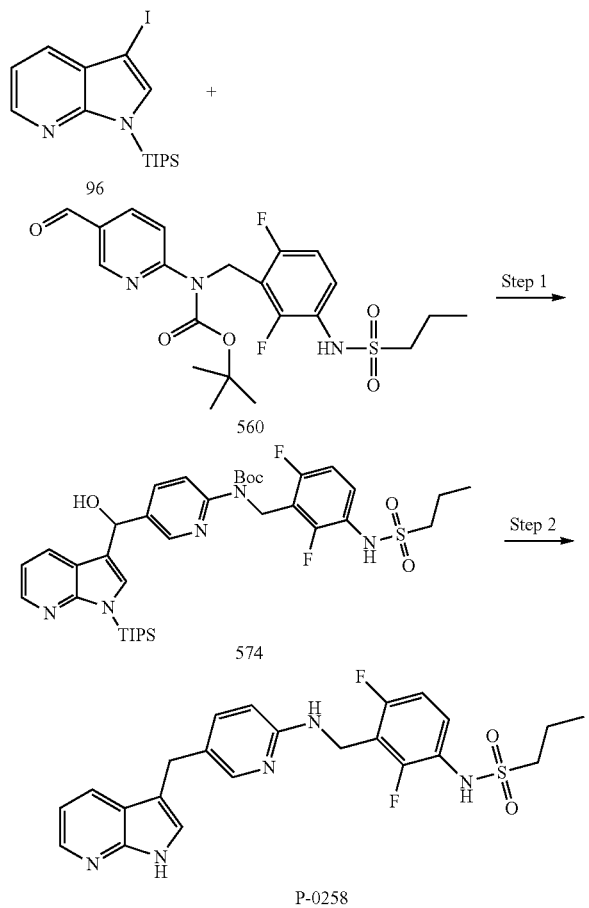

Step 1—Synthesis of [2,6-difluoro-3-(propane-1-sulfonylamino)-benzyl]-5-[hydroxy-(1-triisopropyl-silanyl-1H-pyrrolo[2,3-b]pyridin-3-yl)-methyl]-pyridin-2-yl-carbamic acid tert-butyl ester (574)

To a solution of 3-Iodo-1-triisopropylsilanyl-1H-pyrrolo[2,3-b]pyridine (96, 0.644 g, 1.61 mmol) in tetrahydrofuran (10.0 mL) at −40° C. under nitrogen, isopropylmagnesium chloride (2.0 M in tetrahydrofuran, 0.80 mL) was added slowly. The reaction was allowed to warm to 15° C. over 100 minutes, then cooled to −40° C., followed by adding [2,6-difluoro-3-(propane-1-sulfonylamino)-benzyl]-(5-formyl-pyridin-2-yl)-carbamic acid tert-butyl ester (560, 0.100 g, 0.21 mmol, prepared as described in Example 60, Scheme 175) in tetrahydrofuran (2.0 mL). The reaction was allowed to warm to 5° C. over 2 hours, then poured into aqueous ammonium chloride, and extracted with ethyl acetate. The organic layer was dried over anhydrous sodium sulfate, and filtered. The filtrate was concentrated and purified by silica gel column chromatography eluting with 20% to 100% ethyl acetate in hexane to give a yellow solid (574, 75 mg, 47%). MS (ESI) [M+H⁺]⁺=744.7.

Step 2—Synthesis of Propane-1-sulfonic acid (2,4-difluoro-3-[5-(1H-pyrrolo[2,3-b]pyridin-3-ylmethyl)-pyridin-2-ylamino]-methyl-phenyl)-amide (P-0258)

To [2,6-difluoro-3-(propane-1-sulfonylamino)-benzyl]-5-[hydroxy-(1-triisopropylsilanyl-1H-pyrrolo[2,3-b]pyridin-3-yl)-methyl]-pyridin-2-yl-carbamic acid tert-butyl ester (574, 75.0 mg, 0.10 mmol) in acetonitrile (10.0 mL) were added triethylsilane (0.40 mL, 2.5 mmol) and trifluoroacetic acid (0.20 mL, 2.6 mmol). The reaction was stirred at 80° C. for 4 hours. The reaction was poured into aqueous potassium carbonate, and extracted with ethyl acetate. The organic layer was dried over anhydrous sodium sulfate, and filtered. The filtrate was concentrated and purified by silica gel column chromatography eluting with 2% to 15% methanol in dichloromethane to give an off-white solid (P-0258, 29.3 mg, 61.6%). MS (ESI) [M+H⁺]⁺=472.4.

Propane-1-sulfonic acid (3-{[5-(5-chloro-1H-pyrrolo[2,3-b]pyridin-3-ylmethyl)-pyridin-2-ylamino]-methyl}-2,4-difluoro-phenyl)-amide (P-0259), [6-Fluoro-5-(1H-pyrrolo[2,3-b]pyridin-3-ylmethyl)-pyridin-2-yl]-(6-methoxy-pyridin-3-ylmethyl)-amine (P-0378), and

[5-(5-Chloro-1H-pyrrolo[2,3-b]pyridin-3-ylmethyl)-6-fluoro-pyridin-2-yl]-(6-methoxy-pyridin-3-ylmethyl)-amine (P-0379),

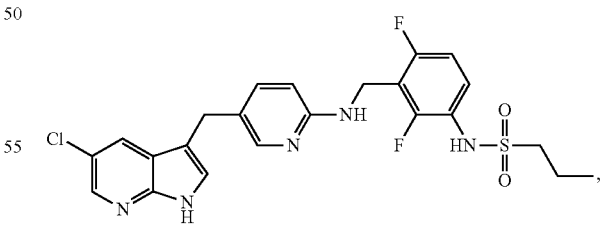

, and

331
-continued

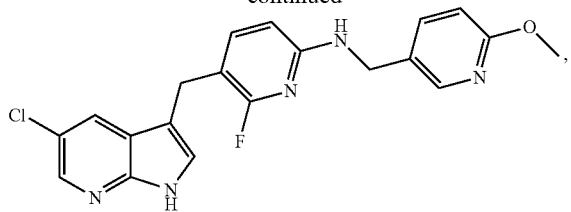

respectively,
were prepared following the protocol of Scheme 178. P-0259 was prepared by replacing 3-iodo-1-triisopropylsilanyl-1H-pyrrolo[2,3-b]pyridine 96 with 5-chloro-3-iodo-1-triisopropylsilanyl-1H-pyrrolo[2,3-b]pyridine in Step 1 (MS [M+H$^+$]$^+$=506.1). P-0378 was prepared by replacing [2,6-difluoro-3-(propane-1-sulfonylamino)-benzyl]-(5-formyl-pyridin-2-yl)-carbamic acid tert-butyl ester 560 with (6-Fluoro-5-formyl-pyridin-2-yl)-(6-methoxy-pyridin-3-yl-methyl)-carbamic acid tert-butyl ester 572 (prepared as described in Example 60, Scheme 177) in Step 1 (MS [M+H$^+$]$^+$=364.1). P-0379 was prepared by replacing both azaindole 96 with 5-chloro-3-iodo-1-triisopropylsilanyl-1H-pyrrolo[2,3-b]pyridine and aldehyde 560 with aldehyde 572 in Step 1 (MS [M+H$^+$]$^+$=400.0).

Example 62

Synthesis of [6-fluoro-5-(5-methoxy-1H-pyrrolo[2,3-b]pyridin-3-ylmethyl)-pyridin-2-yl]-(6-trifluoromethyl-pyridin-3-ylmethyl)-amine P-0187

[6-Fluoro-5-(5-methoxy-1H-pyrrolo[2,3-b]pyridin-3-yl-methyl)-pyridin-2-yl]-(6-trifluoromethyl-pyridin-3-ylmethyl)-amine P-0187 was synthesized in 3 steps from 1-benzenesulfonyl-3-iodo-5-methoxy-1H-pyrrolo[2,3-b]pyridine 575 as shown in Scheme 179.

Scheme 179

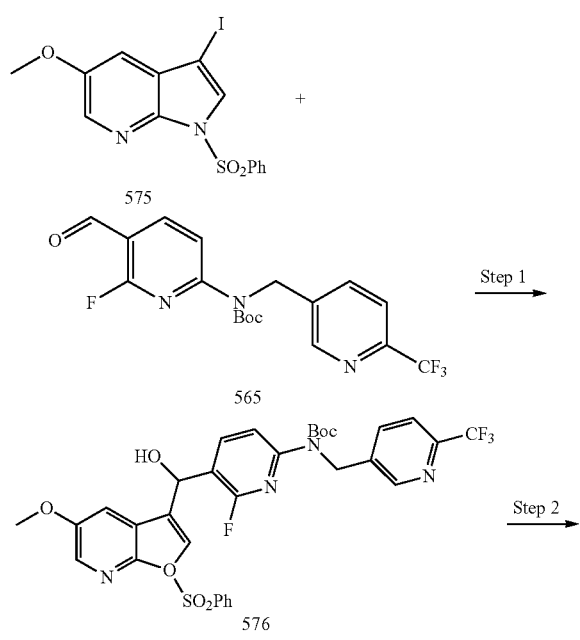

332
-continued

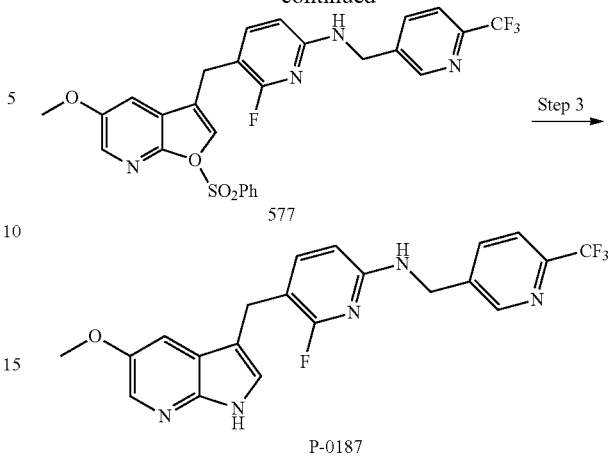

Step 1—Synthesis of 5-[(1-benzenesulfonyl-5-methoxy-1H-pyrrolo[2,3-b]pyridin-3-yl)-hydroxy-methyl]-6-fluoro-pyridin-2-yl-(6-trifluoromethyl-pyridin-3-ylmethyl)-carbamic acid tert-butyl ester (576)

To 1-benzenesulfonyl-3-iodo-5-methoxy-1H-pyrrolo[2,3-b]pyridine (575, 0.326 g, 0.000788 mol) in tetrahydrofuran (3.00 mL) at –45° C. under nitrogen, isopropylmagnesium chloride (2.0 M in tetrahydrofuran, 0.380 mL) was added slowly. The reaction was allowed to warm to –25° C. in 30 minutes, and then cooled to –45° C. followed by adding (6-fluoro-5-formyl-pyridin-2-yl)-(6-trifluoromethyl-pyridin-3-ylmethyl)-carbamic acid tert-butyl ester (565, 80.0 mg, 0.20 mmol, prepared as described in Example 60, Scheme 176) in tetrahydrofuran (1.0 mL). The reaction was allowed to warm to room temperature over 2 hours. The reaction was poured into aqueous ammonium chloride, and extracted with ethyl acetate. The organic layer was dried over anhydrous sodium sulfate and filtered. The filtrate was concentrated and purified by silica gel column chromatography eluting with 20% to 100% ethyl acetate in hexane to give the desired compound (576, 0.080 g, 60%). MS (ESI) [M+H$^+$]$^+$=688.1.

Step 2—Synthesis of [5-(1-Benzenesulfonyl-5-methoxy-1H-pyrrolo[2,3-b]pyridin-3-ylmethyl)-6-fluoro-pyridin-2-yl]-(6-trifluoromethyl-pyridin-3-ylmethyl)-amine (577)

To 5-[(1-benzenesulfonyl-5-methoxy-1H-pyrrolo[2, 3-1)]pyridin-3-yl)-hydroxy-methyl]-6-fluoro-pyridin-2-yl-(6-trifluoromethyl-pyridin-3-ylmethyl)-carbamic acid tert-butyl ester (576, 0.100 g, 0.15 mmol) in acetonitrile (12.6 mL) were added triethylsilane (0.34 mL, 2.10 mmol) and trifluoroacetic acid (0.17 mL, 2.20 mmol). The reaction was heated to 80° C. for 2 hours. The reaction was poured into aqueous potassium carbonate, and extracted with ethyl acetate. The organic layer was dried over anhydrous sodium sulfate, and filtered. The filtrate was concentrated to give the crude compound (577, 90 mg, 100%) that was used in the next step without further purification.

Step 3—Synthesis of [6-Fluoro-5-(5-methoxy-1H-pyrrolo[2,3-b]pyridin-3-ylmethyl)-pyridin-2-yl]-(6-trifluoromethyl-pyridin-3-ylmethyl)-amine (P-0187)

To [5-(1-benzenesulfonyl-5-methoxy-1H-pyrrolo[2,3-b]pyridin-3-ylmethyl)-6-fluoro-pyridin-2-yl]-(6-trifluoromethyl-pyridin-3-ylmethyl)-amine (577, 0.08 g, 0.13 mmol) in tetrahydrofuran (10.0 mL) was added tetrabutylammonium fluoride, trihydrate (0.110 g, 0.35 mmol). The reaction was stirred at room temperature overnight, then poured into water, and extracted with ethyl acetate. The organic layer was dried over anhydrous sodium sulfate and filtered. The filtrate was concentrated and purified by silica gel column chromatography eluting with 20% to 100% ethyl acetate in hexane to give an off-white solid (P-0187, 8.1 mg, 10%). MS (ESI) [M+H$^+$]$^+$=431.9.

[6-Fluoro-5-(5-chloro-1H-pyrrolo[2,3-b]pyridin-3-ylmethyl)-pyridin-2-yl]-(6-trifluoromethyl-pyridin-3-ylmethyl)-amine P-0186 and [6-Fluoro-5-(1H-pyrrolo[2,3-b]pyridin-3-ylmethyl)-pyridin-2-yl]-(6-trifluoromethyl-pyridin-3-ylmethyl)-amine P-0188, respectively, were prepared following the protocol of Scheme 179, substituting 1-benzenesulfonyl-3-iodo-5-methoxy-1H-pyrrolo[2,3-b]pyridine 575 with 1-benzenesulfonyl-3-iodo-5-chloro-1H-pyrrolo[2,3-b]pyridine or 1-Benzenesulfonyl-3-iodo-1H-pyrrolo[2,3-b]pyridine, respectively, in Step 1. MS (ESI) [M+H$^+$]$^+$=435.7 and 401.6, respectively.

Example 63

Synthesis of [6-(2-fluoro-benzylamino)-pyridin-3-yl]-(1H-pyrrolo[2,3-b]pyridin-3-yl)-methanone P-0403

[6-(2-fluoro-benzylamino)-pyridin-3-yl]-(1H-pyrrolo[2,3-b]pyridin-3-yl)-methanone P-0403 was synthesized in 2 steps from 3-Iodo-1-triisopropylsilanyl-1H-pyrrolo[2,3-b]pyridine 96 as shown in Scheme 180.

Scheme 180

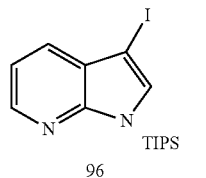

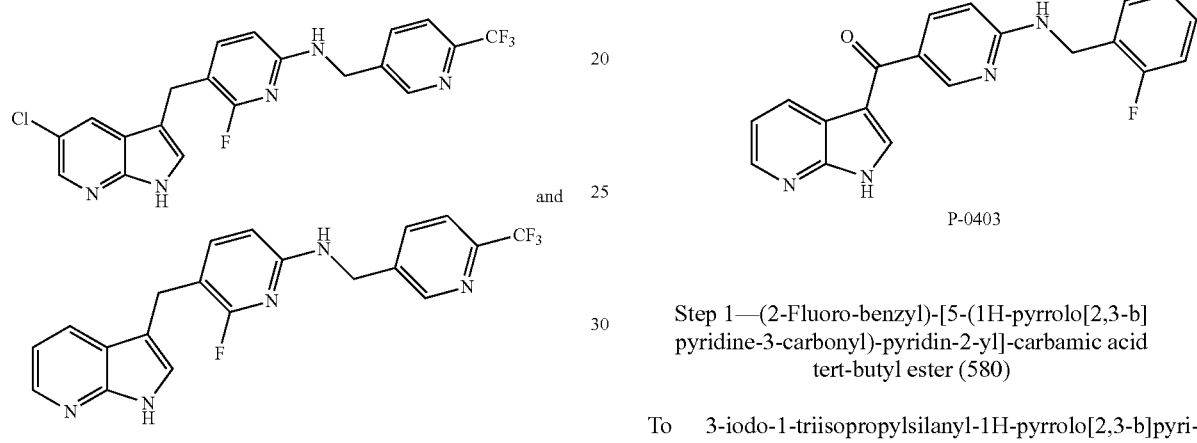

Step 1—(2-Fluoro-benzyl)-[5-(1H-pyrrolo[2,3-b]pyridine-3-carbonyl)-pyridin-2-yl]-carbamic acid tert-butyl ester (580)

To 3-iodo-1-triisopropylsilanyl-1H-pyrrolo[2,3-b]pyridine (96, 0.550 g, 1.37 mmol) in tetrahydrofuran (15.0 mL) at −40° C. under nitrogen, isopropylmagnesium chloride (2.0 M in tetrahydrofuran, 0.65 mL) was added slowly. The reaction was allowed to warm to 5° C. over 70 minutes, then cooled to −40° C., followed by adding (2-fluoro-benzyl)-(5-formyl-pyridin-2-yl)-carbamic acid tert-butyl ester (579, prepared according to the protocol of Example 17, Scheme 19, Steps 1-3, replacing 4-chlorobenzaldehyde 40 with 2-fluoro-benzaldehyde in Step 1) in tetrahydrofuran (4.0 mL). The reaction was allowed to warm to room temperature over 1 hour, then poured into aqueous ammonium chloride, and extracted with ethyl acetate. The organic layer was dried over anhydrous sodium sulfate and filtered. The filtrate was concentrated and purified by silica gel column chromatography eluting with 20% to 100% ethyl acetate in hexane to give the desired compound (580, 0.14 g, 26%). MS (ESI) [M+H$^+$]$^+$=447.0.

Step 2—Synthesis of [6-(2-Fluoro-benzylamino)-pyridin-3-yl]-(1H-pyrrolo[2,3-b]pyridin-3-yl)-methanone (P-0403)

To (2-fluoro-benzyl)-[5-(1H-pyrrolo[2,3-b]pyridine-3-carbonyl)-pyridin-2-yl]-carbamic acid tert-butyl ester (580, 0.080 g, 0.18 mmol) in dichloromethane (3.0 mL) was added trifluoroacetic acid (1.0 mL, 0.013 mol). The reaction was stirred at room temperature overnight, then concentrated, poured into water, and extracted with ethyl acetate. The organic layer was dried over anhydrous sodium sulfate and filtered. The filtrate was concentrated and purified by silica gel column chromatography eluting with 2% to 15% methanol in dichloromethane to give the desired compound (P-0403, 15.0 mg, 23.0%). MS (ESI) [M+H$^+$]$^+$=347.5.

Example 64

Synthesis of (5-chloro-1H-pyrrolo[2,3-b]pyridin-3-yl)-[6-(2-fluoro-benzylamino)-pyridin-3-yl]-methanone P-0404

(5-Chloro-1H-pyrrolo[2, 3-1)]pyridin-3-yl)-[6-(2-fluoro-benzylamino)-pyridin-3-yl]-methanone P-0404 was synthesized in 4 steps from 1-benzenesulfonyl-5-chloro-3-iodo-1H-pyrrolo[2,3-b]pyridine 581 as shown in Scheme 181.

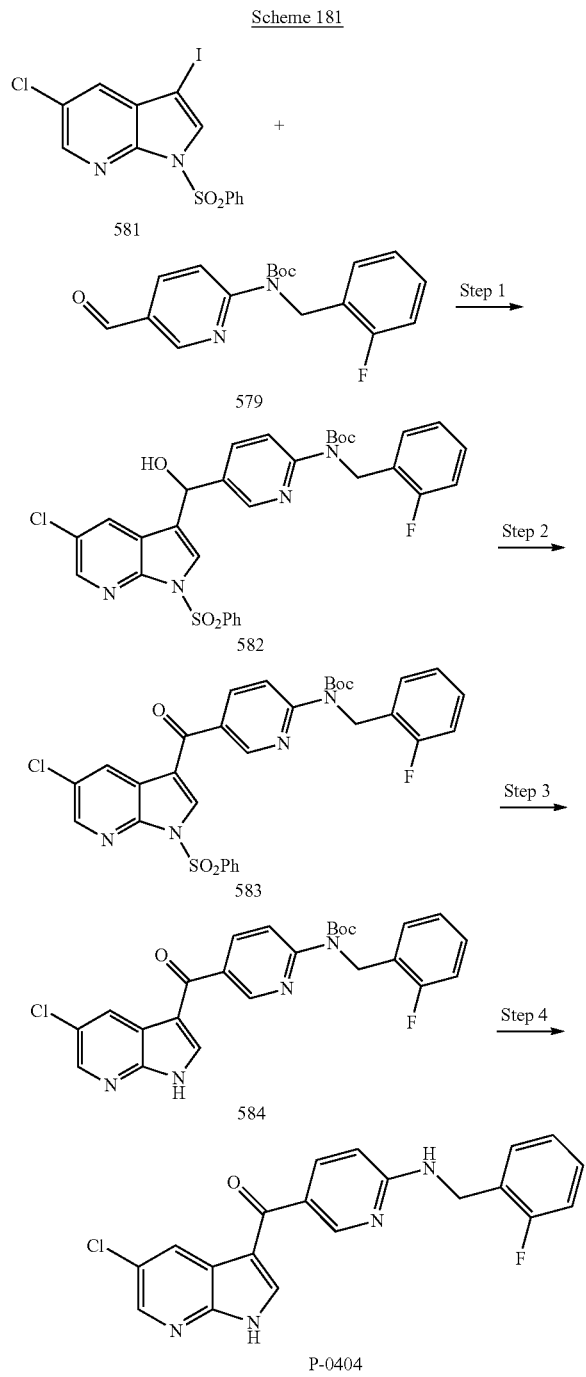

Scheme 181

Step 1—Synthesis of 5-[(1-benzenesulfonyl-5-chloro-1H-pyrrolo[2,3-b]pyridin-3-yl)-hydroxy-methyl]-pyridin-2-yl-(2-fluoro-benzyl)-carbamic acid tert-butyl ester (582)

To a solution of 1-benzenesulfonyl-5-chloro-3-iodo-1H-pyrrolo[2,3-b]pyridine (581, 0.420 g, 1.00 mmol) in tetrahydrofuran (15.0 mL) at −40° C. under nitrogen, isopropylmagnesium chloride (2.0 M in tetrahydrofuran, 0.49 mL) was added slowly. The reaction was allowed to warm to 5° C. over 70 minutes, then cooled to −40° C., followed by adding (2-fluoro-benzyl)-(5-formyl-pyridin-2-yl)-carbamic acid tert-butyl ester 579 in tetrahydrofuran (6.0 mL). The reaction was allowed to warm to room temperature over 1 hour, then poured into aqueous ammonium chloride, and extracted with ethyl acetate. The organic layer was dried over anhydrous sodium sulfate, and filtered. The filtrate was concentrated and purified by silica gel column chromatography eluting with 20% to 100% ethyl acetate in hexane to give the desired compound (582, 0.25 g, 41%). MS (ESI) [M+H$^+$]$^+$=623.1.

Step 2—Synthesis of [5-(1-Benzenesulfonyl-5-chloro-1H-pyrrolo[2,3-b]pyridine-3-carbonyl)-pyridin-2-yl]-(2-fluoro-benzyl)-carbamic acid tert-butyl ester (583)

To 5-[(1-benzenesulfonyl-5-chloro-1H-pyrrolo[2,3-b]pyridin-3-yl)-hydroxy-methyl]-pyridin-2-yl-(2-fluoro-benzyl)-carbamic acid tert-butyl ester (582, 0.25 g, 0.40 mmol) in dichloromethane (5.0 mL) was added Dess-Martin periodinane (0.20 g, 0.48 mmol). The reaction was stirred at room temperature for 10 minutes, then poured into aqueous potassium carbonate, and extracted with ethyl acetate. The organic layer was dried over anhydrous sodium sulfate and filtered. The filtrate was concentrated and purified by silica gel column chromatography eluting with 20% to 100% ethyl acetate in hexane to give the desired compound (583, 0.060 g., 24%).

Step 3—Synthesis of [5-(5-Chloro-1H-pyrrolo[2,3-b]pyridine-3-carbonyl)-pyridin-2-yl]-(2-fluoro-benzyl)-carbamic acid tert-butyl ester (584)

To [5-(1-benzenesulfonyl-5-chloro-1H-pyrrolo[2,3-b]pyridine-3-carbonyl)-pyridin-2-yl]-(2-fluoro-benzyl)-carbamic acid tert-butyl ester (583, 60.0 mg, 0.097 mmol) in tetrahydrofuran (1.0 mL) was added aqueous potassium carbonate (1.0 M, 1.0 mL). The reaction was irradiated with microwave on 300 watts, 100° C. for 10 minutes, then poured into water and extracted with ethyl acetate. The organic layer was dried over anhydrous sodium sulfate and filtered. The filtrate was concentrated to give crude compound (584, 0.040 g, 64%) that was used in the next step without further purification.

Step 4—Synthesis of (5-Chloro-1H-pyrrolo[2,3-b]pyridin-3-yl)-[6-(2-fluoro-benzylamino)-pyridin-3-yl]-methanone (P-0404)

To [5-(5-chloro-1H-pyrrolo[2,3-b]pyridine-3-carbonyl)-pyridin-2-yl]-(2-fluoro-benzyl)-carbamic acid tert-butyl ester (584, 0.030 g, 0.062 mmol) in dichloromethane (1.0 mL) was added trifluoroacetic acid (1.0 mL, 0.013 mol). The reaction was stirred at room temperature overnight, then poured into aqueous potassium carbonate, and extracted with ethyl acetate. The organic layer was dried over anhydrous sodium sulfate and filtered. The filtrate was concentrated and purified by silica gel column chromatography eluting with 2% to 15% methanol in dichloromethane to give the desired compound (P-0404, 2.8 mg, 12%). MS (ESI) [M+H⁺]⁺=381.0.

Example 65

Synthesis of (5-chloro-1H-pyrrolo[2,3-b]pyridin-3-yl)-6-[(6-methoxy-pyridin-3-ylmethyl)-amino]-pyridin-3-yl-methanone P-0405

(5-Chloro-1H-pyrrolo[2,3-b]pyridin-3-yl)-6-[(6-methoxy-pyridin-3-ylmethyl)-amino]-pyridin-3-yl-methanone P-0405 was synthesized in 3 steps from 5-Chloro-1H-pyrrolo[2,3-b]pyridine 532 as shown in Scheme 182.

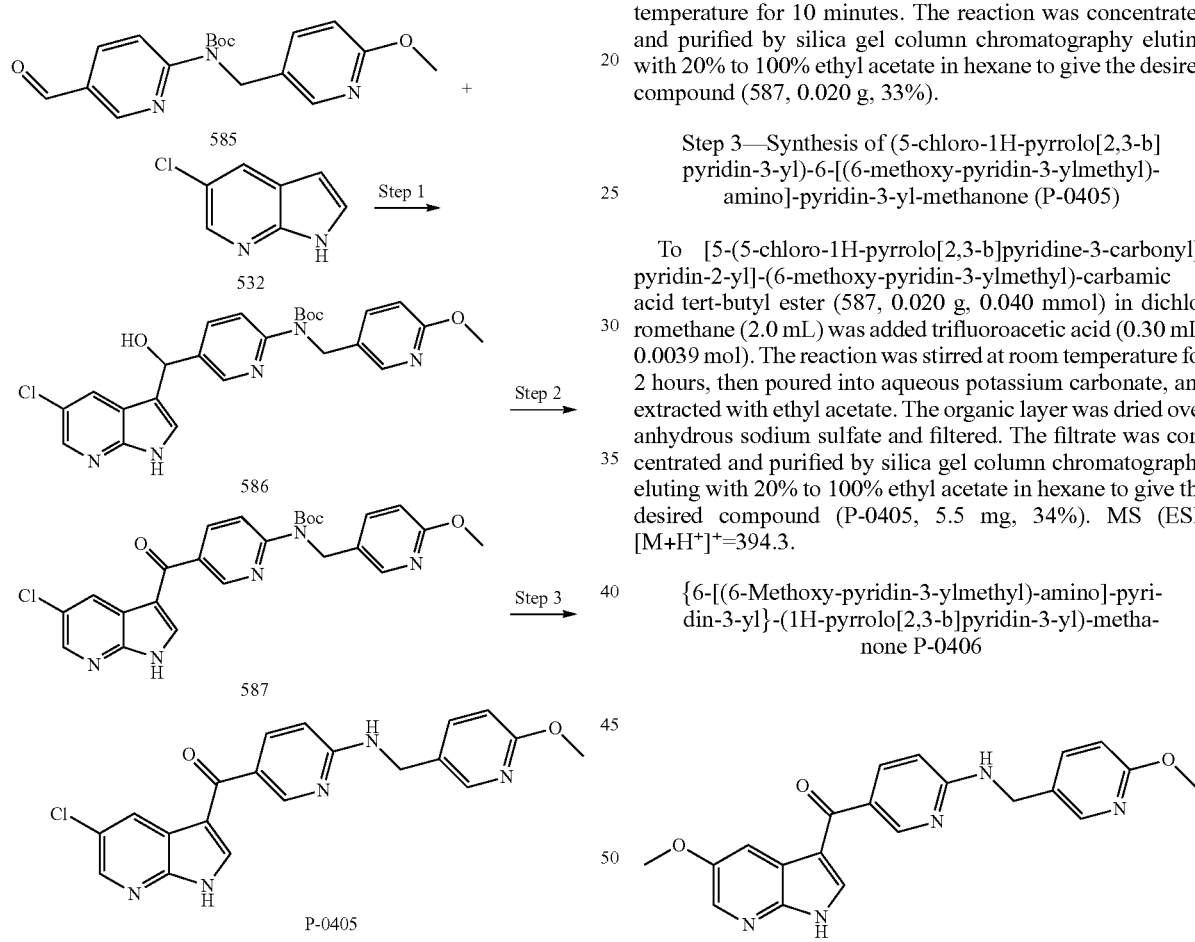

Step 1—Synthesis of 5-[(5-chloro-1H-pyrrolo[2,3-b]pyridin-3-yl)-hydroxy-methyl]-pyridin-2-yl-(6-methoxy-pyridin-3-ylmethyl)-carbamic acid tert-butyl ester (586)

To 5-chloro-1H-pyrrolo[2,3-b]pyridine (532, 0.092 g, 0.60 mmol) in methanol (15.0 mL) were added (5-formyl-pyridin-2-yl)-(6-methoxy-pyridin-3-ylmethyl)-carbamic acid tert-butyl ester (585, 0.240 g, 0.70 mmol, prepared according to the protocol of Example 17, Scheme 19, Steps 1-3, replacing 4-chlorobenzaldehyde 40 with 6-methoxy-pyridine-3-carbaldehyde in Step 1) and potassium hydroxide (1.2 g, 0.021 mol). The reaction was stirred at room temperature overnight, then poured into water, and extracted with ethyl acetate. The organic layer was dried over anhydrous sodium sulfate and filtered. The filtrate was concentrated and purified by silica gel column chromatography eluting with 20% to 100% ethyl acetate in hexane to give the desired compound (586, 0.110 g, 37%).

Step 2—Synthesis of [5-(5-chloro-1H-pyrrolo[2,3-b]pyridine-3-carbonyl)-pyridin-2-yl]-(6-methoxy-pyridin-3-ylmethyl)-carbamic acid tert-butyl ester (587)

To 5-[(5-chloro-1H-pyrrolo[2,3-b]pyridin-3-yl)-hydroxy-methyl]-pyridin-2-yl-(6-methoxy-pyridin-3-ylmethyl)-carbamic acid tert-butyl ester (586, 0.060 g, 0.12 mmol) in dichloromethane (10.0 mL) was added Dess-Martin periodinane (0.062 g, 0.15 mmol). The reaction was stirred at room temperature for 10 minutes. The reaction was concentrated and purified by silica gel column chromatography eluting with 20% to 100% ethyl acetate in hexane to give the desired compound (587, 0.020 g, 33%).

Step 3—Synthesis of (5-chloro-1H-pyrrolo[2,3-b]pyridin-3-yl)-6-[(6-methoxy-pyridin-3-ylmethyl)-amino]-pyridin-3-yl-methanone (P-0405)

To [5-(5-chloro-1H-pyrrolo[2,3-b]pyridine-3-carbonyl)-pyridin-2-yl]-(6-methoxy-pyridin-3-ylmethyl)-carbamic acid tert-butyl ester (587, 0.020 g, 0.040 mmol) in dichloromethane (2.0 mL) was added trifluoroacetic acid (0.30 mL, 0.0039 mol). The reaction was stirred at room temperature for 2 hours, then poured into aqueous potassium carbonate, and extracted with ethyl acetate. The organic layer was dried over anhydrous sodium sulfate and filtered. The filtrate was concentrated and purified by silica gel column chromatography eluting with 20% to 100% ethyl acetate in hexane to give the desired compound (P-0405, 5.5 mg, 34%). MS (ESI) [M+H⁺]⁺=394.3.

{6-[(6-Methoxy-pyridin-3-ylmethyl)-amino]-pyridin-3-yl}-(1H-pyrrolo[2,3-b]pyridin-3-yl)-methanone P-0406

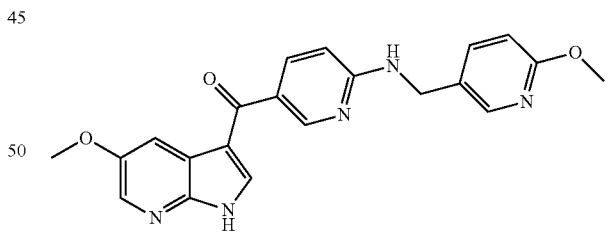

was prepared following the protocol of Scheme 182, substituting 5-chloro-1H-pyrrolo[2,3-b]pyridine 532 with 5-methoxy-1H-pyrrolo[2,3-b]pyridine in step 1. MS (ESI) [M+H⁺]⁺=390.1.

Example 66

Synthesis of intermediate 5-(1-benzenesulfonyl-5-chloro-1H-pyrrolo[2,3-b]pyridin-3-ylmethyl)-4-chloro-thiazol-2-ylamine 592

5-(1-Benzenesulfonyl-5-chloro-1H-pyrrolo[2,3-b]pyridin-3-ylmethyl)-4-chloro-thiazol-2-ylamine 592 was synthesized in 4 steps from 2-amino-4-chloro-thiazole-5-carbaldehyde 588 as shown in Scheme 183.

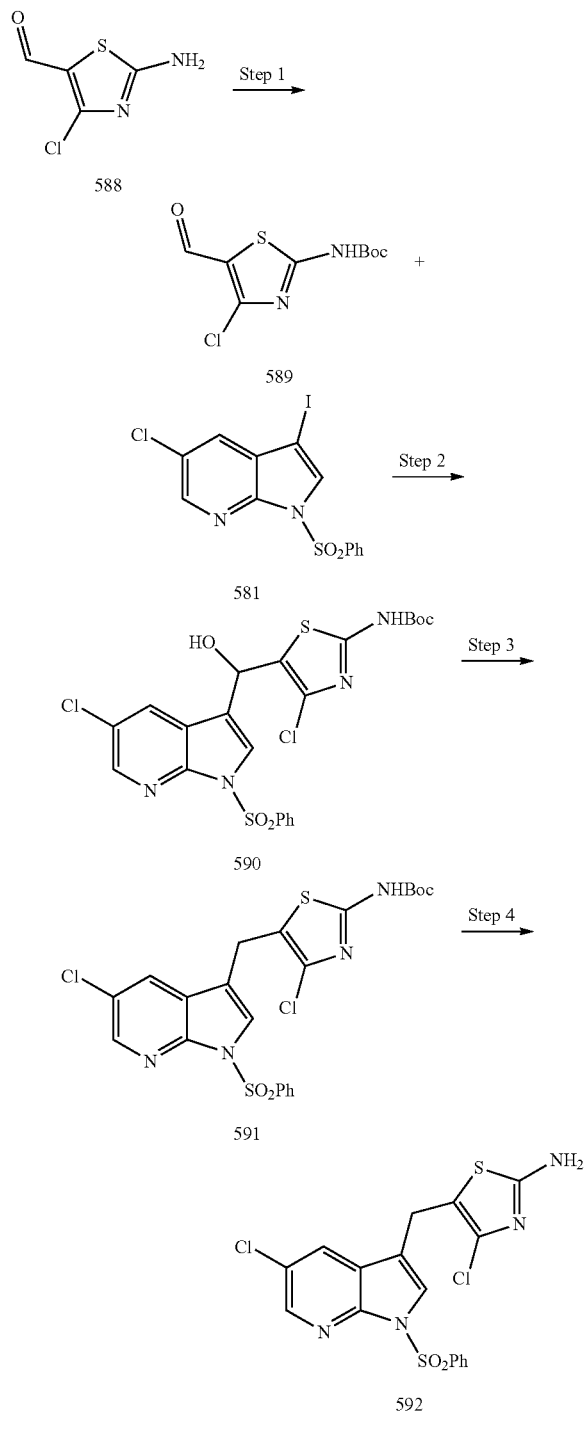

Step 1—Synthesis of (4-chloro-5-formyl-thiazol-2-yl)-carbamic acid tert-butyl ester (589)

To 2-amino-4-chloro-thiazole-5-carbaldehyde (588, 5.00 g, 0.0308 mol) in tetrahydrofuran (122 mL) were added di-tert-butyldicarbonate (7.38 g, 0.0338 mol) and 4-dimethylaminopyridine (0.35 g, 0.0029 mol). The reaction was stirred at 58° C. for 2 hours, then concentrated and purified with silica gel column chromatography eluting with 20% to 80% ethyl acetate in hexane to give a yellow solid (589, 7.0 g, 87%).

Step 2—Synthesis of 5-[(1-benzenesulfonyl-5-chloro-1H-pyrrolo[2,3-b]pyridin-3-yl)-hydroxy-methyl]-4-chloro-thiazol-2-yl-carbamic acid tert-butyl ester (590)

To a solution of 1-benzenesulfonyl-5-chloro-3-iodo-1H-pyrrolo[2,3-b]pyridine (581, 4.40 g, 10.5 mmol) in tetrahydrofuran (30.0 mL) at −45° C. under nitrogen, a solution of isopropylmagnesium chloride (2.0 M in tetrahydrofuran, 5.4 mL) was added slowly over 10 minutes. The reaction was allowed to warm to −25° C. over 30 minutes. The reaction was cooled to −65° C., followed by adding the cold deprotonated (4-chloro-5-formyl-thiazol-2-yl)-carbamic acid tert-butyl ester 589, which was prepared in situ by adding isopropylmagnesium chloride (2.0 M in tetrahydrofuran, 5.0 mL) to (4-chloro-5-formyl-thiazol-2-yl)-carbamic acid tert-butyl ester (589, 2.51 g, 9.55 mmol) in tetrahydrofuran (23.0 mL) at −78° C. under an atmosphere of nitrogen. The reaction was allowed to warm to room temperature in 2 hours, then poured into aqueous ammonium chloride, and extracted with ethyl acetate. The organic layer was dried over anhydrous sodium sulfate and filtered. The filtrate was concentrated and purified by silica gel column chromatography eluting with 25% to 100% ethyl acetate in hexane to give the desired compound (590, 3.70 g, 60.3%). MS (ESI) [M+H$^+$]$^+$=554.2.

Step 3—Synthesis of [5-(1-benzenesulfonyl-5-chloro-1H-pyrrolo[2,3-b]pyridin-3-ylmethyl)-4-chloro-thiazol-2-yl]-carbamic acid tert-butyl ester (591)

To 5-[(1-benzenesulfonyl-5-chloro-1H-pyrrolo[2,3-b]pyridin-3-yl)-hydroxy-methyl]-4-chloro-thiazol-2-yl-carbamic acid tert-butyl ester (590, 0.200 g, 0.32 mmol) in dichloromethane (15.0 mL) were added triethylsilane (0.600 mL, 376 mmol) and trifluoroacetic acid (0.300 mL, 3.89 mmol). The reaction was stirred at room temperature for 3 hours, then concentrated, poured into aqueous potassium carbonate, and extracted with ethyl acetate. The organic layer was dried over anhydrous sodium sulfate and filtered. The filtrate was concentrated and purified by silica gel column chromatography eluting with 25% to 100% ethyl acetate in hexane to give the desired compound (591, 0.155 g, 88.7%). MS (ESI) [M+H$^+$]$^+$=538.9.

Step 4—Synthesis of 5-(1-Benzenesulfonyl-5-chloro-1H-pyrrolo[2,3-b]pyridin-3-ylmethyl)-4-chloro-thiazol-2-ylamine (592)

To [5-(1-benzenesulfonyl-5-chloro-1H-pyrrolo[2,3-b]pyridin-3-ylmethyl)-4-chloro-thiazol-2-yl]-carbamic acid tert-butyl ester (591, 4.30 g, 7.97 mmol) in dichloromethane (70.0 mL) was added a solution of hydrogen chloride (4.00 M in 1,4-dioxane, 42.0 mL). The reaction was stirred at room temperature for 2 days, then concentrated, and triturated with

5-(1-Benzenesulfonyl-1H-pyrrolo[2,3-b]pyridin-3-ylmethyl)-4-chloro-thiazol-2-ylamine 593

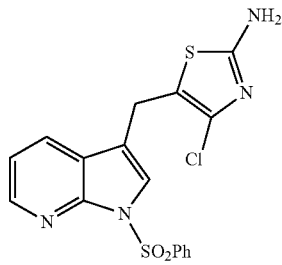

was prepared following the protocol of Scheme 183, substituting 1-benzenesulfonyl-5-chloro-3-iodo-1H-pyrrolo[2,3-b]pyridine 581 with 1-benzenesulfonyl-3-iodo-1H-pyrrolo[2,3-b]pyridine in Step 2. MS (ESI) [M+H$^+$]$^+$=404.4.

Example 67

Synthesis of [4-Chloro-5-(5-chloro-1H-pyrrolo[2,3-b]pyridin-3-ylmethyl)-thiazol-2-yl]-(5-fluoro-pyridin-3-ylmethyl)-amine P-0231

[4-Chloro-5-(5-chloro-1H-pyrrolo[2,3-b]pyridin-3-ylmethyl)-thiazol-2-yl]-(5-fluoro-pyridin-3-ylmethyl)-amine P-0231 was synthesized in 2 steps from 5-(1-benzenesulfonyl-5-chloro-1H-pyrrolo[2,3-b]pyridin-3-ylmethyl)-4-chloro-thiazol-2-ylamine 592 as shown in Scheme 184.

Scheme 184

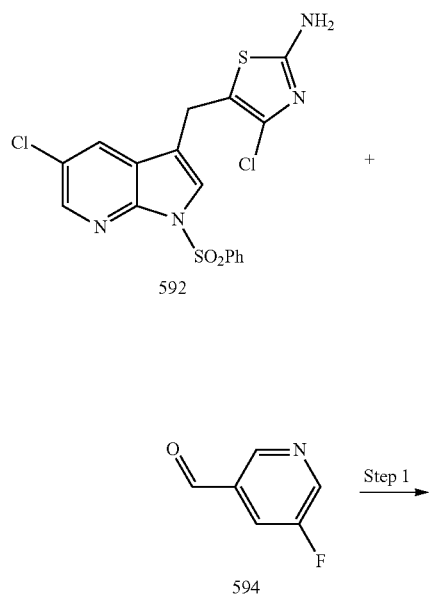

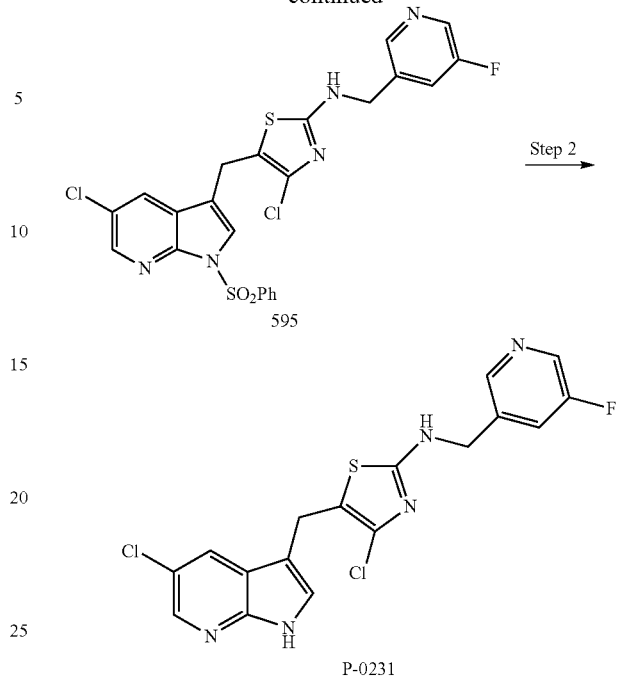

Step 1—Synthesis of [5-(1-benzenesulfonyl-5-chloro-1H-pyrrolo[2,3-b]pyridin-3-ylmethyl)-4-chloro-thiazol-2-yl]-(5-fluoro-pyridin-3-ylmethyl)-amine (595)

To 5-(1-benzenesulfonyl-5-chloro-1H-pyrrolo[2,3-b]pyridin-3-ylmethyl)-4-chloro-thiazol-2-ylamine (592, 50.0 mg, 0.11 mmol, prepared as described in Example 66, Scheme 183) in ethanol (1.60 mL) and acetic acid (0.08 mL) were added 5-fluoro-pyridine-3-carbaldehyde (594, 43 mg, 0.34 mmol) and silica supported cyanoborohydride (1.21 mmol/g, 0.180 g). The reaction was irradiated with microwave on 300 watts, 100° C. for 7 minutes. The reaction was poured into aqueous potassium carbonate, and extracted with ethyl acetate. The organic layer was dried over anhydrous sodium sulfate and filtered. The filtrate was concentrated and purified by silica gel column chromatography eluting with 20% ethyl acetate in hexane to give the desired compound (595, 0.030 g, 48%).

Step 2—Synthesis of [4-chloro-5-(5-chloro-1H-pyrrolo[2,3-b]pyridin-3-ylmethyl)-thiazol-2-yl]-(5-fluoro-pyridin-3-ylmethyl)-amine (P-0231)

To [5-(1-benzenesulfonyl-5-chloro-1H-pyrrolo[2,3-b]pyridin-3-ylmethyl)-4-chloro-thiazol-2-yl]-(5-fluoro-pyridin-3-ylmethyl)-amine (595, 0.030 g, 0.055 mmol) in tetrahydrofuran (6.0 mL) was added tetrabutylammonium fluoride, trihydrate (0.034 g, 0.11 mmol) under an atmosphere of nitrogen. The reaction was stirred at room temperature for 3 hours, then poured into water and extracted with ethyl acetate. The organic layer was dried over anhydrous sodium sulfate and filtered. The filtrate was concentrated and purified by silica gel column chromatography eluting with 20% to 100% ethyl acetate in hexane to give the desired compound (P-0231, 1.5 mg, 6.7%). MS (ESI) [M+H$^+$]$^+$=408.1.

Example 68

Synthesis of 5-(1-benzenesulfonyl-5-chloro-1H-pyrrolo[2,3-b]pyridin-3-ylmethyl)-pyridin-2-ylamine 599

5-(1-Benzenesulfonyl-5-chloro-1H-pyrrolo[2,3-b]pyridin-3-ylmethyl)-pyridin-2-ylamine 599 was synthesized in 4 steps from 5-chloro-1H-pyrrolo[2,3-b]pyridine 532 as shown in Scheme 185.

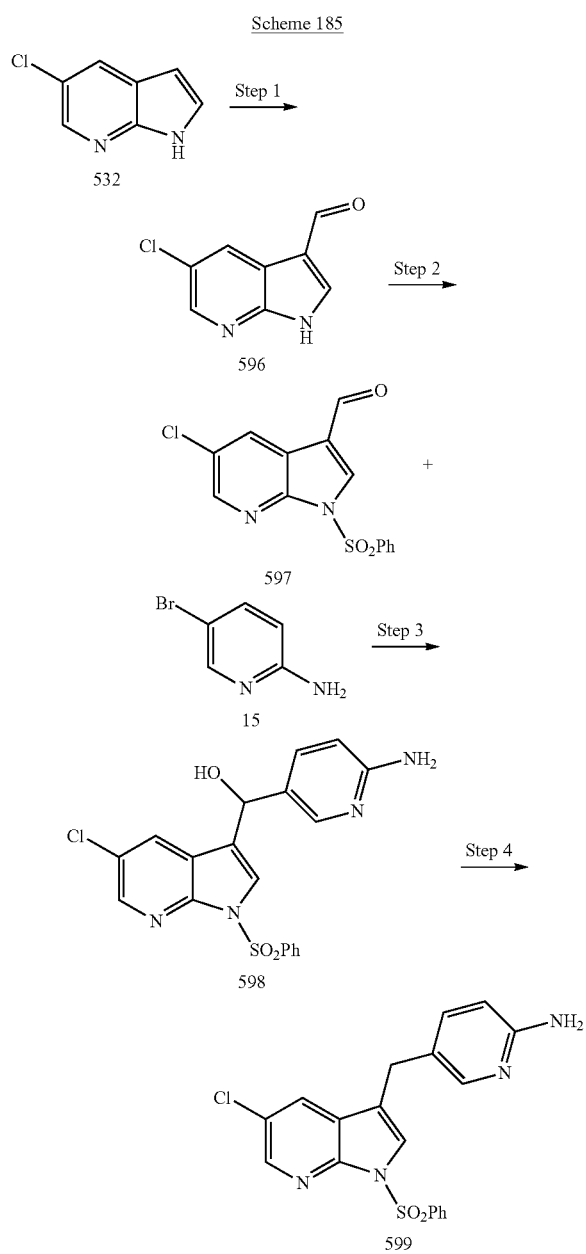

Step 1—Synthesis of 5-chloro-1H-pyrrolo[2,3-b]pyridine-3-carbaldehyde (596)

To 5-chloro-1H-pyrrolo[2,3-b]pyridine (532, 10.0 g, 65.5 mmol) in acetic acid (28.3 mL) were added hexamethylenetetramine (11.9 g, 85.2 mmol) and water (56.7 mL). The reaction was refluxed overnight, followed by addition of 200 mL of water. After 30 minutes, the reaction was filtered to recover the solid, then dried under air to give the desired compound (596, 7.0 g, 59%).

Step 2—Synthesis of 1-benzenesulfonyl-5-chloro-1H-pyrrolo[2,3-b]pyridine-3-carbaldehyde (597)

To 5-chloro-1H-pyrrolo[2,3-b]pyridine-3-carbaldehyde (596, 3.60 g, 0.0199 mol) in dichloromethane (100 mL) were added a solution of potassium hydroxide (9 M in water, 50 mL), tetrabutylammonium hydrogen sulfate (400 mg, 0.001 mol) and benzenesulfonyl chloride (2.9 mL, 0.023 mol). The reaction was stirred at room temperature for 3 hours, then poured into water and extracted with ethyl acetate. The organic layer was dried over anhydrous sodium sulfate and filtered. The filtrate was concentrated and washed with ethyl acetate to give a white solid (597, 2.3 g, 36.0%).

Step 3—Synthesis of (6-amino-pyridin-3-yl)-(1-benzenesulfonyl-5-chloro-1H-pyrrolo[2,3-b]pyridin-3-yl)-methanol (598)

To 2-amino-5-bromopyridine (15, 3.10 g, 17.9 mmol) in tetrahydrofuran (80.0 mL) under an atmosphere of nitrogen at −78° C., a solution n-butyllithium (2.50 M in hexane, 7.10 mL) was added slowly. After 30 minutes, 1,2-bis-(chlorodimethyl-silanyl)-ethane (3.90 g dissolved in tetrahydrofuran 20.0 mL, 18.1 mmol) was added to the reaction mixture slowly, and then allowed to warm to room temperature for 1 hour. The reaction was cooled to −78° C. followed by adding a solution of n-butyllithium (2.50 M in Hexane, 7.10 mL). The reaction mixture was stirred at −78° C. for 30 minutes, then allowed to warm to room temperature for 60 minutes. The reaction mixture was cooled to −78° C., followed by adding a solution of n-butyllithium (2.50 M in Hexane, 7.50 mL) slowly. After 60 minutes, 1-benzenesulfonyl-5-chloro-1H-pyrrolo[2,3-b]pyridine-3-carbaldehyde (597, 1.90 g in 30 mL tetrahydrofuran, 5.92 mmol) was added to the reaction mixture. The reaction mixture was stirred at −78° C. for 2 hours, then allowed to warm to room temperature for 1 hour. The reaction was poured into water and extracted with ethyl acetate. The organic layer was dried over anhydrous sodium sulfate and filtered. The filtrate was concentrated and purified by silica gel column chromatography eluting with 2% to 20% methanol in dichloromethane to give the desired compound (598, 1.25 g, 50.9%). MS (ESI) [M+H$^+$]$^+$=415.2.

Step 4—Synthesis of 5-(1-benzenesulfonyl-5-chloro-1H-pyrrolo[2,3-b]pyridin-3-ylmethyl)-pyridin-2-ylamine (599)

To (6-amino-pyridin-3-yl)-(1-benzenesulfonyl-5-chloro-1H-pyrrolo[2,3-b]pyridin-3-yl)-methanol (598, 1.00 g, 0.00241 mol) in dichloromethane (25.0 mL) were added triethylsilane (3.00 mL, 0.0188 mol) and trifluoroacetic acid (1.50 mL, 0.0195 mol). The reaction was stirred at room temperature overnight, then concentrated, poured into aqueous potassium carbonate, and extracted with ethyl acetate. The organic layer was dried over anhydrous sodium sulfate, and filtered. The filtrate was concentrated and purified by silica gel column chromatography eluting with 20% to 100% ethyl acetate in hexane to give the desired compound (599, 0.70 g, 73%).

5-(1-Benzenesulfonyl-1H-pyrrolo[2,3-b]pyridin-3-ylmethyl)-pyridin-2-ylamine 600

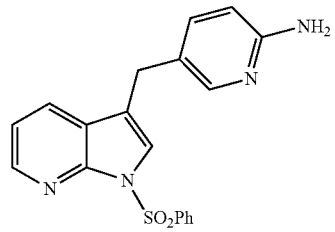

was prepared following the protocol of Scheme 185, substituting 5-chloro-1H-pyrrolo[2,3-b]pyridine 532 with 1H-pyrrolo[2,3-b]pyridine in Step 1. MS (ESI) [M+H$^+$]$^+$=365.2.

Example 69

Synthesis of [5-(5-chloro-1H-pyrrolo[2,3-b]pyridin-3-ylmethyl)-pyridin-2-yl]-(5-fluoro-pyridin-3-ylmethyl)-amine P-0324

[5-(5-Chloro-1H-pyrrolo[2,3-b]pyridin-3-ylmethyl)-pyridin-2-yl]-(5-fluoro-pyridin-3-ylmethyl)-amine P-0324 was synthesized in 2 steps from 5-(1-benzenesulfonyl-5-chloro-1H-pyrrolo[2,3-b]pyridin-3-ylmethyl)-pyridin-2-ylamine 599 as shown in Scheme 186.

Scheme 186

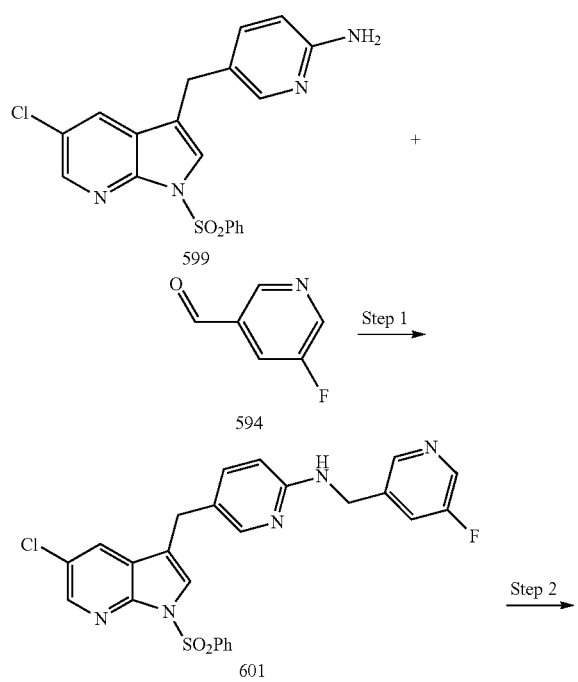

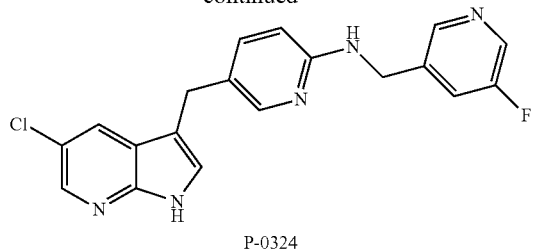

P-0324

Step 1—Synthesis of [5-(1-benzenesulfonyl-5-chloro-1H-pyrrolo[2,3-b]pyridin-3-ylmethyl)-pyridin-2-yl]-(5-fluoro-pyridin-3-ylmethyl)-amine (601)

To 5-(1-benzenesulfonyl-5-chloro-1H-pyrrolo[2,3-b]pyridin-3-ylmethyl)-pyridin-2-ylamine (599, 80.0 mg, 0.20 mmol, prepared as described in Example 68, Scheme 185) in ethanol (2.0 mL) and acetic acid (0.10 mL, 0.0018 mol) were added 5-fluoro-pyridine-3-carbaldehyde (594, 62.7 mg, 0.50 mmol) and sodium cyanoborohydride on silica gel (1.200 mmol/g loading; 0.251 g, 0.30 mmol). The reaction was irradiated with microwave on 300 watts, 100° C. for 10 minutes. The reaction was poured into aqueous potassium carbonate and extracted with ethyl acetate. The organic layer was dried over anhydrous sodium sulfate and filtered. The filtrate was concentrated and purified by silica gel column chromatography eluting with 20% to 100% ethyl acetate in hexane to give the desired compound (601, 0.060 g, 59%).

Step 2—Synthesis of [5-(5-chloro-1H-pyrrolo[2,3-b]pyridin-3-ylmethyl)-pyridin-2-yl]-(5-fluoro-pyridin-3-ylmethyl)-amine (P-0324)

To [5-(1-benzenesulfonyl-5-chloro-1H-pyrrolo[2,3-b]pyridin-3-ylmethyl)-pyridin-2-yl]-(5-fluoro-pyridin-3-ylmethyl)-amine (601, 0.060 g, 0.12 mmol) in tetrahydrofuran (10.0 mL) was added tetrabutylammonium fluoride, trihydrate (0.11 g, 0.35 mmol). The reaction was stirred at room temperature overnight, then poured into water and extracted with ethyl acetate. The organic layer was dried over anhydrous sodium sulfate and filtered. The filtrate was concentrated and purified by silica gel column chromatography eluting with 20% to 100% ethyl acetate in hexane to give the desired compound (P-0324, 13.5 mg, 31%). MS (ESI) [M+H$^+$]$^+$=368.0.

Example 70

Synthesis of (3-Chloro-pyridin-4-ylmethyl)-[5-(1H-pyrrolo[2,3-b]pyridin-3-ylmethyl)-pyridin-2-yl]-amine P-0183

(3-Chloro-pyridin-4-ylmethyl)-[5-(1H-pyrrolo[2,3-b]pyridin-3-ylmethyl)-pyridin-2-yl]-amine P-0183 was synthesized in 2 steps from 5-(1-benzenesulfonyl-1H-pyrrolo[2,3-b]pyridin-3-ylmethyl)-pyridin-2-ylamine 600 as shown in Scheme 187.

Scheme 187

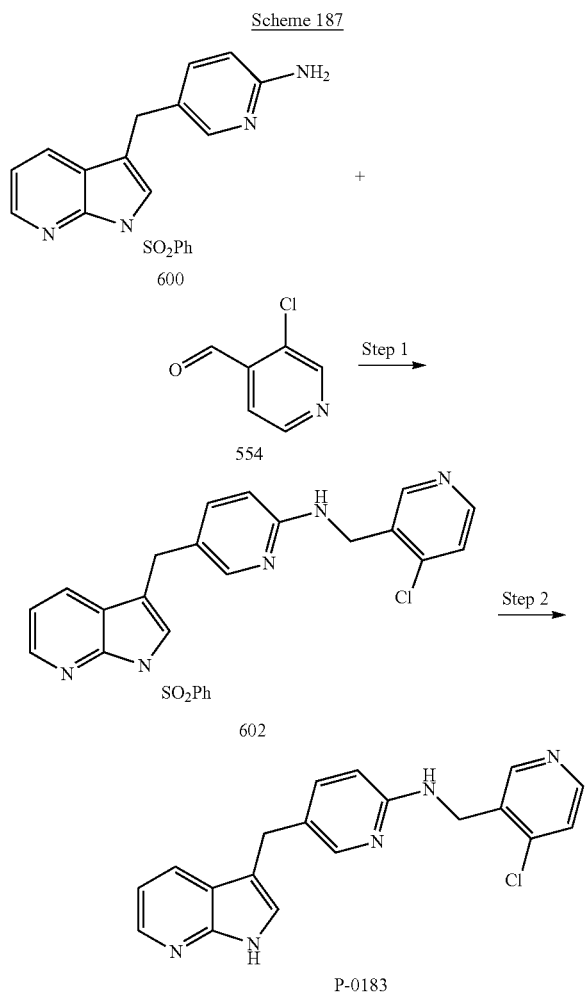

Step 1—Synthesis of [5-(1-benzenesulfonyl-1H-pyrrolo[2,3-b]pyridin-3-ylmethyl)-pyridin-2-yl]-(4-chloro-pyridin-3-ylmethyl)-amine (602)

To 5-(1-benzenesulfonyl-1H-pyrrolo[2,3-b]pyridin-3-ylmethyl)-pyridin-2-ylamine (600, 120.0 mg, 0.33 mmol, prepared as described in Example 68, Scheme 185) in acetonitrile (10.0 mL) were added 3-chloro-pyridine-4-carbaldehyde (554, 51.3 mg, 0.36 mmol), trifluoroacetic acid (0.30 mL, 0.0039 mol) and triethylsilane (0.60 mL, 0.0038 mol). The reaction was heated to reflux overnight, then poured into aqueous potassium carbonate and extracted with ethyl acetate. The organic layer was dried over anhydrous sodium sulfate and filtered. The filtrate was concentrated and purified by silica gel column chromatography eluting with 30% to 100% ethyl acetate in hexane to give the desired compound (602, 80 mg, 49.6%). MS [M+H$^+$]$^+$=490.2.

Step 2—Synthesis of (3-chloro-pyridin-4-ylmethyl)-[5-(1H-pyrrolo[2,3-b]pyridin-3-ylmethyl)-pyridin-2-yl]-amine (P-0183)

To [5-(1-benzenesulfonyl-1H-pyrrolo[2,3-b]pyridin-3-ylmethyl)-pyridin-2-yl]-(4-chloro-pyridin-3-ylmethyl)-amine (602, 0.08 g, 0.16 mmol) in tetrahydrofuran (10.0 mL) was added tetrabutylammonium fluoride, trihydrate (0.240 g, 0.76 mmol). The reaction was stirred at room temperature overnight. The reaction was concentrated and purified by silica gel column chromatography eluting with 20% to 100% ethyl acetate in hexane to give a yellow solid (P-0183, 4.0 mg, 7%). MS (ESI) [M+H$^+$]$^+$=350.2.

Example 71

Synthesis of [5-(5-Chloro-1H-pyrrolo[2,3-b]pyridin-3-ylmethyl)-pyridin-2-yl]-[6-(2,2,2-trifluoro-ethoxy)-pyridin-3-ylmethyl]-amine P-0409

[5-(5-Chloro-1H-pyrrolo[2,3-b]pyridin-3-ylmethyl)-pyridin-2-yl]-(5-fluoro-pyridin-3-ylmethyl)-amine P-0409 was synthesized in 1 step from 5-(1-benzenesulfonyl-5-chloro-1H-pyrrolo[2,3-b]pyridin-3-ylmethyl)-pyridin-2-ylamine 599 as shown in Scheme 188.

Scheme 188

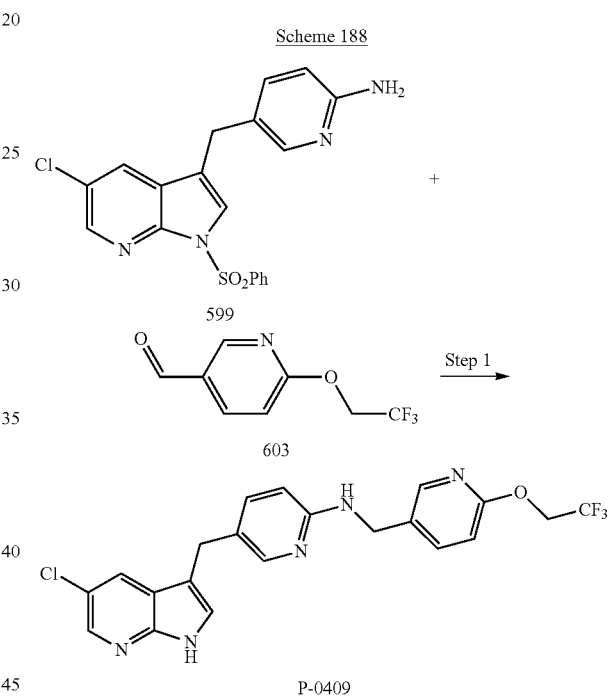

Step 1—Synthesis of [5-(5-chloro-1H-pyrrolo[2,3-b]pyridin-3-ylmethyl)-pyridin-2-yl]-[6-(2,2,2-trifluoro-ethoxy)-pyridin-3-ylmethyl]-amine (P-0409)

To 5-(1-benzenesulfonyl-5-chloro-1H-pyrrolo[2,3-b]pyridin-3-ylmethyl)-pyridin-2-ylamine (599, 124.1 mg, 0.31 mmol, prepared as described in Example 68, Scheme 185) in ethanol (3.00 mL) and acetic acid (0.2 mL) were added 6-(2,2,2-trifluoro-ethoxy)-pyridine-3-carbaldehyde (603, 164.0 mg, 0.80 mmol) and silica supported cyanoborohydride (1.21 mmol/g, 0.700 g). The reaction was irradiated with microwave on 300 watts, 100° C. for 150 minutes. To the reaction was added a solution of potassium hydroxide (9.0 M in water, 1.0 mL). The reaction was irradiated with microwave on 300 watts, 100° C. for 10 minutes. The reaction was poured into aqueous potassium carbonate and extracted with ethyl acetate. The organic layer was dried over anhydrous sodium sulfate and filtered. The filtrate was concentrated and purified by silica gel column chromatography eluting with 20% to

Example 72

Synthesis of 1-(3-fluoro-phenyl)-3-[5-(1H-pyrrolo[2,3-b]pyridin-3-ylmethyl)-pyridin-2-yl]-urea P-0412

1-(3-Fluoro-phenyl)-3-[5-(1H-pyrrolo[2,3-b]pyridin-3-ylmethyl)-pyridin-2-yl]-urea P-0412 was synthesized in 2 steps from 5-(1-benzenesulfonyl-1H-pyrrolo[2,3-b]pyridin-3-ylmethyl)-pyridin-2-ylamine 600 as shown in Scheme 189.

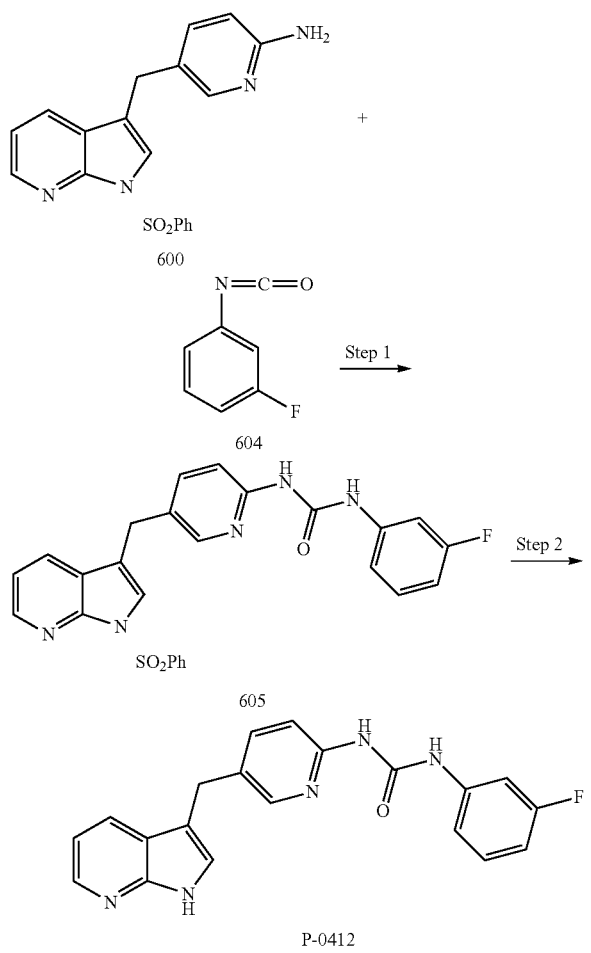

Step 1—Synthesis of 1-[5-(1-benzenesulfonyl-1H-pyrrolo[2,3-b]pyridin-3-ylmethyl)-pyridin-2-yl]-3-(3-fluoro-phenyl)-urea (605)

To 5-(1-benzenesulfonyl-1H-pyrrolo[2,3-b]pyridin-3-ylmethyl)-pyridin-2-ylamine (600, 150.0 mg, 0.41 mmol, prepared as described in Example 68, Scheme 185) in acetonitrile (12.5 mL) were added 3-fluoro-isocyanato-benzene (604, 61.6 mg, 0.45 mmol), 4-dimethylaminopyridine (10.0 mg, 0.082 mmol) and triethylamine (0.25 mL, 0.0018 mol). The reaction mixture was heated at 70° C. overnight, then poured into water, and extracted with ethyl acetate. The organic layer was dried over anhydrous sodium sulfate, and filtered. The filtrate was concentrated and purified by silica gel column chromatography eluting with 20% to 100% ethyl acetate in hexane to give a white solid (605, 0.100 g, 48.4%).

Step 2—Synthesis of 1-(3-Fluoro-phenyl)-3-[5-(1H-pyrrolo[2,3-b]pyridin-3-ylmethyl)-pyridin-2-yl]-urea (P-0412)

To 1-[5-(1-benzenesulfonyl-1H-pyrrolo[2,3-b]pyridin-3-ylmethyl)-pyridin-2-yl]-3-(3-fluoro-phenyl)-urea (605, 0.100 g, 0.20 mmol) in tetrahydrofuran (10.0 mL) was added tetrabutylammonium fluoride, trihydrate (0.240 g, 0.76 mmol). The reaction was stirred at room temperature for 5 hours, then poured into water, and extracted with ethyl acetate. The organic layer was dried over anhydrous sodium sulfate, and filtered. The filtrate was concentrated and purified by silica gel column chromatography eluting with 20% to 100% ethyl acetate in hexane to give a white solid (P-0412, 17.9 mg, 24.8%). MS (ESI) [M+H$^+$]$^+$=362.2.

Example 73

Synthesis of (2-chloro-benzyl)-[6-fluoro-5-(1H-pyrrolo[2,3-b]pyridin-3-ylmethyl)-pyridin-2-yl]-amine P-0335

(2-Chloro-benzyl)-[6-fluoro-5-(1H-pyrrolo[2,3-b]pyridin-3-ylmethyl)-pyridin-2-yl]-amine P-0335 was synthesized in 2 steps from (5-bromo-6-fluoro-pyridin-2-yl)-(2-chloro-benzyl)-amine 571 as shown in Scheme 190.

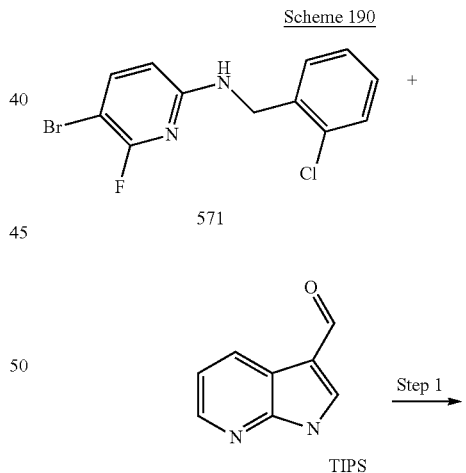

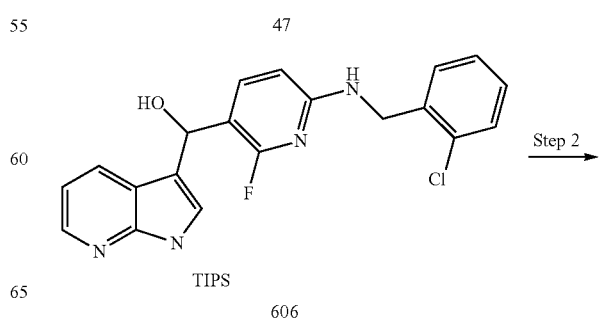

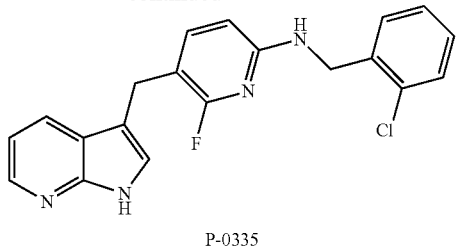

P-0335

Step 1—Synthesis of [6-(2-chloro-benzylamino)-2-fluoro-pyridin-3-yl]-(1-triisopropylsilanyl-1H-pyrrolo[2,3-b]pyridin-3-yl)-methanol (606)

To (5-bromo-6-fluoro-pyridin-2-yl)-(2-chloro-benzyl)-amine (571, 0.635 g, 2.01 mmol, prepared as described in Example 60, Scheme 177) in tetrahydrofuran (25.0 mL) under an atmosphere of nitrogen at −78° C., a solution of n-butyllithium (2.50 M in hexane, 0.80 mL) was added slowly. After 20 minutes, tert-butyllithium (1.7 M in hexane, 2.40 mL) was added to the reaction and after 30 minutes, 1-triisopropylsilanyl-1H-pyrrolo[2,3-b]pyridine-3-carbaldehyde (47, 0.575 g, 1.90 mmol, prepared as described in Example 18) in tetrahydrofuran (8.0 mL) was added to the reaction. The reaction mixture was stirred at −78° C. for 60 minutes, then allowed to warm to room temperature for another 10 minutes. The reaction mixture was poured into aqueous ammonium chloride and extracted with ethyl acetate. The organic layer was washed with brine, dried over sodium sulfate, concentrated and purified by silica gel column chromatography eluting with 20% to 100% ethyl acetate in hexane to give the desired compound (606, 0.180 g, 17.6%). MS (ESI) [M+H$^+$]$^+$=539.2.

Step 2—Synthesis of (2-chloro-benzyl)-[6-fluoro-5-(1H-pyrrolo[2,3-b]pyridin-3-ylmethyl)-pyridin-2-yl]-amine (P-0335)

To [6-(2-chloro-benzylamino)-2-fluoro-pyridin-3-yl]-(1-triisopropylsilanyl-1H-pyrrolo[2,3-b]pyridin-3-yl)-methanol (606, 180.0 mg, 0.33 mmol) in acetonitrile (15.0 mL) were added triethylsilane (1.00 mL, 6.26 mmol) and trifluoroacetic acid (0.50 mL, 6.50 mmol). The reaction was heated to reflux for 2 hours, then poured into aqueous potassium carbonate and extracted with ethyl acetate. The organic layer was dried over anhydrous sodium sulfate and filtered. The filtrate was concentrated and purified by silica gel column chromatography eluting with 20% to 100% ethyl acetate in hexane to give a white solid (P-0335, 24.9 mg, 19.4%). MS (ESI) [M+H$^+$]$^+$=367.0.

Example 74

Synthesis of 1-benzenesulfonyl-5-chloro-3-(2-methanesulfonyl-pyrimidin-5-ylmethyl)-1H-pyrrolo[2,3-b]pyridine 610

1-Benzenesulfonyl-5-chloro-3-(2-methanesulfonyl-pyrimidin-5-ylmethyl)-1H-pyrrolo[2,3-b]pyridine 610 was synthesized in 3 steps from 1-benzenesulfonyl-5-chloro-3-iodo-1H-pyrrolo[2,3-b]pyridine 581 as shown in Scheme 191.

Scheme 191

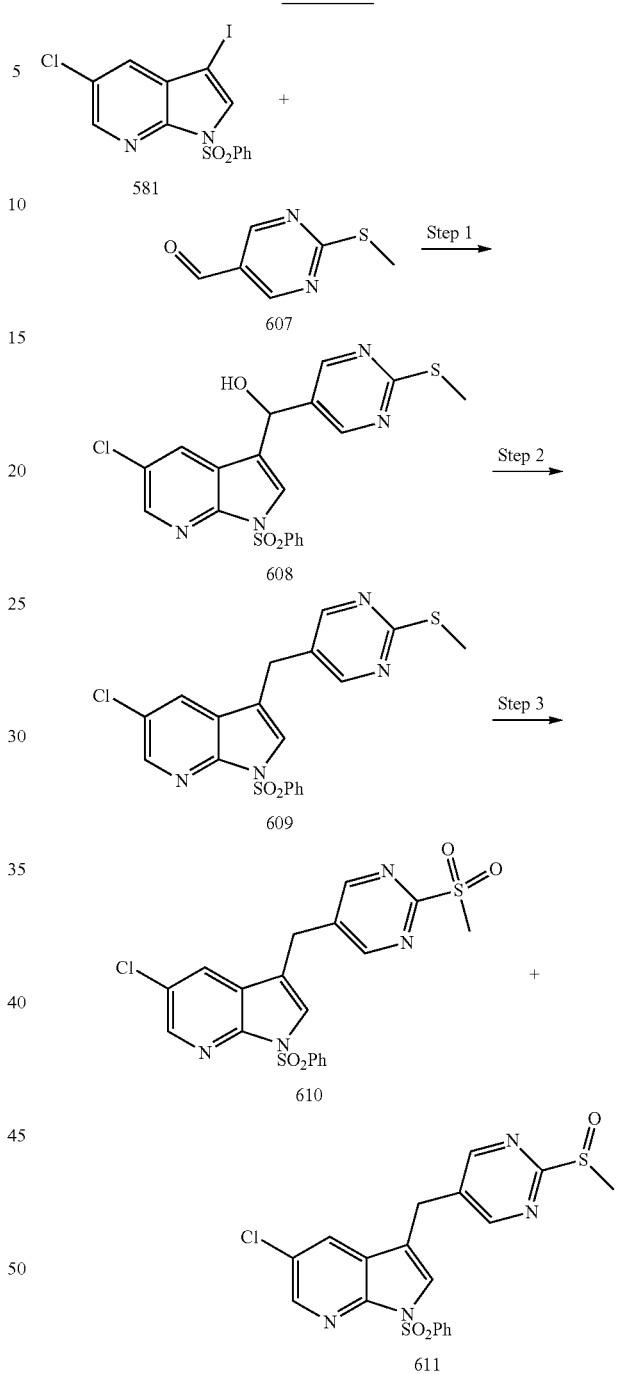

Step 1—Synthesis of (1-benzenesulfonyl-5-chloro-1H-pyrrolo[2,3-b]pyridin-3-yl)-(2-methylsulfanyl-pyrimidin-5-yl)-methanol (608)

To a solution of 1-Benzenesulfonyl-5-chloro-3-iodo-1H-pyrrolo[2,3-b]pyridine (581, 4.36 g, 10.4 mmol) in tetrahydrofuran (100.0 mL) at −40° C. under nitrogen, isopropyl-magnesium chloride (2.0 M in tetrahydrofuran. 5.06 mL) was added slowly. The reaction was allowed to warm to 5° C. over 60 minutes, then cooled to −40° C., followed by adding 2-methylsulfanyl-pyrimidine-5-carbaldehyde (607, 1.30 g, 8.43 mmol, dissolved in tetrahydrofuran 15.0 mL). The reaction was allowed to warm to 10° C. over 2 hours. The reaction was poured into aqueous ammonium chloride and extracted with ethyl acetate. The organic layer was dried over anhydrous sodium sulfate and filtered. The filtrate was concentrated and purified by silica gel column chromatography eluting with 2% to 15% methanol in dichloromethane to give the desired compound (608, 3.00 g, 79.6%). MS (ESI) [M+H$^+$]$^+$=447.2.

Step 2—Synthesis of 1-benzenesulfonyl-5-chloro-3-(2-methylsulfanyl-pyrimidin-5-ylmethyl)-1H-pyrrolo[2,3-b]pyridine (609)

To (1-benzenesulfonyl-5-chloro-1H-pyrrolo[2,3-b]pyridin-3-yl)-(2-methylsulfanyl-pyrimidin-5-yl)-methanol (608, 0.35 g, 0.78 mmol) in dichloromethane (15.0 mL) were added triethylsilane (2.00 mL, 12.52 mmol) and trifluoroacetic acid (1.00 mL, 13.0 mmol). The reaction was stirred at 35° C. overnight, then concentrated, poured into aqueous potassium carbonate, and extracted with ethyl acetate. The organic layer was dried over anhydrous sodium sulfate and filtered. The filtrate was concentrated and purified by silica gel column chromatography eluting with 20% to 100% ethyl acetate in hexane to give the desired compound (609, 0.25 g, 74%). MS (ESI) [M+H$^+$]$^+$=430.9.

Step 3—Synthesis of 1-benzenesulfonyl-5-chloro-3-(2-methanesulfonyl-pyrimidin-5-ylmethyl)-1H-pyrrolo[2,3-b]pyridine (610) and 1-benzenesulfonyl-5-chloro-3-(2-methanesulfinyl-pyrimidin-5-ylmethyl)-1H-pyrrolo[2,3-b]pyridine (611)

To 1-benzenesulfonyl-5-chloro-3-(2-methylsulfanyl-pyrimidin-5-ylmethyl)-1H-pyrrolo[2,3-b]pyridine (609, 0.500 g, 1.16 mmol) in dichloromethane (15.0 mL) was added meta-chloroperoxybenzoic acid (max. 77%, 0.572 g, 2.55 mmol) at 0° C. The reaction was stirred at 0° C. for 70 minutes, then poured into water and extracted with ethyl acetate. The organic layer was dried over anhydrous sodium sulfate and filtered. The filtrate was concentrated and purified by silica gel column chromatography eluting with 20% to 100% ethyl acetate in hexane to give the desired compounds (610, 0.310 g, 57.7%), MS (ESI) [M+H$^+$]$^+$=463.1; and (611, 0.200 g, 38.6%), MS (ESI) [M+H$^+$]$^+$=447.2.

1-Benzenesulfonyl-3-(2-methanesulfonyl-pyrimidin-5-ylmethyl)-1H-pyrrolo[2,3-b]pyridine 612

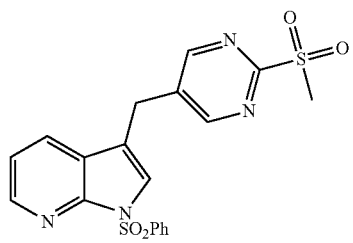

was prepared following the protocol of Scheme 191, substituting 1-benzenesulfonyl-5-chloro-3-iodo-1H-pyrrolo[2,3-b]pyridine 581 with 1-benzenesulfonyl-3-iodo-1H-pyrrolo[2,3-b]pyridine in Step 1.

Example 75

Synthesis of (4-chloro-benzyl)-[5-(5-chloro-1H-pyrrolo[2,3-b]pyridin-3-ylmethyl)-pyrimidin-2-yl]-amine P-0260

(4-Chloro-benzyl)-[5-(5-chloro-1H-pyrrolo[2,3-b]pyridin-3-ylmethyl)-pyrimidin-2-yl]-amine P-0260 was synthesized in 2 steps from 1-benzenesulfonyl-5-chloro-3-(2-methanesulfonyl-pyrimidin-5-ylmethyl)-1H-pyrrolo[2,3-b]pyridine 610 as shown in Scheme 192.

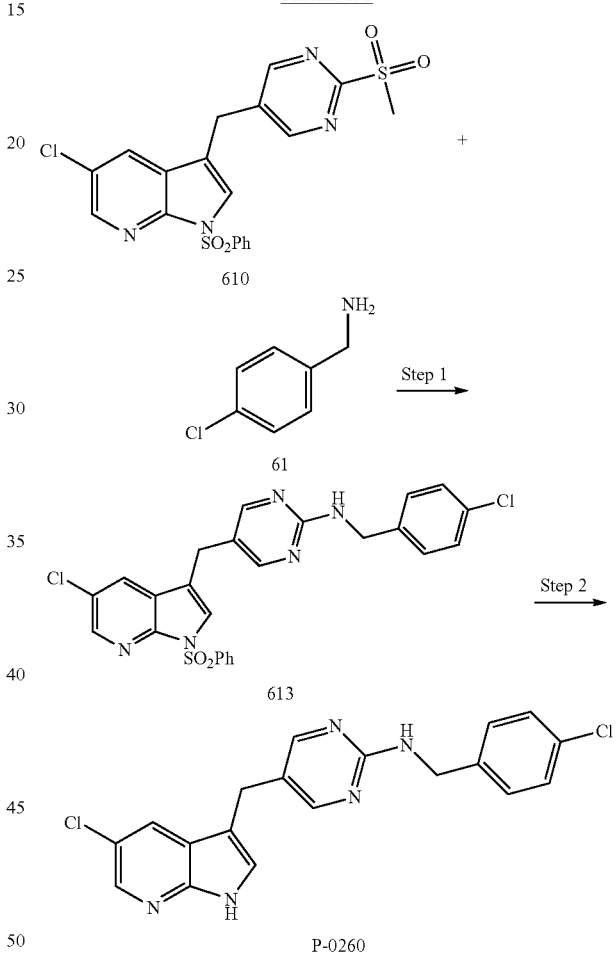

Step 1—Synthesis of [5-(1-benzenesulfonyl-5-chloro-1H-pyrrolo[2,3-b]pyridin-3-ylmethyl)-pyrimidin-2-yl]-(4-chloro-benzyl)-amine (613)

To 1-benzenesulfonyl-5-chloro-3-(2-methanesulfonyl-pyrimidin-5-ylmethyl)-1H-pyrrolo[2,3-b]pyridine (610, 0.060 g, 0.13 mmol, prepared as described in Example 74, Scheme 191) in N-methylpyrrolidinone (1.80 mL) was added p-chlorobenzylamine (61, 0.20 g, 1.4 mmol). The reaction was irradiated with microwave on 300 watts, 150° C. for 15 minutes, then poured into water and extracted with ethyl acetate. The organic layer was dried over anhydrous sodium sulfate and filtered. The filtrate was concentrated and purified by silica gel column chromatography eluting with 20% to 100% ethyl acetate in hexane to give the desired compound (613, 0.05 g, 74%). MS (ESI) [M+H⁺]⁺=524.3.

Step 2—Synthesis of (4-chloro-benzyl)-[5-(5-chloro-1H-pyrrolo[2,3-b]pyridin-3-ylmethyl)-pyrimidin-2-yl]-amine (P-0260)

To [5-(1-benzenesulfonyl-5-chloro-1H-pyrrolo[2,3-b]pyridin-3-ylmethyl)-pyrimidin-2-yl]-(4-chloro-benzyl)-amine (613, 0.050 g, 0.095 mmol) in tetrahydrofuran (10.0 mL) was added tetrabutylammonium fluoride, trihydrate (0.20 g, 0.63 mmol) under an atmosphere of nitrogen. The reaction was stirred at room temperature overnight, then poured into water, and extracted with ethyl acetate. The organic layer was dried over anhydrous sodium sulfate and filtered. The filtrate was concentrated and washed with ethyl acetate in hexane to give an off-white solid (P-0260, 16.9 mg, 46%). MS (ESI) [M+H⁺]⁺=385.9.

Additional compounds were prepared following the protocol of Scheme 192, substituting p-chlorobenzylamine 61 with a suitable amine in Step 1. The following compounds were prepared following this protocol:

[5-(5-Chloro-1H-pyrrolo[2,3-b]pyridin-3-ylmethyl)-pyrimidin-2-yl]-(2,6-difluoro-benzyl)-amine (P-0261),
[5-(5-Chloro-1H-pyrrolo[2,3-b]pyridin-3-ylmethyl)-pyrimidin-2-yl]-(2-trifluoromethyl-benzyl)-amine (P-0262),
(2-Chloro-benzyl)-[5-(5-chloro-1H-pyrrolo[2,3-b]pyridin-3-ylmethyl)-pyrimidin-2-yl]-amine (P-0263),
[5-(5-Chloro-1H-pyrrolo[2,3-b]pyridin-3-ylmethyl)-pyrimidin-2-yl]-(2-fluoro-benzyl)-amine (P-0264),
[5-(5-Chloro-1H-pyrrolo[2,3-b]pyridin-3-ylmethyl)-pyrimidin-2-yl]-(2,4-difluoro-benzyl)-amine (P-0265),
[5-(5-Chloro-1H-pyrrolo[2,3-b]pyridin-3-ylmethyl)-pyrimidin-2-yl]-(4-trifluoromethyl-benzyl)-amine (P-0266),
[5-(5-Chloro-1H-pyrrolo[2,3-b]pyridin-3-ylmethyl)-pyrimidin-2-yl]-(2,5-difluoro-benzyl)-amine (P-0267), and
[5-(5-Chloro-1H-pyrrolo[2,3-b]pyridin-3-ylmethyl)-pyrimidin-2-yl]-(3-trifluoromethyl-benzyl)-amine (P-0268).

The following table indicates the amine (Column 2) used in Scheme 192 to provide the compounds (Column 3). Column 1 provides the compound number and Column 4 the experimental mass spectrometry result.

| Compound number | Amine in Step 1 | Compound | MS (ESI) [M + H⁺]⁺ observed |
|---|---|---|---|
| P-0261 | 2,6-difluorobenzylamine | | 384.1 |
| P-0262 | 2-(trifluoromethyl)benzylamine | | 418.9 |
| P-0263 | 2-chlorobenzylamine | | 384.2 |
| P-0264 | 2-fluorobenzylamine | | 368.2 |

| Compound number | Amine in Step 1 | Compound | MS (ESI) [M + H+]+ observed |
|---|---|---|---|
| P-0265 | H2N-CH2-(2,4-difluorophenyl) | 5-chloro-3-{[2-(2,4-difluorobenzylamino)pyrimidin-5-yl]methyl}-7-azaindole | 386.2 |
| P-0266 | H2N-CH2-(4-CF3-phenyl) | 5-chloro-3-{[2-(4-trifluoromethylbenzylamino)pyrimidin-5-yl]methyl}-7-azaindole | 418.9 |
| P-0267 | H2N-CH2-(2,5-difluorophenyl) | 5-chloro-3-{[2-(2,5-difluorobenzylamino)pyrimidin-5-yl]methyl}-7-azaindole | [M − H+]− = 384.0 |
| P-0268 | H2N-CH2-(3-CF3-phenyl) | 5-chloro-3-{[2-(3-trifluoromethylbenzylamino)pyrimidin-5-yl]methyl}-7-azaindole | 419.2 |

Example 76

Synthesis of (2-fluoro-5-trifluoromethyl-benzyl)-[5-(1H-pyrrolo[2,3-b]pyridin-3-ylmethyl)-pyrimidin-2-yl]-amine P-0291

(2-Fluoro-5-trifluoromethyl-benzyl)-[5-(1H-pyrrolo[2,3-b]pyridin-3-ylmethyl)-pyrimidin-2-yl]-amine P-0291 was synthesized in 1 step from 1-benzenesulfonyl-3-(2-methanesulfonyl-pyrimidin-5-ylmethyl)-1H-pyrrolo[2,3-b]pyridine 612 as shown in Scheme 193.

Scheme 193

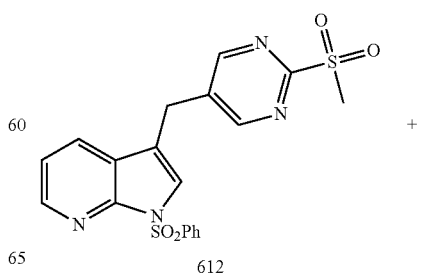

612

+

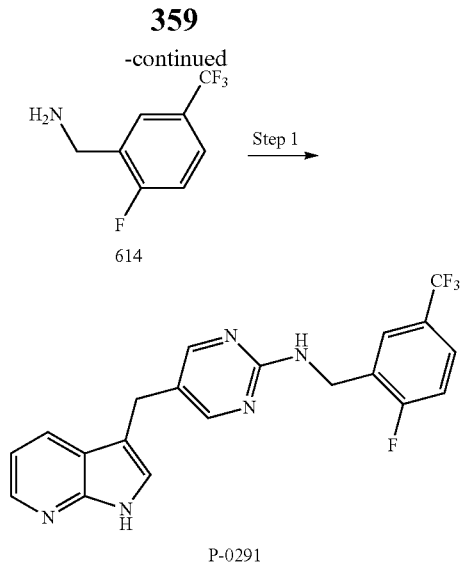

614

P-0291

Step 1—Synthesis of (2-fluoro-5-trifluoromethyl-benzyl)-[5-(1H-pyrrolo[2,3-b]pyridin-3-ylmethyl)-pyrimidin-2-yl]-amine (P-0291)

To 1-benzenesulfonyl-3-(2-methanesulfonyl-pyrimidin-5-ylmethyl)-1H-pyrrolo[2,3-b]pyridine (612, 0.080 g, 0.19 mmol, prepared as described in Example 74, Scheme 191) in N-methylpyrrolidinone (1.00 mL) was added 2-fluoro-5-tri-fluoromethyl-benzylamine (614, 0.20 g, 1.0 mmol). The reaction was irradiated with microwave on 300 watts, 150° C. for 15 minutes. Potassium hydroxide in water (1.00 M, 2.00 mL) was added to the reaction. The reaction was irradiated with microwave on 300 watts, 90° C. for 10 minutes, then poured into water and extracted with ethyl acetate. The organic layer was dried over anhydrous sodium sulfate and filtered. The filtrate was concentrated and purified by silica gel column chromatography eluting with 20% to 100% ethyl acetate in hexane to give a white solid (P-0291, 37.4 mg, 50%). MS (ESI) [M+H$^+$]$^+$=402.6.

Additional compounds were prepared following the protocol of Scheme 193, substituting 2-fluoro-5-trifluoromethyl-benzylamine 614 with a suitable amine. The following compounds were prepared following this protocol:

(2,5-Difluoro-benzyl)-[5-(1H-pyrrolo[2,3-b]pyridin-3-ylmethyl)-pyrimidin-2-yl]-amine (P-0292),
(2-Chloro-5-trifluoromethyl-benzyl)-[5-(1H-pyrrolo[2,3-b]pyridin-3-ylmethyl)-pyrimidin-2-yl]-amine (P-0293),
(3-Fluoro-5-trifluoromethyl-benzyl)-[5-(1H-pyrrolo[2,3-b]pyridin-3-ylmethyl)-pyrimidin-2-yl]-amine (P-0294),
(3,5-Difluoro-benzyl)-[5-(1H-pyrrolo[2,3-b]pyridin-3-ylmethyl)-pyrimidin-2-yl]-amine (P-0295),
(2-Fluoro-benzyl)-[5-(1H-pyrrolo[2,3-b]pyridin-3-ylmethyl)-pyrimidin-2-yl]-amine (P-0300),
(2-Chloro-benzyl)-[5-(1H-pyrrolo[2,3-b]pyridin-3-ylmethyl)-pyrimidin-2-yl]-amine (P-0301),
[5-(1H-Pyrrolo[2,3-b]pyridin-3-ylmethyl)-pyrimidin-2-yl]-(2-trifluoromethyl-benzyl)-amine (P-0302),
[5-(1H-Pyrrolo[2,3-b]pyridin-3-ylmethyl)-pyrimidin-2-yl]-(2-trifluoromethoxy-benzyl)-amine (P-0303),
(5-Chloro-2-fluoro-benzyl)-[5-(1H-pyrrolo[2,3-b]pyridin-3-ylmethyl)-pyrimidin-2-yl]-amine (P-0304),
(2,4-Dichloro-benzyl)-[5-(1H-pyrrolo[2,3-b]pyridin-3-ylmethyl)-pyrimidin-2-yl]-amine (P-0305),
(2,4-Difluoro-benzyl)-[5-(1H-pyrrolo[2,3-b]pyridin-3-ylmethyl)-pyrimidin-2-yl]-amine (P-0306),
(4-Chloro-benzyl)-[5-(1H-pyrrolo[2,3-b]pyridin-3-ylmethyl)-pyrimidin-2-yl]-amine (P-0307),
[5-(1H-Pyrrolo[2,3-b]pyridin-3-ylmethyl)-pyrimidin-2-yl]-(4-trifluoromethyl-benzyl)-amine (P-0308),
(2-Fluoro-3-trifluoromethyl-benzyl)-[5-(1H-pyrrolo[2,3-b]pyridin-3-ylmethyl)-pyrimidin-2-yl]-amine (P-0309),
(2,5-Dichloro-benzyl)-[5-(1H-pyrrolo[2,3-b]pyridin-3-ylmethyl)-pyrimidin-2-yl]-amine (P-0310),
(3-Chloro-2-fluoro-benzyl)-[5-(1H-pyrrolo[2,3-b]pyridin-3-ylmethyl)-pyrimidin-2-yl]-amine (P-0311),
(2-Difluoromethoxy-benzyl)-[5-(1H-pyrrolo[2,3-b]pyridin-3-ylmethyl)-pyrimidin-2-yl]-amine (P-0312),
(2,3-Dichloro-benzyl)-[5-(1H-pyrrolo[2,3-b]pyridin-3-ylmethyl)-pyrimidin-2-yl]-amine (P-0313),
(4-Chloro-2-fluoro-benzyl)-[5-(1H-pyrrolo[2,3-b]pyridin-3-ylmethyl)-pyrimidin-2-yl]-amine (P-0314),
(5-Fluoro-2-trifluoromethyl-benzyl)-[5-(1H-pyrrolo[2,3-b]pyridin-3-ylmethyl)-pyrimidin-2-yl]-amine (P-0315),
(2-Chloro-4-fluoro-benzyl)-[5-(1H-pyrrolo[2,3-b]pyridin-3-ylmethyl)-pyrimidin-2-yl]-amine (P-0316),
(5-Chloro-2-methyl-benzyl)-[5-(1H-pyrrolo[2,3-b]pyridin-3-ylmethyl)-pyrimidin-2-yl]-amine (P-0317),
(5-Fluoro-2-methyl-benzyl)-[5-(1H-pyrrolo[2,3-b]pyridin-3-ylmethyl)-pyrimidin-2-yl]-amine (P-0318),
(2-Fluoro-4-trifluoromethyl-benzyl)-[5-(1H-pyrrolo[2,3-b]pyridin-3-ylmethyl)-pyrimidin-2-yl]-amine (P-0319),
(4-Fluoro-2-trifluoromethyl-benzyl)-[5-(1H-pyrrolo[2,3-b]pyridin-3-ylmethyl)-pyrimidin-2-yl]-amine (P-0320), and
(2-Chloro-5-fluoro-benzyl)-[5-(1H-pyrrolo[2,3-b]pyridin-3-ylmethyl)-pyrimidin-2-yl]-amine (P-0407).

The following table indicates the amine (Column 2) used in Scheme 193 to provide the compounds (Column 3). Column 1 provides the compound number and Column 4 the experimental mass spectrometry result.

| Compound number | Amine | Compound | MS (ESI) [M + H$^+$]$^+$ observed |
|---|---|---|---|
| P-0292 |  |  | 352.3 |

-continued
| Compound number | Amine | Compound | MS (ESI) [M + H+]+ observed |
|---|---|---|---|
| P-0293 | 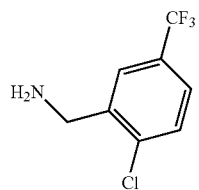 | 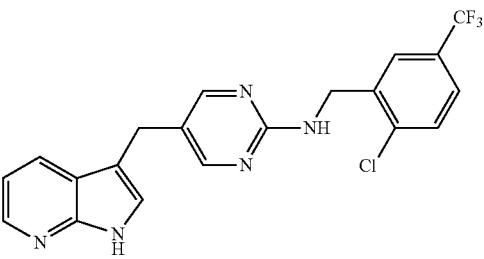 [SMILES: FC(F)(F)c1ccc(Cl)c(CNc2ncc(Cc3c[nH]c4ncccc34)cn2)c1] | 418.2 |
| P-0294 | 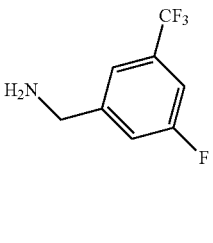 [SMILES: NCc1cc(F)cc(C(F)(F)F)c1] | 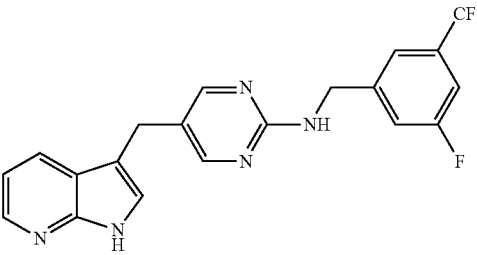 | 402.5 |
| P-0295 | 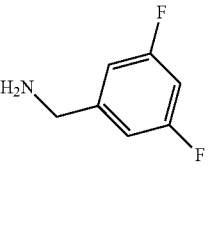 | 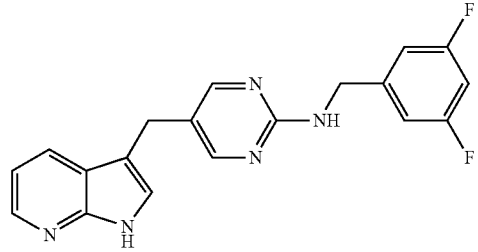 [SMILES: Fc1cc(F)cc(CNc2ncc(Cc3c[nH]c4ncccc34)cn2)c1] | 352.3 |
| P-0300 | 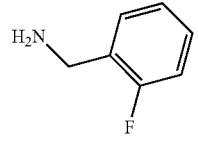 | 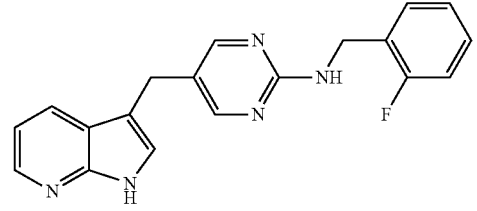 | 334.5 |
| P-0301 | 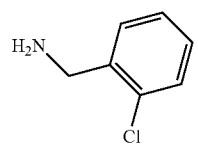 | 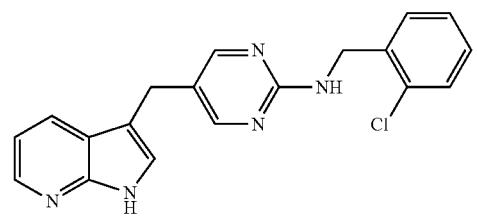 [SMILES: Clc1ccccc1CNc1ncc(Cc2c[nH]c3ncccc23)cn1] | 349.9 |
| P-0302 | 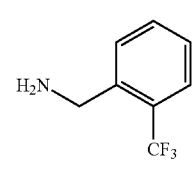 | 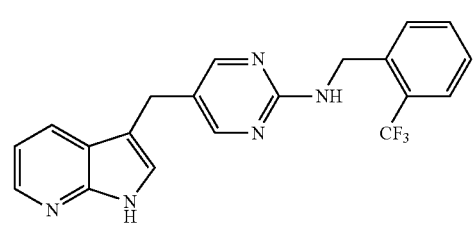 [SMILES: FC(F)(F)c1ccccc1CNc1ncc(Cc2c[nH]c3ncccc23)cn1] | 384.0 |

-continued
| Compound number | Amine | Compound | MS (ESI) [M + H+]+ observed |
|---|---|---|---|
| P-0303 | 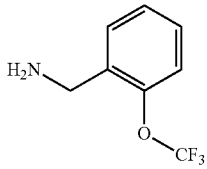 | 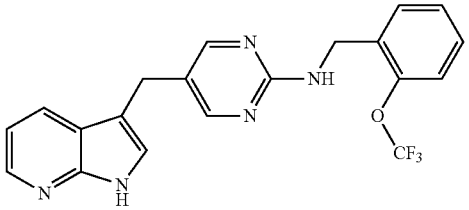 [SMILES: FC(F)(F)Oc1ccccc1CNc1ncc(Cc2c[nH]c3ncccc23)cn1] | 400.5 |
| P-0304 | 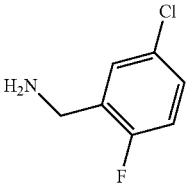 | 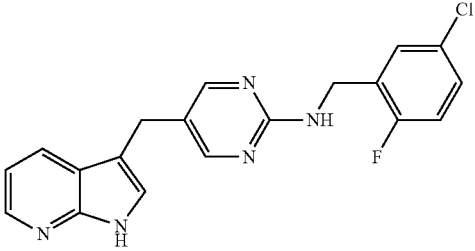 [SMILES: Fc1ccc(Cl)cc1CNc1ncc(Cc2c[nH]c3ncccc23)cn1] | 367.9 |
| P-0305 | 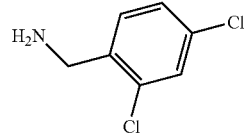 | 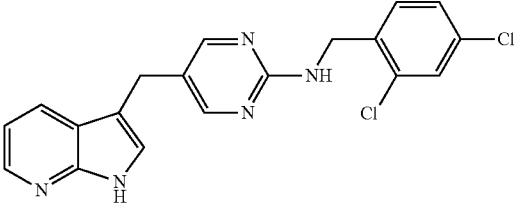 | 383.9 |
| P-0306 | 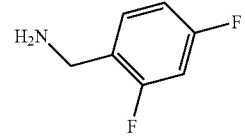 | 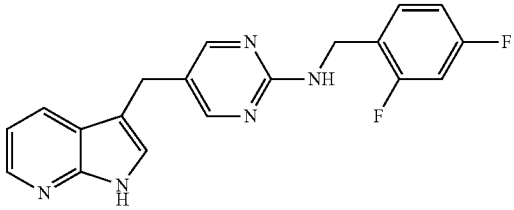 | 352.4 |
| P-0307 | 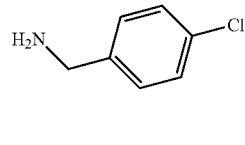 | 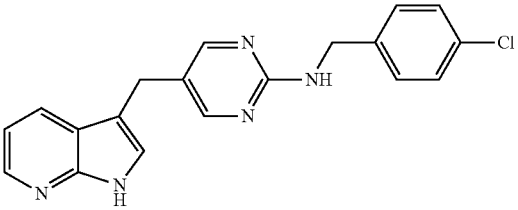 [SMILES: Clc1ccc(CNc2ncc(Cc3c[nH]c4ncccc34)cn2)cc1] | 352.0 |
| P-0308 | 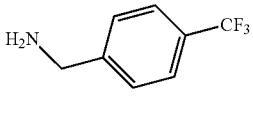 [SMILES: NCc1ccc(C(F)(F)F)cc1] | 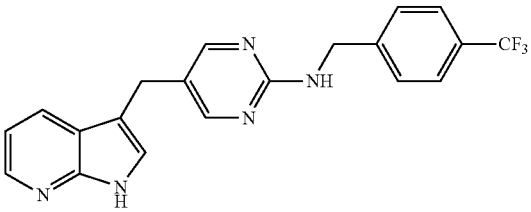 [SMILES: FC(F)(F)c1ccc(CNc2ncc(Cc3c[nH]c4ncccc34)cn2)cc1] | 384.0 |

| Compound number | Amine | Compound | MS (ESI) [M + H⁺]⁺ observed |
|---|---|---|---|
| P-0309 | 3-(aminomethyl)-2-fluoro-CF₃ benzylamine | 7-azaindole-pyrimidine-NH-CH₂-(2-F,3-CF₃-phenyl) | 402.5 |
| P-0310 | 2,5-dichlorobenzylamine | 7-azaindole-pyrimidine-NH-CH₂-(2,5-diCl-phenyl) | 389.0 |
| P-0311 | 2-fluoro-3-chlorobenzylamine | 7-azaindole-pyrimidine-NH-CH₂-(2-F,3-Cl-phenyl) | 368.0 |
| P-0312 | 2-(difluoromethoxy)benzylamine | 7-azaindole-pyrimidine-NH-CH₂-(2-OCHF₂-phenyl) | 382.5 |
| P-0313 | 2,3-dichlorobenzylamine | 7-azaindole-pyrimidine-NH-CH₂-(2,3-diCl-phenyl) | 385.0 |
| P-0314 | 4-chloro-2-fluorobenzylamine | 7-azaindole-pyrimidine-NH-CH₂-(4-Cl,2-F-phenyl) | 367.9 |

-continued

| Compound number | Amine | Compound | MS (ESI) [M + H⁺]⁺ observed |
|---|---|---|---|
| P-0315 | 2-(trifluoromethyl)-5-fluorobenzylamine | 7-azaindole-pyrimidine-NH-CH2-(2-CF3,5-F-phenyl) | 402.4 |
| P-0316 | 2-chloro-4-fluorobenzylamine | 7-azaindole-pyrimidine-NH-CH2-(2-Cl,4-F-phenyl) | 368.2 |
| P-0317 | 5-chloro-2-methylbenzylamine | 7-azaindole-pyrimidine-NH-CH2-(5-Cl,2-Me-phenyl) | 364.8 |
| P-0318 | 5-fluoro-2-methylbenzylamine | 7-azaindole-pyrimidine-NH-CH2-(5-F,2-Me-phenyl) | 348.6 |
| P-0319 | 2-fluoro-4-(trifluoromethyl)benzylamine | 7-azaindole-pyrimidine-NH-CH2-(2-F,4-CF3-phenyl) | 402.5 |
| P-0320 | 4-fluoro-2-(trifluoromethyl)benzylamine | 7-azaindole-pyrimidine-NH-CH2-(4-F,2-CF3-phenyl) | 402.5 |

| Compound number | Amine | Compound | MS (ESI) [M + H⁺]⁺ observed |
|---|---|---|---|
| P-0407 | | | 368.3 |

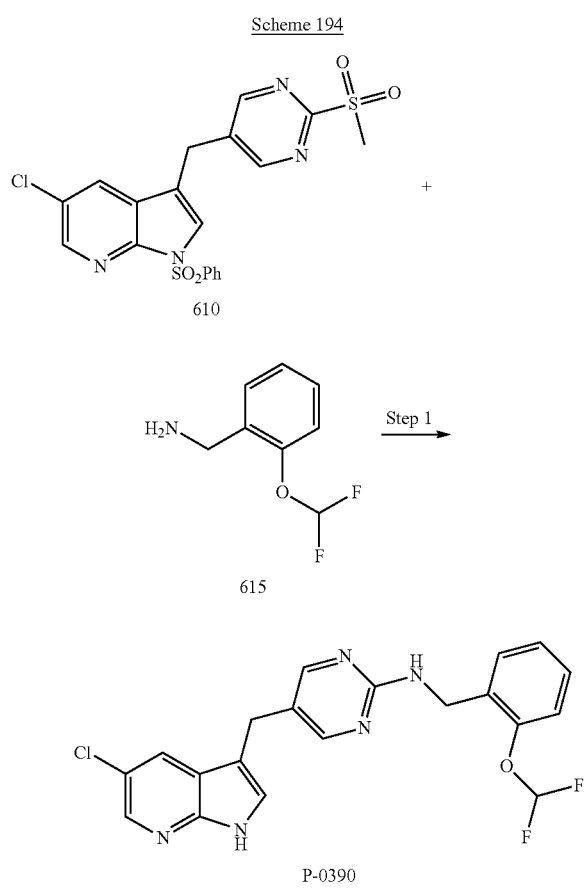

Example 77

Synthesis of [5-(5-Chloro-1H-pyrrolo[2,3-b]pyridin-3-ylmethyl)-pyrimidin-2-yl]-(2-difluoromethoxy-benzyl)-amine P-0390

[5-(5-Chloro-1H-pyrrolo[2,3-b]pyridin-3-ylmethyl)-pyrimidin-2-yl]-(2-difluoromethoxy-benzyl)-amine P-0390 was synthesized in 1 step from 1-benzenesulfonyl-5-chloro-3-(2-methanesulfonyl-pyrimidin-5-ylmethyl)-1H-pyrrolo[2,3-b]pyridine 610 as shown in Scheme 194.

Step 1—Synthesis of [5-(5-Chloro-1H-pyrrolo[2,3-b]pyridin-3-ylmethyl)-pyrimidin-2-yl]-(2-difluoromethoxy-benzyl)-amine (P-0390)

To 1-benzenesulfonyl-5-chloro-3-(2-methanesulfonyl-pyrimidin-5-ylmethyl)-1H-pyrrolo[2,3-b]pyridine (610, 0.060 g, 0.13 mmol, prepared as described in Example 74, Scheme 191) in N-methylpyrrolidinone (1.40 mL) was added 2-difluoromethoxy-benzylamine (615, 0.200 g, 1.16 mmol). The reaction was irradiated with microwave on 300 watts, 150° C. for 15 minutes. Potassium hydroxide in water (1.00 M, 2.00 mL) was added to the reaction. The reaction was irradiated with microwave on 300 watts, 90° C. for 10 minutes, then poured into ethyl acetate and water. The organic layer was concentrated and purified by silica gel column chromatography eluting with 20% to 100% ethyl acetate in hexane to give a white solid (P-0390, 10.9 mg, 20%). MS (ESI) [M+H⁺]⁺ =418.0.

Additional compounds were prepared following the protocol of Scheme 194, substituting 2-difluoromethoxy-benzylamine 615 with a suitable amine. The following compounds were prepared following this protocol:

[5-(5-Chloro-1H-pyrrolo[2,3-b]pyridin-3-ylmethyl)-pyrimidin-2-yl]-(2-fluoro-5-trifluoromethyl-benzyl)-amine (P-0289),

[5-(5-Chloro-1H-pyrrolo[2,3-b]pyridin-3-ylmethyl)-pyrimidin-2-yl]-(5-fluoro-2-trifluoromethyl-benzyl)-amine (P-0391), (3-Chloro-2-fluoro-benzyl)-[5-(5-chloro-1H-pyrrolo[2,3-b]pyridin-3-ylmethyl)-pyrimidin-2-yl]-amine (P-0392),

[5-(5-Chloro-1H-pyrrolo[2,3-b]pyridin-3-ylmethyl)-pyrimidin-2-yl]-(2-fluoro-3-trifluoromethyl-benzyl)-amine (P-0393),

[5-(5-Chloro-1H-pyrrolo[2,3-b]pyridin-3-ylmethyl)-pyrimidin-2-yl]-(2-fluoro-4-trifluoromethyl-benzyl)-amine (P-0394),

[5-(5-Chloro-1H-pyrrolo[2,3-b]pyridin-3-ylmethyl)-pyrimidin-2-yl]-(2,3-difluoro-benzyl)-amine (P-0395), (2-Chloro-4-fluoro-benzyl)-[5-(5-chloro-1H-pyrrolo[2,3-b]pyridin-3-ylmethyl)-pyrimidin-2-yl]-amine (P-0396),

[5-(5-Chloro-1H-pyrrolo[2,3-b]pyridin-3-ylmethyl)-pyrimidin-2-yl]-(2-trifluoromethoxy-benzyl)-amine (P-0402), (2-Chloro-5-fluoro-benzyl)-[5-(5-chloro-1H-pyrrolo[2,3-b]pyridin-3-ylmethyl)-pyrimidin-2-yl]-amine (P-0408),

[5-(5-Chloro-1H-pyrrolo[2,3-b]pyridin-3-ylmethyl)-pyrimidin-2-yl]-pyridin-4-ylmethyl-amine (P-0416),

[5-(5-Chloro-1H-pyrrolo[2,3-b]pyridin-3-ylmethyl)-pyrimidin-2-yl]-(2-pyrrolidin-1-yl-ethyl)-amine (P-0417), Benzyl-[5-(5-chloro-1H-pyrrolo[2,3-b]pyridin-3-ylmethyl)-pyrimidin-2-yl]-amine (P-0418),
Benzyl-[5-(5-chloro-1H-pyrrolo[2,3-b]pyridin-3-ylmethyl)-pyrimidin-2-yl]-methyl-amine (P-0419),
[5-(5-Chloro-1H-pyrrolo[2,3-b]pyridin-3-ylmethyl)-pyrimidin-2-yl]-(4-trifluoromethoxy-benzyl)-amine (P-0420),
(3-Chloro-benzyl)-[5-(5-chloro-1H-pyrrolo[2,3-b]pyridin-3-ylmethyl)-pyrimidin-2-yl]-amine (P-0421),
[5-(5-Chloro-1H-pyrrolo[2,3-b]pyridin-3-ylmethyl)-pyrimidin-2-yl]-pyridin-3-ylmethyl-amine (P-0422),
[5-(5-Chloro-1H-pyrrolo[2,3-b]pyridin-3-ylmethyl)-pyrimidin-2-yl]-(4-fluoro-benzyl)-amine (P-0423),
(3-Chloro-benzyl)-[5-(5-chloro-1H-pyrrolo[2,3-b]pyridin-3-ylmethyl)-pyrimidin-2-yl]-methyl-amine (P-0424),
[5-(5-Chloro-1H-pyrrolo[2,3-b]pyridin-3-ylmethyl)-pyrimidin-2-yl]-(3,5-difluoro-benzyl)-amine (P-0425),
[5-(5-Chloro-1H-pyrrolo[2,3-b]pyridin-3-ylmethyl)-pyrimidin-2-yl]-[1-(2-fluoro-phenyl)-ethyl]-amine (P-0426),
[1-(4-Chloro-phenyl)-ethyl]-[5-(5-chloro-1H-pyrrolo[2,3-b]pyridin-3-ylmethyl)-pyrimidin-2-yl]-amine (P-0427),
[5-(5-Chloro-1H-pyrrolo[2,3-b]pyridin-3-ylmethyl)-pyrimidin-2-yl]-[(S)-1-(4-fluoro-phenyl)-ethyl]-amine (P-0428),
[5-(5-Chloro-1H-pyrrolo[2,3-b]pyridin-3-ylmethyl)-pyrimidin-2-yl]-(6-trifluoromethyl-pyridin-3-ylmethyl)-amine (P-0429),
(2-Chloro-benzyl)-[5-(5-chloro-1H-pyrrolo[2,3-b]pyridin-3-ylmethyl)-pyrimidin-2-yl]-methyl-amine (P-0430),
[5-(5-Chloro-1H-pyrrolo[2,3-b]pyridin-3-ylmethyl)-pyrimidin-2-yl]-(2-methyl-benzyl)-amine (P-0431),
[5-(5-Chloro-1H-pyrrolo[2,3-b]pyridin-3-ylmethyl)-pyrimidin-2-yl]-(2-methoxy-benzyl)-amine (P-0433),
[5-(5-Chloro-1H-pyrrolo[2,3-b]pyridin-3-ylmethyl)-pyrimidin-2-yl]-(2-morpholin-4-yl-ethyl)-amine (P-0434),
[5-(5-Chloro-1H-pyrrolo[2,3-b]pyridin-3-ylmethyl)-pyrimidin-2-yl]-cyclohexylmethyl-amine (P-0435),
[5-(5-Chloro-1H-pyrrolo[2,3-b]pyridin-3-ylmethyl)-pyrimidin-2-yl]-pyridin-2-ylmethyl-amine (P-0436),
[2-(4-Chloro-phenyl)-ethyl]-[5-(5-chloro-1H-pyrrolo[2,3-b]pyridin-3-ylmethyl)-pyrimidin-2-yl]-amine (P-0437),
[5-(5-Chloro-1H-pyrrolo[2,3-b]pyridin-3-ylmethyl)-pyrimidin-2-yl]-(4-difluoromethoxy-benzyl)-amine (P-0438),
[5-(5-Chloro-1H-pyrrolo[2,3-b]pyridin-3-ylmethyl)-pyrimidin-2-yl]-(4-methoxy-benzyl)-amine (P-0439),
[5-(5-Chloro-1H-pyrrolo[2,3-b]pyridin-3-ylmethyl)-pyrimidin-2-yl]-(4-methyl-benzyl)-amine (P-0440),
[5-(5-Chloro-1H-pyrrolo[2,3-b]pyridin-3-ylmethyl)-pyrimidin-2-yl]-(2-methoxy-ethyl)-amine (P-0441),
[5-(5-Chloro-1H-pyrrolo[2,3-b]pyridin-3-ylmethyl)-pyrimidin-2-yl]-(3-fluoro-benzyl)-amine (P-0442),
(3-Chloro-4-fluoro-benzyl)-[5-(5-chloro-1H-pyrrolo[2,3-b]pyridin-3-ylmethyl)-pyrimidin-2-yl]-amine (P-0443),
[5-(5-Chloro-1H-pyrrolo[2,3-b]pyridin-3-ylmethyl)-pyrimidin-2-yl]-(2-ethoxy-benzyl)-amine (P-0444),
[5-(5-Chloro-1H-pyrrolo[2,3-b]pyridin-3-ylmethyl)-pyrimidin-2-yl]-(4-morpholin-4-yl-benzyl)-amine (P-0445),
[5-(5-Chloro-1H-pyrrolo[2,3-b]pyridin-3-ylmethyl)-pyrimidin-2-yl]-(3-difluoromethoxy-benzyl)-amine (P-0446),
(4-Chloro-3-fluoro-benzyl)-[5-(5-chloro-1H-pyrrolo[2,3-b]pyridin-3-ylmethyl)-pyrimidin-2-yl]-amine (P-0447),
[5-(5-Chloro-1H-pyrrolo[2,3-b]pyridin-3-ylmethyl)-pyrimidin-2-yl]-[1-(3-fluoro-phenyl)-ethyl]-amine (P-0448), and
[5-(5-Chloro-1H-pyrrolo[2,3-b]pyridin-3-ylmethyl)-pyrimidin-2-yl]-(2-dimethylamino-benzyl)-amine (P-0449).

The following table indicates the amine (Column 2) used in Scheme 194 to provide the compounds (Column 3). Column 1 provides the compound number and Column 4 the experimental mass spectrometry result.

| Compound number | Amine | Compound | MS (ESI) [M + H⁺]⁺ observed |
|---|---|---|---|
| P-0289 | (2-fluoro-5-trifluoromethyl-benzylamine) | (structure) | 436.0 |
| P-0391 | (5-fluoro-2-trifluoromethyl-benzylamine) | (structure) | 436.0 |

-continued

| Compound number | Amine | Compound | MS (ESI) [M + H⁺]⁺ observed |
|---|---|---|---|
| P-0392 | 3-chloro-2-fluorobenzylamine | 5-chloro-7-azaindole-pyrimidine-NH-CH2-(3-chloro-2-fluorophenyl) | 402.0 |
| P-0393 | 2-fluoro-3-(trifluoromethyl)benzylamine | 5-chloro-7-azaindole-pyrimidine-NH-CH2-(2-fluoro-3-trifluoromethylphenyl) | [M − H⁺]⁻ = 434.1 |
| P-0394 | 2-fluoro-4-(trifluoromethyl)benzylamine | 5-chloro-7-azaindole-pyrimidine-NH-CH2-(2-fluoro-4-trifluoromethylphenyl) | 437.3 |
| P-0395 | 2,3-difluorobenzylamine | 5-chloro-7-azaindole-pyrimidine-NH-CH2-(2,3-difluorophenyl) | 386.0 |
| P-0396 | 2-chloro-4-fluorobenzylamine | 5-chloro-7-azaindole-pyrimidine-NH-CH2-(2-chloro-4-fluorophenyl) | 402.0 |
| P-0402 | 2-(trifluoromethoxy)benzylamine | 5-chloro-7-azaindole-pyrimidine-NH-CH2-(2-trifluoromethoxyphenyl) | 434.3 |

-continued

| Compound number | Amine | Compound | MS (ESI) [M + H⁺]⁺ observed |
|---|---|---|---|
| P-0408 | | | 402.0 |
| P-0416 | | | 351.1 |
| P-0417 | | | 357.1 |
| P-0418 | | | 350.3 |
| P-0419 | | | 364.3 |
| P-0420 | | | 434.3 |

-continued
| Compound number | Amine | Compound | MS (ESI) [M + H+]+ observed |
|---|---|---|---|
| P-0421 | 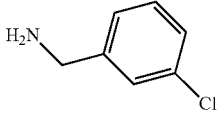 | 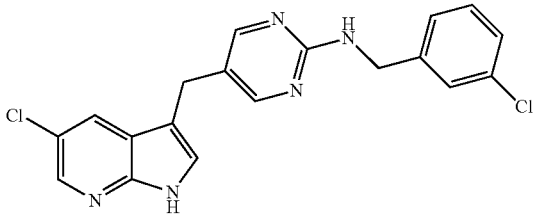 [SMILES: Clc1cccc(CNc2ncc(Cc3c[nH]c4ncc(Cl)cc34)cn2)c1] | 383.9 |
| P-0422 | 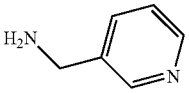 | 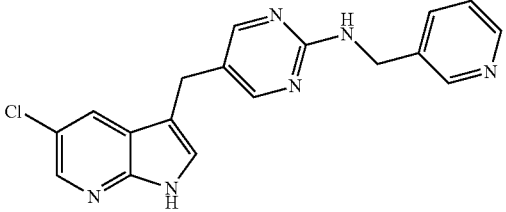 [SMILES: Clc1cnc2[nH]cc(Cc3cnc(NCc4cccnc4)nc3)c2c1] | 351.1 |
| P-0423 | 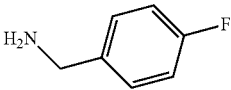 | 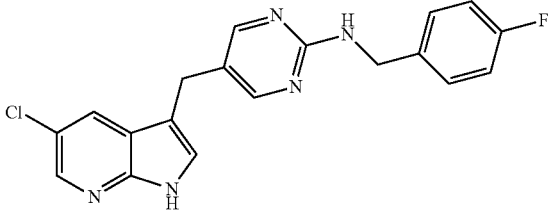 [SMILES: Fc1ccc(CNc2ncc(Cc3c[nH]c4ncc(Cl)cc34)cn2)cc1] | 368.3 |
| P-0424 | 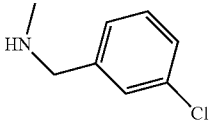 | 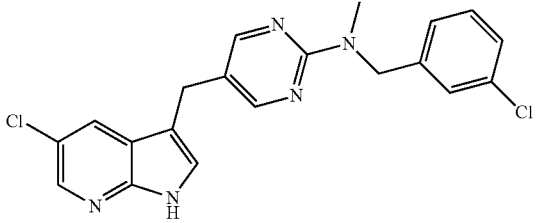 [SMILES: CN(Cc1cccc(Cl)c1)c1ncc(Cc2c[nH]c3ncc(Cl)cc23)cn1] | 398.3 |
| P-0425 | 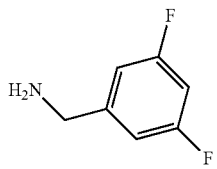 | 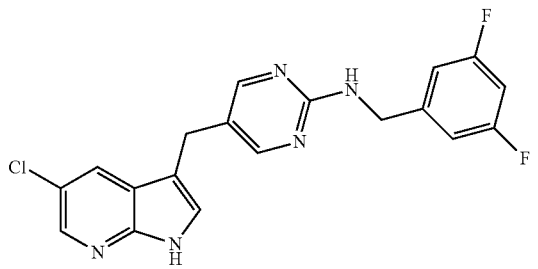 [SMILES: Fc1cc(F)cc(CNc2ncc(Cc3c[nH]c4ncc(Cl)cc34)cn2)c1] | 386.3 |
| P-0426 | 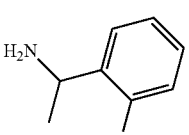 | 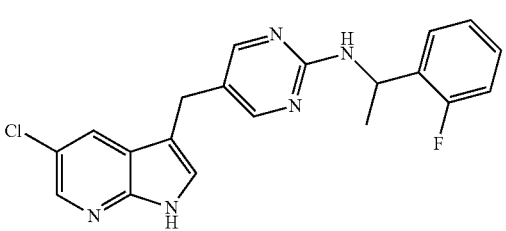 [SMILES: CC(Nc1ncc(Cc2c[nH]c3ncc(Cl)cc23)cn1)c1ccccc1F] | 382.3 |

-continued

| Compound number | Amine | Compound | MS (ESI) [M + H⁺]⁺ observed |
|---|---|---|---|
| P-0427 | H₂N-CH(CH₃)-C₆H₄-Cl (4-Cl) | 5-chloro-7-azaindole-pyrimidine-NH-CH(CH₃)-4-Cl-phenyl | 398.3 |
| P-0428 | H₂N-CH(CH₃)-C₆H₄-F (4-F) | 5-chloro-7-azaindole-pyrimidine-NH-CH(CH₃)-4-F-phenyl | 382.3 |
| P-0429 | H₂N-CH₂-pyridyl-CF₃ | 5-chloro-7-azaindole-pyrimidine-NH-CH₂-pyridyl-CF₃ | 419.1 |
| P-0430 | HN(CH₃)-CH₂-C₆H₄-Cl (2-Cl) | 5-chloro-7-azaindole-pyrimidine-N(CH₃)-CH₂-2-Cl-phenyl | 397.9 |
| P-0431 | H₂N-CH₂-C₆H₄-CH₃ (2-Me) | 5-chloro-7-azaindole-pyrimidine-NH-CH₂-2-Me-phenyl | 364.3 |
| P-0433 | H₂N-CH₂-C₆H₄-OCH₃ (2-OMe) | 5-chloro-7-azaindole-pyrimidine-NH-CH₂-2-OMe-phenyl | 380.3 |

-continued

| Compound number | Amine | Compound | MS (ESI) [M + H⁺]⁺ observed |
|---|---|---|---|
| P-0434 | H₂N-CH₂CH₂-morpholine | 5-chloro-7H-pyrrolo[2,3-b]pyridine-pyrimidine-NH-CH₂CH₂-morpholine | 373.1 |
| P-0435 | H₂N-CH₂-cyclohexyl | 5-chloro-7H-pyrrolo[2,3-b]pyridine-pyrimidine-NH-CH₂-cyclohexyl | 356.3 |
| P-0436 | H₂N-CH₂-(2-pyridyl) | 5-chloro-7H-pyrrolo[2,3-b]pyridine-pyrimidine-NH-CH₂-(2-pyridyl) | 351.1 |
| P-0437 | H₂N-CH₂CH₂-(4-chlorophenyl) | 5-chloro-7H-pyrrolo[2,3-b]pyridine-pyrimidine-NH-CH₂CH₂-(4-chlorophenyl) | 397.9 |
| P-0438 | H₂N-CH₂-(4-OCHF₂-phenyl) | 5-chloro-7H-pyrrolo[2,3-b]pyridine-pyrimidine-NH-CH₂-(4-OCHF₂-phenyl) | 416.3 |
| P-0439 | H₂N-CH₂-(4-methoxyphenyl) | 5-chloro-7H-pyrrolo[2,3-b]pyridine-pyrimidine-NH-CH₂-(4-methoxyphenyl) | 380.3 |

-continued
| Compound number | Amine | Compound | MS (ESI) [M + H⁺]⁺ observed |
|---|---|---|---|
| P-0440 | 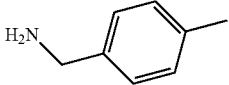 | 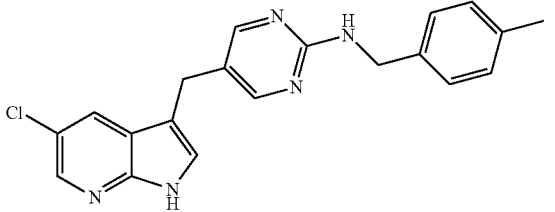 [SMILES: Cc1ccc(CNc2ncc(Cc3c[nH]c4ncc(Cl)cc34)cn2)cc1] | 364.3 |
| P-0441 | 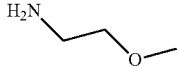 | 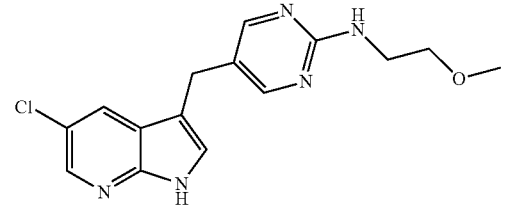 [SMILES: COCCNc1ncc(Cc2c[nH]c3ncc(Cl)cc23)cn1] | 317.9 |
| P-0442 | 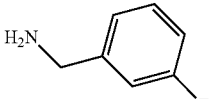 | 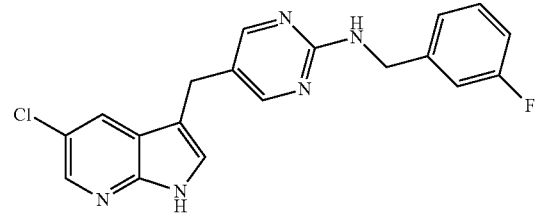 [SMILES: Fc1cccc(CNc2ncc(Cc3c[nH]c4ncc(Cl)cc34)cn2)c1] | 368.3 |
| P-0443 | 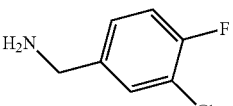 | 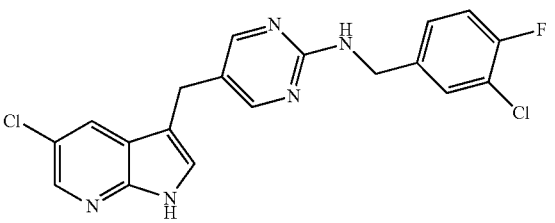 [SMILES: Fc1ccc(CNc2ncc(Cc3c[nH]c4ncc(Cl)cc34)cn2)cc1Cl] | 401.9 |
| P-0444 | 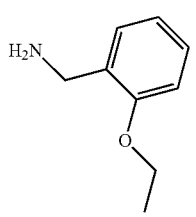 | 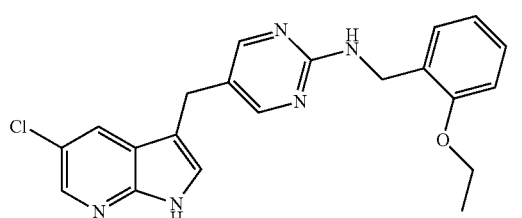 | 393.9 |
| P-0445 | 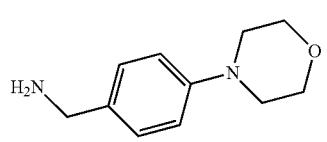 [SMILES: NCc1ccc(N2CCOCC2)cc1] | 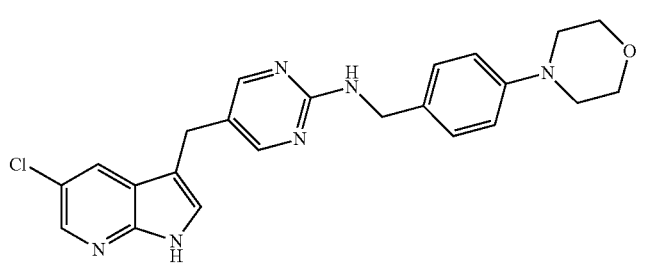 [SMILES: Clc1cnc2[nH]cc(Cc3cnc(NCc4ccc(N5CCOCC5)cc4)nc3)c2c1] | 435.1 |

-continued
| Compound number | Amine | Compound | MS (ESI) [M + H+]+ observed |
|---|---|---|---|
| P-0446 | | | 416.3 |
| P-0447 | | | 402.3 |
| P-0448 | | | 382.3 |
| P-0449 | | | 393.1 |
Example 78
Synthesis of (2-chloro-6-fluoro-benzyl)-[5-(1H-pyrrolo[2,3-b]pyridin-3-ylmethyl)-pyridin-2-yl]-amine P-0210
(2-Chloro-6-fluoro-benzyl)-[5-(1H-pyrrolo[2,3-b]pyridin-3-ylmethyl)-pyridin-2-yl]-amine P-0210 was synthesized in 2 steps from 5-(1-Benzenesulfonyl-1H-pyrrolo[2,3-b]pyridin-3-ylmethyl)-pyridin-2-ylamine 600 as shown in Scheme 195.
Scheme 195
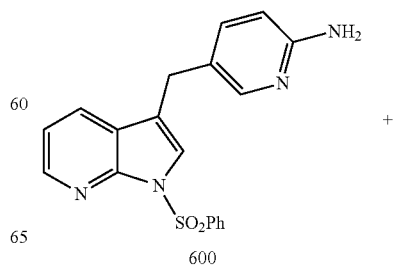

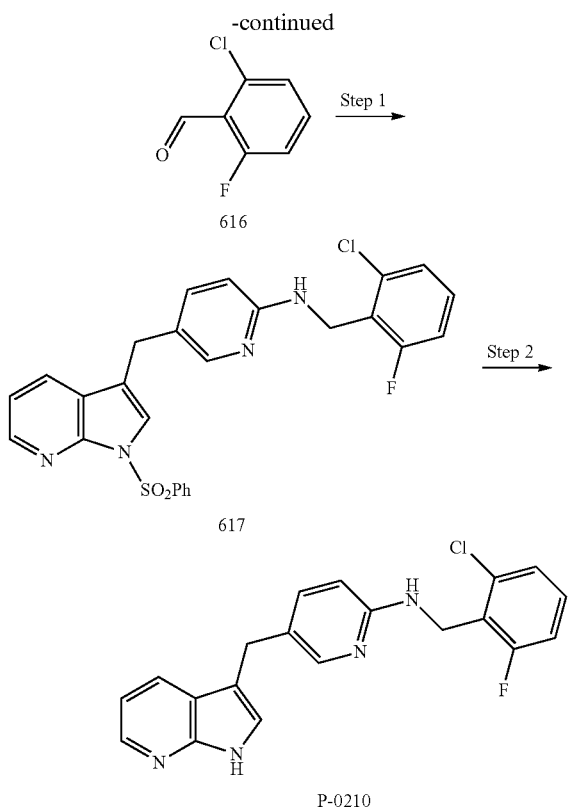

Step 1—Preparation of [5-(1-benzenesulfonyl-1H-pyrrolo[2,3-b]pyridin-3-ylmethyl)-pyridin-2-yl]-(2-chloro-6-fluoro-benzyl)-amine (617)

5-(1-Benzenesulfonyl-1H-pyrrolo[2,3-b]pyridin-3-ylmethyl)-pyridin-2-ylamine (600, 30 mg, 0.083 mmol, prepared as described in Example 68, Scheme 185) was combined with 2-chloro-6-fluoro-benzaldehyde (616, 26.2 mg, 0.165 mmol) in a 2 mL microwave reaction vial. The mixture was dissolved in ethanol:acetic acid (95:5, 0.6 mL). Silica supported cyanoborohydride (1.0 mmol/g, 83 mg, 0.083 mmol) was added and the mixture was irradiated with microwave on 300 watts for 5 minutes at 100° C. The silica was separated by centrifuging and the supernatant solution was decanted. The silica residue was rinsed with ethanol (0.500 mL) and centrifuged. The solvents were combined and removed under reduced pressure to give compound 617, which was used in the next step without further purification.

Step 2—Preparation of (2-chloro-6-fluoro-benzyl)[5-(1H-pyrrolo[2,3-b]pyridin-3-ylmethyl)-pyridin-2-yl]-amine (P-0210)

[5-(1-Benzenesulfonyl-1H-pyrrolo[2,3-b]pyridin-3-ylmethyl)-pyridin-2-yl]-(2-chloro-6-fluoro-benzyl)-amine 617 was combined with methanol:potassium hydroxide (1M) (1:1, 0.5 mL). The mixture was heated at 80° C. for 2 hours. Acetic acid (0.1 mL) was added and the solvents removed under reduced pressure. The remaining residue was dissolved in dimethylsulfoxide (0.4 mL) and purified by reverse phase HPLC on a Phenomenex column (50 mm×10 mm ID) eluting with 0.1% trifluoroacetic acid in water and 20-100% acetonitrile with 0.1% trifluoroacetic acid over 16 minutes at a flow rate of 6 mL/minute to provide the desired compound P-0210. MS (ESI) [M+H$^+$]$^+$=367.1.

Additional compounds were prepared following the protocol of Scheme 195, replacing 2-chloro-6-fluoro-benzaldehyde 616 with an appropriate aldehyde in Step 1. The following compounds were made following this procedure:

Phenethyl-[5-(1H-pyrrolo[2,3-b]pyridin-3-ylmethyl)-pyridin-2-yl]-amine (P-0211),
(2,4-Difluoro-benzyl)-[5-(1H-pyrrolo[2,3-b]pyridin-3-ylmethyl)-pyridin-2-yl]-amine (P-0212),
(2-Fluoro-benzyl)-[5-(1H-pyrrolo[2,3-b]pyridin-3-ylmethyl)-pyridin-2-yl]-amine (P-0213),
(3-Bromo-pyridin-4-ylmethyl)-[5-(1H-pyrrolo[2,3-b]pyridin-3-ylmethyl)-pyridin-2-yl]-amine (P-0214),
(2-Methoxy-pyridin-3-ylmethyl)-[5-(1H-pyrrolo[2,3-b]pyridin-3-ylmethyl)-pyridin-2-yl]-amine (P-0215),
(2-Chloro-benzyl)-[5-(1H-pyrrolo[2,3-b]pyridin-3-ylmethyl)-pyridin-2-yl]-amine (P-0216),
(2-Methyl-benzyl)-[5-(1H-pyrrolo[2,3-b]pyridin-3-ylmethyl)-pyridin-2-yl]-amine (P-0217),
(1-Methyl-1H-benzoimidazol-2-ylmethyl)-[5-(1H-pyrrolo[2,3-b]pyridin-3-ylmethyl)-pyridin-2-yl]-amine (P-0218),
(6-Methoxy-pyridin-3-ylmethyl)-[5-(1H-pyrrolo[2,3-b]pyridin-3-ylmethyl)-pyridin-2-yl]-amine (P-0219),
(1H-Benzoimidazol-2-ylmethyl)-[5-(1H-pyrrolo[2,3-b]pyridin-3-ylmethyl)-pyridin-2-yl]-amine (P-0220),
(2-Chloro-4-fluoro-benzyl)-[5-(1H-pyrrolo[2,3-b]pyridin-3-ylmethyl)-pyridin-2-yl]-amine (P-0221),
(5-Methoxy-pyridin-3-ylmethyl)-[5-(1H-pyrrolo[2,3-b]pyridin-3-ylmethyl)-pyridin-2-yl]-amine (P-0222),
(3-Fluoro-pyridin-4-ylmethyl)-[5-(1H-pyrrolo[2,3-b]pyridin-3-ylmethyl)-pyridin-2-yl]-amine (P-0223),
(6-M ethoxy-pyridin-2-ylmethyl)-[5-(1H-pyrrolo[2, 3-1)]pyridin-3-ylmethyl)-pyridin-2-yl]-amine (P-0224),
(4-Fluoro-2-trifluoromethyl-benzyl)-[5-(1H-pyrrolo[2, 3-1)]pyridin-3-ylmethyl)-pyridin-2-yl]-amine (P-0225),
[5-(1H-Pyrrolo[2,3-b]pyridin-3-ylmethyl)-pyridin-2-yl]-(2-trifluoromethyl-benzyl)-amine (P-0226),
(3,5-Dichloro-pyridin-4-ylmethyl)-[5-(1H-pyrrolo[2, 3-1)]pyridin-3-ylmethyl)-pyridin-2-yl]-amine (P-0227),
(6-Morpholin-4-yl-pyridin-2-ylmethyl)-[5-(1H-pyrrolo[2, 3-1)]pyridin-3-ylmethyl)-pyridin-2-yl]-amine (P-0228),
(3-Fluoro-pyridin-2-ylmethyl)-[5-(1H-pyrrolo[2, 3-1)]pyridin-3-ylmethyl)-pyridin-2-yl]-amine (P-0229),
(5-Fluoro-pyridin-3-ylmethyl)-[5-(1H-pyrrolo[2, 3-1)]pyridin-3-ylmethyl)-pyridin-2-yl]-amine (P-0230),
(2,4-Dichloro-benzyl)-[5-(1H-pyrrolo[2, 3-1)]pyridin-3-ylmethyl)-pyridin-2-yl]-amine (P-0342),
(3-Fluoro-benzyl)-[5-(1H-pyrrolo[2, 3-1)]pyridin-3-ylmethyl)-pyridin-2-yl]-amine (P-0343),
(2-Fluoro-4-trifluoromethyl-benzyl)-[5-(1H-pyrrolo[2, 3-1)]pyridin-3-ylmethyl)-pyridin-2-yl]-amine (P-0344),
(4-Chloro-2-fluoro-benzyl)-[5-(1H-pyrrolo[2, 3-1)]pyridin-3-ylmethyl)-pyridin-2-yl]-amine (P-0345),
(3-Fluoro-5-trifluoromethyl-benzyl)-[5-(1H-pyrrolo[2, 3-1)]pyridin-3-ylmethyl)-pyridin-2-yl]-amine (P-0346),
(2-Morpholin-4-yl-pyridin-3-ylmethyl)-[5-(1H-pyrrolo[2, 3-1)]pyridin-3-ylmethyl)-pyridin-2-yl]-amine (P-0347),
(4-Chloro-3-trifluoromethyl-benzyl)-[5-(1H-pyrrolo[2, 3-1)]pyridin-3-ylmethyl)-pyridin-2-yl]-amine (P-0348),
(2-Chloro-5-trifluoromethyl-benzyl)-[5-(1H-pyrrolo[2, 3-1)]pyridin-3-ylmethyl)-pyridin-2-yl]-amine (P-0349),
(2-Fluoro-5-trifluoromethyl-benzyl)-[5-(1H-pyrrolo[2, 3-1)]pyridin-3-ylmethyl)-pyridin-2-yl]-amine (P-0350),
(2,3-Dichloro-benzyl)-[5-(1H-pyrrolo[2,3-b]pyridin-3-ylmethyl)-pyridin-2-yl]-amine (P-0351),
(2-Fluoro-3-methoxy-benzyl)-[5-(1H-pyrrolo[2,3-b]pyridin-3-ylmethyl)-pyridin-2-yl]-amine (P-0352), Dimethyl-(5-{[5-(1H-pyrrolo[2,3-b]pyridin-3-ylmethyl)-pyridin-2-ylamino]-methyl}-pyrimidin-2-yl)-amine (P-0353),
(3-Chloro-2-fluoro-benzyl)-[5-(1H-pyrrolo[2,3-b]pyridin-3-ylmethyl)-pyridin-2-yl]-amine (P-0354),
(5-Fluoro-pyridin-2-ylmethyl)-[5-(1H-pyrrolo[2,3-b]pyridin-3-ylmethyl)-pyridin-2-yl]-amine (P-0355),
(3,5-Difluoro-benzyl)-[5-(1H-pyrrolo[2,3-b]pyridin-3-ylmethyl)-pyridin-2-yl]-amine (P-0356),
(2-Propoxy-benzyl)-[5-(1H-pyrrolo[2,3-b]pyridin-3-ylmethyl)-pyridin-2-yl]-amine (P-0357),
(2-Morpholin-4-yl-benzyl)-[5-(1H-pyrrolo[2,3-b]pyridin-3-ylmethyl)-pyridin-2-yl]-amine (P-0358),
(2-Chloro-3-methoxy-benzyl)-[5-(1H-pyrrolo[2,3-b]pyridin-3-ylmethyl)-pyridin-2-yl]-amine (P-0359),
(2-Fluoro-6-trifluoromethyl-benzyl)-[5-(1H-pyrrolo[2,3-b]pyridin-3-ylmethyl)-pyridin-2-yl]-amine (P-0360),
[2-(2-Morpholin-4-yl-ethoxy)-benzyl]-[5-(1H-pyrrolo[2,3-b]pyridin-3-ylmethyl)-pyridin-2-yl]-amine (P-0361),
(2,3-Difluoro-benzyl)-[5-(1H-pyrrolo[2,3-b]pyridin-3-ylmethyl)-pyridin-2-yl]-amine (P-0362),
(2-Chloro-3-trifluoromethyl-benzyl)-[5-(1H-pyrrolo[2,3-b]pyridin-3-ylmethyl)-pyridin-2-yl]-amine (P-0363),
(2-Chloro-5-fluoro-benzyl)-[5-(1H-pyrrolo[2,3-b]pyridin-3-ylmethyl)-pyridin-2-yl]-amine (P-0364),
(2-Fluoro-3-trifluoromethyl-benzyl)-[5-(1H-pyrrolo[2,3-b]pyridin-3-ylmethyl)-pyridin-2-yl]-amine (P-0365),
(5-Fluoro-2-methoxy-benzyl)-[5-(1H-pyrrolo[2,3-b]pyridin-3-ylmethyl)-pyridin-2-yl]-amine (P-0366),
(2-Difluoromethoxy-benzyl)-[5-(1H-pyrrolo[2,3-b]pyridin-3-ylmethyl)-pyridin-2-yl]-amine (P-0367),
(2-Fluoro-4-methyl-benzyl)-[5-(1H-pyrrolo[2,3-b]pyridin-3-ylmethyl)-pyridin-2-yl]-amine (P-0368),
[2-(3-Dimethylamino-propoxy)-benzyl]-[5-(1H-pyrrolo[2,3-b]pyridin-3-ylmethyl)-pyridin-2-yl]-amine (P-0369),
(2,6-Dimethoxy-pyridin-3-ylmethyl)-[5-(1H-pyrrolo[2,3-b]pyridin-3-ylmethyl)-pyridin-2-yl]-amine (P-0370),
(2-Fluoro-5-methoxy-benzyl)-[5-(1H-pyrrolo[2,3-b]pyridin-3-ylmethyl)-pyridin-2-yl]-amine (P-0371),
(4-Fluoro-2-methyl-benzyl)-[5-(1H-pyrrolo[2,3-b]pyridin-3-ylmethyl)-pyridin-2-yl]-amine (P-0372),
(3-Chloro-5-fluoro-benzyl)-[5-(1H-pyrrolo[2,3-b]pyridin-3-ylmethyl)-pyridin-2-yl]-amine (P-0373),
(6-Cyclopentyloxy-pyridin-3-ylmethyl)-[5-(1H-pyrrolo[2,3-b]pyridin-3-ylmethyl)-pyridin-2-yl]-amine (P-0374),
(5-Fluoro-2-trifluoromethyl-benzyl)-[5-(1H-pyrrolo[2,3-b]pyridin-3-ylmethyl)-pyridin-2-yl]-amine (P-0375),
[5-(1H-Pyrrolo[2,3-b]pyridin-3-ylmethyl)-pyridin-2-yl]-[2-(2,2,2-trifluoro-ethoxy)-pyridin-3-ylmethyl]-amine (P-0376),
Propane-1-sulfonic acid (2-fluoro-3-{[5-(1H-pyrrolo[2,3-b]pyridin-3-ylmethyl)-pyridin-2-ylamino]-methyl}-phenyl)-amide (P-0377),
(2,5-Dichloro-benzyl)-[5-(1H-pyrrolo[2,3-b]pyridin-3-ylmethyl)-pyridin-2-yl]-amine (P-0380),
Pyrimidin-5-ylmethyl-[5-(1H-pyrrolo[2,3-b]pyridin-3-ylmethyl)-pyridin-2-yl]-amine (P-0381),
(5-Chloro-2-fluoro-benzyl)-[5-(1H-pyrrolo[2,3-b]pyridin-3-ylmethyl)-pyridin-2-yl]-amine (P-0382),
(2-Ethyl-benzyl)-[5-(1H-pyrrolo[2,3-b]pyridin-3-ylmethyl)-pyridin-2-yl]-amine (P-0383),
2,2-Dimethyl-N-(3-{[5-(1H-pyrrolo[2,3-b]pyridin-3-ylmethyl)-pyridin-2-ylamino]-methyl}-pyridin-2-yl)-propionamide (P-0384),
Methyl-(3-{[5-(1H-pyrrolo[2,3-b]pyridin-3-ylmethyl)-pyridin-2-ylamino]-methyl}-pyridin-2-yl)-amine (P-0385),
Methyl-(5-{[5-(1H-pyrrolo[2,3-b]pyridin-3-ylmethyl)-pyridin-2-ylamino]-methyl}-pyrimidin-2-yl)-amine (P-0386),
(2-Chloro-4-methanesulfonyl-benzyl)-[5-(1H-pyrrolo[2,3-b]pyridin-3-ylmethyl)-pyridin-2-yl]-amine (P-0387),
(5-Fluoro-2-methyl-benzyl)-[5-(1H-pyrrolo[2,3-b]pyridin-3-ylmethyl)-pyridin-2-yl]-amine (P-0397),
(2,2-Difluoro-benzo[1,3]dioxol-4-ylmethyl)-[5-(1H-pyrrolo[2,3-b]pyridin-3-ylmethyl)-pyridin-2-yl]-amine (P-0398),
Dimethyl-(3-{[5-(1H-pyrrolo[2,3-b]pyridin-3-ylmethyl)-pyridin-2-ylamino]-methyl}-pyridin-2-yl)-amine (P-0399),
(5-Chloro-pyridin-3-ylmethyl)-[5-(1H-pyrrolo[2,3-b]pyridin-3-ylmethyl)-pyridin-2-yl]-amine (P-0400), and
(2-Methoxy-pyrimidin-5-ylmethyl)-[5-(1H-pyrrolo[2,3-b]pyridin-3-ylmethyl)-pyridin-2-yl]-amine (P-0401).

The following table indicates the aldehyde (Column 2) used in Step 1 of Scheme 195 to provide the compounds (Column 3). Column 1 provides the compound number and Column 4 the experimental mass spectrometry result.

| Compound number | Aldehyde | Compound | MS(ESI) $[M + H^+]^+$ observed |
|---|---|---|---|
| P-0211 | | | 329.1 |
| P-0212 | | | 351.1 |

-continued

| Compound number | Aldehyde | Compound | MS(ESI) [M + H⁺]⁺ observed |
|---|---|---|---|
| P-0213 | 2-fluorobenzaldehyde | | 338.1 |
| P-0214 | 3-bromoisonicotinaldehyde | | 395.9 |
| P-0215 | 2-methoxynicotinaldehyde | | 345.9 |
| P-0216 | 2-chlorobenzaldehyde | | 349.1 |
| P-0217 | 2-methylbenzaldehyde | | 329.1 |
| P-0218 | 1-methyl-1H-benzimidazole-2-carbaldehyde | | 369.1 |

-continued

| Compound number | Aldehyde | Compound | MS(ESI) [M + H⁺]⁺ observed |
|---|---|---|---|
| P-0219 | | | 345.9 |
| P-0220 | | | 355.1 |
| P-0221 | | | 367.1 |
| P-0222 | | | 345.9 |
| P-0223 | | | 334.3 |
| P-0224 | | | 345.9 |

-continued
| Compound number | Aldehyde | Compound | MS(ESI) [M + H+]+ observed |
|---|---|---|---|
| P-0225 | 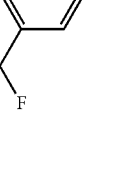 | 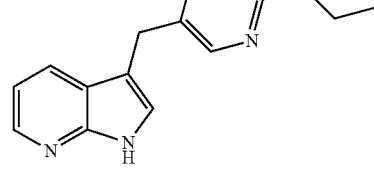 | 401.1 |
| P-0226 | 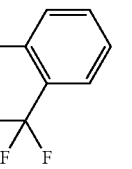 | 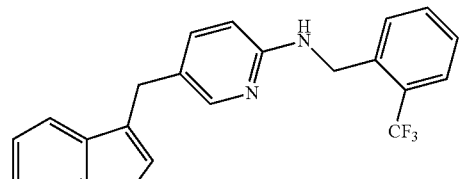 | 383.1 |
| P-0227 | 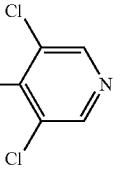 | 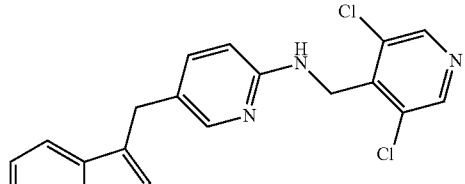 | 383.9 |
| P-0228 | 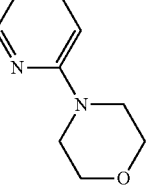 | 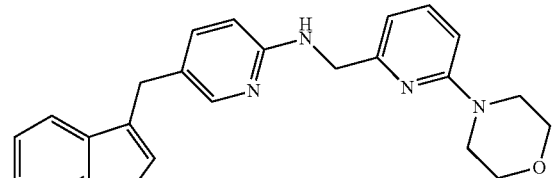 | 401.1 |
| P-0229 | 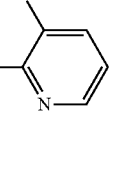 | 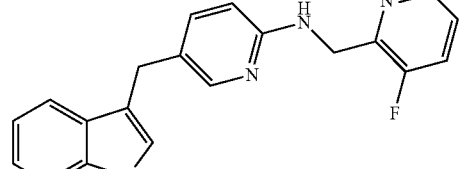 | 334.3 |
| P-0230 | 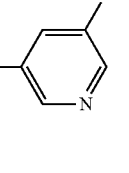 | 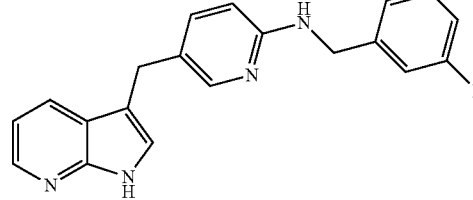 | 334.3 |

| Compound number | Aldehyde | Compound | MS(ESI) [M + H+]+ observed |
|---|---|---|---|
| P-0342 | 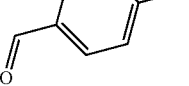 | 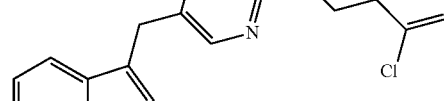 | 383.1 |
| P-0343 | 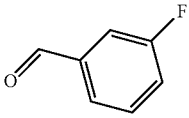 | 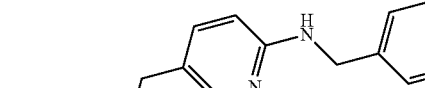 | 333.1 |
| P-0344 | 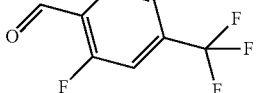 | 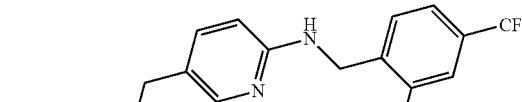 | 401.1 |
| P-0345 | 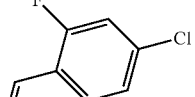 |  | 367.1 |
| P-0346 | 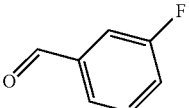 | 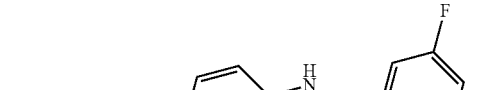 | 401.1 |
| P-0347 | 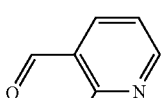 |  | 401.1 |

-continued

| Compound number | Aldehyde | Compound | MS(ESI) [M + H⁺]⁺ observed |
|---|---|---|---|
| P-0348 | | | 417.1 |
| P-0349 | | | 417.1 |
| P-0350 | | | 401.1 |
| P-0351 | | | 383.1 |
| P-0352 | | | 363.1 |
| P-0353 | | | 360.3 |

-continued

| Compound number | Aldehyde | Compound | MS(ESI) [M + H⁺]⁺ observed |
|---|---|---|---|
| P-0354 | 3-chloro-2-fluorobenzaldehyde | 7-azaindole-pyridine-CH₂NH-(3-chloro-2-fluorophenyl) | 367.1 |
| P-0355 | 5-fluoropyridine-2-carbaldehyde | 7-azaindole-pyridine-CH₂NH-(5-fluoropyridin-2-yl) | 334.3 |
| P-0356 | 2,4-difluorobenzaldehyde | 7-azaindole-pyridine-CH₂NH-(3,5-difluorophenyl) | 351.1 |
| P-0357 | 2-propoxybenzaldehyde | 7-azaindole-pyridine-CH₂NH-(2-propoxyphenyl) | 373.1 |
| P-0358 | 2-morpholinobenzaldehyde | 7-azaindole-pyridine-CH₂NH-(2-morpholinophenyl) | 400.3 |
| P-0359 | 2-chloro-3-methoxybenzaldehyde | 7-azaindole-pyridine-CH₂NH-(2-chloro-3-methoxyphenyl) | 379.1 |

-continued

| Compound number | Aldehyde | Compound | MS(ESI) [M + H⁺]⁺ observed |
|---|---|---|---|
| P-0360 | | | 401.1 |
| P-0361 | | | 444.3 |
| P-0362 | | | 351.1 |
| P-0363 | | | 417.1 |
| P-0364 | | | 367.1 |
| P-0365 | | | 401.1 |

-continued

| Compound number | Aldehyde | Compound | MS(ESI) [M + H⁺]⁺ observed |
|---|---|---|---|
| P-0366 | | | 363.1 |
| P-0367 | | | 381.1 |
| P-0368 | | | 347.1 |
| P-0369 | | | 416.3 |
| P-0370 | | | 376.3 |
| P-0371 | | | 363.1 |

-continued

| Compound number | Aldehyde | Compound | MS(ESI) [M + H⁺]⁺ observed |
|---|---|---|---|
| P-0372 | | | 347.1 |
| P-0373 | | | 367.1 |
| P-0374 | | | 400.3 |
| P-0375 | | | 401.1 |
| P-0376 | | | 413.9 |
| P-0377 | | | 453.9 |

-continued
| Compound number | Aldehyde | Compound | MS(ESI) [M + H+]+ observed |
|---|---|---|---|
| P0380 | 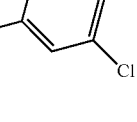 | 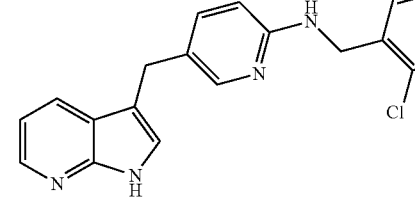 | 383.1 |
| P-0381 | 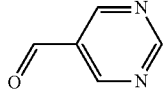 | 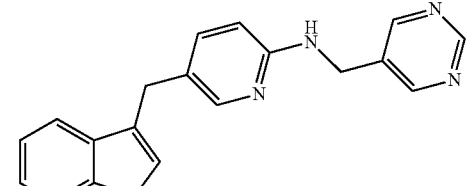 | 317.2 |
| P-0382 | 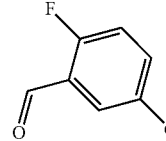 | 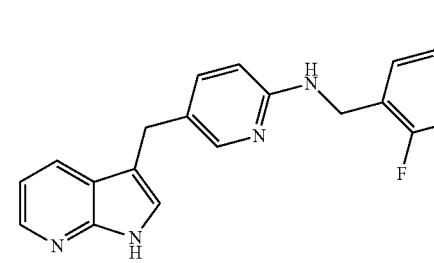 | 367.1 |
| P-0383 | 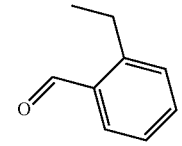 | 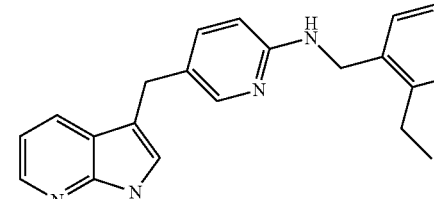 | 343.1 |
| P-0384 | 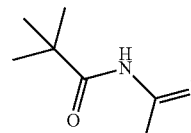 | 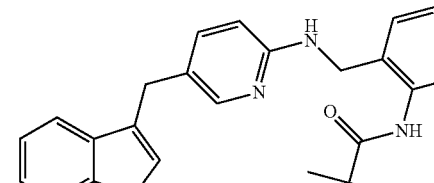 | 415.2 |
| P-0385 | 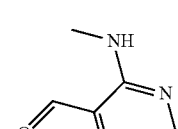 | 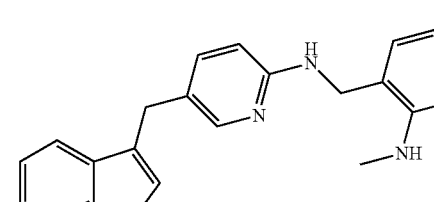 | 345.4 |

-continued

| Compound number | Aldehyde | Compound | MS(ESI) [M + H+]+ observed |
| --- | --- | --- | --- |
| P-0386 | | | 345.2 |
| P-0387 | | | 427.1 |
| P-0397 | | | 347.1 |
| P-0398 | | | 396.1 |
| P-0399 | | | 359.1 |
| P-0400 | | | 350.3 |

| Compound number | Aldehyde | Compound | MS(ESI) [M + H⁺]⁺ observed |
|---|---|---|---|
| P-0401 | (pyrimidine-5-carbaldehyde with 2-methoxy) | (pyrrolopyridine-pyridine-NH-CH2-methoxypyrimidine structure) | 347.1 |

Example 79

Synthesis of [4-Chloro-5-(5-chloro-1H-pyrrolo[2,3-b]pyridin-3-ylmethyl)-thiazol-2-yl]-(6-methoxy-pyridin-3-ylmethyl)-amine P-0190

[4-Chloro-5-(5-chloro-1H-pyrrolo[2,3-b]pyridin-3-ylmethyl)-thiazol-2-yl]-(6-methoxy-pyridin-3-ylmethyl)-amine P-0190 was synthesized in 2 steps from 5-(1-benzenesulfonyl-5-chloro-1H-pyrrolo[2,3-b]pyridin-3-ylmethyl)-4-chloro-thiazol-2-ylamine 592 as shown in Scheme 196.

Scheme 196

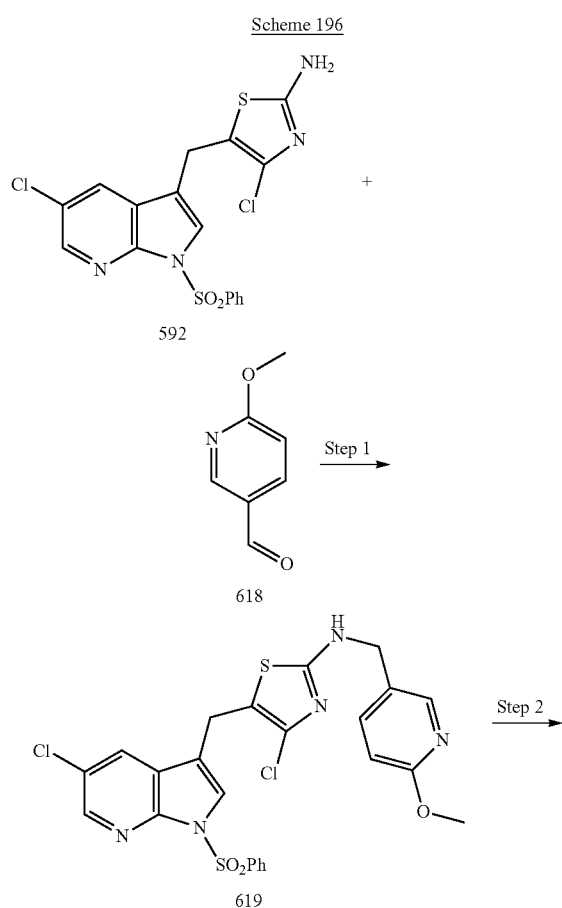

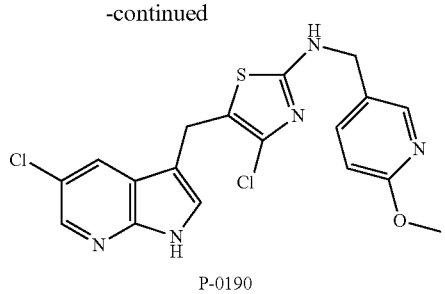

P-0190

Step I—Preparation of [5-(1-benzenesulfonyl-5-chloro-1H-pyrrolo[2,3-b]pyridin-3-ylmethyl)-4-chloro-thiazol-2-yl]-(6-methoxy-pyridin-3-ylmethyl)-amine (619)

5-(1-Benzenesulfonyl-5-chloro-1H-pyrrolo[2,3-b]pyridin-3-ylmethyl)-4-chloro-thiazol-2-ylamine (592, 30 mg, 0.083 mmol, prepared as described in Example 66, Scheme 183) was combined with 6-methoxy-pyridine-3-carbaldehyde (618, 26.2 mg, 0.165 mmol) in a 2 mL microwave reaction vial. The mixture was dissolved in ethanol: acetic acid (95:5, 0.6 mL). Silica supported cyanoborohydride (1.0 mmol/g, 83 mg, 0.083 mmol) was added and the mixture was irradiated with microwave on 300 watts for 5 minutes at 100° C. The silica was separated by centrifuging and the supernatant solution was decanted. The silica residue was rinsed with ethanol (0.500 mL) and centrifuged. The solvents were combined and removed under reduced pressure to give the desired compound 619, which was used without further purification.

Step II—Preparation of [4-chloro-5-(5-chloro-1H-pyrrolo[2,3-b]pyridin-3-ylmethyl)-thiazol-2-yl]-(6-methoxy-pyridin-3-ylmethyl)-amine (P-0190)

[5-(1-Benzenesulfonyl-1H-pyrrolo[2,3-b]pyridin-3-ylmethyl)-4-chloro-thiazol-2-yl]-(6-methoxy-pyridin-3-ylmethyl)-amine 619 was combined with methanol: potassium hydroxide (1M) (1:1, 0.5 mL). The mixture was heated at 80° C. for 2 hours. Acetic acid (0.1 mL) was added and the solvents removed under reduced pressure. The remaining residue was dissolved in dimethylsulfoxide (0.4 mL) and purified by reverse phase HPLC on a Phenomenex column (50 mm×10 mm ID) eluting with 0.1% trifluoroacetic acid in water and 20-100% acetonitrile with 0.1% trifluoroacetic acid over 16 minutes at a flow rate of 6 mL/minute to provide the desired compound P-0190. MS (ESI) [M+H$^+$]$^+$=419.9.

Additional compounds were prepared following the protocol of Scheme 196, replacing 6-methoxy-pyridine-3-carbaldehyde 618 with a suitable aldehyde in Step 1. The following compounds were made following this procedure:

[4-Chloro-5-(5-chloro-1H-pyrrolo[2,3-b]pyridin-3-ylmethyl)-thiazol-2-yl]-thiazol-2-ylmethyl-amine (P-0189),
Benzyl-[4-chloro-5-(5-chloro-1H-pyrrolo[2,3-b]pyridin-3-ylmethyl)-thiazol-2-yl]-amine (P-0192),
[4-Chloro-5-(5-chloro-1H-pyrrolo[2,3-b]pyridin-3-ylmethyl)-thiazol-2-yl]-(3-methoxy-benzyl)-amine (P-0193),
(4-Chloro-benzyl)-[4-chloro-5-(5-chloro-1H-pyrrolo[2,3-b]pyridin-3-ylmethyl)-thiazol-2-yl]-amine (P-0194),
[4-Chloro-5-(5-chloro-1H-pyrrolo[2,3-b]pyridin-3-ylmethyl)-thiazol-2-yl]-(4-fluoro-benzyl)-amine (P-0195),
[4-Chloro-5-(5-chloro-1H-pyrrolo[2,3-b]pyridin-3-ylmethyl)-thiazol-2-yl]-(2,4-dimethyl-thiazol-5-ylmethyl)-amine (P-0196),
[4-Chloro-5-(5-chloro-1H-pyrrolo[2,3-b]pyridin-3-ylmethyl)-thiazol-2-yl]-(2-ethyl-5-methyl-3H-imidazol-4-ylmethyl)-amine (P-0197),
[4-Chloro-5-(5-chloro-1H-pyrrolo[2,3-b]pyridin-3-ylmethyl)-thiazol-2-yl]-(2-ethyl-2H-pyrazol-3-ylmethyl)-amine (P-0198),
[4-Chloro-5-(5-chloro-1H-pyrrolo[2,3-b]pyridin-3-ylmethyl)-thiazol-2-yl]-(6-methoxy-pyridin-2-ylmethyl)-amine (P-0199),
[4-Chloro-5-(5-chloro-1H-pyrrolo[2,3-b]pyridin-3-ylmethyl)-thiazol-2-yl]-(3-fluoro-pyridin-4-ylmethyl)-amine (P-0200),
[4-Chloro-5-(5-chloro-1H-pyrrolo[2,3-b]pyridin-3-ylmethyl)-thiazol-2-yl]-(2-methyl-thiazol-4-ylmethyl)-amine (P-0201),
[4-Chloro-5-(5-chloro-1H-pyrrolo[2,3-b]pyridin-3-ylmethyl)-thiazol-2-yl]-(4-methyl-thiazol-5-ylmethyl)-amine (P-0202),
[4-Chloro-5-(5-chloro-1H-pyrrolo[2,3-b]pyridin-3-ylmethyl)-thiazol-2-yl]-(5-chloro-pyridin-2-ylmethyl)-amine (P-0203),
[4-Chloro-5-(5-chloro-1H-pyrrolo[2,3-b]pyridin-3-ylmethyl)-thiazol-2-yl]-pyridin-3-ylmethyl-amine (P-0236),
[4-Chloro-5-(5-chloro-1H-pyrrolo[2,3-b]pyridin-3-ylmethyl)-thiazol-2-yl]-pyridin-4-ylmethyl-amine (P-0237),
[4-Chloro-5-(5-chloro-1H-pyrrolo[2,3-b]pyridin-3-ylmethyl)-thiazol-2-yl]-(3-chloro-pyridin-4-ylmethyl)-amine (P-0238),
[4-Chloro-5-(5-chloro-1H-pyrrolo[2,3-b]pyridin-3-ylmethyl)-thiazol-2-yl]-(1-ethyl-1H-pyrazol-4-ylmethyl)-amine (P-0239),
[4-Chloro-5-(5-chloro-1H-pyrrolo[2,3-b]pyridin-3-ylmethyl)-thiazol-2-yl]-(5-fluoro-pyridin-2-ylmethyl)-amine (P-0240),
[4-Chloro-5-(5-chloro-1H-pyrrolo[2,3-b]pyridin-3-ylmethyl)-thiazol-2-yl]-(5-methoxy-pyridin-3-ylmethyl)-amine (P-0241),
[4-Chloro-5-(5-chloro-1H-pyrrolo[2,3-b]pyridin-3-ylmethyl)-thiazol-2-yl]-(6-trifluoromethyl-pyridin-3-ylmethyl)-amine (P-0242),
[4-Chloro-5-(5-chloro-1H-pyrrolo[2,3-b]pyridin-3-ylmethyl)-thiazol-2-yl]-(2-chloro-6-fluoro-benzyl)-amine (P-0243),
[4-Chloro-5-(5-chloro-1H-pyrrolo[2,3-b]pyridin-3-ylmethyl)-thiazol-2-yl]-phenethyl-amine (P-0244),
[4-Chloro-5-(5-chloro-1H-pyrrolo[2,3-b]pyridin-3-ylmethyl)-thiazol-2-yl]-(2,4-difluoro-benzyl)-amine (P-0245),
[4-Chloro-5-(5-chloro-1H-pyrrolo[2,3-b]pyridin-3-ylmethyl)-thiazol-2-yl]-(2-fluoro-benzyl)-amine (P-0246),
[4-Chloro-5-(5-chloro-1H-pyrrolo[2,3-b]pyridin-3-ylmethyl)-thiazol-2-yl]-(2-methoxy-pyridin-3-ylmethyl)-amine (P-0247),
(2-Chloro-benzyl)-[4-chloro-5-(5-chloro-1H-pyrrolo[2,3-b]pyridin-3-ylmethyl)-thiazol-2-yl]-amine (P-0248),
[4-Chloro-5-(5-chloro-1H-pyrrolo[2,3-b]pyridin-3-ylmethyl)-thiazol-2-yl]-(2-methyl-benzyl)-amine (P-0249),
[4-Chloro-5-(5-chloro-1H-pyrrolo[2,3-b]pyridin-3-ylmethyl)-thiazol-2-yl]-(2-chloro-4-fluoro-benzyl)-amine (P-0250),
[4-Chloro-5-(5-chloro-1H-pyrrolo[2,3-b]pyridin-3-ylmethyl)-thiazol-2-yl]-(3-fluoro-pyridin-2-ylmethyl)-amine (P-0251),
[4-Chloro-5-(5-chloro-1H-pyrrolo[2,3-b]pyridin-3-ylmethyl)-thiazol-2-yl]-(6-morpholin-4-yl-pyridin-2-ylmethyl)-amine (P-0252),
[4-Chloro-5-(5-chloro-1H-pyrrolo[2,3-b]pyridin-3-ylmethyl)-thiazol-2-yl]-(3,5-dichloro-pyridin-4-ylmethyl)-amine (P-0253),
[4-Chloro-5-(5-chloro-1H-pyrrolo[2,3-b]pyridin-3-ylmethyl)-thiazol-2-yl]-(2-trifluoromethyl-benzyl)-amine (P-0254), and
[4-Chloro-5-(5-chloro-1H-pyrrolo[2,3-b]pyridin-3-ylmethyl)-thiazol-2-yl]-(6-methyl-pyridin-2-ylmethyl)-amine (P-0255).

The following table indicates the aldehyde (Column 2) used in Step 1 of Scheme 196 to provide the compounds (Column 3). Column 1 provides the compound number and Column 4 the experimental mass spectrometry result.

| Compound number | Aldehyde | Compound | MS(ESI) [M + H$^+$]$^+$ observed |
|---|---|---|---|
| P-0189 | | | 395.9 |

-continued

| Compound number | Aldehyde | Compound | MS(ESI) [M + H⁺]⁺ observed |
|---|---|---|---|
| P-0192 | benzaldehyde | | 389.1 |
| P-0193 | 3-methoxybenzaldehyde | | 419.1 |
| P-0194 | 4-chlorobenzaldehyde | | 425.1 |
| P-0195 | 4-fluorobenzaldehyde | | 407.1 |
| P-0196 | 2,4-dimethylthiazole-5-carbaldehyde | | 423.9 |
| P-0197 | 2-ethyl-4-methyl-1H-imidazole-5-carbaldehyde | | 421.1 |

-continued

| Compound number | Aldehyde | Compound | MS(ESI) [M + H+]+ observed |
|---|---|---|---|
| P-0198 | | | 407.1 |
| P-0199 | | | 419.9 |
| P-0200 | | | 407.9 |
| P-0201 | | | 409.9 |
| P-0202 | | | 409.9 |
| P-0203 | | | 423.9 |

-continued
| Compound number | Aldehyde | Compound | MS(ESI) [M + H+]+ observed |
|---|---|---|---|
| P-0236 | 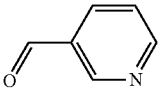 | 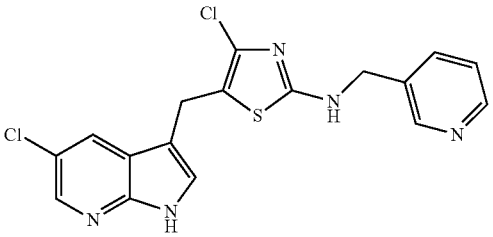 [SMILES: Clc1cnc2[nH]cc(Cc3sc(NCc4cccnc4)nc3Cl)c2c1] | 390.3 |
| P-0237 | 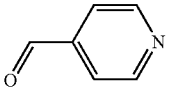 | 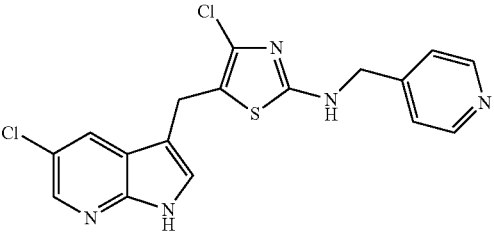 [SMILES: Clc1cnc2[nH]cc(Cc3sc(NCc4ccncc4)nc3Cl)c2c1] | 390.3 |
| P-0238 | 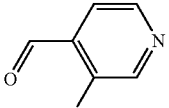 | 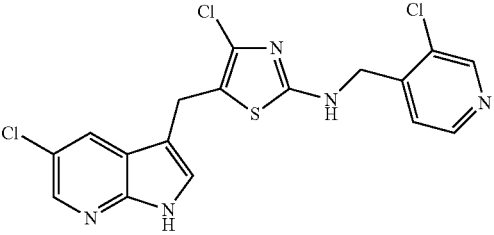 [SMILES: Clc1cnc2[nH]cc(Cc3sc(NCc4ccncc4Cl)nc3Cl)c2c1] | 425.9 |
| P-0239 | 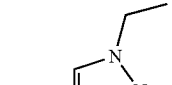 | 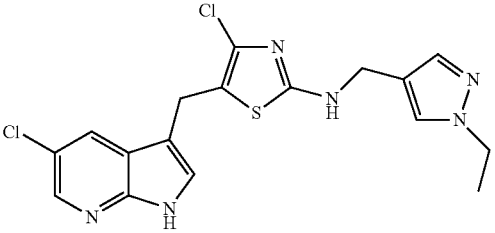 [SMILES: CCn1cc(CNc2nc(Cl)c(Cc3c[nH]c4ncc(Cl)cc34)s2)cn1] | 407.1 |
| P-0240 | 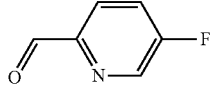 | 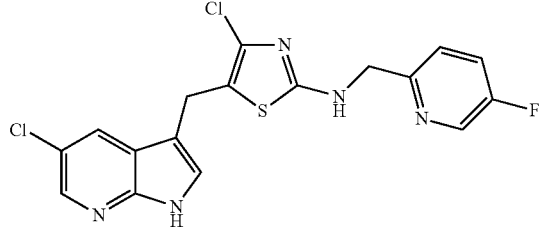 | 407.9 |
| P-0241 | 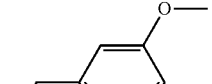 | 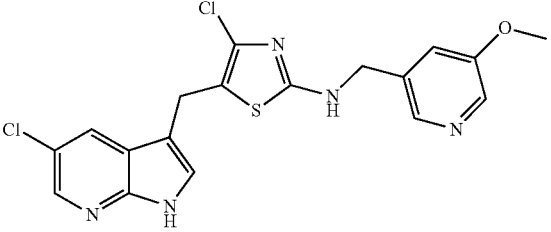 [SMILES: COc1cncc(CNc2nc(Cl)c(Cc3c[nH]c4ncc(Cl)cc34)s2)c1] | 419.9 |

-continued

| Compound number | Aldehyde | Compound | MS(ESI) [M + H⁺]⁺ observed |
|---|---|---|---|
| P-0242 | | | 458.3 |
| P-0243 | | | 443.1 |
| P-0244 | | | 403.1 |
| P-0245 | | | 424.7 |
| P-0246 | | | 407.1 |
| P-0247 | | | 419.9 |

-continued

| Compound number | Aldehyde | Compound | MS(ESI) [M + H⁺]⁺ observed |
|---|---|---|---|
| P-0248 | | | 424.7 |
| P-0249 | | | 403.1 |
| P-0250 | | | 441.1 |
| P-0251 | | | 407.9 |
| P-0252 | | | 475.1 |
| P-0253 | | | 459.9 |

-continued

| Compound number | Aldehyde | Compound | MS(ESI) [M + H⁺]⁺ observed |
|---|---|---|---|
| P-0254 | | | 457.1 |
| P-0255 | | | 404.3 |

Additional compounds were prepared following the protocol of Scheme 196, replacing 5-(1-benzenesulfonyl-5-chloro-1H-pyrrolo[2,3-b]pyridin-3-ylmethyl)-4-chloro-thiazol-2-ylamine 592 with 5-(1-benzenesulfonyl-1H-pyrrolo[2,3-b]pyridin-3-ylmethyl)-4-chloro-thiazol-2-ylamine 593 (prepared as described in Example 66, Scheme 183) in addition to replacing 6-methoxy-pyridine-3-carbaldehyde 618 with a suitable aldehyde in Step 1. The following compounds were made following this procedure:

[4-Chloro-5-(1H-pyrrolo[2,3-b]pyridin-3-ylmethyl)-thiazol-2-yl]-(2,4-dimethyl-thiazol-5-ylmethyl)-amine (P-0204),

[4-Chloro-5-(1H-pyrrolo[2,3-b]pyridin-3-ylmethyl)-thiazol-2-yl]-(2-ethyl-5-methyl-3H-imidazol-4-ylmethyl)-amine (P-0205),

[4-Chloro-5-(1H-pyrrolo[2,3-b]pyridin-3-ylmethyl)-thiazol-2-yl]-(5-fluoro-pyridin-2-ylmethyl)-amine (P-0206),

[4-Chloro-5-(1H-pyrrolo[2,3-b]pyridin-3-ylmethyl)-thiazol-2-yl]-(5-methoxy-pyridin-3-ylmethyl)-amine (P-0207),

[4-Chloro-5-(1H-pyrrolo[2,3-b]pyridin-3-ylmethyl)-thiazol-2-yl]-(4,5-dimethyl-thiophen-2-ylmethyl)-amine (P-0208),

[4-Chloro-5-(1H-pyrrolo[2,3-b]pyridin-3-ylmethyl)-thiazol-2-yl]-(2,5-dimethyl-thiophen-3-ylmethyl)-amine (P-0209), The following table indicates the aldehyde (Column 2) used in Step 1 of Scheme 196 to provide the compounds (Column 3). Column 1 provides the compound number and Column 4 the experimental mass spectrometry result.

| Compound number | Aldehyde | Compound | MS(ESI) [M + H⁺]⁺ observed |
|---|---|---|---|
| P-0204 | | | 390.3 |
| P-0205 | | | 387.1 |

-continued
| Compound number | Aldehyde | Compound | MS(ESI) [M + H⁺]⁺ observed |
|---|---|---|---|
| P-0206 | | | 373.9 |
| P-0207 | | | 386.3 |
| P-0208 | | | 389.1 |
| P-0209 | | | 389.1 |
Example 80
Synthesis of 5-[1-(1H-pyrrolo[2,3-b]pyridin-3-yl)-ethyl]-pyridin-2-yl-(4-trifluoromethyl-benzyl)-amine P-0388
5-[1-(1H-Pyrrolo[2,3-b]pyridin-3-yl)-ethyl]-pyridin-2-yl-(4-trifluoromethyl-benzyl)-amine P-0388 was synthesized from (5-bromo-pyridin-2-yl)-(4-trifluoromethyl-benzyl)-amine 17 as shown in Scheme 197.
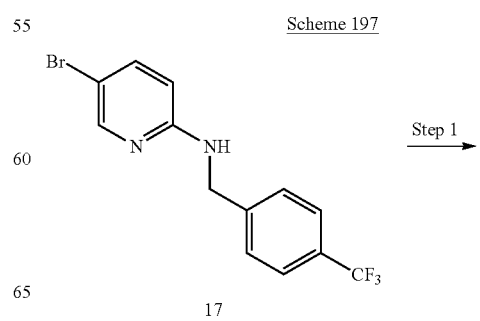
Scheme 197
Step 1

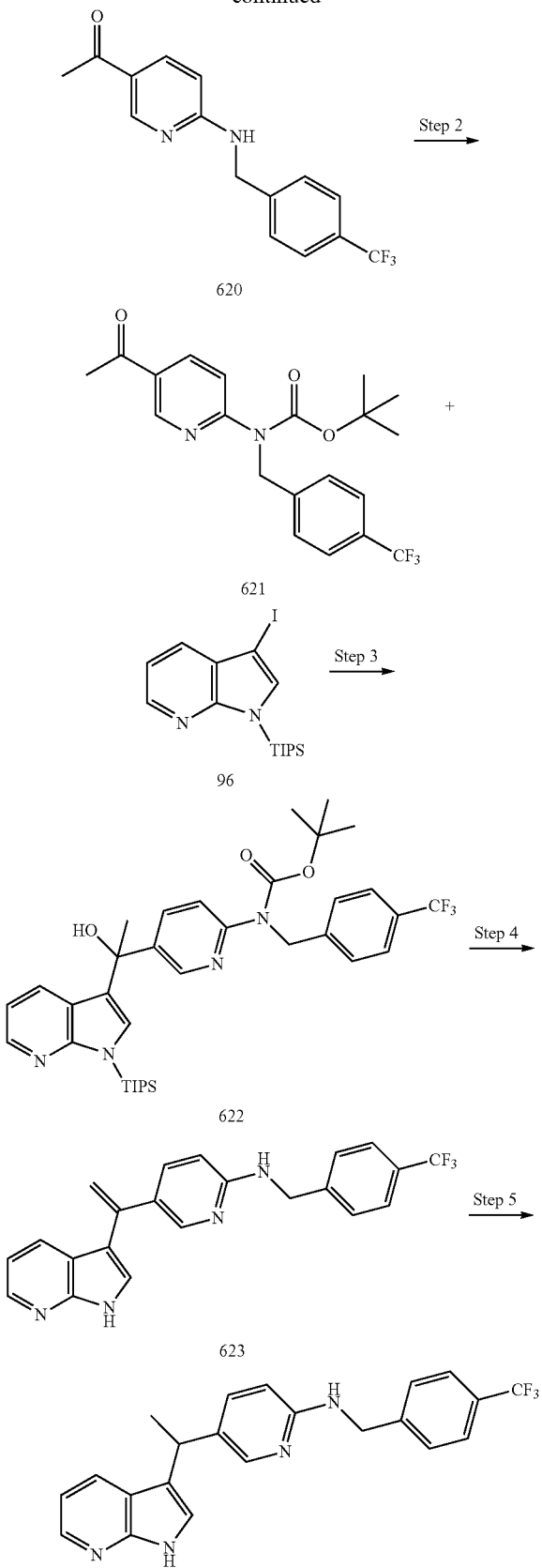

Step 1—Preparation of 1-[6-(4-trifluoromethyl-benzylamino)-pyridin-3-yl]-ethanone (620)

(5-Bromo-pyridin-2-yl)-(4-trifluoromethyl-benzyl)-amine (17, 3.00 g, 9.06 mmol, prepared as described in Example 10, Scheme 12) was dissolved in tetrahydrofuran (80 mL). The reaction was cooled at −78° C. under an atmosphere of argon. 2.5 M n-butyllithium in hexane (10.9 mL) was added. The reaction was stirred at −78° C. for 60 minutes. N-Methoxy-N-methylacetamide (1.93 mL, 18.1 mmol) was added to the reaction, which was allowed to warm to room temperature. The reaction was poured into 1M ammonium chloride and brine and extracted with ethyl acetate. The organic portions were dried with anhydrous sodium sulfate, filtered and the filtrate was adsorbed onto silica. The mixture was purified by silica gel chromatography (ethyl acetate: hexanes) to provide the desired compound as an oil that crystallized to a white solid (620, 1.328 g, 50%), consistent with the compound structure by $^1$H-NMR and MS (ESI): [M+H$^+$]$^+$=295.3.

Step 2—Preparation of (5-acetyl-pyridin-2-yl)-(4-trifluoromethyl-benzyl)-carbamic acid tert-butyl ester (621)

To 1-[6-(4-trifluoromethyl-benzylamino)-pyridin-3-yl]-ethanone (620, 1.30 g, 4.42 mmol) in tetrahydrofuran (15.0 mL) were added di-tert-butyldicarbonate (1.10 g, 5.04 mmol), 4-dimethylaminopyridine (0.0259 g, 0.21 mmol) and N,N-diisopropylethylamine (0.888 mL, 5.10 mmol) under an atmosphere of nitrogen. The reaction was stirred at room temperature for 3 days. The mixture was extracted with ethyl acetate and saturated sodium bicarbonate. The organic portions were dried with anhydrous sodium sulfate, filtered and the filtrate was adsorbed onto silica. The mixture was purified by silica gel chromatography (0-15% ethyl acetate:hexanes) to provide the desired compound as an oil that solidified to a white solid (621, 1.29 g, 74%), consistent with the compound structure by $^1$H-NMR.

Step 3—Preparation of 1-[6-(4-trifluoromethyl-benzylamino)-pyridin-3-yl]-1-(1-triisopropylsilanyl-1H-pyrrolo[2,3-b]pyridin-3-yl)-ethanol (622)

3-Iodo-1-triisopropylsilanyl-1H-pyrrolo[2,3-b]pyridine (96, 485.9 mg, 1.21 mmol) was dissolved in tetrahydrofuran (8 mL) at −20° C. under an atmosphere of nitrogen. 2.0 M isopropylmagnesium chloride in tetrahydrofuran (0.655 mL) was added. The reaction was stirred at −20° C. for 1 hour. Into the reaction was added (5-acetyl-pyridin-2-yl)-(4-trifluoromethyl-benzyl)-carbamic acid tert-butyl ester (621, 300.0 mg, 0.76 mmol) in tetrahydrofuran (6 mL) The reaction was allowed to warm to room temperature overnight. The mixture was extracted with ethyl acetate and saturated sodium bicarbonate. The organic portions were dried with anhydrous sodium sulfate, filtered and the filtrate was adsorbed onto silica. The mixture was purified by silica gel chromatography on the (ethyl acetate:hexanes), to provide the desired compound as an oil (622, 125 mg, 29%), consistent with the compound structure by $^1$H-NMR.

Step 4—Preparation of 5-[1-(1H-pyrrolo[2,3-b]pyridin-3-yl)-vinyl]-pyridin-2-yl-(4-trifluoromethyl-benzyl)-amine (623)

1-[6-(4-Trifluoromethyl-benzylamino)-pyridin-3-yl]-1-(1-triisopropylsilanyl-1H-pyrrolo[2,3-b]pyridin-3-yl)-ethanol (622, 125.0 mg, 0.22 mmol) was dissolved in acetonitrile (11.7 mL) and trifluoroacetic acid (0.175 mL, 2.3 mmol) and triethylsilane (0.292 mL, 1.8 mmol) were added. The reaction was heated to reflux overnight. The reaction was concentrated, then washed with ethyl acetate and saturated sodium bicarbonate. The organic portions were dried with anhydrous sodium sulfate, filtered and the filtrate was adsorbed onto silica. The mixture was purified by silica gel chromatography (0-60% ethyl acetate:hexanes) to provide the desired compound (623, 43 mg, 50%), consistent with the compound structure by $^1$H-NMR.

Step 5—Preparation of 5-[1-(1H-pyrrolo[2,3-b]pyridin-3-yl)-ethyl]-pyridin-2-yl-(4-trifluoromethyl-benzyl)-amine (P-0388)

5-[1-(1H-Pyrrolo[2,3-b]pyridin-3-yl)-vinyl]-pyridin-2-yl-(4-trifluoromethyl-benzyl)-amine (623, 0.043 g, 0.00011 mol) was dissolved in tetrahydrofuran (10 mL) and methanol (10 mL). The reaction was shaken under an atmosphere of hydrogen (30 psi) overnight. The reaction was filtered through Celite and the filtrate adsorbed onto silica and purified by silica gel column chromatography (ethyl acetate:hexanes) to provide the desired compound as a white solid (P-0388, 2.1 mg, 5%), consistent with compound structure by $^1$H-NMR and MS (ESI): [M+H$^+$]$^+$=397.6.

Example 81

Synthesis of [5-(5-Chloro-1H-pyrrolo[2,3-b]pyridin-3-ylmethyl)-thiazol-2-yl]-(4-fluoro-benzyl)-amine P-0290

[5-(5-Chloro-1H-pyrrolo[2,3-b]pyridin-3-ylmethyl)-thiazol-2-yl]-(4-fluoro-benzyl)-amine P-0290 was synthesized in four steps from (4-fluoro-benzyl)-(4-chloro-5-formyl-thiazol-2-yl)-carbamic acid tert-butyl ester 624 as shown in Scheme 198.

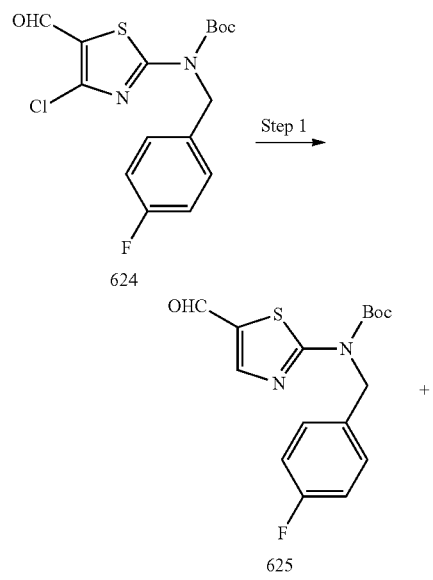

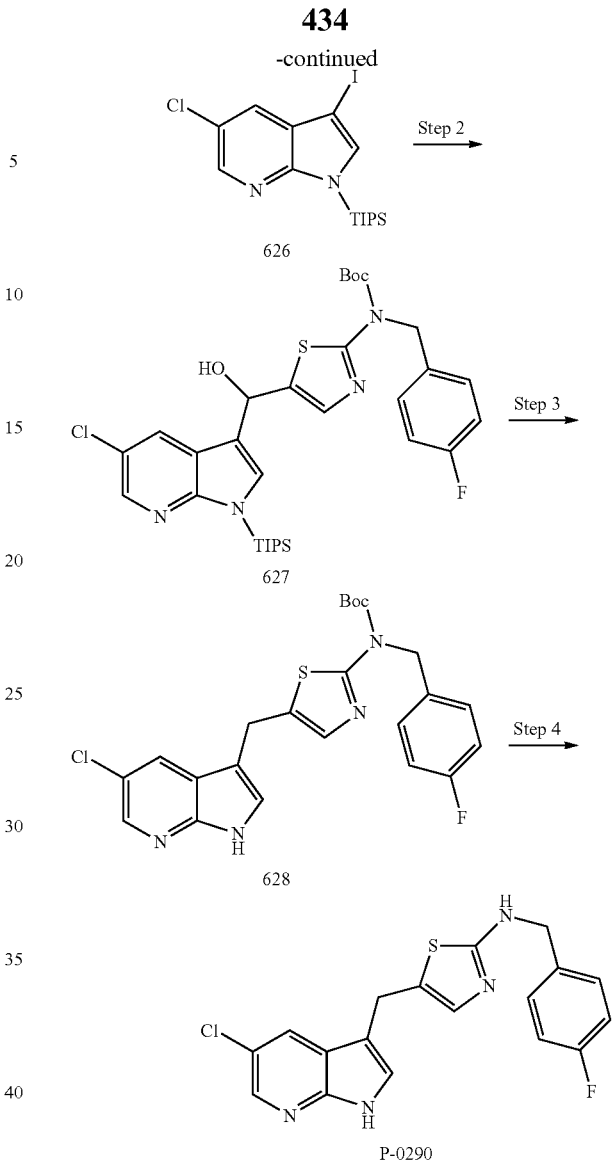

Step 1—Preparation of (4-fluoro-benzyl)-(4-chloro-5-formyl-thiazol-2-yl)-carbamic acid tert-butyl ester (625)

To a solution of (4-fluoro-benzyl)-(4-chloro-5-formyl-thiazol-2-yl)-carbamic acid tert-butyl ester (624, 1 g, 2.70 mmol, prepared as described in Example 44, Scheme 159, Step 2, where 4-(aminomethyl)pyridine 516 is replaced with p-fluorobenzylamine, i.e. intermediate in preparing compound P-0156) in methanol (100 mL) was added Pd/C (100 mg, 50% water wet) and sodium acetate (660 mg, 8.09 mmol) and the mixture was shaken under an atmosphere of hydrogen (50 psi) overnight observing 50% conversion by LCMS. The mixture was filtered over a bed of Celite and the solvent was removed in vacuo and the residue purified by silica gel chromatography (ethyl acetate/heptane) to provide the desired compound as an off-white solid (450 mg, 50%), consistent with compound structure by $^1$H-NMR.

Step 2—Preparation of {5-[(5-chloro-1-triisopropyl-silanyl-1H-pyrrolo[2,3-b]pyridin-3-yl)-hydroxy-methyl]-thiazol-2-yl}-(4-fluoro-benzyl)-carbamic acid tert-butyl ester (627)

To a solution of 5-chloro-3-iodo-1-(triisopropylsilyl)-1H-pyrrolo[2,3-b]pyridine (626, 300 mg, 0.69 mmol) in tetrahydrofuran (10 mL) at −20° C. was added dropwise iso-propyl-magnesium chloride (2M in tetrahydrofuran, 0.44 mL, 0.88 mmol). The reaction mixture was allowed to warm to 0° C. over 10 minutes and then cooled to −40° C. To this reaction mixture was added a solution of (4-fluoro-benzyl)-(4-chloro-5-formyl-thiazol-2-yl)-carbamic acid tert-butyl ester (625, 211 mg, 0.63 mmol) in tetrahydrofuran (5 mL). The reaction mixture was allowed to warm to 0° C. over 30 minutes and then quenched with brine (50 mL). The mixture was transferred to a separatory funnel and the layers were separated. The organic layer was dried over sodium sulfate and evaporated in vacuo to give the crude material which was purified by silica gel column chromatography (0-30% ethyl acetate/heptane) to provide the desired compound as a foam (120 mg, 30%), consistent with structure by $^1$H-NMR.

Step 3—Preparation of [5-(5-chloro-1H-pyrrolo[2,3-b]pyridin-3-ylmethyl)-thiazol-2-yl]-(4-fluoro-benzyl)-carbamic acid tert-butyl ester (628)

To a solution of {5-[(5-chloro-1-triisopropylsilanyl-1H-pyrrolo[2, 3-1)]pyridin-3-yl)-hydroxy-methyl]-thiazol-2-yl}-(4-fluoro-benzyl)-carbamic acid tert-butyl ester (627, 120 mg, 0.186 mmol) in acetonitrile (3 mL) was added trifluoroacetic acid (0.14 mL, 1.86 mmol) and triethylsilane (0.30 mL, 1.86 mmol). The resulting mixture was stirred for 2 hours at 40° C. The solvent was then removed in vacuo and the residue was used directly in the next step.

Step 4: Preparation of [5-(5-chloro-1H-pyrrolo[2,3-b]pyridin-3-ylmethyl)-thiazol-2-yl]-(4-fluoro-benzyl)-amine (P-0290)

To the solution of crude [5-(5-chloro-1H-pyrrolo[2,3-b]pyridin-3-ylmethyl)-thiazol-2-yl]-(4-fluoro-benzyl)-carbamic acid tert-butyl ester (628, 0.186 mmol theory) in dichloromethane (5 mL) at room temperature was added trifluoroacetic acid (1 mL) and the reaction was allowed to stir overnight. The solvent was removed in vacuo and the residue taken up in ethyl acetate and then washed with saturated aqueous potassium carbonate making sure basicity was reached. The layers were separated and the aqueous layer was back-extracted with ethyl acetate. The combined organic layers were dried over sodium sulfate and evaporated in vacuo to give the crude product which was purified by silica gel chromatography (0-10% methanol/ethyl acetate). The solvent was removed in vacuo and the material was triturated with dichloromethane to give the desired compound as an off-white solid (20 mg, 29% over 2 steps) consistent with compound structure by $^1$H-NMR and MS (ESI): [M+H$^+$]$^+$=372.9.

(4-Fluoro-benzyl)-[5-(1H-pyrrolo[2,3-b]pyridin-3-ylmethyl)-thiazol-2-yl]-amine P-0389

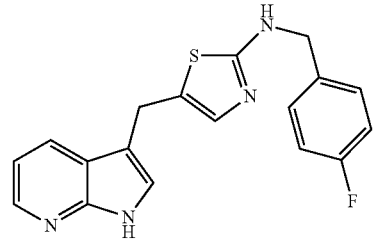 [SMILES: Fc1ccc(CNc2ncc(Cc3c[nH]c4ncccc34)s2)cc1]

was synthesized following the protocol of Scheme 198, replacing 5-chloro-3-iodo-1-(triisopropylsilyl)-1H-pyrrolo[2,3-b]pyridine 626 with 3-iodo-1-triisopropylsilanyl-1H-pyrrolo[2,3-b]pyridine 96, to provide the desired compound, consistent with structure by 1H-NMR and MS (ESI): [M+H$^+$]$^+$=339.0.

Example 82

Synthesis of (5-chloro-1H-pyrrolo[2,3-b]pyridin-3-yl)-[2-ethyl-5-(4-fluoro-benzylamino)-2H-pyrazol-3-yl]-methanone P-0184

(5-Chloro-1H-pyrrolo[2,3-b]pyridin-3-yl)-[2-ethyl-5-(4-fluoro-benzylamino)-2H-pyrazol-3-yl]-methanone P-0184 was synthesized from 5-chloro-1H-pyrrolo[2,3-b]pyridine 532 in 1 step as shown in Scheme 199.

Scheme 199

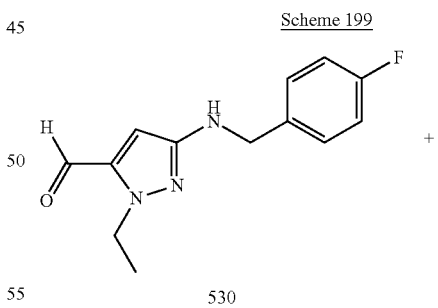

530

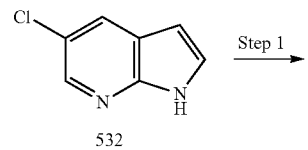

532

Step 1 →

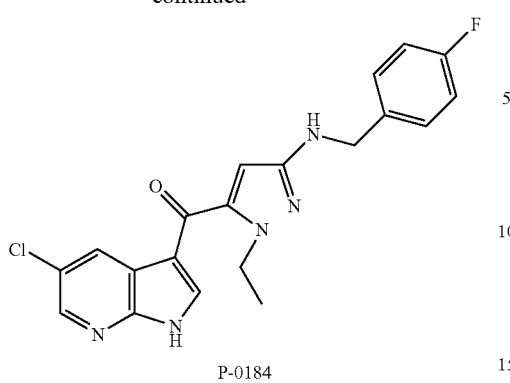

P-0184

Step 1—Synthesis of (5-chloro-1H-pyrrolo[2,3-b]pyridin-3-yl)-[2-ethyl-5-(4-fluoro-benzylamino)-2H-pyrazol-3-yl]-methanone (P-0184)

5-Chloro-1H-pyrrolo[2,3-b]pyridine (532, 0.068 g, 0.44 mmol) was combined with methanol (10 mL) and potassium hydroxide (0.16 g, 2.8 mmol). The mixture was stirred for 50 minutes, then 2-ethyl-5-(4-fluoro-benzylamino)-2H-pyrazole-3-carbaldehyde (530, 0.100 g, 0.40 mmol, prepared as described in Example 47, Scheme 162, Step 5) was added and the reaction was stirred overnight at room temperature and then concentrated. Ethyl acetate was added and the mixture was washed with sodium bicarbonate saturated solution and brine. After drying over anhydrous sodium sulfate the solvent was removed under reduced pressure. Purification with silica gel column chromatography eluting with a gradient of ethyl acetate (10-100%) in hexanes provided the desired compound (0.0033 g, 2%). MS (ESI) [M+H$^+$]$^+$=398.1.

Example 83

Synthesis of [5-(5-chloro-1H-pyrrolo[2,3-b]pyridin-3-ylmethyl)-1-ethyl-1H-pyrazol-3-yl]-(4-fluoro-benzyl)-amine P-0185

[5-(5-Chloro-1H-pyrrolo[2,3-b]pyridin-3-ylmethyl)-1-ethyl-1H-pyrazol-3-yl]-(4-fluoro-benzyl)-amine P-0185 was synthesized from 5-chloro-3-iodo-1-triisopropylsilanyl-1H-pyrrolo[2,3-b]pyridine 629 in 2 steps as shown in Scheme 200.

Scheme 200

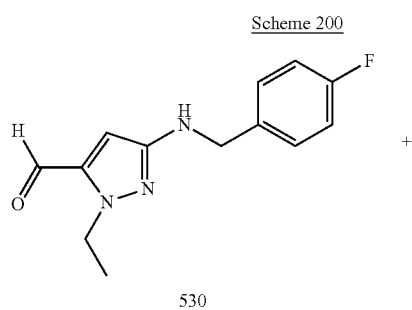

530

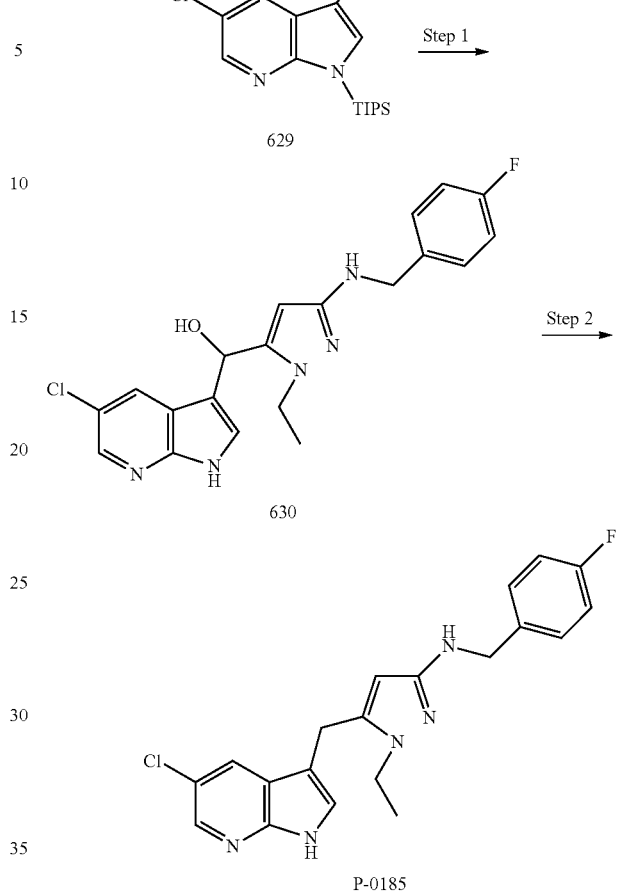

Step 1—Synthesis of (5-chloro-1H-pyrrolo[2,3-b]pyridin-3-yl)-[2-ethyl-5-(4-fluoro-benzylamino)-2H-pyrazol-3-yl]-methanol (630)

5-Chloro-3-iodo-1-triisopropylsilanyl-1H-pyrrolo[2,3-b]pyridine (629, 0.15 g, 0.34 mmol) was dissolved in tetrahydrofuran (3 mL, 40 mmol) and the solution was cooled to −20° C. 2 M isopropylmagnesium chloride in tetrahydrofuran (200 μL) was added dropwise and the reaction was stirred and allowed to warm to −5° C. After the reaction was cooled to −20° C., 2-ethyl-5-(4-fluoro-benzylamino)-2H-pyrazole-3-carbaldehyde (530, 0.043 g, 0.17 mmol, prepared as described in Example 47, Scheme 162, Step 5) in tetrahydrofuran (4 mL) was added to the mixture. The reaction was stirred to −5° C., then concentrated, ethyl acetate was added and the mixture was washed with sodium bicarbonate saturated solution and brine. After drying over anhydrous sodium sulfate, the solvent was removed under reduced pressure. Purification with silica gel column chromatography eluting with a gradient of ethyl acetate (5-80%) in hexanes gave the desired compound (630, 0.038 g, 40%).

Step 2—Synthesis of 5-(5-chloro-1H-pyrrolo[2,3-b]pyridin-3-ylmethyl)-1-ethyl-1H-pyrazol-3-yl]-(4-fluoro-benzyl)-amine (P-0185)

(5-Chloro-1-triisopropylsilanyl-1H-pyrrolo[2,3-b]pyridin-3-yl)-[2-ethyl-5-(4-fluoro-benzylamino)-2H-pyrazol-3- yl]-methanol (630, 0.045 g, 0.081 mmol) was dissolved in acetonitrile (5 mL) and triethylsilane (0.4 mL, 2.0 mmol) was added, followed by trifluoroacetic acid (0.2 mL, 2.0 mmol). The reaction was stirred at room temperature for 45 minutes, then stirred at 60° C. for 45 minutes. The solvent was removed under reduced pressure, ethyl acetate was added and the organic was washed with sodium bicarbonate saturated solution and brine. After drying over anhydrous sodium sulfate, the solvent was evaporated to dryness. Purification with silica gel column chromatography eluting with a gradient of ethyl acetate (40-100%) in hexanes gave the isolation of the desired compound (P-0185, 0.0068 g, 22%). MS (ESI) [M+H$^+$]$^+$=384.1.

Example 84

Synthesis of 3-2-Fluoro-6-[(5-fluoro-pyridin-3-ylmethyl)-amino]-pyridin-3-ylmethyl-1H-pyrrolo[2,3-b]pyridine-5-carbonitrile P-0415

3-2-Fluoro-6-[(5-fluoro-pyridin-3-ylmethyl)-amino]-pyridin-3-ylmethyl-1H-pyrrolo[2,3-b]pyridine-5-carbonitrile P-0415 was synthesized in 5 steps from 1H-Pyrrolo[2,3-b]pyridine-5-carbonitrile 632 as shown in Scheme 201.

Scheme 201

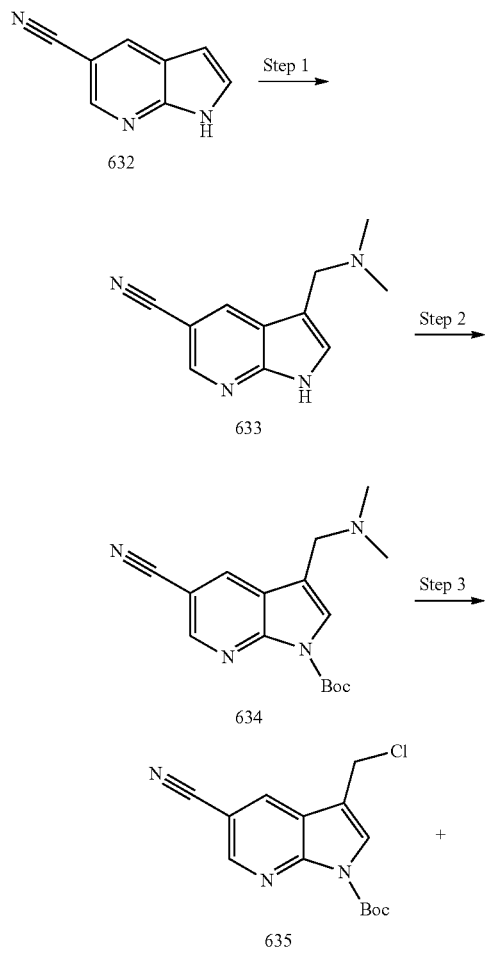

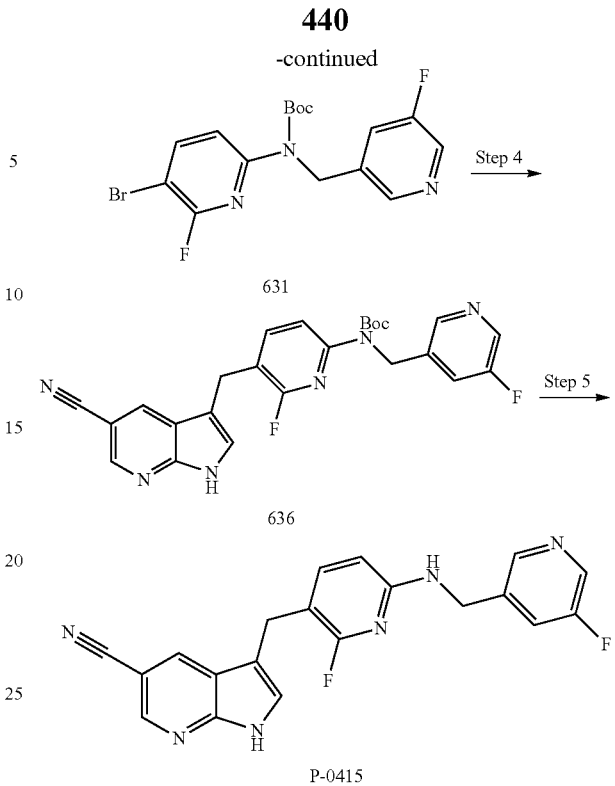

Step 1—Synthesis of 3-dimethylaminomethyl-1H-pyrrolo[2,3-b]pyridine-5-carbonitrile (633)

To 1H-Pyrrolo[2,3-b]pyridine-5-carbonitrile (632, 3.00 g, 0.0210 mol) in isopropyl alcohol (120 mL) were added dimethylamine hydrochloride (1.91 g, 0.0235 mol) and formaldehyde (0.708 g, 0.0236 mol). The reaction was heated to reflux overnight, then concentrated, poured into water, and extracted with ethyl acetate. The organic layer was dried over anhydrous sodium sulfate and filtered. The filtrate was concentrated and purified by silica gel column chromatography eluting with 5% to 30% methanol in dichloromethane containing 0.3% triethyl amine to give the desired compound (633, 2.0 g, 48%).

Step 2—Synthesis of 5-cyano-3-dimethylaminomethyl-pyrrolo[2,3-b]pyridine-1-carboxylic acid tert-butyl ester (634)

To 3-dimethylaminomethyl-1H-pyrrolo[2,3-b]pyridine-5-carbonitrile (633, 2.0 g, 0.010 mol) in tetrahydrofuran (60.0 mL) were added di-tert-butyldicarbonate (2.62 g, 0.0120 mol), 4-dimethylaminopyridine (0.12 g, 0.0010 mol) and triethylamine (4.0 mL, 0.029 mol). The reaction was stirred at 45° C. over a weekend, then concentrated, poured into aqueous potassium carbonate, and extracted with ethyl acetate. The organic layer was dried over anhydrous sodium sulfate and filtered. The filtrate was concentrated and purified by silica gel column chromatography eluting with 2% to 30% methanol in dichloromethane in hexane to give the desired compound (634, 2.50 g, 83%).

Step 3—Synthesis of 3-chloromethyl-5-cyano-pyrrolo[2,3-b]pyridine-1-carboxylic acid tert-butyl ester (635)

To 5-cyano-3-dimethylaminomethyl-pyrrolo[2,3-b]pyridine-1-carboxylic acid tert-butyl ester (634, 2.60 g, 8.66 mmol) in toluene (60.0 mL) under an atmosphere of nitrogen was added ethyl chloroformate (0.828 mL, 8.66 mmol). The reaction was stirred at room temperature for 3 hours, then poured into water and extracted with ethyl acetate. The organic layer was dried over anhydrous sodium sulfate and filtered. The filtrate was concentrated and purified by silica gel column chromatography eluting with 20% to 100% ethyl acetate in hexane to give a white solid (635, 400 mg, 16%).

Step 4—Synthesis of [5-(5-cyano-1H-pyrrolo[2,3-b]pyridin-3-ylmethyl)-6-fluoro-pyridin-2-yl]-(5-fluoro-pyridin-3-ylmethyl)-carbamic acid tert-butyl ester (636)

To (5-bromo-6-fluoro-pyridin-2-yl)-(5-fluoro-pyridin-3-ylmethyl)-carbamic acid tert-butyl ester (631, 0.600 g, 1.50 mmol, prepared as described in Example 60) in tetrahydrofuran (10.0 mL) at −25° C. under an atmosphere of nitrogen, was added a solution of isopropylmagnesium chloride (2.0 M in tetrahydrofuran, 0.730 mL). The reaction was allowed to warm to 5° C. over 1 hour. The reaction was cooled to −35° C., followed by addition of a solution of CuCN.2LiCl (0.65 M in tetrahydrofuran, 2.4 mL). After 5 minutes, 3-chloromethyl-5-cyano-pyrrolo[2,3-b]pyridine-1-carboxylic acid tert-butyl ester (635, 0.086 g, 0.29 mmol) in tetrahydrofuran (4.0 mL) was added to the reaction. The reaction was allowed to warm to room temperature over 1 hour, then poured into a diluted ammonia solution, and extracted with ethyl acetate. The organic layer was dried over anhydrous sodium sulfate and filtered. The filtrate was concentrated and purified by silica gel column chromatography eluting with 20% to 100% ethyl acetate in hexane to give the desired compound (636, 0.13 g, 92%). MS (ESI) [M+H$^+$]$^+$=477.4.

Step 5—Synthesis of 3-2-fluoro-6-[(5-fluoro-pyridin-3-ylmethyl)-amino]-pyridin-3-ylmethyl-1H-pyrrolo[2,3-b]pyridine-5-carbonitrile (P-0415)

To [5-(5-cyano-1H-pyrrolo[2,3-b]pyridin-3-ylmethyl)-6-fluoro-pyridin-2-yl]-(5-fluoro-pyridin-3-ylmethyl)-carbamic acid tert-butyl ester (636, 0.130 g, 0.27 mmol) in dichloromethane (10.0 mL) was added trifluoroacetic acid (1.00 mL, 0.0130 mol). The reaction was stirred at room temperature overnight. The reaction was concentrated, poured into aqueous potassium carbonate, and extracted with ethyl acetate. The organic layer was dried over anhydrous sodium sulfate and filtered. The filtrate was concentrated and purified by silica gel column chromatography eluting with 25% to 100% ethyl acetate in hexane to give a white solid (P-0415, 85.6 mg, 83.4%). MS (ESI) [M+H$^+$]$^+$=377.0.

(5-Fluoro-pyridin-3-ylmethyl)-[6-fluoro-5-(1H-pyrrolo[2,3-b]pyridin-3-ylmethyl)-pyridin-2-yl]-amine P-0414 was prepared following the protocol of Scheme 201, replacing 1H-Pyrrolo[2,3-b]pyridine-5-carbonitrile 632 with 1H-Pyrrolo[2,3-b]pyridine in Step 1. MS (ESI) [M+H$^+$]$^+$=352.5.

3-[6-(4-Chloro-benzylamino)-2-fluoro-pyridin-3-ylmethyl]-1H-pyrrolo[2,3-b]pyridine-5-carbonitrile P-0432

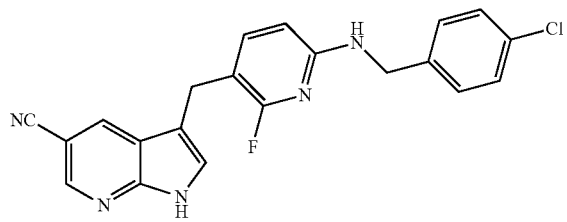 [SMILES: N#Cc1cnc2[nH]cc(Cc3ccc(NCc4ccc(Cl)cc4)nc3F)c2c1]

was prepared following the protocol of Scheme 201, replacing 5-bromo-6-fluoro-pyridin-2-yl)-(5-fluoro-pyridin-3-ylmethyl)-carbamic acid tert-butyl ester 631 with (5-Bromo-6-fluoro-pyridin-2-yl)-(4-chloro-benzyl)-carbamic acid tert-butyl ester 637 (prepared as described in Example 60) in Step 4. MS (ESI) [M+H$^+$]$^+$=391.9.

Example 85

Synthesis of (3-chloro-benzyl)-[5-(5-chloro-1H-pyrrolo[2,3-b]pyridin-3-ylmethyl)-1-methyl-1H-pyrazol-3-yl]-amine P-0410

(3-Chloro-benzyl)-[5-(5-chloro-1H-pyrrolo[2,3-b]pyridin-3-ylmethyl)-1-methyl-1H-pyrazol-3-yl]-amine P-0410 was synthesized in 11 steps from 1H-pyrazole-3,5-dicarboxylic acid monohydrate 638 as shown in Scheme 202.

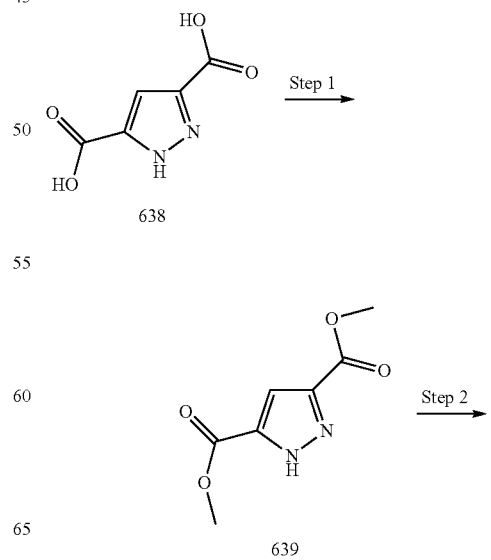

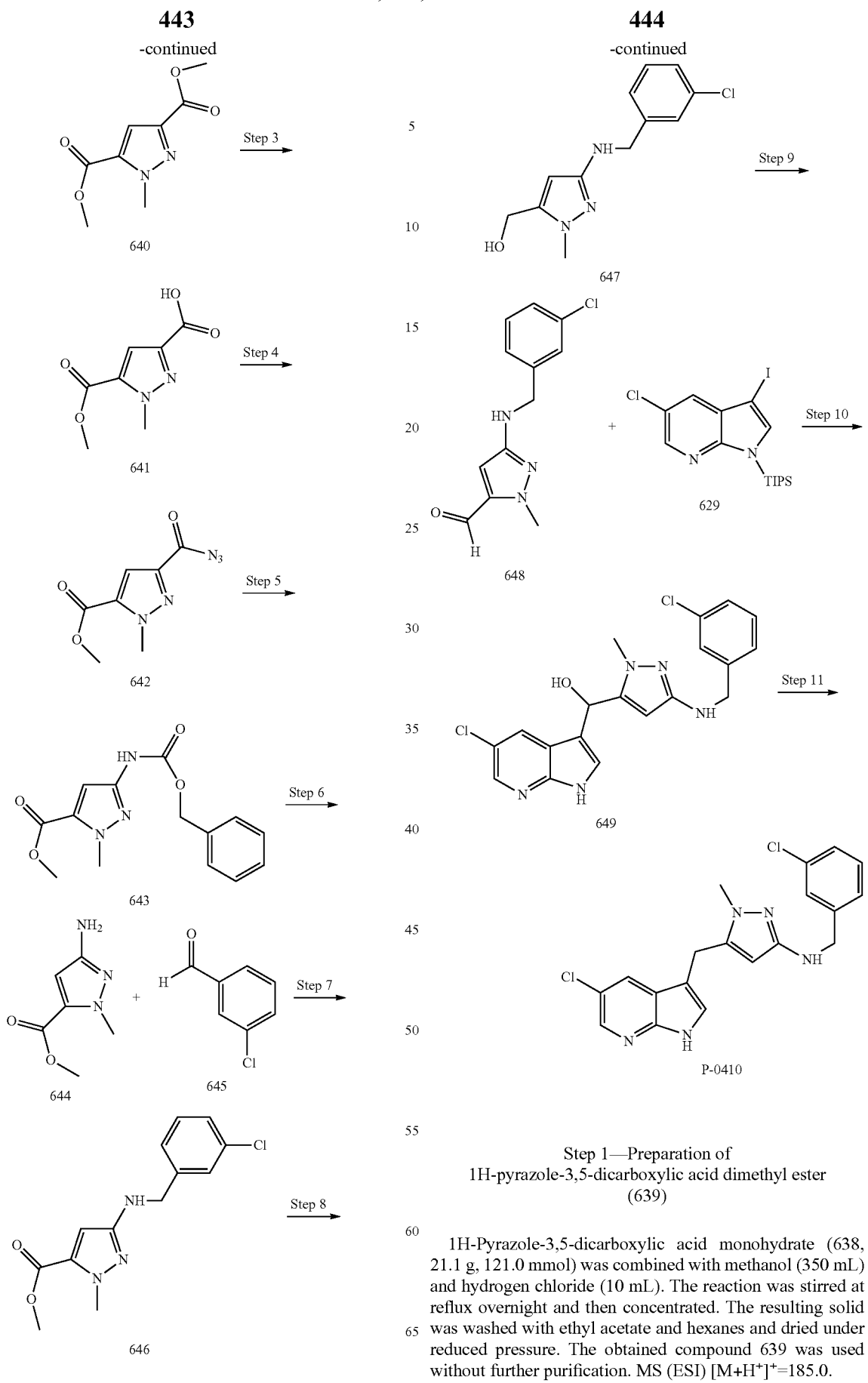

Step 1—Preparation of
1H-pyrazole-3,5-dicarboxylic acid dimethyl ester
(639)

1H-Pyrazole-3,5-dicarboxylic acid monohydrate (638, 21.1 g, 121.0 mmol) was combined with methanol (350 mL) and hydrogen chloride (10 mL). The reaction was stirred at reflux overnight and then concentrated. The resulting solid was washed with ethyl acetate and hexanes and dried under reduced pressure. The obtained compound 639 was used without further purification. MS (ESI) [M+H$^+$]$^+$=185.0.

Step 2—Preparation of 1-methyl-1H pyrazole-3,5-dicarboxylic acid dimethyl ester (640)

1H-Pyrazole-3,5-dicarboxylic acid dimethyl ester (639, 9.1 g, 49.0 mmol) was combined with acetone (400 mL) and potassium carbonate (10.2 g, 74.1 mmol). The mixture was stirred for 40 minutes under an atmosphere of nitrogen. To the stirring suspension, methyl iodide (3.4 mL, 54.0 mmol) was added dropwise. The reaction was stirred at room temperature overnight and then the solvent was evaporated under reduced pressure. The resulting solid was washed with water and filtered. After toluene was added, the solvent was removed under reduced pressure. The resulting compound 640 was used without further purification.

Step 3—Preparation of 1-methyl-1H-pyrazole-3,5-dicarboxylic acid 5-methyl ester (641)

1-Methyl-1H-pyrazole-3,5-dicarboxylic acid dimethyl ester (640, 3.7 g, 19.0 mmol) was combined with 1,4-dioxane (20 mL) and water (60 mL). Concentrated sulfuric acid (1.0 mL) in 2 mL of water was added to the solution. After the reaction was stirred at reflux overnight, it was cooled to room temperature and concentrated until precipitation began. The obtained mixture was left standing overnight. The resulting solid was filtered and dried under reduced pressure. The collected aqueous fractions were extracted with ethyl acetate. The organic portion was dried over anhydrous sodium sulfate and concentrated. Additional solid was crystallized from ethyl acetate to give the desired compound (641, 2.33 g, 68%). MS (ESI) $[M+H^+]^+=185.0$, melting point 175° C.

Step 4—Preparation of 5-azidocarbonyl-2-methyl-2H-pyrazole-3-carboxylic acid methyl ester (642)

1-Methyl-1H-pyrazole-3,5-dicarboxylic acid 5-methyl ester (641, 3.2 g, 17.0 mmol) was combined with thionyl chloride (5 mL). The reaction was heated to reflux for 40 minutes and then concentrated twice from toluene. The resulting solid was dried under reduced pressure overnight. The product was dissolved into acetone (20 mL) and sodium azide (3.5 g, 54.0 mmol) was added in water (10 mL) rapidly at once. The obtained solution was stirred for one minute and then poured into ice-water (50 mL). The precipitate was filtered and dried under reduced pressure. The final compound was used without further purification (642, 2.8 g, 77%).

Step 5—Preparation of 5-benzyloxycarbonylamino-2-methyl-2H-pyrazole-3-carboxylic acid methyl ester (643)

5-Azidocarbonyl-2-methyl-2H-pyrazole-3-carboxylic acid methyl ester (642, 2.8 g, 13.0 mmol) was combined with toluene (35 mL) and benzyl alcohol (2.1 mL, 20.0 mmol). The reaction was heated to reflux for 45 minutes and then the solvent was removed under reduced pressure. The compound (643, 2.4 g, 62%) was washed with methanol and dried under vacuum. MS (ESI) $[M+H^+]^+=290.3$.

Step 6—Preparation of 5-amino-2-methyl-2H-pyrazole-3-carboxylic acid methyl ester (644)

5-Benzyloxycarbonylamino-2-methyl-2H-pyrazole-3-carboxylic acid methyl ester (643, 2.2 g, 7.6 mmol) was combined with methanol (50 mL) and 10% palladium on carbon (500 mg). The mixture was stirred under an atmosphere of hydrogen for three hours. The mixture was filtered through Celite and the solvent was removed under reduced pressure to give the desired compound (644, 1.2 g, 98%). (ESI) $[M+H^+]^+=156.1$.

Step 7—Preparation of 5-(3-chloro-benzylamino)-2-methyl-2H-pyrazole-3-carboxylic acid methyl ester (646)

5-Amino-2-methyl-2H-pyrazole-3-carboxylic acid methyl ester (644, 1.3 g, 8.0 mmol) was combined with 3-chlorobenzaldehyde (645, 0.95 mL, 8.4 mmol) and acetonitrile (40 mL). Trifluoroacetic acid (3.2 mL, 42.0 mmol) was added followed by triethylsilane (6.7 mL, 42.0 mmol). The reaction was heated to reflux overnight and then concentrated. Ethyl acetate was added and the solution was washed with 1N potassium carbonate. The organic portion was dried over anhydrous sodium sulfate, filtered and concentrated. The compound (646, 0.944 g, 42%) was crystallized from a mixture of ethyl acetate:hexane.

Step 8—Preparation of [5-(3-chloro-benzylamino)-2-methyl-2H-pyrazol-3-yl]-methanol (647)

5-(3-Chloro-benzylamino)-2-methyl-2H-pyrazole-3-carboxylic acid methyl ester (646, 0.944 g, 3.37 mmol) was combined with tetrahydrofuran (20 mL) and the solution was cooled to −40° C. 1.0 M lithium tetrahydroaluminate in tetrahydrofuran (3.7 mL) was added and the reaction was stirred for 45 min at −20° C. 1.0 M lithium tetrahydroaluminate in tetrahydrofuran (3.7 mL) was added at −40° C. and the reaction was stirred to 10° C. Sodium sulfate decahydrate was added in small portions and the mixture was stirred for two hours at room temperature, then filtered through Celite and concentrated. The resulting compound (647, 0.821 g, 97%) was washed with a mixture of ethyl acetate:hexanes and dried under reduced pressure.

Step 9—Preparation of 5-(3-chloro-benzylamino)-2-methyl-2H-pyrazole-3-carbaldehyde (648)

[5-(3-Chloro-benzylamino)-2-methyl-2H-pyrazol-3-yl]-methanol (647, 0.821 g, 3.26 mmol) was combined with dichloromethane (70 mL) and manganese(IV) oxide (4 g). The reaction was stirred at room temperature overnight under an atmosphere of nitrogen. The mixture was filtered through Celite and concentrated. Purification by silica gel column chromatography eluting with a gradient of ethyl acetate (10-100%) in hexane gave the desired aldehyde (648, 0.482 g, 60%).

Step 10—Preparation of [5-(3-chloro-benzylamino)-2-methyl-2H-pyrazol-3-yl]-(5-chloro-1-triisopropylsilanyl-1H-pyrrolo[2,3-b]pyridin-3-yl)-methanol (649)

5-Chloro-3-iodo-1-triisopropylsilanyl-1H-pyrrolo[2,3-b]pyridine (629, 0.19 g, 0.44 mmol) was dissolved in tetrahydrofuran (0.9 mL). The solution was cooled to −20° C. 2M isopropylmagnesium chloride in tetrahydrofuran (200 µL) was added dropwise to the mixture, then stirred to −5° C. After the reaction was cooled to −20° C., 5-(3-chloro-benzylamino)-2-methyl-2H-pyrazole-3-carbaldehyde (648, 0.050 g, 0.20 mmol) in 2 mL of tetrahydrofuran was added at once to the mixture. The reaction was stirred to 0° C. and then concentrated. Ethyl acetate was added and the mixture was washed with sodium bicarbonate saturated solution and brine. The organic portion was dried over anhydrous sodium sulfate and concentrated. Purification with silica gel column chromatography eluting with a gradient of ethyl acetate (5-80%) in hexane gave the desired compound (649, 0.033 g, 30%). (ESI) [M+H$^+$]$^+$=558.3, 560.9.

Step 11—Preparation of (3-chloro-benzyl)-[5-(5-chloro-1H-pyrrolo[2,3-b]pyridin-3-ylmethyl)-1-methyl-1H-pyrazol-3-yl]-amine (P-0410)

[5-(3-Chloro-benzylamino)-2-methyl-2H-pyrazol-3-yl]-(5-chloro-1-triisopropylsilanyl-1H-pyrrolo[2,3-b]pyridin-3-yl)-methanol (649, 0.033 g, 0.059 mmol) was combined with dichloromethane (5 mL, 0.08 mol) and triethylsilane (200 µL, 1.0 mmol) was added, followed by trifluoroacetic acid (100 µL, 1.0 mmol). The reaction was stirred at room temperature overnight and then concentrated. Ethyl acetate was added and the organic portion was washed with 1 M potassium carbonate, dried over anhydrous sodium sulfate and concentrated. Purification with silica gel flash chromatography eluting with a gradient of methanol (2-20%) and dichloromethane followed by washes with a mixture of ethyl acetate:hexane gave the desired compound (P-0410, 0.0039 g, 17%). (ESI) [M+H$^+$]$^+$=387.30.

[5-(5-Chloro-1H-pyrrolo[2,3-b]pyridin-3-ylmethyl)-1-methyl-1H-pyrazol-3-yl]-(2,5-difluoro-benzyl)-amine P-0411 and [5-(5-chloro-1H-pyrrolo[2,3-b]pyridin-3-ylmethyl)-1-methyl-1H-pyrazol-3-yl]-(2-fluoro-benzyl)-amine P-0413,

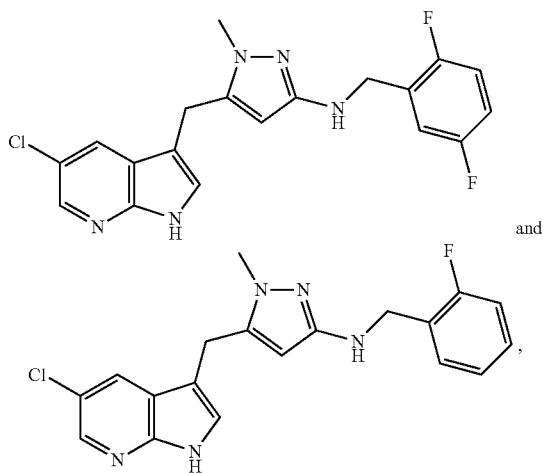

respectively,
were prepared following the protocol of Scheme 202, replacing 3-chlorobenzaldehyde 645 with 2,5-difluorobenzaldehyde and 2-fluorobenzaldehyde, respectively, in Step 7. (ESI) [M+H$^+$]$^+$=389.95 (P-0411) and 370.20 (P-0413).

Example 86

Additional Compounds

The following compounds of the invention were synthesized following the methods of the Examples above, or similar methods known to those of skill in the art:

3-(6-tert-Butoxy-pyridin-3-ylmethyl)-1H-pyrrolo[2,3-b]pyridine (P-0020),
3-(6-Methoxy-pyridin-3-ylmethyl)-4-thiophen-3-yl-1H-pyrrolo[2,3-b]pyridine (P-0022),
(6-Isobutylamino-pyridin-3-yl)-(1H-pyrrolo[2,3-b]pyridin-3-yl)-methanol (P-0029),
[6-(Cyclopropylmethyl-amino)-pyridin-3-yl]-(1H-pyrrolo[2,3-b]pyridin-3-yl)-methanol (P-0034),
[6-(Cyclohexylmethyl-amino)-pyridin-3-yl]-(1H-pyrrolo[2,3-b]pyridin-3-yl)-methanol (P-0035),
(1H-Pyrrolo[2,3-b]pyridin-3-yl)-[6-(4-trifluoromethyl-benzylamino)-pyridin-3-yl]-methanol (P-0036),
[6-(4-Chloro-benzylamino)-pyridin-3-yl]-(1H-pyrrolo[2,3-b]pyridin-3-yl)-methanol (P-0037),
(4-Chloro-benzyl)-{5-[methoxy-(1H-pyrrolo[2,3-b]pyridin-3-yl)-methyl]-pyridin-2-yl}-amine (P-0039),
(4-Chloro-3-trifluoromethyl-benzyl)-{5-[methoxy-(1H-pyrrolo[2,3-b]pyridin-3-yl)-methyl]-pyridin-2-yl}-amine (P-0040),
(4-Chloro-benzyl)-{5-[methoxy-(5-pyridin-3-yl-1H-pyrrolo[2,3-b]pyridin-3-yl)-methyl]-pyridin-2-yl}-amine (P-0041),
[6-(4-Chloro-benzylamino)-2-methyl-pyridin-3-yl]-(1H-pyrrolo[2,3-b]pyridin-3-yl)-methanol (P-0046),
[2,6-Bis-(4-chloro-benzylamino)-pyridin-3-yl]-(1H-pyrrolo[2,3-b]pyridin-3-yl)-methanone (P-0049), and
3-(2-Ethylsulfanyl-4,6-dimethyl-pyrimidin-5-ylmethyl)-1H-pyrrolo[2,3-b]pyridine (P-0052).

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, variations can be made to provide additional compounds of Formulae I, II or III, and all sub-embodiments thereof, and/or various methods of administration can be used. Thus, such additional embodiments are within the scope of the present invention and the following claims.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

SEQUENCE LISTING

SEQ ID NO: 1 Sequence NP_000213
Met Arg Gly Ala Arg Gly Ala Trp Asp Phe Leu Cys Val Leu Leu
Leu Leu Leu Arg Val Gln Thr Gly Ser Ser Gln Pro Ser Val Ser
Pro Gly Glu Pro Ser Pro Pro Ser Ile His Pro Gly Lys Ser Asp
Leu Ile Val Arg Val Gly Asp Glu Ile Arg Leu Leu Cys Thr Asp
Pro Gly Phe Val Lys Trp Thr Phe Glu Ile Leu Asp Glu Thr Asn
Glu Asn Lys Gln Asn Glu Trp Ile Thr Glu Lys Ala Glu Ala Thr
Asn Thr Gly Lys Tyr Thr Cys Thr Asn Lys His Gly Leu Ser Asn
Ser Ile Tyr Val Phe Val Arg Asp Pro Ala Lys Leu Phe Leu Val
Asp Arg Ser Leu Tyr Gly Lys Glu Asp Asn Asp Thr Leu Val Arg
Cys Pro Leu Thr Asp Pro Glu Val Thr Asn Tyr Ser Leu Lys Gly
Cys Gln Gly Lys Pro Leu Pro Lys Asp Leu Arg Phe Ile Pro Asp
Pro Lys Ala Gly Ile Met Ile Lys Ser Val Lys Arg Ala Tyr His
Arg Leu Cys Leu His Cys Ser Val Asp Gln Glu Gly Lys Ser Val
Leu Ser Glu Lys Phe Ile Leu Lys Val Arg Pro Ala Phe Lys Ala
Val Pro Val Val Ser Val Ser Lys Ala Ser Tyr Leu Leu Arg Glu
Gly Glu Glu Phe Thr Val Thr Cys Thr Ile Lys Asp Val Ser Ser
Ser Val Tyr Ser Thr Trp Lys Arg Glu Asn Ser Gln Thr Lys Leu
Gln Glu Lys Tyr Asn Ser Trp His His Gly Asp Phe Asn Tyr Glu
Arg Gln Ala Thr Leu Thr Ile Ser Ser Ala Arg Val Asn Asp Ser
Gly Val Phe Met Cys Tyr Ala Asn Asn Thr Phe Gly Ser Ala Asn
Val Thr Thr Thr Leu Glu Val Val Asp Lys Gly Phe Ile Asn Ile
Phe Pro Met Ile Asn Thr Thr Val Phe Val Asn Asp Gly Glu Asn
Val Asp Leu Ile Val Glu Tyr Glu Ala Phe Pro Lys Pro Glu His
Gln Gln Trp Ile Tyr Met Asn Arg Thr Phe Thr Asp Lys Trp Glu
Asp Tyr Pro Lys Ser Glu Asn Glu Ser Asn Ile Arg Tyr Val Ser
Glu Leu His Leu Thr Arg Leu Lys Gly Thr Glu Gly Gly Thr Tyr
Thr Phe Leu Val Ser Asn Ser Asp Val Asn Ala Ala Ile Ala Phe
Asn Val Tyr Val Asn Thr Lys Pro Glu Ile Leu Thr Tyr Asp Arg
Leu Val Asn Gly Met Leu Gln Cys Val Ala Ala Gly Phe Pro Glu
Pro Thr Ile Asp Trp Tyr Phe Cys Pro Gly Thr Glu Gln Arg Cys
Ser Ala Ser Val Leu Pro Val Asp Val Gln Thr Leu Asn Ser Ser
Gly Pro Pro Phe Gly Lys Leu Val Val Gln Ser Ser Ile Asp Ser
Ser Ala Phe Lys His Asn Gly Thr Val Glu Cys Lys Ala Tyr Asn
Asp Val Gly Lys Thr Ser Ala Tyr Phe Asn Phe Ala Phe Lys Gly

SEQUENCE LISTING

Asn Asn Lys Glu Gln Ile His Pro His Thr Leu Phe Thr Pro Leu
Leu Ile Gly Phe Val Ile Val Ala Gly Met Met Cys Ile Ile Val
Met Ile Leu Thr Tyr Lys Tyr Leu Gln Lys Pro Met Tyr Glu Val
Gln Trp Lys Val Val Glu Glu Ile Asn Gly Asn Asn Tyr Val Tyr
Ile Asp Pro Thr Gln Leu Pro Tyr Asp His Lys Trp Glu Phe Pro
Arg Asn Arg Leu Ser Phe Gly Lys Thr Leu Gly Ala Gly Ala Phe
Gly Lys Val Val Glu Ala Thr Ala Tyr Gly Leu Ile Lys Ser Asp
Ala Ala Met Thr Val Ala Val Lys Met Leu Lys Pro Ser Ala His
Leu Thr Glu Arg Glu Ala Leu Met Ser Glu Leu Lys Val Leu Ser
Tyr Leu Gly Asn His Met Asn Ile Val Asn Leu Leu Gly Ala Cys
Thr Ile Gly Gly Pro Thr Leu Val Ile Thr Glu Tyr Cys Cys Tyr
Gly Asp Leu Leu Asn Phe Leu Arg Arg Lys Arg Asp Ser Phe Ile
Cys Ser Lys Gln Glu Asp His Ala Glu Ala Ala Leu Tyr Lys Asn
Leu Leu His Ser Lys Glu Ser Ser Cys Ser Asp Ser Thr Asn Glu
Tyr Met Asp Met Lys Pro Gly Val Ser Tyr Val Val Pro Thr Lys
Ala Asp Lys Arg Arg Ser Val Arg Ile Gly Ser Tyr Ile Glu Arg
Asp Val Thr Pro Ala Ile Met Glu Asp Asp Glu Leu Ala Leu Asp
Leu Glu Asp Leu Leu Ser Phe Ser Tyr Gln Val Ala Lys Gly Met
Ala Phe Leu Ala Ser Lys Asn Cys Ile His Arg Asp Leu Ala Ala
Arg Asn Ile Leu Leu Thr His Gly Arg Ile Thr Lys Ile Cys Asp
Phe Gly Leu Ala Arg Asp Ile Lys Asn Asp Ser Asn Tyr Val Val
Lys Gly Asn Ala Arg Leu Pro Val Lys Trp Met Ala Pro Glu Ser
Ile Phe Asn Cys Val Tyr Thr Phe Glu Ser Asp Val Trp Ser Tyr
Gly Ile Phe Leu Trp Glu Leu Phe Ser Leu Gly Ser Ser Pro Tyr
Pro Gly Met Pro Val Asp Ser Lys Phe Tyr Lys Met Ile Lys Glu
Gly Phe Arg Met Leu Ser Pro Glu His Ala Pro Ala Glu Met Tyr
Asp Ile Met Lys Thr Cys Trp Asp Ala Asp Pro Leu Lys Arg Pro
Thr Phe Lys Gln Ile Val Gln Leu Ile Glu Lys Gln Ile Ser Glu
Ser Thr Asn His Ile Tyr Ser Asn Leu Ala Asn Cys Ser Pro Asn
Arg Gln Lys Pro Val Val Asp His Ser Val Arg Ile Asn Ser Val
Gly Ser Thr Ala Ser Ser Ser Gln Pro Leu Leu Val His Asp Asp
Val

SEQ ID NO: 2 Sequence NM_000222
   1 gatcccatcg cagctaccgc gatgagaggc gctcgcggcg cctgggattt tctctgcgtt 61 ctgctcctac tgcttcgcgt ccagacaggc tcttctcaac catctgtgag tccaggggaa 121 ccgtctccac catccatcca tccaggaaaa tcagacttaa tagtccgcgt gggcgacgag -continued

SEQUENCE LISTING

```
 181 attaggctgt tatgcactga tccgggcttt gtcaaatgga cttttgagat
cctggatgaa
 241 acgaatgaga ataagcagaa tgaatggatc acggaaaagg cagaagccac
caacaccggc
 301 aaatacacgt gcaccaacaa acacggctta agcaattcca tttatgtgtt
tgttagagat
 361 cctgccaagc ttttccttgt tgaccgctcc ttgtatggga aagaagacaa
cgacacgctg
 421 gtccgctgtc ctctcacaga cccagaagtg accaattatt ccctcaaggg
gtgccagggg
 481 aagcctcttc ccaaggactt gaggtttatt cctgacccca aggcgggcat
catgatcaaa
 541 agtgtgaaac gcgcctacca tcggctctgt ctgcattgtt ctgtggacca
ggagggcaag
 601 tcagtgctgt cggaaaaatt catcctgaaa gtgaggccag ccttcaaagc
tgtgcctgtt
 661 gtgtctgtgt ccaaagcaag ctatcttctt agggaagggg aagaattcac
agtgacgtgc
 721 acaataaaag atgtgtctag ttctgtgtac tcaacgtgga aaagagaaaa
cagtcagact
 781 aaactacagg agaaatataa tagctggcat cacggtgact tcaattatga
acgtcaggca
 841 acgttgacta tcagttcagc gagagttaat gattctggag tgttcatgtg
ttatgccaat
 901 aatacttttg gatcagcaaa tgtcacaaca accttggaag tagtagataa
aggattcatt
 961 aatatcttcc ccatgataaa cactacagta tttgtaaacg atggagaaaa
tgtagatttg
1021 attgttgaat atgaagcatt ccccaaacct gaacaccagc agtggatcta
tatgaacaga
1081 accttcactg ataaatggga agattatccc aagtctgaga atgaaagtaa
tatcagatac
1141 gtaagtgaac ttcatctaac gagattaaaa ggcaccgaag gaggcactta
cacattccta
1201 gtgtccaatt ctgacgtcaa tgctgccata gcatttaatg tttatgtgaa
tacaaaacca
1261 gaaatcctga cttacgacag gctcgtgaat ggcatgctcc aatgtgtggc
agcaggattc
```

| SEQUENCE LISTING |
| --- |
| 1321 ccagagccca aatagattg gtattttgt ccaggaactg agcagagatg
ctctgcttct
1381 gtactgccag tggatgtgca gacactaaac tcatctgggc caccgtttgg
aaagctagtg
1441 gttcagagtt ctatagattc tagtgcattc aagcacaatg gcacggttga
atgtaaggct
1501 tacaacgatg tgggcaagac ttctgcctat tttaactttg catttaaagg
taacaacaaa
1561 gagcaaatcc atccccacac cctgttcact cctttgctga ttggtttcgt
aatcgtagct
1621 ggcatgatgt gcattattgt gatgattctg acctacaaat atttacagaa
acccatgtat
1681 gaagtacagt ggaaggttgt tgaggagata aatggaaaca attatgttta
catagaccca
1741 acacaacttc cttatgatca caaatgggag tttcccagaa acaggctgag
ttttgggaaa
1801 accctgggtg ctggagcttt cgggaaggtt gttgaggcaa ctgcttatgg
cttaattaag
1861 tcagatgcgg ccatgactgt cgctgtaaag atgctcaagc cgagtgccca
tttgacagaa
1921 cgggaagccc tcatgtctga actcaaagtc ctgagttacc ttggtaatca
catgaatatt
1981 gtgaatctac ttgagcctg caccattgga gggcccaccc tggtcattac
agaatattgt
2041 tgctatggtg atcttttgaa tttttgaga agaaaacgtg attcatttat
ttgttcaaag
2101 caggaagatc atgcagaagc tgcacttat aagaatcttc tgcattcaaa
ggagtcttcc
2161 tgcagcgata gtactaatga gtacatggac atgaaacctg gagtttctta
tgttgtccca
2221 accaaggccg acaaaaggag atctgtgaga ataggctcat acatagaaag
agatgtgact
2281 cccgccatca tggaggatga cgagttggcc ctagacttag aagacttgct
gagctttct
2341 taccaggtgg caaagggcat ggctttcctc gcctccaaga attgtattca
cagagacttg
2401 gcagccagaa atatcctcct tactcatggt cggatcacaa agatttgtga
ttttggtcta |

```
2461 gccagagaca tcaagaatga ttctaattat gtggttaaag gaaacgctcg actacctgtg 2521 aagtggatgg cacctgaaag cattttcaac tgtgtataca cgtttgaaag tgacgtctgg 2581 tcctatggga tttttctttg ggagctgttc tctttaggaa gcagcccta tcctggaatg 2641 ccggtcgatt ctaagttcta caagatgatc aaggaaggct tccggatgct cagccctgaa 2701 cacgcacctg ctgaaatgta tgacataatg aagacttgct gggatgcaga tcccctaaaa 2761 agaccaacat tcaagcaaat tgttcagcta attgagaagc agatttcaga gagcaccaat 2821 catatttact ccaacttagc aaactgcagc cccaaccgac agaagcccgt ggtagaccat 2881 tctgtgcgga tcaattctgt cggcagcacc gcttcctcct cccagcctct gcttgtgcac 2941 gacgatgtct gagcagaatc agtgtttggg tcacccctcc aggaatgatc tcttcttttg 3001 gcttccatga tggttatttt cttttctttc aacttgcatc caactccagg atagtgggca 3061 ccccactgca atcctgtctt tctgagcaca ctttagtggc cgatgatttt tgtcatcagc 3121 caccatccta ttgcaaaggt tccaactgta tatattccca atagcaacgt agcttctacc 3181 atgaacagaa acattctga tttggaaaaa gagagggagg tatggactgg gggccagagt 3241 cctttccaag gcttctccaa ttctgcccaa aaatatggtt gatagtttac ctgaataaat 3301 ggtagtaatc acagttggcc ttcagaacca tccatagtag tatgatgata caagattaga 3361 agctgaaaac ctaagtcctt tatgtggaaa acagaacatc attagaacaa aggacagagt 3421 atgaacacct gggcttaaga aatctagtat ttcatgctgg gaatgagaca taggccatga 3481 aaaaaatgat ccccaagtgt gaacaaaaga tgctcttctg tggaccactg catgagcttt 3541 tatactaccg acctggtttt taaatagagt ttgctattag agcattgaat tggagagaag
```

```
                            SEQUENCE LISTING 3601  gcctccctag ccagcacttg tatatacgca tctataaatt gtccgtgttc
      atacatttga
3661  ggggaaaaca ccataaggtt tcgtttctgt atacaaccct ggcattatgt
      ccactgtgta
3721  tagaagtaga ttaagagcca tataagtttg aaggaaacag ttaataccat
      tttttaagga
3781  aacaatataa ccacaaagca cagtttgaac aaaatctcct cttttagctg
      atgaacttat
3841  tctgtagatt ctgtggaaca agcctatcag cttcagaatg gcattgtact
      caatggattt
3901  gatgctgttt gacaaagtta ctgattcact gcatggctcc cacaggagtg
      ggaaaacact
3961  gccatcttag tttggattct tatgtagcag gaaataaagt ataggtttag
      cctccttcgc
4021  aggcatgtcc tggacaccgg gccagtatct atatatgtgt atgtacgttt
      gtatgtgtgt
4081  agacaaatat ttggaggggt attttttgccc tgagtccaag agggtccttt
      agtacctgaa
4141  aagtaacttg gctttcatta ttagtactgc tcttgtttct tttcacatag
      ctgtctagag
4201  tagcttacca gaagcttcca tagtggtgca gaggaagtgg aaggcatcag
      tccctatgta
4261  tttgcagttc acctgcactt aaggcactct gttatttaga ctcatcttac
      tgtacctgtt
4321  ccttagacct tccataatgc tactgtctca ctgaaacatt taaattttac
      cctttagact
4381  gtagcctgga tattattctt gtagtttacc tctttaaaaa caaaacaaaa
      caaaacaaaa
4441  aactcccctt cctcactgcc caatataaaa ggcaaatgtg tacatggcag
      agtttgtgtg
4501  ttgtcttgaa agattcaggt atgttgcctt tatggtttcc cccttctaca
      tttcttagac
4561  tacatttaga gaactgtggc cgttatctgg aagtaaccat ttgcactgga
      gttctatgct
4621  ctcgcacctt tccaaagtta acagattttg gggttgtgtt gtcacccaag
      agattgttgt
4681  ttgccatact ttgtctgaaa aattcctttg tgtttctatt gacttcaatg
      atagtaagaa
```

-continued

SEQUENCE LISTING

```
4741 aagtggttgt tagttataga tgtctaggta cttcaggggc acttcattga
gagttttgtc
4801 ttgccatact ttgtctgaaa aattcctttg tgtttctatt gacttcaatg
atagtaagaa
4861 aagtggttgt tagttataga tgtctaggta cttcaggggc acttcattga
gagttttgtc
4921 aatgtctttt gaatattccc aagcccatga gtccttgaaa atattttta
tatatacagt
4981 aactttatgt gtaaatacat aagcggcgta agtttaaagg atgttggtgt
tccacgtgtt
5041 ttattcctgt atgttgtcca attgttgaca gttctgaaga attc
```

SEQ ID NO: 3 Sequence NP_5202

Met Gly Pro Gly Val Leu Leu Leu Leu Val Ala Thr Ala Trp
His Gly Gln Gly Ile Pro Val Ile Glu Pro Ser Val Pro Glu Leu
Val Val Lys Pro Gly Ala Thr Val Thr Leu Arg Cys Val Gly Asn
Gly Ser Val Glu Trp Asp Gly Pro Pro Ser Pro His Trp Thr Leu
Tyr Ser Asp Gly Ser Ser Ser Ile Leu Ser Thr Asn Asn Ala Thr
Phe Gln Asn Thr Gly Thr Tyr Arg Cys Thr Glu Pro Gly Asp Pro
Leu Gly Gly Ser Ala Ala Ile His Leu Tyr Val Lys Asp Pro Ala
Arg Pro Trp Asn Val Leu Ala Gln Glu Val Val Phe Glu Asp
Gln Asp Ala Leu Leu Pro Cys Leu Leu Thr Asp Pro Val Leu Glu
Ala Gly Val Ser Leu Val Arg Val Arg Gly Arg Pro Leu Met Arg
His Thr Asn Tyr Ser Phe Ser Pro Trp His Gly Phe Thr Ile His
Arg Ala Lys Phe Ile Gln Ser Gln Asp Tyr Gln Cys Ser Ala Leu
Met Gly Gly Arg Lys Val Met Ser Ile Ser Ile Arg Leu Lys Val
Gln Lys Val Ile Pro Gly Pro Pro Ala Leu Thr Leu Val Pro Ala
Glu Leu Val Arg Ile Arg Gly Glu Ala Ala Gln Ile Val Cys Ser
Ala Ser Ser Val Asp Val Asn Phe Asp Val Phe Leu Gln His Asn
Asn Thr Lys Leu Ala Ile Pro Gln Gln Ser Asp Phe His Asn Asn
Arg Tyr Gln Lys Val Leu Thr Leu Asn Leu Asp Gln Val Asp Phe
Gln His Ala Gly Asn Tyr Ser Cys Val Ala Ser Asn Val Gln Gly
Lys His Ser Thr Ser Met Phe Phe Arg Val Val Glu Ser Ala Tyr
Leu Asn Leu Ser Ser Glu Gln Asn Leu Ile Gln Glu Val Thr Val
Gly Glu Gly Leu Asn Leu Lys Val Met Val Glu Ala Tyr Pro Gly
Leu Gln Gly Phe Asn Trp Thr Tyr Leu Gly Pro Phe Ser Asp His
Gln Pro Glu Pro Lys Leu Ala Asn Ala Thr Thr Lys Asp Thr Tyr
Arg His Thr Phe Thr Leu Ser Leu Pro Arg Leu Lys Pro Ser Glu
Ala Gly Arg Tyr Ser Phe Leu Ala Arg Asn Pro Gly Gly Trp Arg
Ala Leu Thr Phe Glu Leu Thr Leu Arg Tyr Pro Pro Glu Val Ser

-continued

SEQUENCE LISTING

```
Val Ile Trp Thr Phe Ile Asn Gly Ser Gly Thr Leu Leu Cys Ala
Ala Ser Gly Tyr Pro Gln Pro Asn Val Thr Trp Leu Gln Cys Ser
Gly His Thr Asp Arg Cys Asp Glu Ala Gln Val Leu Gln Val Trp
Asp Asp Pro Tyr Pro Glu Val Leu Ser Gln Glu Pro Phe His Lys
Val Thr Val Gln Ser Leu Leu Thr Val Glu Thr Leu Glu His Asn
Gln Thr Tyr Glu Cys Arg Ala His Asn Ser Val Gly Ser Gly Ser
Trp Ala Phe Ile Pro Ile Ser Ala Gly Ala His Thr His Pro Pro
Asp Glu Phe Leu Phe Thr Pro Val Val Val Ala Cys Met Ser Ile
Met Ala Leu Leu Leu Leu Leu Leu Leu Leu Leu Leu Tyr Lys Tyr
Lys Gln Lys Pro Lys Tyr Gln Val Arg Trp Lys Ile Ile Glu Ser
Tyr Glu Gly Asn Ser Tyr Thr Phe Ile Asp Pro Thr Gln Leu Pro
Tyr Asn Glu Lys Trp Glu Phe Pro Arg Asn Asn Leu Gln Phe Gly
Lys Thr Leu Gly Ala Gly Ala Phe Gly Lys Val Val Glu Ala Thr
Ala Phe Gly Leu Gly Lys Glu Asp Ala Val Leu Lys Val Ala Val
Lys Met Leu Lys Ser Thr Ala His Ala Asp Glu Lys Glu Ala Leu
Met Ser Glu Leu Lys Ile Met Ser His Leu Gly Gln His Glu Asn
Ile Val Asn Leu Leu Gly Ala Cys Thr His Gly Gly Pro Val Leu
Val Ile Thr Glu Tyr Cys Cys Tyr Gly Asp Leu Leu Asn Phe Leu
Arg Arg Lys Ala Glu Ala Met Leu Gly Pro Ser Leu Ser Pro Gly
Gln Asp Pro Glu Gly Gly Val Asp Tyr Lys Asn Ile His Leu Glu
Lys Lys Tyr Val Arg Arg Asp Ser Gly Phe Ser Ser Gln Gly Val
Asp Thr Tyr Val Glu Met Arg Pro Val Ser Thr Ser Ser Asn Asp
Ser Phe Ser Glu Gln Asp Leu Asp Lys Glu Asp Gly Arg Pro Leu
Glu Leu Arg Asp Leu Leu His Phe Ser Ser Gln Val Ala Gln Gly
Met Ala Phe Leu Ala Ser Lys Asn Cys Ile His Arg Asp Val Ala
Ala Arg Asn Val Leu Leu Thr Asn Gly His Val Ala Lys Ile Gly
Asp Phe Gly Leu Ala Arg Asp Ile Met Asn Asp Ser Asn Tyr Ile
Val Lys Gly Asn Ala Arg Leu Pro Val Lys Trp Met Ala Pro Glu
Ser Ile Phe Asp Cys Val Tyr Thr Val Gln Ser Asp Val Trp Ser
Tyr Gly Ile Leu Leu Trp Glu Ile Phe Ser Leu Gly Leu Asn Pro
Tyr Pro Gly Ile Leu Val Asn Ser Lys Phe Tyr Lys Leu Val Lys
Asp Gly Tyr Gln Met Ala Gln Pro Ala Phe Ala Pro Lys Asn Ile
Tyr Ser Ile Met Gln Ala Cys Trp Ala Leu Glu Pro Thr His Arg
Pro Thr Phe Gln Gln Ile Cys Ser Phe Leu Gln Glu Gln Ala Gln
Glu Asp Arg Arg Glu Arg Asp Tyr Thr Asn Leu Pro Ser Ser Ser
Arg Ser Gly Gly Ser Gly Ser Ser Ser Ser Glu Leu Glu Glu Glu
Ser Ser Ser Glu His Leu Thr Cys Cys Glu Gln Gly Asp Ile Ala
Gln Pro Leu Leu Gln Pro Asn Asn Tyr Gln Phe Cys
```

SEQUENCE LISTING

SEQ ID NO: 4 Sequence NM_005211

```
   1 gaagggcaga cagagtgtcc aaaagcgtga gagcacgaag tgaggagaag gtggagaaga
  61 gagaagagga agaggaagag gaagagagga agcggaggga actgcggcca ggctaaaagg
 121 ggaagaagag gatcagccca aggaggagga agaggaaaac aagacaaaca gccagtgcag
 181 aggagaggaa cgtgtgtcca gtgtcccgat ccctgcggag ctagtagctg agagctctgt
 241 gccctgggca ccttgcagcc ctgcacctgc ctgccacttc cccaccgagg ccatgggccc
 301 aggagttctg ctgctcctgc tggtggccac agcttggcat ggtcagggaa tcccagtgat
 361 agagcccagt gtccctgagc tggtcgtgaa gccaggagca acggtgacct tgcgatgtgt
 421 gggcaatggc agcgtggaat gggatggccc cccatcacct cactggaccc tgtactctga
 481 tggctccagc agcatcctca gcaccaacaa cgctaccttc caaaacacgg ggacctatcg
 541 ctgcactgag cctggagacc ccctgggagg cagcgccgcc atccacctct atgtcaaaga
 601 ccctgcccgg ccctggaacg tgctagcaca ggaggtggtc gtgttcgagg accaggacgc
 661 actactgccc tgtctgctca cagacccggt gctggaagca ggcgtctcgc tggtgcgtgt
 721 gcgtggccgg ccctcatgc gccacaccaa ctactccttc tcgccctggc atggcttcac
 781 catccacagg gccaagttca ttcagagcca ggactatcaa tgcagtgccc tgatgggtgg
 841 caggaaggtg atgtccatca gcatccggct gaaagtgcag aaagtcatcc cagggccccc
 901 agccttgaca ctggtgcctg cagagctggt gcggattcga ggggaggctg cccagatcgt
 961 gtgctcagcc agcagcgttg atgttaactt tgatgtcttc ctccaacaca acaacaccaa
1021 gctcgcaatc cctcaacaat ctgactttca taataccgt taccaaaaag tcctgaccct
1081 caacctcgat caagtagatt tccaacatgc cggcaactac tcctgcgtgg ccagcaacgt
```

SEQUENCE LISTING

```
1141  gcagggcaag cactccacct ccatgttctt ccgggtggta gagagtgcct
      acttgaactt
1201  gagctctgag cagaacctca tccaggaggt gaccgtgggg gaggggctca
      acctcaaagt
1261  catggtggag gcctacccag gcctgcaaggttttaactgga cctacctgg
      gaccctttc
1321  tgaccaccag cctgagccca agcttgctaa tgctaccacc aaggacacat
      acaggcacac
1381  cttcaccctc tctctgcccc gcctgaagcc ctctgaggct ggccgctact
      ccttcctggc
1441  cagaaaccca ggaggctgga gagctctgac gtttgagctc acccttcgat
      acccccaga
1501  ggtaagcgtc atatggacat tcatcaacgg ctctggcacc cttttgtgtg
      ctgcctctgg
1561  gtaccccag cccaacgtga catggctgca gtgcagtggc cacactgata
      ggtgtgatga
1621  ggcccaagtg ctgcaggtct gggatgaccc atacctgag gtcctgagcc
      aggagccctt
1681  ccacaaggtg acggtgcaga gcctgctgac tgttgagacc ttagagcaca
      accaaaccta
1741  cgagtgcagg gcccacaaca gcgtggggag tggctcctgg gccttcatac
      ccatctctgc
1801  aggagcccac acgcatcccc cggatgagtt cctcttcaca ccagtggtgg
      tcgcctgcat
1861  gtccatcatg gccttgctgc tgctgctgct cctgctgcta ttgtacaagt
      ataagcagaa
1921  gcccaagtac caggtccgct ggaagatcat cgagagctat gagggcaaca
      gttatacttt
1981  catcgacccc acgcagctgc cttacaacga gaagtgggag ttccccccgga
      acaacctgca
2041  gtttggtaag accctcggag ctggagcctt tgggaaggtg gtggaggcca
      cggccttttgg
2101  tctgggcaag gaggatgctg tcctgaaggt ggctgtgaag atgctgaagt
      ccacggccca
2161  tgctgatgag aaggaggccc tcatgtccga gctgaagatc atgagccacc
      tgggccagca
2221  cgagaacatc gtcaaccttc tgggagcctg tacccatgga ggccctgtac
      tggtcatcac
```

-continued

SEQUENCE LISTING

```
2281  ggagtactgt tgctatggcg acctgctcaa ctttctgcga aggaaggctg
      aggccatgct
2341  gggacccagc ctgagccccg gccaggaccc cgagggaggc gtcgactata
      agaacatcca
2401  cctcgagaag aaatatgtcc gcagggacag tggcttctcc agccagggtg
      tggacaccta
2461  tgtggagatg aggcctgtct ccacttcttc aaatgactcc ttctctgagc
      aagacctgga
2521  caaggaggat ggacggcccc tggagctccg ggacctgctt cacttctcca
      gccaagtagc
2581  ccagggcatg gccttcctcg cttccaagaa ttgcatccac cgggacgtgg
      cagcgcgtaa
2641  cgtgctgttg accaatggtc atgtggccaa gattggggac ttcgggctgg
      ctagggacat
2701  catgaatgac tccaactaca ttgtcaaggg caatgcccgc ctgcctgtga
      agtggatggc
2761  cccagagagc atctttgact gtgtctacac ggttcagagc gacgtctggt
      cctatggcat
2821  cctcctctgg gagatcttct cacttgggct gaatccctac cctggcatcc
      tggtgaacag
2881  caagttctat aaactggtga aggatggata ccaaatggcc cagcctgcat
      ttgccccaaa
2941  gaatatatac agcatcatgc aggcctgctg ggccttggag cccacccaca
      gacccacctt
3001  ccagcagatc tgctccttcc ttcaggagca ggcccaagag gacaggagag
      agcgggacta
3061  taccaatctg ccgagcagca gcagaagcgg tggcagcggc agcagcagca
      gtgagctgga
3121  ggaggagagc tctagtgagc acctgacctg ctgcgagcaa ggggatatcg
      cccagccctt
3181  gctgcagccc aacaactatc agttctgctg aggagttgac gacagggagt
      accactctcc
3241  cctcctccaa acttcaactc ctccatggat ggggcgacac ggggagaaca
      tacaaactct
3301  gccttcggtc atttcactca acagctcggc ccagctctga aacttgggaa
      ggtgagggat
3361  tcagggagg tcagaggatc ccacttcctg agcatgggcc atcactgcca
      gtcagggct
```

-continued

```
SEQUENCE LISTING 3421  gggggctgag ccctcacccc ccctccccct actgttctca tggtgttggc ctcgtgtttg 3481  ctatgccaac tagtagaacc ttctttccta atcccttat cttcatggaa atggactgac 3541  tttatgccta tgaagtcccc aggagctaca ctgatactga gaaaaccagg ctctttgggg 3601  ctagacagac tggcagagag tgagatctcc ctctctgaga ggagcagcag atgctcacag 3661  accacactca gctcaggccc cttggagcag gatggctcct ctaagaatct cacaggacct 3721  cttagtctct gccctatacg ccgccttcac tccacagcct cacccctccc acccccatac 3781  tggtactgct gtaatgagcc aagtggcagc taaaagttgg gggtgttctg cccagtcccg 3841  tcattctggg ctagaaggca ggggaccttg gcatgtggct ggccacacca agcaggaagc 3901  acaaactccc ccaagctgac tcatcctaac taacagtcac gccgtgggat gtctctgtcc 3961  acattaaact aacagcatta atgca
```

What is claimed is:

1. A pharmaceutical composition comprising a compound of formula:

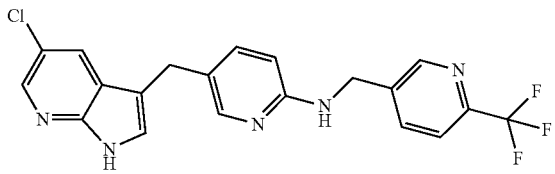 [SMILES: FC(F)(F)c1ccc(CNc2ccc(Cc3c[nH]c4ncc(Cl)cc34)cn2)cn1]

and a pharmaceutically acceptable carrier, diluent or excipient.

2. The pharmaceutical composition of claim 1 in unit dosage form.

3. The pharmaceutical composition of claim 2, wherein the unit dosage form is a capsule or a tablet.

4. The pharmaceutical composition of claim 2, wherein the unit dosage form is a capsule.

5. The pharmaceutical composition of claim 2, wherein the unit dosage form is a tablet.

6. A hydrochloric acid salt of a compound of formula:

7. A pharmaceutical composition comprising the hydrochloric acid salt of claim 6, and a pharmaceutically acceptable carrier, diluent or excipient.

8. The pharmaceutical composition of claim 7 in unit dosage form.

9. The pharmaceutical composition of claim 8, wherein the unit dosage form is a capsule or a tablet.

10. The pharmaceutical composition of claim 8, wherein the unit dosage form is a capsule.

11. The pharmaceutical composition of claim 8, wherein the unit dosage form is a tablet.

12. A polymorphic form of a compound of formula:

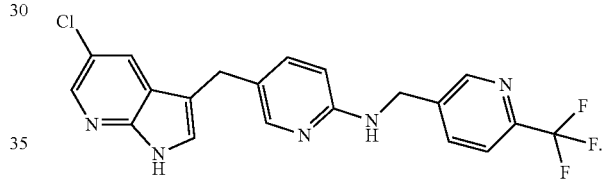

13. A pharmaceutical composition comprising the polymorphic form of claim 12, and a pharmaceutically acceptable carrier, diluent or excipient.

14. The pharmaceutical composition of claim 13 in unit dosage form.

15. The pharmaceutical composition of claim 14, wherein the unit dosage form is a capsule or a tablet.

16. The pharmaceutical composition of claim 14, wherein the unit dosage form is a capsule.

17. The pharmaceutical composition of claim 14, wherein the unit dosage form is a tablet.

* * * * *

```
SEQUENCE LISTING

<160> NUMBER OF SEQ ID NOS: 66

<210> SEQ ID NO 1
<211> LENGTH: 976
<212> TYPE: PRT
<213> ORGANISM: Homo sapiens

<400> SEQUENCE: 1

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
            20                  25                  30

Glu Pro Ser Pro Pro Ser Ile His Pro Gly Lys Ser Asp Leu Ile Val
        35                  40                  45

Arg Val Gly Asp Glu Ile Arg Leu Leu Cys Thr Asp Pro Gly Phe Val
    50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125
```

```
Asp Asn Asp Thr Leu Val Arg Cys Pro Leu Thr Asp Pro Glu Val Thr
130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
            165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
            245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
        275                 280                 285

Met Cys Tyr Ala Asn Asn Thr Phe Gly Ser Ala Asn Val Thr Thr Thr
290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
            325                 330                 335

Tyr Glu Ala Phe Pro Lys Pro Glu His Gln Gln Trp Ile Tyr Met Asn
            340                 345                 350

Arg Thr Phe Thr Asp Lys Trp Glu Asp Tyr Pro Lys Ser Glu Asn Glu
        355                 360                 365

Ser Asn Ile Arg Tyr Val Ser Glu Leu His Leu Thr Arg Leu Lys Gly
370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
            405                 410                 415

Thr Tyr Asp Arg Leu Val Asn Gly Met Leu Gln Cys Val Ala Ala Gly
            420                 425                 430

Phe Pro Glu Pro Thr Ile Asp Trp Tyr Phe Cys Pro Gly Thr Glu Gln
        435                 440                 445

Arg Cys Ser Ala Ser Val Leu Pro Val Asp Val Gln Thr Leu Asn Ser
450                 455                 460

Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
            485                 490                 495

Val Gly Lys Thr Ser Ala Tyr Phe Asn Phe Ala Phe Lys Gly Asn Asn
            500                 505                 510

Lys Glu Gln Ile His Pro His Thr Leu Phe Thr Pro Leu Leu Ile Gly
        515                 520                 525

Phe Val Ile Val Ala Gly Met Met Cys Ile Ile Val Met Ile Leu Thr
530                 535                 540

Tyr Lys Tyr Leu Gln Lys Pro Met Tyr Glu Val Gln Trp Lys Val Val
```

-continued

```
545                 550                 555                 560
Glu Glu Ile Asn Gly Asn Asn Tyr Val Tyr Ile Asp Pro Thr Gln Leu
                565                 570                 575

Pro Tyr Asp His Lys Trp Glu Phe Pro Arg Asn Arg Leu Ser Phe Gly
                580                 585                 590

Lys Thr Leu Gly Ala Gly Ala Phe Gly Lys Val Val Glu Ala Thr Ala
                595                 600                 605

Tyr Gly Leu Ile Lys Ser Asp Ala Ala Met Thr Val Ala Val Lys Met
                610                 615                 620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
                645                 650                 655

Leu Gly Ala Cys Thr Ile Gly Gly Pro Thr Leu Val Ile Thr Glu Tyr
                660                 665                 670

Cys Cys Tyr Gly Asp Leu Leu Asn Phe Leu Arg Arg Lys Arg Asp Ser
                675                 680                 685

Phe Ile Cys Ser Lys Gln Glu Asp His Ala Glu Ala Ala Leu Tyr Lys
                690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
                725                 730                 735

Asp Lys Arg Arg Ser Val Arg Ile Gly Ser Tyr Ile Glu Arg Asp Val
                740                 745                 750

Thr Pro Ala Ile Met Glu Asp Asp Glu Leu Ala Leu Asp Leu Glu Asp
                755                 760                 765

Leu Leu Ser Phe Ser Tyr Gln Val Ala Lys Gly Met Ala Phe Leu Ala
                770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
                805                 810                 815

Ile Lys Asn Asp Ser Asn Tyr Val Val Lys Gly Asn Ala Arg Leu Pro
                820                 825                 830

Val Lys Trp Met Ala Pro Glu Ser Ile Phe Asn Cys Val Tyr Thr Phe
                835                 840                 845

Glu Ser Asp Val Trp Ser Tyr Gly Ile Phe Leu Trp Glu Leu Phe Ser
850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
                885                 890                 895

Ala Glu Met Tyr Asp Ile Met Lys Thr Cys Trp Asp Ala Asp Pro Leu
                900                 905                 910

Lys Arg Pro Thr Phe Lys Gln Ile Val Gln Leu Ile Glu Lys Gln Ile
                915                 920                 925

Ser Glu Ser Thr Asn His Ile Tyr Ser Asn Leu Ala Asn Cys Ser Pro
                930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
                965                 970                 975
```

<210> SEQ ID NO 2
<211> LENGTH: 5084
<212> TYPE: DNA
<213> ORGANISM: Homo sapiens

<400> SEQUENCE: 2

```
gatcccatcg cagctaccgc gatgagaggc gctcgcggcg cctgggattt tctctgcgtt      60
ctgctcctac tgcttcgcgt ccagacaggc tcttctcaac catctgtgag tccaggggaa     120
ccgtctccac catccatcca tccaggaaaa tcagacttaa tagtccgcgt gggcgacgag     180
attaggctgt tatgcactga tccgggcttt gtcaaatgga cttttgagat cctggatgaa     240
acgaatgaga ataagcagaa tgaatggatc acggaaaagg cagaagccac caacaccggc     300
aaatacacgt gcaccaacaa acacggctta agcaattcca tttatgtgtt tgttagagat     360
cctgccaagc ttttccttgt tgaccgctcc ttgtatggga agaagacaa cgacacgctg      420
gtccgctgtc ctctcacaga cccagaagtg accaattatt ccctcaaggg gtgccagggg     480
aagcctcttc ccaaggactt gaggtttatt cctgacccca aggcgggcat catgatcaaa     540
agtgtgaaac gcgcctacca tcggctctgt ctgcattgtt ctgtggacca ggagggcaag     600
tcagtgctgt cggaaaaatt catcctgaaa gtgaggccag ccttcaaagc tgtgcctgtt     660
gtgtctgtgt ccaaagcaag ctatcttctt agggaagggg aagaattcac agtgacgtgc     720
acaataaaag atgtgtctag ttctgtgtac tcaacgtgga aaagagaaaa cagtcagact     780
aaactacagg agaaatataa tagctggcat cacggtgact tcaattatga acgtcaggca     840
acgttgacta tcagttcagc gagagttaat gattctggag tgttcatgtg ttatgccaat     900
aatactttg gatcagcaaa tgtcacaaca accttggaag tagtagataa aggattcatt     960
aatatcttcc ccatgataaa cactacagta tttgtaaacg atggagaaaa tgtagatttg    1020
attgttgaat atgaagcatt ccccaaacct gaacaccagc agtggatcta tatgaacaga    1080
accttcactg ataaatggga agattatccc aagtctgaga atgaaagtaa tatcagatac    1140
gtaagtgaac ttcatctaac gagattaaaa ggcaccgaag gaggcactta cacattccta    1200
gtgtccaatt ctgacgtcaa tgctgccata gcatttaatg tttatgtgaa tacaaaacca    1260
gaaatcctga cttacgacag gctcgtgaat ggcatgctcc aatgtgtggc agcaggattc    1320
ccagagccca aatagattg gtatttttgt ccaggaactg agcagagatg ctctgcttct    1380
gtactgccag tggatgtgca gacactaaac tcatctgggc caccgtttgg aaagctagtg    1440
gttcagagtt ctatagattc tagtgcattc aagcacaatg gcacggttga atgtaaggct    1500
tacaacgatg tgggcaagac ttctgcctat tttaactttg catttaaagg taacaacaaa    1560
gagcaaatcc atccccacac cctgttcact cctttgctga ttggtttcgt aatcgtagct    1620
ggcatgatgt gcattattgt gatgattctg acctacaaat atttacagaa acccatgtat    1680
gaagtacagt ggaaggttgt tgaggagata aatggaaaca attatgttta catagaccca    1740
acacaacttc cttatgatca caatgggag tttcccagaa acaggctgag ttttgggaaa    1800
accctgggtg ctggagcttt cgggaaggtt gttgaggcaa ctgcttatgg cttaattaag    1860
tcagatgcgg ccatgactgt cgctgtaaag atgctcaagc cgagtgccca tttgacagaa    1920
cgggaagccc tcatgtctga actcaaagtc ctgagttacc ttggtaatca catgaatatt    1980
gtgaatctac ttgagcctg caccattgga gggcccaccc tggtcattac agaatattgt    2040
tgctatggtg atcttttgaa ttttttgaga agaaacgtg attcatttat ttgttcaaag    2100
```

```
caggaagatc atgcagaagc tgcactttat aagaatcttc tgcattcaaa ggagtcttcc    2160
tgcagcgata gtactaatga gtacatggac atgaaacctg gagtttctta tgttgtccca    2220
accaaggccg acaaaaggag atctgtgaga ataggctcat acatagaaag agatgtgact    2280
cccgccatca tggaggatga cgagttggcc ctagacttag aagacttgct gagcttttct    2340
taccaggtgg caaagggcat ggctttcctc gcctccaaga attgtattca cagagacttg    2400
gcagccagaa atatcctcct tactcatggt cggatcacaa agatttgtga ttttggtcta    2460
gccagagaca tcaagaatga ttctaattat gtggttaaag␣ gaaacgctcg actacctgtg    2520
aagtggatgg cacctgaaag cattttcaac tgtgtataca cgtttgaaag tgacgtctgg    2580
tcctatggga ttttctttg ggagctgttc tctttaggaa gcagccccta tcctggaatg    2640
ccggtcgatt ctaagttcta caagatgatc aaggaaggct tccggatgct cagccctgaa    2700
cacgcacctg ctgaaatgta tgacataatg aagacttgct gggatgcaga tcccctaaaa    2760
agaccaacat tcaagcaaat tgttcagcta attgagaagc agatttcaga gagcaccaat    2820
catatttact ccaacttagc aaactgcagc cccaaccgac agaagcccgt ggtagaccat    2880
tctgtgcgga tcaattctgt cggcagcacc gcttcctcct cccagcctct gcttgtgcac    2940
gacgatgtct gagcagaatc agtgtttggg tcacccctcc aggaatgatc tcttcttttg    3000
gcttccatga tggttatttt cttttctttc aacttgcatc caactccagg atagtgggca    3060
ccccactgca atcctgtctt tctgagcaca ctttagtggc cgatgatttt tgtcatcagc    3120
caccatccta ttgcaaaggt tccaactgta tatattccca atagcaacgt agcttctacc    3180
atgaacagaa aacattctga tttggaaaaa gagagggagg tatggactgg gggccagagt    3240
cctttccaag gcttctccaa ttctgcccaa aaatatggtt gatagtttac ctgaataaat    3300
ggtagtaatc acagttggcc ttcagaacca tccatagtag tatgatgata caagattaga    3360
agctgaaaac ctaagtcctt tatgtggaaa acagaacatc attagaacaa aggacagagt    3420
atgaacacct gggcttaaga aatctagtat ttcatgctgg gaatgagaca taggccatga    3480
aaaaaatgat ccccaagtgt gaacaaaaga tgctcttctg tggaccactg catgagcttt    3540
tatactaccg acctggtttt taaatagagt ttgctattag agcattgaat tggagagaag    3600
gcctccctag ccagcacttg tatatacgca tctataaatt gtccgtgttc atacatttga    3660
ggggaaaaca cctaaaggtt tcgtttctgt atacaaccct ggcattatgt ccactgtgta    3720
tagaagtaga ttaagagcca tataagtttg aaggaaacag ttaataccat ttttttaagga    3780 aacaatataa ccacaaagca cagtttgaac aaaatctcct cttttagctg atgaacttat    3840
tctgtagatt ctgtggaaca agcctatcag cttcagaatg gcattgtact caatggattt    3900
gatgctgttt gacaaagtta ctgattcact gcatggctcc cacaggagtg ggaaaacact    3960
gccatcttag tttggattct tatgtagcag gaaataaagt ataggtttag cctccttcgc    4020
aggcatgtcc tggacaccgg gccagtatct atatatgtgt atgtacgttt gtatgtgtgt    4080
agacaaatat ttggaggggt attttttgccc tgagtccaag agggtccttt agtacctgaa    4140
aagtaacttg gctttcatta ttagtactgc tcttgtttct tttcacatag ctgtctagag    4200
tagcttacca gaagcttcca tagtggtgca gaggaagtgg aaggcatcag tcctatgta    4260 tttgcagttc acctgcactt aaggcactct gttatttaga ctcatcttac tgtacctgtt    4320
ccttagacct tccataatgc tactgtctca ctgaaacatt taaatttac cctttagact    4380 gtagcctgga tattattctt gtagtttacc tctttaaaaa caaacaaaa caaaacaaaa    4440 aactccccctt cctcactgcc caatataaaa ggcaaatgtg tacatggcag agtttgtgtg    4500
```

-continued

```
ttgtcttgaa agattcaggt atgttgcctt tatggtttcc cccttctaca tttcttagac    4560
tacatttaga gaactgtggc cgttatctgg aagtaaccat ttgcactgga gttctatgct    4620
ctcgcacctt tccaaagtta acagattttg gggttgtgtt gtcacccaag agattgttgt    4680
ttgccatact ttgtctgaaa aattcctttg tgtttctatt gacttcaatg atagtaagaa    4740
aagtggttgt tagttataga tgtctaggta cttcaggggc acttcattga gagttttgtc    4800
ttgccatact ttgtctgaaa aattcctttg tgtttctatt gacttcaatg atagtaagaa    4860
aagtggttgt tagttataga tgtctaggta cttcaggggc acttcattga gagttttgtc    4920
aatgtctttt gaatattccc aagcccatga gtccttgaaa atattttta tatatacagt     4980 aactttatgt gtaaatacat aagcggcgta agtttaaagg atgttggtgt tccacgtgtt    5040
ttattcctgt atgttgtcca attgttgaca gttctgaaga attc                     5084
```

<210> SEQ ID NO 3
<211> LENGTH: 972
<212> TYPE: PRT
<213> ORGANISM: Homo sapiens

<400> SEQUENCE: 3

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
        35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
        115                 120                 125

Leu Thr Asp Pro Val Leu Glu Ala Gly Val Ser Leu Val Arg Val Arg
    130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

```
Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Leu Asn Leu Ser
290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
                340                 345                 350

Asn Ala Thr Thr Lys Asp Thr Tyr Arg His Thr Phe Thr Leu Ser Leu
                355                 360                 365

Pro Arg Leu Lys Pro Ser Glu Ala Gly Arg Tyr Ser Phe Leu Ala Arg
        370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
                420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
        450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
                500                 505                 510

Phe Leu Phe Thr Pro Val Val Ala Cys Met Ser Ile Met Ala Leu
                515                 520                 525

Leu Leu Leu Leu Leu Leu Leu Leu Tyr Lys Tyr Lys Gln Lys Pro
        530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
                580                 585                 590

Phe Gly Lys Val Val Glu Ala Thr Ala Phe Gly Leu Gly Lys Glu Asp
        595                 600                 605

Ala Val Leu Lys Val Ala Val Lys Met Leu Lys Ser Thr Ala His Ala
        610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
                660                 665                 670

Asn Phe Leu Arg Arg Lys Ala Glu Ala Met Leu Gly Pro Ser Leu Ser
        675                 680                 685
```

```
Pro Gly Gln Asp Pro Glu Gly Val Asp Tyr Lys Asn Ile His Leu
    690             695                 700
Glu Lys Lys Tyr Val Arg Arg Asp Ser Gly Phe Ser Ser Gln Gly Val
705             710                 715                 720
Asp Thr Tyr Val Glu Met Arg Pro Val Ser Thr Ser Ser Asn Asp Ser
                725                 730                 735
Phe Ser Glu Gln Asp Leu Asp Lys Glu Asp Gly Arg Pro Leu Glu Leu
            740                 745                 750
Arg Asp Leu Leu His Phe Ser Ser Gln Val Ala Gln Gly Met Ala Phe
            755                 760                 765
Leu Ala Ser Lys Asn Cys Ile His Arg Asp Val Ala Ala Arg Asn Val
770             775                 780
Leu Leu Thr Asn Gly His Val Ala Lys Ile Gly Asp Phe Gly Leu Ala
785             790                 795                 800
Arg Asp Ile Met Asn Asp Ser Asn Tyr Ile Val Lys Gly Asn Ala Arg
                805                 810                 815
Leu Pro Val Lys Trp Met Ala Pro Glu Ser Ile Phe Asp Cys Val Tyr
            820                 825                 830
Thr Val Gln Ser Asp Val Trp Ser Tyr Gly Ile Leu Leu Trp Glu Ile
            835                 840                 845
Phe Ser Leu Gly Leu Asn Pro Tyr Pro Gly Ile Leu Val Asn Ser Lys
850             855                 860
Phe Tyr Lys Leu Val Lys Asp Gly Tyr Gln Met Ala Gln Pro Ala Phe
865             870                 875                 880
Ala Pro Lys Asn Ile Tyr Ser Ile Met Gln Ala Cys Trp Ala Leu Glu
                885                 890                 895
Pro Thr His Arg Pro Thr Phe Gln Gln Ile Cys Ser Phe Leu Gln Glu
            900                 905                 910
Gln Ala Gln Glu Asp Arg Arg Glu Arg Asp Tyr Thr Asn Leu Pro Ser
            915                 920                 925
Ser Ser Arg Ser Gly Gly Ser Gly Ser Ser Ser Glu Leu Glu Glu
930             935                 940
Glu Ser Ser Ser Glu His Leu Thr Cys Cys Glu Gln Gly Asp Ile Ala
945                 950                 955                 960
Gln Pro Leu Leu Gln Pro Asn Asn Tyr Gln Phe Cys
            965                 970

<210> SEQ ID NO 4
<211> LENGTH: 3985
<212> TYPE: DNA
<213> ORGANISM: Homo sapiens

<400> SEQUENCE: 4
gaagggcaga cagagtgtcc aaaagcgtga gagcacgaag tgaggagaag gtggagaaga      60
gagaagagga agaggaagag gaagagagga agcggaggga actgcggcca ggctaaaagg     120
ggaagaagag gatcagccca aggaggagga agaggaaaac aagacaaaca gccagtgcag     180
aggagaggaa cgtgtgtcca gtgtcccgat ccctgcggag ctagtagctg agagctctgt     240
gccctgggca ccttgcagcc ctgcacctgc ctgccacttc ccaccgagg ccatgggccc     300 aggagttctg ctgctcctgc tggtggccac agcttggcat ggtcagggaa tcccagtgat     360
agagcccagt gtccctgagc tggtcgtgaa gccaggagca acggtgacct tgcgatgtgt     420
gggcaatggc agcgtggaat gggatggccc cccatcacct cactggaccc tgtactctga     480
tggctccagc agcatcctca gcaccaacaa cgctaccttc caaaacacgg ggacctatcg     540
```

```
ctgcactgag cctggagacc ccctgggagg cagcgccgcc atccacctct atgtcaaaga    600
ccctgcccgg ccctggaacg tgctagcaca ggaggtggtc gtgttcgagg accaggacgc    660
actactgccc tgtctgctca cagacccggt gctggaagca ggcgtctcgc tggtgcgtgt    720
gcgtggccgg cccctcatgc gccacaccaa ctactccttc tcgccctggc atggcttcac    780
catccacagg gccaagttca ttcagagcca ggactatcaa tgcagtgccc tgatgggtgg    840
caggaaggtg atgtccatca gcatccggct gaaagtgcag aaagtcatcc agggccccc    900 agccttgaca ctggtgcctg cagagctggt gcggattcga ggggaggctg cccagatcgt    960
gtgctcagcc agcagcgttg atgttaactt tgatgtcttc ctccaacaca acaacaccaa   1020
gctcgcaatc cctcaacaat ctgactttca taataaccgt taccaaaaag tcctgaccct   1080
caacctcgat caagtagatt tccaacatgc cggcaactac tcctgcgtgg ccagcaacgt   1140
gcagggcaag cactccacct ccatgttctt ccgggtggta gagagtgcct acttgaactt   1200
gagctctgag cagaacctca tccaggaggt gaccgtgggg gaggggctca acctcaaagt   1260
catggtggag gcctacccag gcctgcaagg ttttaactgg acctacctgg dacccttttc   1320
tgaccaccag cctgagccca agcttgctaa tgctaccacc aaggacacat acaggcacac   1380 cttcacccte tctctgcccc gcctgaagcc ctctgaggct ggccgctact ccttcctggc   1440
cagaaaccca ggaggctgga gagctctgac gtttgagctc acccttcgat acccccaga   1500 ggtaagcgtc atatggacat tcatcaacgg ctctggcacc cttttgtgtg ctgcctctgg   1560 gtaccccag cccaacgtga catggctgca gtgcagtggc cacactgata ggtgtgatga   1620
ggcccaagtg ctgcaggtct gggatgaccc ataccctgag gtcctgagcc aggagcctt   1680 ccacaaggtg acggtgcaga gcctgctgac tgttgagacc ttagagcaca ccaaaaccta   1740
cgagtgcagg gcccacaaca cgtgggggag tggctcctgg gccttcatac ccatctctgc   1800
aggagcccac acgcatcccc cggatgagtt cctcttcaca ccagtggtgg tcgcctgcat   1860
gtccatcatg gccttgctgc tgctgctgct cctgctgcta ttgtacaagt ataagcagaa   1920
gcccaagtac caggtccgct ggaagatcat cgagagctat gagggcaaca gttatactt   1980 catcgacccc acgcagctgc cttacaacga gaagtgggag ttcccccgga caacctgca   2040 gtttggtaag accctcggag ctggagcctt tgggaaggtg gtggaggcca cggcctttgg   2100
tctgggcaag gaggatgctg tcctgaaggt ggctgtgaag atgctgaagt ccacggccca   2160
tgctgatgag aaggaggccc tcatgtccga gctgaagatc atgagccacc tgggccagca   2220
cgagaacatc gtcaaccttc tgggagcctg tacccatgga ggccctgtac tggtcatcac   2280
ggagtactgt tgctatggcg acctgctcaa cttctgcga aggaaggctg aggccatgct   2340
gggacccagc ctgagcccg gccaggaccc cgagggaggc gtcgactata gaacatcca   2400 cctcgagaag aaatatgtcc gcagggacag tggcttctcc agccagggtg tggacaccta   2460
tgtggagatg aggcctgtct ccacttcttc aaatgactcc ttctctgagc aagacctgga   2520
caaggaggat ggacggcccc tggagctccg ggacctgctt cacttctcca gccaagtagc   2580
ccagggcatg gccttcctcg cttccaagaa ttgcatccac cgggacgtgg cagcgcgtaa   2640
cgtgctgttg accaatggtc atgtggccaa gattggggac ttcgggctgg ctaggacat   2700 catgaatgac tccaactaca ttgtcaaggg caatgcccgc ctgcctgtga agtggatggc   2760
cccagagagc atctttgact gtgtctacac ggttcagagc gacgtctggt cctatggcat   2820
cctcctctgg gagatcttct cacttgggct gaatccctac cctggcatcc tggtgaacag   2880
```

-continued

```
caagttctat aaactggtga aggatggata ccaaatggcc cagcctgcat ttgccccaaa    2940
gaatatatac agcatcatgc aggcctgctg ggccttggag cccacccaca gacccacctt    3000
ccagcagatc tgctccttcc ttcaggagca ggcccaagag gacaggagag agcgggacta    3060
taccaatctg ccgagcagca gcagaagcgg tggcagcggc agcagcagca gtgagctgga    3120
ggaggagagc tctagtgagc acctgacctg ctgcgagcaa ggggatatcg cccagccctt    3180
gctgcagccc aacaactatc agttctgctg aggagttgac gacagggagt accactctcc    3240
cctcctccaa acttcaactc ctccatggat ggggcgacac ggggagaaca tacaaactct    3300
gccttcggtc atttcactca acagctcggc ccagctctga aacttgggaa ggtgagggat    3360
tcaggggagg tcagaggatc ccacttcctg agcatgggcc atcactgcca gtcaggggct    3420
gggggctgag ccctcacccc cccctcccct actgttctca tggtgttggc ctcgtgtttg    3480
ctatgccaac tagtagaacc ttctttccta atcccttat  cttcatggaa atggactgac    3540
tttatgccta tgaagtcccc aggagctaca ctgatactga gaaaaccagg ctctttgggg    3600
ctagacagac tggcagagag tgagatctcc ctctctgaga ggagcagcag atgctcacag    3660
accacactca gctcaggccc cttggagcag gatggctcct ctaagaatct cacaggacct    3720
cttagtctct gccctatacg ccgccttcac tccacagcct caccccctccc accccacatac    3780 tggtactgct gtaatgagcc aagtggcagc taaaagttgg gggtgttctg cccagtcccg    3840
tcattctggg ctagaaggca ggggaccttg gcatgtggct ggccacacca agcaggaagc    3900
acaaactccc ccaagctgac tcatcctaac taacagtcac gccgtgggat gtctctgtcc    3960
acattaaact aacagcatta atgca                                          3985
```

<210> SEQ ID NO 5
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 5

```
atgtacgaag ttcagtggaa agttgttgaa gaaatcaacg g                         41
```

<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 6

```
ggtcgatgta aacgtagttg ttaccgttga tttcttcaac aacttt                    46
```

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 7

```
aacaactacg tttacatcga cccgacccag ctgccgtacg ac                        42
```

<210> SEQ ID NO 8

```
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gttacgcggg aactcccatt tgtggtcgta cggcagctgg gtc                          43

<210> SEQ ID NO 9
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aaatgggagt tcccgcgtaa ccgtctgtct ttcggtaaaa ccc                          43

<210> SEQ ID NO 10
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
accgaacgca cccgcaccca gggttttacc gaaagacaga c                            41

<210> SEQ ID NO 11
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggtgcgggtg cgttcggtaa agttgttgaa gcgaccgcgt acg                          43

<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gccgcgtcag atttgatcag accgtacgcg gtcgcttcaa c                            41

<210> SEQ ID NO 13
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctgatcaaat ctgacgcggc gatgaccgtt gcggttaaaa tgc                          43

<210> SEQ ID NO 14
<211> LENGTH: 43
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtcaggtgcg cagacggttt cagcatttta accgcaacgg tca                43

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aaaccgtctg cgcacctgac cgaacgtgaa gcgctgatgt ctg                43

<210> SEQ ID NO 16
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccaggtaaga cagaactttc agttcagaca tcagcgcttc acgt               44

<210> SEQ ID NO 17
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctgaaagttc tgtcttacct gggtaaccac atgaacatcg ttaa               44

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggtgcacgca cccagcaggt taacgatgtt catgtggtta c                  41

<210> SEQ ID NO 19
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctgctgggtg cgtgcaccat cggtggtccg accctggtta tca                43

<210> SEQ ID NO 20
<211> LENGTH: 43
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 20
gtcaccgtag cagcagtatt cggtgataac cagggtcgga cca                    43

<210> SEQ ID NO 21
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gaatactgct gctacggtga cctgctgaac ttcctgcgtc gta                    43

<210> SEQ ID NO 22
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agagcagatg aaagagtcac gtttacgacg caggaagttc agc                    43

<210> SEQ ID NO 23
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgtgactctt tcatctgctc taaacaggaa gaccacgcgg aag                    43

<210> SEQ ID NO 24
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cagcaggttt ttgtacagcg ccgcttccgc gtggtcttcc tgt                    43

<210> SEQ ID NO 25
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcgctgtaca aaaacctgct gcactctaaa gaatcttctt gctc                    44

<210> SEQ ID NO 26
<211> LENGTH: 45
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 26
ccatgtattc gttggtagag tcagagcaag aagattcttt agagt              45

<210> SEQ ID NO 27
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gactctacca acgaatacat ggacatgaaa ccgggtgttt ctta                44

<210> SEQ ID NO 28
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tccgctttgg tcggaacaac gtaagaaaca cccggtttca tgt                 43

<210> SEQ ID NO 29
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gttgttccga ccaaagcgga caaacgtcgt tctgttcgta tcg                 43

<210> SEQ ID NO 30
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
taacgtcacg ttcgatgtaa gaaccgatac gaacagaacg acgttt              46

<210> SEQ ID NO 31
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tcttacatcg aacgtgacgt taccccggcg atcatggaag acg                 43

<210> SEQ ID NO 32
<211> LENGTH: 40
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 32
ccaggtccag cgccagttcg tcgtcttcca tgatcgccgg                            40

<210> SEQ ID NO 33
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gaactggcgc tggacctgga agacctgctg tctttctctt acc                       43

<210> SEQ ID NO 34
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gaacgccata cctttcgcaa cctggtaaga gaaagacagc aggt                      44

<210> SEQ ID NO 35
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gttgcgaaag gtatggcgtt cctggcgtct aaaaactgca tcca                      44

<210> SEQ ID NO 36
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cgcgccgcca ggtcacggtg gatgcagttt ttagacgcc                            39

<210> SEQ ID NO 37
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cgtgacctgg cggcgcgtaa catcctgctg acccacggtc g                         41

<210> SEQ ID NO 38
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
accgaagtcg cagattttgg tgatacgacc gtgggtcagc agg                43

<210> SEQ ID NO 39
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
accaaaatct gcgacttcgg tctggcgcgt gacatcaaaa acg                43

<210> SEQ ID NO 40
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gttaccttta acaacgtagt tagagtcgtt tttgatgtca cgcgcc             46

<210> SEQ ID NO 41
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tctaactacg ttgttaaagg taacgcgcgt ctgccggtta aatg               44

<210> SEQ ID NO 42
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gaagatagat tccggcgcca tccatttaac cggcagacgc gc                 42

<210> SEQ ID NO 43
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
atggcgccgg aatctatctt caactgcgtt tacaccttcg aatc               44

<210> SEQ ID NO 44
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 44
gataccgtaa gaccaaacgt cagattcgaa ggtgtaaacg cag                43

<210> SEQ ID NO 45
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gacgtttggt cttacggtat cttcctgtgg gaactgttct ctc                43

<210> SEQ ID NO 46
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cctgtgggaa ctgttctctc tgggttcttc tccgtacccg g                  41

<210> SEQ ID NO 47
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggttcttctc cgtacccggg tatgccggtt gactctaaat tctat              45

<210> SEQ ID NO 48
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cggaaacctt ctttgatcat tttgtagaat ttagagtcaa ccggc              45

<210> SEQ ID NO 49
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
aaaatgatca agaaggtttc cgtatgctg tctccggaac acg                 43

<210> SEQ ID NO 50
<211> LENGTH: 42
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 50
atgtcgtaca tttccgccgg cgcgtgttcc ggagacagca ta                      42

<210> SEQ ID NO 51
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ccggcggaaa tgtacgacat catgaaaacc tgctgggacg cg                      42

<210> SEQ ID NO 52
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
aaggtcggac gtttcagcgg gtccgcgtcc cagcaggttt tc                      42

<210> SEQ ID NO 53
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ccgctgaaac gtccgacctt caaacagatc gttcagctga tcg                     43

<210> SEQ ID NO 54
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ttggtagatt cagagatctg tttttcgatc agctgaacga tctgtt                  46

<210> SEQ ID NO 55
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
aaacagatct ctgaatctac caaccacatc tactctaacc tggc                    44

<210> SEQ ID NO 56
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
```
tgacggttcg gagagcagtt cgccaggtta gagtagatgt gg          42

<210> SEQ ID NO 57
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
aactgctctc cgaaccgtca gaaaccggtt gttgaccact ctg         43

<210> SEQ ID NO 58
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gtagaaccaa cagagttgat acgaacagag tggtcaacaa ccggt       45

<210> SEQ ID NO 59
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cgtatcaact ctgttggttc taccgcgtct tcttctcagc cg          42

<210> SEQ ID NO 60
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
aacgtcgtcg tgaaccagca gcggctgaga agaagacgcg             40

<210> SEQ ID NO 61
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gttgtttcat atgtacgaag ttcagtggaa ag                     32

<210> SEQ ID NO 62
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62

```
gttgtttgtc gactaaacgt cgtcgtgaac cagcag                                36
```

<210> SEQ ID NO 63
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63

```
gttcttgtcg actatttctg acggttcgga gagc                                  34
```

<210> SEQ ID NO 64
<211> LENGTH: 1325
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (88)..(1302)

<400> SEQUENCE: 64

```
taatacgact cactataggg gaattgtgag cggataacaa ttcccctcta gaaataattt       60
tgtttaactt taagaaggag atatacc atg ggt cac cac cat cac cat cat atg      114
                                Met Gly His His His His His His Met
                                  1               5 tac gaa gtt cag tgg aaa gtt gtt gaa gaa atc aac ggt aac aac tac        162
Tyr Glu Val Gln Trp Lys Val Val Glu Glu Ile Asn Gly Asn Asn Tyr
 10              15                  20                  25 gtt tac atc gac ccg acc cag ctg ccg tac gac cac aaa tgg gag ttc        210
Val Tyr Ile Asp Pro Thr Gln Leu Pro Tyr Asp His Lys Trp Glu Phe
                 30                  35                  40 ccg cgt aac cgt ctg tct ttc ggt aaa acc ctg ggt gcg ggt gcg ttc        258
Pro Arg Asn Arg Leu Ser Phe Gly Lys Thr Leu Gly Ala Gly Ala Phe
             45                  50                  55 ggt aaa gtt gtt gaa gcg acc gcg tac ggt ctg atc aaa tct gac gcg        306
Gly Lys Val Val Glu Ala Thr Ala Tyr Gly Leu Ile Lys Ser Asp Ala
         60                  65                  70 gcg atg acc gtt gcg gtt aaa atg ctg aaa ccg tct gcg cac ctg acc        354
Ala Met Thr Val Ala Val Lys Met Leu Lys Pro Ser Ala His Leu Thr
 75                  80                  85 gaa cgt gaa gcg ctg atg tct gaa ctg aaa gtt ctg tct tac ctg ggt        402
Glu Arg Glu Ala Leu Met Ser Glu Leu Lys Val Leu Ser Tyr Leu Gly
 90                  95                 100                 105 aac cac atg aac atc gtt aac ctg ctg ggt gcg tgc acc atc ggt ggt        450
Asn His Met Asn Ile Val Asn Leu Leu Gly Ala Cys Thr Ile Gly Gly
                110                 115                 120 ccg acc ctg gtt atc acc gaa tac tgc tgc tac ggt gac ctg ctg aac        498
Pro Thr Leu Val Ile Thr Glu Tyr Cys Cys Tyr Gly Asp Leu Leu Asn
            125                 130                 135 ttc ctg cgt cgt aaa cgt gac tct ttc atc tgc tct aaa cag gaa gac        546
Phe Leu Arg Arg Lys Arg Asp Ser Phe Ile Cys Ser Lys Gln Glu Asp
        140                 145                 150 cac gcg gaa gcg gcg ctg tac aaa aac ctg ctg cac tct aaa gaa tct        594
His Ala Glu Ala Ala Leu Tyr Lys Asn Leu Leu His Ser Lys Glu Ser
    155                 160                 165 tct tgc tct gac tct acc aac gaa tac atg gac atg aaa ccg ggt gtt       642
Ser Cys Ser Asp Ser Thr Asn Glu Tyr Met Asp Met Lys Pro Gly Val
170                 175                 180                 185
```

```
tct tac gtt gtt ccg acc aaa gcg gac aaa cgt cgt tct gtt cgt atc    690
Ser Tyr Val Val Pro Thr Lys Ala Asp Lys Arg Arg Ser Val Arg Ile
            190                 195                 200 ggt tct tac atc gaa cgt gac gtt acc ccg gcg atc atg gaa gac gac    738
Gly Ser Tyr Ile Glu Arg Asp Val Thr Pro Ala Ile Met Glu Asp Asp
            205                 210                 215 gaa ctg gcg ctg gac ctg gaa gac ctg ctg tct ttc tct tac cag gtt    786
Glu Leu Ala Leu Asp Leu Glu Asp Leu Leu Ser Phe Ser Tyr Gln Val
            220                 225                 230 gcg aaa ggt atg gcg ttc ctg gcg tct aaa aac tgc atc cac cgt gac    834
Ala Lys Gly Met Ala Phe Leu Ala Ser Lys Asn Cys Ile His Arg Asp
235                 240                 245 ctg gcg gcg cgt aac atc ctg ctg acc cac ggt cgt atc acc aaa atc    882
Leu Ala Ala Arg Asn Ile Leu Leu Thr His Gly Arg Ile Thr Lys Ile
250                 255                 260                 265 tgc gac ttc ggt ctg gcg cgt gac atc aaa aac gac tct aac tac gtt    930
Cys Asp Phe Gly Leu Ala Arg Asp Ile Lys Asn Asp Ser Asn Tyr Val
            270                 275                 280 gtt aaa ggt aac gcg cgt ctg ccg gtt aaa tgg atg gcg ccg gaa tct    978
Val Lys Gly Asn Ala Arg Leu Pro Val Lys Trp Met Ala Pro Glu Ser
            285                 290                 295 atc ttc aac tgc gtt tac acc ttc gaa tct gac gtt tgg tct tac ggt   1026
Ile Phe Asn Cys Val Tyr Thr Phe Glu Ser Asp Val Trp Ser Tyr Gly
            300                 305                 310 atc ttc ctg tgg gaa ctg ttc tct ctg ggt tct tct ccg tac ccg ggt   1074
Ile Phe Leu Trp Glu Leu Phe Ser Leu Gly Ser Ser Pro Tyr Pro Gly
            315                 320                 325 atg ccg gtt gac tct aaa ttc tac aaa atg atc aaa gaa ggt ttc cgt   1122
Met Pro Val Asp Ser Lys Phe Tyr Lys Met Ile Lys Glu Gly Phe Arg
330                 335                 340                 345 atg ctg tct ccg gaa cac gcg ccg gcg gaa atg tac gac atc atg aaa   1170
Met Leu Ser Pro Glu His Ala Pro Ala Glu Met Tyr Asp Ile Met Lys
            350                 355                 360 acc tgc tgg gac gcg gac ccg ctg aaa cgt ccg acc ttc aaa cag atc   1218
Thr Cys Trp Asp Ala Asp Pro Leu Lys Arg Pro Thr Phe Lys Gln Ile
            365                 370                 375 gtt cag ctg atc gaa aaa cag atc tct gaa tct acc aac cac atc tac   1266
Val Gln Leu Ile Glu Lys Gln Ile Ser Glu Ser Thr Asn His Ile Tyr
            380                 385                 390 tct aac ctg gcg aac tgc tct ccg aac cgt cag aaa tagtcgactg        1312
Ser Asn Leu Ala Asn Cys Ser Pro Asn Arg Gln Lys
            395                 400             405 aaaaaggaag agt                                                    1325

<210> SEQ ID NO 65
<211> LENGTH: 405
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Gly His His His His His His Met Tyr Glu Val Gln Trp Lys Val
1               5                   10                  15

Val Glu Glu Ile Asn Gly Asn Asn Tyr Val Tyr Ile Asp Pro Thr Gln
            20                  25                  30

Leu Pro Tyr Asp His Lys Trp Glu Phe Pro Arg Asn Arg Leu Ser Phe
        35                  40                  45

Gly Lys Thr Leu Gly Ala Gly Ala Phe Gly Lys Val Val Glu Ala Thr
```

```
            50                  55                  60
Ala Tyr Gly Leu Ile Lys Ser Asp Ala Ala Met Thr Val Ala Val Lys
 65                  70                  75                  80

Met Leu Lys Pro Ser Ala His Leu Thr Glu Arg Glu Ala Leu Met Ser
                 85                  90                  95

Glu Leu Lys Val Leu Ser Tyr Leu Gly Asn His Met Asn Ile Val Asn
                100                 105                 110

Leu Leu Gly Ala Cys Thr Ile Gly Gly Pro Thr Leu Val Ile Thr Glu
                115                 120                 125

Tyr Cys Cys Tyr Gly Asp Leu Leu Asn Phe Leu Arg Arg Lys Arg Asp
130                 135                 140

Ser Phe Ile Cys Ser Lys Gln Glu Asp His Ala Glu Ala Ala Leu Tyr
145                 150                 155                 160

Lys Asn Leu Leu His Ser Lys Glu Ser Ser Cys Ser Asp Ser Thr Asn
                165                 170                 175

Glu Tyr Met Asp Met Lys Pro Gly Val Ser Tyr Val Val Pro Thr Lys
                180                 185                 190

Ala Asp Lys Arg Arg Ser Val Arg Ile Gly Ser Tyr Ile Glu Arg Asp
                195                 200                 205

Val Thr Pro Ala Ile Met Glu Asp Glu Leu Ala Leu Asp Leu Glu
210                 215                 220

Asp Leu Leu Ser Phe Ser Tyr Gln Val Ala Lys Gly Met Ala Phe Leu
225                 230                 235                 240

Ala Ser Lys Asn Cys Ile His Arg Asp Leu Ala Ala Arg Asn Ile Leu
                245                 250                 255

Leu Thr His Gly Arg Ile Thr Lys Ile Cys Asp Phe Gly Leu Ala Arg
                260                 265                 270

Asp Ile Lys Asn Asp Ser Asn Tyr Val Val Lys Gly Asn Ala Arg Leu
                275                 280                 285

Pro Val Lys Trp Met Ala Pro Glu Ser Ile Phe Asn Cys Val Tyr Thr
                290                 295                 300

Phe Glu Ser Asp Val Trp Ser Tyr Gly Ile Phe Leu Trp Glu Leu Phe
305                 310                 315                 320

Ser Leu Gly Ser Ser Pro Tyr Pro Gly Met Pro Val Asp Ser Lys Phe
                325                 330                 335

Tyr Lys Met Ile Lys Glu Gly Phe Arg Met Leu Ser Pro Glu His Ala
                340                 345                 350

Pro Ala Glu Met Tyr Asp Ile Met Lys Thr Cys Trp Asp Ala Asp Pro
                355                 360                 365

Leu Lys Arg Pro Thr Phe Lys Gln Ile Val Gln Leu Ile Glu Lys Gln
                370                 375                 380

Ile Ser Glu Ser Thr Asn His Ile Tyr Ser Asn Leu Ala Asn Cys Ser
385                 390                 395                 400

Pro Asn Arg Gln Lys
                405
```

```
<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Lys Lys Lys Ser Pro Gly Glu Tyr Val Asn Ile Glu Phe Gly
1               5                   10
```